United States Patent
Oda et al.

(10) Patent No.: US 11,725,210 B2
(45) Date of Patent: Aug. 15, 2023

(54) IMMUNOMODULATORY FUSION PROTEINS AND USES THEREOF

(71) Applicant: Fred Hutchinson Cancer Center, Seattle, WA (US)

(72) Inventors: Shannon K. Oda, Lake Forest Park, WA (US); Philip D. Greenberg, Mercer Island, WA (US); Thomas M. Schmitt, Seattle, WA (US)

(73) Assignee: Fred Hutchinson Cancer Center, Seattle, WA (US)

( * ) Notice: Subject to any disclaimer, the term of this patent is extended or adjusted under 35 U.S.C. 154(b) by 614 days.

(21) Appl. No.: 16/494,729

(22) PCT Filed: Mar. 16, 2018

(86) PCT No.: PCT/US2018/022998
§ 371 (c)(1),
(2) Date: Sep. 16, 2019

(87) PCT Pub. No.: WO2018/170475
PCT Pub. Date: Sep. 20, 2018

(65) Prior Publication Data
US 2020/0009190 A1    Jan. 9, 2020

Related U.S. Application Data

(60) Provisional application No. 62/629,663, filed on Feb. 12, 2018, provisional application No. 62/473,282, filed on Mar. 17, 2017.

(51) Int. Cl.
| C07K 14/705 | (2006.01) |
| C12N 15/62 | (2006.01) |
| A61K 35/17 | (2015.01) |
| C07K 14/47 | (2006.01) |
| C07K 14/725 | (2006.01) |

(52) U.S. Cl.
CPC ............. *C12N 15/62* (2013.01); *A61K 35/17* (2013.01); *C07K 14/4705* (2013.01); *C07K 14/7051* (2013.01); *C07K 14/70521* (2013.01); *C07K 14/70578* (2013.01); *C07K 2319/03* (2013.01); *C07K 2319/33* (2013.01)

(58) Field of Classification Search
None
See application file for complete search history.

(56) References Cited

U.S. PATENT DOCUMENTS

| 5,712,149 A | 1/1998 | Roberts |
| 6,083,751 A | 7/2000 | Feldhaus et al. |
| 9,163,258 B2 | 10/2015 | Riddell et al. |
| 9,987,308 B2 | 6/2018 | Riddell et al. |
| 10,188,749 B2 | 1/2019 | Stephan et al. |
| 10,350,245 B2 | 7/2019 | Adair et al. |
| 2013/0202622 A1 | 8/2013 | Riddell et al. |
| 2014/0219975 A1 | 8/2014 | June et al. |
| 2014/0242049 A1 | 8/2014 | Choi et al. |
| 2014/0314795 A1 | 10/2014 | Riddell et al. |
| 2016/0008399 A1 | 1/2016 | Stephan |
| 2016/0083449 A1 | 3/2016 | Schmitt et al. |
| 2018/0044404 A1 | 2/2018 | Oda et al. |
| 2018/0353588 A1 | 12/2018 | Boyd et al. |
| 2018/0369280 A1 | 12/2018 | Schmitt et al. |
| 2019/0046572 A1 | 2/2019 | Stephan |
| 2019/0054121 A1 | 2/2019 | Stephan |
| 2019/0111153 A1 | 4/2019 | Stephan et al. |
| 2019/0127435 A1 | 5/2019 | Schmitt et al. |
| 2019/0209671 A1 | 7/2019 | Dai et al. |
| 2021/0403532 A1 | 12/2021 | Oda et al. |

FOREIGN PATENT DOCUMENTS

| CN | 110330567 A | 10/2019 |
| WO | 2012/042480 A1 | 4/2012 |
| WO | 2012/079000 A1 | 6/2012 |
| WO | 2012/138858 A1 | 10/2012 |
| WO | 2013/019615 A2 | 2/2013 |
| WO | 2013/123061 A1 | 8/2013 |
| WO | 2014/106839 A1 | 7/2014 |
| WO | 2014/172584 A1 | 10/2014 |
| WO | 2016/014535 A1 | 1/2016 |
| WO | 2016/014565 A2 | 1/2016 |
| WO | 2016/014576 A1 | 1/2016 |
| WO | WO 2016024021 A1 | 2/2016 |
| WO | 2016/102965 A1 | 6/2016 |
| WO | 2016/141357 A1 | 9/2016 |

(Continued)

OTHER PUBLICATIONS

Starling et al. (Biochemistry 1998, 37, 3723-3726). (Year: 1998).*
Starling et al. (J. Exp. Med., vol. 185, No. 8, Apr. 21, 1997 1487-1492). (Year: 1997).*
Orlinick et al. (JBC, vol. 272, No. 46, Issue of Nov. 14, pp. 28889-28894, 1997). (Year: 1997).*
Bajorath (Journal of Computer-Aided Molecular Design, 13: 409-418, 1999). (Year: 1999).*
Ramaswamy (Results and Problems in Cell Differentiation; Springer-Verlag Berlin Heidelberg 2009, "Many Checkpoints on the Road to Cell Death: Regulation of Fas-FasL Interactions and Fas Signaling in Peripheral Immune Responses," pp. 17-47). (Year: 2009).*
Takata et al. (Immunology. Sep. 2005;116(1):21-9). (Year: 2005).*
Jang et al. (Biochemical and Biophysical Research Communications (1998), vol. 242, pp. 613-620). (Year: 1998).*
Arch et al. (MCB, Jan. 1998, p. 558-565). (Year: 1998).*
Barao et al. (Front Immunol. Jan. 4, 2013;3:402). (Year: 2013).*

(Continued)

*Primary Examiner* — Zachary S Skelding
(74) *Attorney, Agent, or Firm* — Seed Intellectual Property Law Group LLP

(57) ABSTRACT

The present disclosure relates to immunomodulatory fusion proteins containing an extracellular binding domain and an intracellular signaling domain, wherein binding of a target can generate a modulatory signal in a host cell, such as a T cell. The present disclosure also relates to uses of immune cells expressing such immunomodulatory fusion proteins to treat certain diseases, such as cancer or infectious disease.

22 Claims, 106 Drawing Sheets

Specification includes a Sequence Listing.

(56) References Cited

FOREIGN PATENT DOCUMENTS

WO         2016203048        12/2016

OTHER PUBLICATIONS

Anderson et al., "Engineering adoptive T cell therapy to co-opt Fas ligand-mediated death signaling in ovarian cancer enhances therapeutic efficacy," Journal for ImmunoTherapy of Cancer 10:e003959, 2022. (14 pages).

Brenner, "Errors in Genome Annotation," Trends in Genetics 15(4):132-133, 1999.

Jena et al., "Redirecting T-cell specificity by introducing a tumor-specific chimeric antigen receptor," Blood 116(7):1035-1044, 2010.

Jones et al., "Lentiviral Vector Design for Optimal T Cell Receptor Gene Expression in the Transduction of Peripheral Blood Lymphocytes and Tumor-Infiltrating Lymphocytes," Human Gene Therapy 20:630-640, 2009.

Leccia et al., "Cytometric and Biochemical Characterization of Human Breast Cancer Cells Reveals Heterogenous Myoepithelial Phenotypes," Cytometry Part A 81A:960-972, 2012.

Ma et al., "Isolation, Culture and Biological Characteristics of Tumor Stem Cells in Human Colorectal Carcinoma," Cancer Res Prev Treat 41(4):345-349, 2014 (5 pages) (with English abstract).

Oda et al., "A Fas-4-1BB fusion protein converts a death to a pro-survival signal and enhances T cell therapy," J. Exp. Med. 217(12): e20191166, 2020 (20 Pages).

Smith et al., "The challenges of genome sequence annotation or "The devil is in the details,"" Nature Biotechnology 15:1222-1223, 1997.

Prosser et al., "Primary Human CD8+ T Cells Engineered to Express a PD1-CD28 Chimeric Receptor are Co-Stimulated through the Exploitation of Tumor Expressed PD-L1," Molecular Therapy 19 (Supplement 1):S192, 2011.

Liu et al., "Synthesis of full length recombinant chimeric receptor anti-erbB2 scFv-CD28-ζ and construction of its eukaryotic expression vector," J Chinese PLA Postgrad Med Sch 31(4):360-362, 2010 (with English Abstract).

Alakoskela et al., "Mechanisms for Size-Dependent Protein Segregation at Immune Synapses Assessed with Molecular Rulers," Biophys. J. 100(12):2865-2874, 2011.

Ankri et al., "Human T Cells Engineered To Express a Programmed Death 1/28 Costimulatory Retargeting Molecule Display Enhanced Antitumor Activity," J. Immunol. 191(8):4121-4129, 2013.

Chen et al., "Fusion Protein Linkers: Property, Design and Functionality," Adv Drug Deliv Rev. 65(10):1357-1369, 2013. (NIH Public Access Author Manuscript, available in PMC Oct. 15, 2014) (32 pages).

Cherkassky et al., "Human CAR T cells with cell-intrinsic PD-1 checkpoint blockade resist tumor-mediated inhibition," J. Clin Invest. 126(8):3130-3144, 2016.

Cheuk et al., "Role of 4-1BB:4-1BB ligand in cancer immunotherapy," Cancer Gene Therapy 11(3):215-226, 2004.

Coles et al., "Expression of CD200 on AML blasts directly suppresses memory T-cell function," Leukemia 26(9):2148-2151, 2012.

Coles et al., "The immunosuppressive ligands PD-L1 and CD200 are linked in AML T-cell immunosuppression: identification of a new immunotherapeutic synapse," Leukemia 29(9):1952-1954, 2015.

Contini et al., "In vivo apoptosis of CD8+lymphocytes in acute myeloid leukemia patients: involvement of soluble HLA-1 and Fas ligand," Leukemia 21:253-260, 2007.

Dustin et al., "Understanding the Structure and Function of the Immunological Synapse," CSH Perspectives in Biology 2(10):a002311, 2010. (14 pages).

Feldhaus et al., "A CD2/CD28 chimeric receptor triggers the CD28 signaling pathway in CTLL.2 cells," Gene Therapy 4(8):833-838, 1997.

Fourcade et al., "CD8+T Cells Specific for Tumor Antigens Can Be Rendered Dysfunctional by the Tumor Microenvironment through Upregulation of the Inhibitory Receptors BTLA and PD-1," Cancer Res. 72(4):887-896, 2012.

Frankel et al., "Characterization of diphtheria fusion proteins targeted to the human interleukin-3 receptor," Protein Engineering 13(8):575-581, 2000.

GenBank, "Homo sapiens Fas cell surface death receptor (FAS), transcript variant 1, mRNA," Accession No. NM_000043.4, Mar. 15, 2015, 6 pages.

GenBank, "Homo sapiens CD2 molecule (CD2), mRNA," Accession No. NM_001767.3, Mar. 15, 2015, 4 pages.

GenBank, "Homo sapiens lymphocyte activating 3 (LAG3), mRNA," Accession No. NM_002286.5, Jun. 17, 2018, 5 pages.

GenBank, "Homo sapiens hepatitis A virus cellular receptor 2 (HAVCR2), mRNA," Accession No. NM_032782.4, Sep. 23, 2018, 5 pages.

Grassmann et al., "S81. Proffered paper: A new PD1-CD28 chimeric receptor overcomes PD-1-mediated immunosuppression in adoptive T cell therapy," J. Immunother. Cancer 2(Suppl. 2):I19, 2014. (1 Page).

Hanada et al., "Augmenting adoptive T cell therapy through universal chimeric costimulators," J. Immunother. Cancer 1(Suppl. 1):P14, 2013. (1 Page).

Hatherley et al., "Structures of CD200/CD200 Receptor Family and Implications for Topology, Regulation, and Evolution," Structure 21(5):820-832, 2013.

Ho et al., "CD200 Is a Marker of LSC Activity in Acute Myeloid Leukemia," Blood 128:1705, 2016 (Abstract only) (6 pages).

James et al., "Biophysical Mechanism of T Cell Receptor Triggering in a Reconstituted System," Nature 487(7405):64-69, 2012. (HHMI Author Manuscript) (18 Pages).

Kawasaki et al., "Cancer stem cells, CD200 and immunoevasion," Trends in Immunology 29(10):464-468, 2008.

Kawasaki et al., "Co-Expression of the Toleragenic Glycoprotein, CD200, With Markers for Cancer Stem Cells," Biochem Biophys Res Commun. 364(4):778-782, 2007 (NIH Public Access Author Manuscript, available in PMC Dec. 28, 2007) (11 pages).

Kawalekar et al., "Distinct Signaling of Coreceptors Regulates Specific Metabolism Pathways and Impacts Memory Development in CAR T Cells," Immunity 44:380-390, 2016.

Keir et al., "PD-1 and its ligands in tolerance and immunity," Annu. Rev. Immunol. 26:677-704, 2008. (Abstract Only)(1 page).

Kharfan-Dabaja et al., "Immunotherapy for chronic lymphocytic leukemia in the era of BTK inhibitors," Leukemia 28(3):507-517, 2014.

Kono, "Current status of cancer immunotherapy," Journal of Stem Cells & Regenerative Medicine 10(1):8-13, 2014.

Kornmann et al., "Fas and Fas-Ligand Expression in Human Pancreatic Cancer," Annals of Surgery 231(3): 368-379, 2000.

Krause et al., "Antigen-dependent CD28 Signaling Selectively Enhances Survival and Proliferation in Genetically Modified Activated Human Primary T Lymphocytes," J. Exp. Med. 188(4):619-626, 1998.

Lavrik, "Regulation of Death Receptor-Induced Apoptosis Induced via CD95/Fas and Other Death Receptors," Molecular Biology 45(1):150-155, 2011.

Lazar-Molnar et al., "The interchain disulfide linkage is not a prerequisite but enhances CD28 costimulatory function," Cell Immunol. 244(2): 125-129, 2006. (NIH Public Access Author Manuscript, available in PMC Sep. 12, 2007) (9 pages).

Ledbetter et al., "CD28 Ligation in T-Cell Activation: Evidence for Two Signal Transduction Pathways," Blood 75(7):1531-1539, 1990.

Liu et al., "The role of N-glycosylation of CD200-CD200R1 interaction of classical microglial activation," Journal of Inflammation 15(28):1-10, 2018.

Ma et al., "CD28 T cell costimulatory receptor function is negatively regulated by N-linked carbohydrates," Biochemical and biophysical research communications 317(1):60-67, 2004.

Maeda et al., "Engineering of functional chimeric protein G-Vargula Luciferase," Analytical biochemistry 249(2):147-152, 1997.

Maus et al., "Antibody-modified T cells: CARs take the front seat for hematologic malignancies," Blood 123(17):2625-2635, 2014.

(56) References Cited

OTHER PUBLICATIONS

Milstein et al., "Nanoscale Increases in CD2-CD48-mediated Intermembrane Spacing Decrease Adhesion and Reorganize the Immunological Synapse," *J. Biol. Chem.* 283(49):34414-34422, 2008.

Moreaux et al., "CD200: a putative therapeutic target in cancer," *Biochemical and biophysical research communications* 366(1):117-122, 2008.

Motz et al., "Tumor Endothelium FasL Establishes a Selective Immune Barrier Promoting Tolerance in Tumors," *Nature Medicine* 20(6): 607-615, 2014 (HHS Public Access Author Manuscript, available in PMC Dec. 1, 2014) (26 pages).

Oda et al., "A CD200R-CD28 fusion protein appropriates an inhibitory signal to enhance T-cell function and therapy of murine leukemia," *Blood* 130(22):2410-2419, 2017.

Oda et al., "Cheating Death: A Fas-41BB Immunomodulatory Fusion Protein Obviates a Death Signal to Enhance T Cell Function and Adoptive Therapy Targeting Leukemia and Solid Tumors," Conference Program, Retrieved from https://www.keystonesymposia.org/index.cfm?e=Web.Meeting.Program&meetingid=1518&subTab=program [Retrieved Jun. 19, 2018}, 22 pages, 2018.

Oda et al., "Cheating Death: A Fas-41BB Immunomodulatory Fusion Protein Obviates a Death Signal to Enhance T Cell Function and Adoptive Therapy Targeting Leukemia and Solid Tumors," *J. Immunol* 200 (1 Supplement) 179.11, 2018 (4 pages).

Pakula et al. "Genetic analysis of protein stability and function," *Annual review of genetics* 23(1):289-310, 1989.

Pardoll, "The blockade of immune checkpoints in cancer immunotherapy," *Nat. Rev. Cancer* 12(4):252-264, 2012. (HHS Public Access Author Manuscript, available in PMC May 4, 2016) (31 pages).

Prosser et al., "Tumor PD-L1 co-stimulates primary human $CD8^+$ cytotoxic T cells modified to express a PD1:CD28 chimeric receptor," *Mol. Immunol.* 51(3-4):263-272, 2012.

Rossy et al., "The integration of signaling and the spatial organization of the T cell synapse," *Front. Immunol.* 3:352, 2012. (12 Pages).

Rudd et al., "CD28 and CTLA-4 coreceptor expression and signal transduction," *Immunol. Rev.* 229(1):12-26, 2009. (Europe PMC Funders Group Author Manuscript, Immunol Rev. Author manuscript available in PMC Oct. 7, 2014) (26 pages).

Siva et al., "Immune modulation by melanoma and ovarian tumor cells through expression of the immunosuppressive molecule CD200," *Cancer Immunol Immunother.* 57:987-996, 2008.

Soto et al., "MHC-class I-restricted CD4 T cells: a nanomolar affinity TCR has improved anti-tumor efficacy in vivo compared to the micromolar wild type TCR," *Cancer Immunol. Immunother.* 62(2):359-369, 2013. (NIH Public Access Author Manuscript, available in PMC Feb. 1, 2014) (20 pages).

Snauwaert et al., "Can immunotherapy specifically target acute myeloid leukemic stem cells?" *OncoImmunology* 2(2):e22943, 10 pages, 2013.

Stromnes et al., "Abrogating Cbl-b in effector $CD8^+T$ cells improves the efficacy of adoptive therapy of leukemia in mice," *The Journal of Clinical Investigation* 120(10):3722-3734, 2010.

Stromnes et al., "Re-adapting T cells for cancer therapy: from mouse models to clinical trials," *Immunol Rev.* 257(1):145-164, 2014 (NIH Public Access Author Manuscript, available in PMC Jan. 1, 2015) (34 pages).

Stromnes et al., "T Cells Engineered against a Native Antigen Can Surmount Immunologic and Physical Barriers to Treat Pancreatic Ductal Adenocarcinoma," *Cancer Cell* 28(5):638-652, 2015. (16 pages).

Stumpfova et al., "The immunosuppressive surface ligand CD200 augments the metastatic capacity of squamous cell carcinoma," *Cancer Res.* 70(7):2962-2972, 2010.

Subramanian et al., "Species- and cell type-specific interactions between CD47 and human SIRPα," *Blood* 107(6): 2548-2556, 2006.

Tang et al., "The advantages of PD1 activating chimeric receptor (PD1-ACR) engineered lymphocytes for $PDL1^+$cancer therapy," *Am. J. Transl. Res.* 7(3):460-473, 2015.

Tonks et al., "CD200 as a prognostic factor in acute myeloid leukaemia," *Leukemia* 21(3):566-568, 2007.

Willingham et al., "The CD47-signal regulatory protein alpha (SIRPa) interaction is a therapeutic target for human solid tumors," *Proc. Natl. Acad. Sci. USA* 109(17):6662-6667, 2012.

Oda et al., Cancer Research, Nov. 2022, vol. 82, No. 22, Supp. Supplement. Abstract No. PR008. Meeting Info: AACR Special Conference: Pancreatic Cancer. Boston, MA, United States. Sep. 13, 2022-Sep. 16, 2022.

Hatherley et al., "Paired Receptor Specificity Explained by Structures of Signal Regulatory Proteins Alone and Complexed with CD47," *Molecular Cell* 31:266-277, 2008.

Kuhlmann, "Unleashing T cells for adoptive immunotherapy," https://www.fredhutch.org/en/news/spotlight/2017/12/crd_oda_blood.html, 2017 (3 pages).

Shirakabe et al., "Mechanistic insights into ectodomain shedding: susceptibility of CADM1 adhesion molecule is determined by alternative splicing and O-glycosylation," *Scientific Reports* 7:46174, 1-12, 2017.

Van den Borne et al. "The CD200-CD200 Receptor Inhibitory Axis Controls Arteriogenesis and Local T Lymphocyte Influx," *PLOS One* 9(6):e98820, 2014 (10 pages).

Yamao et al., "Mouse and Human SHPS-1: Molecular Cloning of cDNAs and Chromosomal Localization of Genes," *Biochemical and Biophysical Research Communications* 231: 61-67, 1997.

\* cited by examiner

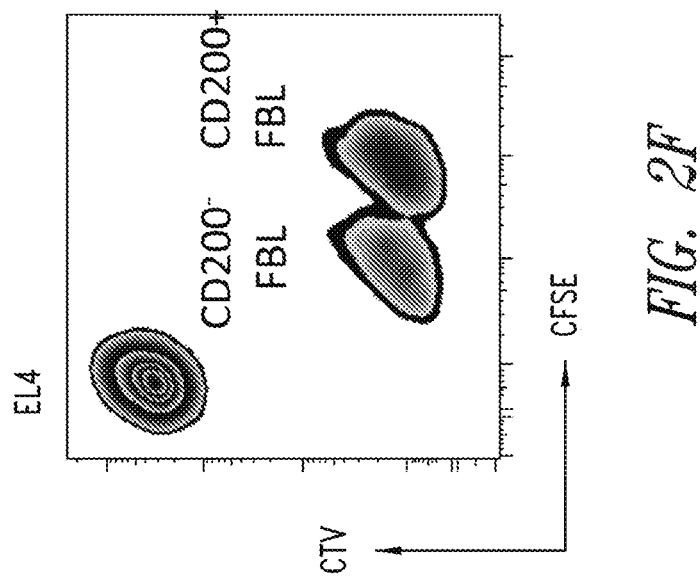

SEQUENCE LISTING

<160> NUMBER OF SEQ ID NOS: 213

<210> SEQ ID NO 1
<211> LENGTH: 915
<212> TYPE: DNA
<213> ORGANISM: Artificial Sequence
<220> FEATURE:
<223> OTHER INFORMATION: huCD200Rtm-CD28 construct

<400> SEQUENCE: 1

```
atgctgtgcc cttggagaac cgccaacctg ggcctgctgc tgatcctgac catcttcctg      60
```

-continued

| | |
|---|---|
| gtggccgcca gcagcagcct gtgcatggac gagaagcaga tcacccagaa ctacagcaag | 120 |
| gtgctggccg aagtgaacac cagctggccc gtgaagatgg ccaccaacgc cgtgctgtgc | 180 |
| tgccctccta tcgccctgcg gaacctgatc atcatcacct gggagatcat cctgcggggc | 240 |
| cagcccagct gtaccaaggc ctaccggaaa gagacaaacg agacaaaaga aacaaactgc | 300 |
| accgacgagc ggatcacatg ggtgtccaga cccgaccaga cagcgacct gcagatcaga | 360 |
| cccgtggcca tcacccacga cggctactac cggtgcatca tggtcacccc cgatggcaac | 420 |
| ttccaccggg gataccatct gcaggtgctc gtgaccccg aagtgaccct gttccagaac | 480 |
| cggaacagaa ccgccgtgtg caaggccgtg gccggaaaac ctgccgccca gatctcttgg | 540 |
| atccccgagg gcgattgcgc caccaagcag gaatactggt ccaacggcac cgtgaccgtg | 600 |
| aagtccacct gtcactggga ggtgcacaac gtgtccaccg tgacatgcca cgtgtcccac | 660 |
| ctgaccggca acaagagcct gtacatcgag ctgctgcctg tgcctggcgc caagaagtcc | 720 |
| gccaagctgt acatcccta catcatcctg acaatcatca ttctgaccat cgtgggcttc | 780 |
| atctggctgc tgcgcagcaa gcggagcaga ggcggccaca gcgactacat gaacatgacc | 840 |
| cctagacggc ctggccccac cagaaagcac taccagcct acgcccctcc ccgggacttt | 900 |
| gccgcctaca gaagc | 915 |

<210> SEQ ID NO 2
<211> LENGTH: 728
<212> TYPE: DNA
<213> ORGANISM: Artificial Sequence
<220> FEATURE:
<223> OTHER INFORMATION: huCD200R entire extracellular domain

<400> SEQUENCE: 2

| | |
|---|---|
| tgctgtgccc ttggagaacc gccaacctgg gcctgctgct gatcctgacc atcttcctgg | 60 |
| tggccgccag cagcagcctg tgcatggacg agaagcagat cacccagaac tacagcaagg | 120 |
| tgctggccga agtgaacacc agctggcccg tgaagatggc caccaacgcc gtgctgtgct | 180 |
| gccctcctat cgccctgcgg aacctgatca tcatcacctg ggagatcatc ctgcggggcc | 240 |
| agcccagctg taccaaggcc taccggaaag acaaacga caaaagaa acaaactgca | 300 |
| ccgacgagcg gatcacatgg gtgtccagac ccgaccagaa cagcgacctg cagatcagac | 360 |
| ccgtggccat cacccacgac ggctactacc ggtgcatcat ggtcacccc gatggcaact | 420 |
| tccaccgggg ataccatctg caggtgctcg tgaccccga agtgaccctg ttccagaacc | 480 |
| ggaacagaac cgccgtgtgc aaggccgtgg ccggaaaacc tgccgccag atctcttgga | 540 |
| tccccgaggg cgattgcgcc accaagcagg aatactggtc caacggcacc gtgaccgtga | 600 |
| agtccacctg tcactgggag gtgcacaacg tgtccaccgt gacatgccac gtgtcccacc | 660 |
| tgaccggcaa caagagcctg tacatcgagc tgctgcctgt gcctggcgcc aagaagtccg | 720 |
| ccaagctg | 728 |

<210> SEQ ID NO 3
<211> LENGTH: 63
<212> TYPE: DNA
<213> ORGANISM: Artificial Sequence
<220> FEATURE:
<223> OTHER INFORMATION: huCD200R transmembrane domain

<400> SEQUENCE: 3

| | |
|---|---|
| tacatcccct acatcatcct gacaatcatc attctgacca tcgtgggctt catctggctg | 60 |
| ctg | 63 |

<210> SEQ ID NO 4
<211> LENGTH: 81
<212> TYPE: DNA
<213> ORGANISM: Artificial Sequence
<220> FEATURE:
<223> OTHER INFORMATION: CD28 transmembrane domain

<400> SEQUENCE: 4
ttctgggtgc tggtggtggt cggaggcgtg ctggcctgct acagcctgct ggtcaccgtg    60
gccttcatca tcttttgggt c                                               81

<210> SEQ ID NO 5
<211> LENGTH: 123
<212> TYPE: DNA
<213> ORGANISM: Artificial Sequence
<220> FEATURE:
<223> OTHER INFORMATION: CD28 intracellular domain

<400> SEQUENCE: 5
cgcagcaagc ggagcagagg cggccacagc gactacatga acatgacccc tagacggcct    60
ggccccacca gaaagcacta ccagccctac gcccctcccc gggactttgc cgcctacaga   120
agc                                                                 123

<210> SEQ ID NO 6
<211> LENGTH: 933
<212> TYPE: DNA
<213> ORGANISM: Artificial Sequence
<220> FEATURE:
<223> OTHER INFORMATION: huCD200R-CD28tm construct

<400> SEQUENCE: 6
atgctgtgcc cttggagaac cgccaacctg gcctgctgc tgatcctgac catcttcctg     60
gtggccgcca gcagcagcct gtgcatggac gagaagcaga tcacccagaa ctacagcaag   120
gtgctggccg aagtgaacac cagctggccc gtgaagatgg ccaccaacgc cgtgctgtgc   180
tgccctccta tcgccctgcg gaacctgatc atcatcacct gggagatcat cctgcggggc   240
cagcccagct gtaccaaggc ctaccggaaa gagacaaacg agacaaaaga aacaaactgc   300
accgacgagc ggatcacatg ggtgtccaga cccgaccaga cagcgacct gcagatcaga   360 cccgtggcca tcacccacga cggctactac cggtgcatca tggtcacccc cgatggcaac   420
ttccaccggg ataccatctg caggtgctc gtgaccccg aagtgaccct gttccagaac   480
cggaacagaa ccgccgtgtg caaggccgtg gccggaaaac tgccgcccca gatctcttgg   540
atccccgagg gcgattgcgc caccaagcag gaatactggt ccaacggcac cgtgaccgtg   600
aagtccacct gtcactggga ggtgcacaac gtgtccaccg tgacatgcca cgtgtcccac   660
ctgaccggca caagagcct gtacatcgag ctgctgcctg tgcctggcgc caagaagtcc   720
gccaagctgt tctgggtgct ggtggtggtc ggaggcgtgc tggcctgcta cagcctgctg   780
gtcaccgtgg ccttcatcat cttttgggtc cgcagcaagc ggagcagagg cggccacagc   840
gactacatga acatgacccc tagacggcct ggccccacca gaaagcacta ccagccctac   900
gcccctcccc gggactttgc cgcctacaga agc                                933

<210> SEQ ID NO 7
<211> LENGTH: 942
<212> TYPE: DNA
<213> ORGANISM: Artificial Sequence
<220> FEATURE:

<223> OTHER INFORMATION: huCD200R-9aas-CD28Cys construct

<400> SEQUENCE: 7

```
atgctgtgcc cttggagaac cgccaacctg ggcctgctgc tgatcctgac catcttcctg      60
gtggccgcca gcagcagcct gtgcatggac gagaagcaga tcacccagaa ctacagcaag     120
gtgctggccg aagtgaacac cagctggccc gtgaagatgg ccaccaacgc cgtgctgtgc     180
tgccctccta tcgccctgcg gaacctgatc atcatcacct gggagatcat cctgcggggc     240
cagcccagct gtaccaaggc ctaccggaaa gagacaaacg agacaaaaga aacaaactgc     300
accgacgagc ggatcacatg ggtgtccaga cccgaccaga cagcgacct gcagatcaga      360
cccgtggcca tcacccacga cggctactac cggtgcatca tggtcacccc cgatggcaac     420
ttccaccggg gataccatct gcaggtgctc gtgaccccg aagtgaccct gttccagaac      480
cggaacagaa ccgccgtgtg caaggccgtg gccggaaaac ctgccgccca gatctcttgg     540
atccccgagg gcgattgcgc caccaagcag gaatactggt ccaacggcac cgtgaccgtg     600
aagtccacct gtcactggga ggtgcacaac gtgtccaccg tgcatgcca cgtgtcccac      660
ctgaccggca acaagagcct gtacatcgag ctgctgcctg tgtgtccag ccctctgttt      720
cccgccccta gcaagccttt ctgggtgctg gtggtggtcg gaggcgtgct ggcctgctac     780
agcctgctgg tcaccgtggc cttcatcatc ttttgggtcc gcagcaagcg gagcagaggc     840
ggccacagcg actacatgaa catgaccct agacggctg ccccaccag aaagcactac         900
cagccctacg cccctccccg ggactttgcc gcctacagaa gc                          942
```

<210> SEQ ID NO 8
<211> LENGTH: 702
<212> TYPE: DNA
<213> ORGANISM: Artificial Sequence
<220> FEATURE:
<223> OTHER INFORMATION: huCD200R-9aas portion of extracellular domain

<400> SEQUENCE: 8

```
atgctgtgcc cttggagaac cgccaacctg ggcctgctgc tgatcctgac catcttcctg      60
gtggccgcca gcagcagcct gtgcatggac gagaagcaga tcacccagaa ctacagcaag     120
gtgctggccg aagtgaacac cagctggccc gtgaagatgg ccaccaacgc cgtgctgtgc     180
tgccctccta tcgccctgcg gaacctgatc atcatcacct gggagatcat cctgcggggc     240
cagcccagct gtaccaaggc ctaccggaaa gagacaaacg agacaaaaga aacaaactgc     300
accgacgagc ggatcacatg ggtgtccaga cccgaccaga cagcgacct gcagatcaga      360
cccgtggcca tcacccacga cggctactac cggtgcatca tggtcacccc cgatggcaac     420
ttccaccggg gataccatct gcaggtgctc gtgaccccg aagtgaccct gttccagaac      480
cggaacagaa ccgccgtgtg caaggccgtg gccggaaaac ctgccgccca gatctcttgg     540
atccccgagg gcgattgcgc caccaagcag gaatactggt ccaacggcac cgtgaccgtg     600
aagtccacct gtcactggga ggtgcacaac gtgtccaccg tgcatgcca cgtgtcccac      660
ctgaccggca acaagagcct gtacatcgag ctgctgcctg tg                         702
```

<210> SEQ ID NO 9
<211> LENGTH: 36
<212> TYPE: DNA
<213> ORGANISM: Artificial Sequence
<220> FEATURE:
<223> OTHER INFORMATION: CD28Cys multimerization domain

<400> SEQUENCE: 9
tgtcccagcc ctctgtttcc cggccctagc aagcct                              36

<210> SEQ ID NO 10
<211> LENGTH: 933
<212> TYPE: DNA
<213> ORGANISM: Artificial Sequence
<220> FEATURE:
<223> OTHER INFORMATION: huCD200R-12aas-CD28Cys construct

<400> SEQUENCE: 10
atgctgtgcc cttggagaac cgccaacctg ggcctgctgc tgatcctgac catcttcctg    60
gtggccgcca gcagcagcct gtgcatggac gagaagcaga tcacccagaa ctacagcaag   120
gtgctggccg aagtgaacac cagctggccc gtgaagatgg ccaccaacgc cgtgctgtgc   180
tgccctccta tcgccctgcg gaacctgatc atcatcacct gggagatcat cctgcggggc   240
cagcccagct gtaccaaggc ctaccggaaa gagacaaacg agacaaaaga aacaaactgc   300
accgacgagc ggatcacatg ggtgtccaga cccgaccaga cagcgacct gcagatcaga   360
cccgtggcca tcacccacga cggctactac cggtgcatca tggtcacccc cgatggcaac   420
ttccaccggg gataccatct gcaggtgctc gtgaccccg aagtgaccct gttccagaac   480
cggaacagaa ccgccgtgtg caaggccgtg gccggaaaac ctgccgccca gatctcttgg   540
atccccgagg gcgattgcgc caccaagcag gaatactggt ccaacggcac cgtgaccgtg   600
aagtccacct gtcactggga ggtgcacaac gtgtccaccg tgacatgcca cgtgtcccac   660
ctgaccggca acaagagcct gtacatcgag ctgtgtccca gccctctgtt tcccggccct   720
agcaagcctt tctgggtgct ggtggtggtc ggaggcgtgc tggcctgcta cagcctgctg   780
gtcaccgtgg ccttcatcat cttttgggtc cgcagcaagc ggagcagagg cggccacagc   840
gactacatga acatgacccc tagacggcct ggccccacca gaaagcacta ccagccctac   900
gcccctcccc gggactttgc cgcctacaga agc                                933

<210> SEQ ID NO 11
<211> LENGTH: 693
<212> TYPE: DNA
<213> ORGANISM: Artificial Sequence
<220> FEATURE:
<223> OTHER INFORMATION: huCD200R-12aas portion of extracellular domain

<400> SEQUENCE: 11
atgctgtgcc cttggagaac cgccaacctg ggcctgctgc tgatcctgac catcttcctg    60
gtggccgcca gcagcagcct gtgcatggac gagaagcaga tcacccagaa ctacagcaag   120
gtgctggccg aagtgaacac cagctggccc gtgaagatgg ccaccaacgc cgtgctgtgc   180
tgccctccta tcgccctgcg gaacctgatc atcatcacct gggagatcat cctgcggggc   240
cagcccagct gtaccaaggc ctaccggaaa gagacaaacg agacaaaaga aacaaactgc   300
accgacgagc ggatcacatg ggtgtccaga cccgaccaga cagcgacct gcagatcaga   360
cccgtggcca tcacccacga cggctactac cggtgcatca tggtcacccc cgatggcaac   420
ttccaccggg gataccatct gcaggtgctc gtgaccccg aagtgaccct gttccagaac   480
cggaacagaa ccgccgtgtg caaggccgtg gccggaaaac ctgccgccca gatctcttgg   540
atccccgagg gcgattgcgc caccaagcag gaatactggt ccaacggcac cgtgaccgtg   600
aagtccacct gtcactggga ggtgcacaac gtgtccaccg tgacatgcca cgtgtcccac   660
ctgaccggca acaagagcct gtacatcgag ctg                                693

<210> SEQ ID NO 12
<211> LENGTH: 945
<212> TYPE: DNA
<213> ORGANISM: Artificial Sequence
<220> FEATURE:
<223> OTHER INFORMATION: huCD200R-9aas-CD28Cys tm-41BBic construct

<400> SEQUENCE: 12

| | | | | | |
|---|---|---|---|---|---|
| atgctgtgcc | cttggagaac | cgccaacctg | ggcctgctgc | tgatcctgac | catcttcctg | 60 |
| gtggccgcca | gcagcagcct | gtgcatggac | gagaagcaga | tcacccagaa | ctacagcaag | 120 |
| gtgctggccg | aagtgaacac | cagctggccc | gtgaagatgg | ccaccaacgc | cgtgctgtgc | 180 |
| tgccctccta | tcgccctgcg | gaacctgatc | atcatcacct | gggagatcat | cctgcggggc | 240 |
| cagcccagct | gtaccaaggc | ctaccggaaa | gagacaaacg | agacaaaaga | aacaaactgc | 300 |
| accgacgagc | ggatcacatg | ggtgtccaga | cccgaccaga | cagcgacct | gcagatcaga | 360 |
| cccgtggcca | tcacccacga | cggctactac | cggtgcatca | tggtcacccc | cgatggcaac | 420 |
| ttccaccggg | gataccatct | gcaggtgctc | gtgaccccg | aagtgaccct | gttccagaac | 480 |
| cggaacagaa | ccgccgtgtg | caaggccgtg | gccggaaaac | ctgccgccca | gatctcttgg | 540 |
| atccccgagg | gcgattgcgc | caccaagcag | gaatactggt | ccaacggcac | cgtgaccgtg | 600 |
| aagtccacct | gtcactggga | ggtgcacaac | gtgtccaccg | tgacatgcca | cgtgtcccac | 660 |
| ctgaccggca | caagagcct | gtacatcgag | ctgctgcctg | tgtgtcccag | ccctctgttt | 720 |
| cccggcccta | gcaagccttt | ctgggtgctg | gtggtggtcg | gaggcgtgct | ggcctgctac | 780 |
| agcctgctgg | tcaccgtggc | cttcatcatc | ttttgggtca | gcggggcag | aaagaagctg | 840 |
| ctgtacatct | tcaagcagcc | tttcatgcgg | cccgtgcaga | ccacccagga | gaggacggc | 900 |
| tgctcctgca | gattccccga | ggaagaagaa | ggcggctgcg | agctg | | 945 |

<210> SEQ ID NO 13
<211> LENGTH: 126
<212> TYPE: DNA
<213> ORGANISM: Artificial Sequence
<220> FEATURE:
<223> OTHER INFORMATION: 4-1BB intracellular component

<400> SEQUENCE: 13

| | | | | | |
|---|---|---|---|---|---|
| aagcggggca | gaaagaagct | gctgtacatc | ttcaagcagc | ctttcatgcg | gcccgtgcag | 60 |
| accacccagg | aagaggacgg | ctgctcctgc | agattccccg | aggaagaaga | aggcggctgc | 120 |
| gagctg | | | | | | 126 |

<210> SEQ ID NO 14
<211> LENGTH: 936
<212> TYPE: DNA
<213> ORGANISM: Artificial Sequence
<220> FEATURE:
<223> OTHER INFORMATION: huCD200R-12aas-CD28Cys tm-41BBic construct

<400> SEQUENCE: 14

| | | | | | |
|---|---|---|---|---|---|
| atgctgtgcc | cttggagaac | cgccaacctg | ggcctgctgc | tgatcctgac | catcttcctg | 60 |
| gtggccgcca | gcagcagcct | gtgcatggac | gagaagcaga | tcacccagaa | ctacagcaag | 120 |
| gtgctggccg | aagtgaacac | cagctggccc | gtgaagatgg | ccaccaacgc | cgtgctgtgc | 180 |
| tgccctccta | tcgccctgcg | gaacctgatc | atcatcacct | gggagatcat | cctgcggggc | 240 |
| cagcccagct | gtaccaaggc | ctaccggaaa | gagacaaacg | agacaaaaga | aacaaactgc | 300 |
| accgacgagc | ggatcacatg | ggtgtccaga | cccgaccaga | cagcgacct | gcagatcaga | 360 |

```
cccgtggcca tcacccacga cggctactac cggtgcatca tggtcacccc cgatggcaac      420
ttccaccggg gataccatct gcaggtgctc gtgaccccg aagtgaccct gttccagaac       480
cggaacagaa ccgccgtgtg caaggccgtg gccggaaaac ctgccgccca gatctcttgg      540
atccccgagg gcgattgcgc caccaagcag gaatactggt ccaacggcac cgtgaccgtg     600
aagtccacct gtcactggga ggtgcacaac gtgtccaccg tgacatgcca cgtgtcccac    660
ctgaccggca caagagcct gtacatcgag ctgtgtccca gccctctgtt tcccggccct     720
agcaagcctt tctgggtgct ggtggtggtc ggaggcgtgc tggcctgcta cagcctgctg    780
gtcaccgtgg ccttcatcat ctttgggtc aagcggggca gaaagaagct gctgtacatc    840
ttcaagcagc ctttcatgcg gcccgtgcag accacccagg aagaggacgg ctgctcctgc   900
agattccccg aggaagaaga aggcggctgc gagctg                              936
```

<210> SEQ ID NO 15
<211> LENGTH: 1059
<212> TYPE: DNA
<213> ORGANISM: Artificial Sequence
<220> FEATURE:
<223> OTHER INFORMATION: huCD200R-12aas-CD28Cys tm ic-41BBic construct

<400> SEQUENCE: 15

```
atgctgtgcc cttggagaac cgccaacctg ggcctgctgc tgatcctgac catcttcctg     60
gtggccgcca gcagcagcct gtgcatggac gagaagcaga tcacccagaa ctacagcaag    120
gtgctggccg aagtgaacac cagctggccc gtgaagatgg ccaccaacgc cgtgctgtgc   180
tgccctccta tcgccctgcg gaacctgatc atcatcacct gggagatcat cctgcggggc   240
cagcccagct gtaccaaggc ctaccggaaa gagacaaacg agacaaaaga aacaaactgc   300
accgacgagc ggatcacatg ggtgtccaga cccgaccaga cagcgacct gcagatcaga    360 cccgtggcca tcacccacga cggctactac cggtgcatca tggtcacccc cgatggcaac    420
ttccaccggg gataccatct gcaggtgctc gtgaccccg aagtgaccct gttccagaac    480
cggaacagaa ccgccgtgtg caaggccgtg gccggaaaac ctgccgccca gatctcttgg    540
atccccgagg gcgattgcgc caccaagcag gaatactggt ccaacggcac cgtgaccgtg    600
aagtccacct gtcactggga ggtgcacaac gtgtccaccg tgacatgcca cgtgtcccac   660
ctgaccggca caagagcct gtacatcgag ctgtgtccca gccctctgtt tcccggccct    720
agcaagcctt tctgggtgct ggtggtggtc ggaggcgtgc tggcctgcta cagcctgctg   780
gtcaccgtgg ccttcatcat ctttgggtc cgcagcaagc ggagcagagg cggccacagc   840
gactacatga acatgacccc tagacggcct ggccccacca gaaagcacta ccagccctac   900 gccctcccc gggactttgc cgcctacaga agcaagcggg gcagaaagaa gctgctgtac    960
atcttcaagc agcctttcat gcggcccgtg cagaccaccc aggaagagga cggctgctcc  1020
tgcagattcc ccgaggaaga agaaggcggc tgcgagctg                          1059
```

<210> SEQ ID NO 16
<211> LENGTH: 1305
<212> TYPE: DNA
<213> ORGANISM: Artificial Sequence
<220> FEATURE:
<223> OTHER INFORMATION: huSIRPalphatm-CD28 construct

<400> SEQUENCE: 16

```
atggaacctg ccggacctgc tcctggcaga ctgggacctc tgctgtgtct gctgctggcc    60
```

```
gcctcttgtg cttggagcgg agtggctggc gaagaggaac tgcaagtgat ccagcccgac      120
aagagcgtgc tggtggccgc tggcgaaacc gccaccctga gatgtacagc caccagcctg      180
atccccgtgg gccccatcca gtggtttaga ggcgctggcc ctggcagaga gctgatctac      240
aaccagaaag agggccactt ccccagagtg accaccgtgt ccgacctgac caagcggaac      300
aacatggact tcagcatccg gatcggcaac atcaccctg ccgatgccgg cacctactac      360
tgcgtgaagt tccggaaggg cagccccgac gacgtggaat caaaagcgg agccggcacc      420
gagctgagcg tgcgggctaa accttctgcc cctgtggtgt ctggacctgc cgccagagct      480
acacctcagc acaccgtgtc ttttacctgc gagagccacg gcttcagccc cagagacatc      540
accctgaagt ggttcaagaa cggcaacgag ctgtccgact ccagaccaa cgtggaccct      600
gtgggcgaga gcgtgtccta cagcatccac agcaccgcca aggtggtgct gacccgcgaa      660
gatgtgcaca gccaagtgat ctgcgaggtg gcccacgtga cactgcaggg cgatcctctg      720
agaggaaccg ccaacctgtc cgagacaatc agagtgcccc ccaccctgga agtgacccag      780
cagcctgtgc gggccgagaa ccaagtgaac gtgacctgcc aagtgcggaa gttctacccc      840
cagcggctgc agctgacctg gctggaaaac ggcaatgtgt cccggaccga cagccagc       900
accgtgacg agaacaagga tggcacctac aattggatga ctggctgct cgtgaacgtg      960
tccgcccacc gggacgatgt gaagctgaca tgccaggtgg aacacgacgg ccagcctgcc     1020
gtgtccaaga gccacgatct gaaggtgtca gcccatccca aagagcaggg ctccaacaca     1080
gccgccgaga acaccggcag caacgagcgg aacatctaca tcgtcgtggg cgtcgtgtgc     1140
accctgctgg tggcactgct gatggccgct ctgtacctcg tgcgcagcaa gcggagcaga     1200
ggcggccaca gcgactacat gaacatgacc cctagacggc ctggccccac cagaaagcac     1260
taccagccct acgcccctcc ccgggacttt gccgcctaca gaagc                     1305
```

<210> SEQ ID NO 17
<211> LENGTH: 1119
<212> TYPE: DNA
<213> ORGANISM: Artificial Sequence
<220> FEATURE:
<223> OTHER INFORMATION: huSIRP alpha entire extracellular domain

<400> SEQUENCE: 17

```
atggaacctg ccggacctgc tcctggcaga ctgggacctc tgctgtgtct gctgctggcc       60
gcctcttgtg cttggagcgg agtggctggc gaagaggaac tgcaagtgat ccagcccgac      120
aagagcgtgc tggtggccgc tggcgaaacc gccaccctga gatgtacagc caccagcctg      180
atccccgtgg gccccatcca gtggtttaga ggcgctggcc ctggcagaga gctgatctac      240
aaccagaaag agggccactt ccccagagtg accaccgtgt ccgacctgac caagcggaac      300
aacatggact tcagcatccg gatcggcaac atcaccctg ccgatgccgg cacctactac      360
tgcgtgaagt tccggaaggg cagccccgac gacgtggaat caaaagcgg agccggcacc      420
gagctgagcg tgcgggctaa accttctgcc cctgtggtgt ctggacctgc cgccagagct      480
acacctcagc acaccgtgtc ttttacctgc gagagccacg gcttcagccc cagagacatc      540
accctgaagt ggttcaagaa cggcaacgag ctgtccgact ccagaccaa cgtggaccct      600
gtgggcgaga gcgtgtccta cagcatccac agcaccgcca aggtggtgct gacccgcgaa      660
gatgtgcaca gccaagtgat ctgcgaggtg gcccacgtga cactgcaggg cgatcctctg      720
agaggaaccg ccaacctgtc cgagacaatc agagtgcccc ccaccctgga agtgacccag      780
cagcctgtgc gggccgagaa ccaagtgaac gtgacctgcc aagtgcggaa gttctacccc      840
```

| | | |
|---|---|---|
| cagcggctgc agctgacctg gctggaaaac ggcaatgtgt cccggaccga dacagccagc | 900 | |
| accgtgaccg agaacaagga tggcacctac aattggatga gctggctgct cgtgaacgtg | 960 | |
| tccgcccacc gggacgatgt gaagctgaca tgccaggtgg aacacgacgg ccagcctgcc | 1020 | |
| gtgtccaaga gccacgatct gaaggtgtca gcccatccca aagagcaggg ctccaacaca | 1080 | |
| gccgccgaga acaccggcag caacgagcgg aacatctac | 1119 | |

<210> SEQ ID NO 18
<211> LENGTH: 63
<212> TYPE: DNA
<213> ORGANISM: Artificial Sequence
<220> FEATURE:
<223> OTHER INFORMATION: huSIRP alpha  transmembrane domain

<400> SEQUENCE: 18

| | | |
|---|---|---|
| atcgtcgtgg gcgtcgtgtg caccctgctg gtggcactgc tgatggccgc tctgtacctc | 60 | |
| gtg | 63 | |

<210> SEQ ID NO 19
<211> LENGTH: 1323
<212> TYPE: DNA
<213> ORGANISM: Artificial Sequence
<220> FEATURE:
<223> OTHER INFORMATION: huSIRP alpha-CD28tm construct

<400> SEQUENCE: 19

| | | |
|---|---|---|
| atggaacctg ccggacctgc tcctggcaga ctgggacctc tgctgtgtct gctgctggcc | 60 | |
| gcctcttgtg cttggagcgg agtggctggc gaagaggaac tgcaagtgat ccagcccgac | 120 | |
| aagagcgtgc tggtggccgc tggcgaaacc gccaccctga tgtacagcca ccagcctgg | 180 | |
| atccccgtgg cccccatcca gtggtttaga ggcgctggcc ctggcagaga gctgatctac | 240 | |
| aaccagaaag agggccactt ccccagagtg accaccgtgt ccgacctgac caagcggaac | 300 | |
| aacatggact tcagcatccg gatcggcaac atcacccctg ccgatgccgg cacctactac | 360 | |
| tgcgtgaagt tccggaaggg cagccccgac gacgtggaat tcaaaagcgg agccggcacc | 420 | |
| gagctgagcg tgcgggctaa ccttctgccc cctgtggtgt ctggacctgc cgccagagct | 480 | |
| acacctcagc acaccgtgtc ttttacctgc gagagccacg gcttcagccc cagagacatc | 540 | |
| accctgaagt ggttcaagaa cggcaacgag ctgtccgact ccagaccaa cgtggaccct | 600 | |
| gtgggcgaga gcgtgtccta cagcatccac agcaccgcca aggtggtgct gacccgcgaa | 660 | |
| gatgtgcaca gccaagtgat ctgcgaggtg gcccacgtga cactgcaggg cgatcctctg | 720 | |
| agaggaaccg ccaacctgtc cgagacaatc agagtgcccc ccaccctgga agtgacccag | 780 | |
| cagcctgtgc gggccgagaa ccaagtgaac gtgacctgcc aagtgcggaa gttctacccc | 840 | |
| cagcggctgc agctgacctg gctggaaaac ggcaatgtgt cccggaccga gacagccagc | 900 | |
| accgtgaccg agaacaagga tggcacctac aattggatga gctggctgct cgtgaacgtg | 960 | |
| tccgcccacc gggacgatgt gaagctgaca tgccaggtgg aacacgacgg ccagcctgcc | 1020 | |
| gtgtccaaga gccacgatct gaaggtgtca gcccatccca aagagcaggg ctccaacaca | 1080 | |
| gccgccgaga acaccggcag caacgagcgg aacatctact ctgggtgct ggtggtggtc | 1140 | |
| ggaggcgtgc tggcctgcta cagcctgctg gtcaccgtgg ccttcatcat cttttgggtc | 1200 | |
| cgcagcaagc ggagcagagg cggccacagc gactacatga acatgacccc tagacggcct | 1260 | |
| ggccccacca gaaagcacta ccagccctac gcccctcccc gggactttgc cgcctacaga | 1320 | |

```
                                                                  agc                             1323

<210> SEQ ID NO 20
<211> LENGTH: 1323
<212> TYPE: DNA
<213> ORGANISM: Artificial Sequence
<220> FEATURE:
<223> OTHER INFORMATION: huSIRP alpha 12aas-CD28Cys construct

<400> SEQUENCE: 20
atggaacctg ccggacctgc tcctggcaga ctgggacctc tgctgtgtct gctgctggcc    60
gcctcttgtg cttggagcgg agtggctggc gaagaggaac tgcaagtgat ccagcccgac   120
aagagcgtgc tggtggccgc tggcgaaacc gccaccctga tgtacagc caccagcctg     180 atccccgtgg gccccatcca gtggtttaga ggcgctggcc ctggcagaga gctgatctac   240
aaccagaaag agggccactt ccccagagtg accaccgtgt ccgacctgac caagcggaac   300
aacatggact tcagcatccg gatcggcaac atcaccctg ccgatgccgg cacctactac     360
tgcgtgaagt tccggaaggg cagccccgac gacgtggaat caaaagcgg agccggcacc   420 gagctgagcg tgcgggctaa accttctgcc cctgtggtgt ctggacctgc cgccagagct   480
acacctcagc acaccgtgtc ttttacctgc gagagccacg gcttcagccc agagacatc   540 accctgaagt ggttcaagaa cggcaacgag ctgtccgact tccagaccaa cgtggaccct   600
gtgggcgaga gcgtgtccta cagcatccac agcaccgcca aggtggtgct gacccgcgaa   660
gatgtgcaca gccaagtgat ctgcgaggtg gcccacgtga cactgcaggg cgatcctctg   720
agaggaaccg ccaacctgtc cgagacaatc agagtgcccc ccaccctgga agtgacccag   780
cagcctgtgc gggccgagaa ccaagtgaac gtgacctgcc aagtgcggaa gttctacccc   840
cagcggctgc agctgacctg gctggaaaac ggcaatgtgt ccggaccgga cagccagc    900 accgtgaccg agaacaagga tgccacctac aattggatga gctggctgct cgtgaacgtg   960
tccgcccacc gggacgatgt gaagctgaca tgccaggtgg aacacgacgg ccagcctgcc  1020
gtgtccaaga gccacgatct gaaggtgtca gcccatccca aagagcaggg ctccaacaca  1080
gcctgtccca gccctctgtt tcccggccct agcaagcctt tctgggtgct ggtggtggtc  1140
ggaggcgtgc tggcctgcta cagcctgctg gtcaccgtgg ccttcatcat cttttgggtc  1200
cgcagcaagc ggagcagagg cggccacagc gactacatga acatgacccc tagacggcct  1260
ggccccacca gaaagcacta ccagccctac gcccctcccc gggactttgc cgcctacaga  1320
agc                                                                1323

<210> SEQ ID NO 21
<211> LENGTH: 1083
<212> TYPE: DNA
<213> ORGANISM: Artificial Sequence
<220> FEATURE:
<223> OTHER INFORMATION: huSIRP alpha 12aas portion of extracellular
      domain

<400> SEQUENCE: 21
atggaacctg ccggacctgc tcctggcaga ctgggacctc tgctgtgtct gctgctggcc    60
gcctcttgtg cttggagcgg agtggctggc gaagaggaac tgcaagtgat ccagcccgac   120
aagagcgtgc tggtggccgc tggcgaaacc gccaccctga tgtacagc caccagcctg     180 atccccgtgg gccccatcca gtggtttaga ggcgctggcc ctggcagaga gctgatctac   240
aaccagaaag agggccactt ccccagagtg accaccgtgt ccgacctgac caagcggaac   300
```

```
aacatggact tcagcatccg gatcggcaac atcacccctg ccgatgccgg cacctactac    360
tgcgtgaagt tccggaaggg cagccccgac gacgtggaat tcaaaagcgg agccggcacc    420
gagctgagcg tgcgggctaa accttctgcc cctgtggtgt ctggacctgc cgccagagct    480
acacctcagc acaccgtgtc ttttacctgc gagagccacg gcttcagccc cagagacatc    540
accctgaagt ggttcaagaa cggcaacgag ctgtccgact tccagaccaa cgtggaccct    600
gtgggcgaga gcgtgtccta cagcatccac agcaccgcca aggtggtgct gacccgcgaa    660
gatgtgcaca gccaagtgat ctgcgaggtg gcccacgtga cactgcaggg cgatcctctg    720
agaggaaccg ccaacctgtc cgagacaatc agagtgcccc ccaccctgga agtgacccag    780
cagcctgtgc gggccgagaa ccaagtgaac gtgacctgcc aagtgcggaa gttctacccc    840
cagcggctgc agctgacctg gctggaaaac ggcaatgtgt cccggaccga gacagccagc    900
accgtgaccg agaacaagga tggcacctac aattggatga gctggctgct cgtgaacgtg    960
tccgcccacc gggacgatgt gaagctgaca tgccaggtgg aacacgacgg ccagcctgcc    1020
gtgtccaaga gccacgatct gaaggtgtca gcccatccca agagcagggg ctccaacaca    1080
gcc                                                                  1083

<210> SEQ ID NO 22
<211> LENGTH: 1326
<212> TYPE: DNA
<213> ORGANISM: Artificial Sequence
<220> FEATURE:
<223> OTHER INFORMATION: huSIRP alpha-12aas-CD28Cys tm-41BBic construct

<400> SEQUENCE: 22
atggaacctg ccggacctgc tcctggcaga ctgggacctc tgctgtgtct gctgctggcc     60
gcctcttgtg cttggagcgg agtggctggc gaagaggaac tgcaagtgat ccagcccgac    120
aagagcgtgc tggtggccgc tggcgaaacc gccaccctga gatgtacagc caccagcctg    180
atccccgtgg gccccatcca gtggtttaga ggcgctggcc ctggcagaga gctgatctac    240
aaccagaaag agggccactt ccccagagtg accacccgtgt ccgacctgac caagcggaac    300
aacatggact tcagcatccg gatcggcaac atcacccctg ccgatgccgg cacctactac    360
tgcgtgaagt tccggaaggg cagccccgac gacgtggaat tcaaaagcgg agccggcacc    420
gagctgagcg tgcgggctaa accttctgcc cctgtggtgt ctggacctgc cgccagagct    480
acacctcagc acaccgtgtc ttttacctgc gagagccacg gcttcagccc cagagacatc    540
accctgaagt ggttcaagaa cggcaacgag ctgtccgact tccagaccaa cgtggaccct    600
gtgggcgaga gcgtgtccta cagcatccac agcaccgcca aggtggtgct gacccgcgaa    660
gatgtgcaca gccaagtgat ctgcgaggtg gcccacgtga cactgcaggg cgatcctctg    720
agaggaaccg ccaacctgtc cgagacaatc agagtgcccc ccaccctgga agtgacccag    780
cagcctgtgc gggccgagaa ccaagtgaac gtgacctgcc aagtgcggaa gttctacccc    840
cagcggctgc agctgacctg gctggaaaac ggcaatgtgt cccggaccga gacagccagc    900
accgtgaccg agaacaagga tggcacctac aattggatga gctggctgct cgtgaacgtg    960
tccgcccacc gggacgatgt gaagctgaca tgccaggtgg aacacgacgg ccagcctgcc   1020
gtgtccaaga gccacgatct gaaggtgtca gcccatccca agagcagggg ctccaacaca   1080
gcctgtccca gccctctgtt tcccggccct agcaagcctt ctgggtgctg gtggtggtc    1140 ggaggcgtgc tggcctgcta cagcctgctg gtcaccgtgg ccttcatcat cttttgggtc   1200
aagcggggca gaaagaagct gctgtacatc ttcaagcagc ctttcatgcg gcccgtgcag   1260
```

| accacccagg | aagaggacgg | ctgctcctgc | agattccccg | aggaagaaga | aggcggctgc | 1320 |
| gagctg | | | | | | 1326 |

<210> SEQ ID NO 23
<211> LENGTH: 1449
<212> TYPE: DNA
<213> ORGANISM: Artificial Sequence
<220> FEATURE:
<223> OTHER INFORMATION: huSIRP alpha-12aas-CD28Cys tm ic-41BBic
      construct

<400> SEQUENCE: 23

| atggaacctg | ccggacctgc | tcctggcaga | ctgggacctc | tgctgtgtct | gctgctggcc | 60 |
| gcctcttgtg | cttggagcgg | agtggctggc | gaagaggaac | tgcaagtgat | ccagcccgac | 120 |
| aagagcgtgc | tggtggccgc | tggcgaaacc | gccaccctga | gatgtacagc | caccagcctg | 180 |
| atccccgtgg | cccccatcca | gtggtttaga | ggcgctggcc | ctggcagaga | gctgatctac | 240 |
| aaccagaaag | agggccactt | ccccagagtg | accaccgtgt | ccgacctgac | caagcggaac | 300 |
| aacatggact | tcagcatccg | gatcggcaac | atcaccctg | ccgatgccgg | cacctactac | 360 |
| tgcgtgaagt | tccggaaggg | cagccccgac | gacgtggaat | caaaagcgg | agccggcacc | 420 |
| gagctgagcg | tgcgggctaa | accttctgcc | cctgtggtgt | ctggacctgc | cgccagagct | 480 |
| acacctcagc | acaccgtgtc | ttttacctgc | gagagccacg | gcttcagccc | cagagacatc | 540 |
| accctgaagt | ggttcaagaa | cggcaacgag | ctgtccgact | ccagaccaa | cgtggaccct | 600 |
| gtgggcgaga | gcgtgtccta | cagcatccac | agcaccgcca | aggtggtgct | gacccgcgaa | 660 |
| gatgtgcaca | gccaagtgat | ctgcgaggtg | gcccacgtga | cactgcaggg | cgatcctctg | 720 |
| agaggaaccg | ccaacctgtc | cgagacaatc | agagtgcccc | ccaccctgga | agtgacccag | 780 |
| cagcctgtgc | gggccgagaa | ccaagtgaac | gtgacctgcc | aagtgcggaa | gttctacccc | 840 |
| cagcggctgc | agctgacctg | gctggaaaac | ggcaatgtgt | cccggaccga | gacagccagc | 900 |
| accgtgaccg | agaacaagga | tggcacctac | aattggatga | gctggctgct | cgtgaacgtg | 960 |
| tccgcccacc | gggacgatgt | gaagctgaca | tgccaggtgg | aacacgacgg | ccagcctgcc | 1020 |
| gtgtccaaga | gccacgatct | gaaggtgtca | gcccatccca | aagagcaggg | ctccaacaca | 1080 |
| gcctgtccca | gccctctgtt | tcccggccct | agcaagcctt | tctgggtgct | ggtggtggtc | 1140 |
| ggaggcgtgc | tggcctgcta | cagcctgctg | gtcaccgtgg | ccttcatcat | cttttgggtc | 1200 |
| cgcagcaagc | ggagcagagg | cggccacagc | gactacatga | acatgacccc | tagacggcct | 1260 |
| ggccccacca | gaaagcacta | ccagccctac | gcccctcccc | gggactttgc | cgcctacaga | 1320 |
| agcaagcggg | gcagaaagaa | gctgctgtac | atcttcaagc | agcctttcat | gcggcccgtg | 1380 |
| cagaccaccc | aggaagagga | cggctgctcc | tgcagattcc | ccgaggaaga | agaaggcggc | 1440 |
| tgcgagctg | | | | | | 1449 |

<210> SEQ ID NO 24
<211> LENGTH: 305
<212> TYPE: PRT
<213> ORGANISM: Artificial Sequence
<220> FEATURE:
<223> OTHER INFORMATION: huCD200Rtm-CD28 protein

<400> SEQUENCE: 24

Met Leu Cys Pro Trp Arg Thr Ala Asn Leu Gly Leu Leu Leu Ile Leu
1               5                   10                  15

```
Thr Ile Phe Leu Val Ala Ala Ser Ser Ser Leu Cys Met Asp Glu Lys
                20                  25                  30

Gln Ile Thr Gln Asn Tyr Ser Lys Val Leu Ala Glu Val Asn Thr Ser
            35                  40                  45

Trp Pro Val Lys Met Ala Thr Asn Ala Val Leu Cys Cys Pro Pro Ile
    50                  55                  60

Ala Leu Arg Asn Leu Ile Ile Thr Trp Glu Ile Leu Arg Gly
65                  70                  75                  80

Gln Pro Ser Cys Thr Lys Ala Tyr Arg Lys Glu Thr Asn Glu Thr Lys
                85                  90                  95

Glu Thr Asn Cys Thr Asp Glu Arg Ile Thr Trp Val Ser Arg Pro Asp
                100                 105                 110

Gln Asn Ser Asp Leu Gln Ile Arg Pro Val Ala Ile Thr His Asp Gly
            115                 120                 125

Tyr Tyr Arg Cys Ile Met Val Thr Pro Asp Gly Asn Phe His Arg Gly
    130                 135                 140

Tyr His Leu Gln Val Leu Val Thr Pro Glu Val Thr Leu Phe Gln Asn
145                 150                 155                 160

Arg Asn Arg Thr Ala Val Cys Lys Ala Val Ala Gly Lys Pro Ala Ala
                165                 170                 175

Gln Ile Ser Trp Ile Pro Glu Gly Asp Cys Ala Thr Lys Gln Glu Tyr
            180                 185                 190

Trp Ser Asn Gly Thr Val Thr Val Lys Ser Thr Cys His Trp Glu Val
    195                 200                 205

His Asn Val Ser Thr Val Thr Cys His Val Ser His Leu Thr Gly Asn
210                 215                 220

Lys Ser Leu Tyr Ile Glu Leu Leu Pro Val Pro Gly Ala Lys Lys Ser
225                 230                 235                 240

Ala Lys Leu Tyr Ile Pro Tyr Ile Ile Leu Thr Ile Ile Leu Thr
                245                 250                 255

Ile Val Gly Phe Ile Trp Leu Leu Arg Ser Lys Arg Ser Arg Gly Gly
                260                 265                 270

His Ser Asp Tyr Met Asn Met Thr Pro Arg Arg Pro Gly Pro Thr Arg
            275                 280                 285

Lys His Tyr Gln Pro Tyr Ala Pro Pro Arg Asp Phe Ala Ala Tyr Arg
    290                 295                 300

Ser
305

<210> SEQ ID NO 25
<211> LENGTH: 243
<212> TYPE: PRT
<213> ORGANISM: Artificial Sequence
<220> FEATURE:
<223> OTHER INFORMATION: huCD200R entire extracellular domain

<400> SEQUENCE: 25

Met Leu Cys Pro Trp Arg Thr Ala Asn Leu Gly Leu Leu Leu Ile Leu
1               5                   10                  15

Thr Ile Phe Leu Val Ala Ala Ser Ser Ser Leu Cys Met Asp Glu Lys
                20                  25                  30

Gln Ile Thr Gln Asn Tyr Ser Lys Val Leu Ala Glu Val Asn Thr Ser
            35                  40                  45

Trp Pro Val Lys Met Ala Thr Asn Ala Val Leu Cys Cys Pro Pro Ile
    50                  55                  60
```

```
Ala Leu Arg Asn Leu Ile Ile Thr Trp Glu Ile Leu Arg Gly
 65                  70                  75                  80

Gln Pro Ser Cys Thr Lys Ala Tyr Arg Lys Glu Thr Asn Glu Thr Lys
                 85                  90                  95

Glu Thr Asn Cys Thr Asp Glu Arg Ile Thr Trp Val Ser Arg Pro Asp
            100                 105                 110

Gln Asn Ser Asp Leu Gln Ile Arg Pro Val Ala Ile Thr His Asp Gly
        115                 120                 125

Tyr Tyr Arg Cys Ile Met Val Thr Pro Asp Gly Asn Phe His Arg Gly
    130                 135                 140

Tyr His Leu Gln Val Leu Val Thr Pro Glu Val Thr Leu Phe Gln Asn
145                 150                 155                 160

Arg Asn Arg Thr Ala Val Cys Lys Ala Val Ala Gly Lys Pro Ala Ala
                165                 170                 175

Gln Ile Ser Trp Ile Pro Glu Gly Asp Cys Ala Thr Lys Gln Glu Tyr
            180                 185                 190

Trp Ser Asn Gly Thr Val Thr Val Lys Ser Thr Cys His Trp Glu Val
        195                 200                 205

His Asn Val Ser Thr Val Thr Cys His Val Ser His Leu Thr Gly Asn
    210                 215                 220

Lys Ser Leu Tyr Ile Glu Leu Leu Pro Val Pro Gly Ala Lys Lys Ser
225                 230                 235                 240

Ala Lys Leu

<210> SEQ ID NO 26
<211> LENGTH: 21
<212> TYPE: PRT
<213> ORGANISM: Artificial Sequence
<220> FEATURE:
<223> OTHER INFORMATION: huCD200R transmembrane domain

<400> SEQUENCE: 26

Tyr Ile Pro Tyr Ile Ile Leu Thr Ile Ile Leu Thr Ile Val Gly
 1               5                  10                  15

Phe Ile Trp Leu Leu
             20

<210> SEQ ID NO 27
<211> LENGTH: 27
<212> TYPE: PRT
<213> ORGANISM: Artificial Sequence
<220> FEATURE:
<223> OTHER INFORMATION: CD28 transmembrane domain protein

<400> SEQUENCE: 27

Phe Trp Val Leu Val Val Val Gly Gly Val Leu Ala Cys Tyr Ser Leu
 1               5                  10                  15

Leu Val Thr Val Ala Phe Ile Ile Phe Trp Val
            20                  25

<210> SEQ ID NO 28
<211> LENGTH: 41
<212> TYPE: PRT
<213> ORGANISM: Artificial Sequence
<220> FEATURE:
<223> OTHER INFORMATION: CD28 intracellular domain protein

<400> SEQUENCE: 28

Arg Ser Lys Arg Ser Arg Gly Gly His Ser Asp Tyr Met Asn Met Thr
 1               5                  10                  15
```

```
Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 29
<211> LENGTH: 311
<212> TYPE: PRT
<213> ORGANISM: Artificial Sequence
<220> FEATURE:
<223> OTHER INFORMATION: huCD200R-CD28tm protein

<400> SEQUENCE: 29

Met Leu Cys Pro Trp Arg Thr Ala Asn Leu Gly Leu Leu Leu Ile Leu
1               5                   10                  15

Thr Ile Phe Leu Val Ala Ala Ser Ser Leu Cys Met Asp Glu Lys
            20                  25                  30

Gln Ile Thr Gln Asn Tyr Ser Lys Val Leu Ala Glu Val Asn Thr Ser
            35                  40                  45

Trp Pro Val Lys Met Ala Thr Asn Ala Val Leu Cys Cys Pro Pro Ile
50                  55                  60

Ala Leu Arg Asn Leu Ile Ile Thr Trp Glu Ile Leu Arg Gly
65                  70                  75                  80

Gln Pro Ser Cys Thr Lys Ala Tyr Arg Lys Glu Thr Asn Glu Thr Lys
                85                  90                  95

Glu Thr Asn Cys Thr Asp Glu Arg Ile Thr Trp Val Ser Arg Pro Asp
            100                 105                 110

Gln Asn Ser Asp Leu Gln Ile Arg Pro Val Ala Ile Thr His Asp Gly
            115                 120                 125

Tyr Tyr Arg Cys Ile Met Val Thr Pro Asp Gly Asn Phe His Arg Gly
130                 135                 140

Tyr His Leu Gln Val Leu Val Thr Pro Glu Val Thr Leu Phe Gln Asn
145                 150                 155                 160

Arg Asn Arg Thr Ala Val Cys Lys Ala Val Ala Gly Lys Pro Ala Ala
                165                 170                 175

Gln Ile Ser Trp Ile Pro Glu Gly Asp Cys Ala Thr Lys Gln Glu Tyr
            180                 185                 190

Trp Ser Asn Gly Thr Val Thr Val Lys Ser Thr Cys His Trp Glu Val
            195                 200                 205

His Asn Val Ser Thr Val Thr Cys His Val Ser His Leu Thr Gly Asn
        210                 215                 220

Lys Ser Leu Tyr Ile Glu Leu Leu Pro Val Pro Gly Ala Lys Lys Ser
225                 230                 235                 240

Ala Lys Leu Phe Trp Val Leu Val Val Val Gly Gly Val Leu Ala Cys
                245                 250                 255

Tyr Ser Leu Leu Val Thr Val Ala Phe Ile Ile Phe Trp Val Arg Ser
            260                 265                 270

Lys Arg Ser Arg Gly Gly His Ser Asp Tyr Met Asn Met Thr Pro Arg
275                 280                 285

Arg Pro Gly Pro Thr Arg Lys His Tyr Gln Pro Tyr Ala Pro Pro Arg
        290                 295                 300

Asp Phe Ala Ala Tyr Arg Ser
305                 310

<210> SEQ ID NO 30
```

<211> LENGTH: 314
<212> TYPE: PRT
<213> ORGANISM: Artificial Sequence
<220> FEATURE:
<223> OTHER INFORMATION: huCD200R-9aas-CD28Cys protein

<400> SEQUENCE: 30

```
Met Leu Cys Pro Trp Arg Thr Ala Asn Leu Gly Leu Leu Leu Ile Leu
1               5                   10                  15

Thr Ile Phe Leu Val Ala Ala Ser Ser Ser Leu Cys Met Asp Glu Lys
            20                  25                  30

Gln Ile Thr Gln Asn Tyr Ser Lys Val Leu Ala Glu Val Asn Thr Ser
        35                  40                  45

Trp Pro Val Lys Met Ala Thr Asn Ala Val Leu Cys Cys Pro Pro Ile
50                  55                  60

Ala Leu Arg Asn Leu Ile Ile Ile Thr Trp Glu Ile Ile Leu Arg Gly
65                  70                  75                  80

Gln Pro Ser Cys Thr Lys Ala Tyr Arg Lys Glu Thr Asn Glu Thr Lys
                85                  90                  95

Glu Thr Asn Cys Thr Asp Glu Arg Ile Thr Trp Val Ser Arg Pro Asp
            100                 105                 110

Gln Asn Ser Asp Leu Gln Ile Arg Pro Val Ala Ile Thr His Asp Gly
        115                 120                 125

Tyr Tyr Arg Cys Ile Met Val Thr Pro Asp Gly Asn Phe His Arg Gly
130                 135                 140

Tyr His Leu Gln Val Leu Val Thr Pro Glu Val Thr Leu Phe Gln Asn
145                 150                 155                 160

Arg Asn Arg Thr Ala Val Cys Lys Ala Val Ala Gly Lys Pro Ala Ala
                165                 170                 175

Gln Ile Ser Trp Ile Pro Glu Gly Asp Cys Ala Thr Lys Gln Glu Tyr
            180                 185                 190

Trp Ser Asn Gly Thr Val Thr Val Lys Ser Thr Cys His Trp Glu Val
        195                 200                 205

His Asn Val Ser Thr Val Thr Cys His Val Ser His Leu Thr Gly Asn
210                 215                 220

Lys Ser Leu Tyr Ile Glu Leu Leu Pro Val Cys Pro Ser Pro Leu Phe
225                 230                 235                 240

Pro Gly Pro Ser Lys Pro Phe Trp Val Leu Val Val Val Gly Gly Val
                245                 250                 255

Leu Ala Cys Tyr Ser Leu Leu Val Thr Val Ala Phe Ile Ile Phe Trp
            260                 265                 270

Val Arg Ser Lys Arg Ser Arg Gly Gly His Ser Asp Tyr Met Asn Met
        275                 280                 285

Thr Pro Arg Arg Pro Gly Pro Thr Arg Lys His Tyr Gln Pro Tyr Ala
    290                 295                 300

Pro Pro Arg Asp Phe Ala Ala Tyr Arg Ser
305                 310
```

<210> SEQ ID NO 31
<211> LENGTH: 234
<212> TYPE: PRT
<213> ORGANISM: Artificial Sequence
<220> FEATURE:
<223> OTHER INFORMATION: huCD200R-9aas protein

<400> SEQUENCE: 31

```
Met Leu Cys Pro Trp Arg Thr Ala Asn Leu Gly Leu Leu Leu Ile Leu
```

```
            1               5                  10                 15
Thr Ile Phe Leu Val Ala Ala Ser Ser Ser Leu Cys Met Asp Glu Lys
            20                  25                 30

Gln Ile Thr Gln Asn Tyr Ser Lys Val Leu Ala Glu Val Asn Thr Ser
            35                  40                 45

Trp Pro Val Lys Met Ala Thr Asn Ala Val Leu Cys Cys Pro Pro Ile
50                  55                  60

Ala Leu Arg Asn Leu Ile Ile Ile Thr Trp Glu Ile Ile Leu Arg Gly
65                  70                  75                  80

Gln Pro Ser Cys Thr Lys Ala Tyr Arg Lys Glu Thr Asn Glu Thr Lys
            85                  90                  95

Glu Thr Asn Cys Thr Asp Glu Arg Ile Thr Trp Val Ser Arg Pro Asp
            100                 105                110

Gln Asn Ser Asp Leu Gln Ile Arg Pro Val Ala Ile Thr His Asp Gly
            115                 120                125

Tyr Tyr Arg Cys Ile Met Val Thr Pro Asp Gly Asn Phe His Arg Gly
            130                 135                140

Tyr His Leu Gln Val Leu Val Thr Pro Glu Val Thr Leu Phe Gln Asn
145                 150                 155                160

Arg Asn Arg Thr Ala Val Cys Lys Ala Val Ala Gly Lys Pro Ala Ala
                165                 170                 175

Gln Ile Ser Trp Ile Pro Glu Gly Asp Cys Ala Thr Lys Gln Glu Tyr
                180                 185                 190

Trp Ser Asn Gly Thr Val Thr Val Lys Ser Thr Cys His Trp Glu Val
                195                 200                 205

His Asn Val Ser Thr Val Thr Cys His Val Ser His Leu Thr Gly Asn
            210                 215                 220

Lys Ser Leu Tyr Ile Glu Leu Leu Pro Val
225                 230
```

<210> SEQ ID NO 32
<211> LENGTH: 12
<212> TYPE: PRT
<213> ORGANISM: Artificial Sequence
<220> FEATURE:
<223> OTHER INFORMATION: CD28Cys (extracellular portion) protein

<400> SEQUENCE: 32

```
Cys Pro Ser Pro Leu Phe Pro Gly Pro Ser Lys Pro
1               5                   10
```

<210> SEQ ID NO 33
<211> LENGTH: 311
<212> TYPE: PRT
<213> ORGANISM: Artificial Sequence
<220> FEATURE:
<223> OTHER INFORMATION: huCD200R-12aas-CD28Cys protein

<400> SEQUENCE: 33

```
Met Leu Cys Pro Trp Arg Thr Ala Asn Leu Gly Leu Leu Leu Ile Leu
1               5                   10                  15

Thr Ile Phe Leu Val Ala Ala Ser Ser Ser Leu Cys Met Asp Glu Lys
            20                  25                  30

Gln Ile Thr Gln Asn Tyr Ser Lys Val Leu Ala Glu Val Asn Thr Ser
            35                  40                  45

Trp Pro Val Lys Met Ala Thr Asn Ala Val Leu Cys Cys Pro Pro Ile
50                  55                  60
```

```
Ala Leu Arg Asn Leu Ile Ile Ile Thr Trp Glu Ile Ile Leu Arg Gly
 65                  70                  75                  80

Gln Pro Ser Cys Thr Lys Ala Tyr Arg Lys Glu Thr Asn Glu Thr Lys
                 85                  90                  95

Glu Thr Asn Cys Thr Asp Glu Arg Ile Thr Trp Val Ser Arg Pro Asp
            100                 105                 110

Gln Asn Ser Asp Leu Gln Ile Arg Pro Val Ala Ile Thr His Asp Gly
        115                 120                 125

Tyr Tyr Arg Cys Ile Met Val Thr Pro Asp Gly Asn Phe His Arg Gly
    130                 135                 140

Tyr His Leu Gln Val Leu Val Thr Pro Glu Val Thr Leu Phe Gln Asn
145                 150                 155                 160

Arg Asn Arg Thr Ala Val Cys Lys Ala Val Ala Gly Lys Pro Ala Ala
                165                 170                 175

Gln Ile Ser Trp Ile Pro Glu Gly Asp Cys Ala Thr Lys Gln Glu Tyr
            180                 185                 190

Trp Ser Asn Gly Thr Val Thr Val Lys Ser Thr Cys His Trp Glu Val
        195                 200                 205

His Asn Val Ser Thr Val Thr Cys His Val Ser His Leu Thr Gly Asn
    210                 215                 220

Lys Ser Leu Tyr Ile Glu Leu Cys Pro Ser Pro Leu Phe Pro Gly Pro
225                 230                 235                 240

Ser Lys Pro Phe Trp Val Leu Val Val Gly Gly Val Leu Ala Cys
                245                 250                 255

Tyr Ser Leu Leu Val Thr Val Ala Phe Ile Ile Phe Trp Val Arg Ser
            260                 265                 270

Lys Arg Ser Arg Gly Gly His Ser Asp Tyr Met Asn Met Thr Pro Arg
                275                 280                 285

Arg Pro Gly Pro Thr Arg Lys His Tyr Gln Pro Tyr Ala Pro Pro Arg
        290                 295                 300

Asp Phe Ala Ala Tyr Arg Ser
305                 310

<210> SEQ ID NO 34
<211> LENGTH: 231
<212> TYPE: PRT
<213> ORGANISM: Artificial Sequence
<220> FEATURE:
<223> OTHER INFORMATION: huCD200R-12aas protein

<400> SEQUENCE: 34

Met Leu Cys Pro Trp Arg Thr Ala Asn Leu Gly Leu Leu Leu Ile Leu
  1               5                  10                  15

Thr Ile Phe Leu Val Ala Ala Ser Ser Ser Leu Cys Met Asp Glu Lys
                 20                  25                  30

Gln Ile Thr Gln Asn Tyr Ser Lys Val Leu Ala Glu Val Asn Thr Ser
             35                  40                  45

Trp Pro Val Lys Met Ala Thr Asn Ala Val Leu Cys Cys Pro Pro Ile
         50                  55                  60

Ala Leu Arg Asn Leu Ile Ile Ile Thr Trp Glu Ile Ile Leu Arg Gly
 65                  70                  75                  80

Gln Pro Ser Cys Thr Lys Ala Tyr Arg Lys Glu Thr Asn Glu Thr Lys
                 85                  90                  95

Glu Thr Asn Cys Thr Asp Glu Arg Ile Thr Trp Val Ser Arg Pro Asp
            100                 105                 110
```

Gln Asn Ser Asp Leu Gln Ile Arg Pro Val Ala Ile Thr His Asp Gly
            115                 120                 125

Tyr Tyr Arg Cys Ile Met Val Thr Pro Asp Gly Asn Phe His Arg Gly
130                 135                 140

Tyr His Leu Gln Val Leu Val Thr Pro Glu Val Thr Leu Phe Gln Asn
145                 150                 155                 160

Arg Asn Arg Thr Ala Val Cys Lys Ala Val Ala Gly Lys Pro Ala Ala
            165                 170                 175

Gln Ile Ser Trp Ile Pro Glu Gly Asp Cys Ala Thr Lys Gln Glu Tyr
            180                 185                 190

Trp Ser Asn Gly Thr Val Thr Val Lys Ser Thr Cys His Trp Glu Val
            195                 200                 205

His Asn Val Ser Thr Val Thr Cys His Val Ser His Leu Thr Gly Asn
            210                 215                 220

Lys Ser Leu Tyr Ile Glu Leu
225                 230

<210> SEQ ID NO 35
<211> LENGTH: 315
<212> TYPE: PRT
<213> ORGANISM: Artificial Sequence
<220> FEATURE:
<223> OTHER INFORMATION: huCD200R-9aas-CD28Cys tm-41BBic protein

<400> SEQUENCE: 35

Met Leu Cys Pro Trp Arg Thr Ala Asn Leu Gly Leu Leu Ile Leu
1               5                   10                  15

Thr Ile Phe Leu Val Ala Ala Ser Ser Ser Leu Cys Met Asp Glu Lys
            20                  25                  30

Gln Ile Thr Gln Asn Tyr Ser Lys Val Leu Ala Glu Val Asn Thr Ser
            35                  40                  45

Trp Pro Val Lys Met Ala Thr Asn Ala Val Leu Cys Cys Pro Pro Ile
50                  55                  60

Ala Leu Arg Asn Leu Ile Ile Thr Trp Glu Ile Ile Leu Arg Gly
65                  70                  75                  80

Gln Pro Ser Cys Thr Lys Ala Tyr Arg Lys Glu Thr Asn Glu Thr Lys
            85                  90                  95

Glu Thr Asn Cys Thr Asp Glu Arg Ile Thr Trp Val Ser Arg Pro Asp
            100                 105                 110

Gln Asn Ser Asp Leu Gln Ile Arg Pro Val Ala Ile Thr His Asp Gly
            115                 120                 125

Tyr Tyr Arg Cys Ile Met Val Thr Pro Asp Gly Asn Phe His Arg Gly
130                 135                 140

Tyr His Leu Gln Val Leu Val Thr Pro Glu Val Thr Leu Phe Gln Asn
145                 150                 155                 160

Arg Asn Arg Thr Ala Val Cys Lys Ala Val Ala Gly Lys Pro Ala Ala
            165                 170                 175

Gln Ile Ser Trp Ile Pro Glu Gly Asp Cys Ala Thr Lys Gln Glu Tyr
            180                 185                 190

Trp Ser Asn Gly Thr Val Thr Val Lys Ser Thr Cys His Trp Glu Val
            195                 200                 205

His Asn Val Ser Thr Val Thr Cys His Val Ser His Leu Thr Gly Asn
            210                 215                 220

Lys Ser Leu Tyr Ile Glu Leu Leu Pro Val Cys Pro Ser Pro Leu Phe
225                 230                 235                 240

```
Pro Gly Pro Ser Lys Pro Phe Trp Val Leu Val Val Gly Gly Val
                245             250             255

Leu Ala Cys Tyr Ser Leu Leu Val Thr Val Ala Phe Ile Ile Phe Trp
            260                 265                 270

Val Lys Arg Gly Arg Lys Lys Leu Leu Tyr Ile Phe Lys Gln Pro Phe
                275                 280                 285

Met Arg Pro Val Gln Thr Thr Gln Glu Glu Asp Gly Cys Ser Cys Arg
        290                 295                 300

Phe Pro Glu Glu Glu Glu Gly Gly Cys Glu Leu
305                 310                 315

<210> SEQ ID NO 36
<211> LENGTH: 42
<212> TYPE: PRT
<213> ORGANISM: Artificial Sequence
<220> FEATURE:
<223> OTHER INFORMATION: 4-1BB intracellular component protein

<400> SEQUENCE: 36

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 37
<211> LENGTH: 312
<212> TYPE: PRT
<213> ORGANISM: Artificial Sequence
<220> FEATURE:
<223> OTHER INFORMATION: huCD200R-12aas-CD28Cys tm-41BBic protein

<400> SEQUENCE: 37

Met Leu Cys Pro Trp Arg Thr Ala Asn Leu Gly Leu Leu Leu Ile Leu
1               5                   10                  15

Thr Ile Phe Leu Val Ala Ala Ser Ser Leu Cys Met Asp Glu Lys
            20                  25                  30

Gln Ile Thr Gln Asn Tyr Ser Lys Val Leu Ala Glu Val Asn Thr Ser
        35                  40                  45

Trp Pro Val Lys Met Ala Thr Asn Ala Val Leu Cys Cys Pro Pro Ile
    50                  55                  60

Ala Leu Arg Asn Leu Ile Ile Ile Thr Trp Glu Ile Leu Arg Gly
65                  70                  75                  80

Gln Pro Ser Cys Thr Lys Ala Tyr Arg Lys Glu Thr Asn Glu Thr Lys
                85                  90                  95

Glu Thr Asn Cys Thr Asp Glu Arg Ile Thr Trp Val Ser Arg Pro Asp
            100                 105                 110

Gln Asn Ser Asp Leu Gln Ile Arg Pro Val Ala Ile Thr His Asp Gly
        115                 120                 125

Tyr Tyr Arg Cys Ile Met Val Thr Pro Asp Gly Asn Phe His Arg Gly
    130                 135                 140

Tyr His Leu Gln Val Leu Val Thr Pro Glu Val Thr Leu Phe Gln Asn
145                 150                 155                 160

Arg Asn Arg Thr Ala Val Cys Lys Ala Val Ala Gly Lys Pro Ala Ala
                165                 170                 175

Gln Ile Ser Trp Ile Pro Glu Gly Asp Cys Ala Thr Lys Gln Glu Tyr
            180                 185                 190
```

Trp Ser Asn Gly Thr Val Thr Val Lys Ser Thr Cys His Trp Glu Val
            195                 200                 205

His Asn Val Ser Thr Val Thr Cys His Val Ser His Leu Thr Gly Asn
210                 215                 220

Lys Ser Leu Tyr Ile Glu Leu Cys Pro Ser Pro Leu Phe Pro Gly Pro
225                 230                 235                 240

Ser Lys Pro Phe Trp Val Leu Val Val Gly Gly Val Leu Ala Cys
            245                 250                 255

Tyr Ser Leu Leu Val Thr Val Ala Phe Ile Ile Phe Trp Val Lys Arg
            260                 265                 270

Gly Arg Lys Lys Leu Leu Tyr Ile Phe Lys Gln Pro Phe Met Arg Pro
            275                 280                 285

Val Gln Thr Thr Gln Glu Glu Asp Gly Cys Ser Cys Arg Phe Pro Glu
            290                 295                 300

Glu Glu Glu Gly Gly Cys Glu Leu
305                 310

<210> SEQ ID NO 38
<211> LENGTH: 353
<212> TYPE: PRT
<213> ORGANISM: Artificial Sequence
<220> FEATURE:
<223> OTHER INFORMATION: huCD200R-12aas-CD28Cys tm ic-41BBic protein

<400> SEQUENCE: 38

Met Leu Cys Pro Trp Arg Thr Ala Asn Leu Gly Leu Leu Leu Ile Leu
1               5                   10                  15

Thr Ile Phe Leu Val Ala Ala Ser Ser Leu Cys Met Asp Glu Lys
            20                  25                  30

Gln Ile Thr Gln Asn Tyr Ser Lys Val Leu Ala Glu Val Asn Thr Ser
            35                  40                  45

Trp Pro Val Lys Met Ala Thr Asn Ala Val Leu Cys Cys Pro Pro Ile
50                  55                  60

Ala Leu Arg Asn Leu Ile Ile Ile Thr Trp Glu Ile Ile Leu Arg Gly
65                  70                  75                  80

Gln Pro Ser Cys Thr Lys Ala Tyr Arg Lys Glu Thr Asn Glu Thr Lys
            85                  90                  95

Glu Thr Asn Cys Thr Asp Glu Arg Ile Thr Trp Val Ser Arg Pro Asp
            100                 105                 110

Gln Asn Ser Asp Leu Gln Ile Arg Pro Val Ala Ile Thr His Asp Gly
            115                 120                 125

Tyr Tyr Arg Cys Ile Met Val Thr Pro Asp Gly Asn Phe His Arg Gly
130                 135                 140

Tyr His Leu Gln Val Leu Val Thr Pro Glu Val Thr Leu Phe Gln Asn
145                 150                 155                 160

Arg Asn Arg Thr Ala Val Cys Lys Ala Val Ala Gly Lys Pro Ala Ala
            165                 170                 175

Gln Ile Ser Trp Ile Pro Glu Gly Asp Cys Ala Thr Lys Gln Glu Tyr
            180                 185                 190

Trp Ser Asn Gly Thr Val Thr Val Lys Ser Thr Cys His Trp Glu Val
            195                 200                 205

His Asn Val Ser Thr Val Thr Cys His Val Ser His Leu Thr Gly Asn
210                 215                 220

Lys Ser Leu Tyr Ile Glu Leu Cys Pro Ser Pro Leu Phe Pro Gly Pro
225                 230                 235                 240

```
Ser Lys Pro Phe Trp Val Leu Val Val Gly Val Leu Ala Cys
            245             250             255

Tyr Ser Leu Leu Val Thr Val Ala Phe Ile Ile Phe Trp Val Arg Ser
        260                 265                 270

Lys Arg Ser Arg Gly Gly His Ser Asp Tyr Met Asn Met Thr Pro Arg
        275                 280                 285

Arg Pro Gly Pro Thr Arg Lys His Tyr Gln Pro Tyr Ala Pro Pro Arg
        290                 295                 300

Asp Phe Ala Ala Tyr Arg Ser Lys Arg Gly Arg Lys Lys Leu Leu Tyr
305                 310                 315                 320

Ile Phe Lys Gln Pro Phe Met Arg Pro Val Gln Thr Thr Gln Glu Glu
            325                 330                 335

Asp Gly Cys Ser Cys Arg Phe Pro Glu Glu Glu Glu Gly Gly Cys Glu
            340                 345                 350

Leu

<210> SEQ ID NO 39
<211> LENGTH: 435
<212> TYPE: PRT
<213> ORGANISM: Artificial Sequence
<220> FEATURE:
<223> OTHER INFORMATION: huSIRP alpha tm-CD28 protein

<400> SEQUENCE: 39

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
    50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
    130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
    210                 215                 220

Gln Val Ile Cys Glu Val Ala His Val Thr Leu Gln Gly Asp Pro Leu
225                 230                 235                 240
```

```
Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285

Glu Asn Gly Asn Val Ser Arg Thr Glu Thr Ala Ser Thr Val Thr Glu
    290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
            340                 345                 350

Pro Lys Glu Gln Gly Ser Asn Thr Ala Ala Glu Asn Thr Gly Ser Asn
        355                 360                 365

Glu Arg Asn Ile Tyr Ile Val Val Gly Val Val Cys Thr Leu Leu Val
    370                 375                 380

Ala Leu Leu Met Ala Ala Leu Tyr Leu Val Arg Ser Lys Arg Ser Arg
385                 390                 395                 400

Gly Gly His Ser Asp Tyr Met Asn Met Thr Pro Arg Arg Pro Gly Pro
                405                 410                 415

Thr Arg Lys His Tyr Gln Pro Tyr Ala Pro Pro Arg Asp Phe Ala Ala
            420                 425                 430

Tyr Arg Ser
        435

<210> SEQ ID NO 40
<211> LENGTH: 373
<212> TYPE: PRT
<213> ORGANISM: Artificial Sequence
<220> FEATURE:
<223> OTHER INFORMATION: huSIRP alpha entire extracellular domain
      protein

<400> SEQUENCE: 40

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
    50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
    130                 135                 140

Arg Ala Lys Pro Ser Ala Pro Val Val Ser Gly Pro Ala Ala Arg Ala
145                 150                 155                 160
```

```
Thr Pro Gln His Thr Val Ser Phe Thr Cys Glu Ser His Gly Phe Ser
            165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
            195                 200                 205

Ile His Ser Thr Ala Lys Val Val Leu Thr Arg Glu Asp Val His Ser
            210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
            245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
            275                 280                 285

Glu Asn Gly Asn Val Ser Arg Thr Glu Thr Ala Ser Thr Val Thr Glu
            290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
            325                 330                 335

Gly Gln Pro Ala Val Ser Lys Ser His Asp Leu Lys Val Ser Ala His
            340                 345                 350

Pro Lys Glu Gln Gly Ser Asn Thr Ala Ala Glu Asn Thr Gly Ser Asn
            355                 360                 365

Glu Arg Asn Ile Tyr
            370

<210> SEQ ID NO 41
<211> LENGTH: 21
<212> TYPE: PRT
<213> ORGANISM: Artificial Sequence
<220> FEATURE:
<223> OTHER INFORMATION: huSIRP alpha transmembrane domain protein

<400> SEQUENCE: 41

Ile Val Val Gly Val Val Cys Thr Leu Leu Val Ala Leu Leu Met Ala
1               5                   10                  15

Ala Leu Tyr Leu Val
            20

<210> SEQ ID NO 42
<211> LENGTH: 441
<212> TYPE: PRT
<213> ORGANISM: Artificial Sequence
<220> FEATURE:
<223> OTHER INFORMATION: huSIRP alpha -CD28tm protein

<400> SEQUENCE: 42

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
            35                  40                  45

Glu Thr Ala Thr Leu Arg Cys Thr Ala Thr Ser Leu Ile Pro Val Gly
```

```
                50              55              60
Pro Ile Gln Trp Phe Arg Gly Ala Gly Pro Arg Glu Leu Ile Tyr
65              70              75              80

Asn Gln Lys Glu Gly His Phe Pro Arg Val Thr Thr Val Ser Asp Leu
            85              90              95

Thr Lys Arg Asn Asn Met Asp Phe Ser Ile Arg Ile Gly Asn Ile Thr
            100             105             110

Pro Ala Asp Ala Gly Thr Tyr Tyr Cys Val Lys Phe Arg Lys Gly Ser
            115             120             125

Pro Asp Asp Val Glu Phe Lys Ser Gly Ala Gly Thr Glu Leu Ser Val
            130             135             140

Arg Ala Lys Pro Ser Ala Pro Val Val Ser Gly Pro Ala Arg Ala
145             150             155             160

Thr Pro Gln His Thr Val Ser Phe Thr Cys Glu Ser His Gly Phe Ser
                165             170             175

Pro Arg Asp Ile Thr Leu Lys Trp Phe Lys Asn Gly Asn Glu Leu Ser
            180             185             190

Asp Phe Gln Thr Asn Val Asp Pro Val Gly Glu Ser Val Ser Tyr Ser
            195             200             205

Ile His Ser Thr Ala Lys Val Val Leu Thr Arg Glu Asp Val His Ser
            210             215             220

Gln Val Ile Cys Glu Val Ala His Val Thr Leu Gln Gly Asp Pro Leu
225             230             235             240

Arg Gly Thr Ala Asn Leu Ser Glu Thr Ile Arg Val Pro Pro Thr Leu
            245             250             255

Glu Val Thr Gln Gln Pro Val Arg Ala Glu Asn Gln Val Asn Val Thr
            260             265             270

Cys Gln Val Arg Lys Phe Tyr Pro Gln Arg Leu Gln Leu Thr Trp Leu
            275             280             285

Glu Asn Gly Asn Val Ser Arg Thr Glu Thr Ala Ser Thr Val Thr Glu
            290             295             300

Asn Lys Asp Gly Thr Tyr Asn Trp Met Ser Trp Leu Leu Val Asn Val
305             310             315             320

Ser Ala His Arg Asp Asp Val Lys Leu Thr Cys Gln Val Glu His Asp
            325             330             335

Gly Gln Pro Ala Val Ser Lys Ser His Asp Leu Lys Val Ser Ala His
            340             345             350

Pro Lys Glu Gln Gly Ser Asn Thr Ala Ala Glu Asn Thr Gly Ser Asn
            355             360             365

Glu Arg Asn Ile Tyr Phe Trp Val Leu Val Val Gly Gly Val Leu
            370             375             380

Ala Cys Tyr Ser Leu Leu Val Thr Val Ala Phe Ile Ile Phe Trp Val
385             390             395             400

Arg Ser Lys Arg Ser Arg Gly Gly His Ser Asp Tyr Met Asn Met Thr
            405             410             415

Pro Arg Arg Pro Gly Pro Thr Arg Lys His Tyr Gln Pro Tyr Ala Pro
            420             425             430

Pro Arg Asp Phe Ala Ala Tyr Arg Ser
            435             440

<210> SEQ ID NO 43
<211> LENGTH: 441
<212> TYPE: PRT
<213> ORGANISM: Artificial Sequence
```

<220> FEATURE:
<223> OTHER INFORMATION: huSIRP alpha-12aas-CD28Cys protein

<400> SEQUENCE: 43

```
Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
    50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
    130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
    210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285

Glu Asn Gly Asn Val Ser Arg Thr Glu Thr Ala Ser Thr Val Thr Glu
    290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
            340                 345                 350

Pro Lys Glu Gln Gly Ser Asn Thr Ala Cys Pro Ser Pro Leu Phe Pro
        355                 360                 365

Gly Pro Ser Lys Pro Phe Trp Val Leu Val Val Val Gly Gly Val Leu
    370                 375                 380

Ala Cys Tyr Ser Leu Leu Val Thr Val Ala Phe Ile Ile Phe Trp Val
385                 390                 395                 400
```

```
Arg Ser Lys Arg Ser Arg Gly His Ser Asp Tyr Met Asn Met Thr
            405                 410                 415

Pro Arg Arg Pro Gly Pro Thr Arg Lys His Tyr Gln Pro Tyr Ala Pro
            420                 425                 430

Pro Arg Asp Phe Ala Ala Tyr Arg Ser
            435                 440

<210> SEQ ID NO 44
<211> LENGTH: 361
<212> TYPE: PRT
<213> ORGANISM: Artificial Sequence
<220> FEATURE:
<223> OTHER INFORMATION: huSIRP alpha-12aas protein

<400> SEQUENCE: 44

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285

Glu Asn Gly Asn Val Ser Arg Thr Glu Thr Ala Ser Thr Val Thr Glu
290                 295                 300

Asn Lys Asp Gly Thr Tyr Asn Trp Met Ser Trp Leu Leu Val Asn Val
305                 310                 315                 320
```

Ser Ala His Arg Asp Asp Val Lys Leu Thr Cys Gln Val Glu His Asp
        325                 330                 335

Gly Gln Pro Ala Val Ser Lys Ser His Asp Leu Lys Val Ser Ala His
        340                 345                 350

Pro Lys Glu Gln Gly Ser Asn Thr Ala
        355                 360

<210> SEQ ID NO 45
<211> LENGTH: 442
<212> TYPE: PRT
<213> ORGANISM: Artificial Sequence
<220> FEATURE:
<223> OTHER INFORMATION: huSIRP alpha-12aas-CD28Cys tm-41BBic protein

<400> SEQUENCE: 45

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
    50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
    130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
    210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285

Glu Asn Gly Asn Val Ser Arg Thr Glu Thr Ala Ser Thr Val Thr Glu
    290                 295                 300

Asn Lys Asp Gly Thr Tyr Asn Trp Met Ser Trp Leu Leu Val Asn Val
305                 310                 315                 320

```
Ser Ala His Arg Asp Asp Val Lys Leu Thr Cys Gln Val Glu His Asp
            325                 330                 335

Gly Gln Pro Ala Val Ser Lys Ser His Asp Leu Lys Val Ser Ala His
            340                 345                 350

Pro Lys Glu Gln Gly Ser Asn Thr Ala Cys Pro Ser Pro Leu Phe Pro
            355                 360                 365

Gly Pro Ser Lys Pro Phe Trp Val Leu Val Val Val Gly Gly Val Leu
370                 375                 380

Ala Cys Tyr Ser Leu Leu Val Thr Val Ala Phe Ile Ile Phe Trp Val
385                 390                 395                 400

Lys Arg Gly Arg Lys Lys Leu Leu Tyr Ile Phe Lys Gln Pro Phe Met
            405                 410                 415

Arg Pro Val Gln Thr Thr Gln Glu Glu Asp Gly Cys Ser Cys Arg Phe
            420                 425                 430

Pro Glu Glu Glu Glu Gly Gly Cys Glu Leu
            435                 440

<210> SEQ ID NO 46
<211> LENGTH: 483
<212> TYPE: PRT
<213> ORGANISM: Artificial Sequence
<220> FEATURE:
<223> OTHER INFORMATION: huSIRP alpha-12aas-CD28Cys tm ic-41BBic protein

<400> SEQUENCE: 46

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
            35                  40                  45

Glu Thr Ala Thr Leu Arg Cys Thr Ala Thr Ser Leu Ile Pro Val Gly
    50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
            85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
            115                 120                 125

Pro Asp Asp Val Glu Phe Lys Ser Gly Ala Gly Thr Glu Leu Ser Val
        130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
            165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
            195                 200                 205

Ile His Ser Thr Ala Lys Val Val Leu Thr Arg Glu Asp Val His Ser
        210                 215                 220

Gln Val Ile Cys Glu Val Ala His Val Thr Leu Gln Gly Asp Pro Leu
225                 230                 235                 240
```

Arg Gly Thr Ala Asn Leu Ser Glu Thr Ile Arg Val Pro Pro Thr Leu
            245                 250                 255

Glu Val Thr Gln Gln Pro Val Arg Ala Glu Asn Gln Val Asn Val Thr
        260                 265                 270

Cys Gln Val Arg Lys Phe Tyr Pro Gln Arg Leu Gln Leu Thr Trp Leu
    275                 280                 285

Glu Asn Gly Asn Val Ser Arg Thr Glu Thr Ala Ser Thr Val Thr Glu
290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
            340                 345                 350

Pro Lys Glu Gln Gly Ser Asn Thr Ala Cys Pro Ser Pro Leu Phe Pro
        355                 360                 365

Gly Pro Ser Lys Pro Phe Trp Val Leu Val Val Val Gly Gly Val Leu
    370                 375                 380

Ala Cys Tyr Ser Leu Leu Val Thr Val Ala Phe Ile Ile Phe Trp Val
385                 390                 395                 400

Arg Ser Lys Arg Ser Arg Gly Gly His Ser Asp Tyr Met Asn Met Thr
                405                 410                 415

Pro Arg Arg Pro Gly Pro Thr Arg Lys His Tyr Gln Pro Tyr Ala Pro
            420                 425                 430

Pro Arg Asp Phe Ala Ala Tyr Arg Ser Lys Arg Gly Arg Lys Lys Leu
        435                 440                 445

Leu Tyr Ile Phe Lys Gln Pro Phe Met Arg Pro Val Gln Thr Thr Gln
    450                 455                 460

Glu Glu Asp Gly Cys Ser Cys Arg Phe Pro Glu Glu Glu Gly Gly
465                 470                 475                 480

Cys Glu Leu

<210> SEQ ID NO 47
<211> LENGTH: 900
<212> TYPE: DNA
<213> ORGANISM: Artificial Sequence
<220> FEATURE:
<223> OTHER INFORMATION: muCD200Rtm-CD28

<400> SEQUENCE: 47
atgttctgct tctggcggac aagcgccctg gccgtgctgc tgatctgggg agtgtttgtg      60
gccggcagca gctgcaccga caagaaccag accacccaga caacagcag cagcccctg     120 acccaagtga caccaccgt gtccgtgcag atcggcacca aggccctgct gtgctgtttc     180
agcatccctc tgaccaaggc tgtgctgatc acctggatca tcaagctgag aggcctgccc     240
agctgcacaa tcgcctacaa ggtggacacc aagaccaacg agacaagctg cctgggcaga     300
aacatcacct gggccagcac cccagaccac agccctgagc tgcagatcag cgccgtgaca     360
ctgcagcacg agggcaccta cacatgcgag acagtgaccc ccgagggcaa cttcgagaag     420
aactacgatc tgcaggtgct ggtgcccccc gaagtgacct acttcccga aagaatag     480 agcgccgtgt gcgaggccat ggctggcaaa cctgccgccc agatctcttg gagccctgac     540
ggcgactgtg tgaccaccag cgagagccac agcaacggca cagtgaccgt gcggagcacc     600
tgtcactggg agcagaacaa cgtgtccgac gtgtcctgca tcgtgtccca cctgaccggc     660

```
aaccagagcc tgagcatcga gctgagcaga ggcggaaacc agtccctgag gccctacatc    720
ccttacatca tccccagcat catcatcctg atcatcatcg ctgcatctg cctgctgaac    780 agcagaagaa acagaggcgg ccagagcgac tacatgaaca tgaccccag aaggcctggc    840 ctgaccagaa agccctacca gccttacgcc cctgccagag acttcgccgc ctacagacct    900
```

<210> SEQ ID NO 48
<211> LENGTH: 918
<212> TYPE: DNA
<213> ORGANISM: Artificial Sequence
<220> FEATURE:
<223> OTHER INFORMATION: muCD200R-CD28tm

<400> SEQUENCE: 48

```
atgttctgct tctggcggac aagcgccctg gccgtgctgc tgatctgggg agtgtttgtg     60
gccggcagca gctgcaccga caagaaccag accacccaga caacagcag cagccccctg    120 acccaagtga acaccaccgt gtccgtgcag atcggcacca aggccctgct gtgctgtttc    180
agcatccctc tgaccaaggc tgtgctgatc acctggatca tcaagctgag aggcctgccc    240
agctgcacaa tcgcctacaa ggtggacacc aagaccaacg agacaagctg cctgggcaga    300
aacatcacct gggccagcac cccagaccac agccctgagc tgcagatcag cgccgtgaca    360
ctgcagcacg agggcaccta cacatgcgag acagtgaccc ccgagggcaa cttcgagaag    420
aactacgatc tgcaggtgct ggtgcccccc gaagtgacct acttccccga agaatagga    480 agcgccgtgt gcgaggccat ggctggcaaa cctgccgccc agatctcttg gagccctgac    540
ggcgactgtg tgaccaccag cgagagccac agcaacggca cagtgaccgt gcggagcacc    600
tgtcactggg agcagaacaa cgtgtccgac gtgtcctgca tcgtgtccca cctgaccggc    660
aaccagagcc tgagcatcga gctgagcaga ggcggaaacc agtccctgag gcccttctgg    720
gccctggtgg tggtggccgg cgtgctgttt tgttacggcc tgctcgtgac cgtggccctg    780
tgcgtgatct ggaccaacag cagaagaaac agaggcggcc agagcgacta catgaacatg    840
acccccagaa ggcctggcct gaccagaaag ccctaccagc cttacgcccc tgccagagac    900
ttcgccgcct acagacct                                                  918
```

<210> SEQ ID NO 49
<211> LENGTH: 945
<212> TYPE: DNA
<213> ORGANISM: Artificial Sequence
<220> FEATURE:
<223> OTHER INFORMATION: muCD200R-CD28Cys

<400> SEQUENCE: 49

```
atgttctgct tctggcggac aagcgccctg gccgtgctgc tgatctgggg agtgtttgtg     60
gccggcagca gctgcaccga caagaaccag accacccaga caacagcag cagccccctg    120 acccaagtga acaccaccgt gtccgtgcag atcggcacca aggccctgct gtgctgtttc    180
agcatccctc tgaccaaggc tgtgctgatc acctggatca tcaagctgag aggcctgccc    240
agctgcacaa tcgcctacaa ggtggacacc aagaccaacg agacaagctg cctgggcaga    300
aacatcacct gggccagcac cccagaccac agccctgagc tgcagatcag cgccgtgaca    360
ctgcagcacg agggcaccta cacatgcgag acagtgaccc ccgagggcaa cttcgagaag    420
aactacgatc tgcaggtgct ggtgcccccc gaagtgacct acttccccga agaatagga    480 agcgccgtgt gcgaggccat ggctggcaaa cctgccgccc agatctcttg gagccctgac    540
```

```
ggcgactgtg tgaccaccag cgagagccac agcaacggca cagtgaccgt gcggagcacc      600
tgtcactggg agcagaacaa cgtgtccgac gtgtcctgca tcgtgtccca cctgaccggc      660
aaccagagcc tgagcatcga gctgagcaga ggcggaaacc agtccctgag gccctgccac      720
acccagagca gccccaagct gttctgggcc ctggtggtgg tggccggcgt gctgttttgt      780
tacggcctgc tcgtgaccgt ggccctgtgc gtgatctgga ccaacagcag aagaaacaga      840
ggcggccaga gcgactacat gaacatgacc cccagaaggc ctggcctgac cagaaagccc      900
taccagcctt acgccctgc cagagacttc gccgcctaca gacct                       945
```

<210> SEQ ID NO 50
<211> LENGTH: 936
<212> TYPE: DNA
<213> ORGANISM: Artificial Sequence
<220> FEATURE:
<223> OTHER INFORMATION: muCD200R-3aas-CD28Cys

<400> SEQUENCE: 50

```
atgttctgct tctggcggac aagcgccctg gccgtgctgc tgatctgggg agtgtttgtg       60
gccggcagca gctgcaccga caagaaccag accacccaga caacagcag cagccccctg      120 acccaagtga acaccaccgt gtccgtgcag atcggcacca aggccctgct gtgctgtttc      180
agcatccctc tgaccaaggc tgtgctgatc acctggatca tcaagctgag aggcctgccc      240
agctgcacaa tcgcctacaa ggtggacacc aagaccaacg agacaagctg cctgggcaga      300
aacatcacct gggccagcac cccagaccac agccctgagc tgcagatcag cgccgtgaca      360
ctgcagcacg agggcaccta cacatgcgag acagtgaccc ccgagggcaa cttcgagaag      420
aactacgatc tgcaggtgct ggtgcccccc gaagtgacct acttccccga agaatgaga      480 agcgccgtgt gcgaggccat ggctggcaaa cctgccgccc agatctcttg agccctgac      540 ggcgactgtg tgaccaccag cgagagccac agcaacggca cagtgaccgt gcggagcacc      600
tgtcactggg agcagaacaa cgtgtccgac gtgtcctgca tcgtgtccca cctgaccggc      660
aaccagagcc tgagcatcga gctgagcaga ggcggaaacc agtcctgcca cacccagagc      720
agccccaagc tgttctgggc cctggtggtg gtggccggcg tgctgttttg ttacggcctg      780
ctcgtgaccg tggccctgtg cgtgatctgg accaacagca agaaaacag aggcggccag      840 agcgactaca tgaacatgac ccccagaagg cctggcctga ccagaaagcc ctaccagcct      900
tacgcccctg ccagagactt cgccgcctac agacct                                 936
```

<210> SEQ ID NO 51
<211> LENGTH: 918
<212> TYPE: DNA
<213> ORGANISM: Artificial Sequence
<220> FEATURE:
<223> OTHER INFORMATION: muCD200R-9aas-CD28Cys

<400> SEQUENCE: 51

```
atgttctgct tctggcggac aagcgccctg gccgtgctgc tgatctgggg agtgtttgtg       60
gccggcagca gctgcaccga caagaaccag accacccaga caacagcag cagccccctg      120 acccaagtga acaccaccgt gtccgtgcag atcggcacca aggccctgct gtgctgtttc      180
agcatccctc tgaccaaggc tgtgctgatc acctggatca tcaagctgag aggcctgccc      240
agctgcacaa tcgcctacaa ggtggacacc aagaccaacg agacaagctg cctgggcaga      300
aacatcacct gggccagcac cccagaccac agccctgagc tgcagatcag cgccgtgaca      360
ctgcagcacg agggcaccta cacatgcgag acagtgaccc ccgagggcaa cttcgagaag      420
```

```
aactacgatc tgcaggtgct ggtgccccc gaagtgacct acttccccga gaagaataga      480
agcgccgtgt gcgaggccat ggctggcaaa cctgccgccc agatctcttg gagccctgac      540
ggcgactgtg tgaccaccag cgagagccac agcaacggca cagtgaccgt gcggagcacc      600
tgtcactggg agcagaacaa cgtgtccgac gtgtcctgca tcgtgtccca cctgaccggc      660
aaccagagcc tgagcatcga gctgagctgc cacacccaga gcagcccaa gctgttctgg       720 gccctggtgg tggtggccgg cgtgctgttt tgttacggcc tgctcgtgac cgtggccctg      780
tgcgtgatct ggaccaacag cagaagaaac agaggcggcc agagcgacta catgaacatg      840 accccagaa ggcctggcct gaccagaaag ccctaccagc cttacgcccc tgccagagac       900
ttcgccgcct acagacct                                                    918

<210> SEQ ID NO 52
<211> LENGTH: 939
<212> TYPE: DNA
<213> ORGANISM: Artificial Sequence
<220> FEATURE:
<223> OTHER INFORMATION: muCD200R-9aas-CD28Cys tm-41BBic

<400> SEQUENCE: 52
atgttctgct ctggcggac aagcgccctg gccgtgctgc tgatctgggg agtgtttgtg        60
gccggcagca gctgcaccga caagaaccag accacccaga caacagcag cagcccctg       120 acccaagtga acaccaccgt gtccgtgcag atcggcacca aggccctgct gtgctgtttc      180
agcatccctc tgaccaaggc tgtgctgatc acctggatca tcaagctgag aggcctgccc      240
agctgcacaa tcgcctacaa ggtggacacc aagaccaacg agacaagctg cctgggcaga      300 aacatcaccct gggccagcac cccagaccac agccctgagc tgcagatcag cgccgtgaca      360
ctgcagcacg agggcaccta cacatgcgag acagtgaccc ccgagggcaa cttcgagaag      420
aactacgatc tgcaggtgct ggtgccccc gaagtgacct acttccccga gaagaataga      480
agcgccgtgt gcgaggccat ggctggcaaa cctgccgccc agatctcttg gagccctgac      540
ggcgactgtg tgaccaccag cgagagccac agcaacggca cagtgaccgt gcggagcacc      600
tgtcactggg agcagaacaa cgtgtccgac gtgtcctgca tcgtgtccca cctgaccggc      660
aaccagagcc tgagcatcga gctgagctgc cacacccaga gcagcccaa gctgttctgg       720 gccctggtgg tggtggccgg cgtgctgttt tgttacggcc tgctcgtgac cgtggccctg      780
tgcgtgatct ggaccagcgt gctgaagtgg atcagaaaga gttccccca catcttcaag      840 cagcccttca gaaaaccac cggcgctgcc caggaagagg acgcctgcag ctgtagatgc       900
cctcaggaag aagaaggcgg cggaggcggc tacgagctg                             939

<210> SEQ ID NO 53
<211> LENGTH: 1062
<212> TYPE: DNA
<213> ORGANISM: Artificial Sequence
<220> FEATURE:
<223> OTHER INFORMATION: muCD200R-9aas-CD28Cys tm ic-41BBic

<400> SEQUENCE: 53
atgttctgct ctggcggac aagcgccctg gccgtgctgc tgatctgggg agtgtttgtg        60
gccggcagca gctgcaccga caagaaccag accacccaga caacagcag cagcccctg       120 acccaagtga acaccaccgt gtccgtgcag atcggcacca aggccctgct gtgctgtttc      180
agcatccctc tgaccaaggc tgtgctgatc acctggatca tcaagctgag aggcctgccc      240
```

| | |
|---|---:|
| agctgcacaa tcgcctacaa ggtggacacc aagaccaacg agacaagctg cctgggcaga | 300 |
| aacatcacct gggccagcac cccagaccac agccctgagc tgcagatcag cgccgtgaca | 360 |
| ctgcagcacg agggcaccta cacatgcgag acagtgaccc ccgagggcaa cttcgagaag | 420 |
| aactacgatc tgcaggtgct ggtgcccccc gaagtgacct acttccccga gaagaataga | 480 |
| agcgccgtgt gcgaggccat ggctggcaaa cctgccgccc agatctcttg gagccctgac | 540 |
| ggcgactgtg tgaccaccag cgagagccac agcaacggca cagtgaccgt gcggagcacc | 600 |
| tgtcactggg agcagaacaa cgtgtccgac gtgtcctgca tcgtgtccca cctgaccggc | 660 |
| aaccagagcc tgagcatcga gctgagctgc acacccaga gcagcccaa gctgttctgg | 720 |
| gccctggtgg tggtggccgg cgtgctgttt tgttacggcc tgctcgtgac cgtggccctg | 780 |
| tgcgtgatct ggaccaacag cagaagaaac agaggcggcc agagcgacta catgaacatg | 840 |
| accccccagaa ggcctggcct gaccagaaag ccctaccagc cttacgcccc tgccagagac | 900 |
| ttcgccgcct acagacctag cgtgctgaag tggatcagaa agaagttccc ccacatcttc | 960 |
| aagcagccct tcaagaaaac caccggcgct gcccaggaag gacgcctg cagctgtaga | 1020 |
| tgccctcagg aagaagaagg cggcggaggc ggctacgagc tg | 1062 |

<210> SEQ ID NO 54
<211> LENGTH: 1305
<212> TYPE: DNA
<213> ORGANISM: Artificial Sequence
<220> FEATURE:
<223> OTHER INFORMATION: muSIRP alpha tm-CD28

<400> SEQUENCE: 54

| | |
|---|---:|
| atggaacctg ctggacctgc ccctggcaga ctgggacctc tgctgctgtg cctgctgctg | 60 |
| agcgccagct gtttctgtac cggcgccacc ggcaaagaac tgaaagtgac ccagcccgag | 120 |
| aagtccgtgt ctgtggccgc tggcgacagc accgtgctga actgtaccct gaccagcctg | 180 |
| ctgcccgtgg gccccatcag atggtataga ggcgtgggcc ctagcagact gctgatctac | 240 |
| agcttcgctg gcgagtacgt gcccagaatc agaaacgtgt ccgacaccac caagcggaac | 300 |
| aacatggact tcagcatcag gatcagcaac gtgacccctg ccgacgccgg catctactac | 360 |
| tgcgtgaagt tccagaaggg cagcagcgag cccgacaccg agattcagtc tggcggcgga | 420 |
| accgaggtgt acgtgctggc taagcccagc cctcctgagg tgtccggccc tgctgataga | 480 |
| ggcatccccg accagaaagt gaacttcaca tgcaagagcc acggcttcag ccccagaaac | 540 |
| atcaccctga gtggttcaa ggacggccag gaactgcacc ccctggaaac caccgtgaac | 600 |
| cccagcggca agaacgtgtc ctacaacatc agctccaccg tgcgggtggt gctgaacagc | 660 |
| atggacgtga cagcaaagt gatctgcgag gtggcccaca tcacactgga cagaagcccc | 720 |
| ctgagaggaa tcgccaacct gagcaacttc atcagagtgt ccccaaccgt gaaagtgaca | 780 |
| cagcagagcc ccaccagcat gaaccaagtg aacctgacct gcagagccga gagattctac | 840 |
| cccgaggacc tgcagctgat ctggctggaa acggcaacg tgtccagaaa cgacaccccc | 900 |
| aagaacctga caaagaacac cgacggcacc tacaactaca cctccctgtt tctcgtgaac | 960 |
| tcctccgccc accgcgagga cgtggtgttc acgtgccaag tgaagcacga ccagcagccc | 1020 |
| gccatcacca gaaaccacac agtgctgggc ttcgcccaca gcagcgacca gggcagcatg | 1080 |
| cagaccttcc ccgacaacaa cgccaccccac aactggaacg tgttcatcgg cgtgggcgtg | 1140 |
| gcctgtgctc tgctggtggt gctgctgatg gccgccctgt ataacagcag aagaaacaga | 1200 |
| ggcggccaga gcgactacat gaacatgacc cccagaaggc ctggcctgac cagaaagccc | 1260 |

<210> SEQ ID NO 55
<211> LENGTH: 1323
<212> TYPE: DNA
<213> ORGANISM: Artificial Sequence
<220> FEATURE:
<223> OTHER INFORMATION: muSIRP alpha-CD28tm

<400> SEQUENCE: 55

```
atggaacctg ctggacctgc ccctggcaga ctgggacctc tgctgctgtg cctgctgctg      60
agcgccagct gtttctgtac cggcgccacc ggcaaagaac tgaaagtgac ccagcccgag     120
aagtccgtgt ctgtggccgc tggcgacagc accgtgctga actgtaccct gaccagcctg     180
ctgcccgtgg gccccatcag atggtataga ggcgtgggcc ctagcagact gctgatctac     240
agcttcgctg gcgagtacgt gcccagaatc agaaacgtgt ccgacaccac caagcggaac     300
aacatggact tcagcatcag gatcagcaac gtgacccctg ccgacgccgg catctactac     360
tgcgtgaagt tccagaaggg cagcagcgag cccgacaccg agattcagtc tggcggcgga     420
accgaggtgt acgtgctggc taagcccagc cctcctgagg tgtccggccc tgctgataga     480
ggcatccccg accagaaagt gaacttcaca tgcaagagcc acggcttcag ccccagaaac     540
atcaccctga gtggttcaa ggacggccag gaactgcacc ccctggaaac caccgtgaac     600
cccagcggca agaacgtgtc ctacaacatc agctccaccg tgcgggtggt gctgaacagc     660
atggacgtga acagcaaagt gatctgcgag gtggcccaca tcacactgga cagaagcccc     720
ctgagaggaa tcgccaacct gagcaacttc atcagagtgt ccccaaccgt gaaagtgaca     780
cagcagagcc ccaccagcat gaaccaagtg aacctgacct gcagagccga gagattctac     840
cccgaggacc tgcagctgat ctggctggaa aacggcaacg tgtccagaaa cgacaccccc     900
aagaacctga caaagaacac cgacggcacc tacaactaca cctcccctgtt tctcgtgaac     960 tcctccgccc accgcgagga cgtggtgttc acgtgccaag tgaagcacga ccagcagccc    1020
gccatcacca gaaaccacac agtgctgggc ttcgcccaca gcagcgacca gggcagcatg    1080
cagaccttcc ccgacaacaa cgccacccac aactggaact tctgggccct ggtggtggtg    1140
gccggcgtgc tgttttgtta cggcctgctc gtgaccgtgg ccctgtgcgt gatctggacc    1200
aacagcagaa gaaacagagg cggccagagc gactacatga acatgacccc cagaaggcct    1260
ggcctgacca gaaagcccta ccagccttac gcccctgcca gagacttcgc cgcctacaga    1320
cct                                                                  1323
```

<210> SEQ ID NO 56
<211> LENGTH: 1350
<212> TYPE: DNA
<213> ORGANISM: Artificial Sequence
<220> FEATURE:
<223> OTHER INFORMATION: muSIRP alpha-CD28cys

<400> SEQUENCE: 56

```
atggaacctg ctggacctgc ccctggcaga ctgggacctc tgctgctgtg cctgctgctg      60
agcgccagct gtttctgtac cggcgccacc ggcaaagaac tgaaagtgac ccagcccgag     120
aagtccgtgt ctgtggccgc tggcgacagc accgtgctga actgtaccct gaccagcctg     180
ctgcccgtgg gccccatcag atggtataga ggcgtgggcc ctagcagact gctgatctac     240
agcttcgctg gcgagtacgt gcccagaatc agaaacgtgt ccgacaccac caagcggaac     300
```

| | |
|---|---|
| aacatggact tcagcatcag gatcagcaac gtgacccctg ccgacgccgg catctactac | 360 |
| tgcgtgaagt tccagaaggg cagcagcgag cccgacaccg agattcagtc tggcggcgga | 420 |
| accgaggtgt acgtgctggc taagcccagc cctcctgagg tgtccggccc tgctgataga | 480 |
| ggcatccccg accagaaagt gaacttcaca tgcaagagcc acggcttcag ccccagaaac | 540 |
| atcaccctga gtggttcaa ggacggccag gaactgcacc ccctggaaac caccgtgaac | 600 |
| cccagcggca agaacgtgtc ctacaacatc agctccaccg tgcgggtggt gctgaacagc | 660 |
| atggacgtga acagcaaagt gatctgcgag gtggcccaca tcacactgga cagaagcccc | 720 |
| ctgagaggaa tcgccaacct gagcaacttc atcagagtgt ccccaaccgt gaaagtgaca | 780 |
| cagcagagcc ccaccagcat gaaccaagtg aacctgacct gcagagccga gagattctac | 840 |
| cccgaggacc tgcagctgat ctggctggaa acggcaacg tgtccagaaa cgacaccccc | 900 |
| aagaacctga caaagaacac cgacggcacc tacaactaca cctcccctgtt tctcgtgaac | 960 |
| tcctccgccc accgcgagga cgtggtgttc acgtgccaag tgaagcacga ccagcagccc | 1020 |
| gccatcacca gaaaccacac agtgctgggc ttcgcccaca gcagcgacca gggcagcatg | 1080 |
| cagaccttcc ccgacaacaa cgccacccac aactggaact gccacaccca gagcagcccc | 1140 |
| aagctgttct gggctctggt ggtggtggcc ggcgtgctgt tttgttacgg cctgctcgtg | 1200 |
| accgtggccc tgtgcgtgat ctggaccaac agcagaagaa acagaggcgg ccagagcgac | 1260 |
| tacatgaaca tgaccccag aaggcctggc ctgaccccgga agccttacca gccttacgcc | 1320 |
| cctgccagag acttcgccgc ctacagacct | 1350 |

<210> SEQ ID NO 57
<211> LENGTH: 1332
<212> TYPE: DNA
<213> ORGANISM: Artificial Sequence
<220> FEATURE:
<223> OTHER INFORMATION: muSIRP alpha -6aas-CD28cys

<400> SEQUENCE: 57

| | |
|---|---|
| atggaacctg ctggacctgc ccctggcaga ctgggacctc tgctgctgtg cctgctgctg | 60 |
| agcgccagct gtttctgtac cggcgccacc ggcaaagaac tgaaagtgac ccagcccgag | 120 |
| aagtccgtgt ctgtggccgc tggcgacagc accgtgctga actgtacct gaccagcctg | 180 |
| ctgcccgtgg cccccatcag atggtataga ggcgtgggcc ctagcagact gctgatctac | 240 |
| agcttcgctg gcgagtacgt gcccagaatc agaaacgtgt ccgacaccac caagcggaac | 300 |
| aacatggact tcagcatcag gatcagcaac gtgacccctg ccgacgccgg catctactac | 360 |
| tgcgtgaagt tccagaaggg cagcagcgag cccgacaccg agattcagtc tggcggcgga | 420 |
| accgaggtgt acgtgctggc taagcccagc cctcctgagg tgtccggccc tgctgataga | 480 |
| ggcatccccg accagaaagt gaacttcaca tgcaagagcc acggcttcag ccccagaaac | 540 |
| atcaccctga gtggttcaa ggacggccag gaactgcacc ccctggaaac caccgtgaac | 600 |
| cccagcggca agaacgtgtc ctacaacatc agctccaccg tgcgggtggt gctgaacagc | 660 |
| atggacgtga acagcaaagt gatctgcgag gtggcccaca tcacactgga cagaagcccc | 720 |
| ctgagaggaa tcgccaacct gagcaacttc atcagagtgt ccccaaccgt gaaagtgaca | 780 |
| cagcagagcc ccaccagcat gaaccaagtg aacctgacct gcagagccga gagattctac | 840 |
| cccgaggacc tgcagctgat ctggctggaa acggcaacg tgtccagaaa cgacaccccc | 900 |
| aagaacctga caaagaacac cgacggcacc tacaactaca cctcccctgtt tctcgtgaac | 960 |
| tcctccgccc accgcgagga cgtggtgttc acgtgccaag tgaagcacga ccagcagccc | 1020 |

```
gccatcacca gaaaccacac agtgctgggc ttcgcccaca gcagcgacca gggcagcatg    1080
cagaccttcc ccgacaacaa ctgccacacc cagagcagcc ccaagctgtt ctgggctctg    1140
gtggtggtgg ccggcgtgct gttttgttac ggcctgctcg tgaccgtggc cctgtgcgtg    1200
atctggacca acagcagaag aaacagaggc ggccagagcg actacatgaa catgaccccc    1260
agaaggcctg gcctgacccg gaagccttac cagccttacg cccctgccag agacttcgcc    1320
gcctacagac ct                                                         1332

<210> SEQ ID NO 58
<211> LENGTH: 1323
<212> TYPE: DNA
<213> ORGANISM: Artificial Sequence
<220> FEATURE:
<223> OTHER INFORMATION: muSIRP alpha -9aas-CD28cys

<400> SEQUENCE: 58
atggaacctg ctggacctgc ccctggcaga ctgggacctc tgctgctgtg cctgctgctg      60
agcgccagct gtttctgtac cggcgccacc ggcaaagaac tgaaagtgac ccagcccgag     120
aagtccgtgt ctgtggccgc tggcgacagc accgtgctga actgtacccc tgaccagcctg    180 ctgcccgtgg gccccatcag atggtataga ggcgtgggcc tagcagact gctgatctac      240 agcttcgctg gcgagtacgt gcccagaatc agaaacgtgt ccgacaccac caagcggaac     300
aacatggact tcagcatcag gatcagcaac gtgacccctg ccgacgccgg catctactac     360
tgcgtgaagt tccagaaggg cagcagcgag cccgacaccg agattcagtc tggcggcgga    420
accgaggtgt acgtgctggc taagcccagc cctcctgagg tgtccggccc tgctgataga    480
ggcatccccg accagaaagt gaacttcaca tgcaagagcc acggcttcag ccccagaaac    540
atcaccctga agtggttcaa ggacggccag gaactgcacc cctggaaaac caccgtgaac    600
cccagcggca agaacgtgtc ctacaacatc agctccaccg tgcgggtggt gctgaacagc    660
atggacgtga acagcaaagt gatctgcgag gtggcccaca tcacactgga cagaagcccc    720
ctgagaggaa tcgccaacct gagcaacttc atcagagtgt ccccaaccgt gaaagtgaca    780
cagcagagcc ccaccagcat gaaccaagtg aacctgacct gcagagccga gagattctac    840
cccgaggacc tgcagctgat ctggctggaa aacggcaacg tgtccagaaa cgacaccccc    900
aagaacctga caaagaacac cgacggcacc tacaactaca ctccctgtt tctcgtgaac    960 tcctccgccc accgcgagga cgtggtgttc acgtgccaag tgaagcacga ccagcagccc   1020
gccatcacca gaaaccacac agtgctgggc ttcgcccaca gcagcgacca gggcagcatg   1080
cagaccttcc cctgccacac ccagagcagc cccaagctgt ctgggctct ggtggtggtg     1140 gccggcgtgc tgttttgtta cggcctgctc gtgaccgtgg ccctgtgcgt gatctggacc    1200
aacagcagaa gaaacagagg cggccagagc gactacatga acatgacccc cagaaggcct    1260
ggcctgaccc ggaagcctta ccagccttac gcccctgcca gagacttcgc cgcctacaga   1320
cct                                                                   1323

<210> SEQ ID NO 59
<211> LENGTH: 1281
<212> TYPE: DNA
<213> ORGANISM: Artificial Sequence
<220> FEATURE:
<223> OTHER INFORMATION: muSIRP alpha-23aas-CD28cys

<400> SEQUENCE: 59
```

```
atggaacctg ctggacctgc ccctggcaga ctgggacctc tgctgctgtg cctgctgctg      60
agcgccagct gtttctgtac cggcgccacc ggcaaagaac tgaaagtgac ccagcccgag     120
aagtccgtgt ctgtggccgc tggcgacagc accgtgctga actgtaccct gaccagcctg     180
ctgcccgtgg cccccatcag atggtataga ggcgtgggcc ctagcagact gctgatctac     240
agcttcgctg gcgagtacgt gcccagaatc agaaacgtgt ccgacaccac caagcggaac     300
aacatggact tcagcatcag gatcagcaac gtgaccccctg ccgacgccgg catctactac     360
tgcgtgaagt tccagaaggg cagcagcgag cccgacaccg agattcagtc tggcggcgga     420
accgaggtgt acgtgctggc taagcccagc cctcctgagg tgtccggccc tgctgataga     480
ggcatccccg accagaaagt gaacttcaca tgcaagagcc acggcttcag ccccagaaac     540
atcaccctga gtggttcaa ggacggccag gaactgcacc ccctggaaac caccgtgaac     600
cccagcggca agaacgtgtc ctacaacatc agctccaccg tgcgggtggt gctgaacagc     660
atggacgtga cagcaaagt gatctgcgag gtggcccaca tcacactgga cagaagcccc     720
ctgagaggaa tcgccaacct gagcaacttc atcagagtgt ccccaaccgt gaaagtgaca     780
cagcagagcc ccaccagcat gaaccaagtg aacctgacct gcagagccga gagattctac     840
cccgaggacc tgcagctgat ctggctggaa acggcaacg tgtccagaaa cgacaccccc     900
aagaacctga caaagaacac cgacggcacc tacaactaca cctccctgtt tctcgtgaac     960
tcctccgccc accgcgagga cgtggtgttc acgtgccaag tgaagcacga ccagcagccc    1020
gccatcacca gaaaccacac agtgctgggc tgccacaccc agagcagccc caagctgttc    1080
tgggctctgg tggtggtggc cggcgtgctg ttttgttacg gctgctcgt gaccgtggcc    1140
ctgtgcgtga tctggaccaa cagcagaaga acagaggcg ccagagcga ctacatgaac    1200
atgaccccca aaggcctgg cctgacccgg aagccttacc agccttacgc ccctgccaga    1260
gacttcgccg cctacagacc t                                             1281
```

<210> SEQ ID NO 60
<211> LENGTH: 137
<212> TYPE: PRT
<213> ORGANISM: Artificial Sequence
<220> FEATURE:
<223> OTHER INFORMATION: huPD-1 ectodomain

<400> SEQUENCE: 60

```
Pro Pro Thr Phe Ser Pro Ala Leu Leu Val Val Thr Glu Gly Asp Asn
1               5                   10                  15
Ala Thr Phe Thr Cys Ser Phe Ser Asn Thr Ser Glu Ser Phe Val Leu
            20                  25                  30
Asn Trp Tyr Arg Met Ser Pro Ser Asn Gln Thr Asp Lys Leu Ala Ala
        35                  40                  45
Phe Pro Glu Asp Arg Ser Gln Pro Gly Gln Asp Cys Arg Phe Arg Val
    50                  55                  60
Thr Gln Leu Pro Asn Gly Arg Asp Phe His Met Ser Val Val Arg Ala
65                  70                  75                  80
Arg Arg Asn Asp Ser Gly Thr Tyr Leu Cys Gly Ala Ile Ser Leu Ala
                85                  90                  95
Pro Lys Ala Gln Ile Lys Glu Ser Leu Arg Ala Glu Leu Arg Val Thr
            100                 105                 110
Glu Arg Arg Ala Glu Val Pro Thr Ala His Pro Ser Pro Ser Pro Arg
        115                 120                 125
Ser Ala Gly Gln Phe Gln Thr Leu Val
```

<210> SEQ ID NO 61
<211> LENGTH: 627
<212> TYPE: DNA
<213> ORGANISM: Artificial Sequence
<220> FEATURE:
<223> OTHER INFORMATION: huCD2 entire extracellular domain

<400> SEQUENCE: 61

```
atgagctttc catgtaaatt tgtagccagc ttccttctga ttttcaatgt ttcttccaaa      60
ggtgcagtct ccaaagagat tacgaatgcc ttggaaacct ggggtgcctt gggtcaggac     120
atcaacttgg acattcctag ttttcaaatg agtgatgata ttgacgatat aaaatgggaa     180
aaaacttcag acaagaaaaa gattgcacaa ttcagaaaag agaaagagac tttcaaggaa     240
aaagatacat ataagctatt taaaaatgga actctgaaaa ttaagcatct gaagaccgat     300
gatcaggata tctacaaggt atcaatatat gatacaaaag gaaaaaatgt gttggaaaaa     360
atatttgatt tgaagattca agagagggtc tcaaaaccaa agatctcctg gacttgtatc     420
aacacaaccc tgacctgtga ggtaatgaat ggaactgacc ccgaattaaa cctgtatcaa     480
gatgggaaac atctaaaact ttctcagagg gtcatcacac acaagtggac caccagcctg     540
agtgcaaaat tcaagtgcac agcagggaac aaagtcagca aggaatccag tgtcgagcct     600
gtcagctgtc agagaaagg tctggac                                          627
```

<210> SEQ ID NO 62
<211> LENGTH: 209
<212> TYPE: PRT
<213> ORGANISM: Artificial Sequence
<220> FEATURE:
<223> OTHER INFORMATION: huCD2 entire extracellular domain

<400> SEQUENCE: 62

```
Met Ser Phe Pro Cys Lys Phe Val Ala Ser Phe Leu Leu Ile Phe Asn
1               5                   10                  15

Val Ser Ser Lys Gly Ala Val Ser Lys Glu Ile Thr Asn Ala Leu Glu
            20                  25                  30

Thr Trp Gly Ala Leu Gly Gln Asp Ile Asn Leu Asp Ile Pro Ser Phe
        35                  40                  45

Gln Met Ser Asp Asp Ile Asp Asp Ile Lys Trp Glu Lys Thr Ser Asp
    50                  55                  60

Lys Lys Lys Ile Ala Gln Phe Arg Lys Glu Lys Glu Thr Phe Lys Glu
65                  70                  75                  80

Lys Asp Thr Tyr Lys Leu Phe Lys Asn Gly Thr Leu Lys Ile Lys His
                85                  90                  95

Leu Lys Thr Asp Asp Gln Asp Ile Tyr Lys Val Ser Ile Tyr Asp Thr
            100                 105                 110

Lys Gly Lys Asn Val Leu Glu Lys Ile Phe Asp Leu Lys Ile Gln Glu
        115                 120                 125

Arg Val Ser Lys Pro Lys Ile Ser Trp Thr Cys Ile Asn Thr Thr Leu
    130                 135                 140

Thr Cys Glu Val Met Asn Gly Thr Asp Pro Glu Leu Asn Leu Tyr Gln
145                 150                 155                 160

Asp Gly Lys His Leu Lys Leu Ser Gln Arg Val Ile Thr His Lys Trp
                165                 170                 175

Thr Thr Ser Leu Ser Ala Lys Phe Lys Cys Thr Ala Gly Asn Lys Val
            180                 185                 190
```

Ser Lys Glu Ser Ser Val Glu Pro Val Ser Cys Pro Glu Lys Gly Leu
        195                 200                 205

Asp

<210> SEQ ID NO 63
<211> LENGTH: 78
<212> TYPE: DNA
<213> ORGANISM: Artificial Sequence
<220> FEATURE:
<223> OTHER INFORMATION: huCD2 transmembrane domain

<400> SEQUENCE: 63
atctatctca tcattggcat atgtggagga ggcagcctct tgatggtctt tgtggcactg    60
ctcgttttct atatcacc                                                  78

<210> SEQ ID NO 64
<211> LENGTH: 26
<212> TYPE: PRT
<213> ORGANISM: Artificial Sequence
<220> FEATURE:
<223> OTHER INFORMATION: huCD2 transmembrane domain

<400> SEQUENCE: 64

Ile Tyr Leu Ile Ile Gly Ile Cys Gly Gly Gly Ser Leu Leu Met Val
1               5                   10                  15

Phe Val Ala Leu Leu Val Phe Tyr Ile Thr
            20                  25

<210> SEQ ID NO 65
<211> LENGTH: 828
<212> TYPE: DNA
<213> ORGANISM: Artificial Sequence
<220> FEATURE:
<223> OTHER INFORMATION: huCD2tm-CD28 DNA

<400> SEQUENCE: 65
atgagctttc catgtaaatt tgtagccagc ttccttctga ttttcaatgt tcttccaaa     60 ggtgcagtct ccaaagagat tacgaatgcc ttggaaacct ggggtgcctt gggtcaggac   120
atcaacttgg acattcctag ttttcaaatg agtgatgata ttgacgatat aaaatgggaa   180
aaaacttcag acaagaaaaa gattgcacaa ttcagaaaag agaaagagac tttcaaggaa   240
aaagatacat ataagctatt taaaaatgga actctgaaaa ttaagcatct gaagaccgat   300
gatcaggata tctacaaggt atcaatatat gatacaaaag gaaaaaatgt gttggaaaaa   360
atatttgatt tgaagattca agagagggtc tcaaaaccaa agatctcctg gacttgtatc   420
aacacaaccc tgacctgtga ggtaatgaat ggaactgacc ccgaattaaa cctgtatcaa   480
gatgggaaac atctaaaact ttctcagagg gtcatcacac acaagtggac caccagcctg   540
agtgcaaaat tcaagtgcac agcagggaac aaagtcagca aggaatccag tgtcgagcct   600
gtcagctgtc cagagaaagg tctggacatc tatctcatca ttggcatatg tggaggaggc   660
agcctcttga tggtctttgt ggcactgctc gttttctata tcacccgcag caagcggagc   720
agaggcggcc acagcgacta catgaacatg ccctagc ggcctggccc caccagaaag    780
cactaccagc cctacgcccc tcccgggac tttgccgcct acagaagc                828

<210> SEQ ID NO 66
<211> LENGTH: 276
<212> TYPE: PRT
<213> ORGANISM: Artificial Sequence
<220> FEATURE:
<223> OTHER INFORMATION: huCD2tm-CD28

<400> SEQUENCE: 66

Met Ser Phe Pro Cys Lys Phe Val Ala Ser Phe Leu Leu Ile Phe Asn
1               5                   10                  15

Val Ser Ser Lys Gly Ala Val Ser Lys Glu Ile Thr Asn Ala Leu Glu
            20                  25                  30

Thr Trp Gly Ala Leu Gly Gln Asp Ile Asn Leu Asp Ile Pro Ser Phe
        35                  40                  45

Gln Met Ser Asp Asp Ile Asp Asp Ile Lys Trp Glu Lys Thr Ser Asp
    50                  55                  60

Lys Lys Lys Ile Ala Gln Phe Arg Lys Glu Lys Glu Thr Phe Lys Glu
65                  70                  75                  80

Lys Asp Thr Tyr Lys Leu Phe Lys Asn Gly Thr Leu Lys Ile Lys His
                85                  90                  95

Leu Lys Thr Asp Asp Gln Asp Ile Tyr Lys Val Ser Ile Tyr Asp Thr
            100                 105                 110

Lys Gly Lys Asn Val Leu Glu Lys Ile Phe Asp Leu Lys Ile Gln Glu
        115                 120                 125

Arg Val Ser Lys Pro Lys Ile Ser Trp Thr Cys Ile Asn Thr Thr Leu
    130                 135                 140

Thr Cys Glu Val Met Asn Gly Thr Asp Pro Glu Leu Asn Leu Tyr Gln
145                 150                 155                 160

Asp Gly Lys His Leu Lys Leu Ser Gln Arg Val Ile Thr His Lys Trp
                165                 170                 175

Thr Thr Ser Leu Ser Ala Lys Phe Lys Cys Thr Ala Gly Asn Lys Val
            180                 185                 190

Ser Lys Glu Ser Ser Val Glu Pro Val Ser Cys Pro Glu Lys Gly Leu
        195                 200                 205

Asp Ile Tyr Leu Ile Ile Gly Ile Cys Gly Gly Gly Ser Leu Leu Met
    210                 215                 220

Val Phe Val Ala Leu Leu Val Phe Tyr Ile Thr Arg Ser Lys Arg Ser
225                 230                 235                 240

Arg Gly Gly His Ser Asp Tyr Met Asn Met Thr Pro Arg Arg Pro Gly
                245                 250                 255

Pro Thr Arg Lys His Tyr Gln Pro Tyr Ala Pro Pro Arg Asp Phe Ala
            260                 265                 270

Ala Tyr Arg Ser
        275

<210> SEQ ID NO 67
<211> LENGTH: 831
<212> TYPE: DNA
<213> ORGANISM: Artificial Sequence
<220> FEATURE:
<223> OTHER INFORMATION: huCD2-CD28tm

<400> SEQUENCE: 67
atgagctttc catgtaaatt tgtagccagc ttccttctga ttttcaatgt tcttccaaa      60 ggtgcagtct ccaaagagat tacgaatgcc ttggaaacct ggggtgcctt gggtcaggac     120
atcaacttgg acattcctag ttttcaaatg agtgatgata ttgacgatat aaaatgggaa     180
aaaacttcag acaagaaaaa gattgcacaa ttcagaaaag agaaagagac tttcaaggaa     240
aaagatacat ataagctatt taaaaatgga actctgaaaa ttaagcatct gaagaccgat     300

```
gatcaggata tctacaaggt atcaatatat gatacaaaag gaaaaaatgt gttggaaaaa    360
atatttgatt tgaagattca agagagggtc tcaaaaccaa agatctcctg gacttgtatc    420
aacacaaccc tgacctgtga ggtaatgaat ggaactgacc ccgaattaaa cctgtatcaa    480
gatgggaaac atctaaaact ttctcagagg gtcatcacac acaagtggac caccagcctg    540
agtgcaaaat tcaagtgcac agcagggaac aaagtcagca aggaatccag tgtcgagcct    600
gtcagctgtc cagagaaagg tctggacttc tgggtgctgg tggtggtcgg aggcgtgctg    660
gcctgctaca gcctgctggt caccgtggcc ttcatcatct tttgggtccg cagcaagcgg    720
agcagaggcg gccacagcga ctacatgaac atgaccccta cggcctgg cccaccaga      780 aagcactacc agccctacgc ccctccccgg gactttgccg cctacagaag c            831
```

<210> SEQ ID NO 68
<211> LENGTH: 277
<212> TYPE: PRT
<213> ORGANISM: Artificial Sequence
<220> FEATURE:
<223> OTHER INFORMATION: huCD2-CD28tm

<400> SEQUENCE: 68

```
Met Ser Phe Pro Cys Lys Phe Val Ala Ser Phe Leu Leu Ile Phe Asn
1               5                   10                  15

Val Ser Ser Lys Gly Ala Val Ser Lys Glu Ile Thr Asn Ala Leu Glu
            20                  25                  30

Thr Trp Gly Ala Leu Gly Gln Asp Ile Asn Leu Asp Ile Pro Ser Phe
        35                  40                  45

Gln Met Ser Asp Asp Ile Asp Asp Ile Lys Trp Glu Lys Thr Ser Asp
    50                  55                  60

Lys Lys Lys Ile Ala Gln Phe Arg Lys Glu Lys Glu Thr Phe Lys Glu
65                  70                  75                  80

Lys Asp Thr Tyr Lys Leu Phe Lys Asn Gly Thr Leu Lys Ile Lys His
                85                  90                  95

Leu Lys Thr Asp Asp Gln Asp Ile Tyr Lys Val Ser Ile Tyr Asp Thr
            100                 105                 110

Lys Gly Lys Asn Val Leu Glu Lys Ile Phe Asp Leu Lys Ile Gln Glu
        115                 120                 125

Arg Val Ser Lys Pro Lys Ile Ser Trp Thr Cys Ile Asn Thr Thr Leu
    130                 135                 140

Thr Cys Glu Val Met Asn Gly Thr Asp Pro Glu Leu Asn Leu Tyr Gln
145                 150                 155                 160

Asp Gly Lys His Leu Lys Leu Ser Gln Arg Val Ile Thr His Lys Trp
                165                 170                 175

Thr Thr Ser Leu Ser Ala Lys Phe Lys Cys Thr Ala Gly Asn Lys Val
            180                 185                 190

Ser Lys Glu Ser Ser Val Glu Pro Val Ser Cys Pro Glu Lys Gly Leu
        195                 200                 205

Asp Phe Trp Val Leu Val Val Val Gly Gly Val Leu Ala Cys Tyr Ser
    210                 215                 220

Leu Leu Val Thr Val Ala Phe Ile Ile Phe Trp Val Arg Ser Lys Arg
225                 230                 235                 240

Ser Arg Gly Gly His Ser Asp Tyr Met Asn Met Thr Pro Arg Arg Pro
                245                 250                 255

Gly Pro Thr Arg Lys His Tyr Gln Pro Tyr Ala Pro Pro Arg Asp Phe
            260                 265                 270
```

```
<210> SEQ ID NO 69
<211> LENGTH: 969
<212> TYPE: DNA
<213> ORGANISM: Artificial Sequence
<220> FEATURE:
<223> OTHER INFORMATION: huCD200R-CD28Cys

<400> SEQUENCE: 69
atgctgtgcc cttggagaac cgccaacctg ggcctgctgc tgatcctgac catcttcctg      60
gtggccgcca gcagcagcct gtgcatggac gagaagcaga tcacccagaa ctacagcaag     120
gtgctggccg aagtgaacac cagctggccc gtgaagatgg ccaccaacgc cgtgctgtgc     180
tgccctccta tcgccctgcg gaacctgatc atcatcacct gggagatcat cctgcggggc     240
cagcccagct gtaccaaggc ctaccggaaa gagacaaacg agacaaaaga acaaaactgc     300
accgacgagc ggatcacatg gtgtccagac cccgaccaga cagcgacct gcagatcaga     360
cccgtggcca tcacccacga cggctactac cggtgcatca tggtcacccc cgatggcaac     420
ttccaccggg gataccatct gcaggtgctc gtgaccccg aagtgaccct gttccagaac      480
cggaacagaa ccgccgtgtg caaggccgtg gccggaaaac ctgccgccca gatctcttgg     540
atccccgagg gcgattgcgc caccaagcag gaatactggt ccaacggcac cgtgaccgtg     600
aagtccacct gtcactggga ggtgcacaac gtgtccaccg tgacatgcca cgtgtcccac     660
ctgaccggca acaagagcct gtacatcgag ctgctgcctg tgcctggcgc caagaagtcc     720
gccaagctgt gtcccagccc tctgtttccc ggccctagca agccttctg gtgctggtg      780
gtggtcggag gcgtgctggc ctgctacagc ctgctggtca ccgtggcctt catcatcttt     840
tgggtccgca gcaagcggag cagaggcggc cacagcgact acatgaacat gaccccctaga     900
cggcctggcc ccaccagaaa gcactaccag ccctacgccc tccccggga ctttgccgcc      960
tacagaagc                                                              969

<210> SEQ ID NO 70
<211> LENGTH: 323
<212> TYPE: PRT
<213> ORGANISM: Artificial Sequence
<220> FEATURE:
<223> OTHER INFORMATION: huCD200R-CD28Cys

<400> SEQUENCE: 70

Met Leu Cys Pro Trp Arg Thr Ala Asn Leu Gly Leu Leu Leu Ile Leu
  1               5                  10                  15

Thr Ile Phe Leu Val Ala Ala Ser Ser Ser Leu Cys Met Asp Glu Lys
                 20                  25                  30

Gln Ile Thr Gln Asn Tyr Ser Lys Val Leu Ala Glu Val Asn Thr Ser
         35                  40                  45

Trp Pro Val Lys Met Ala Thr Asn Ala Val Leu Cys Cys Pro Pro Ile
     50                  55                  60

Ala Leu Arg Asn Leu Ile Ile Ile Thr Trp Glu Ile Ile Leu Arg Gly
 65                  70                  75                  80

Gln Pro Ser Cys Thr Lys Ala Tyr Arg Lys Glu Thr Asn Glu Thr Lys
                 85                  90                  95

Glu Thr Asn Cys Thr Asp Glu Arg Ile Thr Trp Val Ser Arg Pro Asp
            100                 105                 110

Gln Asn Ser Asp Leu Gln Ile Arg Pro Val Ala Ile Thr His Asp Gly
```

```
                115                 120                 125
Tyr Tyr Arg Cys Ile Met Val Thr Pro Asp Gly Asn Phe His Arg Gly
    130                 135                 140

Tyr His Leu Gln Val Leu Val Thr Pro Glu Val Thr Leu Phe Gln Asn
145                 150                 155                 160

Arg Asn Arg Thr Ala Val Cys Lys Ala Val Ala Gly Lys Pro Ala Ala
                165                 170                 175

Gln Ile Ser Trp Ile Pro Glu Gly Asp Cys Ala Thr Lys Gln Glu Tyr
            180                 185                 190

Trp Ser Asn Gly Thr Val Thr Val Lys Ser Thr Cys His Trp Glu Val
        195                 200                 205

His Asn Val Ser Thr Val Thr Cys His Val Ser His Leu Thr Gly Asn
    210                 215                 220

Lys Ser Leu Tyr Ile Glu Leu Leu Pro Val Pro Gly Ala Lys Lys Ser
225                 230                 235                 240

Ala Lys Leu Cys Pro Ser Pro Leu Phe Pro Gly Pro Ser Lys Pro Phe
                245                 250                 255

Trp Val Leu Val Val Val Gly Gly Val Leu Ala Cys Tyr Ser Leu Leu
            260                 265                 270

Val Thr Val Ala Phe Ile Ile Phe Trp Val Arg Ser Lys Arg Ser Arg
        275                 280                 285

Gly Gly His Ser Asp Tyr Met Asn Met Thr Pro Arg Arg Pro Gly Pro
    290                 295                 300

Thr Arg Lys His Tyr Gln Pro Tyr Ala Pro Pro Arg Asp Phe Ala Ala
305                 310                 315                 320

Tyr Arg Ser

<210> SEQ ID NO 71
<211> LENGTH: 519
<212> TYPE: DNA
<213> ORGANISM: Artificial Sequence
<220> FEATURE:
<223> OTHER INFORMATION: huFas entire extracellular domain

<400> SEQUENCE: 71
atgctgggca tctggaccct gctgcctctg gtgctgacaa gcgtggccag actgagcagc        60
aagagcgtga cgcccaagt gaccgacatc aacagcaagg gcctggaact gagaaagacc       120
gtgaccaccg tggaaaccca gaacctggaa ggcctgcacc acgacggcca gttctgccac       180
aagccttgtc ccctggcgcga gcggaaggcc agagactgta ctgtgaacgg cgacgagccc       240
gactgcgtgc cctgtcagga aggcaaagag tacaccgaca ggcccacttc agcagcaag        300 tgccggcggt gcagactgtg tgatgagggc acggcctgg aagtggaaat caactgcacc       360
cggacccaga acaccaagtg cagatgcaag cccaacttct tctgcaacag caccgtgtgc       420
gagcactgcg acccctgtac caagtgcgaa cacggcatca tcaaagagtg cacccctgacc      480 tccaacacaa agtgcaaaga ggaaggcagc agaagcaac                             519

<210> SEQ ID NO 72
<211> LENGTH: 173
<212> TYPE: PRT
<213> ORGANISM: Artificial Sequence
<220> FEATURE:
<223> OTHER INFORMATION: huFas entire extracellular domain

<400> SEQUENCE: 72

Met Leu Gly Ile Trp Thr Leu Leu Pro Leu Val Leu Thr Ser Val Ala
```

```
            1               5                   10                  15
Arg Leu Ser Ser Lys Ser Val Asn Ala Gln Val Thr Asp Ile Asn Ser
                20                  25                  30

Lys Gly Leu Glu Leu Arg Lys Thr Val Thr Thr Val Glu Thr Gln Asn
                35                  40                  45

Leu Glu Gly Leu His His Asp Gly Gln Phe Cys His Lys Pro Cys Pro
            50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                    85                  90                  95

Phe Ser Ser Lys Cys Arg Arg Cys Arg Leu Cys Asp Glu Gly His Gly
                100                 105                 110

Leu Glu Val Glu Ile Asn Cys Thr Arg Thr Gln Asn Thr Lys Cys Arg
                115                 120                 125

Cys Lys Pro Asn Phe Phe Cys Asn Ser Thr Val Cys Glu His Cys Asp
            130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn
                165                 170

<210> SEQ ID NO 73
<211> LENGTH: 498
<212> TYPE: DNA
<213> ORGANISM: Artificial Sequence
<220> FEATURE:
<223> OTHER INFORMATION: huFas extracellular domain -7aas

<400> SEQUENCE: 73
atgctgggca tctggaccct gctgcctctg gtgctgacaa gcgtggccag actgagcagc     60
aagagcgtga acgcccaagt gaccgacatc aacagcaagg gcctggaact gagaaagacc    120
gtgaccaccg tggaaaccca gaacctggaa ggcctgcacc acgacggcca gttctgccac    180
aagccttgtc ccctggcga gcggaaggcc agagactgta ctgtgaacgg cgacgagccc    240
gactgcgtgc cctgtcagga aggcaaagag tacaccgaca ggcccacttc agcagcaag     300 tgccggcggt gcagactgtg tgatgagggc acggcctgg aagtggaaat caactgcacc     360
cggacccaga acaccaagtg cagatgcaag cccaacttct ctgcaacag caccgtgtgc     420 gagcactgcg accctgtac caagtgcgaa cacggcatca tcaaagagtg caccctgacc    480
tccaacacaa agtgcaaa                                                  498

<210> SEQ ID NO 74
<211> LENGTH: 166
<212> TYPE: PRT
<213> ORGANISM: Artificial Sequence
<220> FEATURE:
<223> OTHER INFORMATION: huFas extracellular domain -7aas

<400> SEQUENCE: 74

Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
                20                  25                  30

Lys Gly Leu Glu Leu Arg Lys Thr Val Thr Thr Val Glu Thr Gln Asn
                35                  40                  45
```

-continued

```
Leu Glu Gly Leu His His Asp Gly Gln Phe Cys His Lys Pro Cys Pro
 50                  55                  60

Pro Gly Glu Arg Lys Ala Arg Asp Cys Thr Val Asn Gly Asp Glu Pro
 65                  70                  75                  80

Asp Cys Val Pro Cys Gln Glu Gly Lys Glu Tyr Thr Asp Lys Ala His
                 85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
130                 135                 140

Pro Cys Thr Lys Cys Glu His Gly Ile Ile Lys Glu Cys Thr Leu Thr
145                 150                 155                 160

Ser Asn Thr Lys Cys Lys
                165

<210> SEQ ID NO 75
<211> LENGTH: 483
<212> TYPE: DNA
<213> ORGANISM: Artificial Sequence
<220> FEATURE:
<223> OTHER INFORMATION: huFas extracellular domain -12aas

<400> SEQUENCE: 75
atgctgggca tctggaccct gctgcctctg gtgctgacaa gcgtggccag actgagcagc      60
aagagcgtga acgcccaagt gaccgacatc aacagcaagg gcctggaact gagaaagacc     120
gtgaccaccg tggaaaccca gaacctggaa ggcctgcacc acgacggcca gttctgccac     180
aagccttgtc ccctggcga gcggaaggcc agagactgta ctgtgaacgg cgacgagccc      240
gactgcgtgc cctgtcagga aggcaaagag tacaccgaca aggcccactt cagcagcaag     300
tgccggcggt gcagactgtg tgatgagggc acggcctgg aagtggaaat caactgcacc      360
cggacccaga acaccaagtg cagatgcaag cccaacttct ctgcaacag caccgtgtgc      420 gagcactgcg acccctgtac caagtgcgaa cacggcatca tcaaagagtg caccctgacc     480
tcc                                                                  483

<210> SEQ ID NO 76
<211> LENGTH: 161
<212> TYPE: PRT
<213> ORGANISM: Artificial Sequence
<220> FEATURE:
<223> OTHER INFORMATION: huFas extracellular domain -12aas

<400> SEQUENCE: 76

Met Leu Gly Ile Trp Thr Leu Leu Pro Leu Val Leu Thr Ser Val Ala
  1               5                  10                  15

Arg Leu Ser Ser Lys Ser Val Asn Ala Gln Val Thr Asp Ile Asn Ser
             20                  25                  30

Lys Gly Leu Glu Leu Arg Lys Thr Val Thr Thr Val Glu Thr Gln Asn
         35                  40                  45

Leu Glu Gly Leu His His Asp Gly Gln Phe Cys His Lys Pro Cys Pro
 50                  55                  60

Pro Gly Glu Arg Lys Ala Arg Asp Cys Thr Val Asn Gly Asp Glu Pro
 65                  70                  75                  80

Asp Cys Val Pro Cys Gln Glu Gly Lys Glu Tyr Thr Asp Lys Ala His
                 85                  90                  95
```

```
Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser

<210> SEQ ID NO 77
<211> LENGTH: 51
<212> TYPE: DNA
<213> ORGANISM: Artificial Sequence
<220> FEATURE:
<223> OTHER INFORMATION: huFas transmembrane domain

<400> SEQUENCE: 77
ctgggctggc tgtgcctcct gctgctgccc atccctctga tcgtgtgggt c          51

<210> SEQ ID NO 78
<211> LENGTH: 17
<212> TYPE: PRT
<213> ORGANISM: Artificial Sequence
<220> FEATURE:
<223> OTHER INFORMATION: huFas transmembrane domain

<400> SEQUENCE: 78

Leu Gly Trp Leu Cys Leu Leu Leu Leu Pro Ile Pro Leu Ile Val Trp
1               5                   10                  15

Val

<210> SEQ ID NO 79
<211> LENGTH: 693
<212> TYPE: DNA
<213> ORGANISM: Artificial Sequence
<220> FEATURE:
<223> OTHER INFORMATION: huFAStm-CD28

<400> SEQUENCE: 79
atgctgggca tctggaccct gctgcctctg gtgctgacaa gcgtggccag actgagcagc      60
aagagcgtga acgcccaagt gaccgacatc aacagcaagg gcctggaact gagaaagacc     120
gtgaccaccg tggaaaccca gaacctggaa ggcctgcacc acgacggcca gttctgccac     180
aagccttgtc ccctggcga gcggaaggcc agagactgta ctgtgaacgg cgacgagccc     240
gactgcgtgc cctgtcagga aggcaaagag tacaccgaca ggcccacctt cagcagcaag     300
tgccggcggt gcagactgtg tgatgagggc cacggcctgg aagtggaaat caactgcacc     360
cggacccaga acaccaagtg cagatgcaag cccaacttct ctctgcaacag caccgtgtgc     420 gagcactgcg accctgtac caagtgcgaa acggcatca tcaaagagtg caccctgacc      480
tccaacacaa agtgcaaaga ggaaggcagc agaagcaacc tgggctggct gtgcctcctg     540
ctgctgccca tccctctgat cgtgtgggtc cgcagcaagc ggagcagagg cggccacagc     600
gactacatga acatgacccc tagacggcct ggccccacca gaaagcacta ccagccctac     660
gcccctcccc gggactttgc cgcctacaga agc                                 693

<210> SEQ ID NO 80
<211> LENGTH: 231
```

<212> TYPE: PRT
<213> ORGANISM: Artificial Sequence
<220> FEATURE:
<223> OTHER INFORMATION: huFAStm-CD28

<400> SEQUENCE: 80

```
Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Thr Val Glu Thr Gln Asn
        35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Leu Gly Trp
                165                 170                 175

Leu Cys Leu Leu Leu Leu Pro Ile Pro Leu Ile Val Trp Val Arg Ser
            180                 185                 190

Lys Arg Ser Arg Gly Gly His Ser Asp Tyr Met Asn Met Thr Pro Arg
        195                 200                 205

Arg Pro Gly Pro Thr Arg Lys His Tyr Gln Pro Tyr Ala Pro Pro Arg
    210                 215                 220

Asp Phe Ala Ala Tyr Arg Ser
225                 230
```

<210> SEQ ID NO 81
<211> LENGTH: 723
<212> TYPE: DNA
<213> ORGANISM: Artificial Sequence
<220> FEATURE:
<223> OTHER INFORMATION: huFAS-CD28tm

<400> SEQUENCE: 81

| | | | | | |
|---|---|---|---|---|---|
| atgctgggca | tctggaccct | gctgcctctg | gtgctgacaa | gcgtggccag | actgagcagc | 60 |
| aagagcgtga | acgcccaagt | gaccgacatc | aacagcaagg | gcctggaact | gagaaagacc | 120 |
| gtgaccaccg | tggaaaccca | gaacctggaa | ggcctgcacc | acgacggcca | gttctgccac | 180 |
| aagccttgtc | ccctggcga | gcggaaggcc | agagactgta | ctgtgaacgg | cgacgagccc | 240 |
| gactgcgtgc | cctgtcagga | aggcaaagag | tacaccgaca | aggcccactt | cagcagcaag | 300 |
| tgccggcggt | gcagactgtg | tgatgagggc | cacggcctgg | aagtggaaat | caactgcacc | 360 |
| cggacccaga | acaccaagtg | cagatgcaag | cccaacttct | tctgcaacag | caccgtgtgc | 420 |
| gagcactgcg | acccctgtac | caagtgcgaa | cacggcatca | tcaaagagtg | caccctgacc | 480 |
| tccaacacaa | agtgcaaaga | ggaaggcagc | agaagcaact | tctgggtgct | ggtggtggtc | 540 |

```
ggaggcgtgc tggcctgcta cagcctgctg gtcaccgtgg ccttcatcat ctttgggtc      600 cgcagcaagc ggagcagagg cggccacagc gactacatga acatgacccc tagacggcct      660
ggccccacca gaaagcacta ccagccctac gcccctcccc gggactttgc cgcctacaga      720
agc                                                                    723
```

```
<210> SEQ ID NO 82
<211> LENGTH: 241
<212> TYPE: PRT
<213> ORGANISM: Artificial Sequence
<220> FEATURE:
<223> OTHER INFORMATION: huFAS-CD28tm

<400> SEQUENCE: 82
```

```
Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Thr Val Glu Thr Gln Asn
        35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Phe Trp Val
                165                 170                 175

Leu Val Val Val Gly Val Leu Ala Cys Tyr Ser Leu Leu Val Thr
            180                 185                 190

Val Ala Phe Ile Ile Phe Trp Val Arg Ser Lys Arg Ser Arg Gly Gly
        195                 200                 205

His Ser Asp Tyr Met Asn Met Thr Pro Arg Arg Pro Gly Pro Thr Arg
    210                 215                 220

Lys His Tyr Gln Pro Tyr Ala Pro Pro Arg Asp Phe Ala Ala Tyr Arg
225                 230                 235                 240

Ser
```

```
<210> SEQ ID NO 83
<211> LENGTH: 759
<212> TYPE: DNA
<213> ORGANISM: Artificial Sequence
<220> FEATURE:
<223> OTHER INFORMATION: huFAS-CD28Cys

<400> SEQUENCE: 83
```

```
atgctgggca tctggaccct gctgcctctg gtgctgacaa gcgtggccag actgagcagc      60
aagagcgtga acgcccaagt gaccgacatc aacagcaagg gcctggaact gagaaagacc     120
```

-continued

```
gtgaccaccg tggaaaccca gaacctggaa ggcctgcacc acgacggcca gttctgccac      180
aagccttgtc cccctggcga gcggaaggcc agagactgta ctgtgaacgg cgacgagccc      240
gactgcgtgc cctgtcagga aggcaaagag tacaccgaca aggcccactt cagcagcaag      300
tgccggcggt gcagactgtg tgatgagggc acggcctgga agtggaaat caactgcacc       360 cggacccaga acaccaagtg cagatgcaag cccaacttct tctgcaacag caccgtgtgc      420
gagcactgcg accctgtac caagtgcgaa acggcatca tcaaagagtg caccctgacc        480
tccaacacaa agtgcaaaga ggaaggcagc agaagcaact gtcccagccc tctgtttccc      540
ggccctagca agccttttctg ggtgctggtg gtggtcggag gcgtgctggc ctgctacagc     600
ctgctggtca ccgtggcctt catcatcttt tgggtccgca gcaagcggag cagaggcggc     660
cacagcgact acatgaacat gaccctaga cggcctggcc ccaccagaaa gcactaccag       720
ccctacgccc ctccccggga ctttgccgcc tacagaagc                            759
```

<210> SEQ ID NO 84
<211> LENGTH: 253
<212> TYPE: PRT
<213> ORGANISM: Artificial Sequence
<220> FEATURE:
<223> OTHER INFORMATION: huFAS-CD28Cys

<400> SEQUENCE: 84

```
Met Leu Gly Ile Trp Thr Leu Leu Pro Leu Val Leu Thr Ser Val Ala
 1               5                  10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Thr Val Glu Thr Gln Asn
        35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Cys Pro Ser
                165                 170                 175

Pro Leu Phe Pro Gly Pro Ser Lys Pro Phe Trp Val Leu Val Val Val
            180                 185                 190

Gly Gly Val Leu Ala Cys Tyr Ser Leu Leu Val Thr Val Ala Phe Ile
        195                 200                 205

Ile Phe Trp Val Arg Ser Lys Arg Ser Arg Gly Gly His Ser Asp Tyr
    210                 215                 220

Met Asn Met Thr Pro Arg Arg Pro Gly Pro Thr Arg Lys His Tyr Gln
225                 230                 235                 240

Pro Tyr Ala Pro Pro Arg Asp Phe Ala Ala Tyr Arg Ser
                245                 250
```

<210> SEQ ID NO 85
<211> LENGTH: 738
<212> TYPE: DNA
<213> ORGANISM: Artificial Sequence
<220> FEATURE:
<223> OTHER INFORMATION: huFAS-7aas-CD28Cys

<400> SEQUENCE: 85

```
atgctgggca tctggaccct gctgcctctg gtgctgacaa gcgtggccag actgagcagc      60
aagagcgtga acgcccaagt gaccgacatc aacagcaagg gcctggaact gagaaagacc     120
gtgaccaccg tggaaaccca gaacctggaa ggcctgcacc acgacggcca gttctgccac     180
aagccttgtc ccctggcga gcggaaggcc agagactgta ctgtgaacgg cgacgagccc     240
gactgcgtgc cctgtcagga aggcaaagag tacaccgaca aggcccactt cagcagcaag     300
tgccggcggt gcagactgtg tgatgagggc cacggcctgg aagtggaaat caactgcacc     360
cggacccaga caccaagtg cagatgcaag cccaacttct ctgcaacag caccgtgtgc      420
gagcactgcg accctgtac aagtgcgaa cacggcatca tcaaagagtg caccctgacc     480
tccaacacaa agtgcaaatg cccagccct ctgtttccg ccctagcaa gccttttctgg      540
gtgctggtgg tggtcggagg cgtgctggcc tgctacagcc tgctggtcac cgtggccttc     600
atcatctttt gggtccgcag caagcggagc agaggcggcc acagcgacta catgaacatg     660
acccctagac ggcctggccc caccagaaag cactaccagc cctacgcccc tccccgggac     720
tttgccgcct acagaagc                                                  738
```

<210> SEQ ID NO 86
<211> LENGTH: 246
<212> TYPE: PRT
<213> ORGANISM: Artificial Sequence
<220> FEATURE:
<223> OTHER INFORMATION: huFAS-7aas-CD28Cys

<400> SEQUENCE: 86

```
Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Thr Val Glu Thr Gln Asn
        35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys Cys Pro Ser Pro Leu Phe Pro Gly Pro Ser
```

```
                165                 170                 175
Lys Pro Phe Trp Val Leu Val Val Gly Gly Val Leu Ala Cys Tyr
            180                 185                 190

Ser Leu Leu Val Thr Val Ala Phe Ile Ile Phe Trp Val Arg Ser Lys
        195                 200                 205

Arg Ser Arg Gly Gly His Ser Asp Tyr Met Asn Met Thr Pro Arg Arg
    210                 215                 220

Pro Gly Pro Thr Arg Lys His Tyr Gln Pro Tyr Ala Pro Pro Arg Asp
225                 230                 235                 240

Phe Ala Ala Tyr Arg Ser
                245

<210> SEQ ID NO 87
<211> LENGTH: 723
<212> TYPE: DNA
<213> ORGANISM: Artificial Sequence
<220> FEATURE:
<223> OTHER INFORMATION: FAS-12aas-CD28Cys

<400> SEQUENCE: 87
atgctgggca tctggaccct gctgcctctg gtgctgacaa gcgtggccag actgagcagc      60
aagagcgtga acgcccaagt gaccgacatc aacagcaagg gcctggaact gagaaagacc     120
gtgaccaccg tggaaaccca gaacctggaa ggcctgcacc acgacggcca gttctgccac     180
aagccttgtc ccctggcga gcggaaggcc agagactgta ctgtgaacgg cgacgagccc      240
gactgcgtgc cctgtcagga aggcaaagag tacaccgaca aggcccactt cagcagcaag     300
tgccggcggt gcagactgtg tgatgagggc cacggcctgg aagtggaaat caactgcacc     360
cggacccaga acaccaagtg cagatgcaag cccaacttct tctgcaacag caccgtgtgc     420
gagcactgcg accctgtac caagtgcgaa cacggcatca tcaaagagtg caccctgacc     480
tcctgtccca gccctctgtt tcccggcccc agcaagcctt tctgggtgct ggtggtggtc     540
ggaggcgtgc tggcctgcta cagcctgctg gtcaccgtgg ccttcatcat cttttgggtc     600
cgcagcaagc ggagcagagg cggccacagc gactacatga acatgacccc tagacggcct     660
ggccccacca gaaagcacta ccagccctac gcccctcccc gggactttgc cgcctacaga     720
agc                                                                  723

<210> SEQ ID NO 88
<211> LENGTH: 241
<212> TYPE: PRT
<213> ORGANISM: Artificial Sequence
<220> FEATURE:
<223> OTHER INFORMATION: FAS-12aas-CD28Cys

<400> SEQUENCE: 88

Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Thr Val Glu Thr Gln Asn
        35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
```

```
                    85                  90                  95
Phe Ser Ser Lys Cys Arg Arg Cys Arg Leu Cys Asp Glu Gly His Gly
            100                 105                 110
Leu Glu Val Glu Ile Asn Cys Thr Arg Thr Gln Asn Thr Lys Cys Arg
            115                 120                 125
Cys Lys Pro Asn Phe Phe Cys Asn Ser Thr Val Cys Glu His Cys Asp
            130                 135                 140
Pro Cys Thr Lys Cys Glu His Gly Ile Ile Lys Glu Cys Thr Leu Thr
145                 150                 155                 160
Ser Cys Pro Ser Pro Leu Phe Pro Gly Pro Ser Lys Pro Phe Trp Val
            165                 170                 175
Leu Val Val Val Gly Gly Val Leu Ala Cys Tyr Ser Leu Leu Val Thr
            180                 185                 190
Val Ala Phe Ile Ile Phe Trp Val Arg Ser Lys Arg Ser Arg Gly Gly
            195                 200                 205
His Ser Asp Tyr Met Asn Met Thr Pro Arg Arg Pro Gly Pro Thr Arg
            210                 215                 220
Lys His Tyr Gln Pro Tyr Ala Pro Pro Arg Asp Phe Ala Ala Tyr Arg
225                 230                 235                 240
Ser

<210> SEQ ID NO 89
<211> LENGTH: 510
<212> TYPE: DNA
<213> ORGANISM: Artificial Sequence
<220> FEATURE:
<223> OTHER INFORMATION: huPD1 entire extracellular domain 2

<400> SEQUENCE: 89
atgcagatcc ctcaggcccc ttggcctgtc gtgtgggctg tgctgcagct gggatggcgg      60
cctggctggt ttctggacag ccccgacaga ccctggaacc ccctacatt ttcccctgcc     120 ctgctggtcg tgaccgaggg cgacaatgcc accttcacct gtagcttcag caacaccagc     180
gagagcttcg tgctgaactg gtacagaatg agccccagca accagaccga caagctggcc     240
gccttccccg aggatagatc tcagcccggc caggactgcc ggttcagagt gacccagctg     300
cccaacggcc gggacttcca catgtctgtc gtgcgggcca gacggaacga cagcggcaca     360
tatctgtgcg gcgccatcag cctggccccc aaggcccaga tcaaagagag cctgagagcc     420
gagctgagag tgaccgagag aagggccgaa gtgcctaccg cccaccctag cccatctcca     480
agacctgccg gccagttcca gacactggtc                                      510

<210> SEQ ID NO 90
<211> LENGTH: 170
<212> TYPE: PRT
<213> ORGANISM: Artificial Sequence
<220> FEATURE:
<223> OTHER INFORMATION: huPD1 entire extracellular domain 2

<400> SEQUENCE: 90

Met Gln Ile Pro Gln Ala Pro Trp Pro Val Val Trp Ala Val Leu Gln
1               5                  10                  15
Leu Gly Trp Arg Pro Gly Trp Phe Leu Asp Ser Pro Asp Arg Pro Trp
            20                  25                  30
Asn Pro Pro Thr Phe Ser Pro Ala Leu Leu Val Val Thr Glu Gly Asp
            35                  40                  45
Asn Ala Thr Phe Thr Cys Ser Phe Ser Asn Thr Ser Glu Ser Phe Val
```

```
                    50                  55                  60

Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
                     85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
        130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val
                165                 170
```

<210> SEQ ID NO 91
<211> LENGTH: 474
<212> TYPE: DNA
<213> ORGANISM: Artificial Sequence
<220> FEATURE:
<223> OTHER INFORMATION: huPD1 2 -12aas

<400> SEQUENCE: 91

```
atgcagatcc ctcaggcccc ttggcctgtc gtgtgggctg tgctgcagct gggatggcgg      60
cctggctggt ttctggacag ccccgacaga ccctggaacc cccctacatt ttcccctgcc     120
ctgctggtcg tgaccgaggg cgacaatgcc accttcacct gtagcttcag caacaccagc     180
gagagcttcg tgctgaactg gtacagaatg agccccagca accagaccga caagctggcc     240
gccttccccg aggatagatc tcagcccggc caggactgcc ggttcagagt gacccagctg     300
cccaacggcc gggacttcca catgtctgtc gtgcgggcca acggaacgca gcggcaca      360
tatctgtgcg gcgccatcag cctggccccc aaggcccaga tcaaagagag cctgagagcc     420
gagctgagag tgaccgagag aagggccgaa gtgcctaccg cccacccctag ccca          474
```

<210> SEQ ID NO 92
<211> LENGTH: 158
<212> TYPE: PRT
<213> ORGANISM: Artificial Sequence
<220> FEATURE:
<223> OTHER INFORMATION: huPD1 2 -12aas

<400> SEQUENCE: 92

```
Met Gln Ile Pro Gln Ala Pro Trp Pro Val Val Trp Ala Val Leu Gln
 1               5                  10                  15

Leu Gly Trp Arg Pro Gly Trp Phe Leu Asp Ser Pro Asp Arg Pro Trp
             20                  25                  30

Asn Pro Pro Thr Phe Ser Pro Ala Leu Leu Val Val Thr Glu Gly Asp
         35                  40                  45

Asn Ala Thr Phe Thr Cys Ser Phe Ser Asn Thr Ser Glu Ser Phe Val
     50                  55                  60

Leu Asn Trp Tyr Arg Met Ser Pro Ser Asn Gln Thr Asp Lys Leu Ala
 65                  70                  75                  80

Ala Phe Pro Glu Asp Arg Ser Gln Pro Gly Gln Asp Cys Arg Phe Arg
                 85                  90                  95

Val Thr Gln Leu Pro Asn Gly Arg Asp Phe His Met Ser Val Val Arg
            100                 105                 110
```

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
        130                 135                 140

Thr Glu Arg Arg Ala Glu Val Pro Thr Ala His Pro Ser Pro
145                 150                 155

<210> SEQ ID NO 93
<211> LENGTH: 465
<212> TYPE: DNA
<213> ORGANISM: Artificial Sequence
<220> FEATURE:
<223> OTHER INFORMATION: huPD1 2 -15aas

<400> SEQUENCE: 93
atgcagatcc ctcaggcccc ttggcctgtc gtgtgggctg tgctgcagct gggatggcgg      60
cctggctggt ttctggacag ccccgacaga ccctggaacc ccctacatt tteccctgcc     120 ctgctggtcg tgaccgaggg cgacaatgcc accttcacct gtagcttcag caacaccagc     180
gagagcttcg tgctgaactg gtacagaatg agccccagca accagaccga caagctggcc     240
gccttccccg aggatagatc tcagcccggc caggactgcc ggttcagagt gacccagctg     300
cccaacggcc gggacttcca catgtctgtc gtgcgggcca gacggaacga cagcggcaca     360
tatctgtgcg gcgccatcag cctggccccc aaggcccaga tcaaagagag cctgagagcc     420
gagctgagag tgaccgagag aagggccgaa gtgcctaccg cccac                    465

<210> SEQ ID NO 94
<211> LENGTH: 155
<212> TYPE: PRT
<213> ORGANISM: Artificial Sequence
<220> FEATURE:
<223> OTHER INFORMATION: huPD1 2 -15aas

<400> SEQUENCE: 94

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His
145                 150                 155

<210> SEQ ID NO 95
<211> LENGTH: 447

<212> TYPE: DNA
<213> ORGANISM: Artificial Sequence
<220> FEATURE:
<223> OTHER INFORMATION: huPD1 2 -21aas

<400> SEQUENCE: 95

```
atgcagatcc ctcaggcccc ttggcctgtc gtgtgggctg tgctgcagct gggatggcgg    60
cctggctggt ttctggacag ccccgacaga ccctggaacc ccctacatt tttccctgcc    120
ctgctggtcg tgaccgaggg cgacaatgcc accttcacct gtagcttcag caacaccagc   180
gagagcttcg tgctgaactg gtacagaatg agccccagca accagaccga caagctggcc   240
gccttccccg aggatagatc tcagcccggc caggactgcc ggttcagagt gacccagctg   300
cccaacggcc gggacttcca catgtctgtc gtgcgggcca gacggaacga cagcggcaca   360
tatctgtgcg gcgccatcag cctggccccc aaggcccaga tcaaagagag cctgagagcc   420
gagctgagag tgaccgagag aagggcc                                        447
```

<210> SEQ ID NO 96
<211> LENGTH: 149
<212> TYPE: PRT
<213> ORGANISM: Artificial Sequence
<220> FEATURE:
<223> OTHER INFORMATION: huPD1 -21aas

<400> SEQUENCE: 96

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala
145
```

<210> SEQ ID NO 97
<211> LENGTH: 750
<212> TYPE: DNA
<213> ORGANISM: Artificial Sequence
<220> FEATURE:
<223> OTHER INFORMATION: huPD1-CD28Cys

<400> SEQUENCE: 97

```
atgcagatcc ctcaggcccc ttggcctgtc gtgtgggctg tgctgcagct gggatggcgg    60
cctggctggt ttctggacag ccccgacaga ccctggaacc ccctacatt tttccctgcc    120
ctgctggtcg tgaccgaggg cgacaatgcc accttcacct gtagcttcag caacaccagc   180
```

```
gagagcttcg tgctgaactg gtacagaatg agccccagca accagaccga caagctggcc    240
gccttccccg aggatagatc tcagcccggc caggactgcc ggttcagagt gacccagctg    300
cccaacggcc gggacttcca catgtctgtc gtgcgggcca gacggaacga cagcggcaca    360
tatctgtgcg gcgccatcag cctggccccc aaggcccaga tcaaagagag cctgagagcc    420
gagctgagag tgaccgagag aagggccgaa gtgcctaccg cccaccctag cccatctcca    480
agacctgccg gccagttcca gacactggtc tgtcccagcc ctctgttccc ggccctagc    540 aagcctttct gggtgctggt ggtggtcgga ggcgtgctgg cctgctacag cctgctggtc    600
accgtggcct tcatcatctt ttgggtccgc agcaagcgga gcagaggcgg ccacagcgac    660
tacatgaaca tgaccccctag acggcctggc cccaccagaa agcactacca gccctacgcc    720 cctcccccggg actttgccgc ctacagaagc                                    750
```

```
<210> SEQ ID NO 98
<211> LENGTH: 250
<212> TYPE: PRT
<213> ORGANISM: Artificial Sequence
<220> FEATURE:
<223> OTHER INFORMATION: huPD1-CD28Cys

<400> SEQUENCE: 98

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Cys Pro Ser Pro Leu Phe
                165                 170                 175

Pro Gly Pro Ser Lys Pro Phe Trp Val Leu Val Val Val Gly Gly Val
            180                 185                 190

Leu Ala Cys Tyr Ser Leu Leu Val Thr Val Ala Phe Ile Ile Phe Trp
        195                 200                 205

Val Arg Ser Lys Arg Ser Arg Gly Gly His Ser Asp Tyr Met Asn Met
    210                 215                 220

Thr Pro Arg Arg Pro Gly Pro Thr Arg Lys His Tyr Gln Pro Tyr Ala
225                 230                 235                 240

Pro Pro Arg Asp Phe Ala Ala Tyr Arg Ser
                245                 250
```

```
<210> SEQ ID NO 99
<211> LENGTH: 714
<212> TYPE: DNA
<213> ORGANISM: Artificial Sequence
<220> FEATURE:
<223> OTHER INFORMATION: huPD1-12aas-CD28Cys

<400> SEQUENCE: 99
atgcagatcc ctcaggcccc ttggcctgtc gtgtgggctg tgctgcagct gggatggcgg      60
cctggctggt ttctggacag ccccgacaga ccctggaacc ccctacatt ttcccctgcc      120 ctgctggtcg tgaccgaggg cgacaatgcc accttcacct gtagcttcag caacaccagc     180
gagagcttcg tgctgaactg gtacagaatg agccccagca accagaccga caagctggcc     240
gccttccccg aggatagatc tcagcccggc caggactgcc ggttcagagt gacccagctg     300
cccaacggcc gggacttcca catgtctgtc gtgcgggcca gacggaacga cagcggcaca     360
tatctgtgcg gcgccatcag cctggccccc aaggcccaga tcaaagagag cctgagagcc     420
gagctgagag tgaccgagag aagggccgaa gtgcctaccg cccacccctag cccatgtccc    480 agccctctgt tcccggcccc tagcaagcct ttctgggtgc tggtggtggt cggaggcgtg     540
ctggcctgct acagcctgct ggtcaccgtg gccttcatca tcttttgggt ccgcagcaag     600
cggagcagag gcggccacag cgactacatg aacatgaccc ctagacggcc tggccccacc    660
agaaagcact accagcccta cgcccctccc cgggactttg ccgcctacag aagc          714

<210> SEQ ID NO 100
<211> LENGTH: 238
<212> TYPE: PRT
<213> ORGANISM: Artificial Sequence
<220> FEATURE:
<223> OTHER INFORMATION: huPD1-12aas-CD28Cys

<400> SEQUENCE: 100

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Cys Pro
145                 150                 155                 160

Ser Pro Leu Phe Pro Gly Pro Ser Lys Pro Phe Trp Val Leu Val Val
                165                 170                 175

Val Gly Gly Val Leu Ala Cys Tyr Ser Leu Leu Val Thr Val Ala Phe
            180                 185                 190
```

```
Ile Ile Phe Trp Val Arg Ser Lys Arg Ser Arg Gly Gly His Ser Asp
            195                 200                 205

Tyr Met Asn Met Thr Pro Arg Arg Pro Gly Pro Thr Arg Lys His Tyr
        210                 215                 220

Gln Pro Tyr Ala Pro Pro Arg Asp Phe Ala Ala Tyr Arg Ser
225                 230                 235

<210> SEQ ID NO 101
<211> LENGTH: 705
<212> TYPE: DNA
<213> ORGANISM: Artificial Sequence
<220> FEATURE:
<223> OTHER INFORMATION: huPD1-15aas-CD28Cys

<400> SEQUENCE: 101
atgcagatcc ctcaggcccc ttggcctgtc gtgtgggctg tgctgcagct gggatggcgg      60
cctggctggt ttctggacag ccccgacaga ccctggaacc cccctacatt tccccctgcc     120
ctgctggtcg tgaccgaggg cgacaatgcc accttcacct gtagcttcag caacaccagc     180
gagagcttcg tgctgaactg gtacagaatg agccccagca accagaccga caagctggcc     240
gccttccccg aggatagatc tcagcccggc caggactgcc ggttcagagt gacccagctg     300
cccaacggcc gggacttcca catgtctgtc gtgcgggcca gacggaacga cagcggcaca     360
tatctgtgcg gcgccatcag cctggccccc aaggcccaga tcaaagagag cctgagagcc     420
gagctgagag tgaccgagag aagggccgaa gtgcctaccg ccactgtcc cagccctctg     480 tttccggcc ctagcaagcc tttctgggtg ctggtggtgg tcgaggcgt gctggcctgc     540 tacagcctgc tggtcaccgt ggccttcatc atctttggg tccgcagcaa gcggagcaga     600
ggcggccaca gcgactacat gaacatgacc cctagacggc ctggccccac cagaaagcac     660 taccagcct acgcccctcc ccgggacttt gccgcctaca gaagc                     705

<210> SEQ ID NO 102
<211> LENGTH: 235
<212> TYPE: PRT
<213> ORGANISM: Artificial Sequence
<220> FEATURE:
<223> OTHER INFORMATION: huPD1-15aas-CD28Cys

<400> SEQUENCE: 102

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140
```

Thr Glu Arg Arg Ala Glu Val Pro Thr Ala His Cys Pro Ser Pro Leu
145                 150                 155                 160

Phe Pro Gly Pro Ser Lys Pro Phe Trp Val Leu Val Val Val Gly Gly
            165                 170                 175

Val Leu Ala Cys Tyr Ser Leu Leu Val Thr Val Ala Phe Ile Ile Phe
            180                 185                 190

Trp Val Arg Ser Lys Arg Ser Arg Gly Gly His Ser Asp Tyr Met Asn
            195                 200                 205

Met Thr Pro Arg Arg Pro Gly Pro Thr Arg Lys His Tyr Gln Pro Tyr
    210                 215                 220

Ala Pro Pro Arg Asp Phe Ala Ala Tyr Arg Ser
225                 230                 235

<210> SEQ ID NO 103
<211> LENGTH: 687
<212> TYPE: DNA
<213> ORGANISM: Artificial Sequence
<220> FEATURE:
<223> OTHER INFORMATION: huPD1-21aas-CD28Cys

<400> SEQUENCE: 103
atgcagatcc ctcaggcccc ttggcctgtc gtgtgggctg tgctgcagct gggatggcgg      60
cctggctggt ttctggacag ccccgacaga ccctggaacc ccctacatt ttcccctgcc     120 ctgctggtcg tgaccgaggg cgacaatgcc accttcacct gtagcttcag caacaccagc     180
gagagcttcg tgctgaactg gtacagaatg agcccagca accagaccga caagctggcc     240
gccttccccg aggatagatc tcagcccggc caggactgcc ggttcagagt gacccagctg     300
cccaacggcc gggacttcca catgtctgtc gtgcgggcca cggaacga cagcggcaca     360 tatctgtgcg gcgccatcag cctggccccc aaggcccaga tcaaagagag cctgagagcc     420
gagctgagag tgaccgagag aagggcctgt cccagccctc tgtttcccgg ccctagcaag     480
cctttctggg tgctggtggt ggtcggaggc gtgctggcct gctacagcct gctggtcacc     540
gtggccttca tcatcttttg ggtccgcagc aagcggagca gaggcggcca cagcgactac     600
atgaacatga cccctagacg gcctggcccc accagaaagc actaccagcc ctacgcccct     660
ccccgggact tgccgcctta cagaagc     687

<210> SEQ ID NO 104
<211> LENGTH: 229
<212> TYPE: PRT
<213> ORGANISM: Artificial Sequence
<220> FEATURE:
<223> OTHER INFORMATION: huPD1-21aas-CD28Cys

<400> SEQUENCE: 104

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg

```
            85                  90                  95
Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
            130                 135                 140

Thr Glu Arg Arg Ala Cys Pro Ser Pro Leu Phe Pro Gly Pro Ser Lys
145                 150                 155                 160

Pro Phe Trp Val Leu Val Val Gly Val Leu Ala Cys Tyr Ser
                    165                 170                 175

Leu Leu Val Thr Val Ala Phe Ile Ile Phe Trp Val Arg Ser Lys Arg
            180                 185                 190

Ser Arg Gly Gly His Ser Asp Tyr Met Asn Met Thr Pro Arg Arg Pro
            195                 200                 205

Gly Pro Thr Arg Lys His Tyr Gln Pro Tyr Ala Pro Pro Arg Asp Phe
            210                 215                 220

Ala Ala Tyr Arg Ser
225

<210> SEQ ID NO 105
<211> LENGTH: 810
<212> TYPE: DNA
<213> ORGANISM: Artificial Sequence
<220> FEATURE:
<223> OTHER INFORMATION: muCD2tm-CD28

<400> SEQUENCE: 105
atgaagtgca agttcctggg ctcattcttc ctgctgttca gcctgagcgg caagggcgcc      60
gactgcagag acaacgagac aatctggggc gtgctgggcc acggcatcac cctgaacatc     120
cccaacttcc agatgaccga cgacatcgac gaagtcgcgct gggtgcgaag aggcacactg    180
gtggccgagt tcaagagaaa gaagccccca ttcctgatca gcgagacata cgaggtgctg     240
gccaacggca gcctgaagat caagaaaccc atgatgagaa acgacagcgg cacctacaac     300
gtgatggtgt acggcaccaa cggcatgacc agactggaaa aggacctgga cgtgcggatc     360
ctggaaaggg tgtccaagcc catgatccac tgggagtgcc ccaacaccac cctgacctgt     420
gctgtgctgc agggcaccga cttcgagctg aagctgtacc agggcgagac actgctgaac     480
tccctgcccc agaaaaacat gagctaccag tggaccaacc tgaacgcccc cttcaagtgc     540
gaggccatca ccccgtgtc caaagaaagc aagatggaag tcgtgaactg ccccgagaag      600
ggcctgagct tctacgtgac agtgggcgtg ggagctggcg gactgctgct ggtgctgctg     660
gtggccctgt tcatcttctg catctgcaac agcagacgga acagaggcgg ccagagcgac     720
tacatgaaca tgacccccag aaggcctggc ctgaccagaa agccctacca gccttacgcc     780
cctgccagag acttcgccgc ctacagacct                                      810

<210> SEQ ID NO 106
<211> LENGTH: 270
<212> TYPE: PRT
<213> ORGANISM: Artificial Sequence
<220> FEATURE:
<223> OTHER INFORMATION: muCD2tm-CD28

<400> SEQUENCE: 106

Met Lys Cys Lys Phe Leu Gly Ser Phe Phe Leu Leu Phe Ser Leu Ser
1               5                   10                  15
```

Gly Lys Gly Ala Asp Cys Arg Asp Asn Glu Thr Ile Trp Gly Val Leu
             20                  25                  30

Gly His Gly Ile Thr Leu Asn Ile Pro Asn Phe Gln Met Thr Asp Asp
         35                  40                  45

Ile Asp Glu Val Arg Trp Val Arg Arg Gly Thr Leu Val Ala Glu Phe
 50                  55                  60

Lys Arg Lys Lys Pro Pro Phe Leu Ile Ser Glu Thr Tyr Glu Val Leu
 65                  70                  75                  80

Ala Asn Gly Ser Leu Lys Ile Lys Lys Pro Met Met Arg Asn Asp Ser
                 85                  90                  95

Gly Thr Tyr Asn Val Met Val Tyr Gly Thr Asn Gly Met Thr Arg Leu
            100                 105                 110

Glu Lys Asp Leu Asp Val Arg Ile Leu Glu Arg Val Ser Lys Pro Met
        115                 120                 125

Ile His Trp Glu Cys Pro Asn Thr Thr Leu Thr Cys Ala Val Leu Gln
130                 135                 140

Gly Thr Asp Phe Glu Leu Lys Leu Tyr Gln Gly Glu Thr Leu Leu Asn
145                 150                 155                 160

Ser Leu Pro Gln Lys Asn Met Ser Tyr Gln Trp Thr Asn Leu Asn Ala
                165                 170                 175

Pro Phe Lys Cys Glu Ala Ile Asn Pro Val Ser Lys Glu Ser Lys Met
            180                 185                 190

Glu Val Val Asn Cys Pro Glu Lys Gly Leu Ser Phe Tyr Val Thr Val
        195                 200                 205

Gly Val Gly Ala Gly Leu Leu Val Leu Leu Val Ala Leu Phe
210                 215                 220

Ile Phe Cys Ile Cys Asn Ser Arg Arg Asn Arg Gly Gly Gln Ser Asp
225                 230                 235                 240

Tyr Met Asn Met Thr Pro Arg Arg Pro Gly Leu Thr Arg Lys Pro Tyr
                245                 250                 255

Gln Pro Tyr Ala Pro Ala Arg Asp Phe Ala Ala Tyr Arg Pro
            260                 265                 270

<210> SEQ ID NO 107
<211> LENGTH: 813
<212> TYPE: DNA
<213> ORGANISM: Artificial Sequence
<220> FEATURE:
<223> OTHER INFORMATION: muCD2-CD28tm

<400> SEQUENCE: 107
atgaagtgca agttcctggg ctcattcttc ctgctgttca gcctgagcgg caagggcgcc      60
gactgcagag acaacgagac aatctggggc gtgctggcc acggcatcac cctgaacatc     120
cccaacttcc agatgaccga cgacatcgac gaagtgcgct gggtgcgaag aggcacactg     180
gtggccgagt tcaagagaaa gaagcccca ttcctgatca gcgagacata cgaggtgctg     240
gccaacggca gcctgaagat caagaaaccc atgatgagaa acgacagcgg cacctacaac     300
gtgatggtgt acggcaccaa cggcatgacc agactggaaa aggacctgga cgtgcggatc     360
ctggaaaggg tgtccaagcc catgatccac tgggagtgcc caacaccac cctgacctgt     420 gctgtgctgc agggcaccga cttcgagctg aagctgtacc agggcgagac actgctgaac     480
tccctgcccc agaaaaacat gagctaccag tggaccaacc tgaacgcccc cttcaagtgc     540
gaggccatca cccccgtgtc caagaaagc aagatggaag tcgtgaactg ccccgagaag     600

```
ggcctgagct tctgggccct ggtggtggtg gccggcgtgc tgttttgtta cggcctgctc    660
gtgaccgtgg ccctgtgcgt gatctggacc aacagcagaa gaaacagagg cggccagagc    720
gactacatga acatgacccc cagaaggcct ggcctgacca gaaagcccta ccagccttac    780
gcccctgcca gagacttcgc cgcctacaga ccc                                 813
```

<210> SEQ ID NO 108
<211> LENGTH: 271
<212> TYPE: PRT
<213> ORGANISM: Artificial Sequence
<220> FEATURE:
<223> OTHER INFORMATION: muCD2-CD28tm

<400> SEQUENCE: 108

```
Met Lys Cys Lys Phe Leu Gly Ser Phe Phe Leu Leu Phe Ser Leu Ser
1               5                   10                  15

Gly Lys Gly Ala Asp Cys Arg Asp Asn Glu Thr Ile Trp Gly Val Leu
            20                  25                  30

Gly His Gly Ile Thr Leu Asn Ile Pro Asn Phe Gln Met Thr Asp Asp
        35                  40                  45

Ile Asp Glu Val Arg Trp Val Arg Arg Gly Thr Leu Val Ala Glu Phe
50                  55                  60

Lys Arg Lys Lys Pro Pro Phe Leu Ile Ser Glu Thr Tyr Glu Val Leu
65                  70                  75                  80

Ala Asn Gly Ser Leu Lys Ile Lys Lys Pro Met Met Arg Asn Asp Ser
                85                  90                  95

Gly Thr Tyr Asn Val Met Val Tyr Gly Thr Asn Gly Met Thr Arg Leu
            100                 105                 110

Glu Lys Asp Leu Asp Val Arg Ile Leu Glu Arg Val Ser Lys Pro Met
        115                 120                 125

Ile His Trp Glu Cys Pro Asn Thr Thr Leu Thr Cys Ala Val Leu Gln
    130                 135                 140

Gly Thr Asp Phe Glu Leu Lys Leu Tyr Gln Gly Glu Thr Leu Leu Asn
145                 150                 155                 160

Ser Leu Pro Gln Lys Asn Met Ser Tyr Gln Trp Thr Asn Leu Asn Ala
                165                 170                 175

Pro Phe Lys Cys Glu Ala Ile Asn Pro Val Ser Lys Glu Ser Lys Met
            180                 185                 190

Glu Val Val Asn Cys Pro Glu Lys Gly Leu Ser Phe Trp Ala Leu Val
        195                 200                 205

Val Val Ala Gly Val Leu Phe Cys Tyr Gly Leu Leu Val Thr Val Ala
    210                 215                 220

Leu Cys Val Ile Trp Thr Asn Ser Arg Arg Asn Arg Gly Gly Gln Ser
225                 230                 235                 240

Asp Tyr Met Asn Met Thr Pro Arg Arg Pro Gly Leu Thr Arg Lys Pro
                245                 250                 255

Tyr Gln Pro Tyr Ala Pro Ala Arg Asp Phe Ala Ala Tyr Arg Pro
            260                 265                 270
```

<210> SEQ ID NO 109
<211> LENGTH: 840
<212> TYPE: DNA
<213> ORGANISM: Artificial Sequence
<220> FEATURE:
<223> OTHER INFORMATION: muCD2-CD28Cys

<400> SEQUENCE: 109

```
atgaagtgca agttcctggg ctcattcttc ctgctgttca gcctgagcgg caagggcgcc    60
gactgcagag acaacgagac aatctggggc gtgctgggcc acggcatcac cctgaacatc   120
cccaacttcc agatgaccga cgacatcgac gaagtgcgct gggtgcgaag aggcacactg   180
gtggccgagt tcaagagaaa gaagccccca ttcctgatca gcgagacata cgaggtgctg   240
gccaacggca gcctgaagat caagaaaccc atgatgagaa acgacagcgg cacctacaac   300
gtgatggtgt acggcaccaa cggcatgacc agactggaaa aggacctgga cgtgcggatc   360
ctggaaaggg tgtccaagcc catgatccac tgggagtgcc ccaacaccac cctgacctgt   420
gctgtgctgc agggcaccga cttcgagctg aagctgtacc agggcgagac actgctgaac   480
tccctgcccc agaaaaacat gagctaccag tggaccaacc tgaacgcccc cttcaagtgc   540
gaggccatca cccccgtgtc caaagaaagc aagatggaag tcgtgaactg ccccgagaag   600
ggcctgagct gccacaccca gagcagcccc aagctgttct gggccctggt ggtggtggcc   660
ggcgtgctgt tttgttacgg cctgctcgtg accgtggccc tgtgcgtgat ctggaccaac   720
agcagaagaa acagaggcgg ccagagcgac tacatgaaca tgaccccag aaggcctggc   780
ctgaccagaa agccctacca gccttacgcc cctgccagag acttcgccgc ctacagacct   840
```

<210> SEQ ID NO 110
<211> LENGTH: 280
<212> TYPE: PRT
<213> ORGANISM: Artificial Sequence
<220> FEATURE:
<223> OTHER INFORMATION: muCD2-CD28Cys

<400> SEQUENCE: 110

```
Met Lys Cys Lys Phe Leu Gly Ser Phe Phe Leu Leu Phe Ser Leu Ser
1               5                   10                  15
Gly Lys Gly Ala Asp Cys Arg Asp Asn Glu Thr Ile Trp Gly Val Leu
            20                  25                  30
Gly His Gly Ile Thr Leu Asn Ile Pro Asn Phe Gln Met Thr Asp Asp
        35                  40                  45
Ile Asp Glu Val Arg Trp Val Arg Arg Gly Thr Leu Val Ala Glu Phe
    50                  55                  60
Lys Arg Lys Lys Pro Pro Phe Leu Ile Ser Glu Thr Tyr Glu Val Leu
65                  70                  75                  80
Ala Asn Gly Ser Leu Lys Ile Lys Lys Pro Met Met Arg Asn Asp Ser
                85                  90                  95
Gly Thr Tyr Asn Val Met Val Tyr Gly Thr Asn Gly Met Thr Arg Leu
            100                 105                 110
Glu Lys Asp Leu Asp Val Arg Ile Leu Glu Arg Val Ser Lys Pro Met
        115                 120                 125
Ile His Trp Glu Cys Pro Asn Thr Thr Leu Thr Cys Ala Val Leu Gln
    130                 135                 140
Gly Thr Asp Phe Glu Leu Lys Leu Tyr Gln Gly Glu Thr Leu Leu Asn
145                 150                 155                 160
Ser Leu Pro Gln Lys Asn Met Ser Tyr Gln Trp Thr Asn Leu Asn Ala
                165                 170                 175
Pro Phe Lys Cys Glu Ala Ile Asn Pro Val Ser Lys Glu Ser Lys Met
            180                 185                 190
Glu Val Val Asn Cys Pro Glu Lys Gly Leu Ser Cys His Thr Gln Ser
        195                 200                 205
Ser Pro Lys Leu Phe Trp Ala Leu Val Val Val Ala Gly Val Leu Phe
    210                 215                 220
```

Cys Tyr Gly Leu Leu Val Thr Val Ala Leu Cys Val Ile Trp Thr Asn
225                 230                 235                 240

Ser Arg Arg Asn Arg Gly Gly Gln Ser Asp Tyr Met Asn Met Thr Pro
            245                 250                 255

Arg Arg Pro Gly Leu Thr Arg Lys Pro Tyr Gln Pro Tyr Ala Pro Ala
        260                 265                 270

Arg Asp Phe Ala Ala Tyr Arg Pro
        275                 280

<210> SEQ ID NO 111
<211> LENGTH: 861
<212> TYPE: DNA
<213> ORGANISM: Artificial Sequence
<220> FEATURE:
<223> OTHER INFORMATION: muCD2-CD28Cys-41BBic

<400> SEQUENCE: 111

| | | | |
|---|---|---|---|
| atgaagtgca agttcctggg ctcattcttc ctgctgttca gcctgagcgg caagggcgcc | 60 |
| gactgcagag acaacgagac aatctggggc gtgctgggcc acggcatcac cctgaacatc | 120 |
| cccaacttcc agatgaccga cgacatcgac gaagtgcgct gggtgcgaag aggcacactg | 180 |
| gtggccgagt tcaagagaaa gaagccccca ttcctgatca gcgagacata cgaggtgctg | 240 |
| gccaacggca gcctgaagat caagaaaccc atgatgagaa acgacagcgg cacctacaac | 300 |
| gtgatggtgt acggcaccaa cggcatgacc agactggaaa aggacctgga cgtgcggatc | 360 |
| ctggaaaggg tgtccaagcc catgatccac tgggagtgcc ccaacaccac cctgacctgt | 420 |
| gctgtgctgc agggcaccga cttcgagctg aagctgtacc agggcgagac actgctgaac | 480 |
| tccctgcccc agaaaaacat gagctaccag tggaccaacc tgaacgcccc cttcaagtgc | 540 |
| gaggccatca cccccgtgtc caagaaagc aagatggaag tcgtgaactg ccccgagaag | 600 |
| ggcctgagct gccacaccca gagcagcccc aagctgttct gggccctggt ggtggtggcc | 660 |
| ggcgtgctgt tttgttacgg cctgctcgtg accgtggccc tgtgcgtgat ctggaccagc | 720 |
| gtgctgaagt ggatcagaaa gaagttcccc cacatcttca gcagcccctt caagaaaacc | 780 |
| accggcgctg cccaggaaga ggacgcctgc agctgtagat gccctcagga agaagaaggc | 840 |
| ggcggaggcg gctacgagct g | 861 |

<210> SEQ ID NO 112
<211> LENGTH: 287
<212> TYPE: PRT
<213> ORGANISM: Artificial Sequence
<220> FEATURE:
<223> OTHER INFORMATION: muCD2-CD28Cys-41BBic

<400> SEQUENCE: 112

Met Lys Cys Lys Phe Leu Gly Ser Phe Phe Leu Leu Phe Ser Leu Ser
1               5                   10                  15

Gly Lys Gly Ala Asp Cys Arg Asp Asn Glu Thr Ile Trp Gly Val Leu
            20                  25                  30

Gly His Gly Ile Thr Leu Asn Ile Pro Asn Phe Gln Met Thr Asp Asp
        35                  40                  45

Ile Asp Glu Val Arg Trp Val Arg Arg Gly Thr Leu Val Ala Glu Phe
    50                  55                  60

Lys Arg Lys Lys Pro Pro Phe Leu Ile Ser Glu Thr Tyr Glu Val Leu
65                  70                  75                  80

Ala Asn Gly Ser Leu Lys Ile Lys Lys Pro Met Met Arg Asn Asp Ser

-continued

```
                85                  90                  95
Gly Thr Tyr Asn Val Met Val Tyr Gly Thr Asn Gly Met Thr Arg Leu
            100                 105                 110
Glu Lys Asp Leu Asp Val Arg Ile Leu Glu Arg Val Ser Lys Pro Met
        115                 120                 125
Ile His Trp Glu Cys Pro Asn Thr Thr Leu Thr Cys Ala Val Leu Gln
    130                 135                 140
Gly Thr Asp Phe Glu Leu Lys Leu Tyr Gln Gly Glu Thr Leu Leu Asn
145                 150                 155                 160
Ser Leu Pro Gln Lys Asn Met Ser Tyr Gln Trp Thr Asn Leu Asn Ala
                165                 170                 175
Pro Phe Lys Cys Glu Ala Ile Asn Pro Val Ser Lys Glu Ser Lys Met
            180                 185                 190
Glu Val Val Asn Cys Pro Glu Lys Gly Leu Ser Cys His Thr Gln Ser
        195                 200                 205
Ser Pro Lys Leu Phe Trp Ala Leu Val Val Ala Gly Val Leu Phe
    210                 215                 220
Cys Tyr Gly Leu Leu Val Thr Val Ala Leu Cys Val Ile Trp Thr Ser
225                 230                 235                 240
Val Leu Lys Trp Ile Arg Lys Lys Phe Pro His Ile Phe Lys Gln Pro
                245                 250                 255
Phe Lys Thr Thr Gly Ala Ala Gln Glu Glu Asp Ala Cys Ser Cys
            260                 265                 270
Arg Cys Pro Gln Glu Glu Glu Gly Gly Gly Gly Tyr Glu Leu
        275                 280                 285
```

<210> SEQ ID NO 113
<211> LENGTH: 1080
<212> TYPE: DNA
<213> ORGANISM: Artificial Sequence
<220> FEATURE:
<223> OTHER INFORMATION: muCD200R-3aas-CD28Cys tm ic-41BB

<400> SEQUENCE: 113

```
atgttctgct tctggcggac aagcgccctg gccgtgctgc tgatctgggg agtgtttgtg      60
gccggcagca gctgcaccga caagaaccag accacccaga caacagcag cagccccctg     120
acccaagtga caccaccgt gtccgtgcag atcggcacca aggccctgct gtgctgtttc     180
agcatccctc tgaccaaggc tgtgctgatc acctggatca tcaagctgag aggcctgccc     240
agctgcacaa tcgcctacaa ggtggacacc aagaccaacg agacaagctg cctgggcaga     300
aacatcacct gggccagcac cccagaccac agccctgagc tgcagatcag cgccgtgaca     360
ctgcagcacg agggcaccta cacatgcgag acagtgaccc cgagggcaa cttcgagaag     420
aactacgatc tgcaggtgct ggtgccccc gaagtgacct acttccccga agaaataga     480
agcgccgtgt gcgaggccat ggctggcaaa cctgccgccc agatctcttg gagccctgac     540
ggcgactgtg tgaccaccag cgagagccac agcaacggca cagtgaccgt gcggagcacc     600
tgtcactggg agcagaacaa cgtgtccgac gtgtcctgca tcgtgtccca cctgaccggc     660
aaccagagcc tgagcatcga gctgagcaga ggcggaaacc agtcctgcca cacccagagc     720
agccccaagc tgttctgggc cctggtggtg gtggccggcg tgctgttttg ttacggcctg     780
ctcgtgaccg tggccctgtg cgtgatctgg accaacagca agaaacag aggcggccag     840
agcgactaca tgaacatgac ccccagaagg cctggcctga ccagaaagcc ctaccagcct     900
tacgcccctg ccagagactt cgccgcctac agacctagcg tgctgaagtg gatcagaaag     960
```

```
aagttccccc acatcttcaa gcagcccttc aagaaaacca ccggcgctgc ccaggaagag    1020
gacgcctgca gctgtagatg ccctcaggaa gaagaaggcg gcggaggcgg ctacgagctg    1080
```

<210> SEQ ID NO 114
<211> LENGTH: 360
<212> TYPE: PRT
<213> ORGANISM: Artificial Sequence
<220> FEATURE:
<223> OTHER INFORMATION: muCD200R-3aas-CD28Cys tm ic-41BB

<400> SEQUENCE: 114

```
Met Phe Cys Phe Trp Arg Thr Ser Ala Leu Ala Val Leu Leu Ile Trp
1               5                   10                  15

Gly Val Phe Val Ala Gly Ser Ser Cys Thr Asp Lys Asn Gln Thr Thr
            20                  25                  30

Gln Asn Asn Ser Ser Ser Pro Leu Thr Gln Val Asn Thr Thr Val Ser
        35                  40                  45

Val Gln Ile Gly Thr Lys Ala Leu Leu Cys Cys Phe Ser Ile Pro Leu
    50                  55                  60

Thr Lys Ala Val Leu Ile Thr Trp Ile Ile Lys Leu Arg Gly Leu Pro
65                  70                  75                  80

Ser Cys Thr Ile Ala Tyr Lys Val Asp Thr Lys Thr Asn Glu Thr Ser
                85                  90                  95

Cys Leu Gly Arg Asn Ile Thr Trp Ala Ser Thr Pro Asp His Ser Pro
            100                 105                 110

Glu Leu Gln Ile Ser Ala Val Thr Leu Gln His Glu Gly Thr Tyr Thr
        115                 120                 125

Cys Glu Thr Val Thr Pro Glu Gly Asn Phe Glu Lys Asn Tyr Asp Leu
    130                 135                 140

Gln Val Leu Val Pro Pro Glu Val Thr Tyr Phe Pro Glu Lys Asn Arg
145                 150                 155                 160

Ser Ala Val Cys Glu Ala Met Ala Gly Lys Pro Ala Ala Gln Ile Ser
                165                 170                 175

Trp Ser Pro Asp Gly Asp Cys Val Thr Thr Ser Glu Ser His Ser Asn
            180                 185                 190

Gly Thr Val Thr Val Arg Ser Thr Cys His Trp Glu Gln Asn Asn Val
        195                 200                 205

Ser Asp Val Ser Cys Ile Val Ser His Leu Thr Gly Asn Gln Ser Leu
    210                 215                 220

Ser Ile Glu Leu Ser Arg Gly Gly Asn Gln Ser Cys His Thr Gln Ser
225                 230                 235                 240

Ser Pro Lys Leu Phe Trp Ala Leu Val Val Val Ala Gly Val Leu Phe
                245                 250                 255

Cys Tyr Gly Leu Leu Val Thr Val Ala Leu Cys Val Ile Trp Thr Asn
            260                 265                 270

Ser Arg Arg Asn Arg Gly Gly Gln Ser Asp Tyr Met Asn Met Thr Pro
        275                 280                 285

Arg Arg Pro Gly Leu Thr Arg Lys Pro Tyr Gln Pro Tyr Ala Pro Ala
    290                 295                 300

Arg Asp Phe Ala Ala Tyr Arg Pro Ser Val Leu Lys Trp Ile Arg Lys
305                 310                 315                 320

Lys Phe Pro His Ile Phe Lys Gln Pro Phe Lys Lys Thr Thr Gly Ala
                325                 330                 335

Ala Gln Glu Glu Asp Ala Cys Ser Cys Arg Cys Pro Gln Glu Glu Glu
```

```
                    340                 345                 350
Gly Gly Gly Gly Gly Tyr Glu Leu
                355                 360

<210> SEQ ID NO 115
<211> LENGTH: 966
<212> TYPE: DNA
<213> ORGANISM: Artificial Sequence
<220> FEATURE:
<223> OTHER INFORMATION: muCD200R-CD28Cys tm ic-41BB

<400> SEQUENCE: 115
atgttctgct tctggcggac aagcgccctg gccgtgctgc tgatctgggg agtgtttgtg      60
gccggcagca gctgcaccga caagaaccag accacccaga caacagcag  cagccccctg     120 acccaagtga acaccaccgt gtccgtgcag atcggcacca aggccctgct gtgctgtttc     180
agcatccctc tgaccaaggc tgtgctgatc acctggatca tcaagctgag aggcctgccc     240
agctgcacaa tcgcctacaa ggtggacacc aagaccaacg agacaagctg cctgggcaga     300
aacatcacct gggccagcac cccagaccac agccctgagc tgcagatcag cgccgtgaca     360
ctgcagcacg agggcaccta cacatgcgag acagtgaccc ccgagggcaa cttcgagaag     420
aactacgatc tgcaggtgct ggtgcccccc gaagtgacct acttccccga agaataga       480 agcgccgtgt gcgaggccat ggctggcaaa cctgccgccc agatctcttg gagccctgac     540
ggcgactgtg tgaccaccag cgagagccac agcaacggca gtgaccgt    gcggagcacc    600 tgtcactggg agcagaacaa cgtgtccgac gtgtcctgca tcgtgtccca cctgaccggc     660
aaccagagcc tgagcatcga gctgagcaga ggcggaaacc agtccctgag gccctgccac     720
acccagagca gccccaagct gttctgggcc ctggtggtgg tggccggcgt gctgttttgt     780
tacggcctgc tcgtgaccgt ggccctgtgc gtgatctgga ccagcgtgct gaagtggatc     840
agaaagaagt tcccccacat cttcaagcag cccttcaaga aaaccaccgg cgctgcccag     900
gaagaggacg cctgcagctg tagatgccct caggaagaag aaggcggcgg aggcggctac     960
gagctg                                                                966

<210> SEQ ID NO 116
<211> LENGTH: 322
<212> TYPE: PRT
<213> ORGANISM: Artificial Sequence
<220> FEATURE:
<223> OTHER INFORMATION: muCD200R-CD28Cys tm ic-41BB

<400> SEQUENCE: 116

Met Phe Cys Phe Trp Arg Thr Ser Ala Leu Ala Val Leu Leu Ile Trp
1               5                   10                  15

Gly Val Phe Val Ala Gly Ser Ser Cys Thr Asp Lys Asn Gln Thr Thr
            20                  25                  30

Gln Asn Asn Ser Ser Ser Pro Leu Thr Gln Val Asn Thr Thr Val Ser
        35                  40                  45

Val Gln Ile Gly Thr Lys Ala Leu Leu Cys Cys Phe Ser Ile Pro Leu
    50                  55                  60

Thr Lys Ala Val Leu Ile Thr Trp Ile Ile Lys Leu Arg Gly Leu Pro
65                  70                  75                  80

Ser Cys Thr Ile Ala Tyr Lys Val Asp Thr Lys Thr Asn Glu Thr Ser
                85                  90                  95

Cys Leu Gly Arg Asn Ile Thr Trp Ala Ser Thr Pro Asp His Ser Pro
            100                 105                 110
```

```
Glu Leu Gln Ile Ser Ala Val Thr Leu Gln His Glu Gly Thr Tyr Thr
        115                 120                 125
Cys Glu Thr Val Thr Pro Glu Gly Asn Phe Glu Lys Asn Tyr Asp Leu
    130                 135                 140
Gln Val Leu Val Pro Pro Glu Val Thr Tyr Phe Pro Glu Lys Asn Arg
145                 150                 155                 160
Ser Ala Val Cys Glu Ala Met Ala Gly Lys Pro Ala Ala Gln Ile Ser
                165                 170                 175
Trp Ser Pro Asp Gly Asp Cys Val Thr Thr Ser Glu Ser His Ser Asn
            180                 185                 190
Gly Thr Val Thr Val Arg Ser Thr Cys His Trp Glu Gln Asn Asn Val
        195                 200                 205
Ser Asp Val Ser Cys Ile Val Ser His Leu Thr Gly Asn Gln Ser Leu
    210                 215                 220
Ser Ile Glu Leu Ser Arg Gly Gly Asn Gln Ser Leu Arg Pro Cys His
225                 230                 235                 240
Thr Gln Ser Ser Pro Lys Leu Phe Trp Ala Leu Val Val Val Ala Gly
                245                 250                 255
Val Leu Phe Cys Tyr Gly Leu Leu Val Thr Val Ala Leu Cys Val Ile
            260                 265                 270
Trp Thr Ser Val Leu Lys Trp Ile Arg Lys Lys Phe Pro His Ile Phe
        275                 280                 285
Lys Gln Pro Phe Lys Lys Thr Thr Gly Ala Ala Gln Glu Glu Asp Ala
    290                 295                 300
Cys Ser Cys Arg Cys Pro Gln Glu Glu Glu Gly Gly Gly Gly Gly Tyr
305                 310                 315                 320
Glu Leu

<210> SEQ ID NO 117
<211> LENGTH: 681
<212> TYPE: DNA
<213> ORGANISM: Artificial Sequence
<220> FEATURE:
<223> OTHER INFORMATION: muFas tm-CD28

<400> SEQUENCE: 117
atgctgtgga tctgggccgt gctgcctctg gtgctggctg atcacagct  gagagtgcac    60 acccagggca ccaacagcat cagcgagagc ctgaagctga agaagagt  gcgcgagaca   120 gacaagaact gcagcgaggg cctgtaccag ggcggaccct tctgctgtca gccttgccag   180
cccggcaaga aaaggtgga  agattgcaag atgaacggcg caccCctac  ctgcgcccct   240 tgtacagagg gcaaagagta catggacaag aaccactacg ccgacaagtg cagacggtgc   300
accctgtgcg acgaggaaca cggcctggaa gtggaaacaa actgcaccct gacccagaac   360
accaagtgca gtgcaaaacc cgacttctac tgcgacagcc ccggctgcga gcactgcgtc   420
agatgtgcct cttgcgagca cggcacCctg gaaccttgta ccgccaccag caacaccaac   480
tgccggaagc agagccccag aaacagactg tggctgctga ccatcctggt gctgctgatc   540
cccctggtgt tcatctacaa cagcagaaga aacagaggcg ccagagcga  ctacatgaac   600 atgacccca  gaaggcctgg cctgaccaga aagccctacc agccttacgc ccctgccaga   660
gacttcgccg cctacagacc t                                             681

<210> SEQ ID NO 118
<211> LENGTH: 227
```

<212> TYPE: PRT
<213> ORGANISM: Artificial Sequence
<220> FEATURE:
<223> OTHER INFORMATION: muFas tm-CD28

<400> SEQUENCE: 118

```
Met Leu Trp Ile Trp Ala Val Leu Pro Leu Val Leu Ala Gly Ser Gln
1               5                   10                  15

Leu Arg Val His Thr Gln Gly Thr Asn Ser Ile Ser Glu Ser Leu Lys
            20                  25                  30

Leu Arg Arg Arg Val Arg Glu Thr Asp Lys Asn Cys Ser Glu Gly Leu
        35                  40                  45

Tyr Gln Gly Gly Pro Phe Cys Cys Gln Pro Cys Gln Pro Gly Lys Lys
    50                  55                  60

Lys Val Glu Asp Cys Lys Met Asn Gly Gly Thr Pro Thr Cys Ala Pro
65                  70                  75                  80

Cys Thr Glu Gly Lys Glu Tyr Met Asp Lys Asn His Tyr Ala Asp Lys
                85                  90                  95

Cys Arg Arg Cys Thr Leu Cys Asp Glu His Gly Leu Glu Val Glu
            100                 105                 110

Thr Asn Cys Thr Leu Thr Gln Asn Thr Lys Cys Lys Cys Lys Pro Asp
            115                 120                 125

Phe Tyr Cys Asp Ser Pro Gly Cys Glu His Cys Val Arg Cys Ala Ser
    130                 135                 140

Cys Glu His Gly Thr Leu Glu Pro Cys Thr Ala Thr Ser Asn Thr Asn
145                 150                 155                 160

Cys Arg Lys Gln Ser Pro Arg Asn Arg Leu Trp Leu Leu Thr Ile Leu
                165                 170                 175

Val Leu Leu Ile Pro Leu Val Phe Ile Tyr Asn Ser Arg Arg Asn Arg
            180                 185                 190

Gly Gly Gln Ser Asp Tyr Met Asn Met Thr Pro Arg Arg Pro Gly Leu
        195                 200                 205

Thr Arg Lys Pro Tyr Gln Pro Tyr Ala Pro Ala Arg Asp Phe Ala Ala
    210                 215                 220

Tyr Arg Pro
225
```

<210> SEQ ID NO 119
<211> LENGTH: 711
<212> TYPE: DNA
<213> ORGANISM: Artificial Sequence
<220> FEATURE:
<223> OTHER INFORMATION: muFas-CD28tm

<400> SEQUENCE: 119

| | |
|---|---|
| atgctgtgga tctgggccgt gctgcctctg gtgctggctg gatcacagct gagagtgcac | 60 |
| acccagggca ccaacagcat cagcgagagc ctgaagctga agaagagt gcgcgagaca | 120 |
| gacaagaact gcagcgaggg cctgtaccag ggcggaccct tctgctgtca gccttgccag | 180 |
| cccggcaaga aaaaggtgga agattgcaag atgaacggcg gcacccctac ctgcgcccct | 240 |
| tgtacagagg gcaaagagta catggacaag aaccactacg ccgacaagtg cagacggtgc | 300 |
| accctgtgcg acgaggaaca cggcctggaa gtggaaacaa actgcaccct gacccagaac | 360 |
| accaagtgca agtgcaaacc cgacttctac tgcgacagcc ccggctgcga gcactgcgtc | 420 |
| agatgtgcct cttgcgagca cggcaccctg gaacctgta ccgccaccag caacaccaac | 480 |
| tgccggaagc agagccccag aaacagattc tgggccctgg tggtggtggc cggcgtgctg | 540 |

```
ttttgttacg gcctgctcgt gaccgtggcc ctgtgcgtga tctggaccaa cagcagaaga    600
aacagaggcg gccagagcga ctacatgaac atgacccca gaaggcctgg cctgaccaga     660
aagccctacc agccttacgc ccctgccaga gacttcgccg cctacagacc t             711
```

<210> SEQ ID NO 120
<211> LENGTH: 237
<212> TYPE: PRT
<213> ORGANISM: Artificial Sequence
<220> FEATURE:
<223> OTHER INFORMATION: muFas-CD28tm

<400> SEQUENCE: 120

```
Met Leu Trp Ile Trp Ala Val Leu Pro Leu Val Leu Ala Gly Ser Gln
1               5                   10                  15

Leu Arg Val His Thr Gln Gly Thr Asn Ser Ile Ser Glu Ser Leu Lys
            20                  25                  30

Leu Arg Arg Arg Val Arg Glu Thr Asp Lys Asn Cys Ser Glu Gly Leu
        35                  40                  45

Tyr Gln Gly Gly Pro Phe Cys Cys Gln Pro Cys Gln Pro Gly Lys Lys
    50                  55                  60

Lys Val Glu Asp Cys Lys Met Asn Gly Gly Thr Pro Thr Cys Ala Pro
65                  70                  75                  80

Cys Thr Glu Gly Lys Glu Tyr Met Asp Lys Asn His Tyr Ala Asp Lys
                85                  90                  95

Cys Arg Arg Cys Thr Leu Cys Asp Glu Glu His Gly Leu Glu Val Glu
            100                 105                 110

Thr Asn Cys Thr Leu Thr Gln Asn Thr Lys Cys Lys Cys Lys Pro Asp
        115                 120                 125

Phe Tyr Cys Asp Ser Pro Gly Cys Glu His Cys Val Arg Cys Ala Ser
    130                 135                 140

Cys Glu His Gly Thr Leu Glu Pro Cys Thr Ala Thr Ser Asn Thr Asn
145                 150                 155                 160

Cys Arg Lys Gln Ser Pro Arg Asn Arg Phe Trp Ala Leu Val Val Val
                165                 170                 175

Ala Gly Val Leu Phe Cys Tyr Gly Leu Leu Val Thr Val Ala Leu Cys
            180                 185                 190

Val Ile Trp Thr Asn Ser Arg Arg Asn Arg Gly Gly Gln Ser Asp Tyr
        195                 200                 205

Met Asn Met Thr Pro Arg Arg Pro Gly Leu Thr Arg Lys Pro Tyr Gln
    210                 215                 220

Pro Tyr Ala Pro Ala Arg Asp Phe Ala Ala Tyr Arg Pro
225                 230                 235
```

<210> SEQ ID NO 121
<211> LENGTH: 738
<212> TYPE: DNA
<213> ORGANISM: Artificial Sequence
<220> FEATURE:
<223> OTHER INFORMATION: muFas-CD28Cys

<400> SEQUENCE: 121

```
atgctgtgga tctgggccgt gctgcctctg gtgctggctg gatcacagct gagagtgcac    60
acccagggca ccaacagcat cagcgagagc ctgaagctga agaagagt gcgcgagaca     120 gacaagaact gcagcgaggg cctgtaccag ggcggaccct ctgctgtca gccttgccag    180 cccggcaaga aaaaggtgga agattgcaag atgaacggcg gcacccctac ctgcgcccct   240
```

```
tgtacagagg gcaaagagta catggacaag aaccactacg ccgacaagtg cagacggtgc      300
accctgtgcg acgaggaaca cggcctggaa gtggaaacaa actgcaccct gacccagaac      360
accaagtgca agtgcaaacc cgacttctac tgcgacagcc ccggctgcga gcactgcgtc      420
agatgtgcct cttgcgagca cggcaccctg aaccttgta ccgccaccag caacaccaac       480
tgccggaagc agagcccag aaacagatgc cacacccaga gcagcccaa gctgttctgg        540 gccctggtgg tggtggccgg cgtgctgttt tgttacggcc tgctcgtgac cgtggccctg      600
tgcgtgatct ggaccaacag cagaagaaac agaggcggcc agagcgacta catgaacatg      660 accccccagaa ggcctggcct gaccagaaag ccctaccagc cttacgcccc tgccagagac     720
ttcgccgcct acagacct                                                   738
```

```
<210> SEQ ID NO 122
<211> LENGTH: 246
<212> TYPE: PRT
<213> ORGANISM: Artificial Sequence
<220> FEATURE:
<223> OTHER INFORMATION: muFas-CD28Cys

<400> SEQUENCE: 122

Met Leu Trp Ile Trp Ala Val Leu Pro Leu Val Leu Ala Gly Ser Gln
1               5                   10                  15

Leu Arg Val His Thr Gln Gly Thr Asn Ser Ile Ser Glu Ser Leu Lys
            20                  25                  30

Leu Arg Arg Arg Val Arg Glu Thr Asp Lys Asn Cys Ser Glu Gly Leu
        35                  40                  45

Tyr Gln Gly Gly Pro Phe Cys Cys Gln Pro Cys Gln Pro Gly Lys Lys
    50                  55                  60

Lys Val Glu Asp Cys Lys Met Asn Gly Gly Thr Pro Thr Cys Ala Pro
65                  70                  75                  80

Cys Thr Glu Gly Lys Glu Tyr Met Asp Lys Asn His Tyr Ala Asp Lys
                85                  90                  95

Cys Arg Arg Cys Thr Leu Cys Asp Glu Glu His Gly Leu Glu Val Glu
            100                 105                 110

Thr Asn Cys Thr Leu Thr Gln Asn Thr Lys Cys Lys Cys Lys Pro Asp
        115                 120                 125

Phe Tyr Cys Asp Ser Pro Gly Cys Glu His Cys Val Arg Cys Ala Ser
    130                 135                 140

Cys Glu His Gly Thr Leu Glu Pro Cys Thr Ala Thr Ser Asn Thr Asn
145                 150                 155                 160

Cys Arg Lys Gln Ser Pro Arg Asn Arg Cys His Thr Gln Ser Ser Pro
                165                 170                 175

Lys Leu Phe Trp Ala Leu Val Val Val Ala Gly Val Leu Phe Cys Tyr
            180                 185                 190

Gly Leu Leu Val Thr Val Ala Leu Cys Val Ile Trp Thr Asn Ser Arg
        195                 200                 205

Arg Asn Arg Gly Gly Gln Ser Asp Tyr Met Asn Met Thr Pro Arg Arg
    210                 215                 220

Pro Gly Leu Thr Arg Lys Pro Tyr Gln Pro Tyr Ala Pro Ala Arg Asp
225                 230                 235                 240

Phe Ala Ala Tyr Arg Pro
                245

<210> SEQ ID NO 123
```

<211> LENGTH: 711
<212> TYPE: DNA
<213> ORGANISM: Artificial Sequence
<220> FEATURE:
<223> OTHER INFORMATION: muFas-9aas-CD28Cys

<400> SEQUENCE: 123

```
atgctgtgga tctgggccgt gctgcctctg gtgctggctg gatcacagct gagagtgcac    60
acccagggca ccaacagcat cagcgagagc ctgaagctga agaagagt gcgcgagaca     120
gacaagaact gcagcgaggg cctgtaccag ggcggaccct ctgctgtca gccttgccag    180
cccggcaaga aaaaggtgga agattgcaag atgaacggcg gcaccccta ctgcgccct    240
tgtacagagg gcaaagagta catggacaag aaccactacg ccgacaagtg cagacggtgc    300
accctgtgcg acgaggaaca cggcctggaa gtggaaacaa actgcaccct gacccagaac    360
accaagtgca agtgcaaacc cgacttctac tgcgacagcc ccggctgcga gcactgcgtc    420
agatgtgcct cttgcgagca cggcaccctg aaccttgta ccgccaccag caacaccaac     480
tgccacaccc agagcagccc caagctgttc tgggccctgg tggtggtggc cggcgtgctg    540
ttttgttacg gcctgctcgt gaccgtggcc ctgtgcgtga tctggaccaa cagcagaaga    600
aacagaggcg gccagagcga ctacatgaac atgacccca gaaggcctgg cctgaccaga    660
aagccctacc agccttacgc ccctgccaga gacttcgccg cctacagacc t            711
```

<210> SEQ ID NO 124
<211> LENGTH: 237
<212> TYPE: PRT
<213> ORGANISM: Artificial Sequence
<220> FEATURE:
<223> OTHER INFORMATION: muFas-9aas-CD28Cys

<400> SEQUENCE: 124

Met Leu Trp Ile Trp Ala Val Leu Pro Leu Val Leu Ala Gly Ser Gln
1               5                   10                  15

Leu Arg Val His Thr Gln Gly Thr Asn Ser Ile Ser Glu Ser Leu Lys
            20                  25                  30

Leu Arg Arg Arg Val Arg Glu Thr Asp Lys Asn Cys Ser Glu Gly Leu
        35                  40                  45

Tyr Gln Gly Gly Pro Phe Cys Cys Gln Pro Cys Gln Pro Gly Lys Lys
    50                  55                  60

Lys Val Glu Asp Cys Lys Met Asn Gly Gly Thr Pro Thr Cys Ala Pro
65                  70                  75                  80

Cys Thr Glu Gly Lys Glu Tyr Met Asp Lys Asn His Tyr Ala Asp Lys
                85                  90                  95

Cys Arg Arg Cys Thr Leu Cys Asp Glu Glu His Gly Leu Glu Val Glu
            100                 105                 110

Thr Asn Cys Thr Leu Thr Gln Asn Thr Lys Cys Lys Cys Lys Pro Asp
        115                 120                 125

Phe Tyr Cys Asp Ser Pro Gly Cys Glu His Cys Val Arg Cys Ala Ser
    130                 135                 140

Cys Glu His Gly Thr Leu Glu Pro Cys Thr Ala Thr Ser Asn Thr Asn
145                 150                 155                 160

Cys His Thr Gln Ser Ser Pro Lys Leu Phe Trp Ala Leu Val Val Val
                165                 170                 175

Ala Gly Val Leu Phe Cys Tyr Gly Leu Leu Val Thr Val Ala Leu Cys
            180                 185                 190

Val Ile Trp Thr Asn Ser Arg Arg Asn Arg Gly Gly Gln Ser Asp Tyr

```
                195                 200                 205
Met Asn Met Thr Pro Arg Arg Pro Gly Leu Thr Arg Lys Pro Tyr Gln
    210                 215                 220

Pro Tyr Ala Pro Ala Arg Asp Phe Ala Ala Tyr Arg Pro
225                 230                 235
```

```
<210> SEQ ID NO 125
<211> LENGTH: 693
<212> TYPE: DNA
<213> ORGANISM: Artificial Sequence
<220> FEATURE:
<223> OTHER INFORMATION: muPD1tm-CD28

<400> SEQUENCE: 125
atgtgggtgc gacaggtgcc ctggtctttc acctgggctg tgctgcagct gagctggcag    60
tctggctggc tgctggaagt gcctaacggc ccttggagaa gcctgacctt ctaccccgct   120
tggctgaccg tgtctgaggg cgccaacgcc accttcacct gtagcctgag caattggagc   180
gaggacctga tgctgaactg gaacagactg agccccagca ccagaccgga aagcaggcc   240 gccttctgca acggcctgtc tcagcctgtg caggacgcca gattccagat catccagctg   300
cccaacagac acgacttcca catgaacatc ctggacacca agaaacgca gcgcggcatc   360 tacctgtgcg gcgccatcag cctgcacccc aaggccaaga tcgaggaatc tcctggcgcc   420
gagctggtcg tgaccgagag aatcctggaa acctccacca gataccccag ccccagcct    480 aagcccgagg cagatttca gggcatggtc atcggcatca tgagcgccct cgtgggcatc   540
ccagtgttgc tgctgctggc ctgggccctg aacagcagaa gaaacagagg cggccagagc   600
gactacatga acatgacccc cagaaggcct ggcctgacca aaagccccta ccagccttac   660
gcccctgcca gagacttcgc cgcctacaga cct                                693
```

```
<210> SEQ ID NO 126
<211> LENGTH: 231
<212> TYPE: PRT
<213> ORGANISM: Artificial Sequence
<220> FEATURE:
<223> OTHER INFORMATION: muPD1tm-CD28

<400> SEQUENCE: 126

Met Trp Val Arg Gln Val Pro Trp Ser Phe Thr Trp Ala Val Leu Gln
1               5                  10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140
```

Thr Glu Arg Ile Leu Glu Thr Ser Thr Arg Tyr Pro Ser Pro Ser Pro
145                 150                 155                 160

Lys Pro Glu Gly Arg Phe Gln Gly Met Val Ile Gly Ile Met Ser Ala
            165                 170                 175

Leu Val Gly Ile Pro Val Leu Leu Leu Ala Trp Ala Leu Asn Ser
        180                 185                 190

Arg Arg Asn Arg Gly Gly Gln Ser Asp Tyr Met Asn Met Thr Pro Arg
            195                 200                 205

Arg Pro Gly Leu Thr Arg Lys Pro Tyr Gln Pro Tyr Ala Pro Ala Arg
        210                 215                 220

Asp Phe Ala Ala Tyr Arg Pro
225                 230

<210> SEQ ID NO 127
<211> LENGTH: 711
<212> TYPE: DNA
<213> ORGANISM: Artificial Sequence
<220> FEATURE:
<223> OTHER INFORMATION: muPD1-CD28tm

<400> SEQUENCE: 127
atgtgggtgc gacaggtgcc ctggtctttc acctgggctg tgctgcagct gagctggcag      60
tctggctggc tgctggaagt gcctaacggc ccttggagaa gcctgacctt ctacccgct     120 tggctgaccg tgtctgaggg cgccaacgcc accttcacct gtagcctgag caattggagc    180
gaggacctga tgctgaactg aacagactg agccccagca accagaccga aagcaggcc      240 gccttctgca acggcctgtc tcagcctgtg caggacgcca gattccagat catccagctg    300
cccaacagac acgacttcca catgaacatc ctggacacca agaaaacga cagcggcatc     360 tacctgtgcg gcgccatcag cctgcacccc aaggccaaga tcgaggaatc tcctggcgcc    420
gagctggtcg tgaccgagag aatcctggaa acctccacca gatacccag ccccagccct     480 aagcccgagg gcagatttca gggcatgttc tgggccctgg tggtggtggc cggcgtgctg    540
ttttgttacg gcctgctcgt gaccgtggcc ctgtgcgtga tctggaccaa cagcagaaga    600
aacagaggcg gccagagcga ctacatgaac atgacccca aaggcctgg cctgaccaga     660 aagccctacc agccttacgc ccctgccaga gacttcgccg cctacagacc t             711

<210> SEQ ID NO 128
<211> LENGTH: 237
<212> TYPE: PRT
<213> ORGANISM: Artificial Sequence
<220> FEATURE:
<223> OTHER INFORMATION: muPD1-CD28tm

<400> SEQUENCE: 128

Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
         100                 105                 110

Thr Arg Arg Asn Asp Ser Gly Ile Tyr Leu Cys Gly Ala Ile Ser Leu
         115                 120                 125

His Pro Lys Ala Lys Ile Glu Glu Ser Pro Gly Ala Glu Leu Val Val
         130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met Phe Trp Ala Leu Val Val Val
                 165                 170                 175

Ala Gly Val Leu Phe Cys Tyr Gly Leu Leu Val Thr Val Ala Leu Cys
         180                 185                 190

Val Ile Trp Thr Asn Ser Arg Arg Asn Arg Gly Gly Gln Ser Asp Tyr
         195                 200                 205

Met Asn Met Thr Pro Arg Arg Pro Gly Leu Thr Arg Lys Pro Tyr Gln
         210                 215                 220

Pro Tyr Ala Pro Ala Arg Asp Phe Ala Ala Tyr Arg Pro
225                 230                 235

```
<210> SEQ ID NO 129
<211> LENGTH: 738
<212> TYPE: DNA
<213> ORGANISM: Artificial Sequence
<220> FEATURE:
<223> OTHER INFORMATION: muPD1-CD28Cys

<400> SEQUENCE: 129
atgtgggtgc gacaggtgcc ctggtctttc acctgggctg tgctgcagct gagctggcag      60
tctggctggc tgctggaagt gcctaacggc ccttggagaa gcctgacctt ctaccccgct     120
tggctgaccg tgtctgaggg cgccaacgcc accttcacct gtagcctgag caattggagc     180
gaggacctga tgctgaactg gaacagactg agcccagca accagaccga aagcaggcc      240 gccttctgca cggcctgtc tcagcctgtg caggacgcca gattccagat catccagctg     300
cccaacagac acgacttcca catgaacatc ctggacacca agaaacga cagcggcatc      360 tacctgtgcg gcgccatcag cctgcacccc aaggccaaga tcgaggaatc tcctggcgcc     420
gagctggtcg tgaccgagag aatcctggaa acctccacca gatacccccag ccccagccct     480 aagcccgagg gcagatttca gggcatgtgc cacacccaga gcagcccaa gctgttctgg     540 gctctggtgg tggtggccgg cgtgctgttt tgttacggcc tgctcgtgac cgtggccctg     600
tgcgtgatct ggaccaacag cagacggaac agaggcggcc agagcgacta catgaatatg     660 accccagaa ggcctggcct gaccagaaag ccctaccagc cttacgcccc tgccagagac     720
ttcgccgcct acagacct                                                  738

<210> SEQ ID NO 130
<211> LENGTH: 246
<212> TYPE: PRT
<213> ORGANISM: Artificial Sequence
<220> FEATURE:
<223> OTHER INFORMATION: muPD1-CD28Cys

<400> SEQUENCE: 130
```

Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
             20                  25                  30

```
Arg Ser Leu Thr Phe Tyr Pro Ala Trp Leu Thr Val Ser Glu Gly Ala
            35                  40                  45

Asn Ala Thr Phe Thr Cys Ser Leu Ser Asn Trp Ser Glu Asp Leu Met
        50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Gly Met Cys His Thr Gln Ser Ser Pro
                165                 170                 175

Lys Leu Phe Trp Ala Leu Val Val Val Ala Gly Val Leu Phe Cys Tyr
            180                 185                 190

Gly Leu Leu Val Thr Val Ala Leu Cys Val Ile Trp Thr Asn Ser Arg
        195                 200                 205

Arg Asn Arg Gly Gly Gln Ser Asp Tyr Met Asn Met Thr Pro Arg Arg
    210                 215                 220

Pro Gly Leu Thr Arg Lys Pro Tyr Gln Pro Tyr Ala Pro Ala Arg Asp
225                 230                 235                 240

Phe Ala Ala Tyr Arg Pro
                245

<210> SEQ ID NO 131
<211> LENGTH: 711
<212> TYPE: DNA
<213> ORGANISM: Artificial Sequence
<220> FEATURE:
<223> OTHER INFORMATION: muPD1-9aas-CD28Cys

<400> SEQUENCE: 131
atgtgggtgc gacaggtgcc ctggtctttc acctgggctg tgctgcagct gagctggcag      60
tctggctggc tgctggaagt gcctaacggc ccttggagaa gcctgacctt ctaccccgct     120
tggctgaccg tgtctgaggg cgccaacgcc accttcacct gtagcctgag caattggagc     180
gaggacctga tgctgaactg gaacagactg agccccagca accagaccga aagcaggcc     240 gccttctgca acggcctgtc tcagcctgtg caggacgcca gattccagat catccagctg     300
cccaacagac acgacttcca catgaacatc ctggacacca agaaaacga cagcggcatc     360 tacctgtgcg gcgccatcag cctgcacccc aaggccaaga tcgaggaatc tcctggcgcc     420
gagctggtcg tgaccgagag aatcctggaa acctccacca gatacccag ccccagccct      480 tgccacaccc agagcagccc caagctgttc tgggctctgg tggtggtggc cggcgtgctg     540
ttttgttacg gcctgctcgt gaccgtggcc ctgtgcgtga tctggaccaa cagcagacgg     600
aacagaggcg gccagagcga ctacatgaat atgaccccca aaggcctgg cctgaccaga      660 aagccctacc agccttacgc ccctgccaga gacttcgccg cctacagacc t              711

<210> SEQ ID NO 132
```

<211> LENGTH: 237
<212> TYPE: PRT
<213> ORGANISM: Artificial Sequence
<220> FEATURE:
<223> OTHER INFORMATION: muPD1-9aas-CD28Cys

<400> SEQUENCE: 132

Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140

Thr Glu Arg Ile Leu Glu Thr Ser Thr Arg Tyr Pro Ser Pro Ser Pro
145                 150                 155                 160

Cys His Thr Gln Ser Ser Pro Lys Leu Phe Trp Ala Leu Val Val Val
                165                 170                 175

Ala Gly Val Leu Phe Cys Tyr Gly Leu Leu Val Thr Val Ala Leu Cys
            180                 185                 190

Val Ile Trp Thr Asn Ser Arg Arg Asn Arg Gly Gly Gln Ser Asp Tyr
        195                 200                 205

Met Asn Met Thr Pro Arg Arg Pro Gly Leu Thr Arg Lys Pro Tyr Gln
    210                 215                 220

Pro Tyr Ala Pro Ala Arg Asp Phe Ala Ala Tyr Arg Pro
225                 230                 235

<210> SEQ ID NO 133
<211> LENGTH: 675
<212> TYPE: DNA
<213> ORGANISM: Artificial Sequence
<220> FEATURE:
<223> OTHER INFORMATION: muPD1-21aas-CD28Cys

<400> SEQUENCE: 133
atgtgggtgc gacaggtgcc ctggtctttc acctgggctg tgctgcagct gagctggcag     60
tctggctggc tgctggaagt gcctaacggc ccttggagaa gcctgacctt ctacccgct    120 tggctgaccg tgtctgaggg cgccaacgcc accttcacct gtagcctgag caattggagc    180
gaggacctga tgctgaactg gaacagactg agccccagca accagaccga gaagcaggcc    240
gccttctgca acggcctgtc tcagcctgtg caggacgcca gattccagat catccagctg    300
cccaacagac acgacttcca catgaacatc ctggacacca agaaacgac cagcggcatc    360 tacctgtgcg gcgccatcag cctgcacccc aaggccaaga tcgaggaatc tcctggcgcc    420
gagctggtcg tgaccgagag aatctgccac acccagcagc cccaagct gttctgggct    480

```
ctggtggtgg tggccggcgt gctgttttgt tacggcctgc tcgtgaccgt ggccctgtgc      540
gtgatctgga ccaacagcag acggaacaga ggcggccaga gcgactacat gaatatgacc      600
cccagaaggc ctggcctgac cagaaagccc taccagcctt acgcccctgc cagagacttc      660
gccgcctaca gacct                                                        675
```

<210> SEQ ID NO 134
<211> LENGTH: 225
<212> TYPE: PRT
<213> ORGANISM: Artificial Sequence
<220> FEATURE:
<223> OTHER INFORMATION: muPD1-21aas-CD28Cys

<400> SEQUENCE: 134

```
Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140

Thr Glu Arg Ile Cys His Thr Gln Ser Ser Pro Lys Leu Phe Trp Ala
145                 150                 155                 160

Leu Val Val Val Ala Gly Val Leu Phe Cys Tyr Gly Leu Leu Val Thr
                165                 170                 175

Val Ala Leu Cys Val Ile Trp Thr Asn Ser Arg Arg Asn Arg Gly Gly
            180                 185                 190

Gln Ser Asp Tyr Met Asn Met Thr Pro Arg Arg Pro Gly Leu Thr Arg
        195                 200                 205

Lys Pro Tyr Gln Pro Tyr Ala Pro Ala Arg Asp Phe Ala Ala Tyr Arg
    210                 215                 220

Pro
225
```

<210> SEQ ID NO 135
<211> LENGTH: 1512
<212> TYPE: DNA
<213> ORGANISM: Artificial Sequence
<220> FEATURE:
<223> OTHER INFORMATION: muLag3tm-CD28

<400> SEQUENCE: 135

```
atgagagagg acctgctgct gggctttctg ctgctgggac tgctgtggga ggcccctgtg      60
gtgtcatctg gcctggcaa agaactgccc gtcgtgtggg ctcaggaagg cgctcctgtg      120
catctgccct gcagcctgaa gtcccccaac ctggacccca cttcctgag aagaggcggc      180
```

-continued

| | |
|---|---|
| gtgatctggc agcaccagcc tgattctggc cagcccacac ctatccctgc cctggatctg | 240 |
| caccagggca tgcctagccc tagacagcct gccctggca gataccgt gctgtctgtg | 300 |
| gctcctggcg gcctgagaag tggcagacag cctctgcacc ctcacgtgca gctggaagag | 360 |
| agggactgc agaggggcga cttcagcctg tggctgaggc ctgccctgag aacagatgcc | 420 |
| ggcgagtacc acgctaccgt gcggctgcct aacagagccc tgagctgctc cctgagactg | 480 |
| agagtgggcc aggccagcat gatcgcctct ccatctggcg tgctgaagct gagcgactgg | 540 |
| gtgctgctga actgcagctt ctccagaccc gacagacccg tgtccgtgca ctggttccag | 600 |
| ggacagaaca gagtgcccgt gtacaacagc cccagacact ccctggccga acattcctg | 660 |
| ctgctgcccc aggtgtcccc tctggactct ggcacatggg gctgcgtgct gacatacagg | 720 |
| gacggcttca acgtgtccat cacctacaac ctgaaggtgc tgggcctgga acccgtggct | 780 |
| cctctgacag tgtacgccgc cgagggcagc agagtggaac tgccttgtca tctgccaccc | 840 |
| ggcgtgggca ccttctct gctgatcgcc aagtggaccc ctccaggcgg aggacctgaa | 900 |
| ctgccagtgg ctggcaagag cggcaacttc accctgcacc tggaagcagt gggcctggct | 960 |
| caggccggca cctacacctg tagcatccat ctgcagggcc agcagctgaa cgccaccgtg | 1020 |
| acactggccg tgatcaccgt gacccccaag agctttggcc tgcctggctc cagaggcaag | 1080 |
| ctgctgtgtg aagtgacccc cgccagcggc aaagaaagat cgtgtggcg gcctctgaac | 1140 |
| aacctgagca gatcctgccc caggccccgtg ctggaaatcc aggaagccag actgctggcc | 1200 |
| gagcggtggc agtgccagct gtatgaggga cagcgactgc tgggcgccac tgtgtacgct | 1260 |
| gctgagtcta gctctggcgc ccacagcgcc agaagaatca gcggcgatct gaagggcggc | 1320 |
| cacctggtgc tggtgctgat cctgggcgct ctgagcctgt tcctgctggt ggctggcgct | 1380 |
| ttcggcttta acagcagaag aaacagaggc ggccagagcg actacatgaa catgaccccc | 1440 |
| agaaggcctg gcctgaccag aaagccctac cagccttacg ccctgccag agacttcgcc | 1500 |
| gcctacagac ct | 1512 |

<210> SEQ ID NO 136
<211> LENGTH: 504
<212> TYPE: PRT
<213> ORGANISM: Artificial Sequence
<220> FEATURE:
<223> OTHER INFORMATION: muLag3tm-CD28

<400> SEQUENCE: 136

```
Met Arg Glu Asp Leu Leu Leu Gly Phe Leu Leu Leu Gly Leu Leu Trp
1               5                   10                  15

Glu Ala Pro Val Val Ser Ser Gly Pro Gly Lys Glu Leu Pro Val Val
            20                  25                  30

Trp Ala Gln Glu Gly Ala Pro Val His Leu Pro Cys Ser Leu Lys Ser
        35                  40                  45

Pro Asn Leu Asp Pro Asn Phe Leu Arg Arg Gly Gly Val Ile Trp Gln
    50                  55                  60

His Gln Pro Asp Ser Gly Gln Pro Thr Pro Ile Pro Ala Leu Asp Leu
65                  70                  75                  80

His Gln Gly Met Pro Ser Pro Arg Gln Pro Ala Pro Gly Arg Tyr Thr
                85                  90                  95

Val Leu Ser Val Ala Pro Gly Gly Leu Arg Ser Gly Arg Gln Pro Leu
            100                 105                 110

His Pro His Val Gln Leu Glu Glu Arg Gly Leu Gln Arg Gly Asp Phe
        115                 120                 125
```

```
Ser Leu Trp Leu Arg Pro Ala Leu Arg Thr Asp Ala Gly Glu Tyr His
        130                 135                 140

Ala Thr Val Arg Leu Pro Asn Arg Ala Leu Ser Cys Ser Leu Arg Leu
145                 150                 155                 160

Arg Val Gly Gln Ala Ser Met Ile Ala Ser Pro Ser Gly Val Leu Lys
                165                 170                 175

Leu Ser Asp Trp Val Leu Leu Asn Cys Ser Phe Ser Arg Pro Asp Arg
            180                 185                 190

Pro Val Ser Val His Trp Phe Gln Gly Gln Asn Arg Val Pro Val Tyr
        195                 200                 205

Asn Ser Pro Arg His Phe Leu Ala Glu Thr Phe Leu Leu Leu Pro Gln
210                 215                 220

Val Ser Pro Leu Asp Ser Gly Thr Trp Gly Cys Val Leu Thr Tyr Arg
225                 230                 235                 240

Asp Gly Phe Asn Val Ser Ile Thr Tyr Asn Leu Lys Val Leu Gly Leu
                245                 250                 255

Glu Pro Val Ala Pro Leu Thr Val Tyr Ala Ala Glu Gly Ser Arg Val
            260                 265                 270

Glu Leu Pro Cys His Leu Pro Pro Gly Val Gly Thr Pro Ser Leu Leu
        275                 280                 285

Ile Ala Lys Trp Thr Pro Pro Gly Gly Gly Pro Glu Leu Pro Val Ala
290                 295                 300

Gly Lys Ser Gly Asn Phe Thr Leu His Leu Glu Ala Val Gly Leu Ala
305                 310                 315                 320

Gln Ala Gly Thr Tyr Thr Cys Ser Ile His Leu Gln Gly Gln Gln Leu
                325                 330                 335

Asn Ala Thr Val Thr Leu Ala Val Ile Thr Val Thr Pro Lys Ser Phe
            340                 345                 350

Gly Leu Pro Gly Ser Arg Gly Lys Leu Leu Cys Glu Val Thr Pro Ala
        355                 360                 365

Ser Gly Lys Glu Arg Phe Val Trp Arg Pro Leu Asn Asn Leu Ser Arg
370                 375                 380

Ser Cys Pro Gly Pro Val Leu Glu Ile Gln Glu Ala Arg Leu Leu Ala
385                 390                 395                 400

Glu Arg Trp Gln Cys Gln Leu Tyr Glu Gly Gln Arg Leu Leu Gly Ala
                405                 410                 415

Thr Val Tyr Ala Ala Glu Ser Ser Ser Gly Ala His Ser Ala Arg Arg
            420                 425                 430

Ile Ser Gly Asp Leu Lys Gly Gly His Leu Val Leu Val Leu Ile Leu
        435                 440                 445

Gly Ala Leu Ser Leu Phe Leu Leu Val Ala Gly Ala Phe Gly Phe Asn
450                 455                 460

Ser Arg Arg Asn Arg Gly Gly Gln Ser Asp Tyr Met Asn Met Thr Pro
465                 470                 475                 480

Arg Arg Pro Gly Leu Thr Arg Lys Pro Tyr Gln Pro Tyr Ala Pro Ala
                485                 490                 495

Arg Asp Phe Ala Ala Tyr Arg Pro
            500

<210> SEQ ID NO 137
<211> LENGTH: 1530
<212> TYPE: DNA
<213> ORGANISM: Artificial Sequence
<220> FEATURE:
```

<223> OTHER INFORMATION: muLag3-CD28tm

<400> SEQUENCE: 137

```
atgagagagg aacctgctgct gggctttctg ctgctgggac tgctgtggga ggcccctgtg      60
gtgtcatctg ccctggcaa agaactgccc gtcgtgtggg ctcaggaagg cgctcctgtg     120
catctgccct gcagcctgaa gtcccccaac ctggacccca acttcctgag aagaggcggc     180
gtgatctggc agcaccagcc tgattctggc cagcccacac ctatccctgc cctggatctg     240
caccagggca tgcctagccc tagacagcct gcccctggca gatacaccgt gctgtctgtg     300
gctcctggcg cctgagaag tggcagacag cctctgcacc ctcacgtgca gctggaagag     360
aggggactgc agaggggcga cttcagcctg tggctgaggc ctgccctgag aacagatgcc     420
ggcgagtacc acgctaccgt gcggctgcct aacagagccc tgagctgctc cctgagactg     480
agagtgggcc aggccagcat gatcgcctct ccatctggcg tgctgaagct gagcgactgg     540
gtgctgctga actgcagctt ctccagaccc gacagacccg tgtccgtgca ctggttccag     600
ggacagaaca gagtgcccgt gtacaacagc cccagacact tcctggccga cattcctg      660
ctgctgcccc aggtgtcccc tctggactct ggcacatggg gctgcgtgct gacatacagg     720
gacggcttca cgtgtccat cacctacaac ctgaaggtgc tgggcctgga acccgtggct     780
cctctgacag tgtacgccgc cgagggcagc agagtggaac tgccttgtca tctgccaccc     840
ggcgtgggca ccttctctct gctgatcgcc aagtggaccc tccaggcgg aggacctgaa     900
ctgccagtgg ctggcaagag cggcaacttc accctgcacc tggaagcagt gggcctggct     960
caggccggca cctacacctg tagcatccat ctgcagggcc agcagctgaa cgccaccgtg    1020
acactggccg tgatcaccgt gacccccaag agctttggcc tgcctggctc cagaggcaag    1080
ctgctgtgtg aagtgacccc cgccagcggc aaagaaagat cgtgtggcg gcctctgaac    1140
aacctgagca gatcctgccc aggccccgtg ctggaaatcc aggaagccag actgctggcc    1200
gagcggtggc agtgccagct gtatgaggga cagcgactgc tgggcgccac tgtgtacgct    1260
gctgagtcta gctctggcgc ccacagcgcc agaagaatca gcggcgatct gaagggcggc    1320
cacctgttct gggcccctggt ggtggtggcc ggcgtgctgt tttgttacgg cctgctcgtg    1380
accgtggccc tgtgcgtgat ctggaccaac agcagaagaa acagaggcgg ccagagcgac    1440
tacatgaaca tgaccccccag aaggcctggc ctgaccagaa agccctacca gccttacgcc    1500
cctgccagag acttcgccgc ctacagacct                                      1530
```

<210> SEQ ID NO 138
<211> LENGTH: 510
<212> TYPE: PRT
<213> ORGANISM: Artificial Sequence
<220> FEATURE:
<223> OTHER INFORMATION: muLag3-CD28tm

<400> SEQUENCE: 138

Met Arg Glu Asp Leu Leu Leu Gly Phe Leu Leu Leu Gly Leu Leu Trp
1               5                   10                  15

Glu Ala Pro Val Val Ser Ser Gly Pro Gly Lys Glu Leu Pro Val Val
            20                  25                  30

Trp Ala Gln Glu Gly Ala Pro Val His Leu Pro Cys Ser Leu Lys Ser
        35                  40                  45

Pro Asn Leu Asp Pro Asn Phe Leu Arg Arg Gly Gly Val Ile Trp Gln
    50                  55                  60

His Gln Pro Asp Ser Gly Gln Pro Thr Pro Ile Pro Ala Leu Asp Leu

```
              65                  70                  75                  80
His Gln Gly Met Pro Ser Pro Arg Gln Pro Ala Pro Gly Arg Tyr Thr
                    85                  90                  95

Val Leu Ser Val Ala Pro Gly Gly Leu Arg Ser Gly Arg Gln Pro Leu
                   100                 105                 110

His Pro His Val Gln Leu Glu Glu Arg Gly Leu Gln Arg Gly Asp Phe
                   115                 120                 125

Ser Leu Trp Leu Arg Pro Ala Leu Arg Thr Asp Ala Gly Glu Tyr His
            130                 135                 140

Ala Thr Val Arg Leu Pro Asn Arg Ala Leu Ser Cys Ser Leu Arg Leu
145                 150                 155                 160

Arg Val Gly Gln Ala Ser Met Ile Ala Ser Pro Ser Gly Val Leu Lys
                        165                 170                 175

Leu Ser Asp Trp Val Leu Leu Asn Cys Ser Phe Ser Arg Pro Asp Arg
                180                 185                 190

Pro Val Ser Val His Trp Phe Gln Gly Gln Asn Arg Val Pro Val Tyr
                195                 200                 205

Asn Ser Pro Arg His Phe Leu Ala Glu Thr Phe Leu Leu Leu Pro Gln
210                 215                 220

Val Ser Pro Leu Asp Ser Gly Thr Trp Gly Cys Val Leu Thr Tyr Arg
225                 230                 235                 240

Asp Gly Phe Asn Val Ser Ile Thr Tyr Asn Leu Lys Val Leu Gly Leu
                    245                 250                 255

Glu Pro Val Ala Pro Leu Thr Val Tyr Ala Ala Glu Gly Ser Arg Val
                260                 265                 270

Glu Leu Pro Cys His Leu Pro Pro Gly Val Gly Thr Pro Ser Leu Leu
            275                 280                 285

Ile Ala Lys Trp Thr Pro Pro Gly Gly Gly Pro Glu Leu Pro Val Ala
290                 295                 300

Gly Lys Ser Gly Asn Phe Thr Leu His Leu Glu Ala Val Gly Leu Ala
305                 310                 315                 320

Gln Ala Gly Thr Tyr Thr Cys Ser Ile His Leu Gln Gly Gln Gln Leu
                    325                 330                 335

Asn Ala Thr Val Thr Leu Ala Val Ile Thr Val Thr Pro Lys Ser Phe
                340                 345                 350

Gly Leu Pro Gly Ser Arg Gly Lys Leu Leu Cys Glu Val Thr Pro Ala
            355                 360                 365

Ser Gly Lys Glu Arg Phe Val Trp Arg Pro Leu Asn Asn Leu Ser Arg
370                 375                 380

Ser Cys Pro Gly Pro Val Leu Glu Ile Gln Glu Ala Arg Leu Leu Ala
385                 390                 395                 400

Glu Arg Trp Gln Cys Gln Leu Tyr Glu Gly Gln Arg Leu Leu Gly Ala
                    405                 410                 415

Thr Val Tyr Ala Ala Glu Ser Ser Ser Gly Ala His Ser Ala Arg Arg
                420                 425                 430

Ile Ser Gly Asp Leu Lys Gly Gly His Leu Phe Trp Ala Leu Val Val
            435                 440                 445

Val Ala Gly Val Leu Phe Cys Tyr Gly Leu Leu Val Thr Val Ala Leu
450                 455                 460

Cys Val Ile Trp Thr Asn Ser Arg Arg Asn Arg Gly Gly Gln Ser Asp
465                 470                 475                 480

Tyr Met Asn Met Thr Pro Arg Arg Pro Gly Leu Thr Arg Lys Pro Tyr
                485                 490                 495
```

Gln Pro Tyr Ala Pro Ala Arg Asp Phe Ala Ala Tyr Arg Pro
                500                 505                 510

<210> SEQ ID NO 139
<211> LENGTH: 1557
<212> TYPE: DNA
<213> ORGANISM: Artificial Sequence
<220> FEATURE:
<223> OTHER INFORMATION: muLag3-CD28Cys

<400> SEQUENCE: 139

| | | | | |
|---|---|---|---|---|
| atgagagagg | acctgctgct | gggctttctg | ctgctgggac | tgctgtggga | ggcccctgtg | 60 |
| gtgtcatctg | gccctggcaa | agaactgccc | gtcgtgtggg | ctcaggaagg | cgctcctgtg | 120 |
| catctgccct | gcagcctgaa | gtccccaac | ctggacccca | acttcctgag | aagaggcggc | 180 |
| gtgatctggc | agcaccagcc | tgattctggc | agcccacac | ctatccctgc | cctggatctg | 240 |
| caccagggca | tgcctagccc | tagacagcct | gccctggca | gatacaccgt | gctgtctgtg | 300 |
| gctcctggcg | gcctgagaag | tggcagacag | cctctgcacc | ctcacgtgca | gctggaagag | 360 |
| aggggactgc | agaggggcga | cttcagcctg | tggctgaggc | ctgccctgag | aacagatgcc | 420 |
| ggcgagtacc | acgctaccgt | gcggctgcct | aacagaccc | tgagctgctc | cctgagactg | 480 |
| agagtgggcc | aggccagcat | gatcgcctct | ccatctggcg | tgctgaagct | gagcgactgg | 540 |
| gtgctgctga | actgcagctt | ctccagaccc | gacagaccccg | tgtccgtgca | ctggttccag | 600 |
| ggacagaaca | gagtgcccgt | gtacaacagc | ccagacact | tcctggccga | gacattcctg | 660 |
| ctgctgcccc | aggtgtcccc | tctggactct | ggcacatggg | gctgcgtgct | gacatacagg | 720 |
| gacggcttca | acgtgtccat | cacctacaac | ctgaaggtgc | tgggcctgga | acccgtggct | 780 |
| cctctgacag | tgtacgccgc | cgagggcagc | agagtggaac | tgccttgtca | tctgccaccc | 840 |
| ggcgtgggca | ccttctctct | gctgatcgcc | aagtggaccc | ctccaggcgg | aggacctgaa | 900 |
| ctgccagtgg | ctggcaagag | cggcaacttc | accctgcacc | tggaagcagt | gggcctggct | 960 |
| caggccggca | cctacacctg | tagcatccat | ctgcagggcc | agcagctgaa | cgccaccgtg | 1020 |
| acactggccg | tgatcaccgt | gaccccccaag | agctttggcc | tgcctggctc | cagaggcaag | 1080 |
| ctgctgtgtg | aagtgacccc | cgccagcggc | aaagaaagat | tcgtgtggcg | gcctctgaac | 1140 |
| aacctgagca | gatcctgccc | aggccccgtg | ctggaaatcc | aggaagccag | actgctggcc | 1200 |
| gagcggtggc | agtgccagct | gtatgaggga | cagcgactgc | tgggcgccac | tgtgtacgct | 1260 |
| gctgagtcta | gctctggcgc | ccacagcgcc | agaagaatca | gcggcgatct | gaagggcggc | 1320 |
| cacctgtgcc | acacccagag | cagccccaag | ctgttctggg | ccctggtggt | ggtggccggc | 1380 |
| gtgctgtttt | gttacggcct | gctcgtgacc | gtggccctgt | gcgtgatctg | gaccaacagc | 1440 |
| agaagaaaca | gaggcggcca | gagcgactac | atgaacatga | ccccccagaag | gcctggcctg | 1500 |
| accagaaagc | cctaccagcc | ttacgcccct | gccagagact | cgccgccta | cagacct | 1557 |

<210> SEQ ID NO 140
<211> LENGTH: 519
<212> TYPE: PRT
<213> ORGANISM: Artificial Sequence
<220> FEATURE:
<223> OTHER INFORMATION: muLag3-CD28Cys

<400> SEQUENCE: 140

Met Arg Glu Asp Leu Leu Leu Gly Phe Leu Leu Leu Gly Leu Leu Trp
1               5                   10                  15

Glu Ala Pro Val Val Ser Ser Gly Pro Gly Lys Glu Leu Pro Val Val
                20                  25                  30

Trp Ala Gln Glu Gly Ala Pro Val His Leu Pro Cys Ser Leu Lys Ser
            35                  40                  45

Pro Asn Leu Asp Pro Asn Phe Leu Arg Arg Gly Gly Val Ile Trp Gln
        50                  55                  60

His Gln Pro Asp Ser Gly Gln Pro Thr Pro Ile Pro Ala Leu Asp Leu
65                  70                  75                  80

His Gln Gly Met Pro Ser Pro Arg Gln Pro Ala Pro Gly Arg Tyr Thr
                85                  90                  95

Val Leu Ser Val Ala Pro Gly Gly Leu Arg Ser Gly Arg Gln Pro Leu
            100                 105                 110

His Pro His Val Gln Leu Glu Glu Arg Gly Leu Gln Arg Gly Asp Phe
        115                 120                 125

Ser Leu Trp Leu Arg Pro Ala Leu Arg Thr Asp Ala Gly Glu Tyr His
    130                 135                 140

Ala Thr Val Arg Leu Pro Asn Arg Ala Leu Ser Cys Ser Leu Arg Leu
145                 150                 155                 160

Arg Val Gly Gln Ala Ser Met Ile Ala Ser Pro Ser Gly Val Leu Lys
                165                 170                 175

Leu Ser Asp Trp Val Leu Leu Asn Cys Ser Phe Ser Arg Pro Asp Arg
            180                 185                 190

Pro Val Ser Val His Trp Phe Gln Gly Gln Asn Arg Val Pro Val Tyr
        195                 200                 205

Asn Ser Pro Arg His Phe Leu Ala Glu Thr Phe Leu Leu Leu Pro Gln
210                 215                 220

Val Ser Pro Leu Asp Ser Gly Thr Trp Gly Cys Val Leu Thr Tyr Arg
225                 230                 235                 240

Asp Gly Phe Asn Val Ser Ile Thr Tyr Asn Leu Lys Val Leu Gly Leu
                245                 250                 255

Glu Pro Val Ala Pro Leu Thr Val Tyr Ala Ala Glu Gly Ser Arg Val
            260                 265                 270

Glu Leu Pro Cys His Leu Pro Pro Gly Val Gly Thr Pro Ser Leu Leu
        275                 280                 285

Ile Ala Lys Trp Thr Pro Pro Gly Gly Gly Pro Glu Leu Pro Val Ala
    290                 295                 300

Gly Lys Ser Gly Asn Phe Thr Leu His Leu Glu Ala Val Gly Leu Ala
305                 310                 315                 320

Gln Ala Gly Thr Tyr Thr Cys Ser Ile His Leu Gln Gly Gln Gln Leu
                325                 330                 335

Asn Ala Thr Val Thr Leu Ala Val Ile Thr Val Thr Pro Lys Ser Phe
            340                 345                 350

Gly Leu Pro Gly Ser Arg Gly Lys Leu Leu Cys Glu Val Thr Pro Ala
        355                 360                 365

Ser Gly Lys Glu Arg Phe Val Trp Arg Pro Leu Asn Asn Leu Ser Arg
    370                 375                 380

Ser Cys Pro Gly Pro Val Leu Glu Ile Gln Glu Ala Arg Leu Leu Ala
385                 390                 395                 400

Glu Arg Trp Gln Cys Gln Leu Tyr Glu Gly Gln Arg Leu Leu Gly Ala
                405                 410                 415

Thr Val Tyr Ala Ala Glu Ser Ser Ser Gly Ala His Ser Ala Arg Arg
            420                 425                 430

Ile Ser Gly Asp Leu Lys Gly Gly His Leu Cys His Thr Gln Ser Ser

```
              435                 440                 445
Pro Lys Leu Phe Trp Ala Leu Val Val Val Ala Gly Val Leu Phe Cys
    450                 455                 460

Tyr Gly Leu Leu Val Thr Val Ala Leu Cys Val Ile Trp Thr Asn Ser
465                 470                 475                 480

Arg Arg Asn Arg Gly Gly Gln Ser Asp Tyr Met Asn Met Thr Pro Arg
                485                 490                 495

Arg Pro Gly Leu Thr Arg Lys Pro Tyr Gln Pro Tyr Ala Pro Ala Arg
            500                 505                 510

Asp Phe Ala Ala Tyr Arg Pro
        515

<210> SEQ ID NO 141
<211> LENGTH: 1530
<212> TYPE: DNA
<213> ORGANISM: Artificial Sequence
<220> FEATURE:
<223> OTHER INFORMATION: muLag3-9aas-CD28Cys

<400> SEQUENCE: 141
```

| | | | | | |
|---|---|---|---|---|---|
| atgagagagg | acctgctgct | gggctttctg | ctgctgggac | tgctgtggga | ggcccctgtg | 60 |
| gtgtcatctg | ccctggcaa | agaactgccc | gtcgtgtggg | ctcaggaagg | cgctcctgtg | 120 |
| catctgccct | gcagcctgaa | gtcccccaac | ctggaccca | acttcctgag | aagaggcggc | 180 |
| gtgatctggc | agcaccagcc | tgattctggc | agcccacac | ctatccctgc | cctggatctg | 240 |
| caccagggca | tgcctagccc | tagacagcct | gcccctggca | gataccacgt | gctgtctgtg | 300 |
| gctcctggcg | gcctgagaag | tggcagacag | cctctgcacc | ctcacgtgca | gctggaagag | 360 |
| aggggactgc | agaggggcga | cttcagcctg | tggctgaggc | ctgccctgag | aacagatgcc | 420 |
| ggcgagtacc | acgctaccgt | gcggctgcct | aacagagccc | tgagctgctc | cctgagactg | 480 |
| agagtgggcc | aggccagcat | gatcgcctct | ccatctggcg | tgctgaagct | gagcgactgg | 540 |
| gtgctgctga | actgcagctt | ctccagaccc | gacagacccg | tgtccgtgca | ctggttccag | 600 |
| ggacagaaca | gagtgccccgt | gtacaacagc | cccagacact | tcctggccga | gacattcctg | 660 |
| ctgctgcccc | aggtgtcccc | tctggactct | ggcacatggg | gctgcgtgct | gacatacagg | 720 |
| gacggcttca | acgtgtccat | cacctacaac | ctgaaggtgc | tgggcctgga | acccgtggct | 780 |
| cctctgacag | tgtacgccgc | cgagggcagc | agagtggaaa | tgccttgtca | tctgccaccc | 840 |
| ggcgtgggca | ccttctctct | gctgatcgcc | aagtggaccc | ctccaggcgg | aggacctgaa | 900 |
| ctgccagtgg | ctggcaagag | cggcaacttc | accctgcacc | tggaagcagt | gggcctggct | 960 |
| caggccggca | cctacacctg | tagcatccat | ctgcagggcc | agcagctgaa | cgccaccgtg | 1020 |
| acactggccg | tgatcaccgt | gacccccaag | agctttggcc | tgcctggctc | cagaggcaag | 1080 |
| ctgctgtgtg | aagtgacccc | cgccagcggc | aaagaaagat | tcgtgtggcg | gcctctgaac | 1140 |
| aacctgagca | gatcctgccc | caggccccgtg | ctggaaatcc | aggaagccag | actgctggcc | 1200 |
| gagcggtggc | agtgccagct | gtatgaggga | cagcgactgc | tgggcgccac | tgtgtacgct | 1260 |
| gctgagtcta | gctctggcgc | ccacagcgcc | agaagaatct | gccacaccca | gagcagcccc | 1320 |
| aagctgttct | gggccctggt | ggtggtggcc | ggcgtgctgt | tttgttacgg | cctgctcgtg | 1380 |
| accgtggccc | tgtgcgtgat | ctggaccaac | agcagaagaa | acagaggcgg | ccagagcgac | 1440 |
| tacatgaaca | tgaccccag | aaggcctggc | ctgaccagaa | agccctacca | gccttacgcc | 1500 |
| cctgccagag | acttcgccgc | ctacagacct | | | | 1530 |

<210> SEQ ID NO 142
<211> LENGTH: 510
<212> TYPE: PRT
<213> ORGANISM: Artificial Sequence
<220> FEATURE:
<223> OTHER INFORMATION: muLag3-9aas-CD28Cys

<400> SEQUENCE: 142

```
Met Arg Glu Asp Leu Leu Gly Phe Leu Leu Gly Leu Leu Trp
1               5                   10                  15

Glu Ala Pro Val Val Ser Ser Gly Pro Gly Lys Glu Leu Pro Val Val
                20                  25                  30

Trp Ala Gln Glu Gly Ala Pro Val His Leu Pro Cys Ser Leu Lys Ser
                35                  40                  45

Pro Asn Leu Asp Pro Asn Phe Leu Arg Arg Gly Gly Val Ile Trp Gln
            50                  55                  60

His Gln Pro Asp Ser Gly Gln Pro Thr Pro Ile Pro Ala Leu Asp Leu
65              70                  75                  80

His Gln Gly Met Pro Ser Pro Arg Gln Pro Ala Pro Gly Arg Tyr Thr
                85                  90                  95

Val Leu Ser Val Ala Pro Gly Gly Leu Arg Ser Gly Arg Gln Pro Leu
                100                 105                 110

His Pro His Val Gln Leu Glu Glu Arg Gly Leu Gln Arg Gly Asp Phe
            115                 120                 125

Ser Leu Trp Leu Arg Pro Ala Leu Arg Thr Asp Ala Gly Glu Tyr His
            130                 135                 140

Ala Thr Val Arg Leu Pro Asn Arg Ala Leu Ser Cys Ser Leu Arg Leu
145                 150                 155                 160

Arg Val Gly Gln Ala Ser Met Ile Ala Ser Pro Ser Gly Val Leu Lys
                165                 170                 175

Leu Ser Asp Trp Val Leu Leu Asn Cys Ser Phe Ser Arg Pro Asp Arg
            180                 185                 190

Pro Val Ser Val His Trp Phe Gln Gly Gln Asn Arg Val Pro Val Tyr
            195                 200                 205

Asn Ser Pro Arg His Phe Leu Ala Glu Thr Phe Leu Leu Leu Pro Gln
        210                 215                 220

Val Ser Pro Leu Asp Ser Gly Thr Trp Gly Cys Val Leu Thr Tyr Arg
225                 230                 235                 240

Asp Gly Phe Asn Val Ser Ile Thr Tyr Asn Leu Lys Val Leu Gly Leu
                245                 250                 255

Glu Pro Val Ala Pro Leu Thr Val Tyr Ala Ala Glu Gly Ser Arg Val
                260                 265                 270

Glu Leu Pro Cys His Leu Pro Pro Gly Val Gly Thr Pro Ser Leu Leu
            275                 280                 285

Ile Ala Lys Trp Thr Pro Pro Gly Gly Gly Pro Glu Leu Pro Val Ala
        290                 295                 300

Gly Lys Ser Gly Asn Phe Thr Leu His Leu Glu Ala Val Gly Leu Ala
305                 310                 315                 320

Gln Ala Gly Thr Tyr Thr Cys Ser Ile His Leu Gln Gly Gln Gln Leu
                325                 330                 335

Asn Ala Thr Val Thr Leu Ala Val Ile Thr Val Thr Pro Lys Ser Phe
            340                 345                 350

Gly Leu Pro Gly Ser Arg Gly Lys Leu Leu Cys Glu Val Thr Pro Ala
            355                 360                 365
```

```
Ser Gly Lys Glu Arg Phe Val Trp Arg Pro Leu Asn Asn Leu Ser Arg
    370                 375                 380
Ser Cys Pro Gly Pro Val Leu Glu Ile Gln Glu Ala Arg Leu Leu Ala
385                 390                 395                 400
Glu Arg Trp Gln Cys Gln Leu Tyr Glu Gly Gln Arg Leu Leu Gly Ala
                405                 410                 415
Thr Val Tyr Ala Ala Glu Ser Ser Gly Ala His Ser Ala Arg Arg
            420                 425                 430
Ile Cys His Thr Gln Ser Ser Pro Lys Leu Phe Trp Ala Leu Val Val
        435                 440                 445
Val Ala Gly Val Leu Phe Cys Tyr Gly Leu Leu Val Thr Val Ala Leu
    450                 455                 460
Cys Val Ile Trp Thr Asn Ser Arg Arg Asn Arg Gly Gly Gln Ser Asp
465                 470                 475                 480
Tyr Met Asn Met Thr Pro Arg Arg Pro Gly Leu Thr Arg Lys Pro Tyr
                485                 490                 495
Gln Pro Tyr Ala Pro Ala Arg Asp Phe Ala Ala Tyr Arg Pro
            500                 505                 510

<210> SEQ ID NO 143
<211> LENGTH: 765
<212> TYPE: DNA
<213> ORGANISM: Artificial Sequence
<220> FEATURE:
<223> OTHER INFORMATION: muTim3tm-CD28

<400> SEQUENCE: 143
atgttcagcg gcctgaccct gaactgcgtg ctcctgctgc tgcagctgct gctggccaga      60
agcctggaaa acgcctacgt gttcgaagtg ggcaagaacg cctacctgcc ctgcagctac     120
accctgtcta cacctggcgc cctggtgcct atgtgttggg gcaagggctt ctgcccttgg     180
agccagtgca ccaacgagct gctgagaacc gacgagagaa acgtgaccta ccagaagtcc     240
agcagatacc agctgaaggg cgacctgaac aagggcgacg tgtccctgat catcaagaac     300
gtgaccctgg acgaccacgg cacctactgc tgcagaatcc agttccccgg cctgatgaac     360
gacaagaagc tggaactgaa gctggacatc aaggccgcca agtgacccc tgcccagaca     420
gcccacggcg actctacaac agccagcccc agaaccctga ccaccgagag aacggcagc     480
gagacacaga ccctcgtgac actgcacaac aacaacggca ccaagatcag cacctgggcc     540
gacgagatca aggacagcgg cgagacaatc agaaccgcca tccacatcgg cgtgggcgtg     600
tccgctggac tgacactggc tctgatcatc ggagtgctga tcaacagcag aagaaacaga     660
ggcggccaga gcgactacat gaacatgacc cccagaaggc ctggcctgac cagaaagccc     720
taccagcctt acgcccctgc cagagacttc gccgcctaca gacct                    765

<210> SEQ ID NO 144
<211> LENGTH: 255
<212> TYPE: PRT
<213> ORGANISM: Artificial Sequence
<220> FEATURE:
<223> OTHER INFORMATION: muTim3tm-CD28

<400> SEQUENCE: 144

Met Phe Ser Gly Leu Thr Leu Asn Cys Val Leu Leu Leu Gln Leu
1               5                   10                  15
Leu Leu Ala Arg Ser Leu Glu Asn Ala Tyr Val Phe Glu Val Gly Lys
            20                  25                  30
```

```
Asn Ala Tyr Leu Pro Cys Ser Tyr Thr Leu Ser Thr Pro Gly Ala Leu
         35                  40                  45
Val Pro Met Cys Trp Gly Lys Gly Phe Cys Pro Trp Ser Gln Cys Thr
 50                  55                  60
Asn Glu Leu Leu Arg Thr Asp Glu Arg Asn Val Thr Tyr Gln Lys Ser
 65                  70                  75                  80
Ser Arg Tyr Gln Leu Lys Gly Asp Leu Asn Lys Gly Asp Val Ser Leu
                 85                  90                  95
Ile Ile Lys Asn Val Thr Leu Asp His Gly Thr Tyr Cys Cys Arg
             100                 105                 110
Ile Gln Phe Pro Gly Leu Met Asn Asp Lys Lys Leu Glu Leu Lys Leu
         115                 120                 125
Asp Ile Lys Ala Ala Lys Val Thr Pro Ala Gln Thr Ala His Gly Asp
130                 135                 140
Ser Thr Thr Ala Ser Pro Arg Thr Leu Thr Thr Glu Arg Asn Gly Ser
145                 150                 155                 160
Glu Thr Gln Thr Leu Val Thr Leu His Asn Asn Gly Thr Lys Ile
                 165                 170                 175
Ser Thr Trp Ala Asp Glu Ile Lys Asp Ser Gly Glu Thr Ile Arg Thr
             180                 185                 190
Ala Ile His Ile Gly Val Gly Val Ser Ala Gly Leu Thr Leu Ala Leu
         195                 200                 205
Ile Ile Gly Val Leu Ile Asn Ser Arg Arg Asn Arg Gly Gly Gln Ser
     210                 215                 220
Asp Tyr Met Asn Met Thr Pro Arg Arg Pro Gly Leu Thr Arg Lys Pro
225                 230                 235                 240
Tyr Gln Pro Tyr Ala Pro Ala Arg Asp Phe Ala Ala Tyr Arg Pro
                 245                 250                 255

<210> SEQ ID NO 145
<211> LENGTH: 783
<212> TYPE: DNA
<213> ORGANISM: Artificial Sequence
<220> FEATURE:
<223> OTHER INFORMATION: muTim3-CD28tm

<400> SEQUENCE: 145
atgttcagcg gcctgaccct gaactgcgtg ctcctgctgc tgcagctgct gctggccaga      60
agcctggaaa acgcctacgt gttcgaagtg ggcaagaacg cctacctgcc ctgcagctac     120
accctgtcta cacctggcgc cctggtgcct atgtgttggg gcaagggctt ctgcccttgg     180
agccagtgca ccaacgagct gctgagaacc gacgagagaa acgtgaccta ccagaagtcc     240
agcagatacc agctgaaggg cgacctgaac aagggcgacg tgtccctgat catcaagaac     300
gtgaccctgg acgaccacgg cacctactgc tgcagaatcc agttccccgg cctgatgaac     360
gacaagaagc tggaactgaa gctggacatc aaggccgcca agtgaccccc tgcccagaca     420
gcccacggcg actctacaac agccagcccc agaaccctga ccaccgagag gaacggcagc     480
gagacacaga ccctcgtgac actgcacaac aacaacggca ccaagatcag cacctgggcc     540
gacgagatca aggacagcgg cgagacaatc agaaccgcct ctgggcccct ggtggtggtg     600
gccggcgtgc tgtttttgtta cggcctgctc gtgaccgtgg ccctgtgcgt gatctggacc     660
aacagcagaa gaaacagagg cggccagagc gactacatga acatgacccc cagaaggcct     720
ggcctgacca gaaagcccta ccagccttac gcccctgcca gagacttcgc cgcctacaga     780
cct                                                                  783
```

<210> SEQ ID NO 146
<211> LENGTH: 261
<212> TYPE: PRT
<213> ORGANISM: Artificial Sequence
<220> FEATURE:
<223> OTHER INFORMATION: muTim3-CD28tm

<400> SEQUENCE: 146

```
Met Phe Ser Gly Leu Thr Leu Asn Cys Val Leu Leu Leu Gln Leu
1               5                   10                  15

Leu Leu Ala Arg Ser Leu Glu Asn Ala Tyr Val Phe Glu Val Gly Lys
                20                  25                  30

Asn Ala Tyr Leu Pro Cys Ser Tyr Thr Leu Ser Thr Pro Gly Ala Leu
                35                  40                  45

Val Pro Met Cys Trp Gly Lys Gly Phe Cys Pro Trp Ser Gln Cys Thr
    50                  55                  60

Asn Glu Leu Leu Arg Thr Asp Glu Arg Asn Val Thr Tyr Gln Lys Ser
65                  70                  75                  80

Ser Arg Tyr Gln Leu Lys Gly Asp Leu Asn Lys Gly Asp Val Ser Leu
                85                  90                  95

Ile Ile Lys Asn Val Thr Leu Asp Asp His Gly Thr Tyr Cys Cys Arg
                100                 105                 110

Ile Gln Phe Pro Gly Leu Met Asn Asp Lys Lys Leu Glu Leu Lys Leu
                115                 120                 125

Asp Ile Lys Ala Ala Lys Val Thr Pro Ala Gln Thr Ala His Gly Asp
                130                 135                 140

Ser Thr Thr Ala Ser Pro Arg Thr Leu Thr Thr Glu Arg Asn Gly Ser
145                 150                 155                 160

Glu Thr Gln Thr Leu Val Thr Leu His Asn Asn Asn Gly Thr Lys Ile
                165                 170                 175

Ser Thr Trp Ala Asp Glu Ile Lys Asp Ser Gly Glu Thr Ile Arg Thr
                180                 185                 190

Ala Phe Trp Ala Leu Val Val Val Ala Gly Val Leu Phe Cys Tyr Gly
                195                 200                 205

Leu Leu Val Thr Val Ala Leu Cys Val Ile Trp Thr Asn Ser Arg Arg
        210                 215                 220

Asn Arg Gly Gly Gln Ser Asp Tyr Met Asn Met Thr Pro Arg Arg Pro
225                 230                 235                 240

Gly Leu Thr Arg Lys Pro Tyr Gln Pro Tyr Ala Pro Ala Arg Asp Phe
                245                 250                 255

Ala Ala Tyr Arg Pro
                260
```

<210> SEQ ID NO 147
<211> LENGTH: 810
<212> TYPE: DNA
<213> ORGANISM: Artificial Sequence
<220> FEATURE:
<223> OTHER INFORMATION: muTim3-CD28Cys

<400> SEQUENCE: 147

```
atgttcagcg gcctgaccct gaactgcgtg ctcctgctgc tgcagctgct gctggccaga    60
agcctggaaa acgcctacgt gttcgaagtg ggcaagaacg cctacctgcc ctgcagctac   120
accctgtcta cacctggcgc cctggtgcct atgtgttggg gcaagggctt ctgcccttgg   180
agccagtgca ccaacgagct gctgagaacc gacgagaa acgtgaccta ccagaagtcc    240
```

```
agcagatacc agctgaaggg cgacctgaac aagggcgacg tgtccctgat catcaagaac    300
gtgaccctgg acgaccacgg cacctactgc tgcagaatcc agttccccgg cctgatgaac    360
gacaagaagc tggaactgaa gctggacatc aaggccgcca agtgacccc  tgcccagaca    420
gcccacggcg actctacaac agccagcccc agaaccctga ccaccgagag gaacggcagc    480
gagacacaga ccctcgtgac actgcacaac aacaacggca ccaagatcag cacctgggcc    540
gacgagatca aggacagcgg cgagacaatc agaaccgcct gccacaccca gagcagcccc    600
aagctgttct gggccctggt ggtggtggcc ggcgtgctgt tttgttacgg cctgctcgtg    660
accgtggccc tgtgcgtgat ctggaccaac agcagaagaa acagaggcgg ccagagcgac    720
tacatgaaca tgaccccccag aaggcctggc ctgaccagaa agccctacca gccttacgcc    780
cctgccagag acttcgccgc ctacagacct                                     810
```

<210> SEQ ID NO 148
<211> LENGTH: 270
<212> TYPE: PRT
<213> ORGANISM: Artificial Sequence
<220> FEATURE:
<223> OTHER INFORMATION: muTim3-CD28Cys

<400> SEQUENCE: 148

```
Met Phe Ser Gly Leu Thr Leu Asn Cys Val Leu Leu Leu Gln Leu
1               5                   10                  15

Leu Leu Ala Arg Ser Leu Glu Asn Ala Tyr Val Phe Glu Val Gly Lys
            20                  25                  30

Asn Ala Tyr Leu Pro Cys Ser Tyr Thr Leu Ser Thr Pro Gly Ala Leu
        35                  40                  45

Val Pro Met Cys Trp Gly Lys Gly Phe Cys Pro Trp Ser Gln Cys Thr
    50                  55                  60

Asn Glu Leu Leu Arg Thr Asp Glu Arg Asn Val Thr Tyr Gln Lys Ser
65                  70                  75                  80

Ser Arg Tyr Gln Leu Lys Gly Asp Leu Asn Lys Gly Asp Val Ser Leu
                85                  90                  95

Ile Ile Lys Asn Val Thr Leu Asp Asp His Gly Thr Tyr Cys Cys Arg
            100                 105                 110

Ile Gln Phe Pro Gly Leu Met Asn Asp Lys Lys Leu Glu Leu Lys Leu
        115                 120                 125

Asp Ile Lys Ala Ala Lys Val Thr Pro Ala Gln Thr Ala His Gly Asp
    130                 135                 140

Ser Thr Thr Ala Ser Pro Arg Thr Leu Thr Thr Glu Arg Asn Gly Ser
145                 150                 155                 160

Glu Thr Gln Thr Leu Val Thr Leu His Asn Asn Asn Gly Thr Lys Ile
                165                 170                 175

Ser Thr Trp Ala Asp Glu Ile Lys Asp Ser Gly Glu Thr Ile Arg Thr
            180                 185                 190

Ala Cys His Thr Gln Ser Ser Pro Lys Leu Phe Trp Ala Leu Val Val
        195                 200                 205

Val Ala Gly Val Leu Phe Cys Tyr Gly Leu Leu Val Thr Val Ala Leu
    210                 215                 220

Cys Val Ile Trp Thr Asn Ser Arg Arg Asn Arg Gly Gly Gln Ser Asp
225                 230                 235                 240

Tyr Met Asn Met Thr Pro Arg Arg Pro Gly Leu Thr Arg Lys Pro Tyr
                245                 250                 255
```

Gln Pro Tyr Ala Pro Ala Arg Asp Phe Ala Ala Tyr Arg Pro
         260                 265                 270

<210> SEQ ID NO 149
<211> LENGTH: 783
<212> TYPE: DNA
<213> ORGANISM: Artificial Sequence
<220> FEATURE:
<223> OTHER INFORMATION: muTim3-9aas-CD28Cys

<400> SEQUENCE: 149

```
atgttcagcg gcctgaccct gaactgcgtg ctcctgctgc tgcagctgct gctggccaga      60
agcctggaaa acgcctacgt gttcgaagtg ggcaagaacg cctacctgcc ctgcagctac     120
accctgtcta cacctggcgc cctggtgcct atgtgttggg gcaagggctt ctgcccttgg     180
agccagtgca ccaacgagct gctgagaacc gacgagagaa acgtgaccta ccagaagtcc     240
agcagatacc agctgaaggg cgacctgaac aagggcgacg tgtccctgat catcaagaac     300
gtgaccctgg acgaccacgg cacctactgc tgcagaatcc agttccccgg cctgatgaac     360
gacaagaagc tggaactgaa gctggacatc aaggccgcca agtgaccccc tgcccagaca     420
gcccacggcg actctacaac agccagcccc agaaccctga ccaccgagag gaacggcagc     480
gagacacaga ccctcgtgac actgcacaac aacaacggca ccaagatcag cacctgggcc     540
gacgagatca gtgccacac ccagagcagc cccaagctgt tctgggccct ggtggtggtg     600
gccggcgtgc tgttttgtta cggcctgctc gtgaccgtgg ccctgtgcgt gatctggacc     660
aacagcagaa gaaacagagg cggccagagc gactacatga acatgacccc cagaaggcct     720
ggcctgacca gaaagcccta ccagccttac gcccctgcca gagacttcgc cgcctacaga     780
cct                                                                  783
```

<210> SEQ ID NO 150
<211> LENGTH: 261
<212> TYPE: PRT
<213> ORGANISM: Artificial Sequence
<220> FEATURE:
<223> OTHER INFORMATION: muTim3-9aas-CD28Cys

<400> SEQUENCE: 150

Met Phe Ser Gly Leu Thr Leu Asn Cys Val Leu Leu Leu Gln Leu
1               5                   10                  15

Leu Leu Ala Arg Ser Leu Glu Asn Ala Tyr Val Phe Glu Val Gly Lys
            20                  25                  30

Asn Ala Tyr Leu Pro Cys Ser Tyr Thr Leu Ser Thr Pro Gly Ala Leu
        35                  40                  45

Val Pro Met Cys Trp Gly Lys Gly Phe Cys Pro Trp Ser Gln Cys Thr
    50                  55                  60

Asn Glu Leu Leu Arg Thr Asp Glu Arg Asn Val Thr Tyr Gln Lys Ser
65                  70                  75                  80

Ser Arg Tyr Gln Leu Lys Gly Asp Leu Asn Lys Gly Asp Val Ser Leu
                85                  90                  95

Ile Ile Lys Asn Val Thr Leu Asp Asp His Gly Thr Tyr Cys Cys Arg
            100                 105                 110

Ile Gln Phe Pro Gly Leu Met Asn Asp Lys Lys Leu Glu Leu Lys Leu
        115                 120                 125

Asp Ile Lys Ala Ala Lys Val Thr Pro Ala Gln Thr Ala His Gly Asp
    130                 135                 140

Ser Thr Thr Ala Ser Pro Arg Thr Leu Thr Thr Glu Arg Asn Gly Ser

|     |     |     |     | 145 |     |     |     |     | 150 |     |     |     |     | 155 |     |     |     |     | 160 |
| --- | --- | --- | --- | --- | --- | --- | --- | --- | --- | --- | --- | --- | --- | --- | --- | --- | --- | --- | --- |

Glu Thr Gln Thr Leu Val Thr Leu His Asn Asn Asn Gly Thr Lys Ile
            165                   170             175

Ser Thr Trp Ala Asp Glu Ile Lys Cys His Thr Gln Ser Ser Pro Lys
         180                185             190

Leu Phe Trp Ala Leu Val Val Val Ala Gly Val Leu Phe Cys Tyr Gly
    195                200             205

Leu Leu Val Thr Val Ala Leu Cys Val Ile Trp Thr Asn Ser Arg Arg
      210              215            220

Asn Arg Gly Gly Gln Ser Asp Tyr Met Asn Met Thr Pro Arg Arg Pro
225           230               235           240

Gly Leu Thr Arg Lys Pro Tyr Gln Pro Tyr Ala Pro Ala Arg Asp Phe
         245               250            255

Ala Ala Tyr Arg Pro
         260

<210> SEQ ID NO 151
<211> LENGTH: 1536
<212> TYPE: DNA
<213> ORGANISM: Artificial Sequence
<220> FEATURE:
<223> OTHER INFORMATION: huLag3tm-CD28

<400> SEQUENCE: 151

```
atgtgggaag cgcagtttct tggacttctt tttctccagc cgctgtgggt tgcgccagta    60
aagccgctcc aacccggtgc agaggttccg gtagtgtggg cgcaagaggg tgcaccagcg   120
cagctcccct gcagtccgac gattccgctg caagatttgt cactgcttag aagggcgggc   180
gtaacgtggc agcaccaacc ggatagtggc cctccggctg cagcaccagg cacccactc   240
gcccccggcc ctcatcccgc agcaccgagc agctggggtc ctagaccacg cagatataca   300
gtactctcag taggtcccgg cggcctgcgg tccggtcgct tgccccttca acctagagta   360
cagctggatg aaagaggtcg acaacggggt gatttctccc tctggttgag gcctgcacga   420
cgagcagatg ctggggagta tagggctgcc gtacacctgc agaccgcgc acttagttgt    480
agactccggc tccggctggg acaggcctct atgacagcgt ccccccctgg gtccctgcga   540
gcctctgatt gggtaatact caactgctca ttttctcggc cagatcgccc cgctagtgtt   600
cattggttcc gaaatcgcgg ccaaggtcgc gtgcctgttc gagaatctcc acaccaccat   660
ttggcggagt cttttctttt tctgcctcag gtctccccta tggactctgg accgtggggc   720
tgtattttga catatcggga tgggtttaac gtgagtataa tgtataatct cactgtcttg   780
ggtcttgagc cacctacgcc gctgacggtg tacgcgggag ccggcagccg ggttggtctg   840
ccctgcaggc tgcctgcagg agtcgggaca aggtcattcc ttacagcaaa gtggaccccg   900
ccaggtgggg ggcccgacct ccttgtaacg ggagataatg gagatttcac tctgagactt   960
gaggatgtct ctcaagctca ggctgggact tatacatgtc acattcactt gcaagaacag  1020
cagttgaatg cgacggttac cctggctatc ataacagtaa cacctaaatc tttcggtagt  1080
ccgggtagcc tgggcaaact gttgtgtgag gtaaccccg tgtcaggtca agagcggttc   1140
gtctggagct cattggacac tccctcacag cgatcctta gcggaccctg gctcgaagcc   1200
caagaagccc agctgctttc ccaaccatgg cagtgtcaac tctatcaggg tgagcgcctt  1260
ctcggtgcgg ctgtctactt caccgaattg tcctctccgg gagcgcaaag aagtggacgc  1320
gccccagggg ccctcccggc aggacacctt ctgctgtttt tgattttggg ggtacttagt  1380
```

-continued

```
ttgctgctgc ttgtcacagg cgctttcggt ttccgcagca agcggagcag aggcggccac    1440
agcgactaca tgaacatgac ccctagacgg cctggcccca ccagaaagca ctaccagccc    1500
tacgcccctc cccgggactt tgccgcctac agaagc                              1536
```

<210> SEQ ID NO 152
<211> LENGTH: 512
<212> TYPE: PRT
<213> ORGANISM: Artificial Sequence
<220> FEATURE:
<223> OTHER INFORMATION: huLag3tm-CD28

<400> SEQUENCE: 152

```
Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
    50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
    130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
    290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335
```

| | | | | | | | | | | | | |
|---|---|---|---|---|---|---|---|---|---|---|---|---|
| Leu | Gln | Glu | Gln | Gln | Leu | Asn | Ala | Thr | Val | Thr | Leu | Ala | Ile | Ile | Thr |
| | | | 340 | | | | 345 | | | | 350 | |

| Val | Thr | Pro | Lys | Ser | Phe | Gly | Ser | Pro | Gly | Ser | Leu | Gly | Lys | Leu | Leu |
| | 355 | | | | | 360 | | | | | 365 | | | |

| Cys | Glu | Val | Thr | Pro | Val | Ser | Gly | Gln | Glu | Arg | Phe | Val | Trp | Ser | Ser |
| 370 | | | | | 375 | | | | | 380 | | | | |

| Leu | Asp | Thr | Pro | Ser | Gln | Arg | Ser | Phe | Ser | Gly | Pro | Trp | Leu | Glu | Ala |
| 385 | | | | 390 | | | | | 395 | | | | | 400 |

| Gln | Glu | Ala | Gln | Leu | Ser | Gln | Pro | Trp | Gln | Cys | Gln | Leu | Tyr | Gln |
| | | | 405 | | | | | 410 | | | | 415 |

| Gly | Glu | Arg | Leu | Leu | Gly | Ala | Ala | Val | Tyr | Phe | Thr | Glu | Leu | Ser | Ser |
| | | 420 | | | | | 425 | | | | | 430 | | |

| Pro | Gly | Ala | Gln | Arg | Ser | Gly | Arg | Ala | Pro | Gly | Ala | Leu | Pro | Ala | Gly |
| | 435 | | | | | 440 | | | | | 445 | | | |

| His | Leu | Leu | Leu | Phe | Leu | Ile | Leu | Gly | Val | Leu | Ser | Leu | Leu | Leu | Leu |
| | 450 | | | | 455 | | | | | 460 | | | | |

| Val | Thr | Gly | Ala | Phe | Gly | Phe | Arg | Ser | Lys | Arg | Ser | Arg | Gly | Gly | His |
| 465 | | | | | 470 | | | | | 475 | | | | | 480 |

| Ser | Asp | Tyr | Met | Asn | Met | Thr | Pro | Arg | Arg | Pro | Gly | Pro | Thr | Arg | Lys |
| | | | | 485 | | | | | 490 | | | | | 495 |

| His | Tyr | Gln | Pro | Tyr | Ala | Pro | Pro | Arg | Asp | Phe | Ala | Ala | Tyr | Arg | Ser |
| | | | 500 | | | | | 505 | | | | | 510 |

<210> SEQ ID NO 153
<211> LENGTH: 1350
<212> TYPE: DNA
<213> ORGANISM: Artificial Sequence
<220> FEATURE:
<223> OTHER INFORMATION: huLag3 ectodomain

<400> SEQUENCE: 153

```
atgtgggaag cgcagtttct tggacttctt tttctccagc cgctgtgggt tgcgccagta      60
aagccgctcc aacccggtgc agaggttccg gtagtgtggg cgcaagaggg tgcaccagcg     120
cagctcccct gcagtccgac gattccgctg caagatttgt cactgcttag aagggcgggc     180
gtaacgtggc agcaccaacc ggatagtggc cctccggctg cagcaccagg gcacccactc     240
gccccggcc ctcatcccgc agcaccgagc agctggggtc ctagaccacg cagatataca     300
gtactctcag taggtcccgg cggcctgcgg tccggtcgct tgccccttca acctagagta     360
cagctggatg aaagaggtcg acaacggggt gatttctccc tctggttgag gcctgcacga     420
cgagcagatg ctggggagta tagggctgcc gtacacctgc gagaccgcgc acttagttgt     480
agactccggc tccggctggg acaggcctct atgacagcgt cccccctgg tccctgcga      540
gcctctgatt gggtaatact caactgctca ttttctcggc cagatcgccc cgctagtgtt     600
cattggttcc gaaatcgcgg ccaaggtcgc gtgcctgttc gagaatctcc acaccaccat     660
ttggcggagt cttttctttt tctgcctcag gtctccccta tggactctgg accgtggggc     720
tgtatttga catatcggga tgggtttaac gtgagtataa tgtataatct cactgtcttg      780
ggtcttgagc cacctacgcc gctgacggtg tacgcgggag ccggcagccg ggttggtctg     840
ccctgcaggc tgcctgcagg agtcgggaca aggtcattcc ttacagcaaa gtggaccccg     900
ccaggtgggg ggcccgacct ccttgtaacg ggagataatg agatttcac tctgagactt     960
gaggatgtct ctcaagctca ggctgggact tatacatgtc acattcactt gcaagaacag    1020
cagttgaatg cgacggttac cctggctatc ataacagtaa cacctaaatc tttcggtagt    1080
```

```
ccgggtagcc tgggcaaact gttgtgtgag gtaaccccg tgtcaggtca agagcggttc    1140
gtctggagct cattggacac tccctcacag cgatccttta gcggaccctg gctcgaagcc    1200
caagaagccc agctgctttc ccaaccatgg cagtgtcaac tctatcaggg tgagcgcctt    1260
ctcggtgcgg ctgtctactt caccgaattg tcctctccgg gagcgcaaag aagtggacgc    1320
gccccagggg ccctcccggc aggacacctt                                     1350
```

```
<210> SEQ ID NO 154
<211> LENGTH: 450
<212> TYPE: PRT
<213> ORGANISM: Artificial Sequence
<220> FEATURE:
<223> OTHER INFORMATION: huLag3 ectodomain

<400> SEQUENCE: 154
```

| | | | | | | | | | | | | | | |
|---|---|---|---|---|---|---|---|---|---|---|---|---|---|---|
| Met | Trp | Glu | Ala | Gln | Phe | Leu | Gly | Leu | Leu | Phe | Leu | Gln | Pro | Leu | Trp |
| 1 | | | | 5 | | | | | 10 | | | | | 15 | |
| Val | Ala | Pro | Val | Lys | Pro | Leu | Gln | Pro | Gly | Ala | Glu | Val | Pro | Val | Val |
| | | | 20 | | | | | 25 | | | | | 30 | | |
| Trp | Ala | Gln | Glu | Gly | Ala | Pro | Ala | Gln | Leu | Pro | Cys | Ser | Pro | Thr | Ile |
| | | 35 | | | | | 40 | | | | | 45 | | | |
| Pro | Leu | Gln | Asp | Leu | Ser | Leu | Leu | Arg | Arg | Ala | Gly | Val | Thr | Trp | Gln |
| | 50 | | | | | 55 | | | | | 60 | | | | |
| His | Gln | Pro | Asp | Ser | Gly | Pro | Pro | Ala | Ala | Ala | Pro | Gly | His | Pro | Leu |
| 65 | | | | | 70 | | | | | 75 | | | | | 80 |
| Ala | Pro | Gly | Pro | His | Pro | Ala | Ala | Pro | Ser | Ser | Trp | Gly | Pro | Arg | Pro |
| | | | | 85 | | | | | 90 | | | | | 95 | |
| Arg | Arg | Tyr | Thr | Val | Leu | Ser | Val | Gly | Pro | Gly | Gly | Leu | Arg | Ser | Gly |
| | | | 100 | | | | | 105 | | | | | 110 | | |
| Arg | Leu | Pro | Leu | Gln | Pro | Arg | Val | Gln | Leu | Asp | Glu | Arg | Gly | Arg | Gln |
| | | | 115 | | | | | 120 | | | | | 125 | | |
| Arg | Gly | Asp | Phe | Ser | Leu | Trp | Leu | Arg | Pro | Ala | Arg | Arg | Ala | Asp | Ala |
| | | 130 | | | | | 135 | | | | | 140 | | | |
| Gly | Glu | Tyr | Arg | Ala | Ala | Val | His | Leu | Arg | Asp | Arg | Ala | Leu | Ser | Cys |
| 145 | | | | | 150 | | | | | 155 | | | | | 160 |
| Arg | Leu | Arg | Leu | Arg | Leu | Gly | Gln | Ala | Ser | Met | Thr | Ala | Ser | Pro | Pro |
| | | | | 165 | | | | | 170 | | | | | 175 | |
| Gly | Ser | Leu | Arg | Ala | Ser | Asp | Trp | Val | Ile | Leu | Asn | Cys | Ser | Phe | Ser |
| | | | | 180 | | | | | 185 | | | | | 190 | |
| Arg | Pro | Asp | Arg | Pro | Ala | Ser | Val | His | Trp | Phe | Arg | Asn | Arg | Gly | Gln |
| | | | 195 | | | | | 200 | | | | | 205 | | |
| Gly | Arg | Val | Pro | Val | Arg | Glu | Ser | Pro | His | His | Leu | Ala | Glu | Ser |
| | | 210 | | | | | 215 | | | | | 220 | | | |
| Phe | Leu | Phe | Leu | Pro | Gln | Val | Ser | Pro | Met | Asp | Ser | Gly | Pro | Trp | Gly |
| 225 | | | | | 230 | | | | | 235 | | | | | 240 |
| Cys | Ile | Leu | Thr | Tyr | Arg | Asp | Gly | Phe | Asn | Val | Ser | Ile | Met | Tyr | Asn |
| | | | | 245 | | | | | 250 | | | | | 255 | |
| Leu | Thr | Val | Leu | Gly | Leu | Glu | Pro | Pro | Thr | Pro | Leu | Thr | Val | Tyr | Ala |
| | | | 260 | | | | | 265 | | | | | 270 | | |
| Gly | Ala | Gly | Ser | Arg | Val | Gly | Leu | Pro | Cys | Arg | Leu | Pro | Ala | Gly | Val |
| | | | 275 | | | | | 280 | | | | | 285 | | |
| Gly | Thr | Arg | Ser | Phe | Leu | Thr | Ala | Lys | Trp | Thr | Pro | Pro | Gly | Gly | Gly |
| | | 290 | | | | | 295 | | | | | 300 | | | |
| Pro | Asp | Leu | Leu | Val | Thr | Gly | Asp | Asn | Gly | Asp | Phe | Thr | Leu | Arg | Leu |
| 305 | | | | | 310 | | | | | 315 | | | | | 320 |

-continued

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
    370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
        435                 440                 445

His Leu
    450

<210> SEQ ID NO 155
<211> LENGTH: 63
<212> TYPE: DNA
<213> ORGANISM: Artificial Sequence
<220> FEATURE:
<223> OTHER INFORMATION: huLag3 transmembrane domain

<400> SEQUENCE: 155
ctgctgtttt tgattttggg ggtacttagt ttgctgctgc ttgtcacagg cgctttcggt      60
ttc                                                                   63

<210> SEQ ID NO 156
<211> LENGTH: 21
<212> TYPE: PRT
<213> ORGANISM: Artificial Sequence
<220> FEATURE:
<223> OTHER INFORMATION: huLag3 transmembrane domain

<400> SEQUENCE: 156

Leu Leu Phe Leu Ile Leu Gly Val Leu Ser Leu Leu Leu Leu Val Thr
1               5                   10                  15

Gly Ala Phe Gly Phe
            20

<210> SEQ ID NO 157
<211> LENGTH: 1554
<212> TYPE: DNA
<213> ORGANISM: Artificial Sequence
<220> FEATURE:
<223> OTHER INFORMATION: huLag3-CD28tm

<400> SEQUENCE: 157
atgtgggaag cgcagtttct tggacttctt tttctccagc cgctgtgggt tgcgccagta      60
aagccgctcc aacccggtgc agaggttccg gtagtgtggg cgcaagaggg tgcaccagcg     120
cagctcccct gcagtccgac gattccgctg caagatttgt cactgcttag aagggcgggc     180
gtaacgtggc agcaccaacc ggatagtggc cctccggctg cagcaccagg cacccactc     240 gcccccggcc ctcatcccgc agcaccgagc agctggggtc ctagaccacg cagatataca     300
gtactctcag taggtcccgg cggcctgcgg tccggtcgct tgcccccttca acctagagta    360

```
cagctggatg aaagaggtcg acaacggggt gatttctccc tctggttgag gcctgcacga      420
cgagcagatg ctggggagta tagggctgcc gtacacctgc gagaccgcgc acttagttgt      480
agactccggc tccggctggg acaggcctct atgacagcgt ccccccctgg gtccctgcga      540
gcctctgatt gggtaatact caactgctca ttttctcggc cagatcgccc cgctagtgtt      600
cattggttcc gaaatcgcgg ccaaggtcgc gtgcctgttc gagaatctcc acaccaccat      660
ttggcggagt ctttttcttt tctgcctcag gtctccccta tggactctgg accgtggggc      720
tgtattttga catatcggga tgggtttaac gtgagtataa tgtataatct cactgtcttg      780
ggtcttgagc cacctacgcc gctgacggtg tacgcgggag ccggcagccg ggttggtctg      840
ccctgcaggc tgcctgcagg agtcgggaca aggtcattcc ttacagcaaa gtggaccccg      900
ccaggtgggg gccccgacct ccttgtaacg ggagataatg gagatttcac tctgagactt      960
gaggatgtct ctcaagctca ggctgggact tatacatgtc acattcactt gcaagaacag     1020
cagttgaatg cgacggttac cctggctatc ataacagtaa cacctaaatc tttcggtagt     1080
ccgggtagcc tgggcaaact gttgtgtgag gtaaccccg tgtcaggtca agagcggttc      1140
gtctggagct cattggacac tccctcacag cgatccttta gcggaccctg gctcgaagcc     1200
caagaagccc agctgctttc ccaaccatgg cagtgtcaac tctatcaggg tgagcgcctt     1260
ctcggtgcgg ctgtctactt caccgaattg tcctctccgg gagcgcaaag aagtggacgc     1320
gccccagggg ccctcccggc aggacacctt ttctgggtgc tggtggtggt cggaggcgtg     1380
ctggcctgct acagcctgct ggtcaccgtg gccttcatca tcttttgggt ccgcagcaag     1440
cggagcagag gcggccacag cgactacatg aacatgaccc ctagacggcc tggccccacc     1500
agaaagcact accagcccta cgcccctccc cgggactttg ccgcctacag aagc           1554
```

<210> SEQ ID NO 158
<211> LENGTH: 518
<212> TYPE: PRT
<213> ORGANISM: Artificial Sequence
<220> FEATURE:
<223> OTHER INFORMATION: huLag3-CD28tm

<400> SEQUENCE: 158

```
Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
                20                  25                  30

Trp Ala Gln Glu Gly Ala Pro Ala Gln Leu Pro Cys Ser Pro Thr Ile
            35                  40                  45

Pro Leu Gln Asp Leu Ser Leu Leu Arg Arg Ala Gly Val Thr Trp Gln
        50                  55                  60

His Gln Pro Asp Ser Gly Pro Pro Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
                100                 105                 110

Arg Leu Pro Leu Gln Pro Arg Val Gln Leu Asp Glu Arg Gly Arg Gln
            115                 120                 125

Arg Gly Asp Phe Ser Leu Trp Leu Arg Pro Ala Arg Arg Ala Asp Ala
        130                 135                 140

Gly Glu Tyr Arg Ala Ala Val His Leu Arg Asp Arg Ala Leu Ser Cys
```

```
            145                 150                 155                 160
Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
                180                 185                 190

Arg Pro Asp Arg Pro Ala Ser Val His Trp Phe Arg Asn Arg Gly Gln
            195                 200                 205

Gly Arg Val Pro Val Arg Glu Ser Pro His His His Leu Ala Glu Ser
        210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
                260                 265                 270

Gly Ala Gly Ser Arg Val Gly Leu Pro Cys Arg Leu Pro Ala Gly Val
            275                 280                 285

Gly Thr Arg Ser Phe Leu Thr Ala Lys Trp Thr Pro Pro Gly Gly Gly
        290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
370                 375                 380

Leu Asp Thr Pro Ser Gln Arg Ser Phe Ser Gly Pro Trp Leu Glu Ala
                385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
        435                 440                 445

His Leu Phe Trp Val Leu Val Val Gly Val Leu Ala Cys Tyr
450                 455                 460

Ser Leu Leu Val Thr Val Ala Phe Ile Ile Phe Trp Val Arg Ser Lys
465                 470                 475                 480

Arg Ser Arg Gly Gly His Ser Asp Tyr Met Asn Met Thr Pro Arg Arg
                485                 490                 495

Pro Gly Pro Thr Arg Lys His Tyr Gln Pro Tyr Ala Pro Pro Arg Asp
            500                 505                 510

Phe Ala Ala Tyr Arg Ser
            515

<210> SEQ ID NO 159
<211> LENGTH: 1554
<212> TYPE: DNA
<213> ORGANISM: Artificial Sequence
<220> FEATURE:
<223> OTHER INFORMATION: huLag3-12aas-CD28Cys
```

<400> SEQUENCE: 159

```
atgtgggaag cgcagtttct tggacttctt tttctccagc cgctgtgggt tgcgccagta      60
aagccgctcc aacccggtgc agaggttccg gtagtgtggg cgcaagaggg tgcaccagcg     120
cagctcccct gcagtccgac gattccgctg caagatttgt cactgcttag aagggcgggc     180
gtaacgtggc agcaccaacc ggatagtggc cctccggctg cagcaccagg gcacccactc     240
gcccccggcc ctcatcccgc agcaccgagc agctggggtc ctagaccacg cagatataca     300
gtactctcag taggtcccgg cggcctgcgg tccggtcgct tgccccttca acctagagta     360
cagctggatg aaagaggtcg acaacggggt gatttctccc tctggttgag gcctgcacga     420
cgagcagatg ctggggagta tagggctgcc gtacacctgc gagaccgcgc acttagttgt     480
agactccggc tccggctggg acaggcctct atgacagcgt cccccctgg gtccctgcga      540
gcctctgatt gggtaatact caactgctca ttttctcggc cagatcgccc cgctagtgtt     600
cattggttcc gaaatcgcgg ccaaggtcgc gtgcctgttc gagaatctcc acaccaccat     660
ttggcggagt ctttctttt tctgcctcag gtctcccta tggactctgg accgtggggc       720
tgtattttga catatcggga tgggtttaac gtgagtataa tgtataatct cactgtcttg     780
ggtcttgagc cacctacgcc gctgacggtg tacgcgggag ccggcagccg ggttggtctg     840
ccctgcaggc tgcctgcagg agtcgggaca aggtcattcc ttacagcaaa gtggaccccg     900
ccaggtgggg ggcccgacct ccttgtaacg ggagataatg gagatttcac tctgagactt     960
gaggatgtct ctcaagctca ggctgggact tatacatgtc acattcactt gcaagaacag    1020
cagttgaatg cgacggttac cctggctatc ataacagtaa cacctaaatc tttcggtagt    1080
ccgggtagcc tgggcaaact gttgtgtgag gtaaccccg tgtcaggtca agagcggttc     1140
gtctggagct cattggacac tccctcacag cgatcctta gcggaccctg gctcgaagcc     1200
caagaagccc agctgctttc caaccatgg cagtgtcaac tctatcaggg tgagcgcctt      1260
ctcggtgcgg ctgtctactt caccgaattg tcctctccgg gagcgcaaag aagttgtccc    1320
agccctctgt tcccggccc tagcaagcct ttctgggtgc tggtggtggt cggaggcgtg     1380
ctggcctgct acagcctgct ggtcaccgtg gccttcatca tctttttggt ccgcagcaag    1440
cggagcagag gcggccacag cgactacatg aacatgaccc ctagacggcc tggccccacc    1500
agaaagcact accagcccta cgcccctccc cgggactttg ccgcctacag aagc          1554
```

<210> SEQ ID NO 160
<211> LENGTH: 518
<212> TYPE: PRT
<213> ORGANISM: Artificial Sequence
<220> FEATURE:
<223> OTHER INFORMATION: huLag3-12aas-CD28Cys

<400> SEQUENCE: 160

```
Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
    50                  55                  60

His Gln Pro Asp Ser Gly Pro Pro Ala Ala Ala Pro Gly His Pro Leu
65                  70                  75                  80
```

-continued

```
Ala Pro Gly Pro His Pro Ala Ala Pro Ser Trp Gly Pro Arg Pro
                 85                  90                  95

Arg Arg Tyr Thr Val Leu Ser Val Gly Pro Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
    130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
        275                 280                 285

Gly Thr Arg Ser Phe Leu Thr Ala Lys Trp Thr Pro Pro Gly Gly Gly
    290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
        355                 360                 365

Cys Glu Val Thr Pro Val Ser Gly Gln Glu Arg Phe Val Trp Ser Ser
    370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Cys Pro Ser Pro Leu Phe Pro Gly Pro Ser
        435                 440                 445

Lys Pro Phe Trp Val Leu Val Val Gly Gly Val Leu Ala Cys Tyr
    450                 455                 460

Ser Leu Leu Val Thr Val Ala Phe Ile Ile Phe Trp Val Arg Ser Lys
465                 470                 475                 480

Arg Ser Arg Gly Gly His Ser Asp Tyr Met Asn Met Thr Pro Arg Arg
                485                 490                 495

Pro Gly Pro Thr Arg Lys His Tyr Gln Pro Tyr Ala Pro Pro Arg Asp
```

```
                500               505               510
Phe Ala Ala Tyr Arg Ser
        515
```

<210> SEQ ID NO 161
<211> LENGTH: 1314
<212> TYPE: DNA
<213> ORGANISM: Artificial Sequence
<220> FEATURE:
<223> OTHER INFORMATION: huLag3-12aas

<400> SEQUENCE: 161

| | |
|---|---:|
| atgtgggaag cgcagtttct tggacttctt tttctccagc cgctgtgggt tgcgccagta | 60 |
| aagccgctcc aacccggtgc agaggttccg gtagtgtggg cgcaagaggg tgcaccagcg | 120 |
| cagctcccct gcagtccgac gattccgctg caagatttgt cactgcttag aagggcgggc | 180 |
| gtaacgtggc agcaccaacc ggatagtggc cctccggctg cagcaccagg gcacccactc | 240 |
| gcccccggcc ctcatcccgc agcaccgagc agctggggtc ctagaccacg cagatataca | 300 |
| gtactctcag taggtcccgg cggcctgcgg tccggtcgct gcccccttca acctagagta | 360 |
| cagctggatg aaagaggtcg acaacggggt gatttctccc tctggttgag gcctgcacga | 420 |
| cgagcagatg ctggggagta tagggctgcc gtacacctgc gagaccgcgc acttagttgt | 480 |
| agactccggc tccggctggg acaggcctct atgacagcgt cccccctgg gtccctgcga | 540 |
| gcctctgatt gggtaatact caactgctca ttttctcggc cagatcgccc cgctagtgtt | 600 |
| cattggttcc gaaatcgcgg ccaaggtcgc gtgcctgttc gagaatctcc acaccaccat | 660 |
| ttggcggagt cttttctttt tctgcctcag gtctccccta tggactctgg accgtggggc | 720 |
| tgtatttga catatcggga tgggtttaac gtgagtataa tgtataatct cactgtcttg | 780 |
| ggtcttgagc cacctacgcc gctgacggtg tacgcgggag ccggcagccg ggttggtctg | 840 |
| ccctgcaggc tgcctgcagg agtcgggaca aggtcattcc ttacagcaaa gtggaccccg | 900 |
| ccaggtgggg ggcccgacct ccttgtaacg ggagataatg gagatttcac tctgagactt | 960 |
| gaggatgtct ctcaagctca ggctgggact tatacatgtc acattcactt gcaagaacag | 1020 |
| cagttgaatg cgacggttac cctggctatc ataacagtaa cacctaaatc tttcggtagt | 1080 |
| ccgggtagcc tgggcaaact gttgtgtgag gtaaccccg tgtcaggtca agagcggttc | 1140 |
| gtctggagct cattggacac tccctcacag cgatcctta gcggaccctg gctcgaagcc | 1200 |
| caagaagccc agctgctttc ccaaccatgg cagtgtcaac tctatcaggg tgagcgcctt | 1260 |
| ctcggtgcgg ctgtctactt caccgaattg tcctctccgg gagcgcaaag aagt | 1314 |

<210> SEQ ID NO 162
<211> LENGTH: 438
<212> TYPE: PRT
<213> ORGANISM: Artificial Sequence
<220> FEATURE:
<223> OTHER INFORMATION: huLag3-12aas

<400> SEQUENCE: 162

```
Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
```

```
            50                  55                  60
His Gln Pro Asp Ser Gly Pro Pro Ala Ala Pro Gly His Pro Leu
 65                  70                  75                  80

Ala Pro Gly Pro His Pro Ala Ala Pro Ser Ser Trp Gly Pro Arg Pro
                 85                  90                  95

Arg Arg Tyr Thr Val Leu Ser Val Gly Pro Gly Leu Arg Ser Gly
            100                 105                 110

Arg Leu Pro Leu Gln Pro Arg Val Gln Leu Asp Glu Arg Gly Arg Gln
            115                 120                 125

Arg Gly Asp Phe Ser Leu Trp Leu Arg Pro Ala Arg Arg Ala Asp Ala
        130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
            195                 200                 205

Gly Arg Val Pro Val Arg Glu Ser Pro His His Leu Ala Glu Ser
210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
            275                 280                 285

Gly Thr Arg Ser Phe Leu Thr Ala Lys Trp Thr Pro Pro Gly Gly Gly
            290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
            355                 360                 365

Cys Glu Val Thr Pro Val Ser Gly Gln Glu Arg Phe Val Trp Ser Ser
370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser
            435

<210> SEQ ID NO 163
<211> LENGTH: 1590
<212> TYPE: DNA
<213> ORGANISM: Artificial Sequence
```

<220> FEATURE:
<223> OTHER INFORMATION: huLag3-CD28Cys

<400> SEQUENCE: 163

| | | | | | |
|---|---|---|---|---|---|
| atgtgggaag | cgcagtttct | tggacttctt | tttctccagc | cgctgtgggt | tgcgccagta | 60 |
| aagccgctcc | aacccggtgc | agaggttccg | gtagtgtggg | cgcaagaggg | tgcaccagcg | 120 |
| cagctcccct | gcagtccgac | gattccgctg | caagatttgt | cactgcttag | aagggcgggc | 180 |
| gtaacgtggc | agcaccaacc | ggatagtggc | cctccggctg | cagcaccagg | gcacccactc | 240 |
| gcccccggcc | ctcatcccgc | agcaccgagc | agctggggtc | ctagaccacg | cagatataca | 300 |
| gtactctcag | taggtcccgg | cggcctgcgg | tccggtcgct | tgccccttca | acctagagta | 360 |
| cagctggatg | aaagaggtcg | acaacggggt | gatttctccc | tctggttgag | gcctgcacga | 420 |
| cgagcagatg | ctggggagta | tagggctgcc | gtacacctgc | gagaccgcgc | acttagttgt | 480 |
| agactccggc | tccggctggg | acaggcctct | atgacagcgt | cccccctgg | gtccctgcga | 540 |
| gcctctgatt | gggtaatact | caactgctca | ttttctcggc | cagatcgccc | cgctagtgtt | 600 |
| cattggttcc | gaaatcgcgg | ccaaggtcgc | gtgcctgttc | gagaatctcc | acaccaccat | 660 |
| ttggcggagt | cttttctttt | tctgcctcag | gtctccccta | tggactctgg | accgtggggc | 720 |
| tgtattttga | catatcggga | tgggtttaac | gtgagtataa | tgtataatct | cactgtcttg | 780 |
| ggtcttgagc | cacctacgcc | gctgacggtg | tacgcgggag | ccggcagccg | ggttggtctg | 840 |
| ccctgcaggc | tgcctgcagg | agtcgggaca | aggtcattcc | ttacagcaaa | gtggaccccg | 900 |
| ccaggtgggg | ggcccgacct | ccttgtaacg | ggagataatg | gagatttcac | tctgagactt | 960 |
| gaggatgtct | ctcaagctca | ggctgggact | tatacatgtc | acattcactt | gcaagaacag | 1020 |
| cagttgaatg | cgacggttac | cctggctatc | ataacagtaa | cacctaaatc | tttcggtagt | 1080 |
| ccgggtagcc | tgggcaaact | gttgtgtgag | gtaaccccg | tgtcaggtca | agagcggttc | 1140 |
| gtctggagct | cattggacac | tccctcacag | cgatccttta | gcggaccctg | gctcgaagcc | 1200 |
| caagaagccc | agctgctttc | caaccatgg | cagtgtcaac | tctatcaggg | tgagcgcctt | 1260 |
| ctcggtgcgg | ctgtctactt | caccgaattg | tcctctccgg | gagcgcaaag | aagtggacgc | 1320 |
| gccccagggg | ccctcccggc | aggacacctt | tgtcccagcc | ctctgttcc | cggccctagc | 1380 |
| aagcctttct | gggtgctggt | ggtggtcgga | ggcgtgctgg | cctgctacag | cctgctggtc | 1440 |
| accgtggcct | tcatcatctt | ttgggtccgc | agcaagcgga | gcagaggcgg | ccacagcgac | 1500 |
| tacatgaaca | tgaccctag | acggcctggc | cccaccagaa | agcactacca | gccctacgcc | 1560 |
| cctccccggg | actttgccgc | ctacagaagc | | | | 1590 |

<210> SEQ ID NO 164
<211> LENGTH: 530
<212> TYPE: PRT
<213> ORGANISM: Artificial Sequence
<220> FEATURE:
<223> OTHER INFORMATION: huLag3-CD28Cys

<400> SEQUENCE: 164

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln

-continued

```
            50                  55                  60
His Gln Pro Asp Ser Gly Pro Pro Ala Ala Ala Pro Gly His Pro Leu
 65                  70                  75                  80

Ala Pro Gly Pro His Pro Ala Ala Pro Ser Ser Trp Gly Pro Arg Pro
                 85                  90                  95

Arg Arg Tyr Thr Val Leu Ser Val Gly Pro Gly Leu Arg Ser Gly
            100                 105                 110

Arg Leu Pro Leu Gln Pro Arg Val Gln Leu Asp Glu Arg Gly Arg Gln
            115                 120                 125

Arg Gly Asp Phe Ser Leu Trp Leu Arg Pro Ala Arg Arg Ala Asp Ala
        130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
        195                 200                 205

Gly Arg Val Pro Val Arg Glu Ser Pro His His Leu Ala Glu Ser
    210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
            260                 265                 270

Gly Ala Gly Ser Arg Val Gly Leu Pro Cys Arg Leu Pro Ala Gly Val
            275                 280                 285

Gly Thr Arg Ser Phe Leu Thr Ala Lys Trp Thr Pro Pro Gly Gly Gly
        290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
            340                 345                 350

Val Thr Pro Lys Ser Phe Gly Ser Pro Gly Ser Leu Gly Lys Leu Leu
            355                 360                 365

Cys Glu Val Thr Pro Val Ser Gly Gln Glu Arg Phe Val Trp Ser Ser
        370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
            420                 425                 430

Pro Gly Ala Gln Arg Ser Gly Arg Ala Pro Gly Ala Leu Pro Ala Gly
            435                 440                 445

His Leu Cys Pro Ser Pro Leu Phe Pro Gly Pro Ser Lys Pro Phe Trp
        450                 455                 460

Val Leu Val Val Val Gly Gly Val Leu Ala Cys Tyr Ser Leu Leu Val
465                 470                 475                 480
```

```
Thr Val Ala Phe Ile Ile Phe Trp Val Arg Ser Lys Arg Ser Arg Gly
                485                 490                 495

Gly His Ser Asp Tyr Met Asn Met Thr Pro Arg Arg Pro Gly Pro Thr
            500                 505                 510

Arg Lys His Tyr Gln Pro Tyr Ala Pro Pro Arg Asp Phe Ala Ala Tyr
        515                 520                 525

Arg Ser
    530

<210> SEQ ID NO 165
<211> LENGTH: 792
<212> TYPE: DNA
<213> ORGANISM: Artificial Sequence
<220> FEATURE:
<223> OTHER INFORMATION: huTim3tm-CD28

<400> SEQUENCE: 165
```

| | | | | | |
|---|---|---|---|---|---|
| atgttctccc | atcttcccct | cgactgtgtg | ttgctccttc | tcctcctgct | tctcacccgg | 60 |
| tcaagcgaag | tagagtaccg | ggcggaagta | ggtcagaacg | catatctccc | ctgttttac | 120 |
| acacccgctg | cgccgggaaa | cctggttccc | gtgtgttggg | gaaaggggc | atgccctgtt | 180 |
| ttcgagtgtg | gcaacgtggt | cctccggacg | gatgagcgag | acgtgaatta | ttggacgagc | 240 |
| agatattggt | tgaatggcga | ttttagaaag | ggtgatgtga | gcttgaccat | tgagaatgta | 300 |
| acgcttgctg | atagcgggat | atattgctgt | agaattcaaa | tccctggtat | aatgaacgac | 360 |
| gaaaaattca | atctgaagct | ggtaattaag | ccggccaagg | tgacacccgc | ccgacacga | 420 |
| cagcgcgact | tcacggctgc | ctttccacgc | atgttgacca | aaggggaca | tggtccagcg | 480 |
| gagacccaga | cacttggtag | cctcccggac | ataaacctca | cacaaatatc | cacgttggcg | 540 |
| aacgagctcc | gagattccag | gcttgcgaat | gacctgaggg | attctggagc | taccatcaga | 600 |
| atcggtatct | acataggtgc | cgggatatgc | gccgtctcg | cacttgcctt | gattttcggg | 660 |
| gcactgattc | gcagcaagcg | gagcagaggc | ggccacagcg | actacatgaa | catgaccct | 720 |
| agacggcctg | gccccaccag | aaagcactac | cagccctacg | cccctcccg | ggactttgcc | 780 |
| gcctacagaa | gc | | | | | 792 |

```
<210> SEQ ID NO 166
<211> LENGTH: 264
<212> TYPE: PRT
<213> ORGANISM: Artificial Sequence
<220> FEATURE:
<223> OTHER INFORMATION: huTim3tm-CD28

<400> SEQUENCE: 166

Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95
```

```
Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
        195                 200                 205

Ile Cys Ala Gly Leu Ala Leu Ala Leu Ile Phe Gly Ala Leu Ile Arg
    210                 215                 220

Ser Lys Arg Ser Arg Gly Gly His Ser Asp Tyr Met Asn Met Thr Pro
225                 230                 235                 240

Arg Arg Pro Gly Pro Thr Arg Lys His Tyr Gln Pro Tyr Ala Pro Pro
                245                 250                 255

Arg Asp Phe Ala Ala Tyr Arg Ser
            260
```

<210> SEQ ID NO 167
<211> LENGTH: 606
<212> TYPE: DNA
<213> ORGANISM: Artificial Sequence
<220> FEATURE:
<223> OTHER INFORMATION: huTim3 ectodomain

<400> SEQUENCE: 167

```
atgttctccc atcttcccctt cgactgtgtg ttgctcctcc tcctcctgct tctcacccgg      60
tcaagcgaag tagagtaccg ggcggaagta ggtcagaacg catatctccc ctgttttttac     120
acacccgctg cgccgggaaa cctggttccc gtgtgttggg gaaaggggc atgccctgtt       180
ttcgagtgtg gcaacgtggt cctccggacg gatgagcgag acgtgaatta ttggacgagc      240
agatattggt tgaatggcga ttttagaaag ggtgatgtga gcttgaccat tgagaatgta      300
acgcttgctg atagcgggat atattgctgt agaattcaaa tccctggtat aatgaacgac      360
gaaaaattca atctgaagct ggtaattaag ccggccaagg tgacacccgc cccgacacga      420
cagcgcgact tcacggctgc ctttccacgc atgttgacca aaggggaca tggtccagcg        480
gagacccaga cacttggtag cctcccggac ataaacctca cacaaatatc cacgttggcg      540
aacgagctcc gagattccag gcttgcgaat gacctgaggg attctggagc taccatcaga      600
atcggt                                                                 606
```

<210> SEQ ID NO 168
<211> LENGTH: 202
<212> TYPE: PRT
<213> ORGANISM: Artificial Sequence
<220> FEATURE:
<223> OTHER INFORMATION: huTim3 ectodomain

<400> SEQUENCE: 168

```
Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
```

```
                    20                  25                  30
Asn Ala Tyr Leu Pro Cys Phe Tyr Thr Pro Ala Ala Pro Gly Asn Leu
                35                  40                  45
Val Pro Val Cys Trp Gly Lys Gly Ala Cys Pro Val Phe Glu Cys Gly
 50                  55                  60
Asn Val Val Leu Arg Thr Asp Glu Arg Asp Val Asn Tyr Trp Thr Ser
 65                  70                  75                  80
Arg Tyr Trp Leu Asn Gly Asp Phe Arg Lys Gly Asp Val Ser Leu Thr
                85                  90                  95
Ile Glu Asn Val Thr Leu Ala Asp Ser Gly Ile Tyr Cys Cys Arg Ile
                100                 105                 110
Gln Ile Pro Gly Ile Met Asn Asp Glu Lys Phe Asn Leu Lys Leu Val
                115                 120                 125
Ile Lys Pro Ala Lys Val Thr Pro Ala Pro Thr Arg Gln Arg Asp Phe
                130                 135                 140
Thr Ala Ala Phe Pro Arg Met Leu Thr Thr Arg Gly His Gly Pro Ala
145                 150                 155                 160
Glu Thr Gln Thr Leu Gly Ser Leu Pro Asp Ile Asn Leu Thr Gln Ile
                165                 170                 175
Ser Thr Leu Ala Asn Glu Leu Arg Asp Ser Arg Leu Ala Asn Asp Leu
                180                 185                 190
Arg Asp Ser Gly Ala Thr Ile Arg Ile Gly
                195                 200

<210> SEQ ID NO 169
<211> LENGTH: 63
<212> TYPE: DNA
<213> ORGANISM: Artificial Sequence
<220> FEATURE:
<223> OTHER INFORMATION: huTim3 transmembrane

<400> SEQUENCE: 169
atctacatag gtgccgggat atgcgccggt ctcgcacttg ccttgatttt cggggcactg    60
att                                                                  63

<210> SEQ ID NO 170
<211> LENGTH: 21
<212> TYPE: PRT
<213> ORGANISM: Artificial Sequence
<220> FEATURE:
<223> OTHER INFORMATION: huTim3 transmembrane

<400> SEQUENCE: 170

Ile Tyr Ile Gly Ala Gly Ile Cys Ala Gly Leu Ala Leu Ala Leu Ile
 1               5                  10                  15

Phe Gly Ala Leu Ile
            20

<210> SEQ ID NO 171
<211> LENGTH: 810
<212> TYPE: DNA
<213> ORGANISM: Artificial Sequence
<220> FEATURE:
<223> OTHER INFORMATION: huTim3-CD28tm

<400> SEQUENCE: 171
atgttctccc atcttccctt cgactgtgtg ttgctcctcc tcctcctgct tctcacccgg    60
tcaagcgaag tagagtaccg ggcggaagta ggtcagaacg catatctccc ctgttttttac  120
```

```
acacccgctg cgccgggaaa cctggttccc gtgtgttggg gaaaggggc atgccctgtt    180
ttcgagtgtg gcaacgtggt cctccggacg gatgagcgag acgtgaatta ttggacgagc    240
agatattggt tgaatggcga ttttagaaag ggtgatgtga gcttgaccat tgagaatgta    300
acgcttgctg atagcgggat atattgctgt agaattcaaa tccctggtat aatgaacgac    360
gaaaaattca atctgaagct ggtaattaag ccggccaagg tgacacccgc cccgacacga    420
cagcgcgact tcacggctgc ctttccacgc atgttgacca aaggggaca tggtccagcg    480
gagacccaga cacttggtag cctcccggac ataaacctca cacaaatatc cacgttggcg    540
aacgagctcc gagattccag gcttgcgaat gacctgaggg attctggagc taccatcaga    600
atcggtttct gggtgctggt ggtggtcgga ggcgtgctgg cctgctacag cctgctggtc    660
accgtggcct tcatcatctt tgggtccgc agcaagcgga gcagaggcgg ccacagcgac    720
tacatgaaca tgacccctag acggcctggc cccaccagaa agcactacca gccctacgcc    780
cctccccggg actttgccgc ctacagaagc                                     810
```

<210> SEQ ID NO 172
<211> LENGTH: 270
<212> TYPE: PRT
<213> ORGANISM: Artificial Sequence
<220> FEATURE:
<223> OTHER INFORMATION: huTim3-CD28tm

<400> SEQUENCE: 172

```
Met Phe Ser His Leu Pro Phe Asp Cys Val Leu Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Phe Trp Val Leu Val Val
        195                 200                 205

Val Gly Gly Val Leu Ala Cys Tyr Ser Leu Leu Val Thr Val Ala Phe
    210                 215                 220

Ile Ile Phe Trp Val Arg Ser Lys Arg Ser Arg Gly Gly His Ser Asp
225                 230                 235                 240
```

```
Tyr Met Asn Met Thr Pro Arg Arg Pro Gly Pro Thr Arg Lys His Tyr
            245                 250                 255

Gln Pro Tyr Ala Pro Pro Arg Asp Phe Ala Ala Tyr Arg Ser
        260                 265                 270
```

<210> SEQ ID NO 173
<211> LENGTH: 846
<212> TYPE: DNA
<213> ORGANISM: Artificial Sequence
<220> FEATURE:
<223> OTHER INFORMATION: huTim3-CD28Cys

<400> SEQUENCE: 173

```
atgttctccc atcttcccctt cgactgtgtg ttgctcctcc tcctcctgct tctcacccgg      60
tcaagcgaag tagagtaccg ggcggaagta ggtcagaacg catatctccc ctgtttttac     120
acacccgctg cgccgggaaa cctggttccc gtgtgttggg gaaaggggggc atgccctgtt    180 ttcgagtgtg gcaacgtggt cctccggacg gatgagcgag acgtgaatta ttggacgagc    240
agatattggt tgaatggcga ttttagaaag ggtgatgtga gcttgaccat tgagaatgta    300
acgcttgctg atagcgggat atattgctgt agaattcaaa tccctggtat aatgaacgac    360
gaaaaattca atctgaagct ggtaattaag ccggccaagg tgacacccgc ccgacacga     420 cagcgcgact tcacggctgc ctttccacgc atgttgacca aagggggaca tggtccagcg    480
gagacccaga cacttggtag cctcccggac ataaacctca cacaaatatc cacgttggcg    540
aacgagctcc gagattccag gcttgcgaat gacctgaggg attctggagc taccatcaga    600
atcggttgtc ccagccctct gtttcccggc cctagcaagc cttctgggt gctggtggtg      660 gtcggaggcg tgctggcctg ctacagcctg ctggtcaccg tggccttcat catcttttgg    720
gtccgcagca gcggagcag aggcggccac agcgactaca tgaacatgac ccctagacgg    780
cctggcccca ccagaaagca ctaccagccc tacgcccctc cccgggactt tgccgcctac    840
agaagc                                                              846
```

<210> SEQ ID NO 174
<211> LENGTH: 282
<212> TYPE: PRT
<213> ORGANISM: Artificial Sequence
<220> FEATURE:
<223> OTHER INFORMATION: huTim3-CD28Cys

<400> SEQUENCE: 174

```
Met Phe Ser His Leu Pro Phe Asp Cys Val Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
        35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125
```

Ile Lys Pro Ala Lys Val Thr Pro Ala Pro Thr Arg Gln Arg Asp Phe
130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
            165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Cys Pro Ser Pro Leu Phe
            195                 200                 205

Pro Gly Pro Ser Lys Pro Phe Trp Val Leu Val Val Val Gly Gly Val
            210                 215                 220

Leu Ala Cys Tyr Ser Leu Leu Val Thr Val Ala Phe Ile Ile Phe Trp
225                 230                 235                 240

Val Arg Ser Lys Arg Ser Arg Gly Gly His Ser Asp Tyr Met Asn Met
                245                 250                 255

Thr Pro Arg Arg Pro Gly Pro Thr Arg Lys His Tyr Gln Pro Tyr Ala
            260                 265                 270

Pro Pro Arg Asp Phe Ala Ala Tyr Arg Ser
            275                 280

<210> SEQ ID NO 175
<211> LENGTH: 810
<212> TYPE: DNA
<213> ORGANISM: Artificial Sequence
<220> FEATURE:
<223> OTHER INFORMATION: huTim3-12aas-CD28Cys

<400> SEQUENCE: 175
atgttctccc atcttccctt cgactgtgtg ttgctccttc cctcctgct tctcacccgg      60 tcaagcgaag tagagtaccg ggcggaagta ggtcagaacg catatctccc ctgtttttac    120
acacccgctg cgccgggaaa cctggttccc gtgtgttggg gaaaggggggc atgccctgtt   180 ttcgagtgtg gcaacgtggt cctccggacg gatgagcgag acgtgaatta ttggacgagc    240
agatattggt tgaatggcga ttttagaaag ggtgatgtga gcttgaccat tgagaatgta    300
acgcttgctg atagcgggat atattgctgt agaattcaaa tccctggtat aatgaacgac    360
gaaaaattca atctgaagct ggtaattaag ccggccaagg tgacacccgc ccgacacga    420 cagcgcgact tcacggctgc ctttccacgc atgttgacca aaggggaca tggtccagcg    480 gagacccaga cacttggtag cctcccggac ataaacctca cacaaatatc acgttggcg    540 aacgagctcc gagattccag gcttgcgaat tgtcccagcc ctctgtttcc cggccctagc    600
aagcctttct gggtgctggt ggtggtcgga ggcgtgctgg cctgctacag cctgctggtc    660
accgtggcct tcatcatctt tgggtccgc agcaagcgga gcagaggcgg ccacagcgac    720
tacatgaaca tgaccctag acggcctggc ccaccagaa agcactacca gccctacgcc    780
cctccccggg actttgccgc ctacagaagc                                    810

<210> SEQ ID NO 176
<211> LENGTH: 270
<212> TYPE: PRT
<213> ORGANISM: Artificial Sequence
<220> FEATURE:
<223> OTHER INFORMATION: huTim3-12aas-CD28Cys

<400> SEQUENCE: 176

```
Met Phe Ser His Leu Pro Phe Asp Cys Val Leu Leu Leu Leu Leu
1               5                   10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
                35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
                100                 105                 110

Gln Ile Pro Gly Ile Met Asn Asp Glu Lys Phe Asn Leu Lys Leu Val
            115                 120                 125

Ile Lys Pro Ala Lys Val Thr Pro Ala Pro Thr Arg Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Cys Pro
                180                 185                 190

Ser Pro Leu Phe Pro Gly Pro Ser Lys Pro Phe Trp Val Leu Val Val
            195                 200                 205

Val Gly Gly Val Leu Ala Cys Tyr Ser Leu Leu Val Thr Val Ala Phe
    210                 215                 220

Ile Ile Phe Trp Val Arg Ser Lys Arg Ser Arg Gly Gly His Ser Asp
225                 230                 235                 240

Tyr Met Asn Met Thr Pro Arg Arg Pro Gly Pro Thr Arg Lys His Tyr
                245                 250                 255

Gln Pro Tyr Ala Pro Pro Arg Asp Phe Ala Ala Tyr Arg Ser
            260                 265                 270
```

<210> SEQ ID NO 177
<211> LENGTH: 570
<212> TYPE: DNA
<213> ORGANISM: Artificial Sequence
<220> FEATURE:
<223> OTHER INFORMATION: huTim3-12aas

<400> SEQUENCE: 177

```
atgttctccc atcttcccctt cgactgtgtg ttgctccttc cctcctgct tctcacccgg      60
tcaagcgaag tagagtaccg ggcggaagta ggtcagaacg catatctccc ctgtttttac    120
acacccgctg cgccgggaaa cctggttccc gtgtgttggg gaaaggggc atgccctgtt    180
ttcgagtgtg gcaacgtggt cctccggacg gatgagcgag acgtgaatta ttggacgagc    240
agatattggt tgaatggcga ttttagaaag ggtgatgtga gcttgaccat tgagaatgta    300
acgcttgctg atagcgggat atattgctgt agaattcaaa tccctggtat aatgaacgac    360
gaaaaattca atctgaagct ggtaattaag ccggccaagg tgacacccgc ccgacacga    420
cagcgcgact tcacggctgc ctttccacgc atgttgacca aaggggaca tggtccagcg    480
gagacccaga cacttggtag cctcccggac ataaacctca cacaaatatc cacgttggcg    540
```
aacgagctcc gagattccag gcttgcgaat                                     570

<210> SEQ ID NO 178
<211> LENGTH: 190
<212> TYPE: PRT
<213> ORGANISM: Artificial Sequence
<220> FEATURE:
<223> OTHER INFORMATION: huTim3-12aas

<400> SEQUENCE: 178

Met Phe Ser His Leu Pro Phe Asp Cys Val Leu Leu Leu Leu Leu
1               5                  10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
            35                  40                  45

Val Pro Val Cys Trp Gly Lys Gly Ala Cys Pro Val Phe Glu Cys Gly
        50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Arg Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn
            180                 185                 190

<210> SEQ ID NO 179
<211> LENGTH: 792
<212> TYPE: DNA
<213> ORGANISM: Artificial Sequence
<220> FEATURE:
<223> OTHER INFORMATION: Synthetic sequence hu_trCD200R

<400> SEQUENCE: 179
atgctgtgcc cttggagaac cgccaacctg gcctgctgc tgatcctgac catcttcctg      60
gtggccgcca gcagcagcct gtgcatggac gagaagcaga tcacccagaa ctacagcaag    120
gtgctggccg aagtgaacac cagctggccc gtgaagatgg ccaccaacgc cgtgctgtgc    180
tgccctccta tcgccctgcg gaacctgatc atcatcacct gggagatcat cctgcggggc    240
cagcccagct gtaccaaggc ctaccggaaa gagacaaacg agacaaaaga aacaaactgc    300
accgacgagc ggatcacatg ggtgtccaga cccgaccaga acagcgacct gcagatcaga    360
cccgtggcca tcacccacga cggctactac cggtgcatca tggtcacccc cgatggcaac    420
ttccaccggg ataccatctg caggtgctc gtgaccccg aagtgaccct gttccagaac      480
cggaacagaa ccgccgtgtg caaggccgtg gccggaaaac ctgccgccca gatctcttgg    540
atccccgagg gcgattgcgc caccaagcag gaatactggt ccaacggcac cgtgaccgtg    600
aagtccacct gtcactggga ggtgcacaac gtgtccaccg tgacatgcca cgtgtcccac    660

```
ctgaccggca acaagagcct gtacatcgag ctgctgcctg tgcctggcgc caagaagtcc    720
gccaagctgt acatccccta catcatcctg acaatcatca ttctgaccat cgtgggcttc    780
atctggctgc tg                                                        792
```

<210> SEQ ID NO 180
<211> LENGTH: 264
<212> TYPE: PRT
<213> ORGANISM: Artificial Sequence
<220> FEATURE:
<223> OTHER INFORMATION: Synthetic sequence hu_trCD200R

<400> SEQUENCE: 180

```
Met Leu Cys Pro Trp Arg Thr Ala Asn Leu Gly Leu Leu Leu Ile Leu
1               5                   10                  15

Thr Ile Phe Leu Val Ala Ala Ser Ser Leu Cys Met Asp Glu Lys
            20                  25                  30

Gln Ile Thr Gln Asn Tyr Ser Lys Val Leu Ala Glu Val Asn Thr Ser
        35                  40                  45

Trp Pro Val Lys Met Ala Thr Asn Ala Val Leu Cys Cys Pro Pro Ile
    50                  55                  60

Ala Leu Arg Asn Leu Ile Ile Thr Trp Glu Ile Leu Arg Gly
65                  70                  75                  80

Gln Pro Ser Cys Thr Lys Ala Tyr Arg Lys Glu Thr Asn Glu Thr Lys
                85                  90                  95

Glu Thr Asn Cys Thr Asp Glu Arg Ile Thr Trp Val Ser Arg Pro Asp
            100                 105                 110

Gln Asn Ser Asp Leu Gln Ile Arg Pro Val Ala Ile Thr His Asp Gly
        115                 120                 125

Tyr Tyr Arg Cys Ile Met Val Thr Pro Asp Gly Asn Phe His Arg Gly
    130                 135                 140

Tyr His Leu Gln Val Leu Val Thr Pro Glu Val Thr Leu Phe Gln Asn
145                 150                 155                 160

Arg Asn Arg Thr Ala Val Cys Lys Ala Val Ala Gly Lys Pro Ala Ala
                165                 170                 175

Gln Ile Ser Trp Ile Pro Glu Gly Asp Cys Ala Thr Lys Gln Glu Tyr
            180                 185                 190

Trp Ser Asn Gly Thr Val Thr Val Lys Ser Thr Cys His Trp Glu Val
        195                 200                 205

His Asn Val Ser Thr Val Thr Cys His Val Ser His Leu Thr Gly Asn
    210                 215                 220

Lys Ser Leu Tyr Ile Glu Leu Leu Pro Val Pro Gly Ala Lys Lys Ser
225                 230                 235                 240

Ala Lys Leu Tyr Ile Pro Tyr Ile Ile Leu Thr Ile Ile Leu Thr
                245                 250                 255

Ile Val Gly Phe Ile Trp Leu Leu
            260
```

<210> SEQ ID NO 181
<211> LENGTH: 684
<212> TYPE: DNA
<213> ORGANISM: Artificial Sequence
<220> FEATURE:
<223> OTHER INFORMATION: Synthetic sequence huCD200R-15aas portion of
    extracellular domain

<400> SEQUENCE: 181

```
atgctgtgcc cttggagaac cgccaacctg gcctgctgc tgatcctgac catcttcctg      60
gtggccgcca gcagcagcct gtgcatggac gagaagcaga tcacccagaa ctacagcaag    120
gtgctggccg aagtgaacac cagctggccc gtgaagatgg ccaccaacgc cgtgctgtgc    180
tgccctccta tcgccctgcg gaacctgatc atcatcacct gggagatcat cctgcggggc    240
cagcccagct gtaccaaggc ctaccggaaa gagacaaacg agacaaaaga acaaactgc     300
accgacgagc ggatcacatg ggtgtccaga cccgaccaga cagcgacct gcagatcaga     360
cccgtggcca tcacccacga cggctactac cggtgcatca tggtcacccc cgatggcaac   420
ttccaccggg gataccatct gcaggtgctc gtgaccccg aagtgaccct gttccagaac    480
cggaacagaa ccgccgtgtg caaggccgtg gccggaaaac ctgccgccca gatctcttgg   540
atccccgagg gcgattgcgc caccaagcag gaatactggt ccaacggcac cgtgaccgtg   600
aagtccacct gtcactggga ggtgcacaac gtgtccaccg tgacatgcca cgtgtcccac   660
ctgaccggca caagagcct gtac                                           684
```

```
<210> SEQ ID NO 182
<211> LENGTH: 228
<212> TYPE: PRT
<213> ORGANISM: Artificial Sequence
<220> FEATURE:
<223> OTHER INFORMATION: Synthetic sequence huCD200R-15aas protein

<400> SEQUENCE: 182

Met Leu Cys Pro Trp Arg Thr Ala Asn Leu Gly Leu Leu Ile Leu
1               5                   10                  15

Thr Ile Phe Leu Val Ala Ala Ser Ser Ser Leu Cys Met Asp Glu Lys
            20                  25                  30

Gln Ile Thr Gln Asn Tyr Ser Lys Val Leu Ala Glu Val Asn Thr Ser
        35                  40                  45

Trp Pro Val Lys Met Ala Thr Asn Ala Val Leu Cys Cys Pro Pro Ile
    50                  55                  60

Ala Leu Arg Asn Leu Ile Ile Ile Thr Trp Glu Ile Ile Leu Arg Gly
65                  70                  75                  80

Gln Pro Ser Cys Thr Lys Ala Tyr Arg Lys Glu Thr Asn Glu Thr Lys
                85                  90                  95

Glu Thr Asn Cys Thr Asp Glu Arg Ile Thr Trp Val Ser Arg Pro Asp
            100                 105                 110

Gln Asn Ser Asp Leu Gln Ile Arg Pro Val Ala Ile Thr His Asp Gly
        115                 120                 125

Tyr Tyr Arg Cys Ile Met Val Thr Pro Asp Gly Asn Phe His Arg Gly
    130                 135                 140

Tyr His Leu Gln Val Leu Val Thr Pro Glu Val Thr Leu Phe Gln Asn
145                 150                 155                 160

Arg Asn Arg Thr Ala Val Cys Lys Ala Val Ala Gly Lys Pro Ala Ala
                165                 170                 175

Gln Ile Ser Trp Ile Pro Glu Gly Asp Cys Ala Thr Lys Gln Glu Tyr
            180                 185                 190

Trp Ser Asn Gly Thr Val Thr Val Lys Ser Thr Cys His Trp Glu Val
        195                 200                 205

His Asn Val Ser Thr Val Thr Cys His Val Ser His Leu Thr Gly Asn
    210                 215                 220

Lys Ser Leu Tyr
225
```

<210> SEQ ID NO 183
<211> LENGTH: 924
<212> TYPE: DNA
<213> ORGANISM: Artificial Sequence
<220> FEATURE:
<223> OTHER INFORMATION: Synthetic sequence huCD200R-15aas-CD28Cys construct

<400> SEQUENCE: 183

```
atgctgtgcc cttggagaac cgccaacctg ggcctgctgc tgatcctgac catcttcctg      60
gtggccgcca gcagcagcct gtgcatggac gagaagcaga tcacccagaa ctacagcaag     120
gtgctggccg aagtgaacac cagctggccc gtgaagatgg ccaccaacgc cgtgctgtgc     180
tgccctccta tcgccctgcg gaacctgatc atcatcacct gggagatcat cctgcggggc     240
cagcccagct gtaccaaggc ctaccggaaa gagacaaacg agacaaaaga aacaaactgc     300
accgacgagc ggatcacatg ggtgtccaga cccgaccaga cagcgacct gcagatcaga      360
cccgtggcca tcacccacga cggctactac cggtgcatca tggtcacccc cgatggcaac     420
ttccaccggg gataccatct gcaggtgctc gtgaccccg aagtgaccct gttccagaac      480
cggaacagaa ccgccgtgtg caaggccgtg gccggaaaac ctgccgccca gatctcttgg     540
atccccgagg gcgattgcgc caccaagcag gaatactggt ccaacggcac cgtgaccgtg     600
aagtccacct gtcactggga ggtgcacaac gtgtccaccg tgacatgcca cgtgtcccac     660
ctgaccggca caagagcct gtactgtccc agccctctgt ttcccggccc tagcaagcct      720
ttctgggtgc tggtggtggt cggaggcgtg ctggcctgct acagcctgct ggtcaccgtg     780
gccttcatca tcttttgggt ccgcagcaag cggagcagag cggccacag cgactacatg     840
aacatgaccc ctagcggcc tggccccacc agaaagcact accagccta cgcccctccc      900
cgggactttg ccgcctacag aagc                                            924
```

<210> SEQ ID NO 184
<211> LENGTH: 308
<212> TYPE: PRT
<213> ORGANISM: Artificial Sequence
<220> FEATURE:
<223> OTHER INFORMATION: Synthetic sequence huCD200R-15aas-CD28Cys protein

<400> SEQUENCE: 184

```
Met Leu Cys Pro Trp Arg Thr Ala Asn Leu Gly Leu Leu Leu Ile Leu
1               5                   10                  15

Thr Ile Phe Leu Val Ala Ala Ser Ser Ser Leu Cys Met Asp Glu Lys
            20                  25                  30

Gln Ile Thr Gln Asn Tyr Ser Lys Val Leu Ala Glu Val Asn Thr Ser
        35                  40                  45

Trp Pro Val Lys Met Ala Thr Asn Ala Val Leu Cys Cys Pro Pro Ile
    50                  55                  60

Ala Leu Arg Asn Leu Ile Ile Ile Thr Trp Glu Ile Ile Leu Arg Gly
65                  70                  75                  80

Gln Pro Ser Cys Thr Lys Ala Tyr Arg Lys Glu Thr Asn Glu Thr Lys
                85                  90                  95

Glu Thr Asn Cys Thr Asp Glu Arg Ile Thr Trp Val Ser Arg Pro Asp
            100                 105                 110

Gln Asn Ser Asp Leu Gln Ile Arg Pro Val Ala Ile Thr His Asp Gly
        115                 120                 125

Tyr Tyr Arg Cys Ile Met Val Thr Pro Asp Gly Asn Phe His Arg Gly
```

```
                130               135               140
Tyr His Leu Gln Val Leu Val Thr Pro Glu Val Thr Leu Phe Gln Asn
145                 150                 155                 160

Arg Asn Arg Thr Ala Val Cys Lys Ala Val Ala Gly Lys Pro Ala Ala
                165                 170                 175

Gln Ile Ser Trp Ile Pro Glu Gly Asp Cys Ala Thr Lys Gln Glu Tyr
                180                 185                 190

Trp Ser Asn Gly Thr Val Thr Val Lys Ser Thr Cys His Trp Glu Val
                195                 200                 205

His Asn Val Ser Thr Val Thr Cys His Val Ser His Leu Thr Gly Asn
                210                 215                 220

Lys Ser Leu Tyr Cys Pro Ser Pro Leu Phe Pro Gly Pro Ser Lys Pro
225                 230                 235                 240

Phe Trp Val Leu Val Val Gly Gly Val Leu Ala Cys Tyr Ser Leu
                245                 250                 255

Leu Val Thr Val Ala Phe Ile Ile Phe Trp Val Arg Ser Lys Arg Ser
                260                 265                 270

Arg Gly Gly His Ser Asp Tyr Met Asn Met Thr Pro Arg Arg Pro Gly
                275                 280                 285

Pro Thr Arg Lys His Tyr Gln Pro Tyr Ala Pro Pro Arg Asp Phe Ala
290                 295                 300

Ala Tyr Arg Ser
305

<210> SEQ ID NO 185
<211> LENGTH: 700
<212> TYPE: DNA
<213> ORGANISM: Artificial Sequence
<220> FEATURE:
<223> OTHER INFORMATION: Synthetic sequence huFAStm-41BB construct

<400> SEQUENCE: 185
caccatgctg ggcatctgga ccctgctgcc tctggtgctg acaagcgtgg ccagactgag      60
cagcaagagc gtgaacgccc aagtgaccga catcaacagc aagggcctgg aactgagaaa     120
gaccgtgacc accgtggaaa cccagaacct ggaaggcctg caccacgacg ccagttctg     180 ccacaagcct tgtccccctg cgagcggaa ggccagagac tgtactgtga cggcgacga      240 gcccgactgc gtgccctgtc aggaaggcaa agagtacacc gacaaggccc acttcagcag     300
caagtgccgg cggtgcagac tgtgtgatga gggccacggc ctggaagtgg aaatcaactg     360
cacccggacc cagaacacca gtgcagatg caagcccaac ttcttctgca acagcaccgt     420
gtgcgagcac tgcgaccct gtaccaagtg cgaacacggc atcatcaaag agtgcaccct     480
gacctccaac acaaagtgca agaggaagg cagcagaagc aacctgggct ggctgtgcct     540
cctgctgctg cccatccctc tgatcgtgtg ggtcaagcgg ggcagaaaga agctgctgta     600
catcttcaag cagcctttca tgcggcccgt gcagaccacc caggaagagg acggctgctc     660
ctgcagattc cccgaggaag aagaaggcgg ctgcgagctg                            700

<210> SEQ ID NO 186
<211> LENGTH: 232
<212> TYPE: PRT
<213> ORGANISM: Artificial Sequence
<220> FEATURE:
<223> OTHER INFORMATION: Synthetic sequence huFAStm-41BB protein

<400> SEQUENCE: 186
```

Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Val Glu Thr Gln Asn
            35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65              70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
            115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Leu Gly Trp
                165                 170                 175

Leu Cys Leu Leu Leu Leu Pro Ile Pro Leu Ile Val Trp Val Lys Arg
            180                 185                 190

Gly Arg Lys Lys Leu Leu Tyr Ile Phe Lys Gln Pro Phe Met Arg Pro
            195                 200                 205

Val Gln Thr Thr Gln Glu Glu Asp Gly Cys Ser Cys Arg Phe Pro Glu
            210                 215                 220

Glu Glu Glu Gly Gly Cys Glu Leu
225                 230

<210> SEQ ID NO 187
<211> LENGTH: 730
<212> TYPE: DNA
<213> ORGANISM: Artificial Sequence
<220> FEATURE:
<223> OTHER INFORMATION: Synthetic sequence huFAS-41BBtm construct

<400> SEQUENCE: 187
caccatgctg ggcatctgga ccctgctgcc tctggtgctg acaagcgtgg ccagactgag      60
cagcaagagc gtgaacgccc aagtgaccga catcaacagc aagggcctgg aactgagaaa     120
gaccgtgacc accgtggaaa cccagaacct ggaaggcctg caccacgacg gccagttctg     180
ccacaagcct tgtccccctg cgagcggaa ggccagagac tgtactgtga acggcgacga     240
gcccgactgc gtgccctgtc aggaaggcaa agagtacacc gacaaggccc acttcagcag     300
caagtgccgg cggtgcagac tgtgtgatga gggccacggc ctggaagtgg aaatcaactg     360
caccccggac cagaacacca gtgcagatg caagcccaac ttcttctgca acagcaccgt     420
gtgcgagcac tgcgaccct gtaccaagtg cgaacacggc atcatcaaag agtgcaccct     480
gacctccaac acaaagtgca agaggaagg cagcagaagc aacatcatat ccttcttcct     540
ggcgttgacc tctaccgcgc tgcttttctt gctgttcttc cttacgctcc gcttcagtgt     600
ggttaagcgg ggcagaaaga agctgctgta catcttcaag cagccttca tgcggcccgt     660
gcagaccacc caggaagagg acggctgctc ctgcagattc cccgaggaag aagaggcgg     720 ctgcgagctg 730

<210> SEQ ID NO 188
<211> LENGTH: 242
<212> TYPE: PRT
<213> ORGANISM: Artificial Sequence
<220> FEATURE:
<223> OTHER INFORMATION: Synthetic sequence huFAS-41BBtm protein

<400> SEQUENCE: 188

Met Leu Gly Ile Trp Thr Leu Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Thr Val Glu Thr Gln Asn
        35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Ile Ile Ser
                165                 170                 175

Phe Phe Leu Ala Leu Thr Ser Thr Ala Leu Leu Phe Leu Leu Phe Phe
            180                 185                 190

Leu Thr Leu Arg Phe Ser Val Val Lys Arg Gly Arg Lys Lys Leu Leu
        195                 200                 205

Tyr Ile Phe Lys Gln Pro Phe Met Arg Pro Val Gln Thr Thr Gln Glu
    210                 215                 220

Glu Asp Gly Cys Ser Cys Arg Phe Pro Glu Glu Glu Glu Gly Gly Cys
225                 230                 235                 240

Glu Leu

<210> SEQ ID NO 189
<211> LENGTH: 705
<212> TYPE: DNA
<213> ORGANISM: Artificial Sequence
<220> FEATURE:
<223> OTHER INFORMATION: Synthetic sequence muFas tm-41BB construct

<400> SEQUENCE: 189
atgctgtgga tctgggccgt gctgcctctg gtgctggctg atcacagct gagagtgcac      60 acccagggca ccaacagcat cagcgagagc ctgaagctga agaagagt gcgcgagaca     120 gacaagaact gcagcgaggg cctgtaccag ggcggaccct tctgctgtca gccttgccag     180
cccggcaaga aaaaggtgga agattgcaag atgaacggcg gcacccctac ctgcgcccct     240
tgtacagagg gcaaagagta catggacaag aaccactacg ccgacaagtg cagacggtgc     300

-continued

```
accctgtgcg acgaggaaca cggcctggaa gtggaaacaa actgcaccct gacccagaac    360
accaagtgca agtgcaaacc cgacttctac tgcgacagcc ccggctgcga gcactgcgtc    420
agatgtgcct cttgcgagca cggcaccctg gaaccttgta ccgccaccag caacaccaac    480
tgccggaagc agagcccag aaacagactg tggctgctga ccatcctggt gctgctgatc     540
cccctggtgt tcatctacag cgtgctgaag tggatcagaa agaagttccc ccacatcttc    600
aagcagccct tcaagaaaac caccggcgct gcccaggaag aggacgcctg cagctgtaga    660
tgccctcagg aagaagaagg cggcggaggc ggctacgagc tgtga                    705
```

<210> SEQ ID NO 190
<211> LENGTH: 234
<212> TYPE: PRT
<213> ORGANISM: Artificial Sequence
<220> FEATURE:
<223> OTHER INFORMATION: Synthetic sequence muFas tm-41BB protein

<400> SEQUENCE: 190

```
Met Leu Trp Ile Trp Ala Val Leu Pro Leu Val Leu Ala Gly Ser Gln
1               5                   10                  15

Leu Arg Val His Thr Gln Gly Thr Asn Ser Ile Ser Glu Ser Leu Lys
            20                  25                  30

Leu Arg Arg Arg Val Arg Glu Thr Asp Lys Asn Cys Ser Glu Gly Leu
        35                  40                  45

Tyr Gln Gly Gly Pro Phe Cys Cys Gln Pro Cys Pro Gly Lys Lys
    50                  55                  60

Lys Val Glu Asp Cys Lys Met Asn Gly Gly Thr Pro Thr Cys Ala Pro
65                  70                  75                  80

Cys Thr Glu Gly Lys Glu Tyr Met Asp Lys Asn His Tyr Ala Asp Lys
                85                  90                  95

Cys Arg Arg Cys Thr Leu Cys Asp Glu Glu His Gly Leu Glu Val Glu
            100                 105                 110

Thr Asn Cys Thr Leu Thr Gln Asn Thr Lys Cys Lys Cys Lys Pro Asp
        115                 120                 125

Phe Tyr Cys Asp Ser Pro Gly Cys Glu His Cys Val Arg Cys Ala Ser
    130                 135                 140

Cys Glu His Gly Thr Leu Glu Pro Cys Thr Ala Thr Ser Asn Thr Asn
145                 150                 155                 160

Cys Arg Lys Gln Ser Pro Arg Asn Arg Leu Trp Leu Leu Thr Ile Leu
                165                 170                 175

Val Leu Leu Ile Pro Leu Val Phe Ile Tyr Ser Val Leu Lys Trp Ile
            180                 185                 190

Arg Lys Lys Phe Pro His Ile Phe Lys Gln Pro Phe Lys Lys Thr Thr
        195                 200                 205

Gly Ala Ala Gln Glu Glu Asp Ala Cys Ser Cys Arg Cys Pro Gln Glu
    210                 215                 220

Glu Glu Gly Gly Gly Gly Gly Tyr Glu Leu
225                 230
```

<210> SEQ ID NO 191
<211> LENGTH: 718
<212> TYPE: DNA
<213> ORGANISM: Artificial Sequence
<220> FEATURE:
<223> OTHER INFORMATION: Synthetic sequence muFas-41BBtm construct

<400> SEQUENCE: 191

```
caccatgctg tggatctggg ccgtgctgcc tctggtgctg gctggatcac agctgagagt    60
gcacacccag gcaccaaca gcatcagcga gagcctgaag ctgagaagaa gagtgcgcga   120
gacagacaag aactgcagcg agggcctgta ccagggcgga cccttctgct gtcagccttg   180
ccagcccggc aagaaaaagg tggaagattg caagatgaac ggcggcaccc ctacctgcgc   240
cccttgtaca gagggcaaag agtacatgga caagaaccac tacgccgaca gtgcagacg    300
gtgcaccctg tgcgacgagg aacacggcct ggaagtggaa acaaactgca ccctgaccca   360
gaacaccaag tgcaagtgca acccgactt ctactgcgac agccccggct gcgagcactg    420
cgtcagatgt gcctcttgcg agcacggcac cctggaacct tgtaccgcca ccagcaacac   480
caactgccgg aagcagagcc cagaaacag aacccttttc ctggctttga cctccgctct    540
cctcttggct ctgatcttca tcacccttct gtttagcgtg ctgaagtgga tcagaaagaa   600
gttcccccac atcttcaagc agcccttcaa gaaaaccacc ggcgctgccc aggaagagga   660
cgcctgcagc tgtagatgcc ctcaggaaga agaaggcggc ggaggcggct acgagctg     718
```

<210> SEQ ID NO 192
<211> LENGTH: 238
<212> TYPE: PRT
<213> ORGANISM: Artificial Sequence
<220> FEATURE:
<223> OTHER INFORMATION: Synthetic sequence muFas-41BBtm protein

<400> SEQUENCE: 192

```
Met Leu Trp Ile Trp Ala Val Leu Pro Leu Val Leu Ala Gly Ser Gln
1               5                   10                  15

Leu Arg Val His Thr Gln Gly Thr Asn Ser Ile Ser Glu Ser Leu Lys
            20                  25                  30

Leu Arg Arg Arg Val Arg Glu Thr Asp Lys Asn Cys Ser Glu Gly Leu
        35                  40                  45

Tyr Gln Gly Gly Pro Phe Cys Cys Gln Pro Cys Gln Pro Gly Lys Lys
    50                  55                  60

Lys Val Glu Asp Cys Lys Met Asn Gly Gly Thr Pro Thr Cys Ala Pro
65                  70                  75                  80

Cys Thr Glu Gly Lys Glu Tyr Met Asp Lys Asn His Tyr Ala Asp Lys
                85                  90                  95

Cys Arg Arg Cys Thr Leu Cys Asp Glu Glu His Gly Leu Glu Val Glu
            100                 105                 110

Thr Asn Cys Thr Leu Thr Gln Asn Thr Lys Cys Lys Cys Lys Pro Asp
        115                 120                 125

Phe Tyr Cys Asp Ser Pro Gly Cys Glu His Cys Val Arg Cys Ala Ser
    130                 135                 140

Cys Glu His Gly Thr Leu Glu Pro Cys Thr Ala Thr Ser Asn Thr Asn
145                 150                 155                 160

Cys Arg Lys Gln Ser Pro Arg Asn Arg Thr Leu Phe Leu Ala Leu Thr
                165                 170                 175

Ser Ala Leu Leu Leu Ala Leu Ile Phe Ile Thr Leu Leu Phe Ser Val
            180                 185                 190

Leu Lys Trp Ile Arg Lys Lys Phe Pro His Ile Phe Lys Gln Pro Phe
        195                 200                 205

Lys Lys Thr Thr Gly Ala Ala Gln Glu Glu Asp Ala Cys Ser Cys Arg
    210                 215                 220

Cys Pro Gln Glu Glu Glu Gly Gly Gly Gly Tyr Glu Leu
225                 230                 235
```

<210> SEQ ID NO 193
<211> LENGTH: 735
<212> TYPE: DNA
<213> ORGANISM: Artificial Sequence
<220> FEATURE:
<223> OTHER INFORMATION: Synthetic sequencemuFas-9aas-CD28Cys tm-41BBic construct

<400> SEQUENCE: 193

```
atgctgtgga tctgggccgt gctgcctctg gtgctggctg gatcacagct gagagtgcac     60
acccagggca ccaacagcat cagcgagagc ctgaagctga agaagagt gcgcgagaca      120
gacaagaact gcagcgaggg cctgtaccag ggcggaccct tctgctgtca gccttgccag    180
cccggcaaga aaaggtgga agattgcaag atgaacggcg gcacccctac ctgcgcccct    240
tgtacagagg gcaaagagta catggacaag aaccactacg ccgacaagtg cagacggtgc    300
accctgtgcg acgaggaaca cggcctggaa gtggaaacaa actgcaccct gacccagaac    360
accaagtgca gtgcaaacc cgacttctac tgcgacagcc ccggctgcga gcactgcgtc    420
agatgtgcct cttgcgagca cggcacctg gaaccttgta ccgccaccag caacaccaac    480
tgccacaccc agagcagccc caagctgttc tgggccctgg tggtggtggc cggcgtgctg    540
ttttgttacg gcctgctcgt gaccgtggcc ctgtgcgtga tctggaccag cgtgctgaag    600
tggatcagaa agaagttccc ccacatcttc aagcagccct tcaagaaaac caccggcgct    660
gcccaggaag aggacgcctg cagctgtaga tgccctcagg aagaagaagg cggcggaggc    720
ggctacgagc tgtga                                                     735
```

<210> SEQ ID NO 194
<211> LENGTH: 244
<212> TYPE: PRT
<213> ORGANISM: Artificial Sequence
<220> FEATURE:
<223> OTHER INFORMATION: Synthetic sequence muFas-9aas-CD28Cys tm-41BBic protein

<400> SEQUENCE: 194

Met Leu Trp Ile Trp Ala Val Leu Pro Leu Val Leu Ala Gly Ser Gln
1               5                   10                  15

Leu Arg Val His Thr Gln Gly Thr Asn Ser Ile Ser Glu Ser Leu Lys
            20                  25                  30

Leu Arg Arg Arg Val Arg Glu Thr Asp Lys Asn Cys Ser Glu Gly Leu
        35                  40                  45

Tyr Gln Gly Gly Pro Phe Cys Cys Gln Pro Cys Gln Pro Gly Lys Lys
    50                  55                  60

Lys Val Glu Asp Cys Lys Met Asn Gly Gly Thr Pro Thr Cys Ala Pro
65                  70                  75                  80

Cys Thr Glu Gly Lys Glu Tyr Met Asp Lys Asn His Tyr Ala Asp Lys
                85                  90                  95

Cys Arg Arg Cys Thr Leu Cys Asp Glu Glu His Gly Leu Glu Val Glu
            100                 105                 110

Thr Asn Cys Thr Leu Thr Gln Asn Thr Lys Cys Lys Cys Lys Pro Asp
        115                 120                 125

Phe Tyr Cys Asp Ser Pro Gly Cys Glu His Cys Val Arg Cys Ala Ser
    130                 135                 140

Cys Glu His Gly Thr Leu Glu Pro Cys Thr Ala Thr Ser Asn Thr Asn
145                 150                 155                 160

Cys His Thr Gln Ser Ser Pro Lys Leu Phe Trp Ala Leu Val Val Val

```
                    165                 170                 175
Ala Gly Val Leu Phe Cys Tyr Gly Leu Leu Val Thr Val Ala Leu Cys
                180                 185                 190

Val Ile Trp Thr Ser Val Leu Lys Trp Ile Arg Lys Lys Phe Pro His
            195                 200                 205

Ile Phe Lys Gln Pro Phe Lys Lys Thr Thr Gly Ala Ala Gln Glu Glu
        210                 215                 220

Asp Ala Cys Ser Cys Arg Cys Pro Gln Glu Glu Glu Gly Gly Gly Gly
225                 230                 235                 240

Gly Tyr Glu Leu

<210> SEQ ID NO 195
<211> LENGTH: 735
<212> TYPE: DNA
<213> ORGANISM: Artificial Sequence
<220> FEATURE:
<223> OTHER INFORMATION: Synthetic sequence muFas-CD28tm-41BBic
      construct

<400> SEQUENCE: 195
atgctgtgga tctgggccgt gctgcctctg gtgctggctg gatcacagct gagagtgcac      60
acccagggca ccaacagcat cagcgagagc ctgaagctga agaagagt gcgcgagaca      120 gacaagaact gcagcgaggg cctgtaccag ggcggacccct tctgctgtca gccttgccag      180
cccggcaaga aaaggtgga agattgcaag atgaacggcg gcacccctac ctgcgcccct      240
tgtacagagg gcaaagagta catggacaag aaccactacg ccgacaagtg cagacggtgc      300
accctgtgcg acgaggaaca cggcctggaa gtggaaacaa actgcaccct gacccagaac      360
accaagtgca gtgcaaacc cgacttctac tgcgacagcc ccggctgcga gcactgcgtc      420
agatgtgcct cttgcgagca cggcacctg gaaccttgta ccgccaccag caacaccaac      480
tgccggaagc agagccccag aaacagattc tgggccctgg tggtggtggc cggcgtgctg      540
ttttgttacg gcctgctcgt gaccgtggcc ctgtgcgtga tctggaccag cgtgctgaag      600
tggatcagaa agaagttccc ccacatcttc aagcagccct tcaagaaaac caccggcgct      660
gcccaggaag aggacgcctg cagctgtaga tgccctcagg aagaagaagg cggcggaggc      720
ggctacgagc tgtga                                                     735

<210> SEQ ID NO 196
<211> LENGTH: 244
<212> TYPE: PRT
<213> ORGANISM: Artificial Sequence
<220> FEATURE:
<223> OTHER INFORMATION: Synthetic sequence muFas-CD28tm-41BBic protein

<400> SEQUENCE: 196

Met Leu Trp Ile Trp Ala Val Leu Pro Leu Val Leu Ala Gly Ser Gln
1               5                   10                  15

Leu Arg Val His Thr Gln Gly Thr Asn Ser Ile Ser Glu Ser Leu Lys
            20                  25                  30

Leu Arg Arg Arg Val Arg Glu Thr Asp Lys Asn Cys Ser Glu Gly Leu
        35                  40                  45

Tyr Gln Gly Gly Pro Phe Cys Cys Gln Pro Cys Gln Pro Gly Lys Lys
    50                  55                  60

Lys Val Glu Asp Cys Lys Met Asn Gly Gly Thr Pro Thr Cys Ala Pro
65                  70                  75                  80

Cys Thr Glu Gly Lys Glu Tyr Met Asp Lys Asn His Tyr Ala Asp Lys
```

```
                        85                  90                  95
Cys Arg Arg Cys Thr Leu Cys Asp Glu Glu His Gly Leu Glu Val Glu
            100                 105                 110

Thr Asn Cys Thr Leu Thr Gln Asn Thr Lys Cys Lys Cys Lys Pro Asp
        115                 120                 125

Phe Tyr Cys Asp Ser Pro Gly Cys Glu His Cys Val Arg Cys Ala Ser
    130                 135                 140

Cys Glu His Gly Thr Leu Glu Pro Cys Thr Ala Thr Ser Asn Thr Asn
145                 150                 155                 160

Cys Arg Lys Gln Ser Pro Arg Asn Arg Phe Trp Ala Leu Val Val Val
                165                 170                 175

Ala Gly Val Leu Phe Cys Tyr Gly Leu Leu Val Thr Val Ala Leu Cys
            180                 185                 190

Val Ile Trp Thr Ser Val Leu Lys Trp Ile Arg Lys Lys Phe Pro His
        195                 200                 205

Ile Phe Lys Gln Pro Phe Lys Lys Thr Thr Gly Ala Ala Gln Glu Glu
    210                 215                 220

Asp Ala Cys Ser Cys Arg Cys Pro Gln Glu Glu Gly Gly Gly Gly
225                 230                 235                 240

Gly Tyr Glu Leu

<210> SEQ ID NO 197
<211> LENGTH: 81
<212> TYPE: DNA
<213> ORGANISM: Artificial Sequence
<220> FEATURE:
<223> OTHER INFORMATION: Synthetic sequence hu41BB transmembrane domain

<400> SEQUENCE: 197
atcatatcct tcttcctggc gttgacctct accgcgctgc ttttcttgct gttcttcctt    60
acgctccgct tcagtgtggt t                                               81

<210> SEQ ID NO 198
<211> LENGTH: 27
<212> TYPE: PRT
<213> ORGANISM: Artificial Sequence
<220> FEATURE:
<223> OTHER INFORMATION: Synthetic sequence hu41BB transmembrane protein

<400> SEQUENCE: 198

Ile Ile Ser Phe Phe Leu Ala Leu Thr Ser Thr Ala Leu Leu Phe Leu
1               5                   10                  15

Leu Phe Phe Leu Thr Leu Arg Phe Ser Val Val
            20                  25

<210> SEQ ID NO 199
<211> LENGTH: 507
<212> TYPE: DNA
<213> ORGANISM: Artificial Sequence
<220> FEATURE:
<223> OTHER INFORMATION: Synthetic sequence muFas extracellular domain

<400> SEQUENCE: 199
atgctgtgga tctgggccgt gctgcctctg gtgctggctg atcacagct gagagtgcac    60 acccagggca ccaacagcat cagcgagagc ctgaagctga agaagagt gcgcgagaca    120 gacaagaact gcagcgaggg cctgtaccag ggcggaccct tctgctgtca gccttgccag    180
cccggcaaga aaaaggtgga agattgcaag atgaacggcg gcaccccta ctgcgcccct    240
```

```
tgtacagagg gcaaagagta catggacaag aaccactacg ccgacaagtg cagacggtgc    300
accctgtgcg acgaggaaca cggcctggaa gtggaaacaa actgcaccct gacccagaac    360
accaagtgca agtgcaaacc cgacttctac tgcgacagcc ccggctgcga gcactgcgtc    420
agatgtgcct cttgcgagca cggcaccctg aaccttgta ccgccaccag caacaccaac    480
tgccggaagc agagccccag aaacaga                                        507
```

```
<210> SEQ ID NO 200
<211> LENGTH: 169
<212> TYPE: PRT
<213> ORGANISM: Artificial Sequence
<220> FEATURE:
<223> OTHER INFORMATION: Synthetic sequence muFas extracellular domain
      protein

<400> SEQUENCE: 200

Met Leu Trp Ile Trp Ala Val Leu Pro Leu Val Leu Ala Gly Ser Gln
1               5                   10                  15

Leu Arg Val His Thr Gln Gly Thr Asn Ser Ile Ser Glu Ser Leu Lys
            20                  25                  30

Leu Arg Arg Arg Val Arg Glu Thr Asp Lys Asn Cys Ser Glu Gly Leu
        35                  40                  45

Tyr Gln Gly Gly Pro Phe Cys Cys Gln Pro Cys Gln Pro Gly Lys Lys
    50                  55                  60

Lys Val Glu Asp Cys Lys Met Asn Gly Gly Thr Pro Thr Cys Ala Pro
65                  70                  75                  80

Cys Thr Glu Gly Lys Glu Tyr Met Asp Lys Asn His Tyr Ala Asp Lys
                85                  90                  95

Cys Arg Arg Cys Thr Leu Cys Asp Glu Glu His Gly Leu Glu Val Glu
            100                 105                 110

Thr Asn Cys Thr Leu Thr Gln Asn Thr Lys Cys Lys Cys Lys Pro Asp
        115                 120                 125

Phe Tyr Cys Asp Ser Pro Gly Cys Glu His Cys Val Arg Cys Ala Ser
    130                 135                 140

Cys Glu His Gly Thr Leu Glu Pro Cys Thr Ala Thr Ser Asn Thr Asn
145                 150                 155                 160

Cys Arg Lys Gln Ser Pro Arg Asn Arg
                165
```

```
<210> SEQ ID NO 201
<211> LENGTH: 51
<212> TYPE: DNA
<213> ORGANISM: Artificial Sequence
<220> FEATURE:
<223> OTHER INFORMATION: Synthetic sequence muFas transmembrane domain

<400> SEQUENCE: 201
ctgtggctgc tgaccatcct ggtgctgctg atccccctgg tgttcatcta c              51
```

```
<210> SEQ ID NO 202
<211> LENGTH: 17
<212> TYPE: PRT
<213> ORGANISM: Artificial Sequence
<220> FEATURE:
<223> OTHER INFORMATION: Synthetic sequence muFas transmembrane domain
      protein

<400> SEQUENCE: 202

Leu Trp Leu Leu Thr Ile Leu Val Leu Leu Ile Pro Leu Val Phe Ile
1               5                   10                  15
```

Tyr

<210> SEQ ID NO 203
<211> LENGTH: 63
<212> TYPE: DNA
<213> ORGANISM: Artificial Sequence
<220> FEATURE:
<223> OTHER INFORMATION: Synthetic sequence mu41BB transmembrane domain

<400> SEQUENCE: 203

```
acccttttcc tggctttgac ctccgctctc ctcttggctc tgatcttcat caccttctg      60 ttt                                                                   63
```

<210> SEQ ID NO 204
<211> LENGTH: 21
<212> TYPE: PRT
<213> ORGANISM: Artificial Sequence
<220> FEATURE:
<223> OTHER INFORMATION: Synthetic sequence mu41BB transmembrane protein

<400> SEQUENCE: 204

Thr Leu Phe Leu Ala Leu Thr Ser Ala Leu Leu Leu Ala Leu Ile Phe
1               5                   10                  15

Ile Thr Leu Leu Phe
            20

<210> SEQ ID NO 205
<211> LENGTH: 144
<212> TYPE: DNA
<213> ORGANISM: Artificial Sequence
<220> FEATURE:
<223> OTHER INFORMATION: Synthetic sequence mu41BB intracellular domain

<400> SEQUENCE: 205

```
agcgtgctga gtggatcag aaagaagttc ccccacatct tcaagcagcc cttcaagaaa      60
accaccggcg ctgcccagga agaggacgcc tgcagctgta gatgccctca ggaagaagaa     120
ggcggcggag cggctacga gctg                                             144
```

<210> SEQ ID NO 206
<211> LENGTH: 48
<212> TYPE: PRT
<213> ORGANISM: Artificial Sequence
<220> FEATURE:
<223> OTHER INFORMATION: Synthetic sequence mu41BB intracellular protein

<400> SEQUENCE: 206

Ser Val Leu Lys Trp Ile Arg Lys Lys Phe Pro His Ile Phe Lys Gln
1               5                   10                  15

Pro Phe Lys Lys Thr Thr Gly Ala Ala Gln Glu Glu Asp Ala Cys Ser
            20                  25                  30

Cys Arg Cys Pro Gln Glu Glu Glu Gly Gly Gly Gly Tyr Glu Leu
        35                  40                  45

<210> SEQ ID NO 207
<211> LENGTH: 480
<212> TYPE: DNA
<213> ORGANISM: Artificial Sequence
<220> FEATURE:
<223> OTHER INFORMATION: Synthetic sequence muFas extracellular domain
      -9aas

<400> SEQUENCE: 207

```
atgctgtgga tctgggccgt gctgcctctg gtgctggctg atcacagct gagagtgcac      60 acccagggca ccaacagcat cagcgagagc ctgaagctga aagaagagt gcgcgagaca    120 gacaagaact gcagcgaggg cctgtaccag ggcggaccct tctgctgtca gccttgccag    180
cccggcaaga aaaaggtgga agattgcaag atgaacggcg caccctac ctgcgcccct     240 tgtacagagg gcaaagagta catggacaag aaccactacg ccgacaagtg cagacggtgc    300
accctgtgcg acgaggaaca cggcctggaa gtgaaacaa actgcaccct gacccagaac    360
accaagtgca agtgcaaacc cgacttctac tgcgacagcc ccggctgcga gcactgcgtc    420
agatgtgcct cttgcgagca cggcaccctg gaaccttgta ccgccaccag caacaccaac    480
```

<210> SEQ ID NO 208
<211> LENGTH: 160
<212> TYPE: PRT
<213> ORGANISM: Artificial Sequence
<220> FEATURE:
<223> OTHER INFORMATION: Synthetic sequence muFas extracellular domain
      -9aas  protein

<400> SEQUENCE: 208

```
Met Leu Trp Ile Trp Ala Val Leu Pro Leu Val Leu Ala Gly Ser Gln
1               5                   10                  15

Leu Arg Val His Thr Gln Gly Thr Asn Ser Ile Ser Glu Ser Leu Lys
            20                  25                  30

Leu Arg Arg Val Arg Glu Thr Asp Lys Asn Cys Ser Glu Gly Leu
        35                  40                  45

Tyr Gln Gly Gly Pro Phe Cys Cys Gln Pro Cys Gln Pro Gly Lys Lys
    50                  55                  60

Lys Val Glu Asp Cys Lys Met Asn Gly Gly Thr Pro Thr Cys Ala Pro
65                  70                  75                  80

Cys Thr Glu Gly Lys Glu Tyr Met Asp Lys Asn His Tyr Ala Asp Lys
                85                  90                  95

Cys Arg Arg Cys Thr Leu Cys Asp Glu Glu His Gly Leu Glu Val Glu
            100                 105                 110

Thr Asn Cys Thr Leu Thr Gln Asn Thr Lys Cys Lys Cys Lys Pro Asp
        115                 120                 125

Phe Tyr Cys Asp Ser Pro Gly Cys Glu His Cys Val Arg Cys Ala Ser
    130                 135                 140

Cys Glu His Gly Thr Leu Glu Pro Cys Thr Ala Thr Ser Asn Thr Asn
145                 150                 155                 160
```

<210> SEQ ID NO 209
<211> LENGTH: 108
<212> TYPE: DNA
<213> ORGANISM: Artificial Sequence
<220> FEATURE:
<223> OTHER INFORMATION: Synthetic sequence muCD28Cys (108 nt)

<400> SEQUENCE: 209

```
tgccacaccc agagcagccc caagctgttc tgggccctgg tggtggtggc cggcgtgctg      60
ttttgttacg gcctgctcgt gaccgtggcc ctgtgcgtga tctggacc                 108
```

<210> SEQ ID NO 210
<211> LENGTH: 36
<212> TYPE: PRT
<213> ORGANISM: Artificial Sequence
<220> FEATURE:
<223> OTHER INFORMATION: Synthetic sequence muCD28Cys protein

```
<400> SEQUENCE: 210

Cys His Thr Gln Ser Ser Pro Lys Leu Phe Trp Ala Leu Val Val
1               5                   10                  15

Ala Gly Val Leu Phe Cys Tyr Gly Leu Leu Val Thr Val Ala Leu Cys
            20                  25                  30

Val Ile Trp Thr
        35

<210> SEQ ID NO 211
<211> LENGTH: 81
<212> TYPE: DNA
<213> ORGANISM: Artificial Sequence
<220> FEATURE:
<223> OTHER INFORMATION: Synthetic sequence muCD28tm

<400> SEQUENCE: 211
ttctgggccc tggtggtggt ggccggcgtg ctgttttgtt acggcctgct cgtgaccgtg     60
gccctgtgcg tgatctggac c                                              81

<210> SEQ ID NO 212
<211> LENGTH: 27
<212> TYPE: PRT
<213> ORGANISM: Artificial Sequence
<220> FEATURE:
<223> OTHER INFORMATION: Synthetic sequence muCD28tm protein

<400> SEQUENCE: 212

Phe Trp Ala Leu Val Val Val Ala Gly Val Leu Phe Cys Tyr Gly Leu
1               5                   10                  15

Leu Val Thr Val Ala Leu Cys Val Ile Trp Thr
            20                  25

<210> SEQ ID NO 213
<211> LENGTH: 9
<212> TYPE: PRT
<213> ORGANISM: Artificial Sequence
<220> FEATURE:
<223> OTHER INFORMATION: Synthetic sequence virus gag epitope

<400> SEQUENCE: 213

Cys Cys Leu Cys Leu Thr Val Phe Leu
1               5
```

IMMUNOMODULATORY FUSION PROTEINS AND USES THEREOF

STATEMENT REGARDING SEQUENCE LISTING

The Sequence Listing associated with this application is provided in text format in lieu of a paper copy, and is hereby incorporated by reference into the specification. The name of the text file containing the Sequence Listing is 360056_447USPC_SEQUENCE_LISTING.txt. The text file is 322 KB, was created on Sep. 16, 2019, and is being submitted electronically via EFS-Web.

BACKGROUND

T cell-based immunotherapies began to be developed when tumor-reactive T cells were found among a population of tumor-infiltrating lymphocytes (TILs) (Clark et al., *Cancer Res.* 29:705, 1969). One strategy, known as adoptive T cell transfer, in some contexts involves the isolation of tumor infiltrating lymphocytes pre-selected for tumor-reactivity, clonal expansion of the tumor-reactive T cells induced by anti-CD3 and anti-CD28 antibodies in the presence of IL-2, and finally infusing the expanded cell population back to the tumor-bearing patient (together with chemotherapy and repetitive administration of IL-2) (Dudley et al., Science 298:850, 2002). This form of adoptive T cell therapy with tumor infiltrating lymphocytes can be technically cumbersome and leads to complete remission in only a minor fraction of patients with melanoma and is rarely effective in other cancers (Besser et al., *Clin. Cancer Res.* 16:2646, 2010).

Isolation of tumor-reactive T cell clones led to the development of another immunotherapeutic approach—the generation of recombinant T cell receptors (TCRs) specific for particular antigens, which may be introduced into T cells, e.g., using a vector delivery system, to confer specificity for a desired target such as a tumor-associated peptide presented by a major histocompatibility complex (MHC) molecule expressed on a tumor cell (known as human leukocyte antigen (HLA) molecule in humans). Another approach introduces a synthetic receptor, termed a chimeric antigen receptor (CAR), which generally contains an antigen-binding domain, which, e.g., in the context of anti-tumor therapy can bind to a tumor-specific or associated antigen, linked to one or more intracellular component comprising an effector domains, such as a primary signaling domain such as a TCR signaling domain or in some contexts costimulatory signaling domains. Unlike administration of TILs, the basic procedure for engineered TCR or CAR T cell immunotherapy is generally to genetically modify human T cells with a transgene encoding a tumor targeting moiety, ex vivo expansion of the recombinant T cells, and transfusing the expanded recombinant T cells back into patients.

Adoptive T cell therapy using T cells expressing recombinant TCRs has been shown to have a promising clinical benefit, especially in certain B cell cancers. However, effective T cell activation often requires or is enhanced by a concurrent co-stimulatory signal (Chen and Flies, *Nat. Rev. Immunol.* 13: 227-242, 2013). In the tumor microenvironment, co-stimulatory molecules are generally downregulated. As a result, exogenous stimulus via IL-2 is typically needed for T cells that express recombinant TCRs specific for cancer antigens.

Activation of T cells is initiated when the TCR engages a specific peptide presented in MHC on an antigen-presenting cell (APC) (Rossy et al., *Frontiers in Immunol.* 3: 1-12, 2012). The point of interaction of the T cell and the APC becomes the immunological synapse, which is comprised of three concentric supramolecular activation clusters (SMACs), including the central cSMAC, peripheral pSMAC, and the distal dSMAC (Rossy et al., *Frontiers in Immunol.* 3: 1-12, 2012). Within the cSMAC, co-stimulatory receptors can recruit signaling molecules to amplify the TCR signal. Such co-stimulatory receptors can include CD28, and in some contexts form microclusters with the TCR to lower the threshold of activation (Chen and Flies, *Nat. Rev. Immunol.* 13: 227-242, 2013). Access to the cSMAC by transmembrane proteins expressed by T cells may be restricted by the size of the extracellular domain. For example, CD45 has a large ectodomain and is generally excluded from the immunological synapse, thereby preventing its ability to inhibit TCR signaling (James and Vale, *Nature* 487:64-69, 2012).

There remains a need in the immunotherapy field for alternative compositions and methods that provide immunomodulatory signals to host cells for treating various diseases, such as cancer or infections. Presently disclosed embodiments address these needs and provide other related advantages.

BRIEF SUMMARY

In certain aspects, the present disclosure is directed to a fusion protein, comprising an extracellular component that contains a binding domain that specifically binds a target, an intracellular component comprised of an intracellular signaling domain, and a hydrophobic component connecting the extracellular and intracellular components, provided that the length of a fusion protein::target complex spans a distance similar to a distance between membranes in an immunological synapse.

In some embodiments, a length or spatial distance of a complex formed between the fusion protein and the target or a portion of such fusion protein::target complex (generally the extracellular portion of such complex) is or spans a particular distance, e.g., in some embodiments, is a distance that is less than or less than about a certain distance. In some aspects, a distance of the fusion protein::target complex (or, typically, the extracellular portion thereof) is less than at or about 50 nm, less than at or about 40 nm, less than at or about 30 nm, or less than at or about 20 nm or equal to or less than at or about 15 nm. In some embodiments, it is at or about 10, 11, 12, 13, 14, 15, 16, 17, 18, 19, or 20 nm, such as at or about 14 or 15 nm. In some aspects, the distance is one that is similar to a distance between membranes in an immunological synapse or is a distance that is the same, about the same, or substantially the same, as a distance between the membrane proximal-most portion, e.g., residue, of the extracellular domain of a TCR and the membrane proximal-most portion, e.g., residue, of an MHC (e.g., HLA, such as an MHCI or MHCII) molecule, with respect to a TCR-peptide/MHC complex or the distance spanned by the extracellular portions of such a complex (or spatial distance spanned by the extracellular portion known to be contained within a synapse, such as a complex containing CD8, CD4, CD28, and the respective binding partner or ligand thereof). In some embodiments, spatial distances of complexes refer to a distance between membranes of two different cells, wherein a first cell and a second cell each express on their surface a binding partner that can form a complex between the membranes when the cells are in proximity to each other. In some aspects, the distance is a distance that is the same, about the same, or substantially the same, as a distance spanned by the extracellular portions of a complex formed between a TCR and cognate interaction with an MHC molecule. In some aspects, such as where a fusion protein comprises a binding domain from a molecule ordinarily capable of entering an immunological synapse or co-localizing with an antigen receptor, the distance is similar to or the same as that spanned by a complex formed between the molecule (having the binding domain used in the fusion protein), and a natural binding partner thereof. In some aspects, such as where the fusion protein comprises a binding domain from a molecule ordinarily not capable of entering an immunological synapse or ordinarily not capable of co-localizing with an antigen receptor, the distance is different than, e.g., less than or substantially less than, that spanned by a complex formed between the molecule (having the binding domain or functional portion thereof used in the fusion protein), and a natural binding partner thereof.

In some embodiments, a binding domain within the extracellular component of a fusion protein of this disclosure contains a target-binding portion of a molecule capable of delivering an inhibitory signal, such as of an inhibitory molecule, e.g., an immunoinhibitory molecule, such as an immunoinhibitory receptor or immune checkpoint molecule. In some aspects, such a molecule is a glycoprotein, checkpoint family member. In certain embodiments, the fusion protein comprising a binding domain from a glycoprotein, checkpoint family member or is not a B7 or B7-binding molecule or is not a CD28-B7-superfamily member (e.g., is not a CD28, CTLA4, ICOS, or other B7 family binding molecule) Exemplary glycoprotein, checkpoint family members include CD200R, SIRPα, CD279 (PD-1), CD2, CD95 (Fas), CTLA4 (CD152), CD223 (LAG3), CD272 (BTLA), A2aR, KIR, TIM3, CD300, or LPA5, or a binding variant of any such molecule. In some embodiments, a binding domain within the extracellular component of a fusion protein of this disclosure comprises a binding partner of any of the foregoing, or a binding variant of any such molecule. In some aspects of such embodiments, the intracellular portion of a fusion protein includes a signaling domain capable of delivering a stimulatory, such as a costimulatory, signal to a lymphocyte, such as a T cell, such as a costimulatory region of CD28, 4-1BB, ICOS, or other costimulatory molecule. In some aspects, the intracellular portion of the fusion protein does not include an intracellular signaling domain of the inhibitory molecule, such as of a checkpoint or immunoinhibitory molecule, when the extracellular binding portion is from a checkpoint or immunoinhibitory molecule. In some aspects, a fusion protein does not include a primary signaling domain such as a CD3ζ signaling domain or other domain capable of delivering a primary signal to a T cell.

In certain aspects, the extracellular component or the binding portion thereof contains or is a binding domain of a molecule or ectodomain capable of specifically binding to CD200, such as a binding portion of a CD200R or variant thereof. In some embodiments, the binding domain is or includes a binding region of a molecule or of an ectodomain that is capable of specifically binding to a CD47, such as a SIRP ectodomain or CD47-binding region thereof, such as a SIRPα ectodomain or CD47-binding region thereof. In some embodiments, the binding domain is capable of binding to a PD-L1 or a PD-L2 or a LAG3 molecule. Exemplary targets may be one or more proteins whose expression is increased or upregulated in certain cells or tissues associated with or of a disease or condition to be treated or ameliorated with the fusion proteins and compositions provided herein, such as a tumor cell or tumor microenvironment, or is bound by a receptor generally upregulated on immune cells such as lymphocytes infiltrating a diseased tissue, such as a tumor.

In some embodiments, the extracellular component further includes one or more additional regions or domains, for example, from a molecule other than that from which the binding domain is derived or other than the molecule with which the binding domain shares identity. The one or more additional extracellular domain(s) may include a spacer region, such as one from an immunoglobulin molecule, which may contain all or a portion of a hinge, or constant region domain such as CH2 or CH3 domain, or from another cell surface molecule such as a costimulatory receptor, such as CD28. The additional extracellular domain(s) may include, in some aspects, a multimerization domain, e.g., a dimerization domain or sequence that may promote homo- or heterodimerization with another molecule, such as multimerization of two or more of the fusion proteins. In some embodiments, such a domain includes a portion of an extracellular domain of a CD28 molecule including at least the transmembrane-proximal-most cysteine, and generally an extracellular portion between such cysteine and the membrane, or modified variant thereof. In some aspects, such a domain includes an amino acid sequence as set forth in SEQ ID NO: 32, or portion thereof, or variant thereof such as having at least 90%, 95%, or 99% identity thereto. In some aspects, such a domain may be included in order to facilitate or promote multimerization. In some embodiments, a fusion protein contains an extracellular component including a CD200-binding domain, such as an extracellular portion (or portion thereof, such as a binding domain thereof) of a CD200R, such as an extracellular portion of CD200R having an amino acid sequence as set forth in SEQ ID NO: 25 or encoded by a nucleic acid molecule as set forth in SEQ ID NO: 2, or a CD200-binding portion thereof or variant thereof or binding portion thereof. In some aspects of such embodiments, the extracellular portion of the fusion protein further includes a portion of an extracellular region of CD28, such as up to about 9 to about 12 amino acids thereof (e.g., 9 amino acids or 12 amino acids), and in some aspects including a membrane-proximal-most cysteine residue of a CD28 extracellular region. In some such embodiments, the length of the CD200R portion of the extracellular region is reduced in length corresponding to the number of additional residues in the CD28-derived portion, such as by about 9 to about 12 amino acids (e.g., 9 amino acids or 12 amino acids), or by a sufficient number of amino acids that the distance spanned by the extracellular portion of a complex between the fusion protein and a CD200 molecule is similar to, substantially similar to, or the same as that spanned by the extracellular portion of a complex between a human CD200R, e.g., a CD200R, and CD200; or that spanned by the extracellular portion of a complex between a TCR in cognate interaction with an MHC molecule (e.g., MHC I or MHCII) in binding to a cognate peptide-MHC complex; or that of an immunological synapse. In some aspects, the fusion protein further includes a transmembrane domain, such as a CD28 transmembrane, such as a transmembrane domain encoded by the sequence set forth as SEQ ID NO: 4 or portion thereof, or a modified version thereof, such as a variant modified to contain additional charged regions or residues or hydrophilic residues to facilitate intermolecular interactions. In some embodiments, the protein further includes a CD28 intracellular signaling domain, such as a costimulatory domain of CD28, such as one that is capable of recruiting one or more adapter molecules to a CD28 in response to ligation. In some aspects, the CD28 intracellular domain includes or is a sequence encoded by the nucleotide sequence of SEQ ID NO: 5 or a portion or functional variant thereof.

In some embodiments, the present disclosure is directed to a fusion protein comprising an extracellular component comprised of a binding domain that specifically binds a target, an intracellular component comprised of an intracellular signaling domain, and a hydrophobic component connecting the extracellular and intracellular components, provided that the length of a fusion protein:target complex spans a distance similar to a distance between membranes in an immunological synapse, wherein (a) the extracellular component comprises an extracellular portion of a CD200R, (b) the hydrophobic component comprises a transmembrane domain of a CD28, and (c) the intracellular component comprises an intracellular signaling domain of a CD28.

In some embodiments, the present disclosure is directed to a fusion protein comprising an extracellular component comprised of a binding domain that specifically binds a target, an intracellular component comprised of an intracellular signaling domain, and a hydrophobic component connecting the extracellular and intracellular components, provided that the length of a fusion protein:target complex spans a distance similar to a distance between membranes in an immunological synapse, wherein (a) the extracellular component comprises an extracellular portion of a CD200R, (b) the hydrophobic component comprises a transmembrane domain of a CD28, and (c) the intracellular component comprises an intracellular signaling domain of a CD28 and an intracellular signaling domain of a CD137 (4-1BB).

In some embodiments, the present disclosure is directed to a fusion protein comprising an extracellular component comprised of a binding domain that specifically binds a target, an intracellular component comprised of an intracellular signaling domain, and a hydrophobic component connecting the extracellular and intracellular components, provided that the length of a fusion protein::target complex spans a distance similar to a distance between membranes in an immunological synapse, wherein (a) the extracellular component comprises an extracellular portion of a CD200R, (b) the hydrophobic component comprises a transmembrane domain of a CD28, and (c) the intracellular component comprises an intracellular signaling domain of a CD137 (4-1BB).

In some embodiments, the present disclosure is directed to a fusion protein comprising an extracellular component comprised of a binding domain that specifically binds a target, an intracellular component comprised of an intracellular signaling domain, and a hydrophobic component connecting the extracellular and intracellular components, provided that the length of a fusion protein:target complex spans a distance similar to a distance between membranes in an immunological synapse, wherein (a) the extracellular component comprises an extracellular portion of a SIRPα, (b) the hydrophobic component comprises a transmembrane domain of a CD28, and (c) the intracellular component comprises an intracellular signaling domain of a CD28.

In some embodiments, the present disclosure is directed to a fusion protein comprising an extracellular component comprised of a binding domain that specifically binds a target, an intracellular component comprised of an intracellular signaling domain, and a hydrophobic component connecting the extracellular and intracellular components, provided that the length of a fusion protein::target complex spans a distance similar to a distance between membranes in an immunological synapse, wherein (a) the extracellular component comprises an extracellular portion of a CD279 (PD-1), (b) the hydrophobic component comprises a transmembrane domain of a CD28, and (c) the intracellular component comprises an intracellular signaling domain of a CD28.

In some embodiments, the present disclosure is directed to a fusion protein comprising an extracellular component comprised of a binding domain that specifically binds a target, an intracellular component comprised of an intracellular signaling domain, and a hydrophobic component connecting the extracellular and intracellular components, provided that the length of a fusion protein::target complex spans a distance similar to a distance between membranes in an immunological synapse, wherein (a) the extracellular component comprises an extracellular portion of a CD95 (Fas), (b) the hydrophobic component comprises a transmembrane domain of a CD28, and (c) the intracellular component comprises an intracellular signaling domain of a CD28.

In some embodiments, the present disclosure is directed to a fusion protein comprising an extracellular component comprised of a binding domain that specifically binds a target, an intracellular component comprised of an intracellular signaling domain, and a hydrophobic component connecting the extracellular and intracellular components, provided that the length of a fusion protein:target complex spans a distance similar to a distance between membranes in an immunological synapse, wherein (a) the extracellular component comprises an extracellular portion of a TIM3, (b) the hydrophobic component comprises a transmembrane domain of a CD28, and (c) the intracellular component comprises an intracellular signaling domain of a CD28.

In some embodiments, the present disclosure is directed to a fusion protein comprising an extracellular component comprised of a binding domain that specifically binds a target, an intracellular component comprised of an intracellular signaling domain, and a hydrophobic component connecting the extracellular and intracellular components, provided that the length of a fusion protein:target complex spans a distance similar to a distance between membranes in an immunological synapse, wherein (a) the extracellular component comprises an extracellular portion of a LAG3, (b) the hydrophobic component comprises a transmembrane domain of a CD28, and (c) the intracellular component comprises an intracellular signaling domain of a CD28.

In some embodiments, the present disclosure is directed to a fusion protein comprising an extracellular component comprised of a binding domain that specifically binds a target, an intracellular component comprised of an intracellular signaling domain, and a hydrophobic component connecting the extracellular and intracellular components, provided that the length of a fusion protein::target complex spans a distance similar to a distance between membranes in an immunological synapse, wherein (a) the extracellular component comprises an extracellular portion of a CD2, (b) the hydrophobic component comprises a transmembrane domain of a CD28, and (c) the intracellular component comprises an intracellular signaling domain of a CD28.

In some embodiments, the present disclosure is directed to a fusion protein, comprising (a) an extracellular component comprised of a binding domain that specifically binds a target, (b) an intracellular component comprised of an intracellular signaling domain, and (c) a hydrophobic component connecting the extracellular and intracellular components, wherein the extracellular portion of a complex formed by specific binding of the fusion protein to the target (fusion protein::target complex) is of a size, or spans a distance, of (i) up to about a distance between two cell membranes of an immunological synapse, (ii) up to about or substantially the same as a distance spanned by the extracellular portion of a complex between a T cell receptor (TCR) and an MHC-peptide complex specifically bound by the TCR, (iii) up to about or substantially the same as a distance spanned by the extracellular portion of a complex between a natural molecule comprising the binding domain and its cognate binding partner; (iii) less than or up to about 40 nm, 25 nm, 20 nm, 15 nm, or 14 nm; or (iv) any combination thereof; and wherein the extracellular component is or comprises a CD95 (Fas) ectodomain or a functional fragment thereof, and the intracellular component is or comprises a CD137 (4-1BB) intracellular signaling domain or a functional portion thereof.

In some embodiments, the present disclosure is directed to a fusion protein comprising (a) an extracellular component comprised of a binding domain that specifically binds a target, (b) an intracellular component comprised of an intracellular signaling domain, and (c) a hydrophobic component connecting the extracellular and intracellular components, wherein the binding domain is, or has at least 95% identity to, an inhibitory molecule binding domain and the intracellular signaling domain is, or contains at least 95% identity to, a costimulatory or stimulatory molecule binding domain, and wherein the inhibitory molecule is or comprises a CD95 (Fas) ectodomain or a functional fragment thereof, and the costimulatory or stimulatory molecule is or comprises an intracellular signaling domain or a functional portion thereof from CD137 (4-1BB).

In some embodiments, the present disclosure is directed to a fusion protein comprising: (a) an extracellular component comprising an amino acid sequence encoded by a nucleic acid molecule as set forth in SEQ ID NO.:71, (b) a hydrophobic component comprising an amino acid sequence encoded by a nucleic acid molecule as set forth in SEQ ID NO.:197, and (c) an intracellular component comprising an amino acid sequence encoded by a nucleic acid molecule as set forth in SEQ ID NO.:13.

In some embodiments, the present disclosure is directed to a fusion protein comprising: (a) an extracellular component comprising a binding domain with an amino acid sequence as set forth in SEQ ID NO.:72; (b) a hydrophobic component comprising an amino acid sequence as set forth in SEQ ID NO.:198; and (c) an intracellular component comprising an amino acid sequence as set forth in SEQ ID NO.:36.

In certain aspects, the present disclosure is directed to a nucleic acid molecule encoding a fusion protein as described herein.

In certain aspects, the present disclosure is directed to a vector comprising a nucleic molecule that encodes a fusion protein as described herein.

In certain other aspects, the present disclosure is directed to a host cell comprising a fusion protein, nucleic acid, or vector as described herein.

In certain other aspects, a method of increasing the activity of an immune cell is provided, comprising administering to a subject in need of increased immune cell activity an effective amount of a host cell as described herein.

In other aspects, the present disclosure is directed to a method of enhancing or prolonging an immune response, comprising administering to a subject in need of enhanced or prolonged immune cell activity an effective amount of a host cell as described herein.

In still other aspects, the present disclosure provides a method of stimulating an antigen-specific T cell response, comprising administering to a subject in need of increased immune cell activity an effective amount of a host cell as described herein.

In other aspects, the present disclosure is directed to a method of inhibiting an immunosuppressive signaling pathway, comprising administering to a subject in need thereof an effective amount of a host cell as described herein.

In other aspects, the present disclosure is directed to a method of treating cancer, comprising administering to a subject having cancer a therapeutically effective amount of a host cell as described herein.

In other aspects, the present disclosure is directed to a method of inhibiting immune resistance of cancer cells, comprising administering to a subject in need thereof an effective amount of a host cell as described herein.

In still other aspects, the present disclosure provides a method for treating a tumor, comprising administering to a subject having a tumor a therapeutically effective amount of a host cell as described herein, wherein the administered host cell is capable of proliferating in an immunosuppressive tumor microenvironment.

A method of treating an infection, comprising administering to a subject having the infection a therapeutically effective amount of a host cell as described herein, is also provided by the present disclosure.

These and other aspects of the present invention will become apparent upon reference to the following detailed description and attached drawings.

BRIEF DESCRIPTION OF THE DRAWINGS

FIGS. 2A to 2G show that CD200R-CD28 constructs promote proliferation, accumulation, and effector function in response to CD200$^-$ tumor target cells in vitro, and accumulate in the immunological synapse. Splenocytes from naive TCR$_{gag}$ mice were stimulated in vitro with anti-CD3, anti-CD28, and recombinant human IL-2 (100 U/ml) and transduced with retroviral supernatant for 2 days. Cells were restimulated every 7 days with irradiated FBL and splenocytes and cultured with rhIL-2 (50 U/mL) for up to three stimulations. T cells were used for assays 5-7 days after the last stimulation. (A) Proliferation of CD200R-CD28 and GFP control $TCR_{gag}$ T cells as measured by CellTrace Violet dilution. T cells were stimulated with CD200⁻ FBL (upper panels) or CD200⁺ FBL (lower panels) for 3 days. (B) Preferential expansion/survival of transduced $TCR_{gag}$ T cells during co-culture with non-transduced $TCR_{gag}$ T cells during weekly cycles of stimulation with irradiated CD200⁺ FBL and splenocytes. (C) Enrichment of transduced T cells. Repeated restimulation with irradiated CD200⁺ tumor cells enriched the cells transduced with CD200R-9aas-CD28Cys compared to wild-type T cells transduced with an empty GFP control vector. (D) Increased CD200R and CD200 signal intensity at T cell:FBL synapse. Lipid rafts are increased at the immunological synapse (I). CD200R-9aas-CD28Cys fusion proteins co-localized with lipid rafts, indicating that the fusion proteins concentrate within the immunological synapse (III, IV). (E) CD200R-CD28⁺ CD8⁺ T cells display enhanced ability to lyse CD200⁺ FBL cells in vitro. Target tumor cells were labeled with different dilutions of the fluorescent dye 5,6-carboxyfluorescein diacetate succinimidyl ester (CFSE), as indicated. Effector $TCR_{gag}$ T cells transduced with the indicated CD200R-CD28 fusion protein or an empty vector control were incubated at the indicated effector to target ratio with a 1:1 mix of CD200⁺ FBL ($CFSE^{hi}$) and non-specific EL4 ($CFSE^{lo}$) control targets for 5 hours. The percentage of FBL of the sum of FBL and control tumor cells was determined by flow cytometry. The percentage lysis was determined by dividing the percent of FBL incubated with T cells by the percent of FBL incubated without T cells. (F) Target tumor cells for CFSE assay in (G). Target tumor cells were labeled with different dilutions of the fluorescent dyes CellTrace Violet (CTV) or CFSE. A 1:1:1 mix of EL4 cells (CTV+), CD200⁺ FBL ($CFSE^{hi}$) and non-specific EL4 ($CFSE^{lo}$) control targets was generated. (G) CFSE cytotoxicity assay. $TCR_{gag}$ T cells were transduced with CD200R-CD28 receptor or GFP control vector. Effector $TCR_{gag}$ T cells were incubated at the indicated effector to target ratio with a 1:1 mix of CD200⁻ FBL or CD200⁻ FBL and non-specific EL4 control targets for 4 hours. The percentage of FBL of the sum of FBL and control tumor cells was determined by flow cytometry. The percentage lysis was determined by dividing the percent of FBL incubated with T cells by the percent of FBL incubated without T cells.

Expression of Fas-CD28 constructs but not full-length (FL) Fas promoted survival or expansion of T cells upon multiple stimulations in vitro.

Figure 12A:
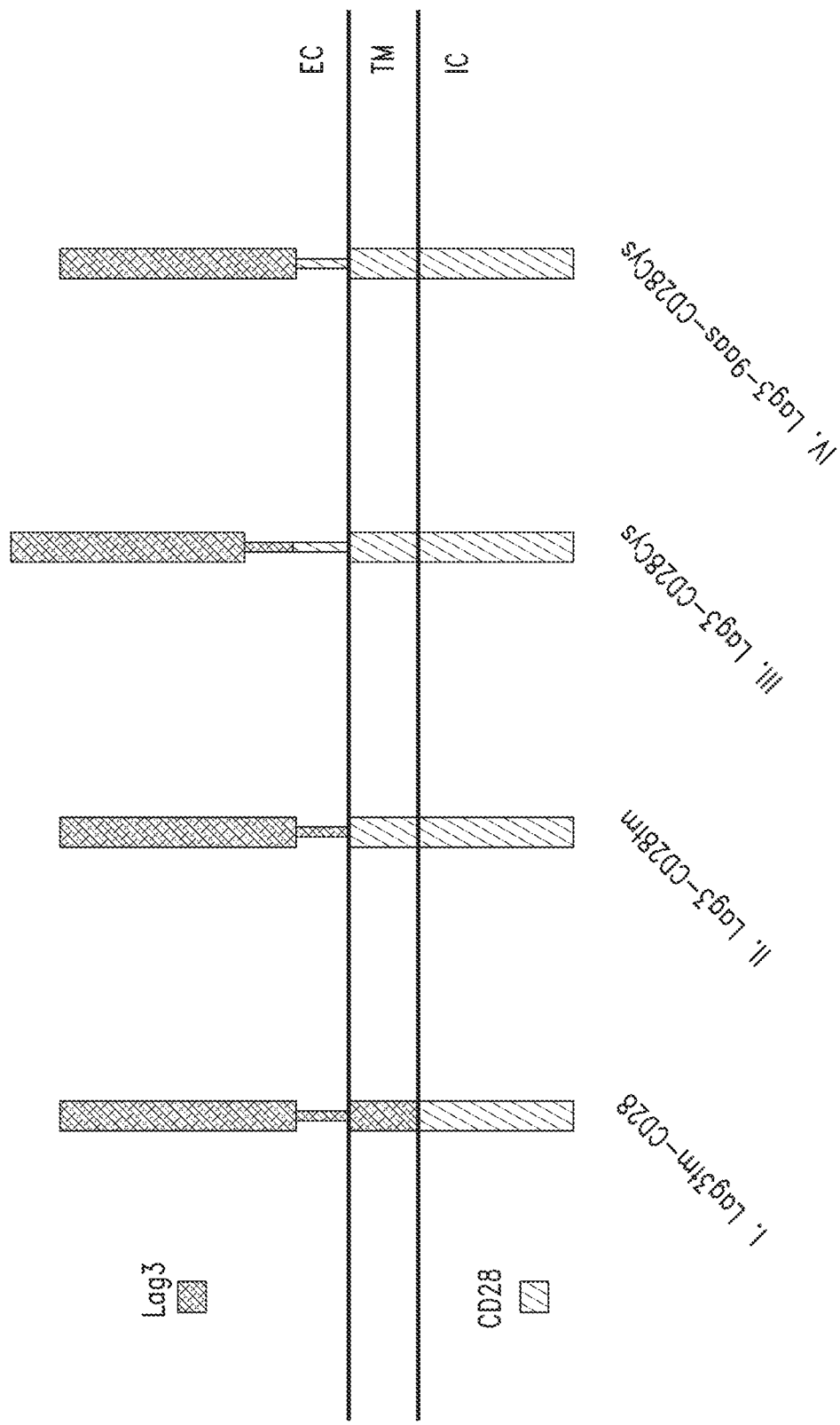
Figure 12B:
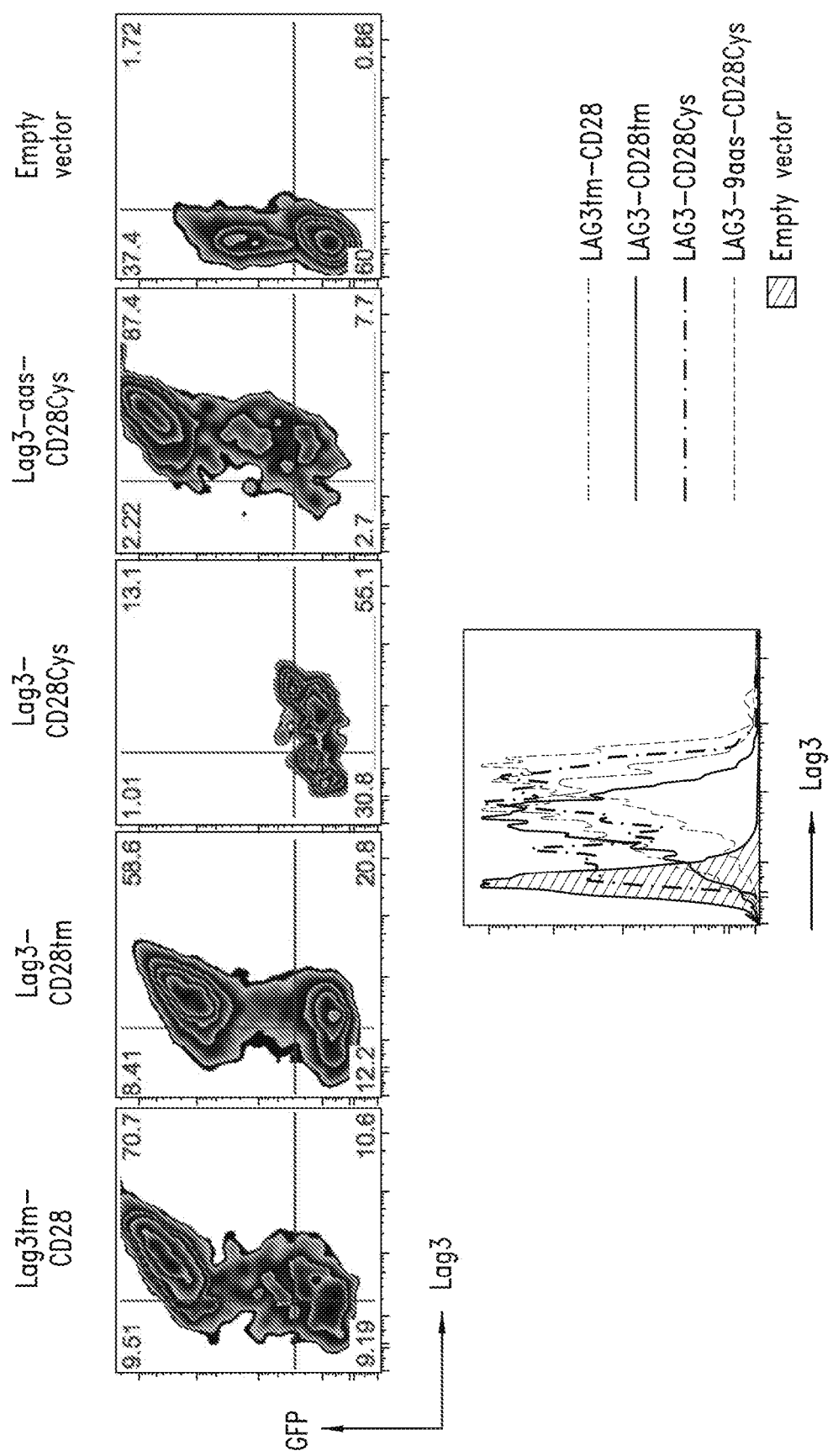

FIGS. 12A and 12B show the structure and expression of fusion proteins comprising LAG3 extracellular components and CD28 co-stimulatory signaling domains. (A) Schematic representation of exemplary LAG3-CD28 constructs. Construct "I" contains LAG3 extracellular ("EC") and transmembrane ("TM") domains and a CD28 intracellular ("IC") signaling domain (LAG3tm-CD28). Construct "II" contains the extracellular domain of LAG3 and the transmembrane and intracellular domains of CD28 (LAG3-CD28tm). Constructs "III" and "IV" also incorporate a portion of the extracellular domain of CD28 adjacent to the transmembrane-proximal cysteine to promote multimerization and enhance CD28 signaling. To account for the extra extracellular amino acids (e.g., extra nine (9) amino acids for murine constructs, or twelve (12) amino acids for human constructs), construct IV has a truncated portion of LAG3, wherein the LAG3 extracellular domain is truncated 9 amino acids. Constructs "I", "II", and "IV" maintain the short spatial distance between the cells (e.g., between a T cell and an antigen presenting cell) and may co-localize with the TCR within the cSMAC and deliver a strong co-stimulatory signal. (B) Expression of LAG3-CD28 constructs by murine $CD8^+$ T cells, as determined by anti-LAG3 antibody staining and flow cytometry. T cells transduced to express LAG3-CD28 constructs (LAG3tm-CD28; LAG3-CD28tm; LAG3-CD28Cys; LAG3-9aas-CD28Cys) exhibited expression of the constructs, in contrast with control T cells that received empty vector.

Figure 13A:
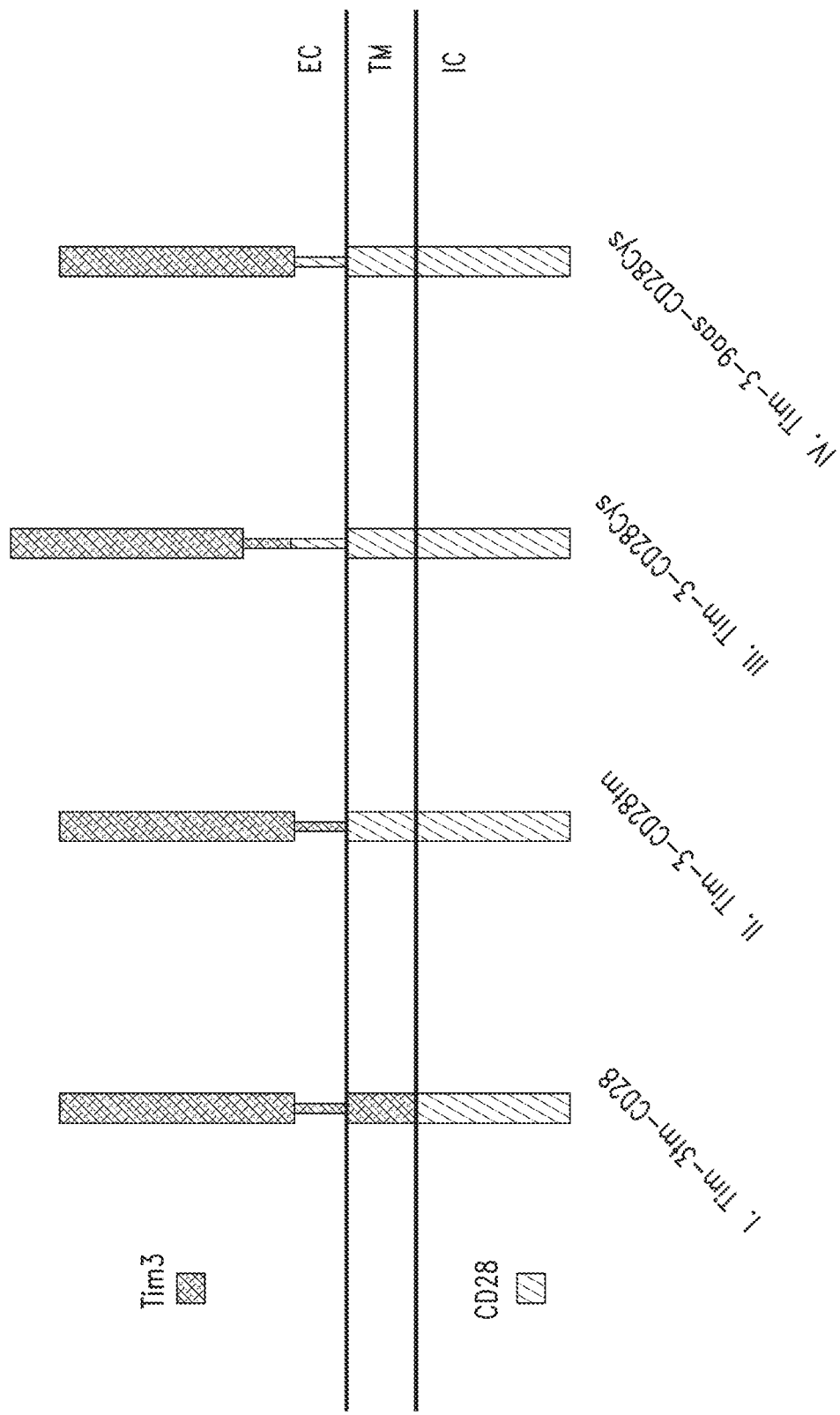
Figure 13B:
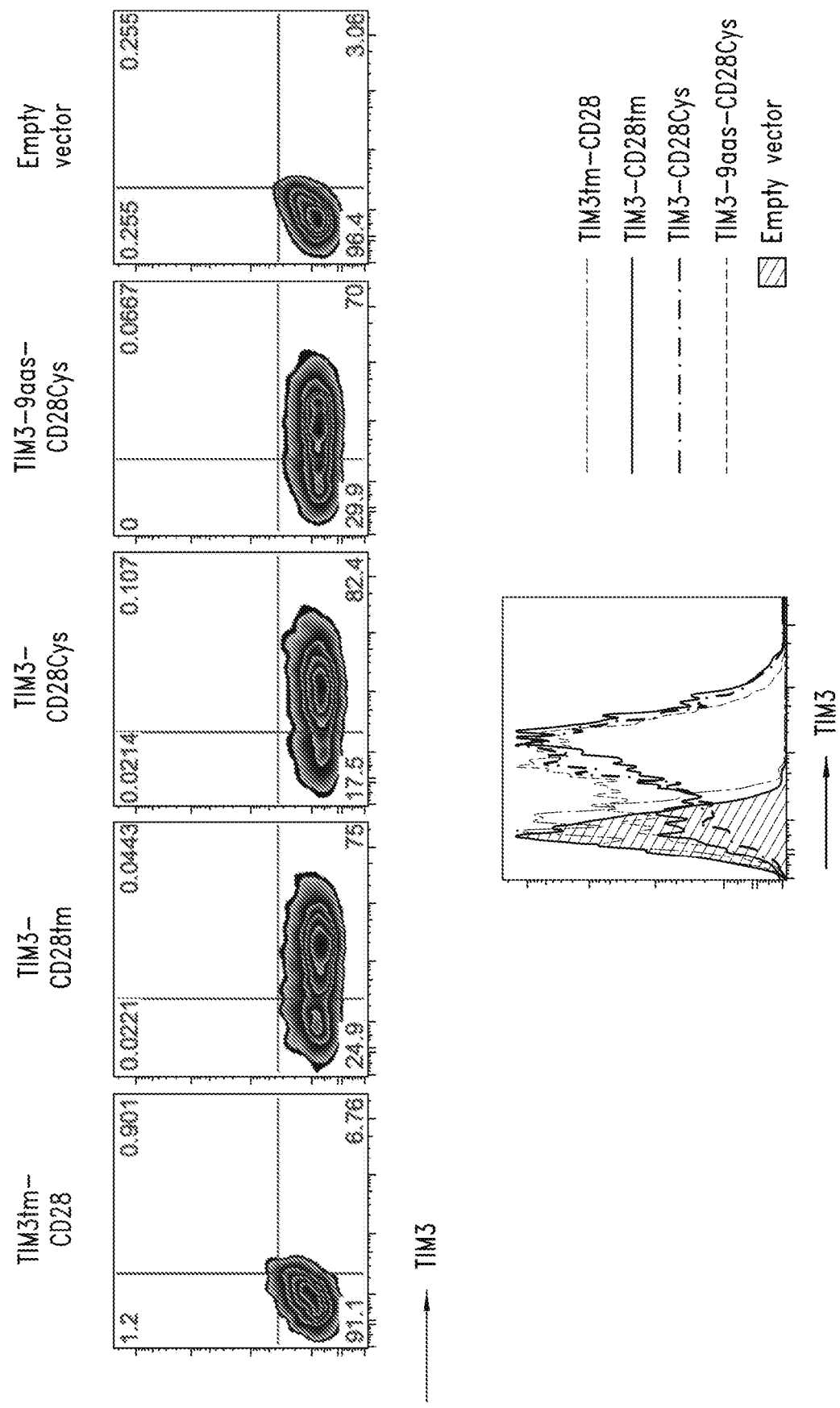

FIGS. 13A and 13B show the structure and expression of fusion proteins comprising TIM3 extracellular components and CD28 co-stimulatory signaling domains. (A) Schematic representation of exemplary TIM3-CD28 constructs. Construct "I" contains TIM3 extracellular ("EC") and transmembrane ("TM") domains and a CD28 intracellular ("IC") signaling domain (TIM3tm-CD28). Construct "II" contains the extracellular domain of TIM3 and the transmembrane and intracellular domains of CD28 (TIM3-CD28tm). Constructs "III" and "IV" also incorporate a portion of the extracellular domain of CD28 adjacent to the transmembrane-proximal cysteine to promote multimerization and enhance CD28 signaling. To account for the extra extracellular amino acids (e.g., extra nine (9) amino acids for murine constructs, or twelve (12) amino acids for human constructs), construct IV has a truncated portion of TIM3, wherein the TIM3 extracellular domain is truncated 9 amino acids. Constructs "I", "II", and "IV" maintain the short spatial distance between the cells (e.g., between a T cell and an antigen presenting cell) and may co-localize with the TCR within the cSMAC and deliver a strong co-stimulatory signal. (B) Expression of TIM3-CD28 constructs by murine $CD8^+$ T cells, as determined by anti-TIM3 antibody staining and flow cytometry. T cells transduced to express TIM3-CD28 constructs (TIM3tm-CD28; TIM3-CD28tm; TIM3-CD28Cys; TIM3-9aas-CD28Cys) typically exhibited expression of the constructs, in contrast with control T cells that received empty vector.

Figure 14A:
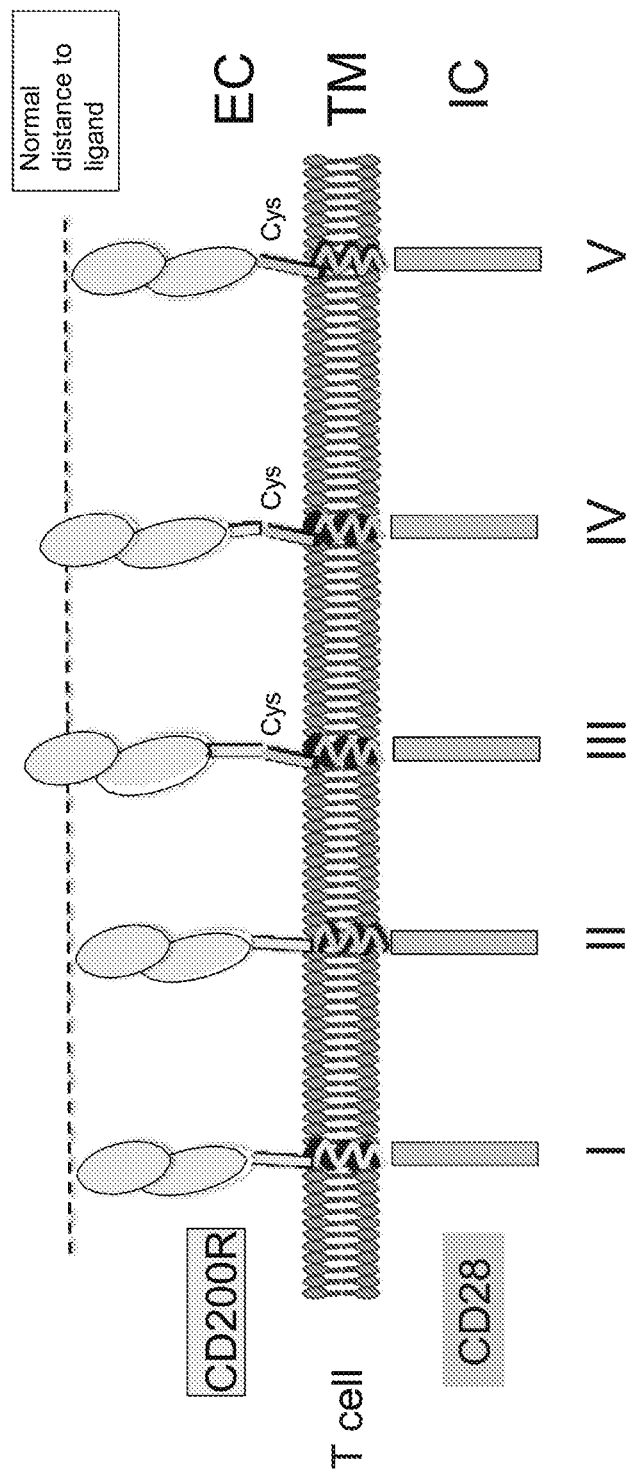
Figure 14B:
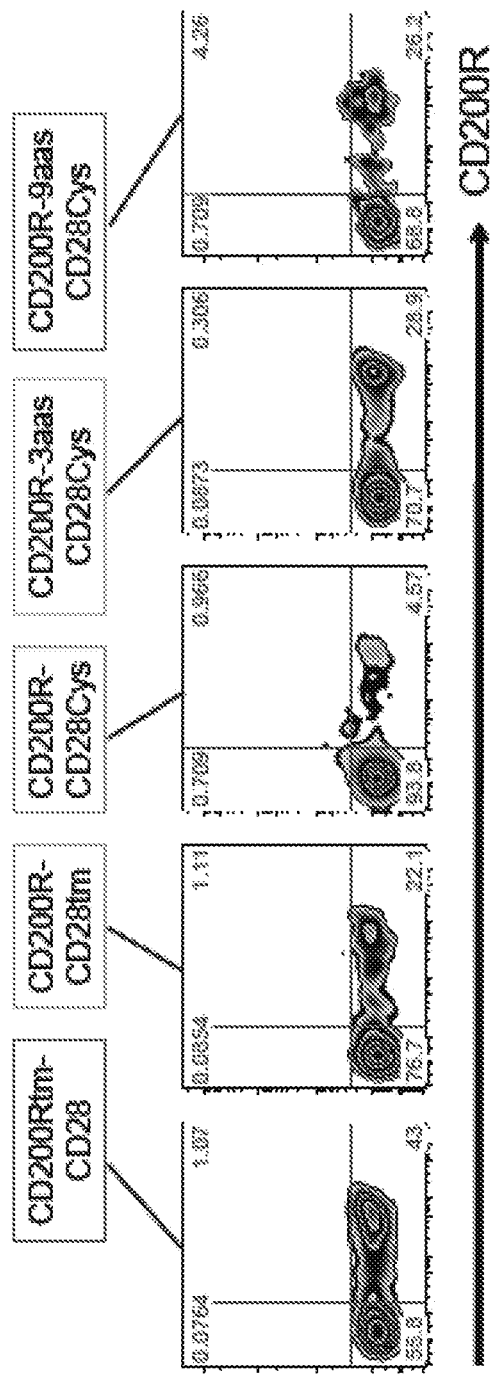

FIGS. 14A and 14B show CD200R-CD28 constructs expressed at high levels on primary murine $CD8^+$ T cells. (A) Schematic illustration of representative CD200R-CD28 constructs. Construct "I" contains CD200R extracellular ("EC") and transmembrane ("TM") domains and a CD28 intracellular ("IC") signaling domain (CD200Rtm-CD28). Construct "II" contains the extracellular domain of CD200R and the transmembrane and intracellular domains of CD28 (CD200R-CD28tm). Constructs "III-V" also incorporate a portion of the extracellular domain of CD28 to the transmembrane-proximal cysteine to promote multimerization and enhance CD28 signaling. To account for any extra extracellular amino acids caused by incorporating the portion of the extracellular domain of CD28 (e.g., from one to about 50 amino acids; such as exemplary murine constructs disclosed here containing an extra three (3) or nine (9) amino acids and exemplary human constructs disclosed here containing an extra nine (9) or twelve (12) amino acids), some constructs have a truncated portion of an extracellular or intracellular domain (e.g., a CD200R that preserves an N linked glycosylation site). For example, construct IV has a truncated portion of CD200R that is truncated by 3 amino acids. Construct V has a truncated portion of CD200R that is truncated 9 amino acids. Constructs "I", "II", and "V" maintain the spatial distance between the cells (e.g., between a T cell and an antigen presenting cell) as indicated by the dashed line, and may co-localize with the TCR within the cSMAC and deliver a strong co-stimulatory signal. (B) Transgenic expression of murine CD200R-CD28 constructs on $TCR_{gag}$ T cells as detected by anti-CD200R antibody.

Figure 15A:
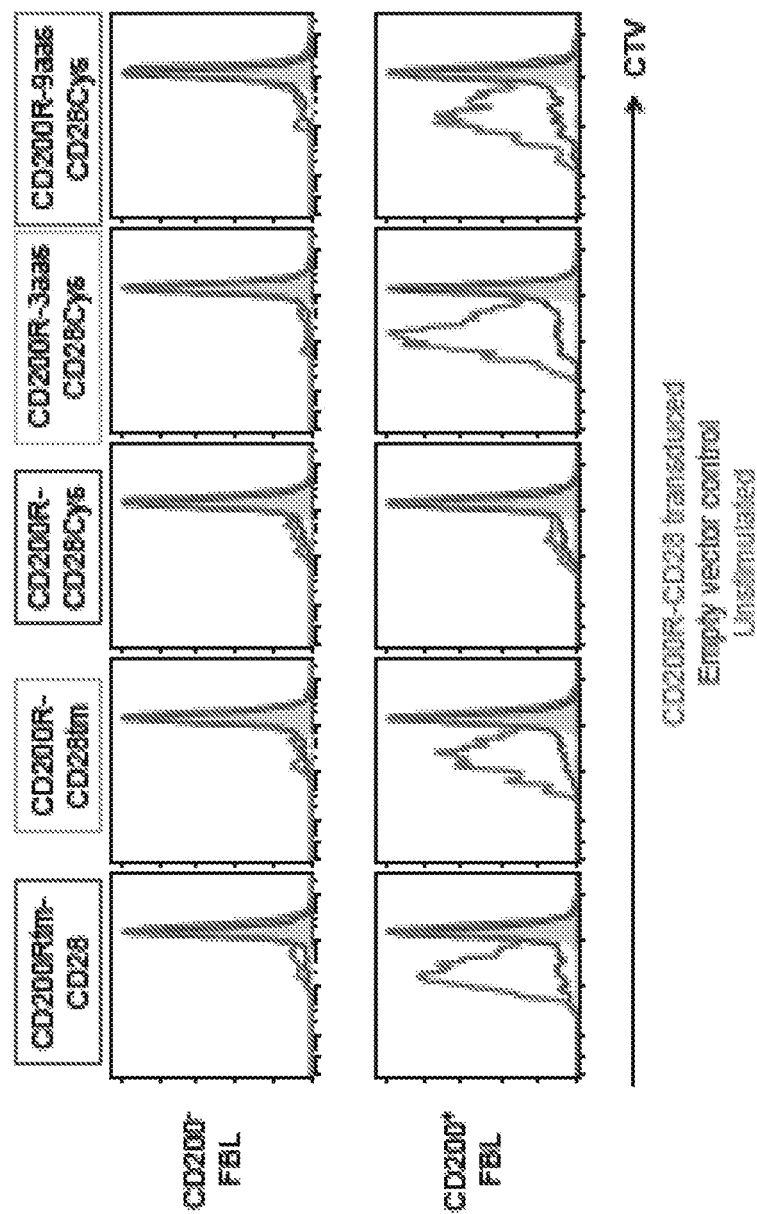
Figure 15B:
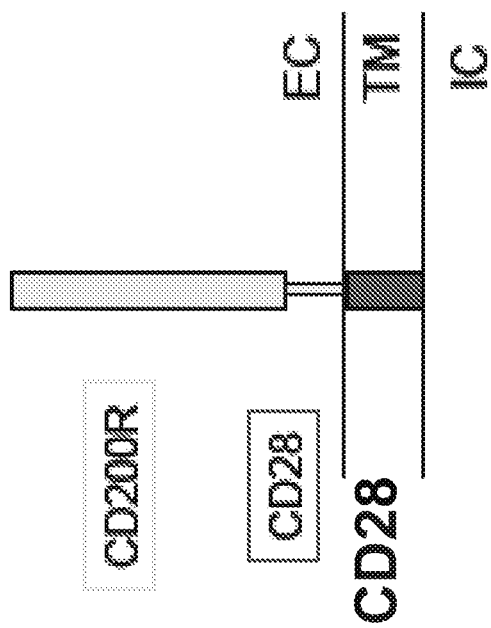
Figure 15C:
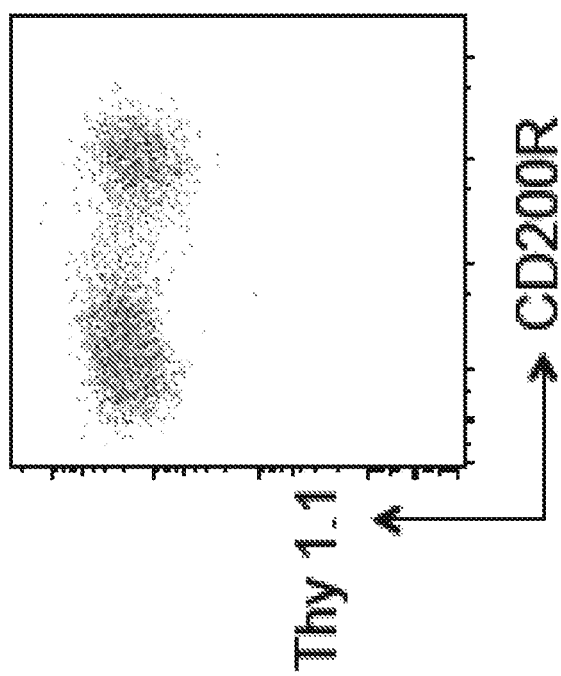
Figure 15D:
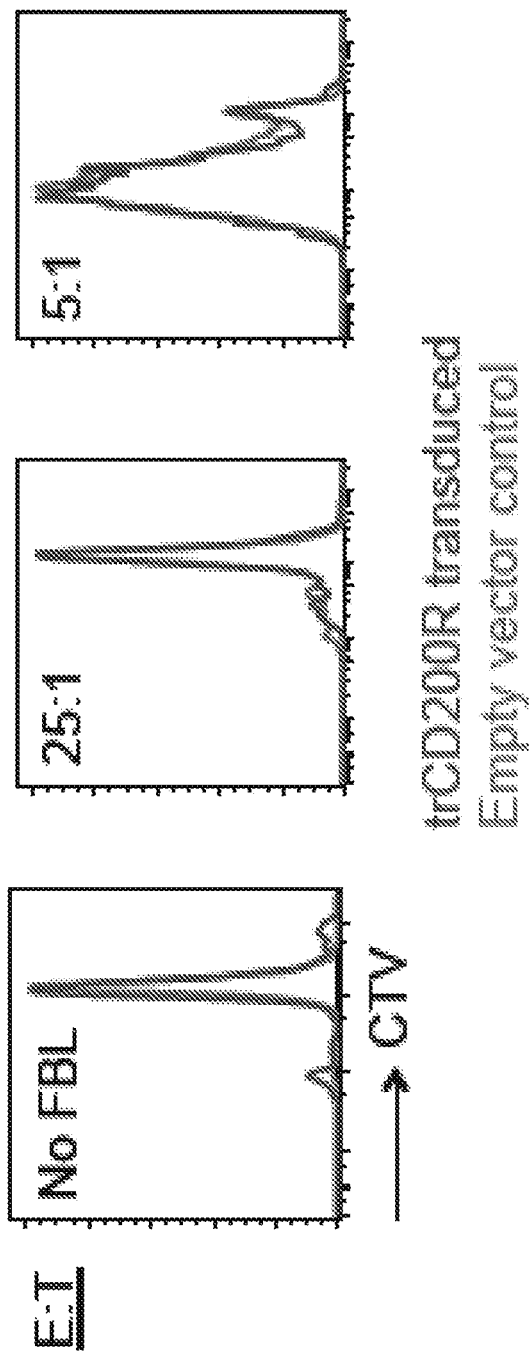
Figure 15E:
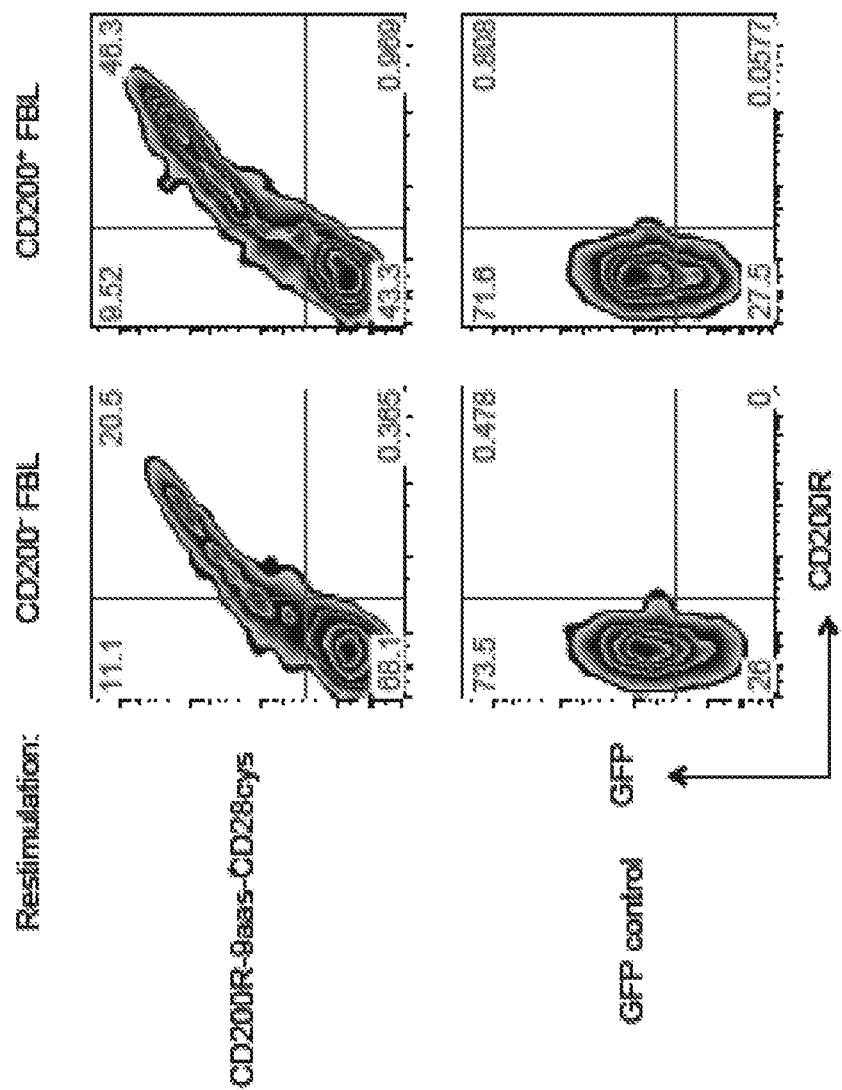
Figure 15F:
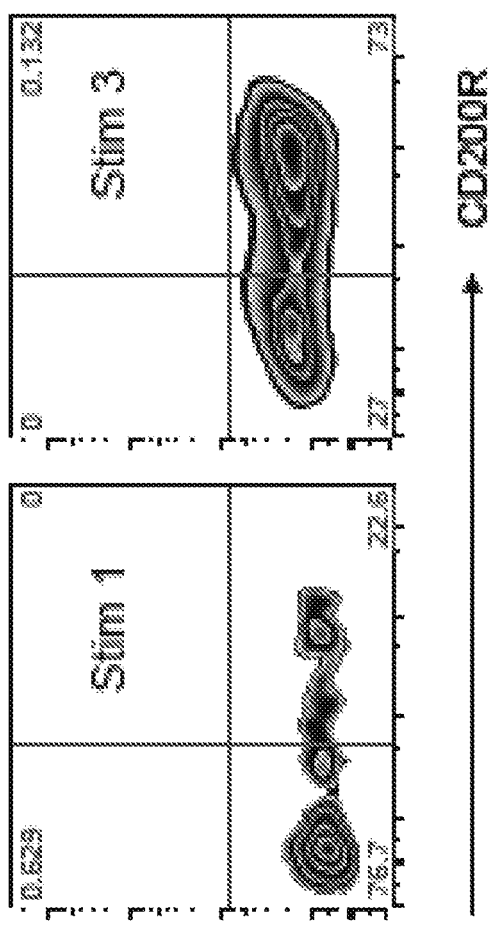
Figure 15G:
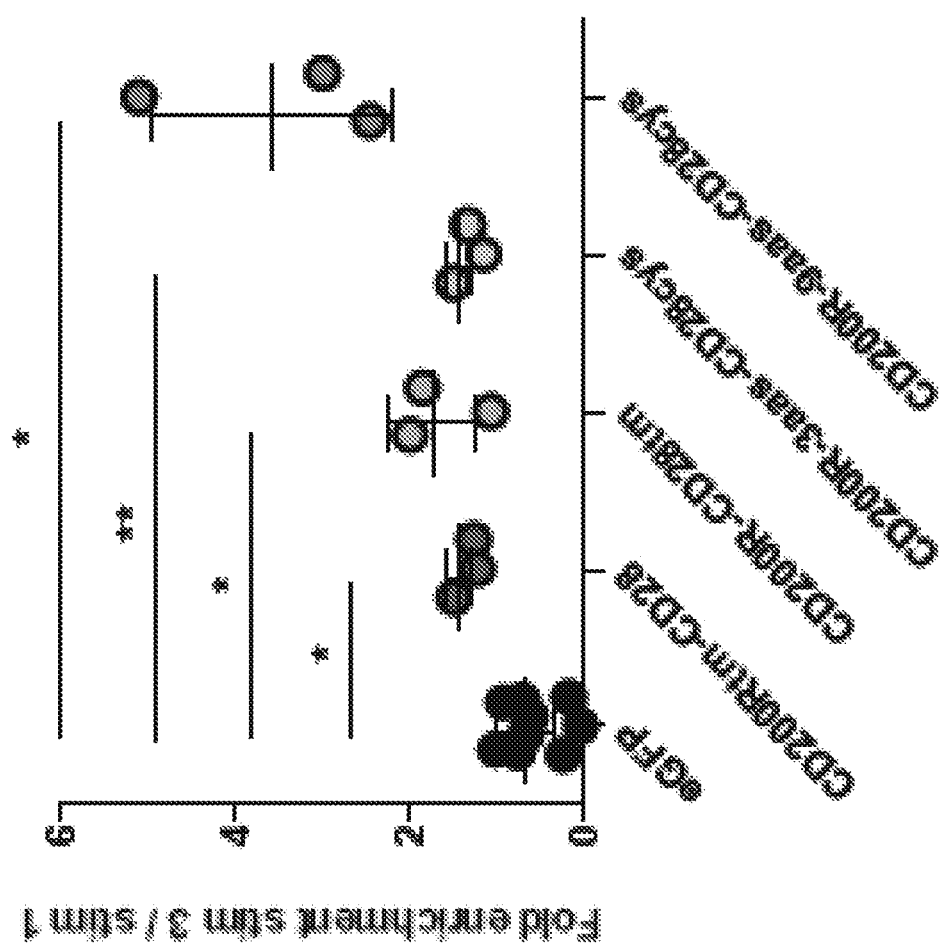
Figure 15H:
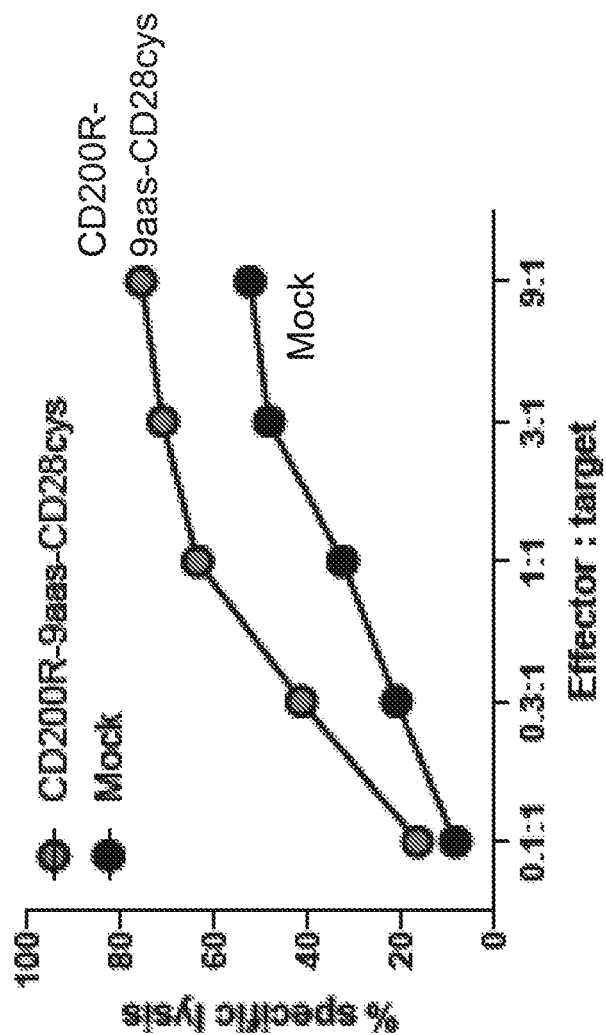
Figure 15H:
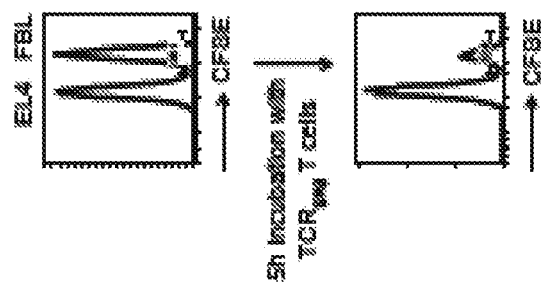
Figure 15I:
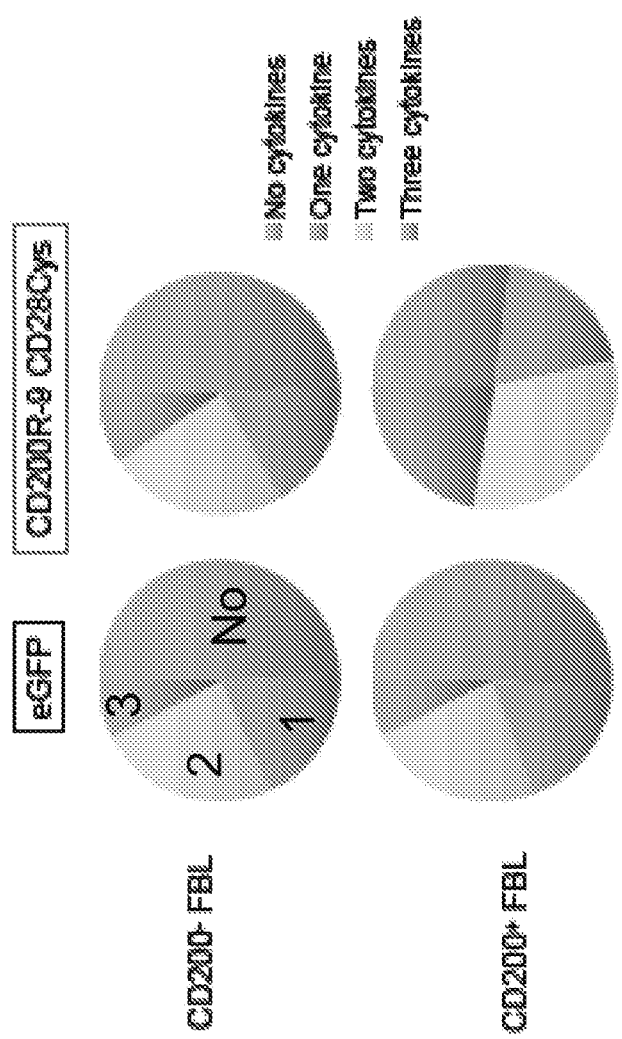
Figure 15J:
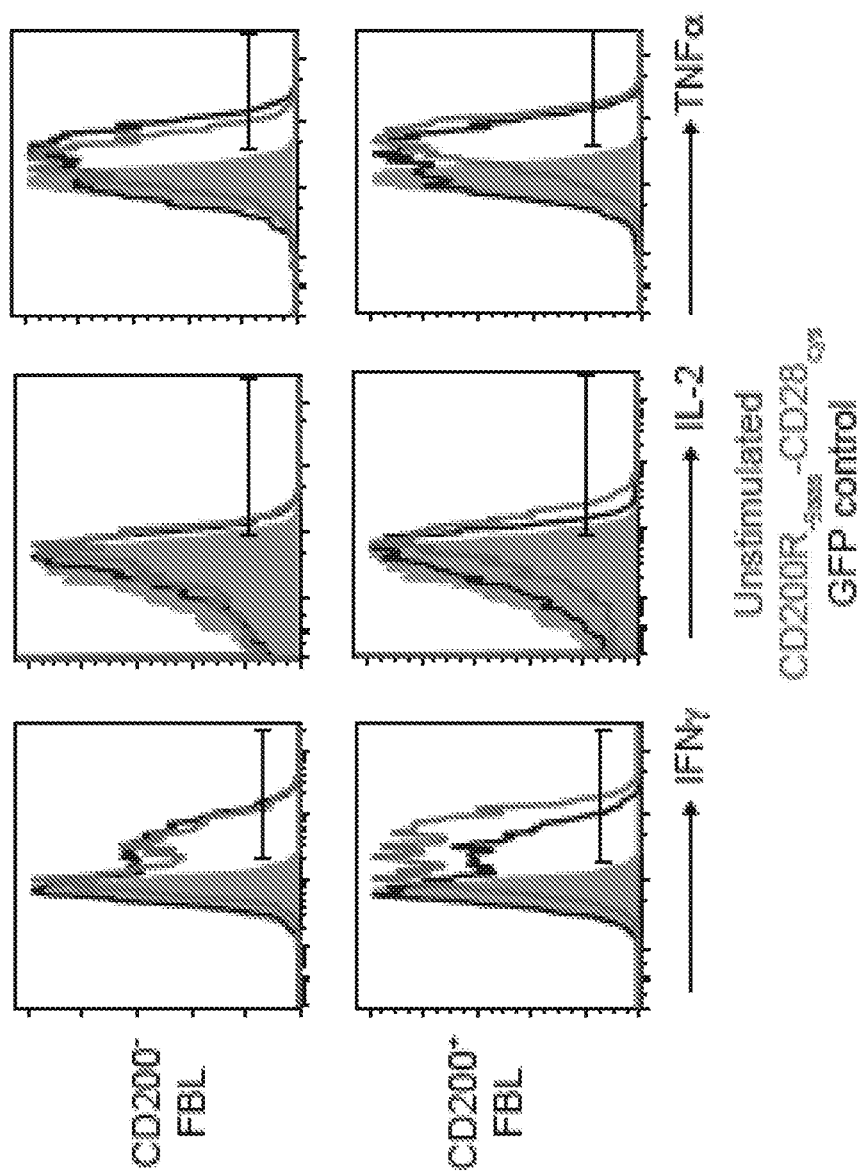
Figure 15K:
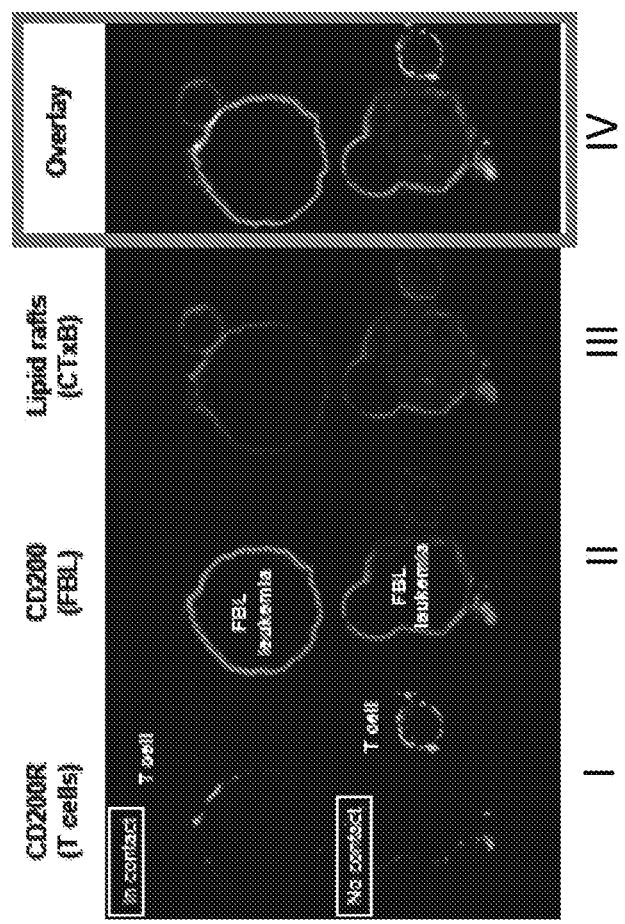
Figure 15L:
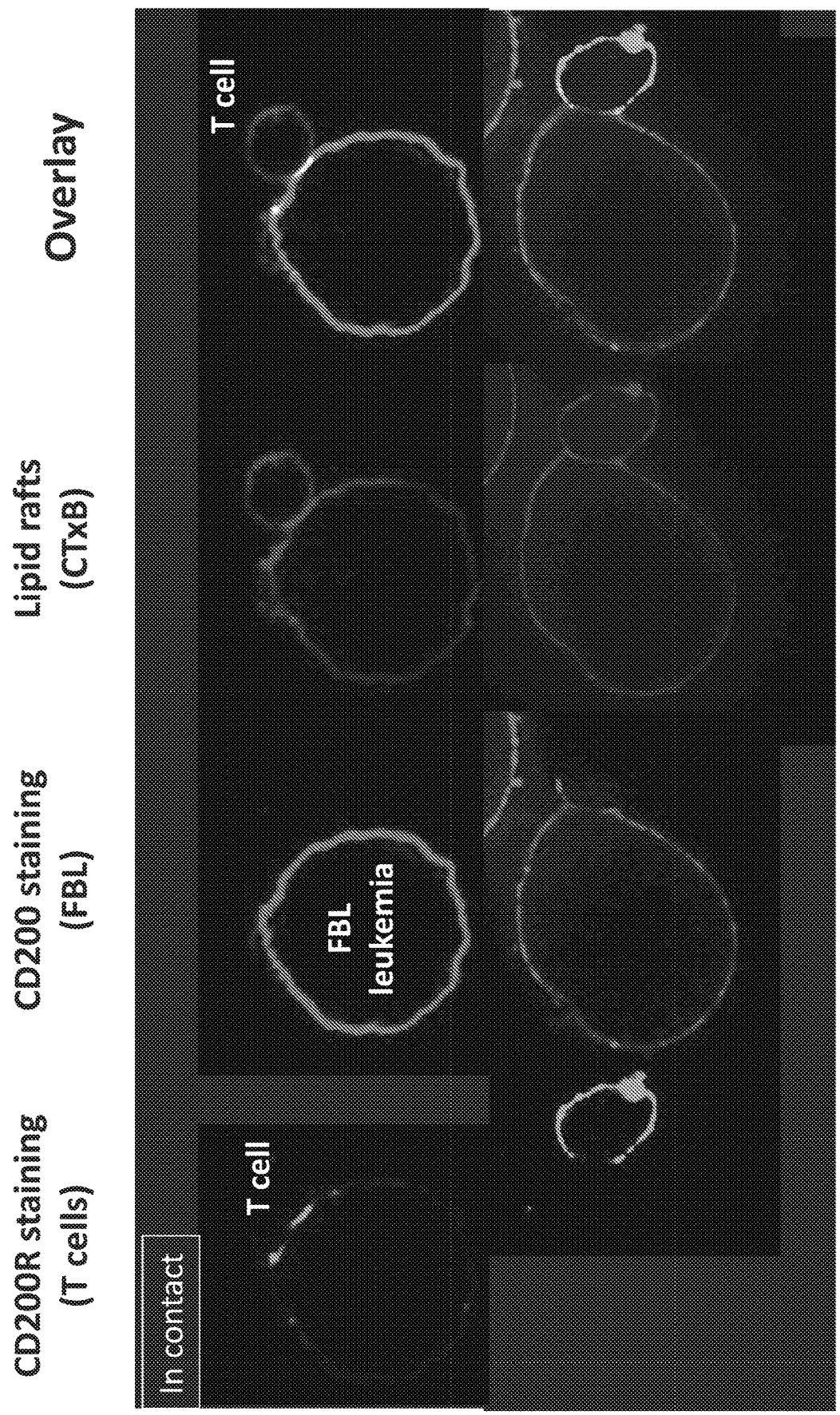
Figure 15M:
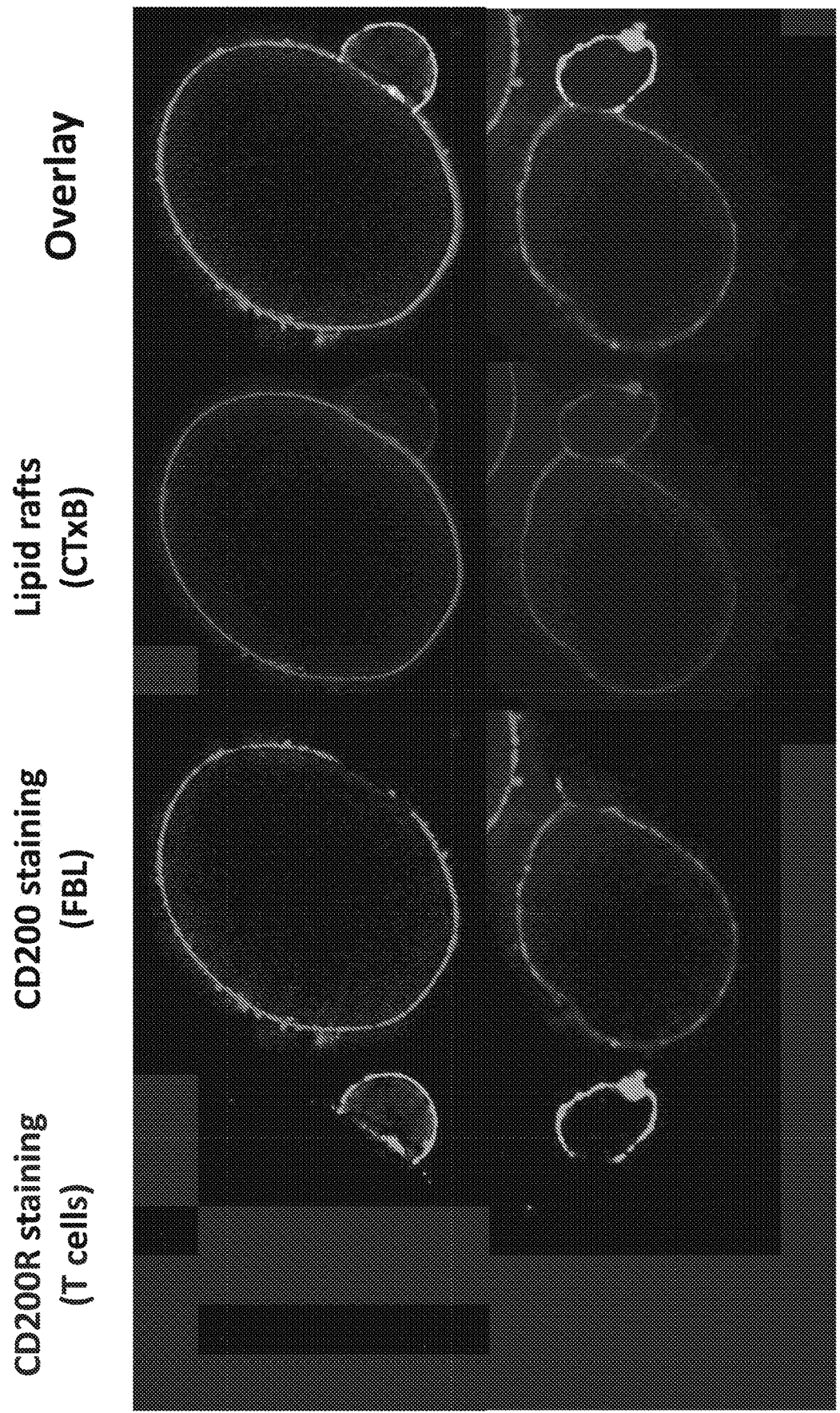
Figure 15N:
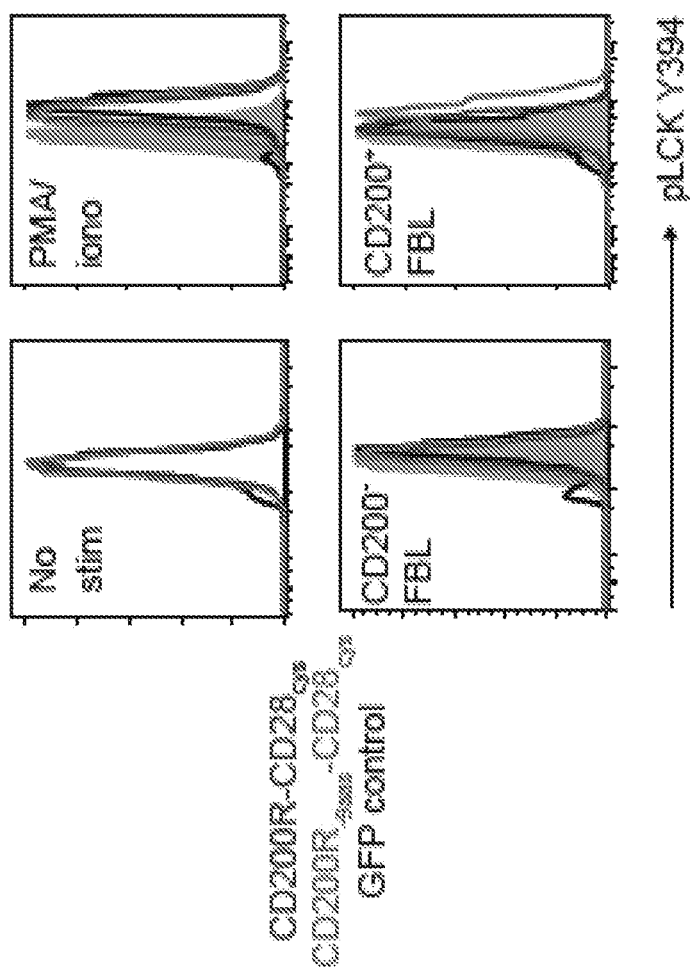

FIGS. 15A to 15N show that CD200R-CD28 constructs promote proliferation, accumulation, and effector function of T cells stimulated by $CD200^+$ tumor target cells in vitro, and accumulate in the immunological synapse. Unless otherwise indicated, all results are representative of at least 2 experiments with similar results. Splenocytes from naive $TCR_{gag}$ mice were stimulated in vitro with anti-CD3, anti-CD28, and recombinant human IL-2 (rhIL-2, 100 U/ml) and transduced with retroviral supernatant for 2 days. Cells were restimulated every 7 days with irradiated FBL and splenocytes and cultured with rhIL-2 (50 U/mL) for up to three stimulations. T cells were used for assays 5-7 days after the last stimulation. (A) Proliferation of CD200R-CD28 and GFP control $TCR_{gag}$ T cells as measured by CellTrace Violet (CTV) dilution, relative to unstimulated cells (shaded). T cells were stimulated with $CD200^-$ FBL (upper panels) or $CD200^+$ FBL (lower panels) for 3 days. (B) Schematic of truncated CD200R (trCD200R). (C) CD28 signaling domain is required for costimulation. Transgenic expression of trCD200R construct on TCRgag T cells as detected by anti-CD200R antibody. (D) Proliferation of trCD200R (blue lines) and GFP control (red lines) $TCR_{gag}$ T cells as measured by CellTrace Violet dilution. T cells were stimulated with $CD200^+$ FBL for 3 days. (E) Restimulation with $CD200^+$ FBL enriches CD200R IFP-transduced T cells. Enrichment of transduced $TCR_{gag}$ T cells in a mixed population including non-transduced $TCR_{gag}$ T cells during 1 cycle of restimulation with irradiated $CD200^-$ (left panels) or $CD200^+$ (right panels) FBL, and splenocytes. $TCR_{gag}$ T cells were transduced with CD200R-CD28 (upper panels) or GFP control (lower panels). (F, G) Enrichment of transduced $TCR_{gag}$ T cells in a mixed population including non-transduced $TCR_{gag}$ T cells during weekly cycles of stimulation with irradiated $CD200^-$ FBL and splenocytes. *P<0.05, **P<0.01 (t test). (H) CD200R-9aas-$CD28Cys^+CD8^-$ T cells display enhanced ability to lyse $CD200^+$ FBL cells in vitro. Target tumor cells were labeled with the fluorescent dye 5,6-carboxyfluorescein diacetate succinimidyl ester (CFSE). $TCR_{gag}$ T cells were transduced with CD200R-9aas-CD28Cys or mock-transduced cells (black symbols). Effector $TCR_{gag}$ T cells were incubated at the indicated effector to target ratio with a 1:1 mix of $CD200^+$ FBL and non-specific EL4 control targets for 4 hours. The percentage of FBL of the sum of FBL and control tumor cells was determined by flow cytometry. The percentage lysis was determined by dividing the percent of FBL incubated with T cells by the percent of FBL incubated without T cells. (I) Pie charts depicting the pattern of cytokine production in $TCR_{gag}$ T cells in response to FBL stimulation at a 1:1 ratio. Each slice within the pie chart represents a combination of cytokine staining, including IFNγ, TNFα, and IL-2. (J) Histograms of cytokine production shown in (I), as measured by flow cytometry. Shaded histograms represent GFP control-transduced cells. (K-M) CD200R-9aas-CD28Cys fusion proteins co-localized with lipid rafts, indicating that the fusion proteins concentrate at the region of T cell:target contact, suggesting that the size of the fusion protein can be accommodated within the immunological synapse. Vector transduced $TCR_{gag}$ in vitro expanded effector T cells were combined with FBL at a E:T of 10:1 at 37° C. for 20 minutes. Conjugates were loaded on a p.-Slide VI.4 chamber (Ibidi) for an additional 15 minutes. Fixed cells were stained and visualized by microscopy. In FIG. 15K, the upper panel shows cells in contact, and the lower panel shows cells not in contact. (N) LCK Y394 expression of $TCR_{gag}$ T cells transduced with CD200R-9aas-CD28Cys (red line), CD200R-CD28Cys (blue line), and GFP control (black line) and stimulated for 10 minutes as labeled.

FIGS. 16A to 16E show that T cells transduced with CD200R-9aas-CD28Cys preferentially accumulate in response to tumor challenge in vivo and enhance adoptive immunotherapy of disseminated leukemia. Transduced $TCR_{gag}$ T cells were generated as described in Example 15. C57BL/6 mice were injected with $4\times10^6$ CD200⁻ FBL cells. Five days later, CD200R9aas-CD28Cys (Thy1.1 homozygous) and eGFP (Thy1.1 heterozygous) $TCR_{gag}$ T cells were co-injected into Cy-treated FBL-bearing B6 mice at $4\times10^6$ cells/mouse. IL-2 was administered every 2 days ($2\times10^4$ U/dose). On day 8 post-T cell transfer, mice were euthanized and spleens and inguinal lymph nodes harvested. (A) CD200R-9aas-CD28Cys$TCR_{gag}$ T cells accumulate in the spleen in response to FBL, relative to empty vector control $TCR_{gag}$ T cells. (B) Phenotype of IFP-transduced T cells is similar to control. Expression of surface markers on $TCR_{gag}$ T cells transduced with CD200R-CD28 (red lines) or non-transduced (blue lines) 5 days after stimulation in vitro. (C) Accumulation of CD200R-9aas-CD28Cys and empty vector control $TCR_{gag}$ T cells in the lymph node (LN) and spleen (Spl) in response to FBL. The fold increase of CD200R-9aas-CD28Cys $TCR_{gag}$ T cells (Thy1.1 hom) was calculated by dividing by the percentage of empty vector control (Thy1.1⁺ Thy1.2⁺) $TCR_{gag}$ T cells. (D, E) Expression of surface markers on CD200R-9aas-CD28Cys $TCR_{gag}$ T cells (blue lines), control $TCR_{gag}$ T cells (red lines), and endogenous T cells (shaded) at days 8 (D) and 15 (E). At 15 days post-transfer, CD200R-9aas-CD28Cys $TCR_{gag}$ T cells expressed similar levels of cell surface proteins compared to empty vector control $TCR_{gag}$ T cells.

Figure 17A:
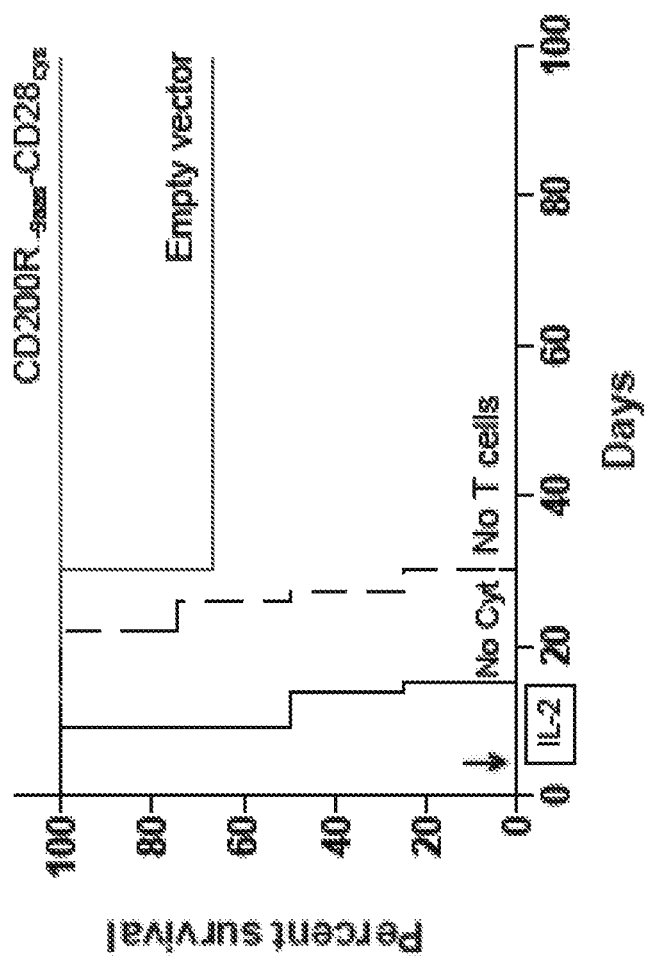
Figure 17B:
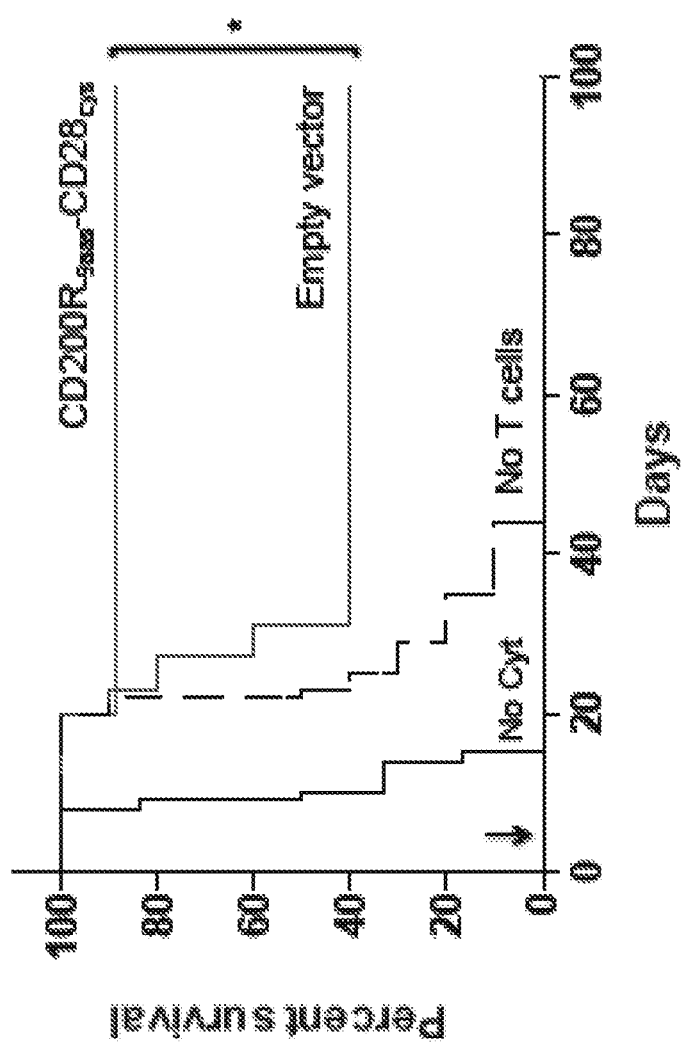

FIGS. 17A and 17B show survival of mice treated in the presence (A) or absence (B) of IL-2 injections. C57BL/6 mice were injected with $4\times10^6$ CD200⁺ FBL cells. Five days later, CD200R-9aas-CD28Cys, and eGFP $TCR_{gag}$ T cells were injected i.p. into Cy-treated FBL-bearing mice at $10^5$ cells/mouse (indicated by arrow). IL-2 was administered every 2 days for a total of 10 days ($2\times10^4$ U/dose) in a cohort of mice (A). Transfer of CD200R-9aas-CD28Cys $TCR_{gag}$ T cells significantly improved survival in the absence of IL-2 injections (P<0.05, log-rank Mantel-Cox test) (B). In (A), data are from 1 experiment (n=3-4 mice/group). In (B), data were pooled from 3 independent experiments (n=6-10 mice/group).

FIGS. 18A to 18E show that human primary T cells transduced to express a WT1-specific TCR and a CD200Rtm-CD28 fusion protein exhibit enhanced proliferation to target cells that express CD200 and increased cytokine production in response to tumor cells that express CD200. (A) Expression of CD200 on CD34⁺ cells from a healthy donor leukapheresis (upper panels) or leukemic blasts (lower panels). (B) Expression of the $WT1_{126}$-specific TCR, $TCR_{C4}$, and CD200Rtm-CD28 in primary human T cells. Diagram shows construct combining IFP, TCRα, and TCRβ chains. (C, D) Proliferation of T cells as indicated by CFSE. Cells that proliferate in response to antigen show reduced CFSE fluorescence intensity. T cells transduced with $TCR_{C4}$ or with $TCR_{C4}$ and CD200Rtm-CD28 were stimulated with $WT1_{126}$-pulsed T2 cells. (E) Cytokine production in response to exposure to T2 cells, as measured by flow cytometry. T cells transduced with the $TCR_{C4}$ alone (upper panels) or with both $TCR_{C4}$ and the CD200-targeted IFP (lower panels) were stimulated with a titration of $WT1_{126}$-pulsed T2 cells, as indicated. Relative to control T cells transduced with the $TCR_{C4}$ alone, T cells transduced with both $TCR_{C4}$ and the IFP CD200Rtm-CD28 showed increased cytokine production.

Figure 19A:
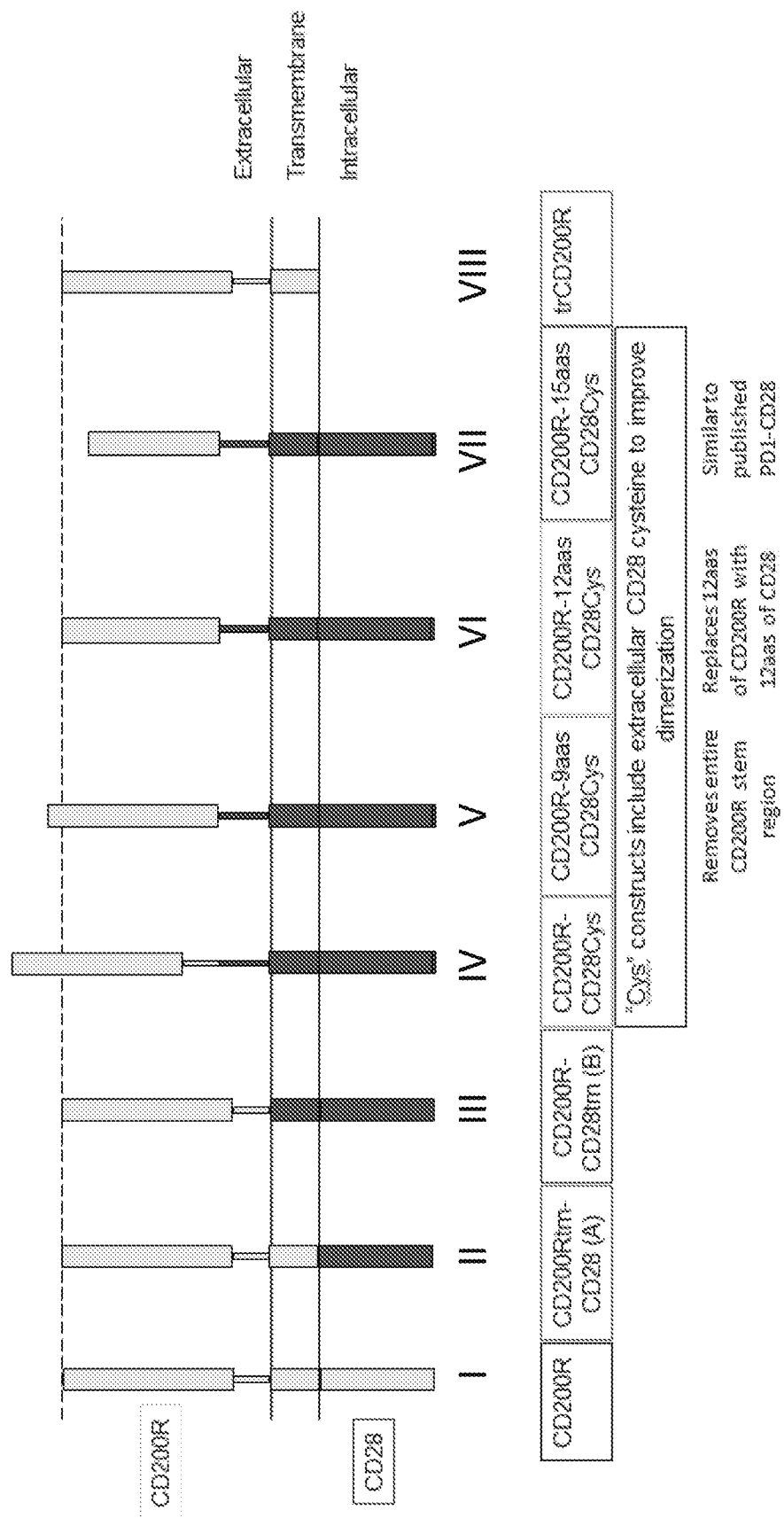
Figure 19B:
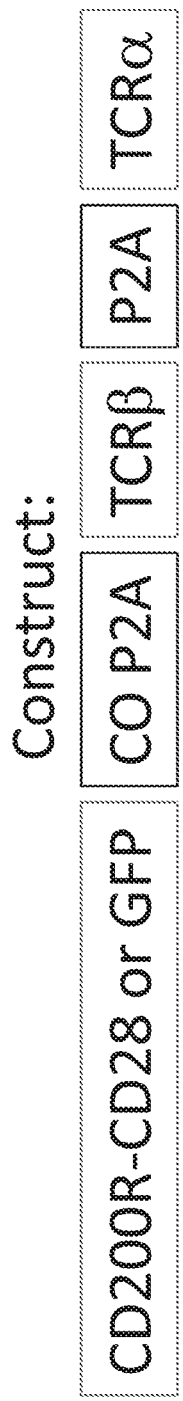
Figure 19C:
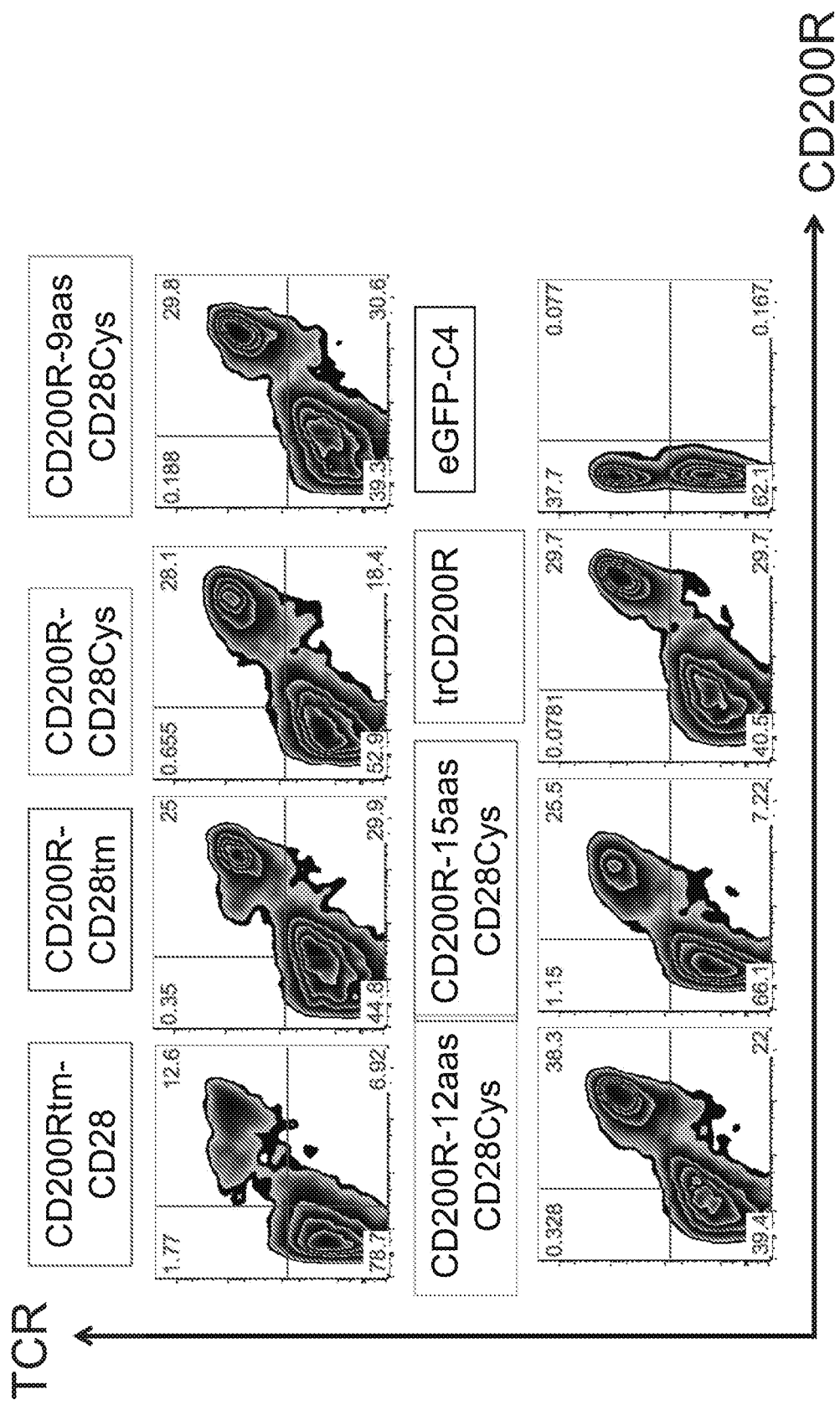

FIGS. 19A to 19C show CD200R-CD28 constructs co-expressed with WT1-specific TCR in primary human T cells. (A) Schematic illustration of representative CD200R-CD28 constructs. (B) Diagram showing construct combining IFP, TCRα, and TCRβ chains. (C) Expression of the $WT1_{126}$-specific TCR, $TCR_{C4}$, and CD200R-CD28 fusion proteins in primary human T cells.

FIGS. 20A to 20D show the results of assays for enrichment of T cells expressing CD200R-CD28 constructs.

FIGS. 21A to 21K show effector function assays (cytokine production, cytotoxicity) for T cells expressing CD200R-CD28 constructs.

Figure 22A:
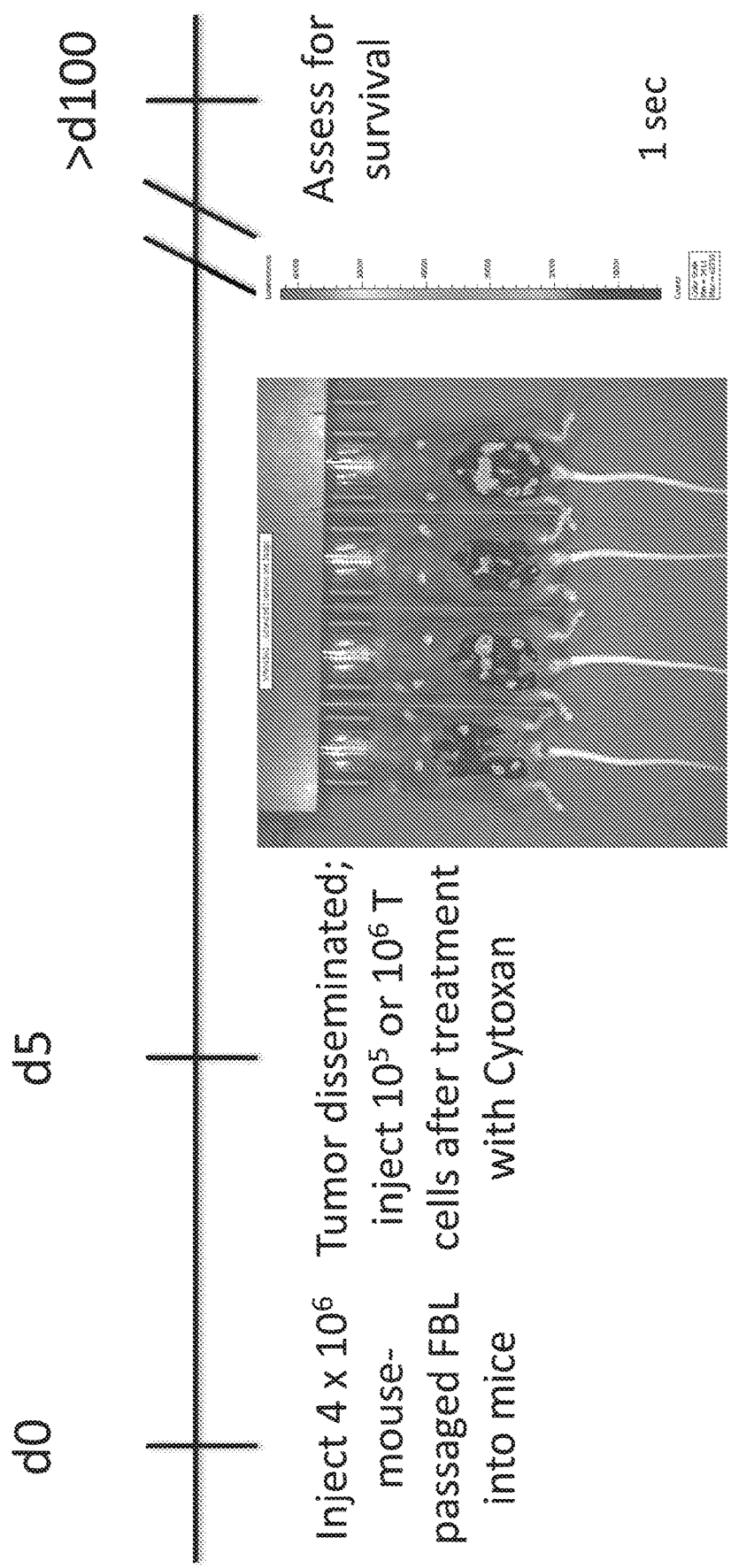
Figure 22B:
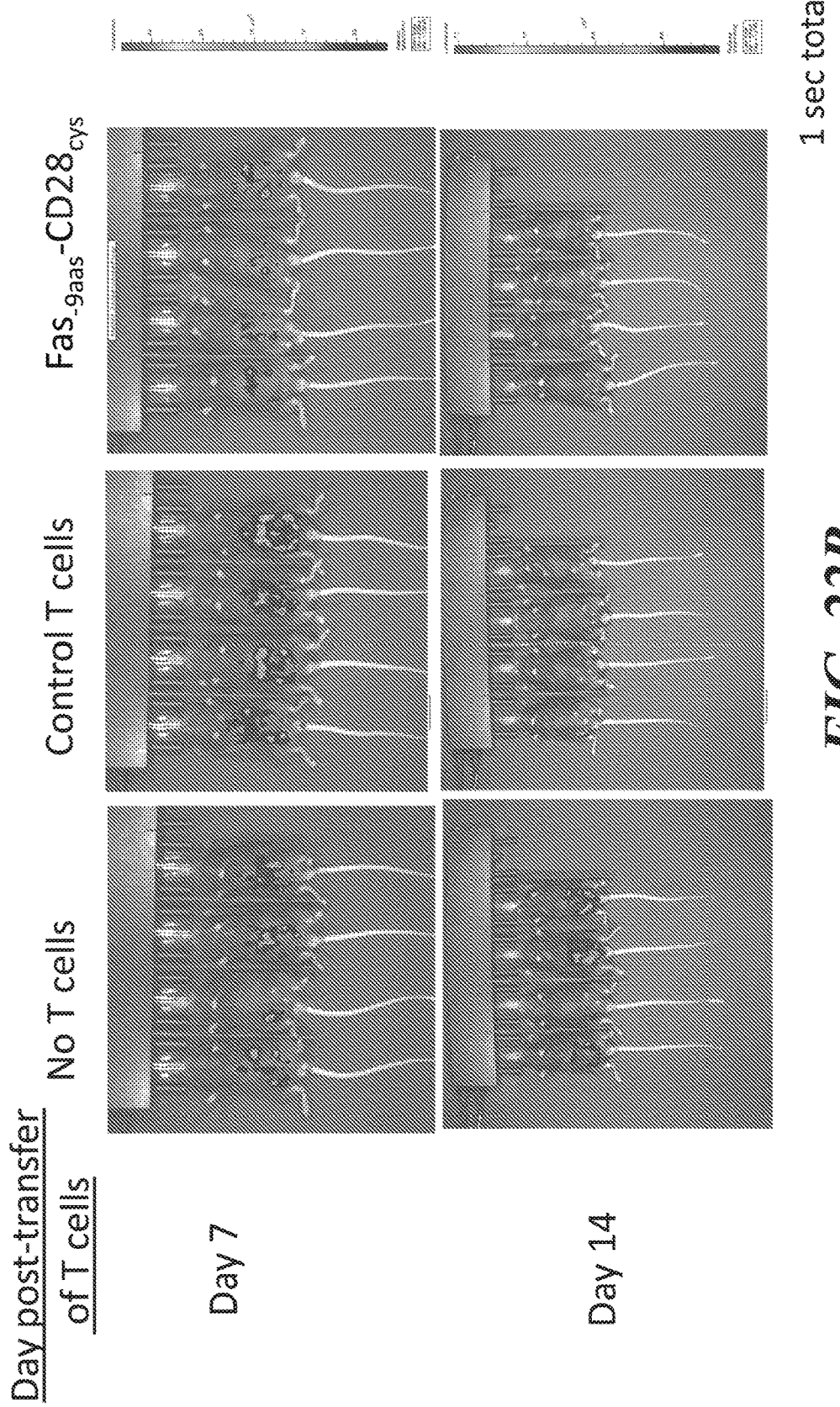
Figure 22C:
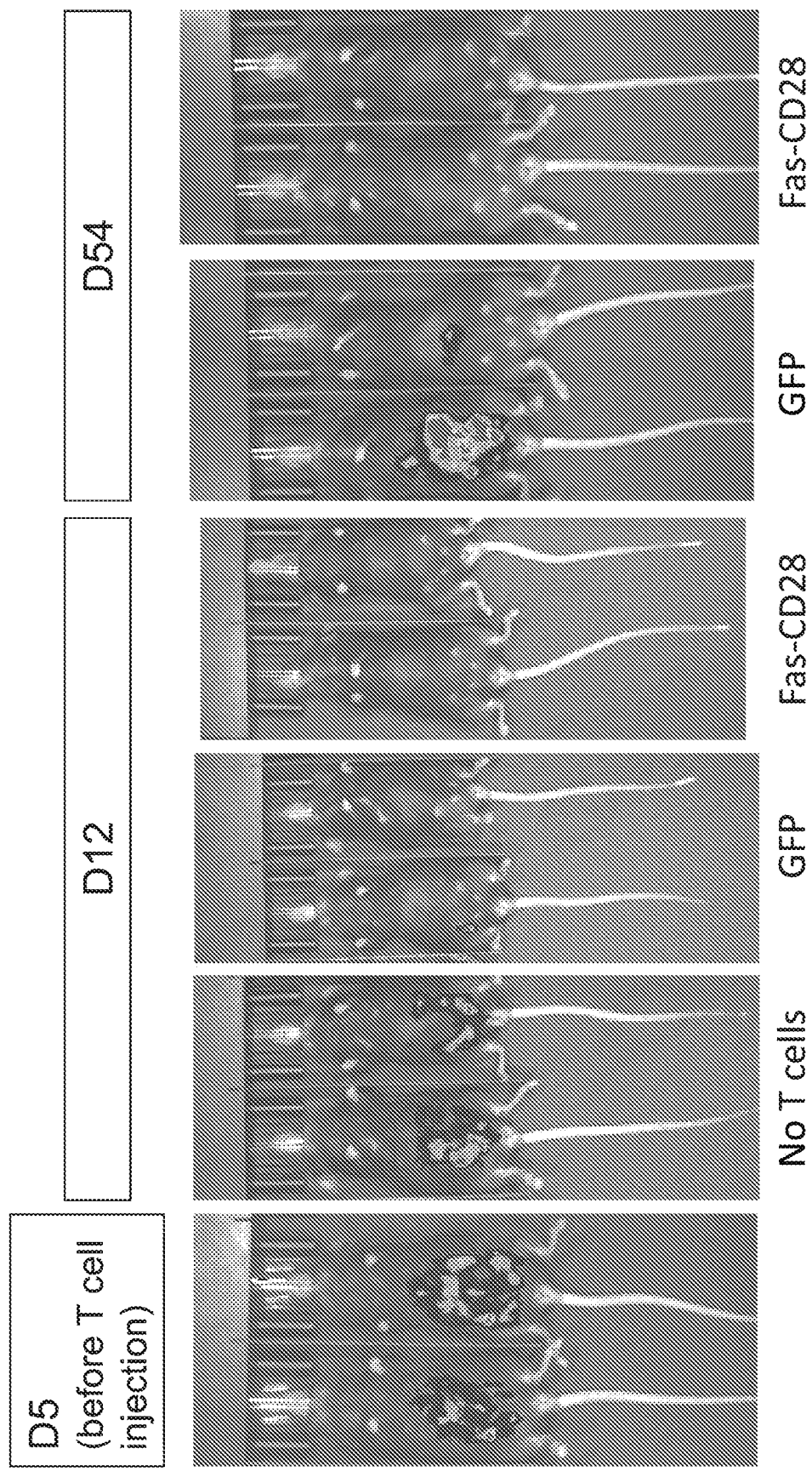
Figure 22D:
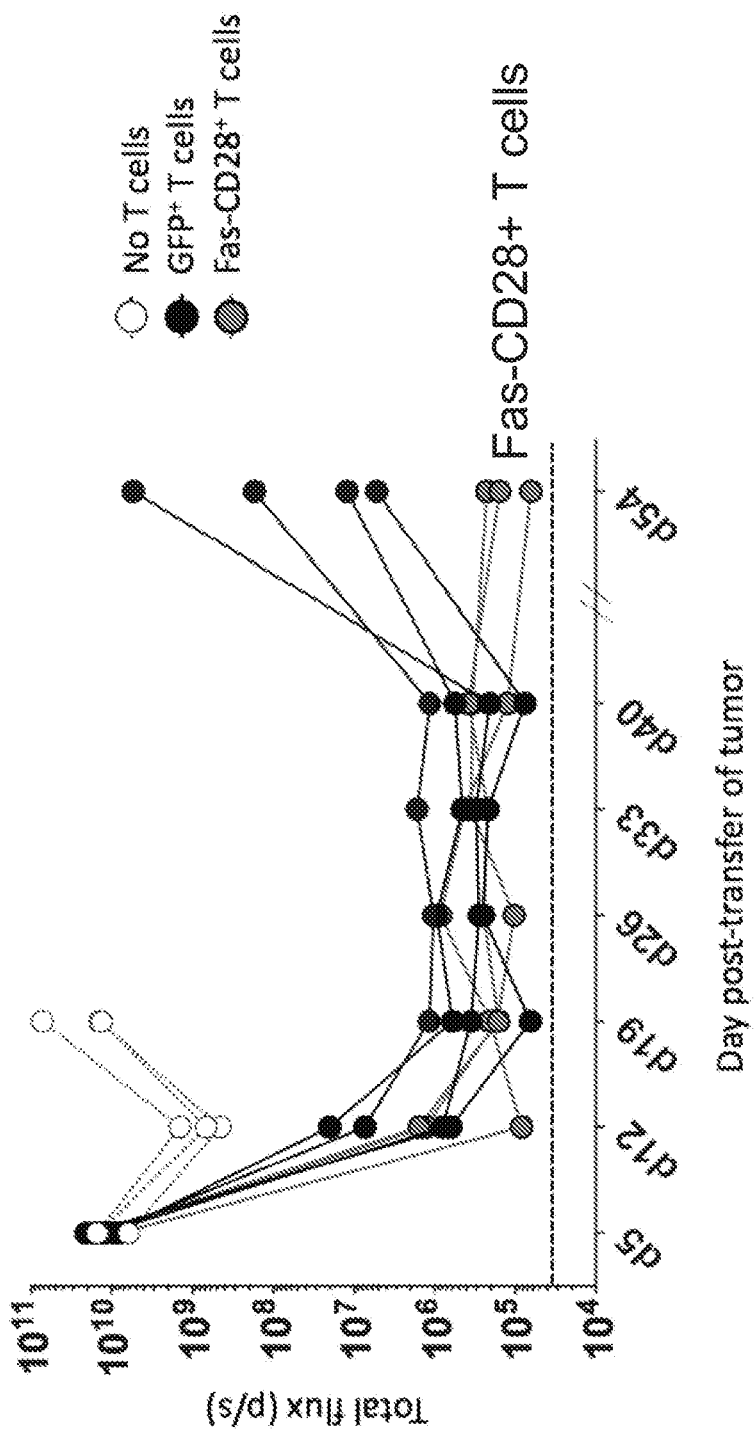

FIGS. 22A to 22D show results of an in vivo study of immunotherapy with T cells expressing Fas IFP constructs. (A) Study design. (B-C) In vivo bioluminescence imaging of firefly luciferase⁺ FBL tumors in C57BL/6 mice at indicated time points after intraperitoneal inoculation with $4\times10^6$ tumor cells (day 0) and after cyclophosphamide treatment, followed by no additional treatment or adoptive transfer of $10^6$ GFP-transduced or Fas-CD28-transduced $TCR_{gag}$ transgenic CD8⁺ T cells (day 5). The two mice shown in FIG. 22C are representative of n=4 mice. (D) Biodistribution of FBL tumor cells as quantified by IVIS imaging. FBL tumors in C57BL/6 mice at indicated time points after intraperitoneal inoculation with $4\times10^6$ tumor cells (day 0) and after cyclophosphamide treatment, followed by no additional treatment (white circles) or adoptive transfer of $10^6$ GFP-transduced (black circles) or Fas-CD28-transduced (red circles) $TCR_{gag}$ transgenic CD8⁺ T cells (day 5).

FIGS. 23A to 23D show that fusion proteins comprising Fas extracellular components and 4-1BB co-stimulatory signaling domains accumulate and proliferate in vitro upon stimulation with tumor cells, and also reduce Fas-induced cell death. (A) Schematic representation of an exemplary Fas-4-1BB construct. The construct contains a Fas extracellular ("EC") domain and 4-1BB transmembrane ("TM") and intracellular ("IC") signaling domains ("Fas-4-1BBtm"). (B) Co-expression of a transgenic TCR and a Fas-4-1BB IFP (Fas-4-1BBtm) in murine T cells. Retroviral supernatant was generated by transfection of Plat-E cells with DNA constructs encoding either $TCR_{gag}$ alone, or $TCR_{gag}$ and Fas-4-1BBtm (SEQ ID NO.:187). Naive P14 T cells were stimulated with anti-CD3 and anti-CD28, then transduced for 2 days with retroviral supernatant. Five days post-stimulation, transduced T cells were stained with specific antibodies to the TCR and to Fas, and analyzed by flow cytometry. (C) Proliferation of T cells transduced with $TCR_{gag}$ alone or with $TCR_{gag}$ and Fas-4-1BBtm, as measured by CellTrace Violet (CTV) dilution. Transduced P14 T cells were stained with CellTrace Violet (CTV) proliferation dye and were unstimulated (left) or stimulated with FBL tumor cells for 6 days at an effector-to-target ratio of 8:1 (right). T cells were then harvested and analyzed by flow cytometry. (D) Cell death Fas signaling pathway activity in (i) T cells expressing transgenic $TCR_{gag}$ but lacking Fas expression; (ii) wild-type T cells expressing transgenic $TCR_{gag}$; and (iii) T cells expressing transgenic $TCR_{gag}$ and Fas-4-1BBtm. P14 T cells were stimulated and transduced with $TCR_{gag}$ or $TCR_{gag}$+Fas-4-1BBtm IFP. 7 days later, T cells were stained for active caspase-8 expression using the FLICA methodology, as a measure of cell death by the Fas pathway.

Figure 24A:
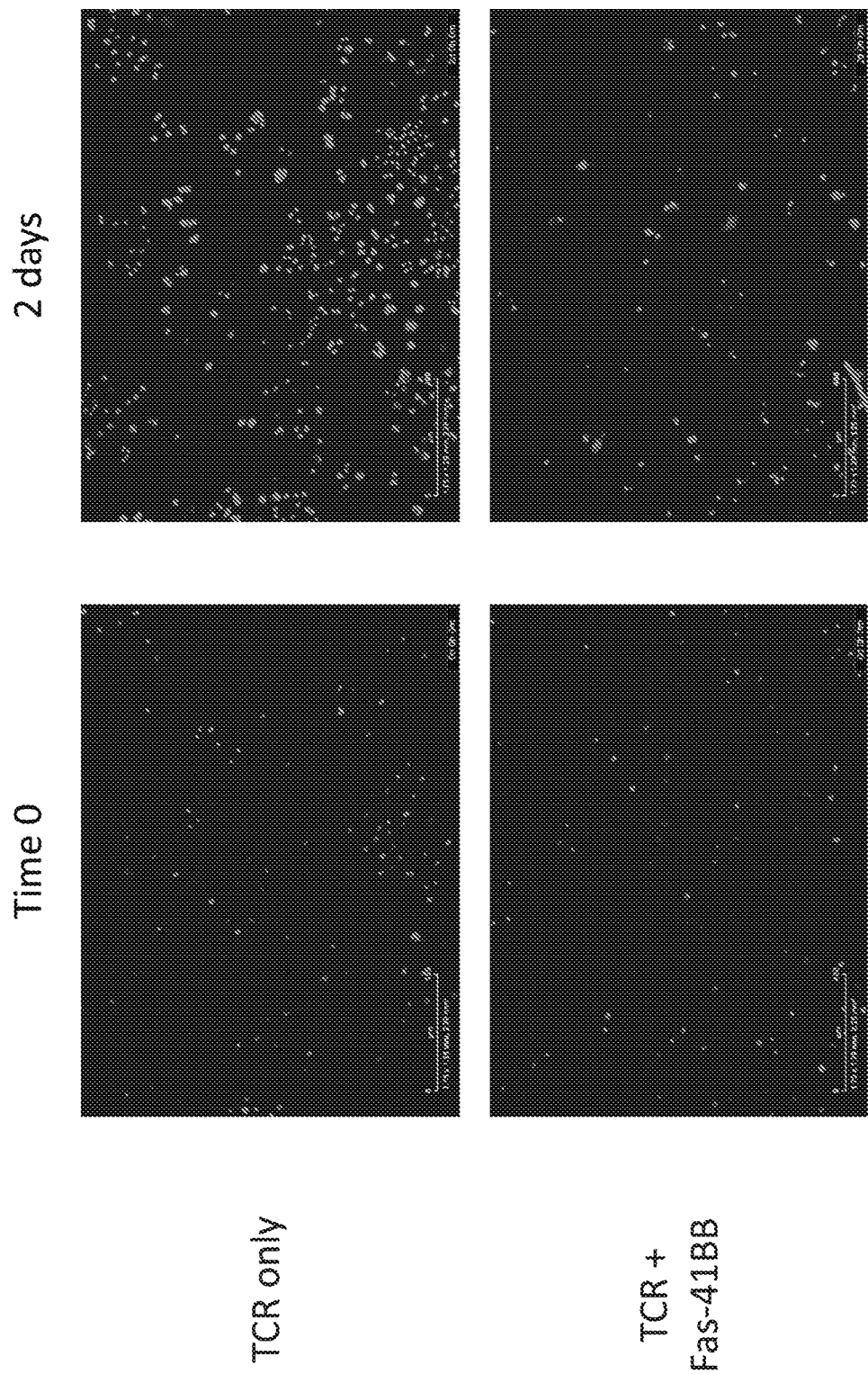
Figure 24B:
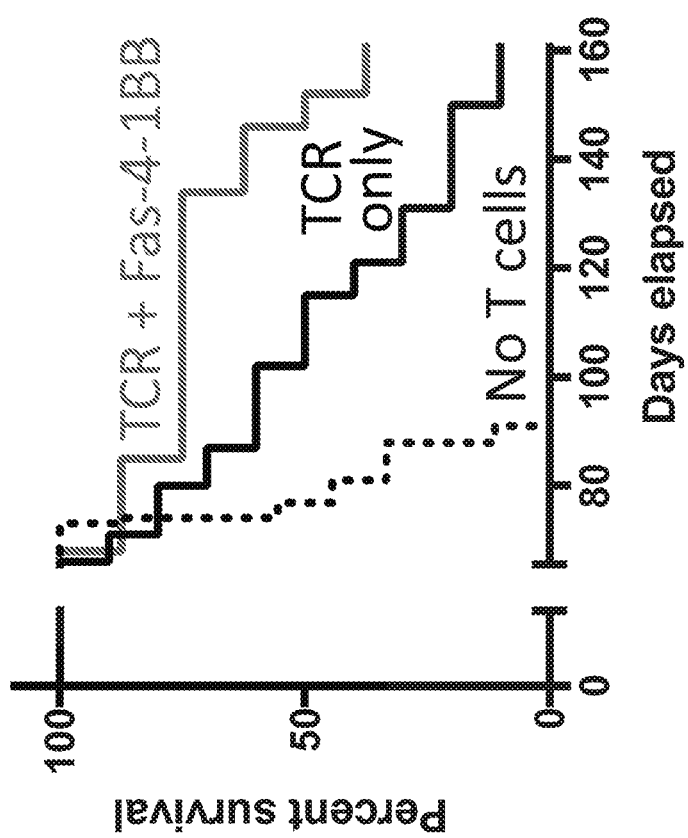

FIGS. 24A to 24B show that Fas-4-1BB T cells control tumor growth and promote survival in an ID8 model of ovarian cancer. (A) Results of an IncuCyte® assay used to quantify killing of ID8 ovarian tumor cells. Murine transduced T cells (anti-mesothelin TCR or anti-mesothelin TCR+Fas-4-1BBtm) were co-incubated with red fluorescent ID8 ovarian tumor cells for two days and ID8 cell growth was quantified by IncuCyte® analysis. Loss of red signal indicates killing of tumor cells. (B) Survival of ID8 mice treated with (i) anti-mesothelin TCR cells or (ii) with anti-mesothelin TCR+Fas-4-1BBtm cells. In the ID8 murine ovarian cancer model, $5 \times 10^6$ ID8 tumor cells were implanted and allowed to disseminate for 6 weeks. Following cyclophosphamide treatment, mice received $10^7$ T cells and $5.0 \times 10^8$ mesothelin-pulsed splenocytes, followed by IL-2 injections for 10 days. Mice were treated every two weeks until euthanized.

FIGS. 25A to 25D show that Fas-4-1BB T cells exhibit greater persistence and promote survival in a KPC mouse model of pancreatic cancer. (A) Ultrasound image of a healthy mouse with normal pancreas (left) and a pancreatic tumor in an "enrolled" mouse (a KPC genetically engineered mouse) (right). (B) Experiment schematic. KPC mice were screened by ultrasound to determine when tumors arise, and were enrolled in the study when a tumor was detected, at approximately 8 weeks of age. Mice were randomly assigned to treatment groups; mice were treated with cyclophosphamide, and those receiving TCR-T cells were injected with $10^7$ each of mesothelin-specific-T cells and mesothelin peptide-pulsed splenocytes post-cyclophosphamide. Beginning 14 days post-enrollment, the T cell/APC infusion (but without cyclophosphamide) was repeated every 2 weeks for a total of 3 infusions, without IL-2 injections. At the end of the study, the mice were assessed for survival. (C) Mice that survived 28 days post final T cell infusion were bled and the persistence of transferred T cells was assessed by detection of congenically marked T cells by flow cytometry. (D) Survival of KPC mice treated with (i) anti-mesothelin TCR cells or (ii) with anti-mesothelin TCR+Fas-4-1BBtm cells.

Figure 26:
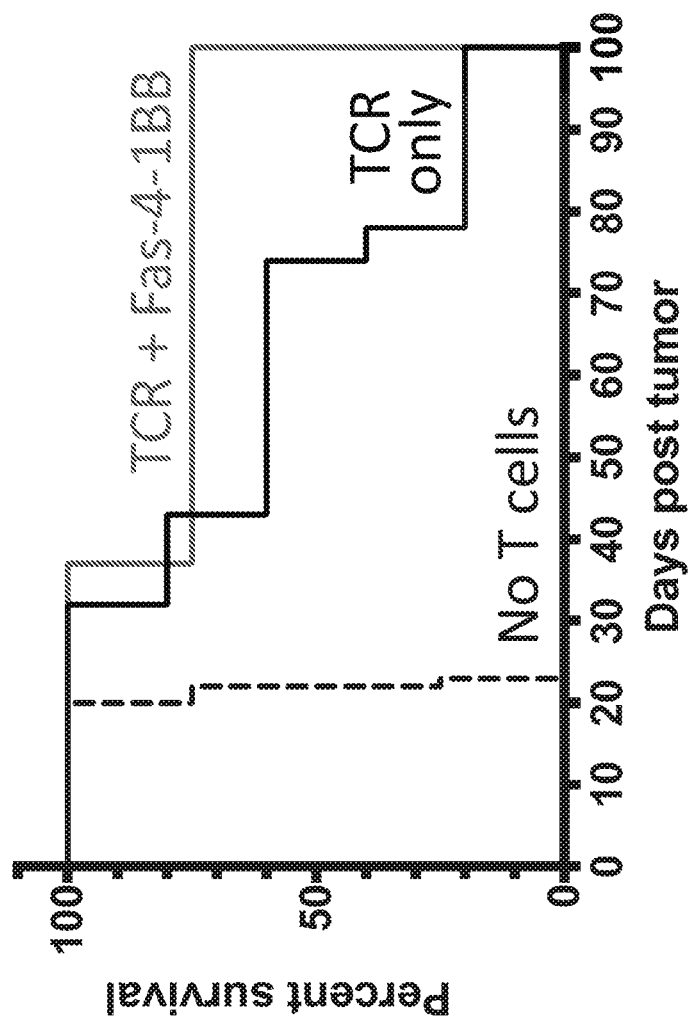

FIG. 26 shows survival of AML model (FBL-injected) mice treated with (i) $TCR_{gag}$ T cells or (ii) with $TCR_{gag}$+Fas-4-1BBtm T cells. Mice were injected with FBL cells. Five days later, mice were treated with cyclophosphamide with or without administration of $10^6$ T cells.

DETAILED DESCRIPTION

The instant disclosure provides fusion proteins that modulate signaling in a host cell, such as an immune cell. For example, fusion proteins of this disclosure can provide an activation or co-stimulatory signal in a human T cell, wherein the T cell may optionally be engineered to have a preferred antigen-specific TCR. These immunomodulatory fusion proteins (IFPs) can interact with ubiquitously expressed targets or with targets that are commonly upregulated or overexpressed in non-normal cells (e.g., a cancer cell). Such IFPs have an extracellular binding domain and an intracellular signaling domain. By transducing T cells with engineered TCRs (e.g., high affinity TCRs) and fusion proteins of this disclosure that generate activation signals, certain embodiments of T cells may no longer require exogenous co-stimulation upon interaction with, for example, a tumor cell.

In certain aspects, the present disclosure provides host cells (e.g., immune cells such as T cells, dendritic cells, NK cells or the like) comprising an IFP, vectors encoding IFPs, and methods of activating T cells comprising an IFP for various therapeutic applications, including the treatment of a disease in subject (e.g., cancer, infectious disease).

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

The term "consisting essentially of" limits the scope of a claim to the specified materials or steps, or to those that do not materially affect the basic characteristics of a claimed invention. For example, a protein domain, region, or module (e.g., a binding domain, hinge region, linker module) or a protein (which may have one or more domains, regions, or modules) "consists essentially of" a particular amino acid sequence when the amino acid sequence of a domain, region, or module or protein includes extensions, deletions, mutations, or any combination thereof (e.g., amino acids at the amino- or carboxy-terminus or between domains) that, in combination, contribute to at most 20% (e.g., at most 15%, 10%, 8%, 6%, 5%, 4%, 3%, 2%, or 1%) of the length of a domain, region, or module or protein and do not substantially affect (i.e., do not reduce the activity by more than 50%, such as no more than 40%, 30%, 25%, 20%, 15%, 10%, 5%, or 1%) the activity of the domain(s), region(s), module(s), or protein (e.g., the target binding affinity of a binding protein).

As used herein, "heterologous" or "non-endogenous" or "exogenous" refers to any gene, protein, compound, molecule, or activity that is not native to a host cell or a subject, or is any gene, protein, compound, molecule, or activity native to a host or host cell that has been altered or mutated such that the structure, activity or both is different as between the native and mutated molecules. In certain embodiments, heterologous, non-endogenous or exogenous molecules (e.g., receptors, ligands) may not be endogenous to a host cell or subject, but instead nucleic acids encoding such molecules may have been added to a host cell by conjugation, transformation, transfection, electroporation, or the like, wherein the added nucleic acid molecule may integrate into a host cell genome or can exist as extra-chromosomal genetic material (e.g., as a plasmid or other self-replicating vector). The term "homologous" or "homolog" refers to a molecule or activity found in or derived from a host cell, species, or strain. For example, a heterologous or exogenous molecule or gene encoding the molecule may be homologous to a native host or host cell molecule or gene that encodes the molecule, respectively, but may have an altered structure, sequence, expression level or combinations thereof. A non-endogenous molecule may be from the same species, a different species, or a combination thereof.

As used herein, the term "endogenous" or "native" refers to a gene, protein, compound, molecule, or activity that is normally present in a host or host cell and has no engineered alterations.

A "binding domain" (also referred to as a "binding region" or "binding moiety"), as used herein, refers to a molecule, such as a peptide, oligopeptide, polypeptide or protein, that possesses the ability to specifically and non-covalently associate, unite, or combine with a target molecule (e.g., CD200, CD47, CD19, CD20, CD22, ROR1, mesothelin, PD-L1, PD-L2, PSMA, WT-1, cyclin-A1). A binding domain includes any naturally occurring, synthetic, semi-synthetic, or recombinantly produced binding partner for a biological molecule or other target of interest or binding protein thereof. In some embodiments, the binding domain is an antigen-binding domain, such as an antibody or T cell receptor (TCR) or functional binding domain or antigen-binding fragment thereof. Exemplary binding domains include receptor ectodomains (e.g., those of CD200R, PD-1, CTLA4, BTLA, CD2, Fas) or binding portions thereof, ligands (e.g., cytokines such as IL35, chemokines) or binding portions thereof, single chain antibody variable regions (e.g., domain antibodies, sFv, scFv, Fab) or binding portions thereof, antigen-binding regions of T cell receptors (TCRs), such as single chain TCRs (scT-CRs), or synthetic polypeptides selected for the specific ability to bind to a biological molecule.

In some embodiments, "specifically binds" refers to an association or union of a binding domain, or a fusion protein thereof, to a target molecule with an affinity or $K_a$ (i.e., an equilibrium association constant of a particular binding interaction with units of 1/M) equal to or greater than $10^5$ $M^{-1}$, or binds to such target molecule while not significantly associating or uniting with any other molecules or components in a sample. Binding domains (or fusion proteins thereof) may be classified as "high affinity" binding domains (or fusion proteins thereof) or "low affinity" binding domains (or fusion proteins thereof). "High affinity" binding domains refer to those binding domains with a $K_a$ of at least $10^7 M^{-1}$, at least $10^8 M^{-1}$, at least $10^9 M^{-1}$, at least $10^{10} M^{-1}$, at least $10^{11} M^{-1}$, at least $10^{12} M^{-1}$, or at least $10^{13} M^{-1}$. "Low affinity" binding domains refer to those binding domains with a $K_a$ of up to $10^7 M^{-1}$, up to $10^6 M^{-1}$, up to $10^5 M^{-1}$. Alternatively, affinity may be defined as an equilibrium dissociation constant ($K_d$) of a particular binding interaction with units of M (e.g., $10^{-5}$ M to $10^{-13}$ M). In certain embodiments, a binding domain may have "enhanced affinity," which refers to a selected or engineered binding domain with stronger binding to a target antigen than a wild type (or parent) binding domain. For example, enhanced affinity may be due to a $K_a$ (equilibrium association constant) for the target antigen that is higher than the wild type binding domain, or due to a $K_d$ (dissociation constant) for the target antigen that is less than that of the wild type binding domain, or due to an off-rate ($K_{off}$) for the target antigen that is less than that of the wild type binding domain. A variety of assays are known for identifying binding domains of the present disclosure that specifically bind a particular target, as well as determining binding domain or fusion protein affinities, such as Western blot, ELISA, and Biacore® analysis (see also, e.g., Scatchard et al., Ann. N.Y. Acad. Sci. 51:660, 1949; and U.S. Pat. Nos. 5,283,173, 5,468,614, or the equivalent).

As used herein, a "fusion protein" refers to a polypeptide that, in a single chain, has at least two distinct domains, wherein the domains are not naturally found together in a protein. A nucleic acid molecule encoding a fusion protein may be constructed using PCR, recombinantly engineered, or the like, or such fusion proteins can be made using methods of protein synthesis. A fusion protein may further contain other components (e.g., covalently bound), such as a tag or bioactive molecule. In certain embodiments, a fusion protein expressed or produced by a host cell (e.g., T cell) locates to the cell surface, where the fusion protein is anchored to the cell membrane with a portion of the fusion protein located extracellularly (e.g., containing a binding domain) and a portion of the fusion protein located intracellularly (e.g., containing a signaling domain).

A "hydrophobic component," as used herein, means any amino acid sequence having a three-dimensional structure that is thermodynamically stable in a cell membrane, and generally ranges in length from about 15 amino acids to about 30 amino acids. The structure of a hydrophobic component may comprise an alpha helix, a beta barrel, a beta sheet, a beta helix, or any combination thereof. In certain embodiments, a hydrophobic component is comprised of a "transmembrane domain" from a known transmembrane protein, which is a portion of a transmembrane protein that can insert into or span a cell membrane. In further embodiments, a hydrophobic component or transmembrane domain can be disposed between and connect the extracellular and intracellular portions of a fusion protein. Additionally, the hydrophobic component may be modified to contain charged regions or hydrophilic residues to facilitate intermolecular interactions.

As used herein, an "intracellular signaling domain" is an intracellular portion of molecule, such as one used in a fusion protein of this disclosure, that can directly or indirectly promote a response such as a co-stimulatory, positive, or activating biological or physiological response in a cell when receiving the appropriate signal. In certain embodiments, an intracellular signaling domain is part of a protein or protein complex that receives a signal when bound, or itself can bind directly to a target molecule to transmit a signal to other components in the cell. An intracellular signaling domain may directly promote a cellular response when it contains one or more signaling domains or motifs, such as an immunoreceptor tyrosine-based activation motif (ITAM), a kinase domain, a co-stimulatory domain, or the like. In other embodiments, an intracellular signaling domain will indirectly promote a cellular response by associating with one or more other proteins that in turn directly promote a cellular response. In some embodiments, an intracellular signaling domain or functional fragment thereof may be from a CD3ε, CD3δ, CD3ζ, CD25, CD27, CD28, CD40, CD47, CD79A, CD79B, CD134 (OX40), CD137 (4-1BB), CD150 (SLAMF1), CD278 (ICOS), CD357 (GITR), CARD11, DAP10, DAP12, FcRα, FcRβ, FcRγ, Fyn, Lck, LAT, LRP, NKG2D, NOTCH1, NOTCH2, NOTCH3, NOTCH4, ROR2, Ryk, Slp76, pTα, TCRα, TCRβ, TRIM, Zap70, PTCH2, or any combination thereof. In some embodiments, an intracellular signaling domain or functional fragment thereof does not comprise a CD3ζ.

A "multimerization domain," as used herein, refers to a polypeptide molecule or region that preferentially interacts or associates with another polypeptide molecule or region, directly or indirectly, wherein the interaction of multimerization domains substantially contribute to or efficiently promote multimerization (i.e., the formation of a dimer, trimer, tetramer, or higher order multimers, which may be a homodimer, heterodimer, homotrimer, heterotrimer, homomultimer, heteromultimer, or the like). For example, multimerization may be due to one or more types of molecular forces, including covalent bonds (e.g., disulfide bonds or bridges), ionic bonds, metallic bonds, electrostatic interactions, salt bridges, dipole-dipole forces, hydrogen bonding, Van der Waals forces, hydrophobic interactions, or any combination thereof. A multimer is stable under appropriate conditions (e.g., physiological conditions, in an aqueous solution suitable for expressing, purifying, or storing recombinant or engineered proteins, or under conditions for non-denaturing or non-reducing electrophoresis). Exemplary multimerization domains may comprise one or more disulfide bonds, zinc finger motif, a leucine zipper motif, helix-turn-helix, helix-loop-helix, or the like.

In certain embodiments, a fusion protein may contain a "linker," which can provide a spacer function to facilitate the interaction of two single chain fusion proteins, or positioning of one or more binding domains, so that the resulting polypeptide structure maintains a specific binding affinity to a target molecule or maintains signaling activity (e.g., effector domain activity) or both. Exemplary linkers include from one to about ten repeats of $Gly_xSer_y$, wherein x and y are independently an integer from 1 to 5.

"Junction amino acids" or "junction amino acid residues" refer to one or more (e.g., about 2-20) amino acid residues between two adjacent motifs, regions, or domains of a fusion protein, such as between a binding domain and an adjacent hydrophobic component, or on one or both ends of a hydrophobic component. Junction amino acids may result from the construct design of a fusion protein (e.g., amino acid residues resulting from the use of a restriction enzyme site during the construction of a nucleic acid molecule encoding a fusion protein). In certain embodiments, junction amino acids form a linker, such as those having from one to about ten repeats of $Gly_xSer_y$, wherein x and y are independently an integer from 1 to 5.

As used herein, an "immune system cell" means any cell of the immune system that originates from a hematopoietic stem cell in the bone marrow, which gives rise to two major lineages, a myeloid progenitor cell (which give rise to myeloid cells such as monocytes, macrophages, dendritic cells, megakaryocytes and granulocytes) and a lymphoid progenitor cell (which give rise to lymphoid cells such as T cells, B cells and natural killer (NK) cells). Exemplary immune system cells include a CD4+ T cell, a CD8+ T cell, a CD4− CD8− double negative T cell, a γδ T cell, a regulatory T cell, a natural killer cell, and a dendritic cell. Macrophages and dendritic cells may be referred to as "antigen presenting cells" or "APCs," which are specialized cells that can activate T cells when a major histocompatibility complex (MHC) receptor on the surface of the APC complexed with a peptide interacts with a TCR on the surface of a T cell.

A "T cell" is an immune system cell that matures in the thymus and produces T cell receptors (TCRs). T cells can be naïve (not exposed to antigen; increased expression of CD62L, CCR7, CD28, CD3, CD127, and CD45RA, and decreased expression of CD45RO as compared to $T_{CM}$), memory T cells ($T_M$) (antigen-experienced and long-lived), and effector cells (antigen-experienced, cytotoxic). $T_M$ can be further divided into subsets of central memory T cells ($T_{CM}$, increased expression of CD62L, CCR7, CD28, CD127, CD45RO, and CD95, and decreased expression of CD54RA as compared to naïve T cells) and effector memory T cells ($T_{EM}$, decreased expression of CD62L, CCR7, CD28, CD45RA, and increased expression of CD127 as compared to naïve T cells or $T_{CM}$). Effector T cells ($T_E$) refers to antigen-experienced CD8+ cytotoxic T lymphocytes that have decreased expression of CD62L, CCR7, CD28, and are positive for granzyme and perforin as compared to $T_{CM}$. Other exemplary T cells include regulatory T cells, such as CD4+CD25+ (Foxp3+) regulatory T cells and Treg17 cells, as well as Tr1, Th3, CD8+CD28−, and Qa-1 restricted T cells.

"T cell receptor" (TCR) refers to a molecule found on the surface of T cells (or T lymphocytes) that, in association with CD3, is generally responsible for recognizing antigens bound to major histocompatibility complex (MHC) molecules. The TCR has a disulfide-linked heterodimer of the highly variable α and β chains (also known as TCRα and TCRβ, respectively) in most T cells. In a small subset of T cells, the TCR is made up of a heterodimer of variable γ and δ chains (also known as TCRγ and TCRδ, respectively). Each chain of the TCR is a member of the immunoglobulin superfamily and possesses one N-terminal immunoglobulin variable domain, one immunoglobulin constant domain, a transmembrane region, and a short cytoplasmic tail at the C-terminal end (see Janeway et al., *Immunobiology: The Immune System in Health and Disease*, $3^{rd}$ Ed., Current Biology Publications, p. 4:33, 1997). TCR, as used in the present disclosure, may be from various animal species, including human, mouse, rat, cat, dog, goat, horse, or other mammals. TCRs may be cell-bound (i.e., have a transmembrane region or domain) or in soluble form.

"Major histocompatibility complex molecules" (MHC molecules), which is used interchangeably and is understood to also refer to the human counterpart human leukocyte antigen (HLA molecules), refer to glycoproteins that deliver peptide antigens to a cell surface. MHC class I molecules are heterodimers consisting of a membrane spanning α chain (with three α domains) and a non-covalently associated β2 microglobulin. MHC class II molecules are composed of two transmembrane glycoproteins, α and β, both of which span the membrane. Each chain has two domains. MHC (HLA) class I molecules deliver peptides originating in the cytosol to the cell surface, where peptide:MHC (or peptide:HLA in humans) complex is recognized by $CD8^+$ T cells. MHC (HLA) class II molecules deliver peptides originating in the vesicular system to the cell surface, where they are recognized by $CD4^+$ T cells. An MHC molecule may be from various animal species, including human, mouse, rat, or other mammals.

"Nucleic acid molecule", or polynucleotide, may be in the form of RNA or DNA, which includes cDNA, genomic DNA, and synthetic DNA. A nucleic acid molecule may be double stranded or single stranded, and if single stranded, may be the coding strand or non-coding (anti-sense strand).

A coding molecule may have a coding sequence identical to a coding sequence known in the art or may have a different coding sequence, which, as the result of the redundancy or degeneracy of the genetic code, or by splicing, can encode the same polypeptide.

Variants of the nucleic acid molecules or polynucleotides of this disclosure are also contemplated. Variant polynucleotides are at least 80%, and preferably at least 85%, 90%, 95%, 99%, or 99.9% identical to one of the polynucleotides of defined sequence as described herein, or that hybridizes to one of those polynucleotides of defined sequence under stringent hybridization conditions of 0.015M sodium chloride, 0.0015M sodium citrate at about 65-68° C. or 0.015M sodium chloride, 0.0015M sodium citrate, and 50% formamide at about 42° C. The polynucleotide variants retain the capacity to encode a binding domain or fusion protein thereof having the functionality described herein.

The term "stringent" is used to refer to conditions that are commonly understood in the art as stringent. Hybridization stringency is principally determined by temperature, ionic strength, and the concentration of denaturing agents such as formamide. Examples of stringent conditions for hybridization and washing are 0.015M sodium chloride, 0.0015M sodium citrate at about 65-68° C. or 0.015M sodium chloride, 0.0015M sodium citrate, and 50% formamide at about 42° C. (see Sambrook et al., *Molecular Cloning: A Laboratory Manual*, 2nd Ed., Cold Spring Harbor Laboratory, Cold Spring Harbor, N.Y., 1989).

More stringent conditions (such as higher temperature, lower ionic strength, higher formamide, or other denaturing agent) may also be used; however, the rate of hybridization will be affected. In instances wherein hybridization of deoxyoligonucleotides is concerned, additional exemplary stringent hybridization conditions include washing in 6×SSC, 0.05% sodium pyrophosphate at 37° C. (for 14-base oligonucleotides), 48° C. (for 17-base oligonucleotides), 55° C. (for 20-base oligonucleotides), and 60° C. (for 23-base oligonucleotides).

A "vector" is a nucleic acid molecule that is capable of transporting another nucleic acid. Vectors may be, for example, plasmids, cosmids, viruses, or phage. An "expression vector" is a vector that is capable of directing the expression of a protein encoded by one or more genes carried by the vector when it is present in the appropriate environment.

"Retroviruses" are viruses having an RNA genome. "Gammaretrovirus" refers to a genus of the retroviridae family. Exemplary gammaretroviruses include mouse stem cell virus, murine leukemia virus, feline leukemia virus, feline sarcoma virus, and avian reticuloendotheliosis viruses.

"Lentivirus" refers to a genus of retroviruses that are capable of infecting dividing and non-dividing cells. Several examples of lentiviruses include HIV (human immunodeficiency virus: including HIV type 1, and HIV type 2); equine infectious anemia virus; feline immunodeficiency virus (FIV); bovine immune deficiency virus (BIV); and simian immunodeficiency virus (SIV).

The terms "identical" or "percent identity," in the context of two or more polypeptide or nucleic acid molecule sequences, means two or more sequences or subsequences that are the same or have a specified percentage of amino acid residues or nucleotides that are the same over a specified region (e.g., 60%, 65%, 70%, 75%, 80%, 85%, 90%, 91%, 92%, 93%, 94%, 95%, 96%, 97%, 98%, 99%, or 100% identity), when compared and aligned for maximum correspondence over a comparison window, or designated region, as measured using methods known in the art, such as a sequence comparison algorithm, by manual alignment, or by visual inspection. For example, preferred algorithms suitable for determining percent sequence identity and sequence similarity are the BLAST and BLAST 2.0 algorithms, which are described in Altschul et al. (1977) Nucleic Acids Res. 25:3389 and Altschul et al. (1990) J. Mol. Biol. 215:403, respectively.

"Treat" or "treatment" or "ameliorate" refers to medical management of a disease, disorder, or condition of a subject (e.g., a human or non-human mammal, such as a primate, horse, dog, mouse, or rat). In general, an appropriate dose or treatment regimen comprising a host cell expressing a fusion protein of this disclosure, and optionally an adjuvant or adjunctive therapy, is administered in an amount sufficient to elicit a therapeutic or prophylactic benefit. Therapeutic or prophylactic/preventive benefit includes improved clinical outcome; lessening or alleviation of symptoms associated with a disease; decreased occurrence of symptoms; improved quality of life; longer disease-free status; diminishment of extent of disease, stabilization of disease state; delay of disease progression; remission; survival; prolonged survival; or any combination thereof.

A "therapeutically effective amount" or "effective amount" of a fusion protein or cell expressing a fusion protein of this disclosure (e.g., CD200R-CD28, SIRPα-CD28, CD200R-41BB, SIRPα-41BB, CD200R-CD28-41BB, SIRPα-CD28-4-1BB or other such fusion proteins), in the context of a disease or condition being treated, refers to that amount of fusion protein or number of cells sufficient to result in amelioration of one or more symptoms of the disease being treated in a statistically significant manner (e.g., reducing infection, reducing tumor size, inhibiting cancer growth or the like).

Immunomodulatory Fusion Proteins (IFPs)

In certain aspects, the present disclosure provides a fusion protein, comprising an extracellular component, a hydrophobic component, and an intracellular component. In some embodiments, the extracellular component includes a binding domain such as one that specifically binds to a target. In some embodiments, the binding domain is from a molecule that ordinarily, e.g., in its natural setting, is capable of delivering a negative or inhibitory signal when bound to its binding partner or ligand or receptor, such as an immunoinhibitory receptor or checkpoint molecule, or the target is an inhibitory receptor or ligand or checkpoint molecule or other inhibitory ligand. In some embodiments, the intracellular component includes a signaling domain, such as a costimulatory signaling domain or signaling region of a molecule generally capable of delivering a costimulatory or positive signal, e.g., to an immune cell. Thus, in some aspects, the fusion proteins are capable of delivering a positive or costimulatory signal in response to a binding event that in a natural setting would result in an inhibitory signal.

In some embodiments, the fusion protein is such that a particular distance is achieved. For example, in some embodiments, a fusion protein::target complex (such as one comprised of an extracellular portion of a complex formed between the fusion protein and the target by specific binding thereto) is of a particular length or spans a particular distance, such as a distance of up to a distance between membranes in an immunological synapse, or that spanned by the extracellular portion of a cognate complex between a TCR and MHC molecule, e.g., following specific recognition thereof by a TCR, or the distance spanned by the extracellular portion of a complex formed between the natural molecule and its natural binding partner. In some embodiments, the distance or length is sufficient to promote the colocalization of a fusion protein with antigen receptor or other signaling molecule when expressed in an immune cell, such as a T cell, or entry into an immunologic synapse.

By way of background, an immunological synapse is an interface between cells, which can form between a variety of cells, such as between immune cells (Rossy et al., *Frontiers in Immunol.* 3: 1-12, 2012; Hatherley et al., *Structure* 21:820, 2013). For example, in the case of a T cell contacting an antigen-presenting cell (APC), an immunological synapse can be formed by the binding of a TCR (found on the surface of a T cell) with an HLA-peptide (MHC-peptide for non-human) complex (found on the surface of, for example, APCs; HLA class I molecules can be found on the surface of all nucleated cells, while HLA class II can conditionally be expressed on all cell types but are regularly found on APCs). In addition, an immunological synapse may be organized into supramolecular activation clusters (SMACs), which can affect lymphocyte activation, direct antigen-HLA (or antigen-MHC) complex presentation to lymphocytes, and direct secretion of cytokines or lytic granules between cells. A SMAC can be comprised of three structures arranged in concentric circles: a central region (cSMAC) containing a high number of TCRs as well as co-stimulatory and inhibitory molecules, a peripheral region (pSMAC) where LFA-1 and talins are clustered, and a distal region (dSMAC) that is enriched for CD43 and CD45 molecules. In certain embodiments, an immunological synapse will span from about 10 nm to about 15 nm. For example, protein interactions found within the immunological synapse, such as the TCR::HLA-peptide interaction or a fusion protein-target interaction, generally span about 14 nm between membranes. In certain embodiments, the width of a SMAC in an immunological synapse does not exceed 15 nm.

In some embodiments, the extracellular span of a fusion protein::target complex is such that it can localize to a particular compartment of an immunological synapse. Some complexes thought to localize to various compartments of the immunological synapse are well-characterized with regard to the length of their extracellular span. For example, the MHC-TCR complex is thought to have an extracellular span of approximately 10-15 nm and more integrin-based complexes are thought to have extracellular spans on the order of approximately 40 nm (Alakoskela et al., *Biophys J* 100:2865, 2011). Additional exemplary complexes include the CD2-CD48 complex, which is thought to have an extracellular span of approximately 12.8 nm (Milstein et al., *J Biol Chem* 283:34414, 2008). Additionally, exemplary ligand-binding molecules thought to localize to the cSMAC include the TCR and MHC complexes, CD2, CD4, CD8, CD28, and ligands thereof (Dustin et al., *CSH Perspectives in Biology* 2:a002311, 2010); thus, it is contemplated that these molecules complexed with their natural ligands are of an appropriate size to localize to the cSMAC.

In some aspects, the length or distance or approximate length or distance of a particular construct or engineered extracellular portion thereof such as an extracellular portion of a fusion protein, or complex of any of the foregoing such as with a binding partner thereof, may be determined or modeled by known methods. In some exemplary models, a protein's tertiary structure, binding domains, and other characteristics may be approximated using an input amino acid or nucleic acid sequence. The tertiary structure of a protein may be used to approximate extracellular portion size, flexibility, and other characteristics useful for determining the approximate length of the extracellular portion of the protein or complex thereof. In general, methods for modeling or approximating the length of the extracellular portion of a protein are known. For example, molbiol-tools.ca and Swiss-Model contain multiple tools useful for predicting protein structure (see also Schwede, T., *Structure* 21:1531, 2013).

In certain embodiments, a fusion protein of this disclosure complexed, associated or interacting with a target is capable of residing within an immunological synapse. In some embodiments, the extracellular portion of a fusion protein:: target complex spans an immunological synapse. In other embodiments, a fusion protein::target complex is localized in a supramolecular activation cluster (SMAC), such as a cSMAC. In further embodiments, the extracellular portion of a fusion protein::target complex spans an immunological synapse defined by the extracellular portion of a TCR::HLA-peptide interaction. In still further embodiments, the length of the extracellular portion of a fusion protein::target complex is about 12 nm to about 15 nm, or is about 14 nm.

The distance between the cell membranes of cells interacting in an immunological synapse may be measured by any method known in the art. For example, in particular embodiments, the distance may be measured by a subdiffraction-resolution method or electron microscopy (James and Vale, *Nature* 487:64-69, 2012).

In particular embodiments, a fusion protein as disclosed herein comprises an extracellular portion that extends less than 40 nm from the cell membrane. In some embodiments, a fusion protein as disclosed herein comprises an extracellular portion that extends less than 30 nm from the cell membrane. In some embodiments, a fusion protein as disclosed herein comprises an extracellular portion that extends less than 20 nm from the cell membrane. In some embodiments, a fusion protein as disclosed herein comprises an extracellular portion that extends less than 15 nm from the cell membrane.

In some embodiments, the provided fusion proteins provide the advantage of having an extracellular length or spatial distance as compared to the distance between cell membrane(s) that allows for entry into a synapse or co-localization with antigen receptor, or that mimic a distance or length present in the natural proteins. In some embodiments, where the extracellular portion of the fusion protein includes domain(s) from an additional molecule, which is from a different molecule from which a binding domain is obtained, the length of the extracellular component containing the binding domain is reduced, e.g., truncated, as compared to the extracellular region of the natural molecule, to provide for such similar length or distance. In some embodiments, a fusion protein as described herein comprises an extracellular component comprising an extracellular domain of a cell-surface receptor and a second domain (e.g., a linker or an extracellular domain of a second cell-surface receptor). In some such embodiments, to maintain an extracellular component capable of residing within an immunological synapse or spanning an immunological synapse when complexed with a target molecule, one or more domains of the extracellular component may be truncated.

In some diseases (e.g., cancer), the amplitude and quality of a T cell response resulting from antigen recognition by a T cell receptor (TCR) can be dysregulated (e.g., reduced) due to an imbalance between co-stimulatory and inhibitory signals, which can result in immune resistance. One advantage of certain fusion proteins of the instant disclosure is that a first signal can be converted into a qualitatively different second signal. For example, in some embodiments, the fusion proteins are such that a negative or inhibitory signal can effectively be converted into a positive or co-stimulatory signal to thereby relieve or minimize immune resistance associated with a disease, such as cancer. For example, upon binding to a target that, if bound by its natural binding partner, would result in inhibition or delivery of a negative signal, a fusion protein as provided herein, in some embodiments, is capable of instead delivering a positive, e.g., costimulatory signal, to a cell in which it is expressed, such as in a T cell. In certain embodiments, a fusion protein of this disclosure comprises an extracellular component associated with a negative signal and an intracellular component associated with a positive signal. An exemplary receptor found on the surface of T cells, cytotoxic T-lymphocyte-associated antigen 4 (CTLA4 or CD152), can receive an inhibitory signal when bound by one of its ligands, CD80 or CD86, found on APCs. CTLA4 regulates the amplitude of early stage T cell activation by counteracting the T cell co-stimulatory receptor CD28 (see Rudd et al., *Immunol. Rev.* 229:12, 2009). Another exemplary receptor found on the surface of T cells, programmed cell death protein 1 (PD-1 or CD279), can receive an inhibitory signal when bound by one of its ligands, PD-L1 (B7-H1, CD274) or PD-L2 (B7-DC, CD73), found on APCs. PD-1 limits the activity of T cells in peripheral tissues during inflammation and to minimize autoimmunity (see Keir et al., *Annu. Rev. Immunol.* 26:677, 2008). Representative fusion proteins of this disclosure comprising an extracellular component associated with a negative signal (e.g., CTLA4 or PD-1) and an intracellular component associated with a positive signal (e.g., CD28, CD137) include a CTLA4-CD28 fusion protein, a CTLA4-CD137 fusion protein, a CTLA4-CD28-CD137 fusion protein, a PD1-CD28 fusion protein, a PD1-CD137 fusion protein, or a PD1-CD28-CD137 fusion protein.

Fusion proteins of the instant disclosure may block or reduce the number of inhibitory signals received by an immune cell. For example, in some embodiments, a fusion protein as disclosed herein converts an inhibitory signal into a positive signal, thereby reducing the total number of inhibitory signals received by an immune cell or converting an ordinarily negative or inhibitory signal to a positive one. In other embodiments, a fusion protein as disclosed herein blocks the signaling of a wild-type receptor. For example, dominant negative fusion proteins are included within the scope of the disclosure. In some embodiments, a fusion protein as disclosed herein binds to a wild-type receptor and blocks signaling of the wild-type receptor by forming an oligomer with the wild-type receptor.

Yet another advantage of certain fusion proteins of the instant disclosure is that more than one such fusion protein may be expressed by a cell, providing multiple stimulatory signals. It has been observed that recombinant TCRs possessing multiple co-stimulatory domains may not produce adequate co-stimulatory signaling. Co-expressing multiple immunomodulatory fusion proteins, especially those capable of residing within an immunological synapse, may provide the co-stimulatory signaling necessary for T cells to avoid anergy and proliferate.

In some embodiments, a fusion protein of the instant disclosure operates in trans relative to a TCR or chimeric antigen receptor (CAR) or other antigen receptor. In some embodiments, a fusion protein as disclosed herein operates outside of the immunological synapse.

In yet another aspect, a fusion protein of the instant disclosure allows for enrichment of transduced T cells by restimulation with tumor cells expressing a ligand that binds to the fusion protein, without the need for sorting.

In one exemplary embodiment, a fusion protein comprising (a) an extracellular portion of a CD200R, (b) a transmembrane domain of a CD28, and (c) an intracellular signaling domain of a CD28 is provided. In some embodiments, the extracellular portion further comprises an extracellular portion of a CD28 extending from the CD28 transmembrane domain. In further embodiments, the extracellular portion of the CD200R comprises at least about 231 amino acids from the N-terminus of CD200R. In still further embodiments, the fusion protein further comprises an intracellular signaling domain of a CD137 (4-1BB).

In another exemplary embodiment, the present disclosure provides a fusion protein comprising (a) an extracellular portion of a SIRPα, (b) a transmembrane domain of a CD28, and (c) an intracellular signaling domain of a CD28. In some embodiments, the fusion protein further comprises an extracellular portion of a CD28 extending from the CD28 transmembrane domain. In further embodiments, the extracellular portion of the SIRPα comprises at least about 361 amino acids from the N-terminus of SIRPα. In still further embodiments, the fusion protein further comprises an intracellular signaling domain of a CD137 (4-1BB).

In another exemplary embodiment, the present disclosure provides a fusion protein comprising (a) an extracellular portion of a CD95 (Fas), (b) a transmembrane domain of a CD137 (4-1BB), and (c) an intracellular signaling domain of a CD137 (4-1BB).

In another exemplary embodiment, the present disclosure provides a fusion protein comprising (a) an extracellular portion of a CD95 (Fas), (b) a transmembrane domain of a CD28, and (c) an intracellular signaling domain of a CD137 (4-1BB). In some embodiments, the fusion protein further comprises an extracellular portion of a CD28 extending from the CD28 transmembrane domain.

In another exemplary embodiment, the present disclosure provides a fusion protein, comprising (a) an extracellular component comprised of a binding domain that specifically binds a target, (b) an intracellular component comprised of an intracellular signaling domain, and (c) a hydrophobic component connecting the extracellular and intracellular components, wherein the extracellular portion of a complex formed by specific binding of the fusion protein to the target (fusion protein::target complex) is of a size, or spans a distance, of (i) up to about a distance between two cell membranes of an immunological synapse, (ii) up to about or substantially the same as a distance spanned by the extracellular portion of a complex between a T cell receptor (TCR) and an MHC-peptide complex specifically bound by the TCR, (iii) up to about or substantially the same as a distance spanned by the extracellular portion of a complex between a natural molecule comprising the binding domain and its cognate binding partner; (iii) less than or up to about 40 nm, 25 nm, 20 nm, 15 nm, or 14 nm; or (iv) any combination thereof; and wherein the extracellular component is or comprises a CD95 (Fas) ectodomain or a functional fragment thereof, and the intracellular component is or comprises a CD137 (4-1BB) intracellular signaling domain or a functional portion thereof.

In another exemplary embodiment, the present disclosure provides a fusion protein comprising (a) an extracellular component comprised of a binding domain that specifically binds a target, (b) an intracellular component comprised of an intracellular signaling domain, and (c) a hydrophobic component connecting the extracellular and intracellular components, wherein the binding domain is, or has at least 95% identity to, an inhibitory molecule binding domain and the intracellular signaling domain is, or contains at least 95% identity to, a costimulatory or stimulatory molecule binding domain, and wherein the inhibitory molecule is or comprises a CD95 (Fas) ectodomain or a functional fragment thereof, and the costimulatory or stimulatory molecule is or comprises an intracellular signaling domain or a functional portion thereof from CD137 (4-1BB).

In another exemplary embodiment, the present disclosure provides a fusion protein comprising: (a) an extracellular component comprising an amino acid sequence encoded by a nucleic acid molecule as set forth in SEQ ID NO.:71, (b) a hydrophobic component comprising an amino acid sequence encoded by a nucleic acid molecule as set forth in SEQ ID NO.:197, and (c) an intracellular component comprising an amino acid sequence encoded by a nucleic acid molecule as set forth in SEQ ID NO.:13.

In another exemplary embodiment, the present disclosure provides a fusion protein comprising: (a) an extracellular component comprising a binding domain with an amino acid sequence as set forth in SEQ ID NO.:72; (b) a hydrophobic component comprising an amino acid sequence as set forth in SEQ ID NO.:198; and (c) an intracellular component comprising an amino acid sequence as set forth in SEQ ID NO.:36.

Component parts of the fusion proteins of the present disclosure are further described in detail herein.

Extracellular Component

As described herein, a fusion protein of the present disclosure generally comprises an extracellular component comprising a binding domain that specifically binds a target. Binding of a target by the fusion protein binding domain may (1) block the interaction of target with another molecule (e.g., block or interfere with a receptor-ligand interaction), (2) interfere, reduce or eliminate certain functions of the target (e.g., inhibitory signal transduction), (3) induce certain biological pathways not normally induced when the target is bound (e.g., converting an inhibitory or negative signal into a stimulatory or positive signal), such as in a cell in which the fusion protein is expressed, or any combination thereof. In some embodiments, the fusion proteins as described herein comprise an extracellular portion, wherein the extracellular portion comprises an extracellular portion of protein associated with a negative signal.

Exemplary binding domains of this disclosure may be ectodomains of cell-surface receptors, or binding portions thereof, ectodomains of cell-surface ligands, cytokines (e.g., IL35), chemokines, antibody-based binding domains, TCR-based binding domains, non-conventional binding domains, or any combination thereof. For example, binding domains comprising an ectodomain of CD200R, SIRPα, CD279 (PD-1), CD2, CD95 (Fas), CTLA4 (CD152), CD223 (LAG3), CD272 (BTLA), A2aR, KIR, TIM3, CD300, or LPA5 are within the scope of this disclosure. As used herein, an "ectodomain" from a cell-surface receptor or ligand includes a complete extracellular domain or a functional (binding) fragment thereof. In certain embodiments, an ectodomain comprises a mutated extracellular domain or a functional (binding) fragment thereof that has a higher avidity for target as compared to a wild-type or reference protein. In certain embodiments, an ectodomain comprises a variable-like domain or a CDR of a variable-like domain.

In some embodiments, a fusion protein contains an extracellular component comprising a CD200-binding domain, such as a CD200R ectodomain or CD200-binding portion thereof. By way of background, CD200R is a receptor that binds to CD200, a type-1 membrane protein of the immunoglobulin superfamily (Tonks et al., *Leukemia* 21:566-568, 2007). CD200 has been reported to be upregulated on various malignancies, including leukemias, multiple myeloma, and various solid tumors (e.g., melanoma, breast, and squamous cell carcinoma). In fact, high levels of CD200 expression have been linked with poor prognosis for acute myeloid leukemia (AML), and CD200R signaling has been shown to have an inhibitory effect on T cells (Coles et al., *Leukemia* 26: 2148-2151, 2012). In certain embodiments, a CD200R ectodomain includes a full length extracellular portion of a CD200R protein, a full length mature extracellular portion of a CD200R protein, a binding fragment of an extracellular portion of a CD200R protein, or a binding fragment of an extracellular portion of a CD200R protein along with a portion of the transmembrane domain of CD200R, or any combination thereof.

In further embodiments, a CD200R is encoded by a nucleic acid molecule as set forth in SEQ ID NO.:2. In certain other embodiments, a CD200R ectodomain comprises at least 200 amino acids from the N-terminus of CD200R. In some other embodiments, a CD200R is encoded by a nucleic acid molecule as set forth in SEQ ID NO.:11. In yet other embodiments, an extracellular portion of the CD200R comprises at least 180, 190, 200, 210, 220, 230, 231, 234, or 243 amino acids from the N-terminus of CD200R. For example, in certain embodiments, a CD200R is encoded by the nucleic acid molecule as set forth in SEQ ID NO.:8. In any of the aforementioned embodiments, a CD200R, a CD200R ectodomain, or any CD200R fragment thereof used in a fusion protein of this disclosure is a human CD200R. In further embodiments, there are provided CD200R ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence encoded by a nucleic acid molecule as set forth in SEQ ID NO.:2.

In some embodiments, a CD200R comprises an amino acid sequence as set forth in SEQ ID NO.:25. In some embodiments, a CD200R comprises an amino acid sequence as set forth in SEQ ID NO.:34. In certain embodiments, a CD200R comprises an amino acid sequence as set forth in SEQ ID NO.:31. In any of the aforementioned embodiments, a CD200R, a CD200R ectodomain, or any CD200R fragment thereof used in a fusion protein of this disclosure is a human CD200R. In further embodiments, there are provided CD200R ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence as set forth in SEQ ID NO.:25.

In some embodiments, a fusion protein contains an extracellular component comprising a CD47-binding domain such as a SIRPα ectodomain or binding portion thereof. By way of background, CD47 is a widely expressed transmembrane protein that plays a role in protecting cells from phagocytosis (Willingham et al., *PNAS* 109: 6662-6667, 2012). Binding of CD47 to SIRPα initiates SIRPα signaling, which inhibits phagocytosis by macrophages. Accordingly, downregulation of SIRPα will result in increased phagocytosis by macrophages. SIRPα is expressed on multiple human tumor types including AML, chronic myelogenous leukemia (CML), acute lymphoblastic leukemia (ALL), Non-Hodgkin lymphoma (NHL), multiple myeloma (MM), lung, bladder, and other solid tumors. In certain embodiments, a SIRPα ectodomain includes a full length extracellular portion of a SIRPα protein, a full length mature extracellular portion of a SIRPα protein, a binding fragment of an extracellular portion of a SIRPα protein, and a binding fragment of an extracellular portion of a SIRPα protein along with a portion of the transmembrane domain of SIRPα, or any combination thereof.

In further embodiments, a SIRPα ectodomain or binding portion thereof is encoded by a nucleic acid molecule as set forth in SEQ ID NO.:17. In certain embodiments, a SIRPα ectodomain comprises at least 300, 310, 320, 330, 340, 350, 360, 361, 370, 373, or more amino acids from the N-terminus of SIRPα. In some other embodiments, a SIRPα is encoded by a nucleic acid molecule as set forth in SEQ ID NO.:21. In any of the aforementioned embodiments, a SIRPα, a SIRPα ectodomain, or any SIRPα fragment thereof used in a fusion protein of this disclosure is a human SIRPα. In further embodiments, there are provided SIRPα ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence encoded by a nucleic acid molecule as set forth in SEQ ID NO.:17.

In further embodiments, a SIRPα ectodomain comprises an amino acid sequence as set forth in SEQ ID NO.:40. In some embodiments, a SIRPα comprises an amino acid sequence as set forth in SEQ ID NO.:44. In any of the aforementioned embodiments, a SIRPα, a SIRPα ectodomain, or any SIRPα fragment thereof used in a fusion protein of this disclosure is a human SIRPα. In further embodiments, there are provided SIRPα ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence as set forth in SEQ ID NO.:40.

In some embodiments, a fusion protein contains an extracellular component comprising a binding domain that binds to PD-L1, PD-L2, or both. In some embodiments, a fusion protein contains an extracellular component comprising a PD-1 ectodomain or ligand-binding portion thereof. In certain embodiments, a PD-1 ectodomain includes a full length extracellular portion of a PD-1 protein, a full length mature extracellular portion of a PD-1 protein, a binding fragment of an extracellular portion of a PD-1 protein, or a binding fragment of an extracellular portion of a PD-1 protein along with a portion of the transmembrane domain of PD-1, or any combination thereof. In certain embodiments, a PD-1 ectodomain comprises at least 80, 90, 100, 110, 120, 125, 130, 132, 135, 137, 140, 149, 150, 155, 158, 160, or 170 amino acids from the N-terminus of PD-1. For example, in certain embodiments, a PD-1 ectodomain is encoded by the nucleic acid molecule as set forth in SEQ ID NO.:91, 93, or 95. In further embodiments, a PD-1 ectodomain comprises at least from about 90 amino acids to at least about 130 amino acids from a PD-1 as set forth in SEQ ID NO.:60. In still further embodiments, a PD-1 ectodomain comprises 170 amino acids from the N-terminus of a PD-1 ectodomain, as set forth in SEQ ID NO.:90. In some embodiments, a PD-1 is encoded by a nucleic acid molecule as set forth in SEQ ID NO.:89. In any of the aforementioned embodiments, a PD-1, a PD-1 ectodomain, or any PD-1 fragment thereof used in a fusion protein of this disclosure is a human PD-1. In further embodiments, there are provided PD-1 ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence as set forth in SEQ ID NO.:60. In further embodiments, there are provided PD-1 ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence as set forth in SEQ ID NO.:90. In still further embodiments, there are provided PD-1 binding domains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence encoded by a nucleic acid molecule as set forth in SEQ ID NO.:89.

In certain embodiments, a PD-1 ectodomain comprises the amino acid sequence as set forth in SEQ ID NO.:92, 94, or 96. In further embodiments, there are provided PD-1 ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence as set forth in SEQ ID NO.: 92, 94, or 96. In any of the aforementioned embodiments, a PD-1, a PD-1 ectodomain, or any PD-1 fragment thereof used in a fusion protein of this disclosure is a human PD-1.

In some embodiments, a fusion protein contains an extracellular component comprising a CD2 ectodomain. In certain embodiments, a CD2 ectodomain is encoded by a nucleic acid molecule as set forth in SEQ ID NO.:61. In certain embodiments, a CD2 ectodomain includes a full length extracellular portion of a CD2 protein, a full length mature extracellular portion of a CD2 protein, a binding fragment of an extracellular portion of a CD2 protein, or a binding fragment of an extracellular portion of a CD2 protein along with a portion of the transmembrane domain of CD2, or any combination thereof. In any of the aforementioned embodiments, a CD2, a CD2 ectodomain, or any CD2 fragment thereof used in a fusion protein of this disclosure is a human CD2. In further embodiments, there are provided CD2 ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence encoded by a nucleic acid molecule as set forth in GenBank Accession No. NM 001767.3. In further embodiments, there are provided CD2 ectodomains s that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence encoded by a nucleic acid molecule as set forth in SEQ ID NO.:61.

In some embodiments, a CD2 ectodomain comprises an amino acid sequence as set forth in SEQ ID NO.:62. In further embodiments, there are provided CD2 ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence as set forth in SEQ ID NO.:62. In any of the aforementioned embodiments, a CD2, a CD2 ectodomain, or any CD2 fragment thereof used in a fusion protein of this disclosure is a human CD2.

In some embodiments, a fusion protein contains an extracellular component comprising a binding domain that binds to FasL. In some embodiments, a fusion protein contains an extracellular component comprising a Fas (CD95) ectodomain. Fas is expressed on tumor-associated vasculature and prevents CD8 cell infiltration by inducing cell death. FasL is expressed in AML, pancreatic, ovarian, and other cancers (Kornmann et al., *Annals of Surgery* 231: 368-379, 2000; Contini et al., *Leukemia* 21: 253-260, 2007; Motz et al., *Nature Medicine* 20: 607-615, 2014). Additionally, many chemotherapeutics have been reported to cause upregulation of FasL on tumors, and FasL can also be upregulated on T cells in response to CD44 engagement. In certain embodiments, a Fas ectodomain includes a full length extracellular portion of a Fas protein, a full length mature extracellular portion of a Fas protein, a binding fragment of an extracellular portion of a Fas protein, and a binding fragment of an extracellular portion of a Fas protein along with a portion of the transmembrane domain of Fas, or any combination thereof. In some embodiments, a Fas ectodomain is encoded by a nucleic acid molecule as set forth in SEQ ID NO.:71. In yet other embodiments, a Fas ectodomain comprises at least 150, 160, 161, 166, 170, or 173 amino acids from the N-terminus of Fas. For example, in certain embodiments, a Fas is encoded by the nucleic acid molecule as set forth in SEQ ID NO.:73. In certain other embodiments, a Fas is encoded by the nucleic acid molecule as set forth in SEQ ID NO.:75. In any of the aforementioned embodiments, a Fas, a Fas ectodomain, or any Fas fragment thereof used in a fusion protein of this disclosure is a human Fas. In further embodiments, there are provided Fas ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence encoded by a nucleic acid molecule as set forth in GenBank Accession No. NM 000043.4. In still further embodiments, there are provided Fas ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence encoded by a nucleic acid molecule as set forth in SEQ ID NO.:71.

In some embodiments, a Fas ectodomain comprises an amino acid sequence as set forth in SEQ ID NO.:72. In certain embodiments, a Fas ectodomain comprises the amino acid sequence as set forth in SEQ ID NO.:74. In certain other embodiments, a Fas ectodomain comprises the amino acid sequence as set forth in SEQ ID NO.:76. In any of the aforementioned embodiments, a Fas, a Fas ectodomain, or any Fas fragment thereof used in a fusion protein of this disclosure is a human Fas. In further embodiments, there are provided Fas ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence as set forth in SEQ ID NO.:72.

In some embodiments, a fusion protein contains an extracellular component comprising a LAG3 (CD223) ectodomain. In certain embodiments, a LAG3 ectodomain includes a full length extracellular portion of a LAG3 protein, a full length mature extracellular portion of a LAG3 protein, a binding fragment of an extracellular portion of a LAG3 protein, and a binding fragment of an extracellular portion of a LAG3 protein along with a portion of the transmembrane domain of LAG3, or any combination thereof. For example, in some embodiments, a LAG3 ectodomain comprises about 420, 416, 415, 413, or 410 amino acids from the N terminus of LAG3. In any of the aforementioned embodiments, a LAG3, a LAG3 ectodomain, or any LAG3 fragment thereof used in a fusion protein of this disclosure is a human LAG3. In further embodiments, there are provided LAG3 ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence encoded by a nucleic acid molecule as set forth in GenBank Accession No. NM_002286.5.

In further embodiments, a LAG3 is encoded by a nucleic acid molecule as set forth in SEQ ID NO.:153. In certain other embodiments, a LAG3 ectodomain comprises at least 430, 435, 438, 440, 445, or 450 amino acids from the N-terminus of LAG3. For example, in certain embodiments, a LAG3 is encoded by the nucleic acid molecule as set forth in SEQ ID NO.:161. In any of the aforementioned embodiments, a LAG3, LAG3 ectodomain, or any LAG3 fragment thereof used in a fusion protein of this disclosure is a human LAG3. In further embodiments, there are provided LAG3 ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence encoded by a nucleic acid molecule as set forth in SEQ ID NO.:153.

In some embodiments, a LAG3 comprises an amino acid sequence as set forth in SEQ ID NO.:154. In some embodiments, a LAG3 comprises an amino acid sequence as set forth in SEQ ID NO.:162. In any of the aforementioned embodiments, a LAG3, a LAG3 ectodomain, or any LAG3 fragment thereof used in a fusion protein of this disclosure is a human LAG3. In further embodiments, there are provided LAG3 ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence as set forth in SEQ ID NO.:154.

In some embodiments, a fusion protein contains an extracellular component comprising a TIM3 ectodomain. In certain embodiments, a TIM3 ectodomain includes a full length extracellular portion of a TIM3 protein, a full length mature extracellular portion of a TIM3 protein, a binding fragment of an extracellular portion of a TIM3 protein, and a binding fragment of an extracellular portion of a TIM3 protein along with a portion of the transmembrane domain of TIM3, or any combination thereof. In any of the aforementioned embodiments, a TIM3, a TIM3 ectodomain, or any TIM3 fragment thereof used in a fusion protein of this disclosure is a human TIM3. In further embodiments, there are provided TIM3 ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence encoded by a nucleic acid molecule as set forth in GenBank Accession No. NM 032782.4.

In further embodiments, a TIM3 is encoded by a nucleic acid molecule as set forth in SEQ ID NO.:167. In certain other embodiments, a TIM3 ectodomain comprises at least 180, 185, 190, 195, or 200 amino acids from the N-terminus of TIM3. For example, in certain embodiments, a TIM3 is encoded by the nucleic acid molecule as set forth in SEQ ID NO.:177. In any of the aforementioned embodiments, a TIM3, TIM3 ectodomain, or any TIM3 fragment thereof used in a fusion protein of this disclosure is a human TIM3. In further embodiments, there are provided TIM3 ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence encoded by a nucleic acid molecule as set forth in SEQ ID NO.:167.

In some embodiments, a TIM3 comprises an amino acid sequence as set forth in SEQ ID NO.:168. In some embodiments, a TIM3 comprises an amino acid sequence as set forth in SEQ ID NO.:178. In any of the aforementioned embodiments, a TIM3, a TIM3 ectodomain, or any TIM3 fragment thereof used in a fusion protein of this disclosure is a human TIM3. In further embodiments, there are provided TIM3 ectodomains that have a sequence that is at least 80%, at least 85%, at least 90%, at least 91%, at least 92%, at least 93%, at least 94%, at least 95%, at least 96%, at least 97%, at least 98%, at least 99%, at least 99.5%, or at least 100% identical to an ectodomain of a molecule having an amino acid sequence as set forth in SEQ ID NO.:168.

A binding domain may be any peptide that specifically binds a target of interest. Sources of binding domains include antibody variable regions from various species (which can be in the form of antibodies, sFvs, scFvs, Fabs, scFv-based grababody, or soluble VH domain or domain antibodies), including human, rodent, avian, or ovine. Additional sources of binding domains include variable regions of antibodies from other species, such as camelid (from camels, dromedaries, or llamas; Ghahroudi et al., FEBS Lett. 414:521, 1997; Vincke et al., J. Biol. Chem. 284:3273, 2009; Hamers-Casterman et al., Nature 363:446, 1993 and Nguyen et al., J. Mol. Biol. 275:413, 1998), nurse sharks (Roux et al., Proc. Nat'l. Acad. Sci. (USA) 95:11804, 1998), spotted raffish (Nguyen et al., Immunogen. 54:39, 2002), or lamprey (Herrin et al., Proc. Nat'l. Acad. Sci. (USA) 105:2040, 2008 and Alder et al. Nat. Immunol. 9:319, 2008). These antibodies can form antigen-binding regions using only a heavy chain variable region, i.e., these functional antibodies are homodimers of heavy chains only (referred to as "heavy chain antibodies") (Jespers et al., Nat. Biotechnol. 22:1161, 2004; Cortez-Retamozo et al., Cancer Res. 64:2853, 2004; Baral et al., Nature Med. 12:580, 2006; and Barthelemy et al., J. Biol. Chem. 283:3639, 2008).

An alternative source of non-conventional binding domains of this disclosure includes sequences that encode random peptide libraries or sequences that encode an engineered diversity of amino acids in loop regions of alternative non-antibody scaffolds, such as scTCR (see, e.g., Lake et al., Int. Immunol. 11:745, 1999; Maynard et al., J. Immunol. Methods 306:51, 2005; U.S. Pat. No. 8,361,794), fibrinogen domains (see, e.g., Weisel et al., Science 230:1388, 1985), Kunitz domains (see, e.g., U.S. Pat. No. 6,423,498), designed ankyrin repeat proteins (DARPins) (Binz et al., J. Mol. Biol. 332:489, 2003 and Binz et al., Nat. Biotechnol. 22:575, 2004), fibronectin binding domains (adnectins or monobodies) (Richards et al., J. Mol. Biol. 326:1475, 2003; Parker et al., Protein Eng. Des. Selec. 18:435, 2005 and Hackel et al. (2008) J. Mol. Biol. 381:1238-1252), cysteine-knot miniproteins (Vita et al. (1995) Proc. Nat'l. Acad. Sci. (USA) 92:6404-6408; Martin et al. (2002) Nat. Biotechnol. 21:71, 2002 and Huang et al. (2005) Structure 13:755, 2005), tetratricopeptide repeat domains (Main et al., Structure 11:497, 2003 and Cortaj arena et al., ACS Chem. Biol. 3:161, 2008), leucine-rich repeat domains (Stumpp et al., J. Mol. Biol. 332:471, 2003), lipocalin domains (see, e.g., WO 2006/095164, Beste et al., Proc. Nat'l. Acad. Sci. (USA) 96:1898, 1999 and Schonfeld et al., Proc. Nat'l. Acad. Sci. (USA) 106:8198, 2009), V-like domains (see, e.g., US Patent Application Publication No. 2007/0065431), C-type lectin domains (Zelensky and Gready, FEBS J. 272:6179, 2005; Beavil et al., Proc. Nat'l. Acad. Sci. (USA) 89:753, 1992 and Sato et al., Proc. Nat'l. Acad. Sci. (USA) 100: 7779, 2003), mAb$^2$ or Fcab™ (see, e.g., PCT Patent Application Publication Nos. WO 2007/098934; WO 2006/072620), armadillo repeat proteins (see, e.g., Madhurantakam et al., Protein Sci. 21: 1015, 2012; PCT Patent Application Publication No. WO 2009/040338), affilin (Ebersbach et al., J. Mol. Biol. 372: 172, 2007), affibody, avimers, knottins, fynomers, atrimers, cytotoxic T-lymphocyte associated protein-4 (Weidle et al., Cancer Gen. Proteo. 10:155, 2013) or the like (Nord et al., Protein Eng. 8:601, 1995; Nord et al., Nat. Biotechnol. 15:772, 1997; Nord et al., Euro. J. Biochem. 268:4269, 2001; Binz et al., Nat. Biotechnol. 23:1257, 2005; Boersma and PlUckthun, Curr. Opin. Biotechnol. 22:849, 2011).

In some embodiments, a binding domain is a single chain T cell receptor (scTCR) comprising $V_{\alpha/\beta}$ and $C_{\alpha/\beta}$ chains (e.g., $V_\alpha$-$C_\alpha$, $V_\beta$-$C_\beta$, $V_\alpha$-$V_\beta$) or comprising $V_\alpha$-$C_\alpha$, $V_\beta$-$C_\beta$, $V_\alpha$-$V_\beta$ pair specific for a target of interest (e.g., peptide-MHC complex or peptide-HLA complex).

In certain embodiments, a binding domain comprises or is a sequence that is at least 90%, at least 91%, at least 92%, at least 93%, at least 94%, at least 95%, at least 96%, at least 97%, at least 98%, at least 99%, at least 99.5%, or 100% identical to an ectodomain of a molecule having an amino acid sequence of a TCR $V_\alpha$, $V_\beta$, $C_\alpha$, or $C_\beta$, wherein each CDR comprises zero changes or at most one, two, or three changes, from a TCR or fragment or derivative thereof that specifically binds to a target of interest.

In certain embodiments, a binding domain $V_\alpha$, $V_\beta$, $C_\alpha$, or $C_\beta$ region of the present disclosure can be derived from or based on a $V_\alpha$, $V_\beta$, $C_\alpha$, or $C_\beta$ of a known TCR (e.g., a high-affinity TCR) and contains one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions or non-conservative amino acid substitutions), or a combination of the above-noted changes, when compared with the $V_\alpha$, $V_\beta$, $C_\alpha$, or $C_\beta$ of a known TCR. An insertion, deletion or substitution may be anywhere in a $V_\alpha$, $V_\beta$, $C_\alpha$, or $C_\beta$ region, including at the amino- or carboxy-terminus or both ends of these regions, provided that each CDR comprises zero changes or at most one, two, or three changes and provided a binding domain containing a modified $V_\alpha$, $V_\beta$, $C_\alpha$, or $C_\beta$ region can still specifically bind its target with an affinity similar to wild type. In certain embodiments, a TCR has an affinity for a peptide-HLA complex ranging from about 10 μM to about 500 μM. In further embodiments, a TCR has a high affinity for a peptide-HLA complex ranging from about 10 nM to about 200 pM.

In certain aspects, a fusion protein according to the present disclosure has an extracellular component comprised of a binding domain that specifically binds a target (e.g., a ligand or receptor), wherein the extracellular component optionally includes one or more other functional subcomponents or domains, such as a multimerization domain, a linker, junction amino acids, or any combination thereof.

In certain embodiments, a fusion protein disclosed herein further comprises an additional extracellular region in addition to the binding domain or in addition to the portion derived from the molecule from which the binding domain is derived, such as a spacer or a multimerization domain. For example, in some aspects a multimerization domain is contained in or is a part of the extracellular component of the fusion protein. For example, a multimerization domain may be created by altering (e.g., mutating) the extracellular component, or a multimerization domain may be created by adding 1 to about 50 amino acid residues to the extracellular component. A multimerization domain may be located between the binding domain of the extracellular component and hydrophobic component of a fusion protein of this disclosure. In certain embodiments, a fusion protein expressed on a cell surface comprises a multimerization domain within the extracellular component and is proximal to the cell membrane, within one to 50 amino acids from the hydrophobic component. For example, a fusion protein multimerization domain may comprise one or more cysteine residues located within 30, 25, 20, 15, 14, 13, 12, 11, 10, 9, 8, 7, 6, 5, 4, 3, 2, 1 or 0 amino acids from the fusion protein hydrophobic component, wherein such one or more cysteine residues from one fusion protein can form one or more disulfide bridges with one or more other fusion proteins. In some embodiments, the additional extracellular portion is derived from the same molecule from which a transmembrane or stimulatory region of the fusion protein is derived.

In further embodiments, interaction(s) between multimerization domains of two or more fusion proteins substantially contribute to or efficiently promote signal transduction (e.g., immune cell stimulation or activation) as compared to a fusion protein monomer. In certain embodiments, multimerization of fusion proteins promote signal transduction in a host cell in a statistically significant manner over fusion protein monomers. In further embodiments, multimerization of fusion proteins that promotes or enhances signal transduction in a host cell is via a disulfide bridge.

An exemplary multimer is a "dimer," which refers to a biological entity containing two molecules, such as two fusion proteins, associated with each other. Such a dimer is considered a "homodimer" when the two associated fusion proteins have substantially similar or identical amino acid sequences. Similarly, multimerization of three substantially or fully identical fusion proteins is referred to as a "homotrimer." In some embodiments, a multimerization domain comprises at least one cysteine residue, wherein a multimerization domain cysteine residue from a first fusion protein can form a disulfide bridge with a multimerization domain cysteine residue from a second fusion protein. In certain embodiments, a fusion protein dimer forms via a disulfide bridge. In other embodiments, a fusion protein trimer forms via two or more disulfide bridges. Alternatively, a dimer, homodimer, trimer or homotrimer may multimerize via a zinc finger motif or a leucine zipper motif. In still further embodiments, a fusion protein comprises a plurality of multimerization domains, which can be located extracellularly, intracellularly or both.

In some embodiments, a multimerization domain contained in the extracellular component of a fusion protein comprises an extracellular portion extending from the hydrophobic component. For example, in some embodiments, a multimerization domain contained in the extracellular component of a fusion protein comprises an extracellular portion of a CD28 extending from a CD28 transmembrane domain. In some embodiments, an extracellular portion of the CD28 comprises about 5, 6, 7, 8, 9, 10, 11, 12, 13, 14, 15, or up to about 25 amino acids adjacent to the transmembrane domain. In some embodiments, the extracellular portion of the CD28 comprises 9 amino acids or 12 amino acids adjacent to the transmembrane domain. In some embodiments, the extracellular portion of a CD28 comprises the amino acid sequence encoded by a nucleic acid molecule as set forth in SEQ ID NO.:9. In some embodiments, the extracellular portion of a CD28 comprises the amino acid sequence as set forth in SEQ ID NO.:32. In yet another exemplary embodiment, a multimerization domain contained in the extracellular component of a fusion protein comprises an extracellular portion of a CD137 (4-1BB) (e.g., ranging from one to about 50 amino acids) extending from a CD137 (4-1BB) transmembrane domain. In certain embodiments, the multimerization domain and the hydrophobic component are from different proteins. For example, a multimerization domain contained in the extracellular component of a fusion protein comprises an extracellular portion of a CD28 extending from a CD137 transmembrane domain, or comprises an extracellular portion of a CD137 extending from a CD28 transmembrane domain. In any of the aforementioned embodiments, a multimerization domain may further comprise a glycosylation site.

In some embodiments, a fusion protein may contain a linker or junction amino acids connecting, for example, an extracellular component with a multimerization domain or connecting an extracellular component with a hydrophobic component or connecting a hydrophobic component with an intracellular component. In some embodiments, the linker is a $Gly_xSer_y$, wherein x and y are independently an integer from 1 to 5.

In some embodiments, the extracellular component is or comprises a molecule, or portion thereof, that forms a multimer, and the intracellular component is or comprises a molecule, or portion thereof, that forms a multimer of the same number. For example, in some embodiments, the extracelluar component is or comprises a molecule, or portion thereof, that forms a dimer, and the intracellular component is or comprises a molecule, or portion thereof, that also forms a dimer. In some embodiments, the extracelluar component is or comprises a molecule, or portion thereof, that forms a trimer, and the intracellular component is or comprises a molecule, or portion thereof, that also forms a trimer.

A target molecule, which is specifically bound by a binding domain contained in a fusion protein of the present disclosure, may be found on or in association with a cell of interest ("target cell"). Exemplary target cells include an immune cell, a cancer cell, a cell associated with an autoimmune disease or disorder or with an inflammatory disease or disorder, and an infectious organism or cell (e.g., bacteria, virus, virus-infected cell), or any cell presenting antigen complexed with a MHC or human leukocyte antigen (HLA). A cell of an infectious organism, such as a mammalian parasite, is also contemplated as a target cell. In some embodiments, the target is an immunosuppressive ligand. In some embodiments, the target is selected from a CD47, CD58, CD80, CD86, CD95L (FasL), CD200, CD270 (HVEM), CD274 (PD-L1), or GAL9.

Intracellular Component

An intracellular component contained in a fusion protein of the present disclosure will have an intracellular signaling domain, such as an activating domain or a co-stimulatory domain, capable of transmitting functional signals to a cell. In certain embodiments, an intracellular signaling domain will indirectly promote a cellular response by associating with one or more other proteins that directly promote a cellular response. An intracellular signaling domain may include one, two, three or more receptor signaling domains, costimulatory domains, or combinations thereof. Any intracellular component comprising an activating domain, co-stimulatory domain, or both from any of a variety of signaling molecules (e.g., signal transduction receptors) may be used in the fusion proteins of this disclosure.

As used herein, an "intracellular signaling domain" from a cell-surface receptor or ligand includes a complete intracellular domain, a portion comprising an intracellular signaling domain, or a functional (signaling) fragment thereof. In certain embodiments, an intracellular signaling domain comprises a mutated intracellular domain or a functional (signaling) fragment thereof that has increased signaling activity as compared to a wild-type or reference intracellular signaling domain.

A "co-stimulatory molecule" as used herein refers to a receptor or cell-surface molecule that can transduce signals into T cells to positively modulate T cell activation (Chen and Flies, *Nat. Rev. Immunol.* 13: 227-242, 2013). By way of background, T cell activation and proliferation requires two signals mediated through engagement of the T cell antigen-specific receptor (TCR) and a co-stimulatory signal, most typically binding of CD28 by CD80 and CD86 (Ledbetter et al., *Blood* 75:1531, 1990).

An intracellular signaling domain or functional fragment thereof useful in the fusion proteins of this disclosure may be from a CD3ε, CD3δ, CD3ζ, CD25, CD27, CD28, CD40, CD47, CD79A, CD79B, CD134 (OX40), CD137 (4-1BB), CD150 (SLAMF1), CD278 (ICOS), CD357 (GITR), CARD11, DAP10, DAP12, FcRα, FcRβ, FcRγ, Fyn, Lck, LAT, LRP, NKG2D, NOTCH1, NOTCH2, NOTCH3, NOTCH4, ROR2, Ryk, Slp76, pTα, TCRα, TCRβ, TRIM, Zap70, PTCH2, or any combination thereof. In some embodiments, an intracellular signaling domain or functional fragment thereof does not comprise a primary signal. In some embodiments, an intracellular signaling domain does not comprise a CD3.

In some embodiments, an intracellular signaling domain of a fusion protein of this disclosure comprises a CD28. CD28 signaling promotes proliferation of T cells stimulated via the TCR (Chen and Flies, *Nat. Rev. Immunol.* 13: 227-242, 2013). CD28 forms disulfide-linked homodimers, as a result of the cysteine residue proximal to the transmembrane domain (Lazar-Molnar et al., *Cell Immunol.* 244: 125-129, 2006). In certain embodiments, a CD28 signaling domain includes a full length intracellular portion of a CD28 protein, a full length mature intracellular portion of a CD28 protein, a signaling fragment of an intracellular portion of a CD28 protein, and a signaling fragment of an intracellular portion of a CD28 protein along with a transmembrane domain or fragment thereof of CD28, or any combination thereof.

In some embodiments, an intracellular signaling domain of a fusion protein contains an intracellular signaling domain of a CD137 (4-1BB). CD137 is a co-stimulatory molecule, wherein binding of CD137 to its ligand (4-1BBL or CD137L) is associated with T cell activation and proliferation (Cheuk et al., *Cancer Gene Therapy* 11: 215-226, 2004). In certain embodiments, a CD137 signaling domain includes a full length intracellular portion of a CD137 protein, a full length mature intracellular portion of a CD137 protein, a signaling fragment of an intracellular portion of a CD137 protein, and a signaling fragment of an intracellular portion of a CD137 protein along with a transmembrane domain or fragment thereof of CD137, or any combination thereof.

In certain embodiments, an intracellular signaling domain comprises a lymphocyte receptor signaling domain or comprises an amino acid sequences having one or a plurality of immunoreceptor tyrosine-based activation motifs (ITAMs). In still further embodiments, an intracellular signaling domain comprises a cytoplasmic portion that associates with a cytoplasmic signaling protein, wherein the cytoplasmic signaling protein is a lymphocyte receptor or signaling domain thereof, a protein comprising a plurality of ITAMs, a costimulatory factor, or any combination thereof.

In some exemplary embodiments, the present disclosure provides a fusion protein having an extracellular component comprising an extracellular portion of a CD200R that specifically binds CD200, an intracellular component comprising an intracellular portion of CD28, and a hydrophobic component connecting the extracellular and intracellular components, provided that a fusion protein::target complex spans a distance similar to a distance between membranes in an immunological synapse.

In particular embodiments, an intracellular component of a fusion protein of the instant disclosure comprises a CD28, a CD137 (4-1BB) or both. For example, in some embodiments, an intracellular component comprises the amino acid sequence encoded by a nucleic acid molecule as set forth in in SEQ ID NO.:5. In some other embodiments, an intracellular component comprises an amino acid sequence encoded by a nucleic acid molecule as set forth in SEQ ID NO.:13. In some embodiments, an intracellular component comprises two intracellular signaling domains, for example, a CD28 and a CD137 (4-1BB). In some embodiments, an intracellular component comprises an amino acid sequence encoded by a nucleic acid molecule as set forth in SEQ ID NO.:5 and the amino acid sequence encoded by the nucleotide sequence as set SEQ ID NO.:13.

Hydrophobic Component

A hydrophobic portion contained in a single chain fusion protein of the present disclosure will allow a fusion protein of this disclosure to associate with a cellular membrane such that a portion of the fusion protein will be located extracellularly and a portion will be located intracellularly (e.g., intracellular signaling domain). A hydrophobic component will generally be disposed within the cellular membrane phospholipid bilayer. In certain embodiments, one or more junction amino acids may be disposed between and connecting a hydrophobic portion with an intracellular signaling domain.

In certain embodiments, a hydrophobic domain is a transmembrane domain, such as one derived from an integral membrane protein (e.g., receptor, cluster of differentiation (CD) molecule, enzyme, transporter, cell adhesion molecule, or the like). In some embodiments, the hydrophobic domain comprises a transmembrane domain found in or derived from an integral membrane protein, wherein the transmembrane domain has been modified by the addition, removal, or replacement of one or more amino acids with at least one different amino acid, or any combination thereof, such as charged or hydrophilic residues that facilitate intermolecular interactions. Thus, the term "hydrophobic domain" includes transmembrane domains having, for example, modifications that may reduce hydrophobicity.

In some embodiments, the hydrophobic component comprises a transmembrane domain of a CD2, CD3ε, CD3δ, CD3ζ, CD25, CD27, CD28, CD40, CD47, CD79A, CD79B, CD80, CD86, CD95 (Fas), CD134 (OX40), CD137 (4-1BB), CD150 (SLAMF1), CD152 (CTLA4), CD200R, CD223 (LAG3), CD270 (HVEM), CD272 (BTLA), CD273 (PD-L2), CD274 (PD-L1), CD278 (ICOS), CD279 (PD-1), TIM3, CD300, CD357 (GITR), A2aR, DAP10, FcRα, FcRβ, FcRγ, Fyn, GALS, KIR, Lck, LAT, LPA5, LRP, NKG2D, NOTCH1, NOTCH2, NOTCH3, NOTCH4, PTCH2, ROR2, Ryk, Slp76, SIRPα, pTα, TCRα, TCRβ, TIM3, TRIM, or Zap70. In particular embodiments, a hydrophobic portion is a transmembrane domain from CD28, CD4, CD8, CD27, or CD137 (4-1BB).

In certain embodiments, a transmembrane domain comprises a CD28 transmembrane domain. In some embodiments, a transmembrane domain comprises or consists of a CD28 transmembrane domain having an amino acid sequence encoded by a polynucleotide having at least 80%, 85%, 90%, 95% or more sequence identity with the polynucleotide of SEQ ID NO.:4. In further embodiments, a transmembrane domain is a CD28 transmembrane domain comprising or consisting of an amino acid sequence encoded by the nucleic acid molecule as set forth in SEQ ID NO.:4. In still further embodiments, a transmembrane domain is a CD28 transmembrane domain having at least 90%, 95% or more sequence identity with the amino acid sequence of SEQ ID NO.:27. In yet further embodiments, a transmembrane domain is a CD28 transmembrane domain comprising or consisting of an amino acid sequence as set forth in SEQ ID NO.:27.

In certain embodiments, a transmembrane domain comprises a CD137 (4-1BB) transmembrane domain. In further embodiments, a transmembrane domain comprises or consists of a CD137 transmembrane domain having an amino acid sequence encoded by a polynucleotide having at least 80%, 85%, 90%, 95% or more sequence identity with the polynucleotide of SEQ ID NO.:197. In particular embodiments, a transmembrane domain is a CD137 transmembrane domain comprising or consisting of an amino acid sequence encoded by the nucleic acid molecule of SEQ ID NO.:197.

In certain other embodiments, a transmembrane domain comprises a CD200R transmembrane domain. In some embodiments, a transmembrane domain comprises or consists of a CD200R transmembrane domain having an amino acid sequence encoded by a polynucleotide having at least 80%, 85%, 90%, 95% or more sequence identity with the polynucleotide of SEQ ID NO.:3. In further embodiments, a transmembrane domain is a CD200R transmembrane domain comprising or consisting of an amino acid sequence encoded by the nucleic acid molecule as set forth in SEQ ID NO.:3.

In certain embodiments, a transmembrane domain comprises a SIRPα transmembrane domain. In some embodiments, a transmembrane domain comprises or consists of a SIRPα transmembrane domain having an amino acid sequence encoded by a polynucleotide having at least 80%, 85%, 90%, 95% or more sequence identity with the polynucleotide of SEQ ID NO.:18. In further embodiments, a transmembrane domain is a SIRPα transmembrane domain comprising or consisting of an amino acid sequence encoded by the nucleic acid molecule as set forth in SEQ ID NO.:18.

In certain embodiments, a transmembrane domain comprises a CD2 transmembrane domain. In some embodiments, a transmembrane domain comprises or consists of a CD2 transmembrane domain having an amino acid sequence encoded by a polynucleotide having at least 80%, 85%, 90%, 95% or more sequence identity with the polynucleotide of SEQ ID NO.:63. In further embodiments, a transmembrane domain is a CD2 transmembrane domain comprising or consisting of an amino acid sequence encoded by the nucleic acid molecule as set forth in SEQ ID NO.:63.

In certain embodiments, a transmembrane domain comprises a Fas transmembrane domain. In some embodiments, a transmembrane domain comprises or consists of a Fas transmembrane domain having an amino acid sequence encoded by a polynucleotide having at least 80%, 85%, 90%, 95% or more sequence identity with the polynucleotide of SEQ ID NO.:77. In further embodiments, a transmembrane domain is a Fas transmembrane domain comprising or consisting of an amino acid sequence encoded by the nucleic acid molecule as set forth in SEQ ID NO.:77.

In certain embodiments, a transmembrane domain comprises a TIM3 transmembrane domain. In some embodiments, a transmembrane domain comprises or consists of a TIM3 transmembrane domain having an amino acid sequence encoded by a polynucleotide having at least 80%, 85%, 90%, 95% or more sequence identity with the polynucleotide of SEQ ID NO.:169. In further embodiments, a transmembrane domain is a TIM3 transmembrane domain comprising or consisting of an amino acid sequence encoded by the nucleic acid molecule as set forth in SEQ ID NO.:169.

In certain embodiments, a transmembrane domain comprises a LAG3 transmembrane domain. In some embodiments, a transmembrane domain comprises or consists of a LAG3 transmembrane domain having an amino acid sequence encoded by a polynucleotide having at least 80%, 85%, 90%, 95% or more sequence identity with the polynucleotide of SEQ ID NO.:155. In further embodiments, a transmembrane domain is a LAG3 transmembrane domain comprising or consisting of an amino acid sequence encoded by the nucleic acid molecule as set forth in SEQ ID NO.:155.

Nucleic Acids and Host Cells

In certain aspects, the present disclosure provides nucleic acid molecules that encode any one or more of the fusion proteins described herein, which may be immunomodulatory fusion proteins (IFPs). Such nucleic acid molecules can be inserted into an appropriate vector (e.g., viral vector or non-viral plasmid vector) for introduction in a host cell of interest (e.g., hematopoietic progenitor cell, T cell).

As used herein, the term "recombinant" or "non-natural" refers to an organism, microorganism, cell, nucleic acid molecule, or vector that includes at least one genetic alteration or has been modified by introduction of an exogenous nucleic acid molecule, wherein such alterations or modifications are introduced by genetic engineering. Genetic alterations include, for example, modifications introducing expressible nucleic acid molecules encoding proteins, fusion proteins or enzymes, or other nucleic acid molecule additions, deletions, substitutions or other functional disruption of a cell's genetic material. Additional modifications include, for example, non-coding regulatory regions in which the modifications alter expression of a gene or operon. In certain embodiments, a cell, such as a T cell, obtained from a subject may be converted into a non-natural or recombinant cell (e.g., a non-natural or recombinant T cell) by introducing a nucleic acid that encodes a fusion protein as described herein and whereby the cell expresses a fusion protein.

In certain embodiments, nucleic acid molecules encoding fusion proteins may be codon optimized to enhance or maximize expression in certain types of cells, such as T cells (Scholten et al., *Clin. Immunol.* 119: 135-145, 2006).

In one exemplary embodiment, the present disclosure provides a nucleic acid molecule that encodes a CD200R-CD28 construct (huCD200Rtm-CD28), wherein the extracellular component comprises a CD200R ectodomain, the hydrophobic component comprises the transmembrane domain of a CD200R, and the intracellular component comprises the intracellular signaling domain of a CD28. For example, in one embodiment, a nucleic acid molecule as set forth in SEQ ID NO.:1 is provided. In certain embodiments, the present disclosure provides a huCD200Rtm-CD28 comprising a polynucleotide that is at least 80% or at least 90% identical to a polynucleotide sequence of SEQ ID NO.:1. In other embodiments, the present disclosure provides a huCD200Rtm-CD28 comprising or consisting of a polynucleotide sequence of SEQ ID NO.:1.

In another exemplary embodiment, the present disclosure provides a nucleic acid molecule that encodes a CD200R-CD28 construct (huCD200R-CD28tm), wherein the hydrophobic component comprises the transmembrane domain of a CD28. For example, in one embodiment, the disclosure provides a nucleic acid molecule as set forth in SEQ ID NO.:6. In certain embodiments, the present disclosure provides a huCD200R-CD28tm comprising a polynucleotide that is at least 80% or at least 90% identical to a polynucleotide sequence of SEQ ID NO.:6. In other embodiments, the present disclosure provides a huCD200R-CD28tm comprising or consisting of a polynucleotide sequence of SEQ ID NO.:6. In further embodiments, a huCD200R-CD28tm protein has an amino acid sequence that is at least 90%, at least 91%, at least 92%, at least 93%, at least 94%, at least 95%, at least 96%, at least 97%, at least 98%, at least 99%, at least 99.5%, or 100% identical to an amino acid sequence as set forth in SEQ ID NO.: 29.

In other exemplary embodiments, the present disclosure provides a nucleic acid molecule that encodes a CD200R-CD28 construct, wherein the extracellular comprises a truncated extracellular domain of CD200R and an extracellular portion of CD28. For example, the CD200R extracellular domain may be truncated by about 9 to about 15 amino acids. Exemplary CD200R-CD28 constructs of the instant disclosure include those with a 9 amino acid truncation (e.g., huCD200R-9aas-CD28Cys, SEQ ID NO.:7), a 12 amino acid truncation (e.g., huCD200R-12aas-CD28Cys, SEQ ID NO.:10), or a 15 amino acid truncation (e.g., huCD200R-15aas-CD28Cys, SEQ ID NO.:183). The extracellular portion of CD28 comprises, in some embodiments, an amino acid sequence encoded by a nucleic acid molecule as set forth in SEQ ID NO.:9. In certain embodiments, an extracellular portion of CD28 comprises an amino acid sequence that is at least 90%, at least 91%, at least 92%, at least 93%, at least 94%, at least 95%, at least 96%, at least 97%, at least 98%, at least 99%, at least 99.5%, or 100% identical to an amino acid sequence as set forth in SEQ ID NO.:32. In further embodiments, an extracellular portion of CD28 comprises or consists of an amino acid sequence as set forth in SEQ ID NO.:32. In certain other embodiments, a huCD200R-9aas-CD28Cys protein comprises an amino acid sequence that is at least 90%, at least 91%, at least 92%, at least 93%, at least 94%, at least 95%, at least 96%, at least 97%, at least 98%, at least 99%, at least 99.5%, or 100% identical to an amino acid sequence as set forth in SEQ ID NO.:30. An exemplary huCD200R-9aas-CD28Cys protein comprises or consists of an amino acid sequence as set forth in SEQ ID NO.: 30. In certain other embodiments, a huCD200R-12aas-CD28Cys protein comprises an amino acid sequence that is at least 90%, at least 91%, at least 92%, at least 93%, at least 94%, at least 95%, at least 96%, at least 97%, at least 98%, at least 99%, at least 99.5%, or 100% identical to an amino acid sequence as set forth in SEQ ID NO.:33. An exemplary huCD200R-12aas-CD28Cys protein comprises or consists of an amino acid sequence as set forth in SEQ ID NO.: 33. In certain other embodiments, a huCD200R-15aas-CD28Cys protein comprises an amino acid sequence that is at least 90%, at least 91%, at least 92%, at least 93%, at least 94%, at least 95%, at least 96%, at least 97%, at least 98%, at least 99%, at least 99.5%, or 100% identical to an amino acid sequence as set forth in SEQ ID NO.:184. An exemplary huCD200R-15aas-CD28Cys protein comprises or consists of an amino acid sequence as set forth in SEQ ID NO.:184.

In one exemplary embodiment, the present disclosure provides a nucleic acid molecule that encodes a CD200R-CD28-4-1BB construct (huCD200R-9aas-CD28Cystm-41BBic or huCD200R-12aas-CD28Cystm-41BBic), wherein the intracellular component comprises the intracellular signaling domain of CD137 (4-1BB). For example, in one embodiment, the nucleic acid molecule has the nucleotide sequence as set forth in SEQ ID NO.:12 or SEQ ID NO.:14.

In another exemplary embodiment, the present disclosure provides a nucleic acid molecule that encodes a CD200R-CD28-4-1BB construct (huCD200R-9aas-CD28Cys tm is 41BBic or huCD200R-12aas-CD28Cys tm ic-41BBic), wherein the intracellular component comprises the intracellular signaling domain of CD28 and of CD137 (4-1BB). In one embodiment, for example, the nucleic acid of the present disclosure has the nucleotide sequence as set forth in SEQ ID NO.:9 or SEQ ID NO.:15.

In other exemplary embodiments, the present disclosure provides a nucleic acid molecule that encodes a SIRPα-CD28 construct. For example, the present disclosure includes a nucleic acid molecule as set forth in SEQ ID NO.:16 (huSIRPαtm-CD28) or SEQ ID NO.:19 (huSIRPα-CD28tm).

In other exemplary embodiments, the present disclosure provides a nucleic acid molecule that encodes a SIRPα-CD28 construct, wherein the extracellular component comprises a truncated extracellular domain of SIRPα and an extracellular portion of CD28. For example, the SIRPα extracellular domain may be truncated by about 8 amino acids to about 15 amino acids. An exemplary SIRPα-CD28 constructs has the CD95 (Fas) extracellular domain truncated by 12 amino acids (e.g., huSIRPα-12aas-CD28Cys, SEQ ID NO.:20).

In one exemplary embodiment, the present disclosure provides a nucleic acid molecule that encodes a SIRPα-CD28-4-1BB construct (huSIRPα-12aas-CD28Cystm-41BBic), wherein the intracellular component comprises the intracellular signaling domain of CD137 (4-1BB). For example, in one embodiment, the nucleic acid of the present disclosure has the nucleotide sequence as set forth in SEQ ID NO.:22.

In another exemplary embodiment, the present disclosure provides a nucleic acid molecule that encodes a SIRPα-CD28-4-1BB construct (huSIRPα-12aas-CD28Cys tm ic-41BBic), wherein the intracellular component comprises the intracellular signaling domain of CD28 and of CD137 (4-1BB). In one embodiment, for example, the nucleic acid of the present disclosure has the nucleotide sequence as set forth in SEQ ID NO.:23.

In other exemplary embodiments, the present disclosure provides a nucleic acid molecule that encodes a PD-1-CD28 construct. For example, the present disclosure includes a nucleic acid molecule as set forth in SEQ ID NO.:97 (huPD1-CD28Cys).

In other exemplary embodiments, the present disclosure provides a nucleic acid molecule that encodes a PD-1-CD28 construct, wherein the extracellular component comprises a truncated extracellular domain of PD-1 and an extracellular portion of CD28. For example, the PD-1 extracellular domain may be truncated by about 10 amino acids to about 25 amino acids. Exemplary PD-1-CD28 constructs have the PD-1 extracellular domain truncated by 12 amino acids (e.g., huPD1-12aas-CD28Cys, SEQ ID NO.:99), 15 amino acids (e.g., huPD1-15aas-CD28Cys, SEQ ID NO.:101), or 21 amino acids (e.g., huPD1-21aas-CD28Cys, SEQ ID NO.:103).

In other exemplary embodiments, the present disclosure provides a nucleic acid molecule that encodes a CD2-CD28 construct. For example, the present disclosure includes a nucleic acid molecule as set forth in SEQ ID NO.:69 (huCD2-CD28Cys).

In other exemplary embodiments, the present disclosure provides a nucleic acid molecule that encodes a Fas-CD28 construct. For example, the present disclosure includes a nucleic acid molecule as set forth in SEQ ID NO.:83 (huFas-CD28Cys).

In other exemplary embodiments, the present disclosure provides a nucleic acid molecule that encodes a Fas-CD28 construct, wherein the extracellular component comprises a truncated extracellular domain of Fas and an extracellular portion of CD28. For example, the Fas extracellular domain may be truncated by about 7 amino acids to about 15 amino acids. Exemplary Fas-CD28 constructs have the CD95 (Fas) extracellular domain truncated by 7 amino acids (e.g., huFas-7aas-CD28Cys, SEQ ID NO.:85) or 12 amino acids (e.g., huFas-12aas-CD28Cys, SEQ ID NO.:87).

In another exemplary embodiment, the present disclosure provides a nucleic acid molecule that encodes a Fas-4-IBB construct, wherein the extracellular component comprises the entire extracellular domain or a truncated extracellular domain of CD95 (Fas), and the intracellular component comprises the signaling domain of CD137 (4-1BB). In a further embodiment, the nucleic acid molecule encodes a Fas-4-1BB construct wherein the hydrophobic component further comprises the transmembrane portion of CD95 (Fas) or CD137 (4-1BB). For example, in certain embodiments, a Fas-4-1BB construct is encoded by a the nucleic acid molecule having at least 80%, 85%, 90%, 95% or more sequence identity with the polynucleotide sequence of SEQ ID NO.:185. In some embodiments, a Fas-4-1BB construct is encoded by a polynucleotide comprising or consisting of the polynucleotide sequence of SEQ ID NO.:185. In other embodiments, a Fas-4-1BB construct is encoded by a nucleic acid molecule having at least 80%, 85%, 90%, 95% or more sequence identity with the polynucleotide sequence of SEQ ID NO.:187. In some embodiments, a Fas-4-1BB construct is encoded by a polynucleotide comprising or consisting of the polynucleotide sequence of SEQ ID NO.: 187. In certain other embodiments, a Fas-4-1BB construct is a huFastm-41BB protein comprising an amino acid sequence that is at least 90%, at least 91%, at least 92%, at least 93%, at least 94%, at least 95%, at least 96%, at least 97%, at least 98%, at least 99%, at least 99.5%, or 100% identical to an amino acid sequence as set forth in SEQ ID NO.:186. An exemplary huFastm-41BB protein comprises or consists of an amino acid sequence as set forth in SEQ ID NO.:186. In certain other embodiments, a Fas-4-1BB construct is a huFas-41BBtm protein comprising an amino acid sequence that is at least 90%, at least 91%, at least 92%, at least 93%, at least 94%, at least 95%, at least 96%, at least 97%, at least 98%, at least 99%, at least 99.5%, or 100% identical to an amino acid sequence as set forth in SEQ ID NO.:188. An exemplary huFas-41BBtm protein comprises or consists of an amino acid sequence as set forth in SEQ ID NO.:188.

In other exemplary embodiments, the present disclosure provides a nucleic acid molecule that encodes a Fas-CD28-41BB construct, wherein the extracellular component comprises an extracellular domain of CD95 (Fas), the hydrophobic component comprises a transmembrane domain of CD28, and the intracellular component comprises the signaling domain of CD137 (4-1BB). In some embodiments, the extracellular component comprises a truncated extracellular domain of CD95 (Fas) and an extracellular portion of CD28. For example, the CD95 (Fas) extracellular domain may be truncated by about 7 to about 15 amino acids. Exemplary Fas-CD28-41BB constructs have the CD95 (Fas) extracellular domain truncated by 7, 9, 12, or 15 amino acids. For example, in some embodiments, the CD95 (Fas) extracellular domain may comprise an amino acid sequence encoded by the nucleic acid sequence as set forth in SEQ ID NO.:73 or 75. The extracellular portion of CD28 may comprise a multimerization domain. The extracellular portion of CD28 may comprise, for example, an amino acid sequence encoded by a nucleic acid sequence as set forth in SEQ ID NO.:9.

In other exemplary embodiments, the present disclosure provides a nucleic acid molecule that encodes a TIM3-CD28 construct. For example, the present disclosure includes a nucleic acid molecule as set forth in SEQ ID NO.:173 (huTIM3-CD28Cys). Also included within the scope of the disclosure is a TIM3-CD28 fusion protein, wherein the extracellular component comprises a truncated extracellular domain of TIM3 and an extracellular portion of CD28. For example, the TIM3 extracellular domain may be truncated by about 8 to about 15 amino acids (e.g., huTIM3-12aas-CD28Cys, SEQ ID NO.:175, has a 12 amino acid truncation).

In other exemplary embodiments, the present disclosure provides a nucleic acid molecule that encodes a LAG3-CD28 construct. For example, the present disclosure includes a nucleic acid molecule as set forth in SEQ ID NO.:163 (huLAG3-CD28Cys). Also included within the scope of the disclosure is a LAG3-CD28 fusion protein, wherein the extracellular component comprises a truncated extracellular domain of LAG3 and an extracellular portion of CD28. For example, the LAG3 extracellular domain may be truncated by about 8 to about 15 amino acids (e.g., huLAG3-12aas-CD28Cys, SEQ ID NO.:159, has a 12 amino acid truncation).

A vector that encodes a core virus is referred to herein as a "viral vector." There are a large number of available viral vectors suitable for use with the compositions of the instant disclosure, including those identified for human gene therapy applications (see Pfeifer and Verma, *Ann. Rev. Genomics Hum. Genet.* 2:177, 2001). Suitable viral vectors include vectors based on RNA viruses, such as retrovirus-derived vectors, e.g., Moloney murine leukemia virus (MLV)-derived vectors, and include more complex retrovirus-derived vectors, e.g., lentivirus-derived vectors. HIV-1-derived vectors belong to this category. Other examples include lentivirus vectors derived from HIV-2, FIV, equine infectious anemia virus, SIV, and Maedi-Visna virus (ovine lentivirus). Methods of using retroviral and lentiviral viral vectors and packaging cells for transducing mammalian host cells with viral particles containing chimeric antigen receptor transgenes are known in the art and have been previous described, for example, in U.S. Pat. No. 8,119,772; Walchli et al., *PLoS One* 6:327930, 2011; Zhao et al., *J. Immunol.* 174:4415, 2005; Engels et al., *Hum. Gene Ther.* 14:1155, 2003; Frecha et al., *Mol. Ther.* 18:1748, 2010; Verhoeyen et al., *Methods Mol. Biol.* 506:97, 2009. Retroviral and lentiviral vector constructs and expression systems are also commercially available.

In certain embodiments, a viral vector is used to introduce a non-endogenous nucleic acid sequence encoding a fusion protein or a non-endogenous nucleic acid sequence encoding a fusion protein specific for a target. A viral vector may be a retroviral vector or a lentiviral vector. A viral vector may also include nucleic acid sequences encoding a marker for transduction. Transduction markers for viral vectors are known in the art and include selection markers, which may confer drug resistance, or detectable markers, such as fluorescent markers or cell surface proteins that can be detected by methods such as flow cytometry. In particular embodiments, a viral vector further comprises a gene marker for transduction comprising green fluorescent protein (GFP), an extracellular domain of human CD2, or a truncated human EGFR (huEGFRt; see Wang et al., *Blood* 118:1255, 2011). When a viral vector genome comprises a plurality of nucleic acid sequences to be expressed in a host cell as separate transcripts, the viral vector may also comprise additional sequences between the two (or more) transcripts allowing bicistronic or multicistronic expression. Examples of such sequences used in viral vectors include internal ribosome entry sites (IRES), furin cleavage sites, viral 2A peptide, or any combination thereof.

Other vectors also can be used for polynucleotide delivery including DNA viral vectors, including, for example adenovirus-based vectors and adeno-associated virus (AAV)-based vectors; vectors derived from herpes simplex viruses (HSVs), including amplicon vectors, replication-defective HSV and attenuated HSV (Krisky et al., *Gene Ther.* 5: 1517, 1998).

Other vectors recently developed for gene therapy uses can also be used with the compositions and methods of this disclosure. Such vectors include those derived from baculoviruses and α-viruses (Jolly, D J. 1999. Emerging Viral Vectors. pp 209-40 in Friedmann T. ed. The Development of Human Gene Therapy. New York: Cold Spring Harbor Lab), or plasmid vectors (such as sleeping beauty or other transposon vectors). In some embodiments, a viral or plasmid vector further comprises a gene marker for transduction (e.g. green fluorescent protein, huEGFRt).

In some embodiments, a vector encoding a fusion protein as disclosed herein may encode more than one fusion protein. For example, a vector may encode two different fusion proteins (e.g., a first fusion protein comprising a PD-1 ectodomain and a second fusion protein comprising a TIM3 ectodomain).

In some embodiments, a vector encoding a fusion protein as disclosed herein may further comprise an antigen-specific TCR. In some embodiments, the antigen-specific TCR is exogenous. In some embodiments, the antigen-specific TCR is specific to a HLA (MHC) class I restricted antigen. In some embodiments, the antigen is a cancer-specific antigen. Embodiments wherein the cancer-specific antigen comprises WT-1, mesothelin, or cyclin-A1 are also within the scope of the disclosure. In still other embodiments, a vector that encodes a fusion protein as disclosed herein further encodes a ligand, which may be CD200, CD47, PD-L1, or CD58. In yet further embodiments, a vector that encodes a fusion protein as disclosed herein further encodes an siRNA for reducing the expression of an endogenous receptor. In some particular embodiments, the endogenous receptor is CD200R, SIRPα, CD279 (PD-1), CD95 (Fas) or CD2.

In some embodiments, host cells capable of expressing a fusion protein of this disclosure on the cell surface are immune cells. In some embodiments, host cells capable of expressing a fusion protein of this disclosure on the cell surface are T cells, including primary cells or cell lines derived from human, mouse, rat, or other mammals. If obtained from a mammal, a T cell can be obtained from numerous sources, including blood, bone marrow, lymph node, thymus, or other tissues or fluids. A T cell may be enriched or purified. T cell lines are well known in the art, some of which are described in Sandberg et al., *Leukemia* 21:230, 2000. In certain embodiments, T cells that lack endogenous expression of TCRα and β chains are used. Such T cells may naturally lack endogenous expression of TCRα and β chains or may have been modified to block expression (e.g., T cells from a transgenic mouse that does not express TCR α and β chains or cells that have been manipulated to inhibit expression of TCR α and β chains) or to knockout TCRα chain, TCRβ chain, or both genes. In some embodiments, T cells may be engineered to express a TCR specific to a particular antigen.

In certain embodiments, a host cell transfected to express a fusion protein of this disclosure is a functional T cell, such as a virus-specific T cell, a tumor antigen specific cytotoxic T cell, a naïve T cell, a memory stem T cell, a central or effector memory T cell, γδ T cells, or a CD4+ CD25+ regulatory T cell. In further embodiments, a nucleic acid molecule encoding a fusion protein of this disclosure is introduced into bulk CD8+ T cells, naïve CD8+ T cells, CD8+ $T_{CM}$ cells, CD8+ $T_{EM}$ cells, or any combination thereof. In still further embodiments, a nucleic acid molecule encoding a fusion protein of this disclosure is introduced into bulk CD4+ T cells, naïve CD4+ T cells, CD4+ $T_{CM}$ cells, CD4+ $T_{EM}$ cells, or any combination thereof. In other embodiments, a nucleic acid molecule encoding a fusion protein of this disclosure is introduced into a population of T cells enriched for naïve CD8+ T cells and CD8+ $T_{CM}$ cells. In still other embodiments, a nucleic acid molecule encoding a fusion protein of this disclosure is introduced into a population of T cells enriched for naïve CD4+ T cells and CD4+ $T_{CM}$ cells. In any of the aforementioned embodiments, the T cells further contain a nucleic acid molecule encoding an engineered antigen-specific T cell receptor (TCR), an engineered antigen-specific high affinity TCR, an exogenous co-stimulatory molecule, a chimeric antigen receptor (CAR), or any combination thereof.

In certain embodiments, a host cell transfected to express a fusion protein of this disclosure is a functional natural killer cell.

One or more growth factor cytokines that promote proliferation of T cells expressing a fusion protein of this disclosure may be added to the culture used to expand T cells. The cytokines may be human or non-human. Exemplary growth factor cytokines that may be used promote T cell proliferation include IL2, IL15, or the like.

In certain embodiments, a host T cell transfected to express a fusion protein of this disclosure is a CD4⁻ T cell that also expresses an antigen-specific high-affinity TCR specific to a HLA (MHC) class I restricted antigen (see Soto et al., *Cancer Immunol Immunother.* 62: 359-369, 2013).

In certain embodiments, a host T cell transfected to express a fusion protein of this disclosure also expresses a recombinant TCR specific to a cancer antigen. In some embodiments, the cancer antigen is a WT1. "WT1" refers to Wilm's tumor 1, a transcription factor that contains four zinc-finger motifs at the C-terminus and a proline/glutamine-rich DNA binding domain at the N-terminus. WT1 has an essential role in the normal development of the urogenital system and is mutated in a small subset of patients with Wilm's tumors. High expression of WT1 has been observed in various cancers, including, breast cancer, ovarian cancer, acute leukemias, vascular neoplasms, melanomas, colon cancer, lung cancer, thyroid cancer, bone and soft tissue sarcoma, and esophageal cancer. Alternative splicing has been noted for WT1.

In certain embodiments, a host T cell transfected to express a fusion protein of this disclosure also expresses a recombinant TCR specific to mesothelin. "Mesothelin" (MSLN) refers to a gene that encodes a precursor protein that is cleaved into two products, megakaryocyte potentiating factor and mesothelin. Megakaryocyte potentiation factor functions as a cytokine that can stimulate colony formation in bone marrow megakaryocytes. Mesothelin is a glycosylphosphatidylinositol-anchored cell-surface protein that may function as a cell adhesion protein. This protein is overexpressed in epithelial mesotheliomas, ovarian cancers and in specific squamous cell carcinomas. Alternative splicing results in multiple transcript variants.

In certain embodiments, a host T cell transfected to express a fusion protein of this disclosure also expresses a recombinant TCR specific to cyclin-A1.

In certain embodiments, a host T cell transfected to express a fusion protein of this disclosure also expresses a CAR.

In still other embodiments, a host cell that expresses a fusion protein as disclosed herein further comprises a ligand, which may be CD200, CD47, PD-L1, or CD58. In yet further embodiments, a host cell that expresses a fusion protein as disclosed herein further expresses an siRNA for reducing the expression of an endogenous receptor. In some particular embodiments, the endogenous receptor is CD200R, SIRPα, CD279 (PD-1), CD95 (Fas), or CD2.

In some embodiments, a host cell that expresses a fusion protein as disclosed herein may express more than one fusion protein. For example, the host cell may express two different fusion proteins (e.g., a first fusion protein comprising a PD-1 ectodomain and a second fusion protein comprising a TIM3 ectodomain).

Uses

Diseases that may be treated with cells expressing fusion proteins as described in the present disclosure include cancer, infectious diseases (viral, bacterial, protozoan infections), immune diseases (e.g., autoimmune), or aging-related diseases (e.g., senescence). Adoptive immune and gene therapy are promising treatments for various types of cancer (Morgan et al., Science 314:126, 2006; Schmitt et al., Hum. Gene Ther. 20:1240, 2009; June, J. Clin. Invest. 117:1466, 2007) and infectious disease (Kitchen et al., PLoS One 4:38208, 2009; Rossi et al., Nat. Biotechnol. 25:1444, 2007; Zhang et al., PLoS Pathog. 6:e1001018, 2010; Luo et al., J. Mol. Med. 89:903, 2011).

A wide variety of cancers, including solid tumors and leukemias are amenable to the compositions and methods disclosed herein. Exemplary types of cancer that may be treated include adenocarcinoma of the breast, prostate, and colon; all forms of bronchogenic carcinoma of the lung; myeloid leukemia; melanoma; hepatoma; neuroblastoma; papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, Merkel cell, mucinous, non-small cell lung, oat cell, papillary, scirrhous, bronchiolar, bronchogenic, squamous cell, and transitional cell). Additional types of cancers that may be treated include histiocytic disorders; malignant histiocytosis; leukemia; Hodgkin's disease; immunoproliferative small; non-Hodgkin's lymphoma; plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; trophoblastic tumor. Further, the following types of cancers are also contemplated as amenable to treatment: adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; sertoli cell tumor; theca cell tumor; leimyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin. The types of cancers that may be treated also include angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

Exemplifying the variety of hyperproliferative disorders amenable to a fusion protein T cell therapy are B-cell cancers, including B-cell lymphomas (such as various forms of Hodgkin's disease, non-Hodgkins lymphoma (NHL) or central nervous system lymphomas), leukemias (such as acute lymphoblastic leukemia (ALL), chronic lymphocytic leukemia (CLL), Hairy cell leukemia, B cell blast transformation of chronic myeloid leukemia, and acute myeloid leukemia (AML)) and myelomas (such as multiple myeloma). Additional B cell cancers include small lymphocytic lymphoma, B-cell prolymphocytic leukemia, lymphoplasmacytic lymphoma, splenic marginal zone lymphoma, plasma cell myeloma, solitary plasmacytoma of bone, extraosseous plasmacytoma, extra-nodal marginal zone B-cell lymphoma of mucosa-associated (MALT) lymphoid tissue, nodal marginal zone B-cell lymphoma, follicular lymphoma, mantle cell lymphoma, diffuse large B-cell lymphoma, mediastinal (thymic) large B-cell lymphoma, intravascular large B-cell lymphoma, primary effusion lymphoma, Burkitt's lymphoma/leukemia, B-cell proliferations of uncertain malignant potential, lymphomatoid granulomatosis, and post-transplant lymphoproliferative disorder.

Inflammatory and autoimmune diseases include arthritis, rheumatoid arthritis, juvenile rheumatoid arthritis, osteoarthritis, polychondritis, psoriatic arthritis, psoriasis, dermatitis, polymyositis/dermatomyositis, inclusion body myositis, inflammatory myositis, toxic epidermal necrolysis, systemic scleroderma and sclerosis, CREST syndrome, inflammatory bowel disease, Crohn's disease, ulcerative colitis, respiratory distress syndrome, adult respiratory distress syndrome (ARDS), meningitis, encephalitis, uveitis, colitis, glomerulonephritis, allergic conditions, eczema, asthma, conditions involving infiltration of T cells and chronic inflammatory responses, atherosclerosis, autoimmune myocarditis, leukocyte adhesion deficiency, systemic lupus erythematosus (SLE), subacute cutaneous lupus erythematosus, discoid lupus, lupus myelitis, lupus cerebritis, juvenile onset diabetes, multiple sclerosis, allergic encephalomyelitis, neuromyelitis optica, rheumatic fever, Sydenham's chorea, immune responses associated with acute and delayed hypersensitivity mediated by cytokines and T-lymphocytes, tuberculosis, sarcoidosis, granulomatosis including Wegener's granulomatosis and Churg-Strauss disease, agranulocytosis, vasculitis (including hypersensitivity vasculitis/angiitis, ANCA and rheumatoid vasculitis), aplastic anemia, Diamond Blackfan anemia, immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, central nervous system (CNS) inflammatory disorders, multiple organ injury syndrome, myasthenia gravis, antigen-antibody complex mediated diseases, anti-glomerular basement membrane disease, anti-phospholipid antibody syndrome, allergic neuritis, Behcet disease, Castleman's syndrome, Goodpasture's syndrome, Lambert-Eaton Myasthenic Syndrome, Reynaud's syndrome, Sjorgen's syndrome, Stevens-Johnson syndrome, solid organ transplant rejection, graft versus host disease (GVHD), bullous pemphigoid, pemphigus, autoimmune polyendocrinopathies, seronegative spondyloarthropathies, Reiter's disease, stiff-man syndrome, giant cell arteritis, immune complex nephritis, IgA nephropathy, IgM polyneuropathies or IgM mediated neuropathy, idiopathic thrombocytopenic purpura (ITP), thrombotic throbocytopenic purpura (TTP), Henoch-Schonlein purpura, autoimmune thrombocytopenia, autoimmune disease of the testis and ovary including autoimmune orchitis and oophoritis, primary hypothyroidism; autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular endocrinopathy syndromes), Type I diabetes also referred to as insulin-dependent diabetes mellitus (IDDM) and Sheehan's syndrome; autoimmune hepatitis, lymphoid interstitial pneumonitis (HIV), bronchiolitis obliterans (non-transplant), non-specific interstitial pneumonia (NSIP), Guillain-Barr-Syndrome, large vessel vasculitis (including polymyalgia rheumatica and giant cell (Takayasu's) arteritis), medium vessel vasculitis (including Kawasaki's disease and polyarteritis nodosa), polyarteritis nodosa (PAN) ankylosing spondylitis, Berger's disease (IgA nephropathy), rapidly progressive glomerulonephritis, primary biliary cirrhosis, Celiac sprue (gluten enteropathy), cryoglobulinemia, cryoglobulinemia associated with hepatitis, amyotrophic lateral sclerosis (ALS), coronary artery disease, familial Mediterranean fever, microscopic polyangiitis, Cogan's syndrome, Whiskott-Aldrich syndrome and thromboangiitis obliterans.

In particular embodiments, a method of treating a subject with the fusion protein as disclosed herein includes treating acute myelocytic leukemia, acute lymphocytic leukemia, acute myeloid leukemia (AML), and chronic myelocytic leukemia.

In particular embodiments, a method of treating a subject with the fusion protein as disclosed herein includes treating pancreatic cancer.

In particular embodiments, a method of treating a subject with the fusion protein as disclosed herein includes treating ovarian cancer.

In particular embodiments, a method of treating disease with a fusion protein as disclosed herein is provided, wherein the disease comprises a solid tumor that expresses CD200 or a tumor that is infiltrated with myeloid cells that are CD200⁻, and the fusion protein has an extracellular component comprising an extracellular portion of a CD200R.

In particular embodiments, a method of treating disease with a fusion protein as disclosed herein is provided, wherein the disease comprises acute myeloid leukemia (AML) and the fusion protein has an extracellular component comprising an extracellular portion of a CD200R, a SIRPα, a CD95 (Fas), a CD279 (PD-1), or a CD2.

In particular embodiments, a method of treating disease with a fusion protein as disclosed herein is provided, wherein the disease comprises a solid tumor and the fusion protein has an extracellular component comprising an extracellular portion of a TIM3, a CD223 (LAG3), a CD95 (Fas), a CD279 (PD-1), or a CD2.

In particular embodiments, a method of treating disease with a fusion protein as disclosed herein is provided, wherein the disease comprises breast cancer, ovarian cancer, colon cancer, prostate cancer, or multiple myeloma, and the fusion protein has an extracellular component comprising an extracellular portion of a CD200R. In some such embodiments, a CD200R-9aas-CD28Cys fusion protein is encoded by a polynucleotide that is at least 60%, at least 70%, at least 75%, at least 80%, at least 85%, at least 90%, at least 95%, or 100% identical to a polynucleotide sequence as set forth in SEQ ID NO.:7. In certain embodiments, a CD200R-9aas-CD28Cys fusion protein is encoded by a polynucleotide comprising or consisting of a polynucleotide sequence as set forth in SEQ ID NO.:7. In other embodiments, a CD200R-9aas-CD28Cys fusion protein comprises an amino acid sequence that is at least 90%, at least 91%, at least 92%, at least 93%, at least 94%, at least 95%, at least 96%, at least 97%, at least 98%, at least 99%, at least 99.5%, or 100% identical to an amino acid sequence as set forth in SEQ ID NO.:30. In further embodiments, a CD200R-9aas-CD28Cys fusion protein comprises or consists of an amino acid sequence as set forth in SEQ ID NO.:30.

In particular embodiments, a method of treating disease with a fusion protein as disclosed herein is provided, wherein the disease comprises ovarian cancer, pancreatic cancer, or AML, and the fusion protein has an extracellular component comprising an extracellular portion of a CD95 (Fas). In some such embodiments, a Fastm-4-1BB fusion protein is encoded by a polynucleotide that is at least 60%, at least 70%, at least 75%, at least 80%, at least 85%, at least 90%, at least 95%, or 100% identical to a polynucleotide sequence as set forth in SEQ ID NO.:185. In certain embodiments, a Fastm-4-1BB fusion protein is encoded by a polynucleotide comprising or consisting of a polynucleotide sequence as set forth in SEQ ID NO.:185. In other embodiments, a Fastm-4-1BB fusion protein comprises an amino acid sequence that is at least 90%, at least 91%, at least 92%, at least 93%, at least 94%, at least 95%, at least 96%, at least 97%, at least 98%, at least 99%, at least 99.5%, or 100% identical to an amino acid sequence as set forth in SEQ ID NO.:186. In further embodiments, a Fastm-4-1BB fusion protein comprises or consists of an amino acid sequence as set forth in SEQ ID NO.:186.

In particular embodiments, a method of treating disease with a fusion protein as disclosed herein is provided, wherein the disease comprises ovarian cancer, pancreatic cancer, or AML, and the fusion protein has an extracellular component comprising an extracellular portion of a CD95 (Fas). In some such embodiments, a Fas-4-1BBtm fusion protein is encoded by a polynucleotide that is at least 60%, at least 70%, at least 75%, at least 80%, at least 85%, at least 90%, at least 95%, or 100% identical to a polynucleotide sequence as set forth in SEQ ID NO.:187. In certain embodiments, a Fas-4-1BBtm fusion protein is encoded by a polynucleotide comprising or consisting of a polynucleotide sequence as set forth in SEQ ID NO.:187. In other embodiments, a Fas-4-1BBtm fusion protein comprises an amino acid sequence that is at least 90%, at least 91%, at least 92%, at least 93%, at least 94%, at least 95%, at least 96%, at least 97%, at least 98%, at least 99%, at least 99.5%, or 100% identical to an amino acid sequence as set forth in SEQ ID NO.:188. In further embodiments, a Fas-4-1BBtm fusion protein comprises or consists of an amino acid sequence as set forth in SEQ ID NO.:188.

Infectious diseases include those associated with infectious agents and include any of a variety of bacteria (e.g., pathogenic *E. coli, S. typhimurium, P. aeruginosa, B. anthracis, C. botulinum, C. difficile, C. perfringens, H. pylori, V. cholerae, Listeria* spp., *Rickettsia* spp., *Chlamydia* spp., and the like), mycobacteria, and parasites (including any known parasitic member of the Protozoa). Infectious viruses include eukaryotic viruses, such as adenovirus, bunyavirus, herpesvirus, papovavirus, papillomavirus (e.g., HPV), paramyxovirus, picornavirus, rhabdovirus (e.g., Rabies), orthomyxovirus (e.g., influenza), poxvirus (e.g., Vaccinia), reovirus, retrovirus, lentivirus (e.g., HIV), flavivirus (e.g., HCV, HBV) or the like. In certain embodiments, infection with cytosolic pathogens whose antigens are processed and displayed with HLA (MHC) Class I molecules, are treated with fusion proteins of this disclosure.

A fusion protein of this disclosure may be administered to a subject in cell-bound form (e.g., gene therapy of target cell population (mature T cells (e.g., CD8$^+$ or CD4$^+$ T cells) or other cells of T cell lineage)). In a particular embodiment, cells of T cell lineage expressing fusion proteins administered to a subject are syngeneic, allogeneic, or autologous cells.

Pharmaceutical compositions including fusion proteins of this disclosure may be administered in a manner appropriate to the disease or condition to be treated (or prevented) as determined by persons skilled in the medical art. An appropriate dose, suitable duration, and frequency of administration of the compositions will be determined by such factors as the condition of the patient, size, type and severity of the disease, particular form of the active ingredient, and the method of administration. The present disclosure provides pharmaceutical compositions comprising cells expressing a fusion protein as disclosed herein and a pharmaceutically acceptable carrier, diluents, or excipient. Suitable excipients include water, saline, dextrose, glycerol, or the like and combinations thereof.

In some embodiments, the disclosure is directed to a method of increasing the activity of an immune cell, enhancing or prolonging an immune response, stimulating an antigen-specific T cell response, inhibiting an immunosuppressive signaling pathway, treating cancer or a tumor, inhibiting immune resistance of cancer cells, or treating an infection, comprising administering to a subject in need thereof an effective amount of a host cell expressing a fusion protein as described herein. In further embodiments, a host cell for use in any of the aforementioned methods further expresses an engineered antigen-specific TCR, an engineered antigen-specific high affinity TCR, a CAR, a co-stimulatory molecule, or any combination thereof. In particular embodiments, methods of treating leukemia are provided, comprising co-expressing a fusion protein as disclosed herein and a recombinant, antigen-specific TCR.

In some embodiments, there are provided methods of inducing or enhancing a Class I HLA response by a CD4+ T cell, comprising administering to a subject in need thereof an effective amount of a CD4+ T cell expressing a fusion protein as described herein. In further embodiments, a host cell for use in inducing or enhancing a Class I HLA response by a CD4+ T cell further expresses an engineered antigen-specific TCR, an engineered antigen-specific high affinity TCR, a CAR, a co-stimulatory molecule, or any combination thereof.

In any of the aforementioned embodiments, the methods are effective in the absence of administering exogenous IL-2.

In some embodiments, there are provided methods for increasing cytokine production in an immune cell (e.g., CD4$^+$ T cell or a CD8$^+$ T cell) of a subject, comprising administering to a subject in need thereof an effective amount of a fusion protein, or a vector encoding the fusion protein, as disclosed herein.

In some embodiments, there are provided methods for increasing cytokine production in an immune cell (e.g., CD4$^+$ T cell or a CD8$^+$ T cell), comprising contacting the immune cell with a fusion protein, or a vector encoding the fusion protein, as disclosed herein. In further embodiments, the immune cell further expresses an engineered antigen-specific TCR, an engineered antigen-specific high affinity TCR, a CAR, a co-stimulatory molecule, or any combination thereof. In some embodiments, the cytokine that is increased comprises interferon gamma (IFNγ), tumor necrosis factor (TNFα), or interleukin-2 (IL-2).

In still other embodiments, a subject of any of the aforementioned methods is further treated with an adjunctive therapy, such as a chemotherapy. Exemplary chemotherapeutic agents include, for example, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSKTM; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (Taxol™, Bristol-Myers Squibb Oncology, Princeton, N.J.) and docetaxel (Taxotere™, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DNIFO); retinoic acid; esperamicins, capecitabine; and pharmaceutically acceptable salts, acids or derivatives of any of the above.

In some embodiments, the adjunctive therapy is a vaccine, an inhibitor of an immunosuppression signal, a B-Raf inhibitor, a MEK inhibitor, a tyrosine kinase inhibitor, a cytotoxic agent, a chemotherapeutic, or any combination thereof. In some embodiments, the inhibitor of an immunosuppression signal is an antibody or siRNA. In some embodiments, the antibody or siRNA is specific for PD-1, PD-L1, PD-L2, CTLA4, LAG3, KIR, CD244, B7-H3, B7-H4, BTLA, HVEM, GALS, TIM3, A2aR, or any combination thereof.

EXAMPLES

Example 1

CD200R-CD28 Fusion Protein Constructions

Figure 1A:
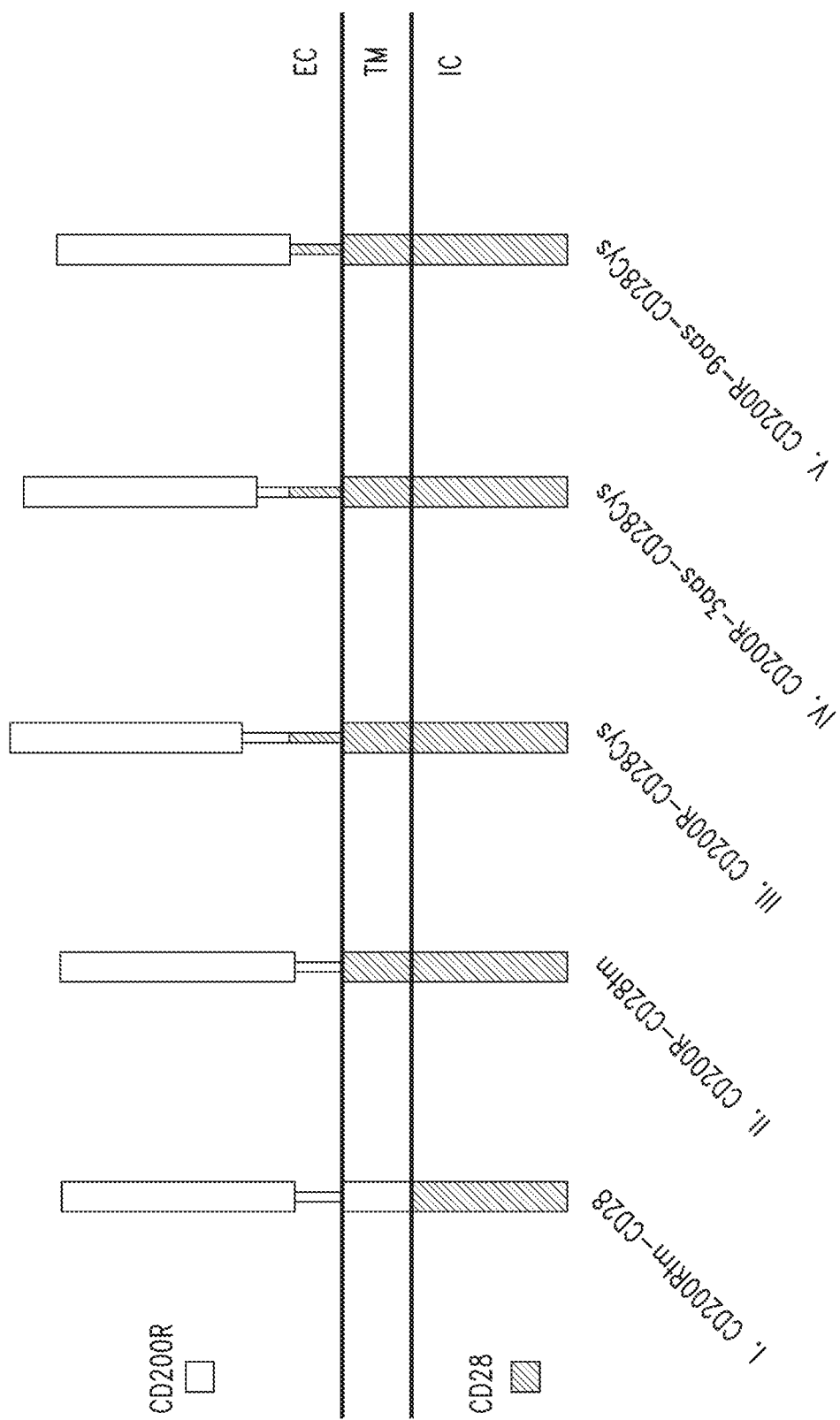
FIGS. 1A and 1B show CD200R-CD28 constructs expressed at high levels on primary murine CD8$^+$ T cells. (A) Schematic representation of exemplary CD200R-CD28 constructs. Construct "I" contains CD200R extracellular ("EC") and transmembrane ("TM") domains and a CD28 intracellular ("IC") signaling domain (CD200Rtm-CD28). Construct "II" contains the extracellular domain of CD200R and the transmembrane and intracellular domains of CD28 (CD200R-CD28tm). Constructs "III-V" also incorporate a portion of the extracellular domain of CD28 to the transmembrane-proximal cysteine to promote multimerization and enhance CD28 signaling. To account for any extra extracellular amino acids (e.g., from one to about 50 amino acids; such as exemplary murine constructs disclosed here contain an extra nine (9) amino acids and exemplary human constructs disclosed here contain twelve (12) amino acids), some constructs have a truncated portion of an extracellular or intracellular domain (e.g., a CD200R that preserves an N linked glycosylation site). For example, construct IV has a truncated portion of CD200R that is truncated by 3 amino acids. Construct V has a truncated portion of CD200R that is truncated 9 amino acids. Constructs "I", "II", and "V" maintain the short spatial distance between the cells (e.g., between a T cell and an antigen presenting cell) and may co-localize with the TCR within the cSMAC and deliver a strong co-stimulatory signal. (B) Transgenic expression of murine CD200R-CD28 constructs on TCR$_{gag}$ T cells as detected by anti-CD200R antibody. The control vector contains green fluorescent protein (GFP).

Exemplary fusion proteins as described herein are illustrated using schematic representations in FIG. 1A. Exemplary fusion proteins include immunomodulatory fusion proteins (IFPs) comprised of the extracellular domain of CD200R or a portion thereof, and an intracellular signaling domain of CD28 or a portion thereof (FIG. 1A, constructs I-V). The hydrophobic component may be comprised of the transmembrane domain of either CD200R (FIG. 1A, construct I) or CD28 (FIG. 1A, constructs II-V), or portions thereof. In some exemplary CD200R-CD28 fusion proteins, the hydrophobic component comprises the transmembrane domain of CD28 and the extracellular component further comprises an extracellular portion of CD28, particularly an extracellular cysteine residue adjacent to the hydrophobic component (e.g., FIG. 1A construct III, CD200R-CD28Cys; construct IV, CD200R-3aas-CD28Cys; and construct V, CD200R-9aas-CD28Cys). The extracellular component may comprise all or a portion of the extracellular domain of CD200R. In some embodiments, the extracellular component comprises the entire extracellular domain of CD200R (FIG. 1A, constructs In other examples, the extracellular component comprises the first 235 amino acids (preserving an N-linked glycosylation site) (e.g., FIG. 1A, construct IV, CD200R-3aas-CD28Cys) or the first 229 amino acids (e.g., FIG. 1A, construct V, CD200R-9aas-CD28Cys) from the N-terminus of CD200R. The size of the extracellular component, which may be manipulated by adjusting the fusion protein construct, may affect the ability of the fusion protein to enter the immunological synapse and co-localize with the TCR within the cSMAC to deliver a strong co-stimulatory signal. Additionally, the CD200R-CD28 construct has the capacity to convert what would typically be an inhibitory signal from the binding of CD200R to its target into a positive signal generated by the CD28 intracellular signaling domain.

An exemplary nucleic acid molecule encoding a CD200R-CD28 fusion protein comprises the following elements (5' to 3'): Extracellular Component (CD200R)-Multimerization Domain (CD28 Cysteine)-Hydrophobic Component (CD28 transmembrane)-Intracellular Component (CD28 intracellular). In some embodiments, a nucleic acid molecule encoding a CD200R-CD28 fusion protein comprises a nucleic acid molecule as set forth in any one of SEQ ID NOS.:47-51 or 1, 6, 7, 10, 12, 14, or 15.

Nucleic acids encoding the constructs were ordered from Invitrogen or generated in-house by PCR then directionally TOPO-cloned into the pENTR™/D-TOPO® vector (Invitrogen), and transferred into the retroviral vector pMP71-attR using Gateway® technology (Invitrogen). In certain embodiments, the nucleic acid molecules encoding IFPs of the instant disclosure were codon optimized before cloning into the pMP71-attR retroviral vector.

Example 2

Transgenic Expression of CD200R-CD28 Constructs

A preclinical mouse model for disseminated leukemia, based on the murine C57BL/6 Friend virus-induced erythroleukemia (FBL) and $TCR_{gag}$ transgenic mice, was used to determine if CD200R-CD28 chimeric receptors can improve T cell function.

TCR transgenic mice were generated to produce CD8⁺ T cells specific for the gag epitope ($TCR_{gag}$). C57BL/6 (B6) mice were purchased from the Jackson Laboratory. $TCR_{gag}$ transgenic mice express a TCR transgene specific for the Friend virus gag epitope in CD8⁺ T cell (Öhlén et al., *J. Immunol.* 166: 2863-2870, 2001). All animal studies performed were approved under the University of Washington Institutional Animal Care and Use Committee protocol (Protocol #2013-01). The murine B6 Friend virus induced erythroleukemia (FBL) expresses the F-MuLV encoded gag epitope (peptide CCLCLTVFL (SEQ ID NO.:213)).

CD200R-CD28 chimeric constructs based on murine genes were inserted into the pMP71 retroviral vector and used to transduce primary mouse splenocytes stimulated with anti-CD3 and anti-CD28 antibodies. Constructs were designed as described in Example 1, and ordered from Invitrogen or generated in-house by PCR. The constructs were then directionally TOPO-cloned into the pENTR™/D-TOPO® vector (Invitrogen), and transferred into the retroviral vector pMP71-attR using Gateway® technology (Invitrogen). The retroviral packaging cell line Plat-E (Morita et al., 2000, *Gene Therapy* 7:1063-1066, 2000; Cell Biolabs, Inc.) was transduced with the retroviral vector using effectene transduction reagent (Qiagen). Viral supernatant was collected on days 2 and 3 and then used to transduce TCR$_{gag}$ T cells.

One day prior to the transfection, TCR$_{gag}$ T cells were stimulated with anti-CD3/CD28 and 100 U/mL rhIL-2. Transduction of TCR$_{gag}$ T cells was performed in 12 well plates in the presence of IL-2 and polybrene by spinfection for 90 minutes at 1000 g. FBL cells were transduced with CD200 with polybrene spinfection, similar to T cell transduction, and subsequently sorted to generate a homogenous population.

Figure 1B:
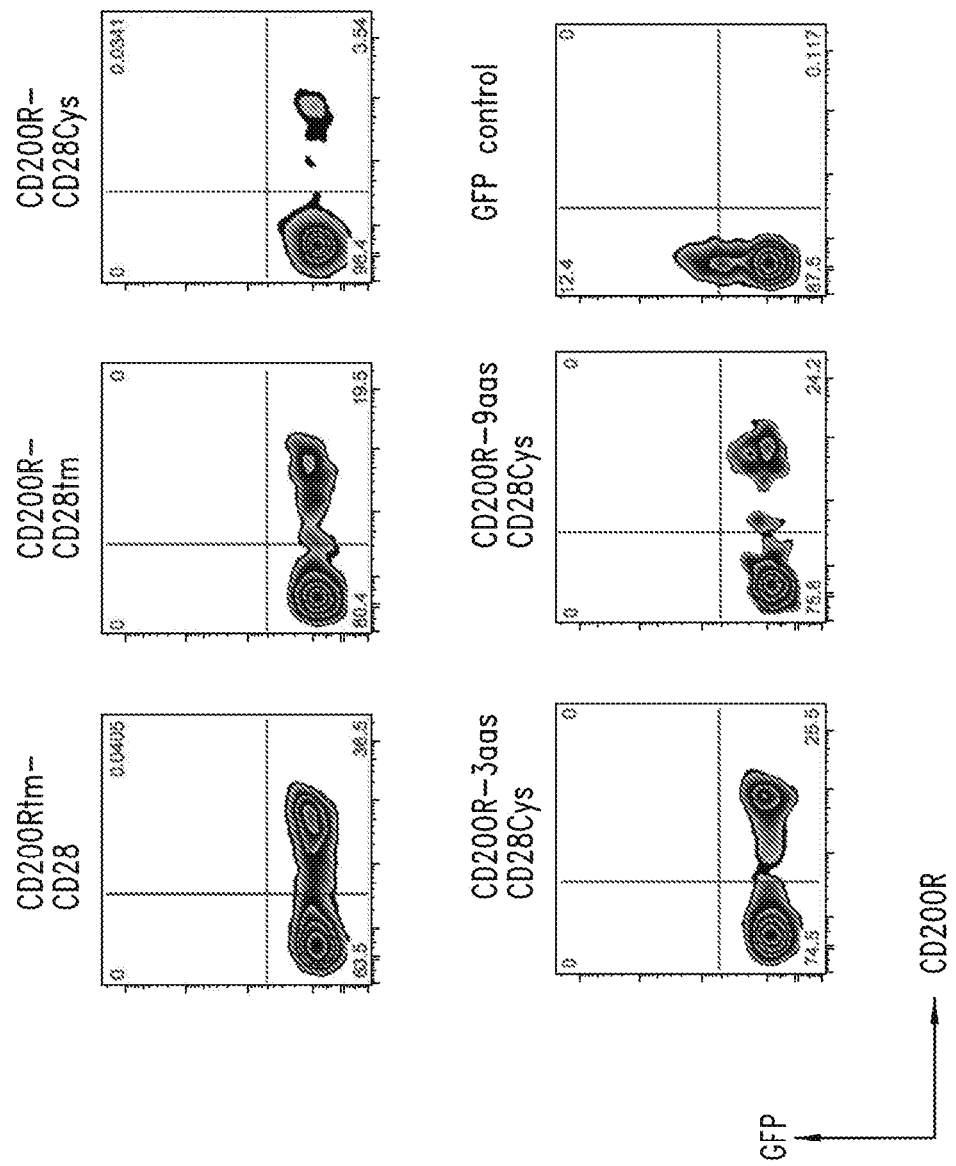

Five days after transduction, CD8$^+$ T cells were analyzed for construct expression by anti-CD200R antibody staining and flow cytometry (FIG. 1B). A vector encoding green fluorescent protein (GFP) was used as a control. Transduction efficiency ranged from 4-36% and the mean fluorescent intensity (MFI) of the transduced cells was similar between constructs.

Example 3

CD200R-CD28 Constructs Promote In Vitro Proliferation, Accumulation, and Effector Function of Transduced T Cells The CD200R-CD28 constructs described in Examples 1 and 2 were assessed for their abilities to promote proliferation, accumulation, and effector function of TCR$_{gag}$ T cells.

Expansion of Effector Cells In Vitro

TCR$_{gag}$ effector cells were generated in vitro as previously described (Stromnes et al., *J. Clin. Invest.* 120: 3722-34, 2010). Irradiated antigen presenting splenocytes (5×10$^6$), irradiated FBL (3×10$^6$), and TCR$_{gag}$ tg cells (10$^6$) were cultured together with IL-2 (50 U/mL) in 10 mL of culture media (IMDM supplemented with non-essential amino acids, 2 µM glutamine, 100 U/mL penicillin/streptomycin, 10% FBS, and 50 µM 2-mercapatoethanol). T cells were restimulated weekly and assessed by flow cytometry 5-7 days after the last stimulation.

In Vitro T Cell Proliferation Assay

TCR$_{gag}$ T cells were transduced as in Example 2. To assess T cell proliferation in vitro, TCR$_{gag}$ T cells were stained with CellTrace Violet (CTV, Life Technologies) according to the manufacturer's protocol. CTV-labeled Tg T cells (10$^5$) and GFP control T cells were stimulated with titrating numbers of CD200$^-$ FBL or CD200$^+$ FBL cells. After 3 days, CTV dilution of TCR$_{gag}$ T cells was assessed by flow cytometry.

Figure 2A:
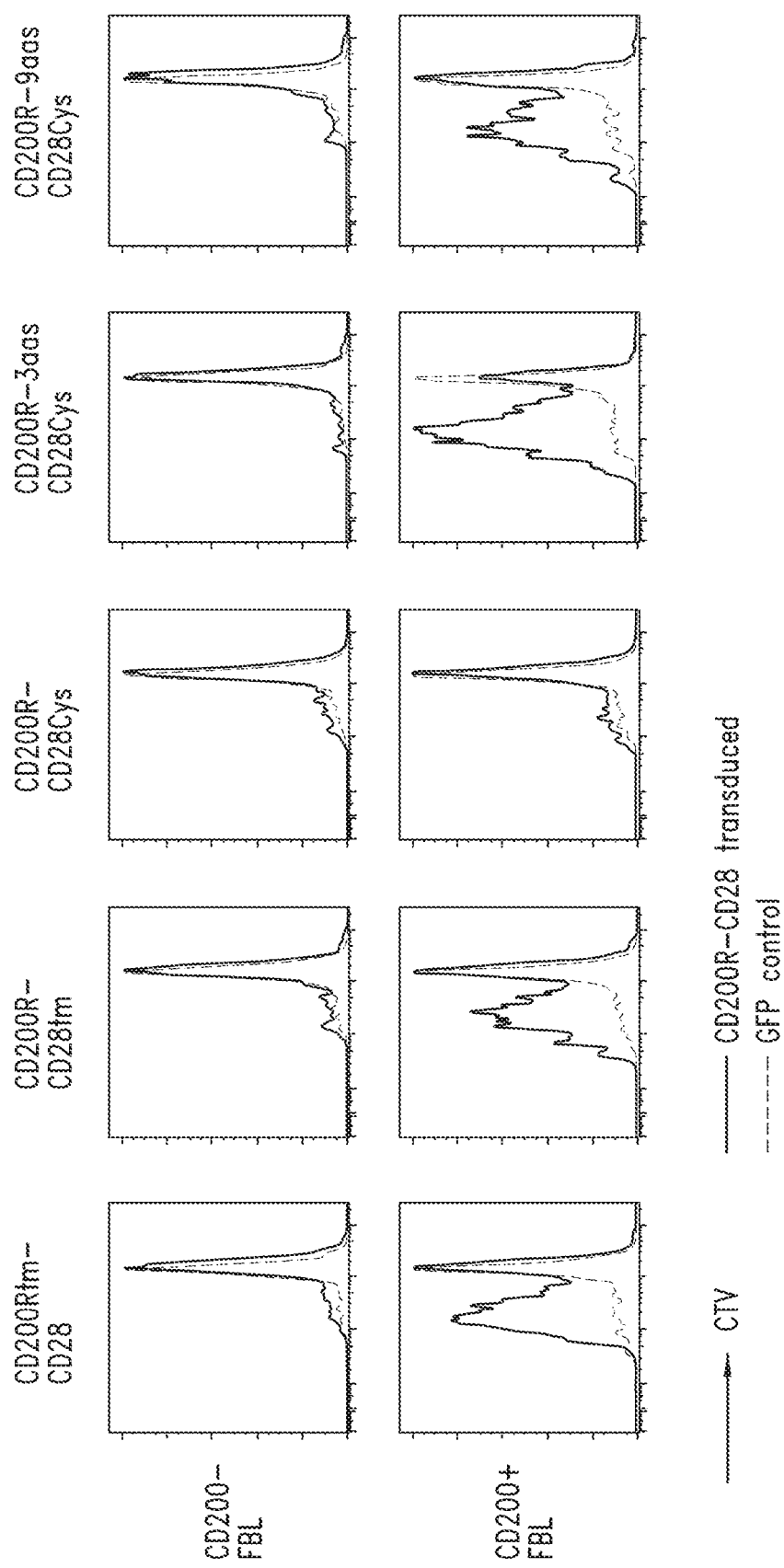

Flow cytometry results indicating the number of TCR$_{gag}$ T cells after stimulation with titrating numbers of CD200$^+$ FBL cells (upper) or CD200$^-$ FBL (lower) are shown in FIG. 2A. Four of the five CD200R-CD28 constructs tested dramatically improved proliferation of TCR$_{gag}$ T cells in response to CD200$^+$ FBL (blue lines) compared to GFP control-transduced T cells (red lines).

In Vitro T Cell Accumulation Assay

To determine if the enhanced proliferation also resulted in increased accumulation of transduced cells, the proportion of transduced cells in the total TCR$_{gag}$ population over multiple cycles of stimulation with irradiated CD200$^+$ FBL was measured.

Figure 2B:
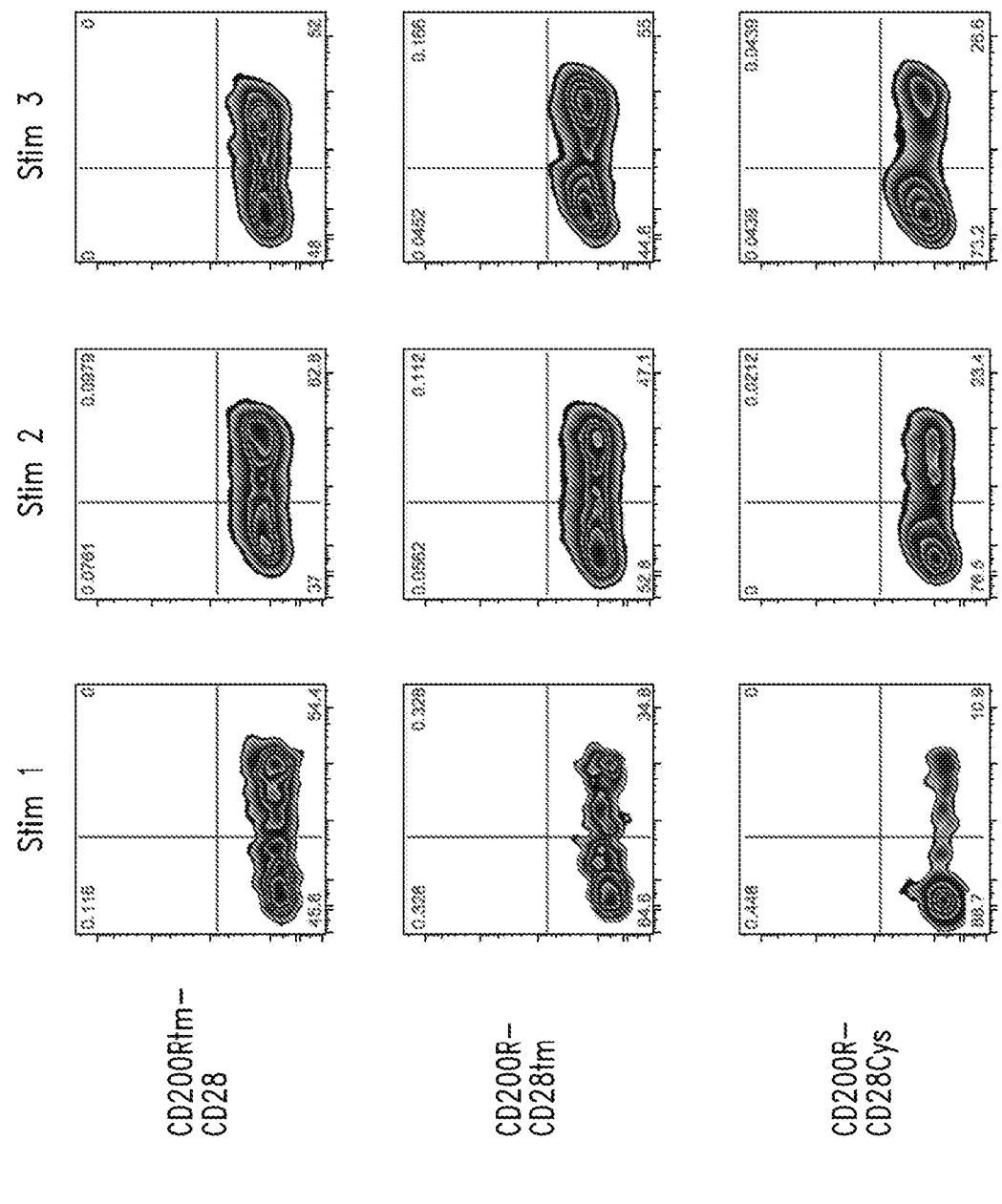
Figure 2B:
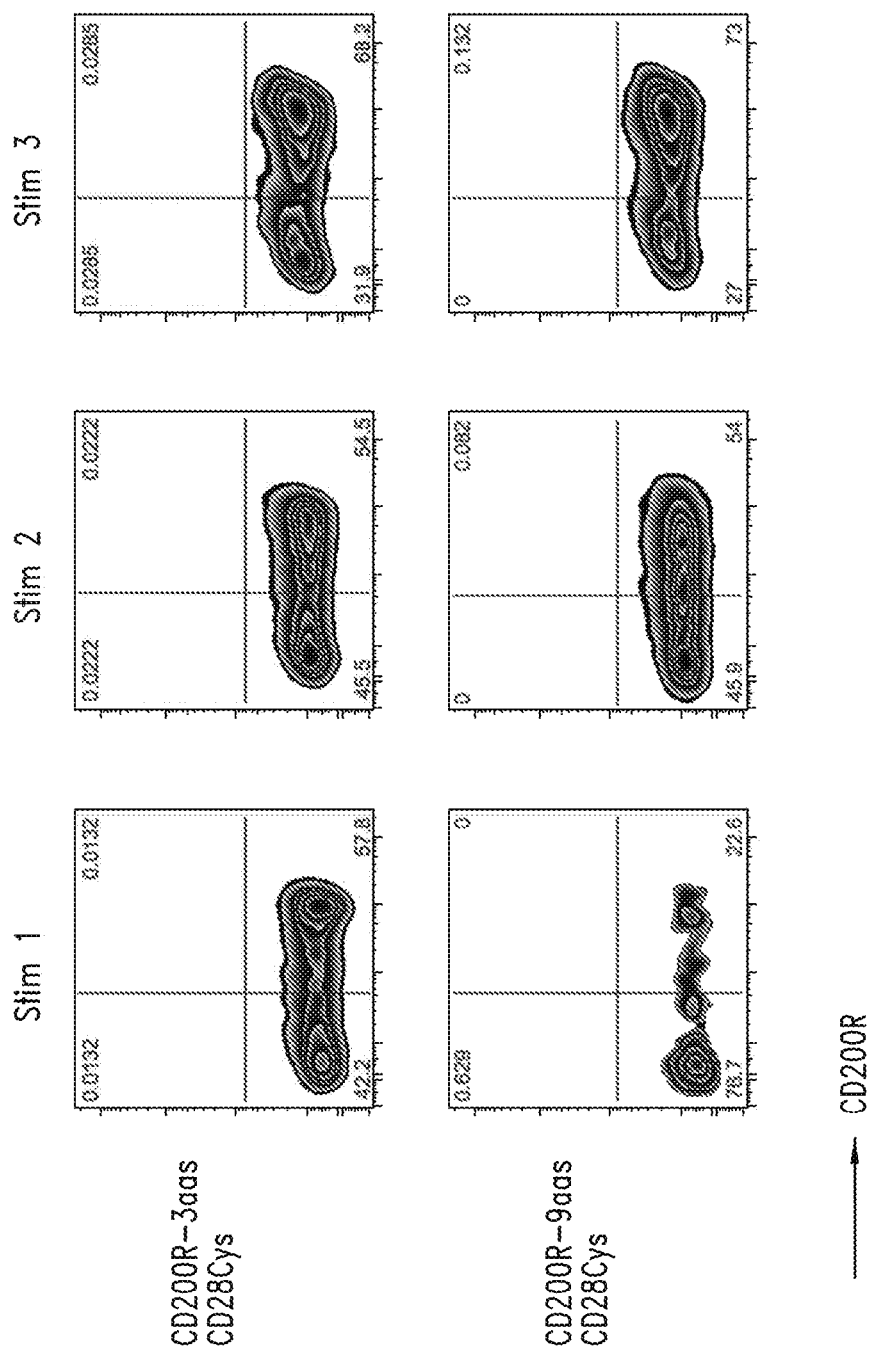

Several of the constructs promoted accumulation of transduced T cells, including CD200R-CD28tm, CD200R-CD28Cys, CD200R-3aas-CD28Cys, and CD200R-9aas-CD28Cys (FIG. 2B). Of these constructs, CD200R-9aas-CD28Cys exhibited the greatest increase in transduced T cells over multiple stimulations, resulting in more than a 3-fold expansion over 3 stimulations.

In Vitro T Cell Enrichment Assay

Figure 2C:
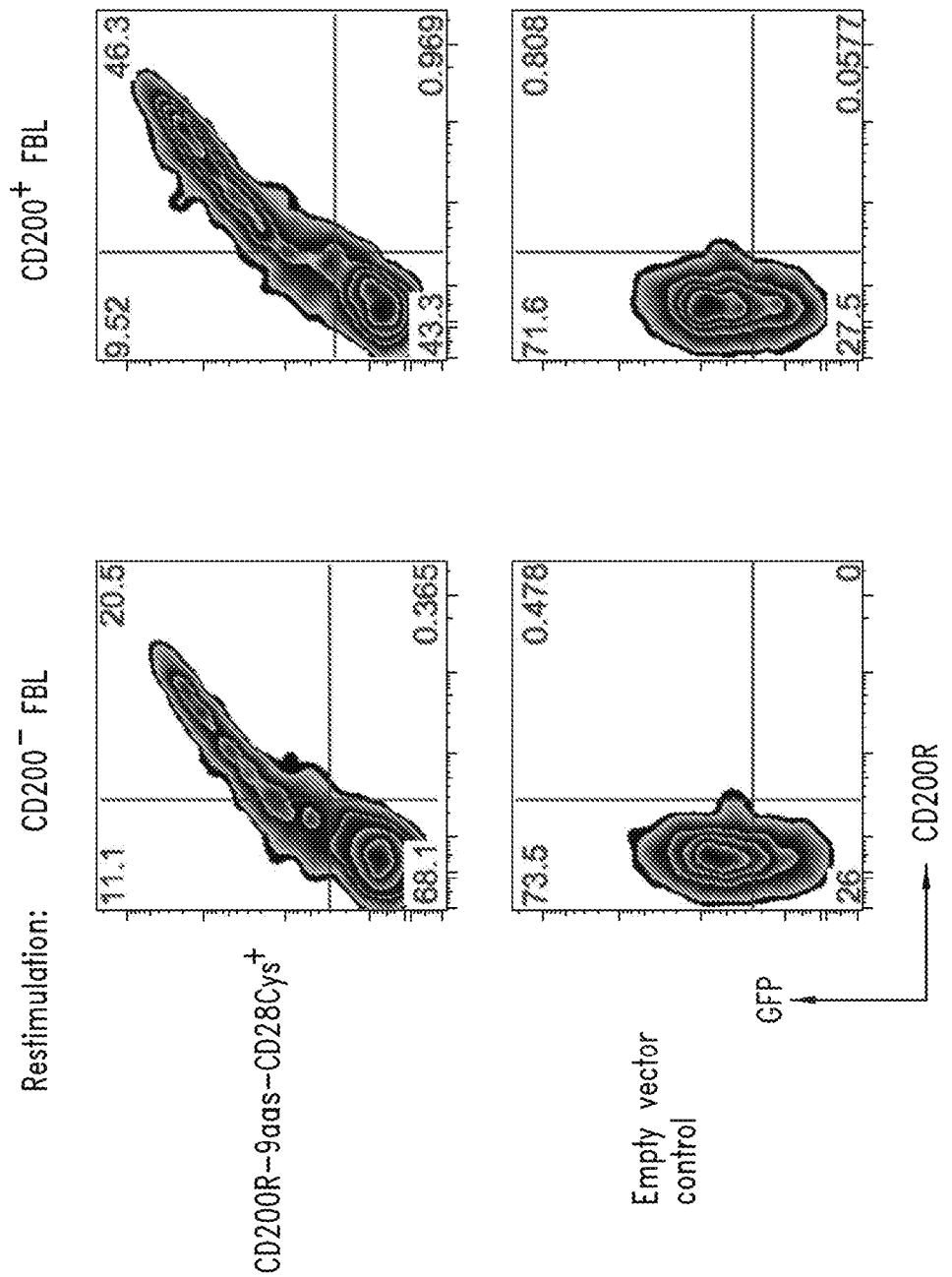

A mixed population of transduced and nontransduced CD8$^-$ T cells were restimulated with CD200$^+$ or CD200$^-$ irradiated FBL cells to determine if restimulation would enrich the population for the transduced CD200R-9aas-CD28Cys IFP$^+$ T cells. Repeated restimulation with irradiated CD200$^-$ tumor cells enriched the cells transduced with the IFP compared to wild type T cells, demonstrating that recognition of a target expressing the ligand for the CD200R-9aas-CD28Cys IFP enhances the response (FIG. 2C).

In Vitro Colocalization Assay

Figure 2D:
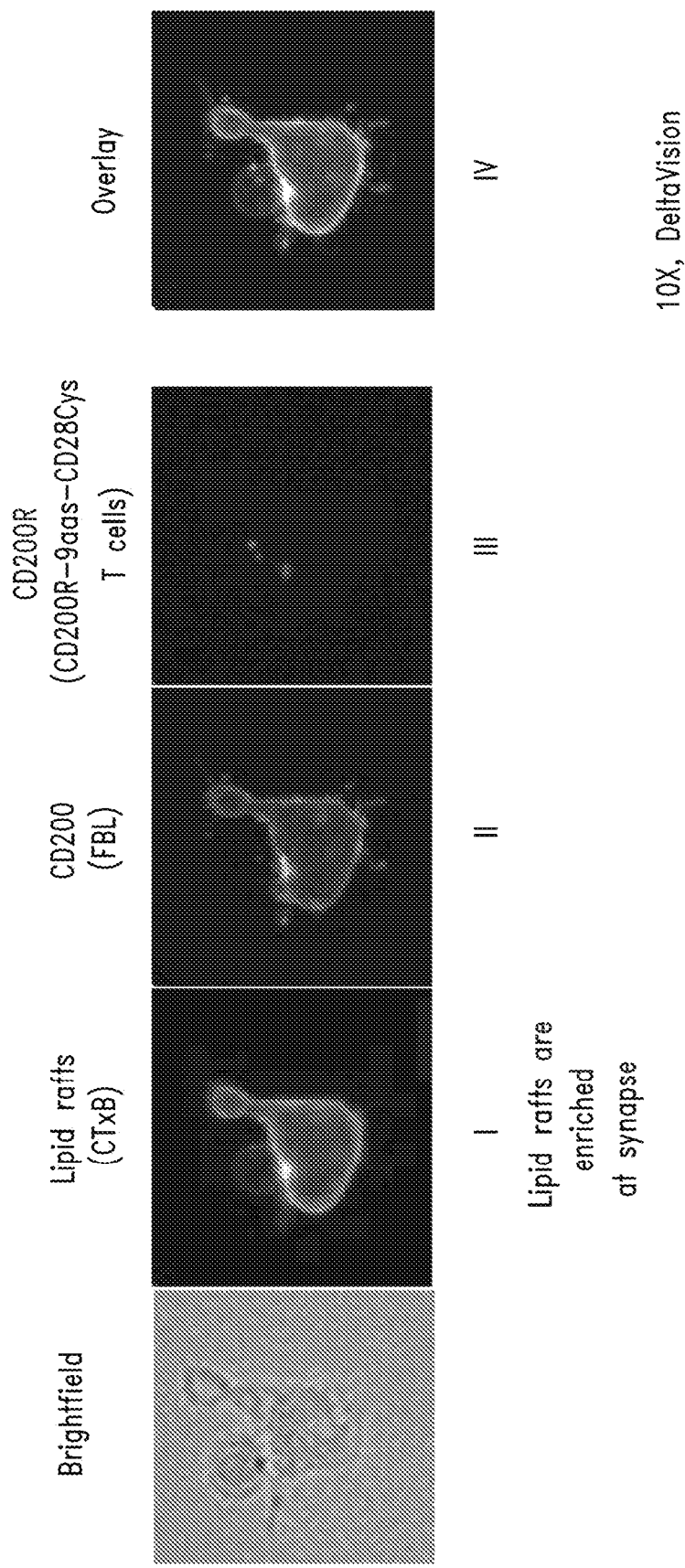

Transduced T cells were imaged by microscopy to determine if the CD200R-9aas-CD28Cys IFP colocalized with the cognate ligand in the immunological synapse (IS) during T cell activation. CTxB was used to stain lipids within the cell membrane, which are enriched at the synapse (FIG. 2D, panel I). Labeled antibodies that target CD200 expressed by the FBL cell (FIG. 2D, panel II) or CD200R expressed by the T cell (FIG. 2D, panel III) were used to visualize the location of the molecules in relation to the IS. CD200 ligand and CD200R colocalized within the IS (FIG. 2D, panel IV), demonstrating that the construct is sized appropriately to be accommodated by the immunologic synapse.

CFSE-Based Cytotoxicity Assay

Increased CD28 signaling also promotes effector function (Chen and Flies, *Nat. Rev. Immunol.* 13: 227-242, 2013). CD200R-CD28 fusion protein-transduced T cells were tested for increased killing of target tumor cells. FBL and control EL4 tumors were incubated for 10 minutes at room temperature with 2.5 µM (CFSE$_{hi}$) or 0.25 µM) (CFSE$^{lo}$) CFSE in PBS, respectively. Excess dye was removed by washing tumor cells in serum-containing media. A 1:1 mixture of EL4 and FBL tumor cells was incubated with titrated numbers of CD200R-CD28 or GFP vector transduced TCR$_{gag}$ in vitro expanded effector T cells for 4 hours in 96-well, round-bottom plates at 37° C. and 5% CO$_2$. Specific FBL lysis was determined by flow cytometric analyses of the % CFSE$_{hi}$ (FBL) of total CFSE positive cells (FBL+EL4) remaining in the well.

Figure 2E:
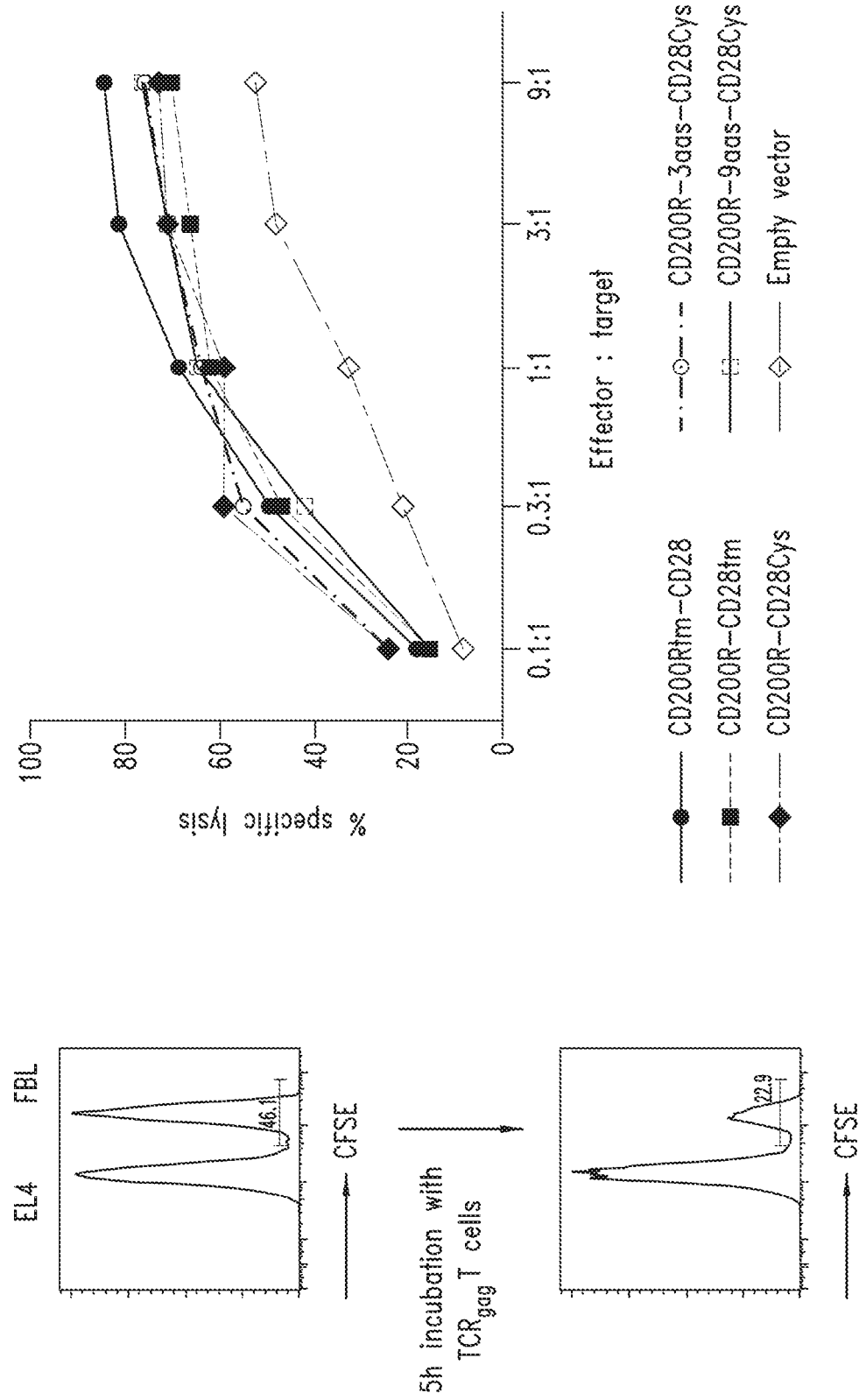
Figure 2G:
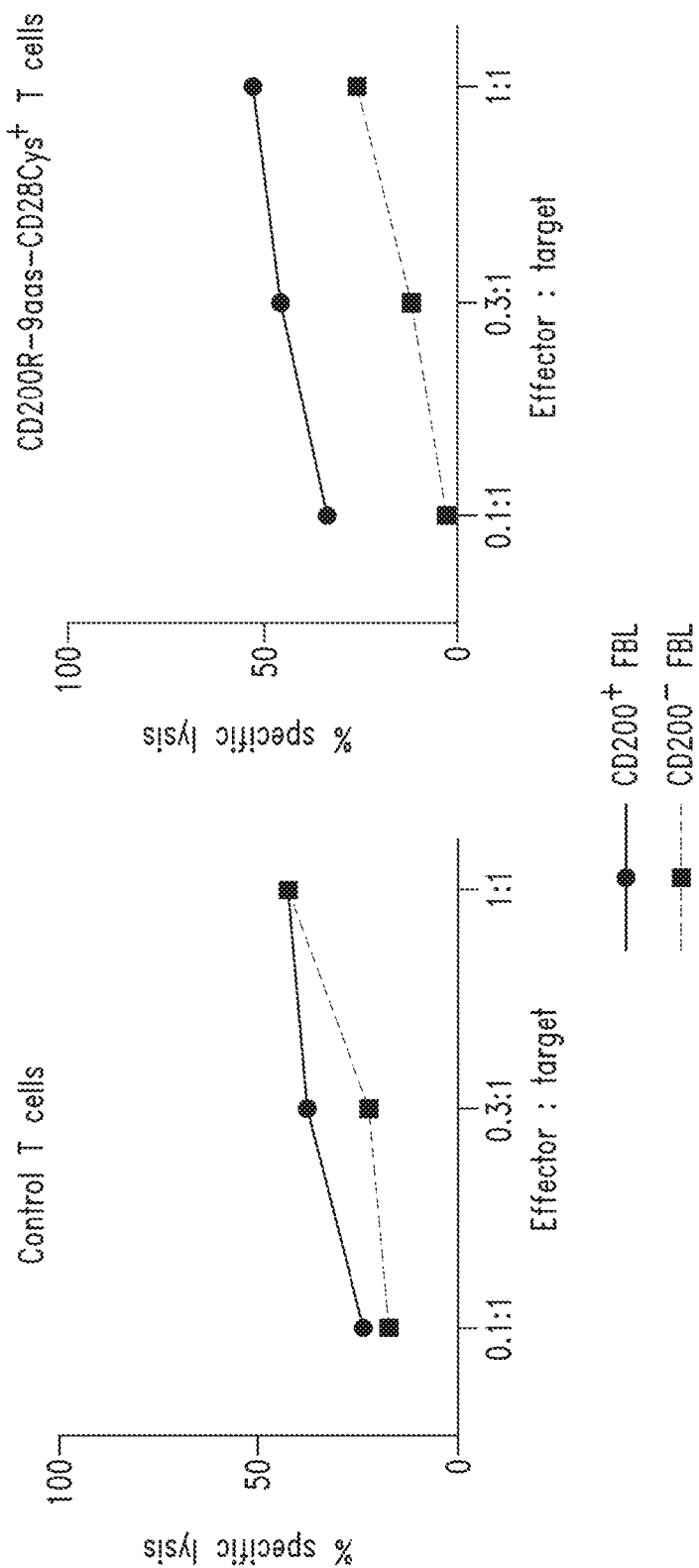

TCR$_{gag}$ T cells transduced with CD200R-CD28 constructs displayed an enhanced ability to lyse FBL tumor in vitro compared to TCR$_{gag}$ T cells transduced with an empty vector (FIGS. 2E, 2G). Target tumor cells were labeled with different dilutions of the fluorescent dyes CellTrace Violet (CTV) or CF SE to generate a 1:1:1 mix of EL4 cells (CTV+), CD200$^-$ FBL (CFSE) and non-specific EL4) (CFSE$^{lo}$) control targets (FIG. 2F). Additionally, control GFP-transduced TCR$_{gag}$ T cells lysed CD200$^-$ FBL and CD200$^+$ FBL at equal efficiencies (FIG. 2G). By contrast, TCR$_{gag}$ T cells transduced with CD200R-9aas-CD28Cys exhibited increased killing of CD200$^+$ FBL cells compared to control T cells, lysing over 40% of CD200$^+$ FBL at the lowest E:T ratio tested (FIG. 2G).

Taken together, these data show that CD200R-CD28 constructs function to increase accumulation and the lytic activity of transduced T cells in response to tumor cell stimulation.

Example 4

T Cells Transduced with CD200R-9AAS-CD28CYS Exhibit Enhanced Accumulation In Vivo in Response to Recognition of FBL B6 mice were injected with $4 \times 10^6$ live FBL leukemia intraperitoneal (i.p.) as previously described (Stromnes et al., *J. Clin. Invest.* 120: 3722-34, 2010). After allowing 5 days for the FBL to disseminate, mice received 180 mg/kg cyclophosphamide (Cy, commercially available as Cytoxan®) i.p. at least 6 hours before transfer of the effector T cells. For survival studies, $10^5$ $TCR_{gag}$ T cells which previously underwent 1-3 stimulations in vitro were transferred into tumor-bearing mice. To assess short-term proliferation and accumulation, $2 \times 10^6$ of each of fusion protein-transduced and a GFP-control-transduced T cells were co-injected into tumor-bearing mice and the mice euthanized for analysis 8 days later. Mice were regularly monitored for tumor burden and euthanized if evidence of tumor progression predicted mortality would occur within 24-48 hours.

Figure 3A:
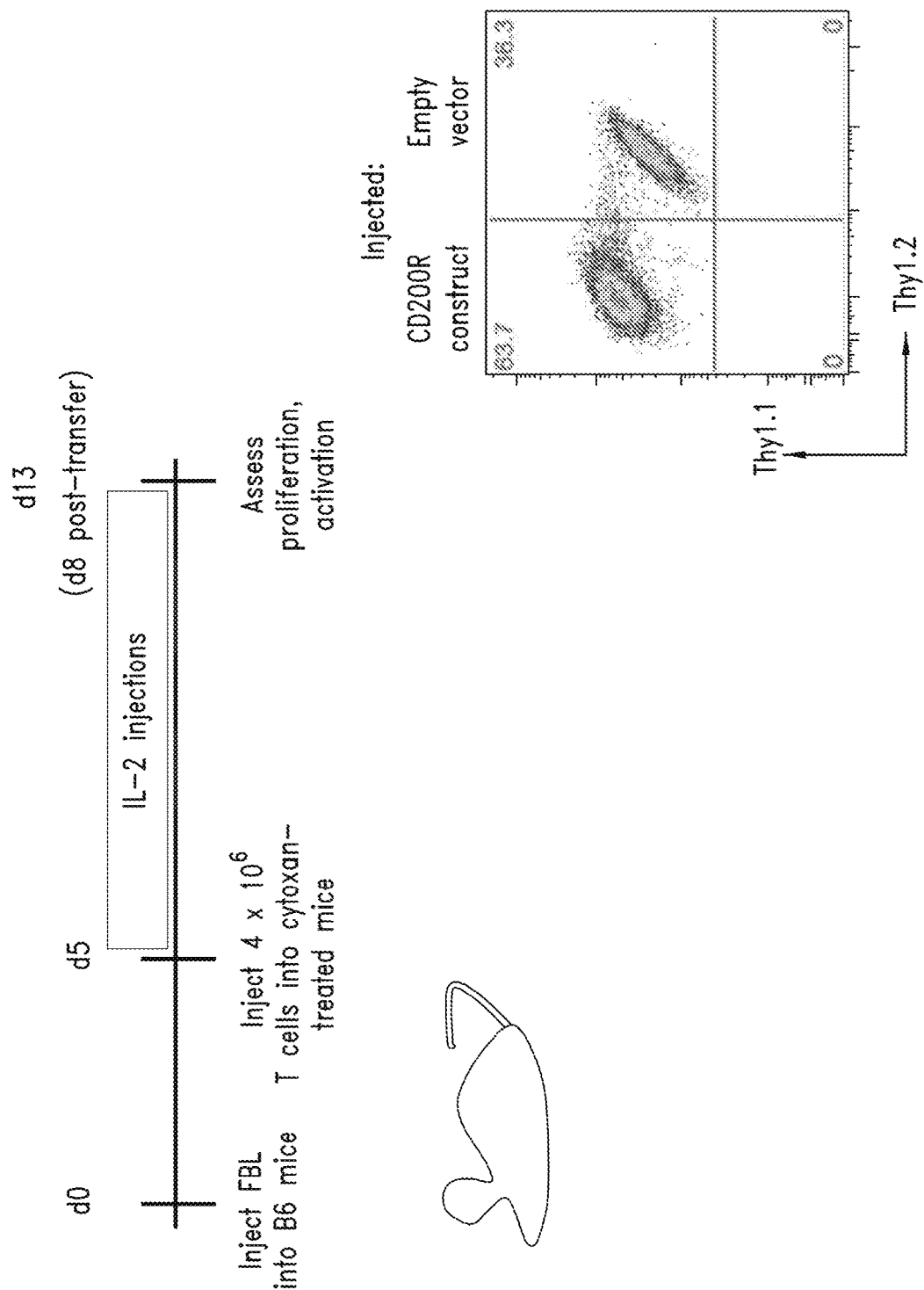
FIGS. 3A to 3D show that T cells transduced with CD200R-9aas-CD28Cys preferentially accumulate in response to tumor challenge in vivo and express surface proteins consistent with an effector phenotype after injection into cyclophosphamide-treated, FBL-bearing mice. Transduced $TCR_{gag}$ T cells were generated as described in Example 2. (A) Experimental schematic. C57BL/6 mice were injected with $4 \times 10^6$ CD200⁺ FBL cells. Five days later, CD200R-9aas-CD28Cys (Thy1.1 homozygous) and eGFP control (Thy1.1 heterozygous) $TCR_{gag}$ T cells were co-injected into cyclophosphamide-treated FBL-bearing B6 mice at $4 \times 10^6$ cells/mouse. IL-2 was administered every 2 days ($2 \times 10^4$ U/dose). On day 8 post-T cell transfer, mice were euthanized and spleens and inguinal lymph nodes harvested. (B) CD200R-9aas-CD28Cys $TCR_{gag}$ T cells accumulate in the spleen in response to FBL. (LN=lymph node; Spl=spleen). (C) Comparison of surface proteins 3 days post-transfer for T cells transduced to express CD200R-9aas-CD28Cys, T cells transduced with an empty vector, and endogenous T cells. CD200R-9aas-CD28Cys $TCR_{gag}$ T cells expressed reduced CD62L compared to control $TCR_{gag}$ T cells, suggesting an effector T cell phenotype. (D) Comparison of surface proteins 15 days post-transfer for cells transduced to express CD200R-9aas-CD28Cys⁺ T cells, T cells transduced with an empty vector, and endogenous T cells. CD200R-9aas-CD28Cys $TCR_{gag}$ T cells express similar levels of cell surface proteins compared to control $TCR_{gag}$ T cells.
Figure 3B:
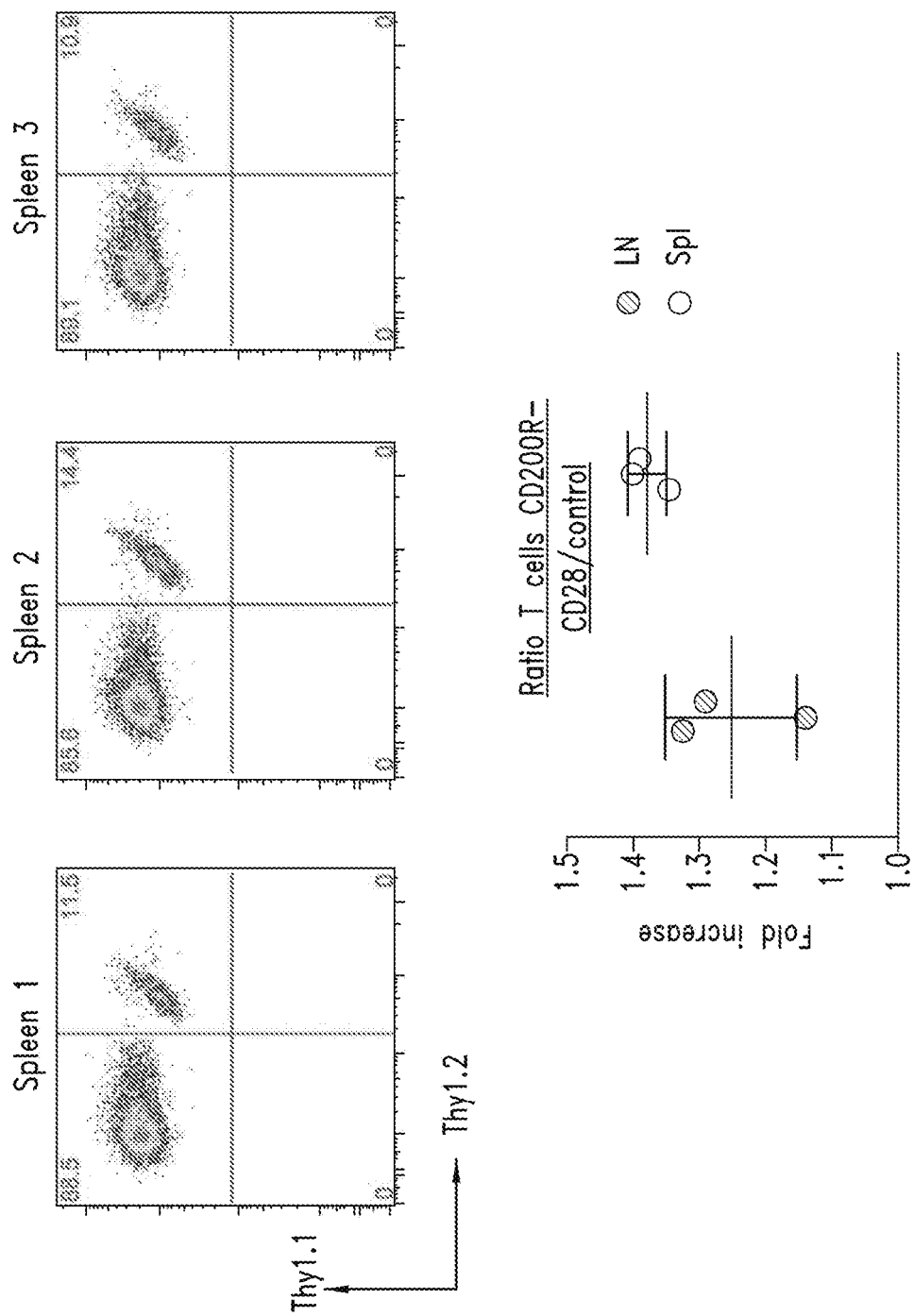
Figure 3C:
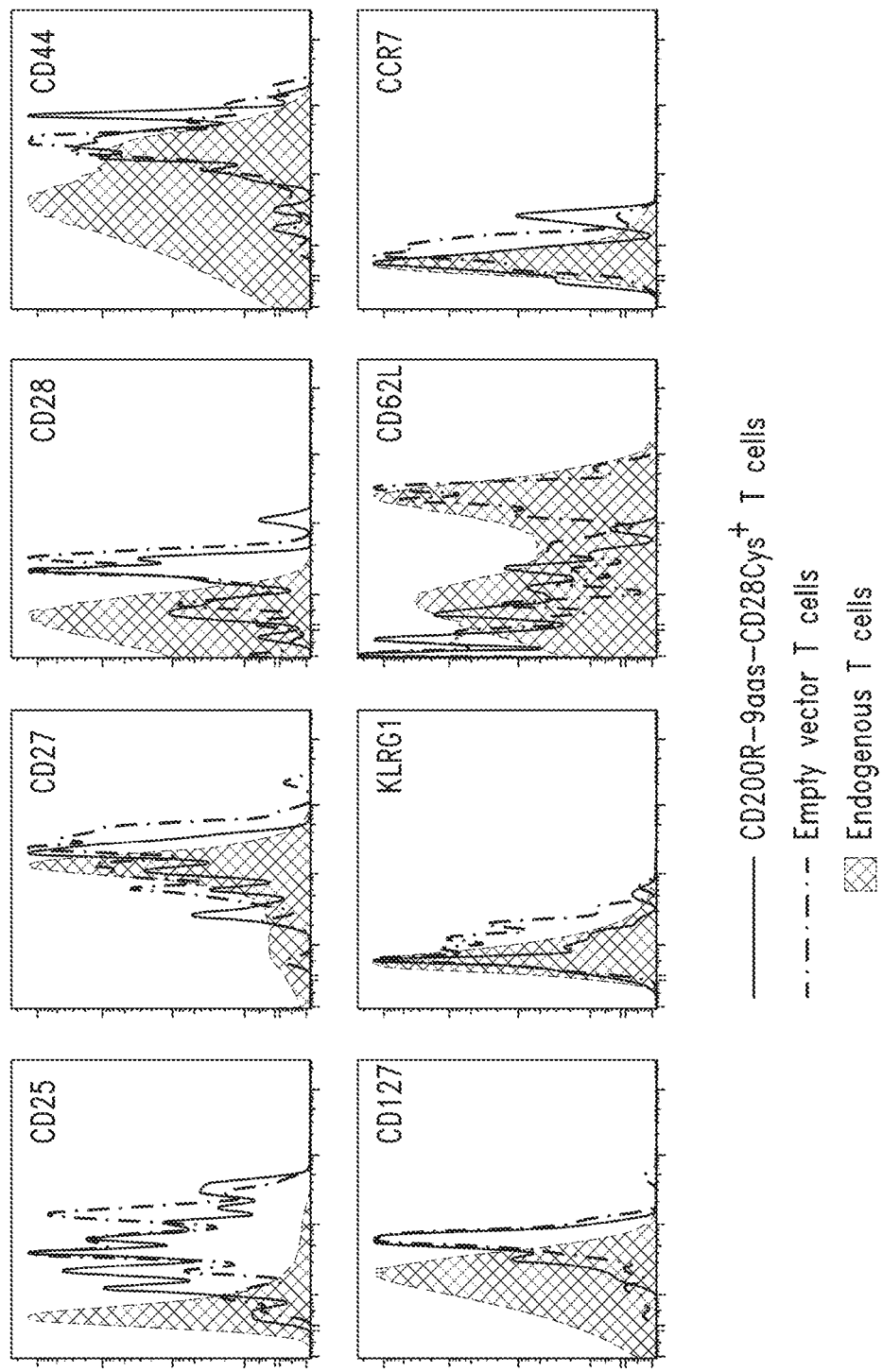
Figure 3D:
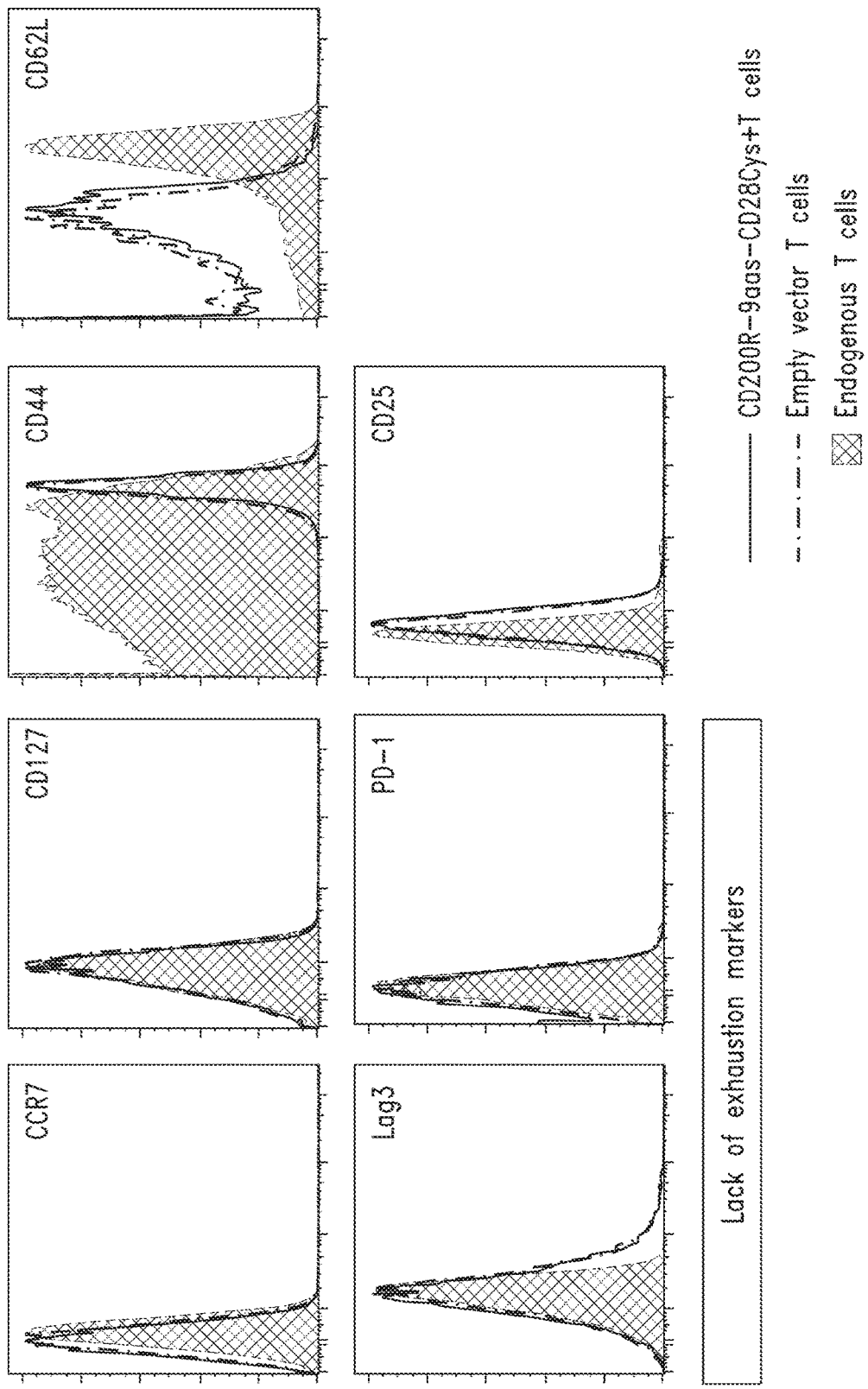

To assess whether CD200R-9aas-CD28Cys fusion protein-transduced T cells exhibited greater proliferation and accumulation in vivo in response to recognition of FBL, a mixed population of fusion protein-transduced and control cells were transferred into tumor-bearing mice and the ratio of cells by ex vivo analysis were compared 8 days after transfer (FIG. 3A). By use of congenic markers, transduced T cells were detected at a 1.2-1.4-fold greater ratio over control cells in both the spleen and lymph nodes relative to the ratio that was injected (FIG. 3B). Transduced CD200R-9aas-CD28Cys$^+$ $TCR_{gag}$ T cells exhibited reduced CD62L expression 3 days post-transfer to tumor-bearing mice, suggesting an effector T cell phenotype (FIG. 3C). By day 15, transduced and control T cells exhibited similar phenotypes, including a lack of exhaustion markers (FIG. 3D). Similar to the in vitro findings, T cells that expressed CD200R-9aas-CD28Cys displayed increased accumulation in response to tumor stimulation in vivo. Furthermore, they exhibited protein expression patterns consistent with an effector T cell phenotype for at least 3 days following transfer to tumor-bearing mice.

Example 5

Adoptive Immunotherapy With CD200R-CDd28$^+$ T Cells Exhibits Greater Activity in Therapy of Disseminated Leukemia Adoptive immunotherapy with T cells transduced with CD200R-CD28 mediated increased therapeutic activity in the preclinical mouse model of disseminated leukemia.

Figure 4A:
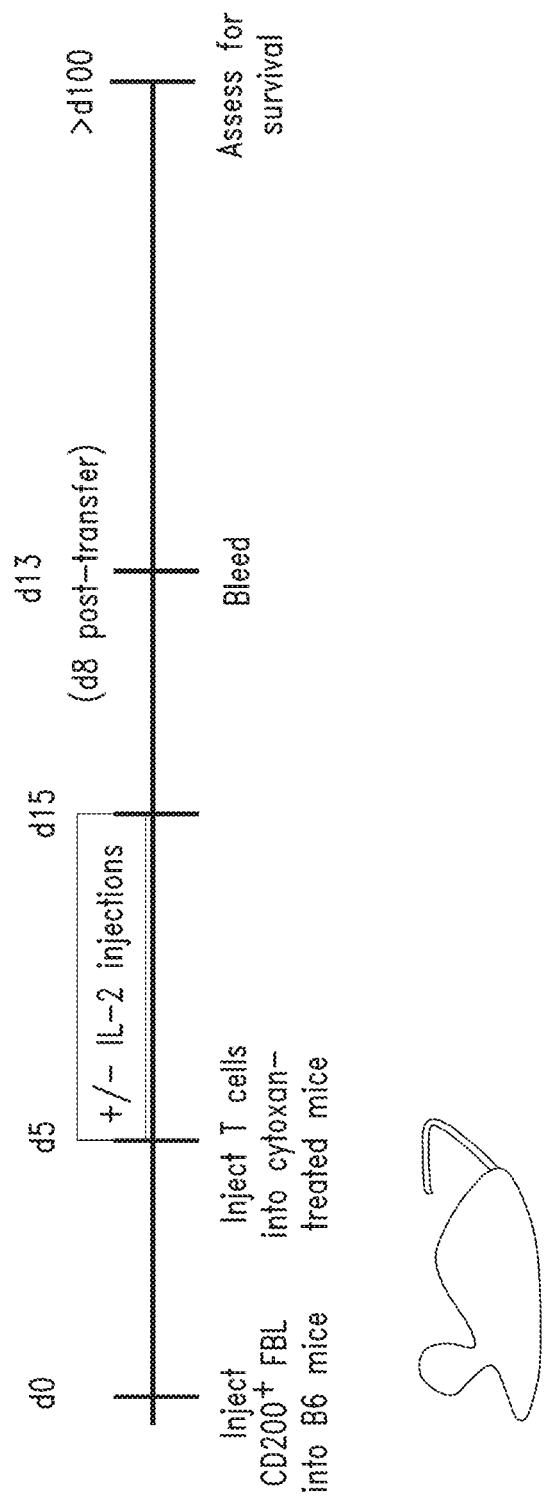
FIGS. 4A to 4D show that adoptive immunotherapy with CD200R-CD28-transduced T cells can eradicate disseminated leukemia. (A) Experiment schematic. C57BL/6 mice were injected with $4 \times 10^6$ CD200⁺ FBL cells. Five days later, CD200R-CD28tm, CD200R-CD28Cys, CD200R-9aas-CD28Cys, or eGFP $TCR_{gag}$ T cells were injected i.p. into Cy-treated FBL-bearing mice at $10^5$ cells/mouse. IL-2 was administered every 2 days ($2 \times 10^4$ U/dose) in a cohort of mice as indicated. (B) Representative example of expression of cell surface proteins in CD200R-CD28tm transduced T cells and non-transduced T cells on day of injection with IL-2, as determined by flow cytometry. (C) Survival of mice treated in the presence of IL-2 injections. (D) Survival of mice treated in the absence of IL-2 injections. Transfer of CD200R-9aas-CD28Cys $TCR_{gag}$ T cells significantly improved survival in the absence of IL-2 injections ($P<0.05$, log-rank Mantel-Cox test).
Figure 4B:
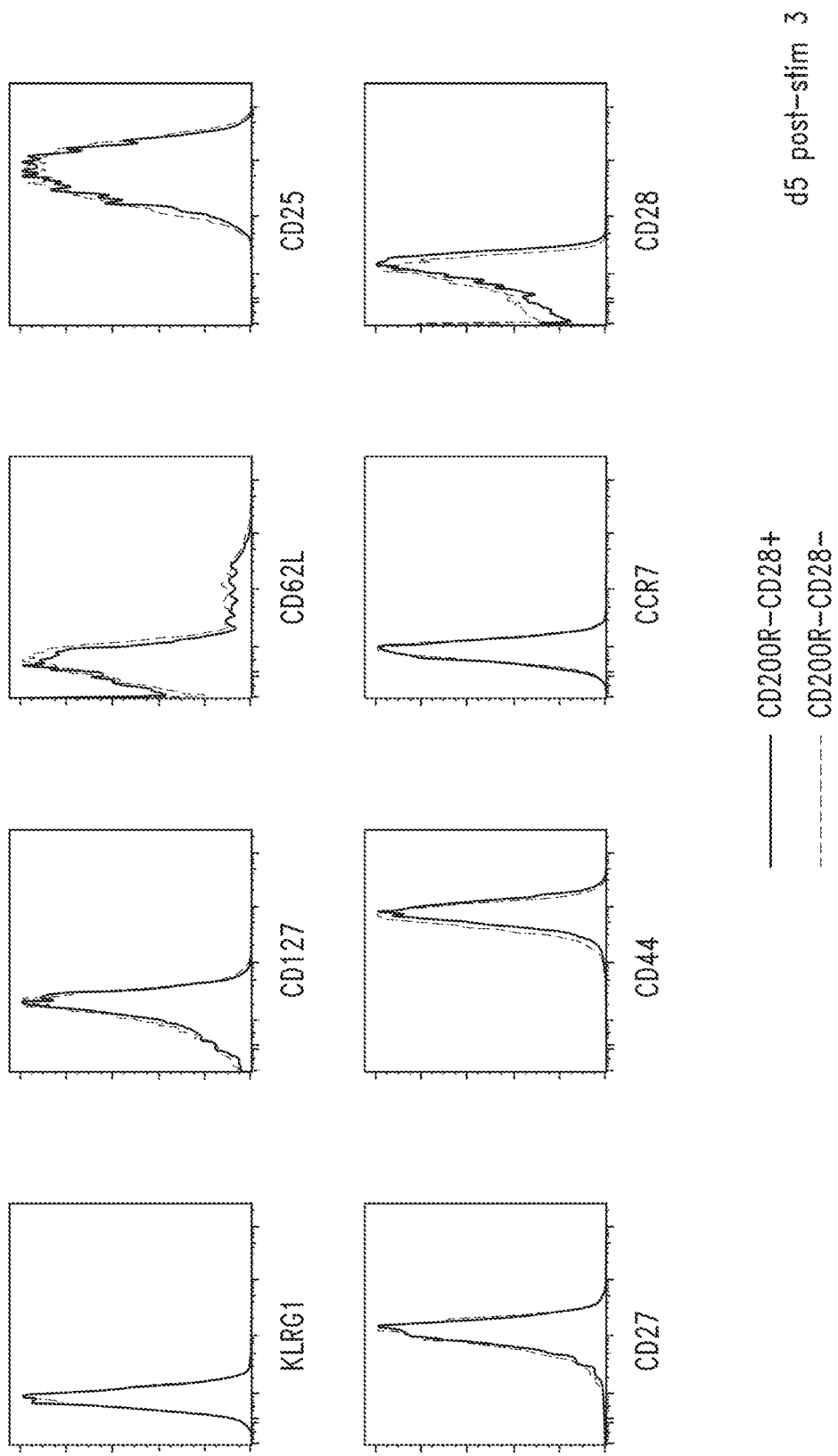

Mice were injected with a lethal dose of CD200$^+$ FBL leukemia and five days later, cohorts of Cy-treated mice received additional therapy with $10^5$ T cells (FIG. 4A). The contribution of the CD28 cysteine bond to efficacy mediated by the CD200R-CD28 construct was assessed by comparing T cells transduced with CD200R-CD28tm, CD200R-9aas-CD28Cys, and GFP control constructs as shown in FIG. 1A. IL-2 was administered for 10 days as an additional therapeutic reagent to a cohort of mice to promote the activity of the T cells (Stromnes et al., *J. Clin. Invest.* 120: 3722-34, 2010). Before injection, T cells were assessed for various surface proteins by flow cytometry. Transduced and control $TCR_{gag}$ T cells displayed similar phenotypes, indicating that transduction did not alter the phenotype of the cells prior to injection (FIG. 4B).

Figure 4C:
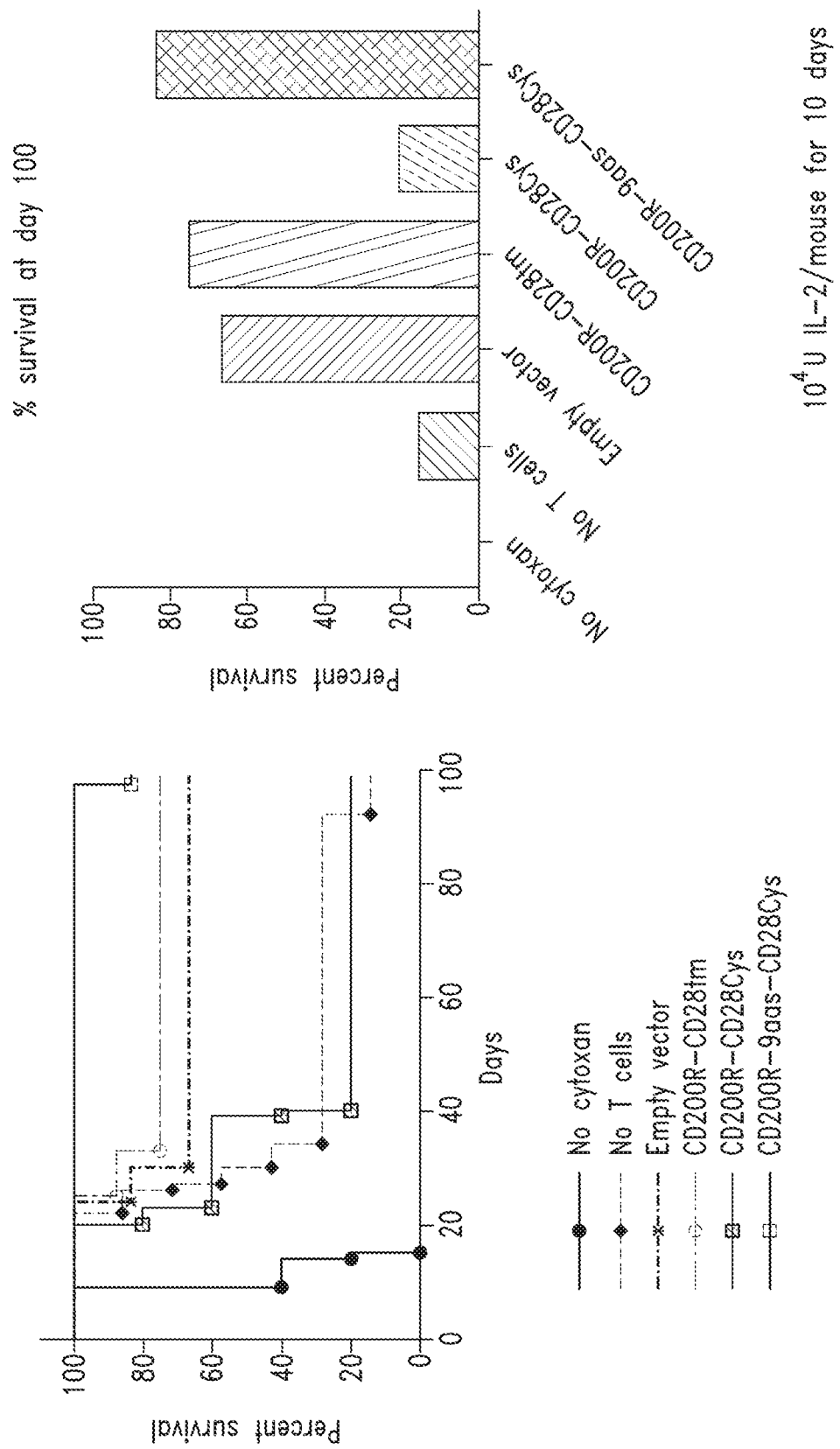
Figure 4D:
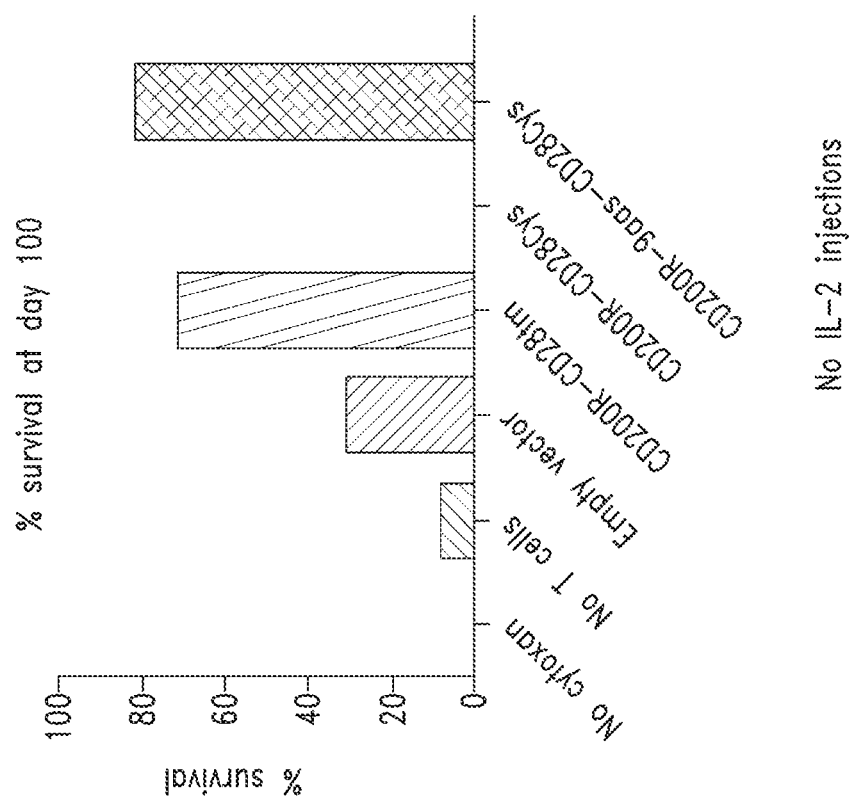
Figure 4D:
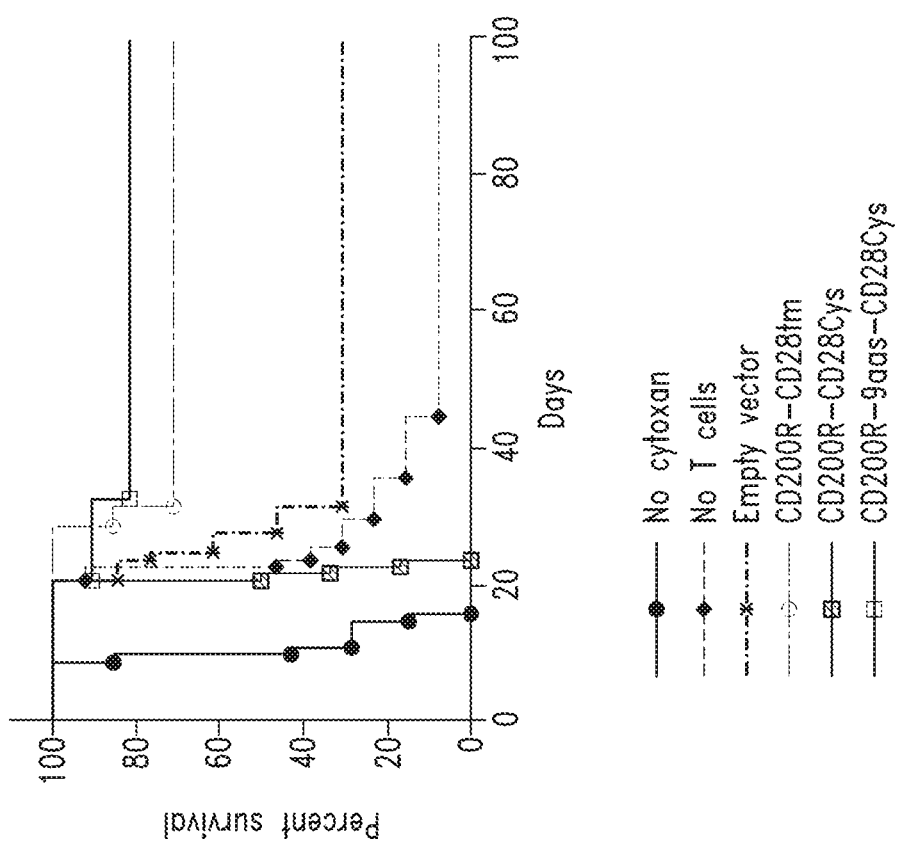

In the small cohort of mice that received IL-2 injections, T cells improved survival but a significant difference in the survival of mice that received the different groups of T cells could not be detected (FIG. 4C). However, in the cohort of mice that did not receive IL-2 injections, there was a significant improvement in the survival of mice that received T cells transduced with CD200R-CD28 constructs appropriately sized to fit within the immunological synapse (FIG. 4D). The majority of the mice not receiving T cells, receiving T cells transduced with the GFP control vector or T cells transduced with the largest ectodomain (CD200R-CD28Cys IFP) did not survive beyond day 30 (FIGS. 4C and 4D, black solid, dashed, and orange lines, respectively). In contrast, 71% of mice that received CD200R-CD28tm$^+$ T cells and 83% of mice that received CD200R-9aas-CD28Cys$^+$ T cells survived more than 100 days post-therapy (FIGS. 4C and 4D, green and red lines, respectively). These data suggest that transduction of T cells with CD200R-CD28 constructs that span a distance similar to a distance between membranes in an immunological synapse provides sufficient costimulation to overcome the dependence of T cell immunotherapy on injection of exogenous IL-2. Furthermore, although there were differences in proliferation and accumulation between the CD200Rtm-CD28 and CD200R-9aas-CD28Cys constructs tested in mice that did not receive injections of exogenous IL-2, both IFPs effectively enhanced T cell immunotherapy to significantly improve the clinical outcome from otherwise progressive leukemia.

Example 6

Figure 5A:
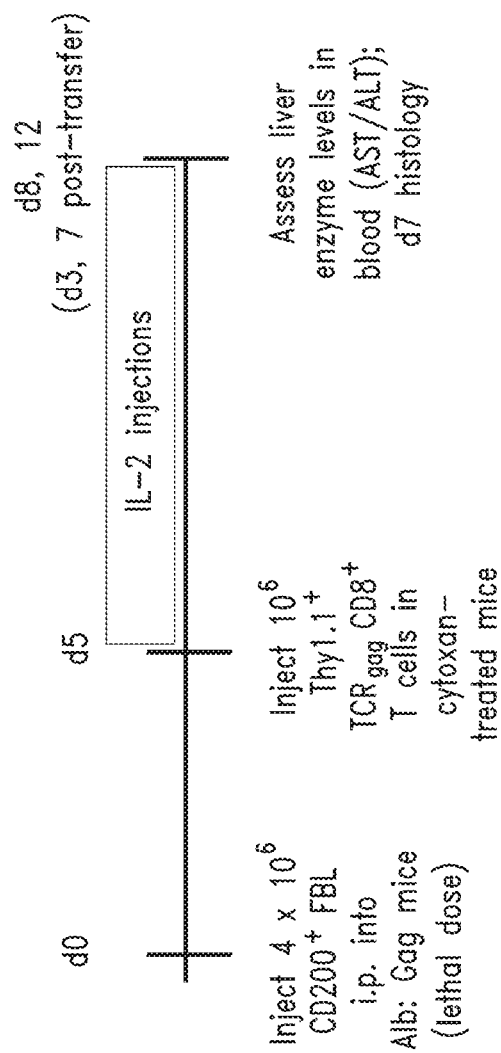
FIGS. 5A to 5C show that T cells expressing CD200R-9aas-CD28Cys do not induce detectable autoimmune liver damage or infiltrate normal tissues. (A) Experiment schematic. Cyclophosphamide-treated Alb/Gag mice were injected with $4 \times 10^6$ CD200⁺ FBL cells. Five days later, CD200R-9aas-CD28Cys, and eGFP $TCR_{gag}$ T cells were injected i.p. into the cyclophosphamide-treated FBL-bearing mice at $10^5$ cells/mouse. IL-2 was administered every 2 days ($2 \times 10^4$ U/dose) in a cohort of mice as indicated. Three and 7 days post-transfer, liver damage was assessed by quantification of serum levels of liver enzymes aspartate aminotransferase (AST) and alanine aminotransferase (ALT). (B) AST and ALT levels measured at 3 and 7 days post-transfer for mice receiving no T cells, control T cells expressing GFP, or T cells expressing CD200R-9aas-CD28Cys did not vary by treatment. (C) Assessment of T cell infiltration of normal tissue. Limited presence of T cells in liver tissue was observed using antibodies specific to the T cell marker CD3 (left panel), with no significant difference between recipients of CD200R-9aas-CD28Cys $TCR_{gag}$ or control $TCR_{gag}$ T cells (right panel).
Figure 5A:
Figure 5B:
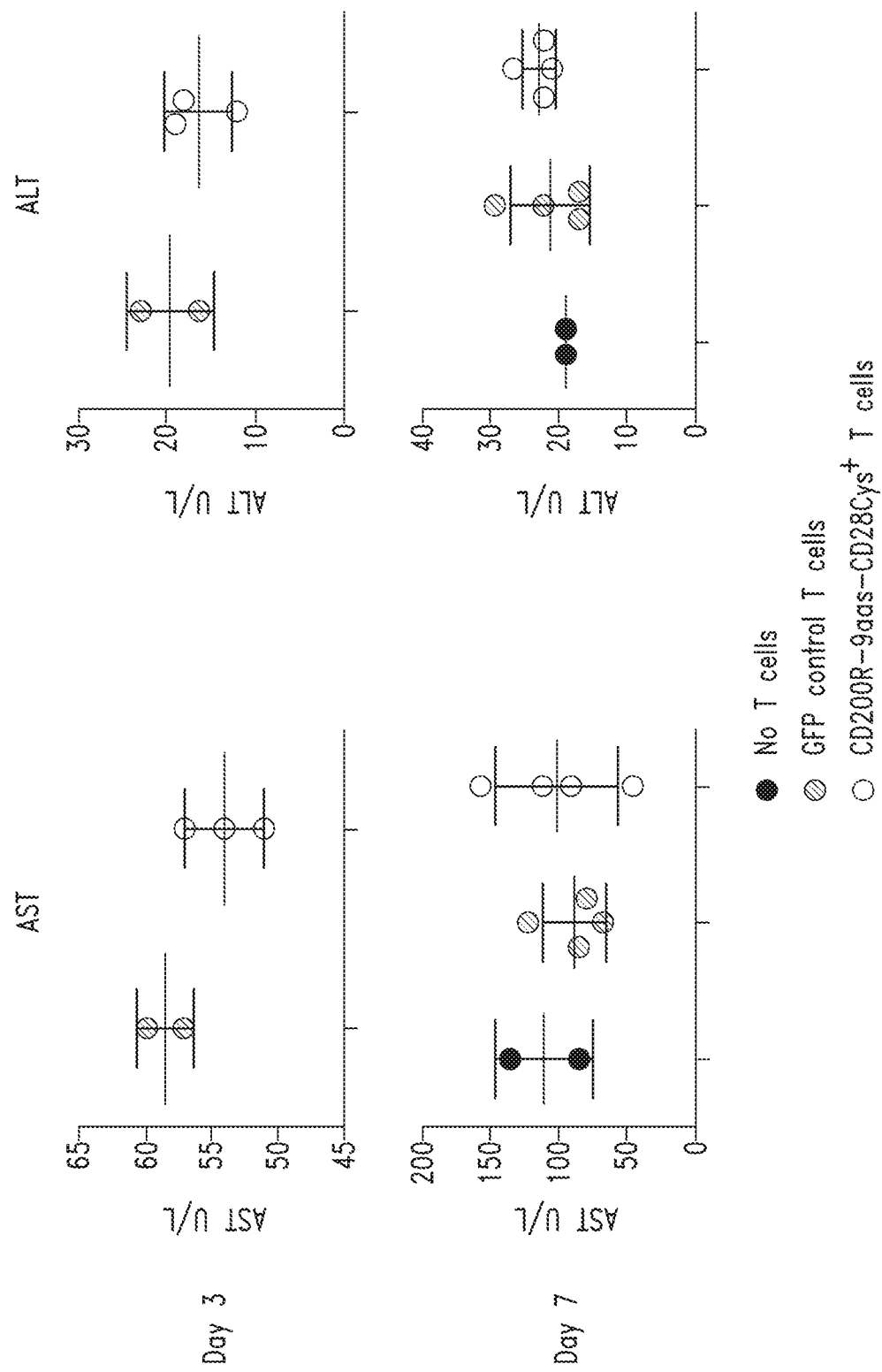

CD200R-9AAs-CD28Cys$^+$ T Cells Do Not Cause Autoreactivity with Endogenous Tissues and Do Not Exhibit Infiltration of Normal Tissues In Vivo To determine if transduction of $TCR_{gag}$ T cells lowered the threshold of activation sufficiently to result in autoreactivity with endogenous tissues, autoimmune toxicity was assessed in transgenic mice engineered to express the FBL gag tumor Ag as a self-antigen in hepatocytes, under control of the albumin promoter (FIG. 5A). $TCR_{gag}$ effectors were generated in vitro and $10^6$ were transferred into cyclophosphamide-treated Alb:Gag mice with disseminated leukemia. At 3 and 7 days post-transfer, liver damage was assessed by quantification of serum levels of the liver enzymes aspartate aminotransferase (AST) and alanine aminotransferase (ALT). Adoptive therapy with control or CD200R-9aas-CD28Cys$^+$ $TCR_{gag}$ cells in mice did not affect serum levels of AST or ALT at days 3 or 7 post-transfer, indicating that CD200R-9aas-CD28Cys does not induce detectable autoimmune liver damage in Alb:Gag mice (FIG. 5B).

Figure 5C:
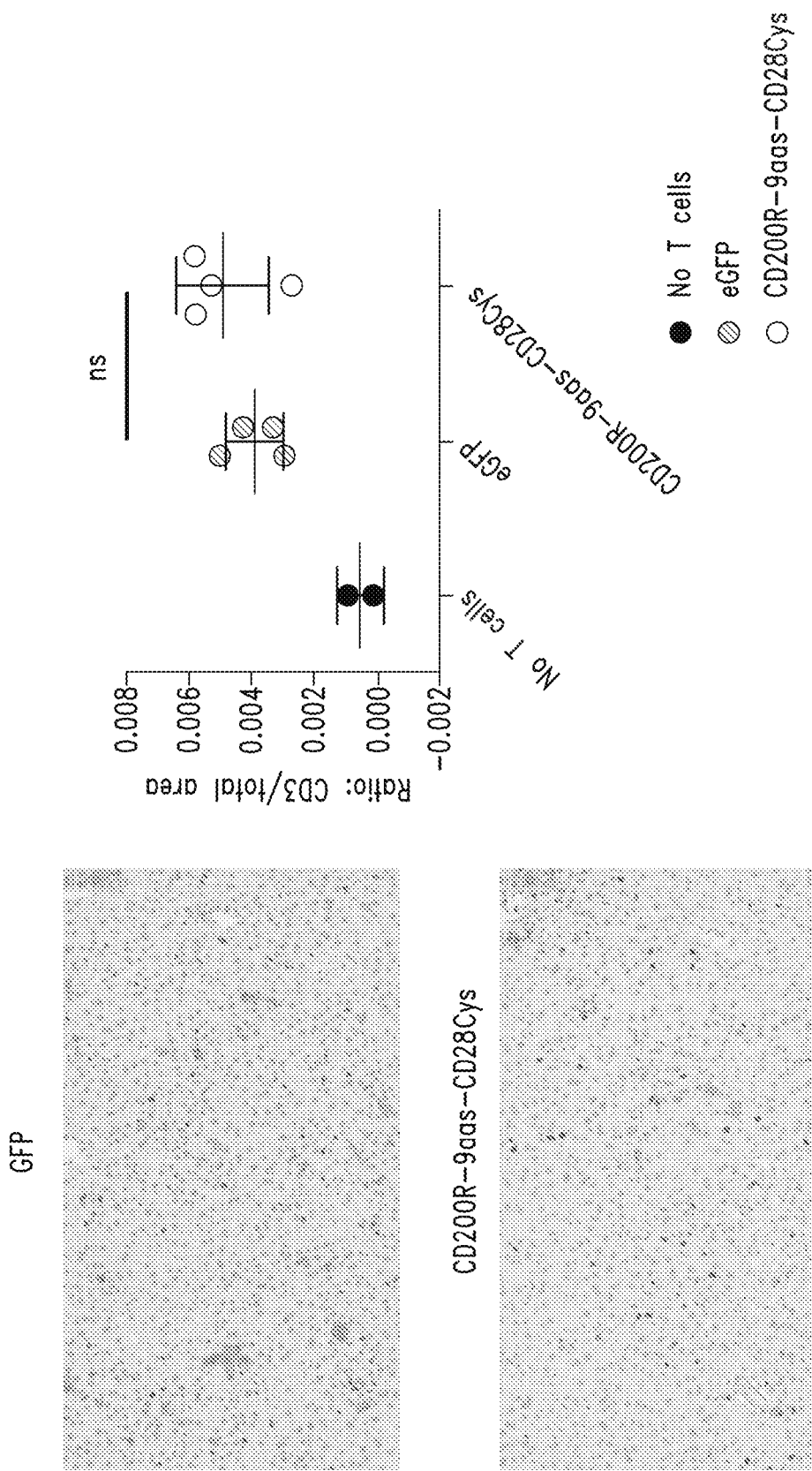

T cells transduced with IFP do not exhibit increased infiltration of normal tissues compared to control T cells. Mice were euthanized 7 days post-transfer and liver sections were stained with an antibody to the T cell marker CD3 to quantify T cell infiltration. Limited presence of T cells in liver tissue was observed, with no significant difference between recipients of CD200R-9aas-CD28Cys$^+$ or control $TCR_{gag}$, indicating no increased lymphocytic cellular infiltration as a result of IFP expression (FIG. 5C).

Example 7

Figure 6A:
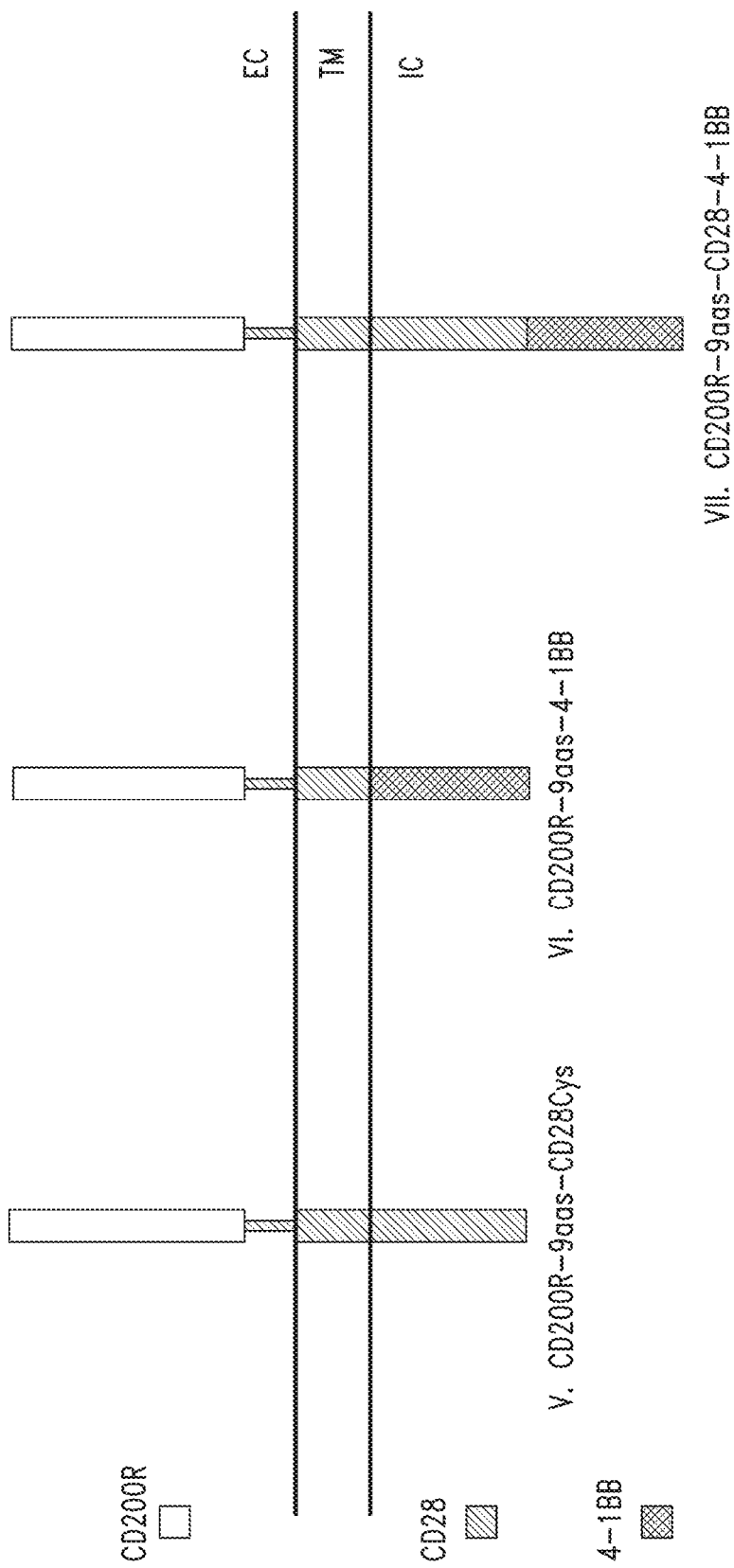
FIGS. 6A to 6D show that 4-1BB co-stimulatory signaling domains promote accumulation and effector function of transduced T cells in vitro and promote survival of tumor-bearing recipients of transduced T cell in response to CD200⁺ tumor target cells. (A) Schematic representation of CD200R-CD28 ("V"), -4-1BB ("VI"), and—CD28-4-1BB ("VII") constructs. (B) Expansion of transduced $TCR_{gag}$ T cells relative to non-transduced $TCR_{gag}$ T cells after weekly stimulation with irradiated CD200⁺ FBL and splenocytes. CD200R-4-1BB and CD200R-CD28-4-1BB also promote accumulation of transduced T cells in vitro. (C) CD200R-9aas-4-1BB⁻ CD8⁺ T cells displayed an enhanced ability to lyse CD200⁺ FBL cells in vitro relative to controls, using a standard CFSE-based cytotoxicity assay. The percentage of FBL of the sum of FBL and control tumor cells was determined by flow cytometry. The percentage lysis was determined by dividing the percent of FBL incubated with T cells by the percent of FBL incubated without T cells. (D) CD200R-41BB-transduced T cells also promote survival relative to controls. C57BL/6 mice were injected with $4 \times 10^6$ CD200⁺ FBL cells. Five days later, CD200R-9aas-CD28, CD200R-9aas-4-1BB, CD200R-9aas-CD28-4-1BB, or eGFP TCR$_{gag}$ T cells were injected i.p. into cyclophosphamide-treated FBL-bearing mice at $10^5$ cells/mouse.

4-1BB Co-Stimulatory Signaling Domain Promotes Accumulation of Transduced T Cells In Vitro Co-stimulatory receptor 4-1BB is upregulated on activated T cells, which promotes T cell survival and cytokine production (Chen and Flies, *Nat. Rev. Immunol.* 13: 227-242, 2013). To assess if the intracellular signaling domain of 4-1BB, with or without the intracellular signaling domain of CD28, could induce increased T cell proliferation and accumulation, IFPs using 4-1BB (CD200R-9aas-4-1BB) or combining 4-1BB with CD28 (CD200R-9aas-CD28-4-1BB) were generated (FIG. 6A) using the methods described in Example 2. TCR$_{gag}$ T cells were transduced as in Example 2, and TCR$_{gag}$ effector cells were generated in vitro as in Example 3.

Figure 6B:
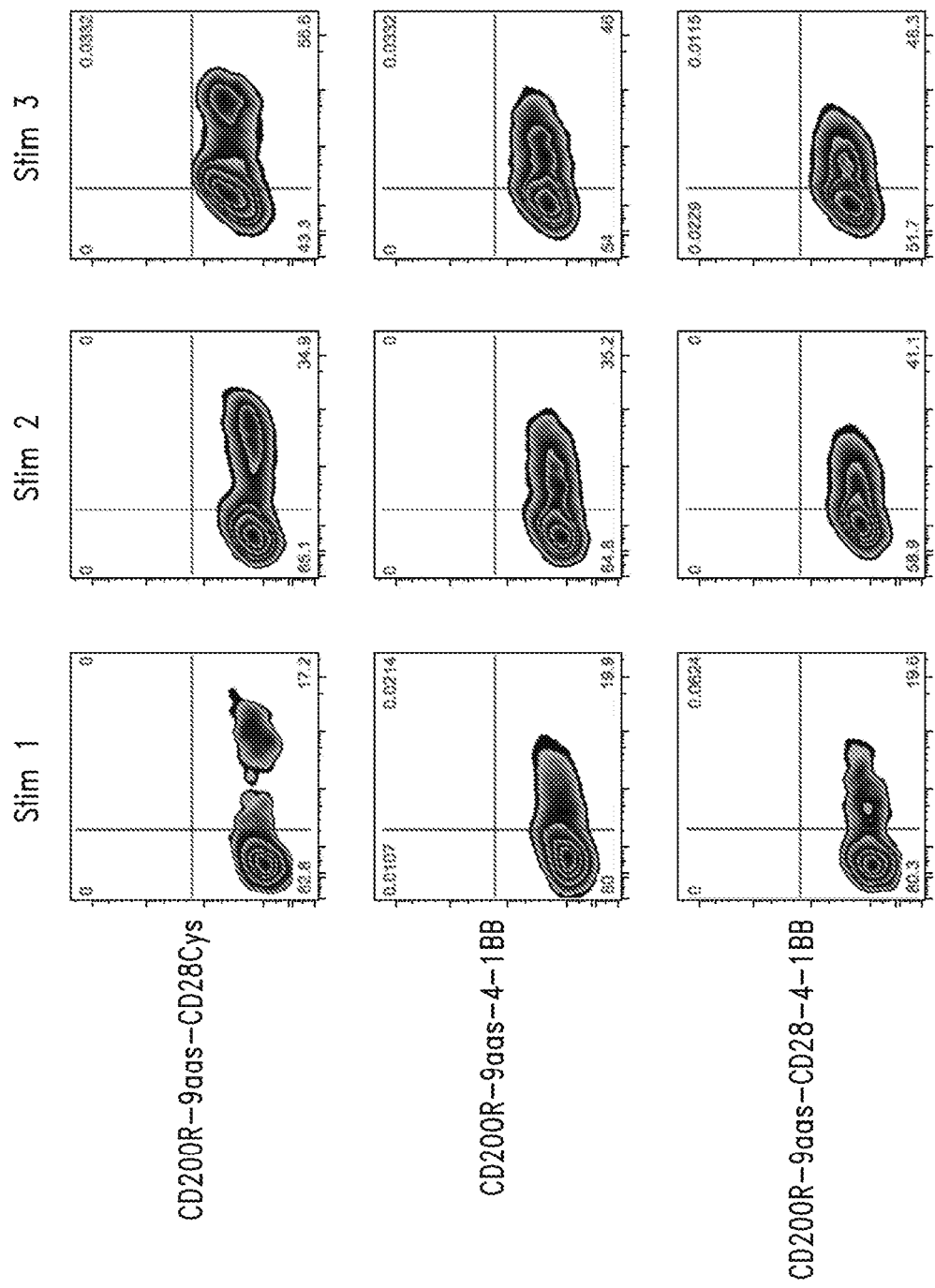

As was observed with CD200R-9aas-CD28Cys, T cells transduced with the 4-1BB constructs accumulated over multiple rounds of stimulation in vitro (FIG. 6B). These data indicate that 4-1BB IFPs also promote proliferation and survival of T cells.

Figure 6C:
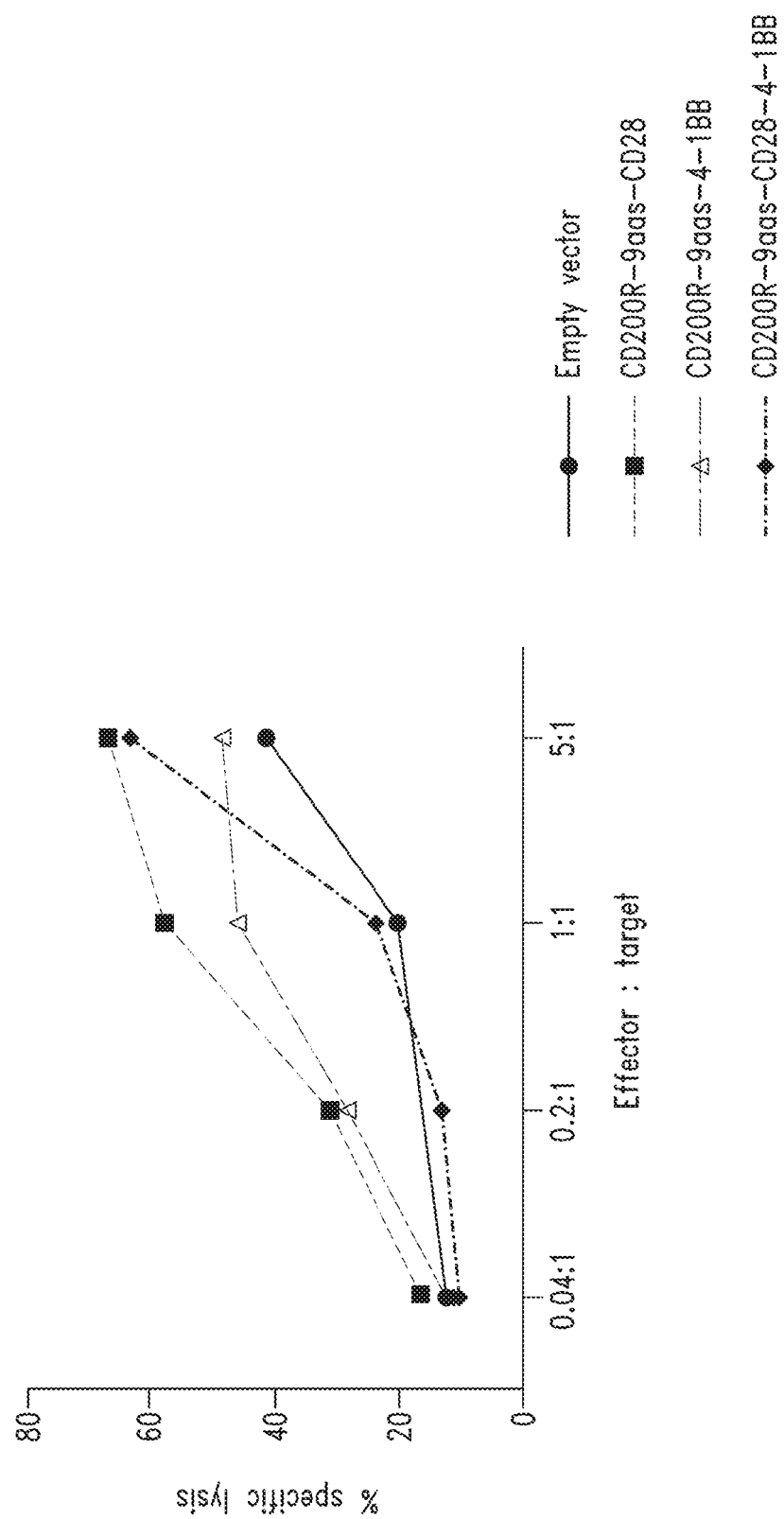
Figure 6D:
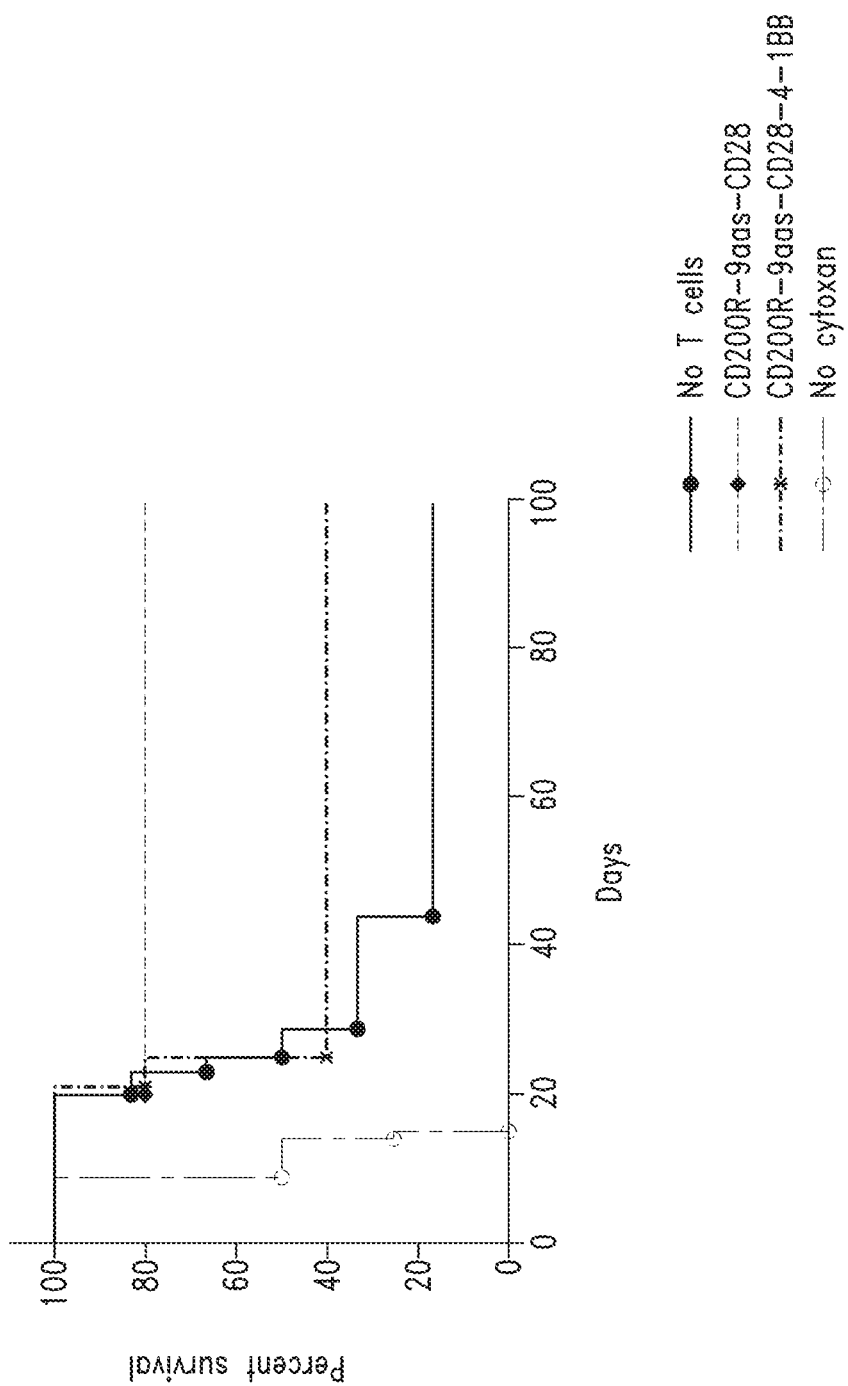

TCR$_{gag}$ T cells transduced with a CD200R-4-1BB displayed an enhanced ability to lyse FBL tumor in vitro using the CFSE-based cytotoxicity assay described in Example 3 (FIG. 6C). CD200R-41BB-transduced T cells also promote survival (FIG. 6D).

Example 8

Figure 7A:
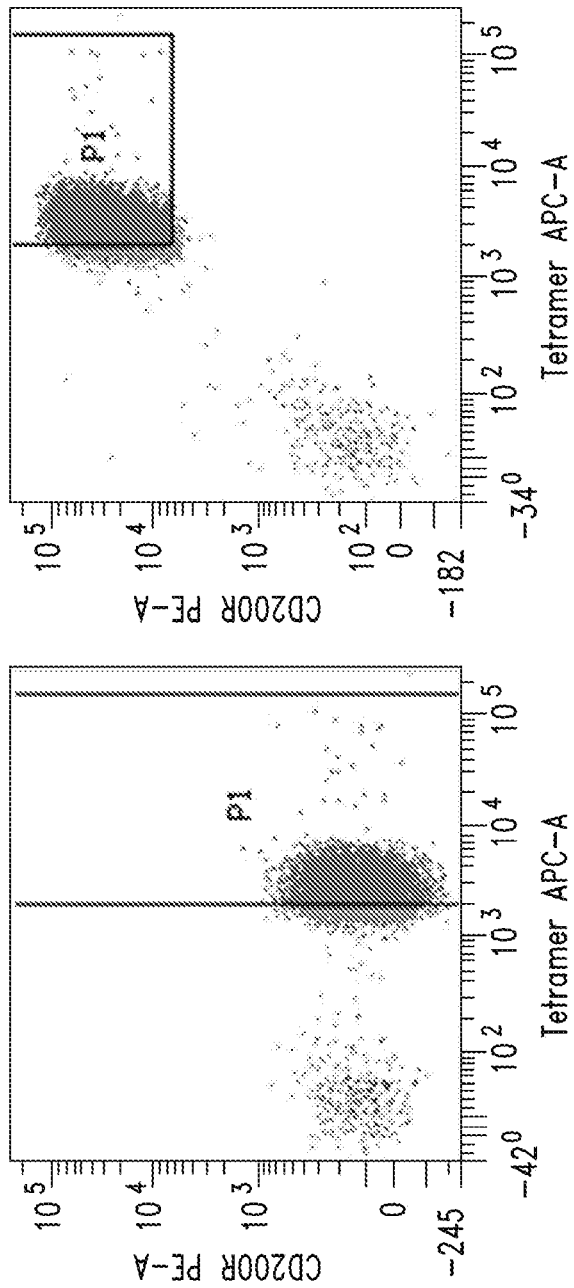
FIGS. 7A to 7D show that human primary T cells transduced to express a WT1-specific TCR and a CD200Rtm-CD28 fusion protein exhibit enhanced proliferation to target cells that express CD200 and increased cytokine production in response to tumor cells that express CD200. (A) Expression of the WT1$_{126}$-specific TCR, C4, and CD200Rtm-CD28. (B) Expression of CD200 in T2 and K562 cells. T2 cells exhibit low-level endogenous CD200 expression. (C) Proliferation of T cells as indicated by CFSE. Cells that proliferate in response to antigen show reduced CFSE fluorescence intensity. T cells transduced with both C4 and the IFP show enhanced proliferation to target cells expressing low levels of CD200 relative to T cells transduced with C4 only. (D) Cytokine production in response to exposure to CD200dim tumor cells, as measured by flow cytometry. Relative to control T cells transduced with the TCR C4 alone, T cells transduced with both C4 and the IFP CD200Rtm-CD28 show increased cytokine production.

Co-Expression of CD200RTm-CD28 Enhances Function in WT1-Specific TCR Primary T Cells A human CD200Rtm-CD28 construct (SEQ ID NO.:1) was generated to determine if IFP expression enhanced T cell function of human primary T cells. The construct was combined with the beta and alpha chains of the HLA-A2-restricted WT1$_{126}$-specific TCR "C4" by linking the genes with P2A elements (FIG. 7A). The first P2A sequence was codon optimized to prevent genetic recombination with the second P2A sequence. To generate lentiviruses, 293 T/17 cells (3×10$^6$ cells/plate) were transduced with human constructs in the pRRLSIN and the packaging vectors pMDLg/pRRE, pMD2-G, and pRSV-REV using Effectene (Qiagen). Culture media was changed on day 1 post-transfection and virus-containing supernatant collected on days 2 and 3, and aliquots frozen for future use.

The Jurkat human T cell subline, which lacks an endogenous TCR, was used to test expression of the IFP and TCRs. These Jurkat T cells were transduced by spinfection of 2×10$^6$ cells with 2 ml of retroviral supernatant at 1000 g for 90 min at 32° C. Transduction of the Jurkat human T cell line with the three-gene construct resulted in high expression of the IFP and expression of the TCR at a similar MFI as T cells transduced with the TCR only (FIG. 7A).

To transduce primary human T cells, peripheral blood mononuclear cells (PBMC) were harvested from HLA-A2+ donors. CD8$^+$ T cells were purified using Miltenyi magnetic beads and stimulated with Human T cell Expander CD3/CD28 Dynabeads (Life Technologies) and 50 IU/ml IL-2. Four hours following stimulation, T cells were transduced as described above for Jurkat T cells. T cells were restimulated every 10-14 days with a rapid expansion protocol (REP), as has been previously described (Ho et al., *J Immunol Methods* 310:40-52, 2006).

Figure 7B:
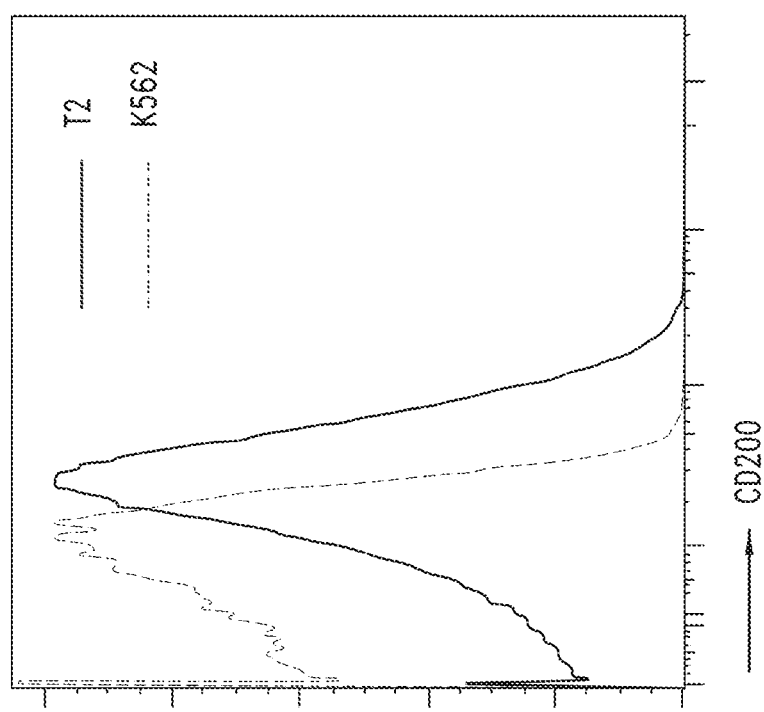

The human cell line T2 was used as an APC, because it is deficient in TAP and thus cannot present endogenous peptides, while low level MHCI expression allows presentation of exogenously loaded peptides. Expression of CD200 by the T2 cells was assessed by flow cytometry (FIG. 7B). T2 cells exhibited a low level of endogenous CD200 expression (FIG. 7B).

Figure 7C:
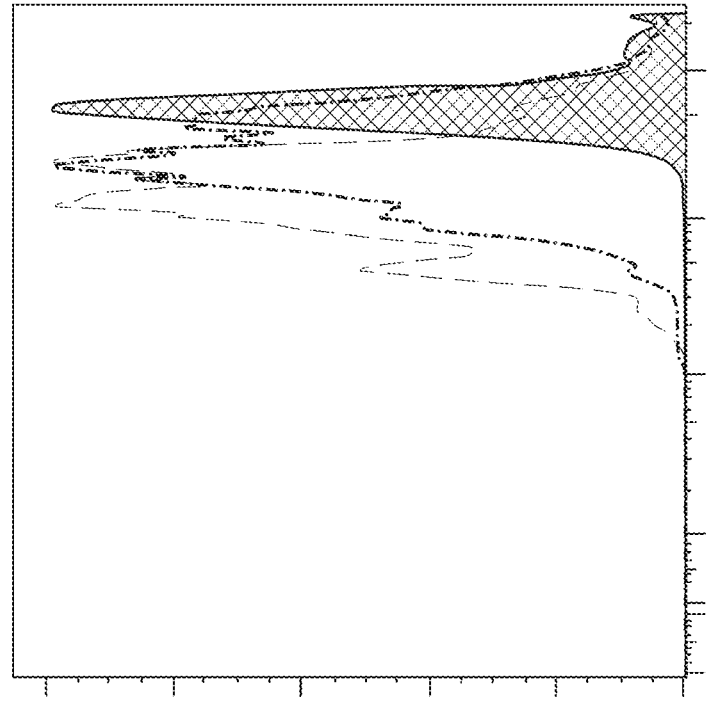
Figure 7C:
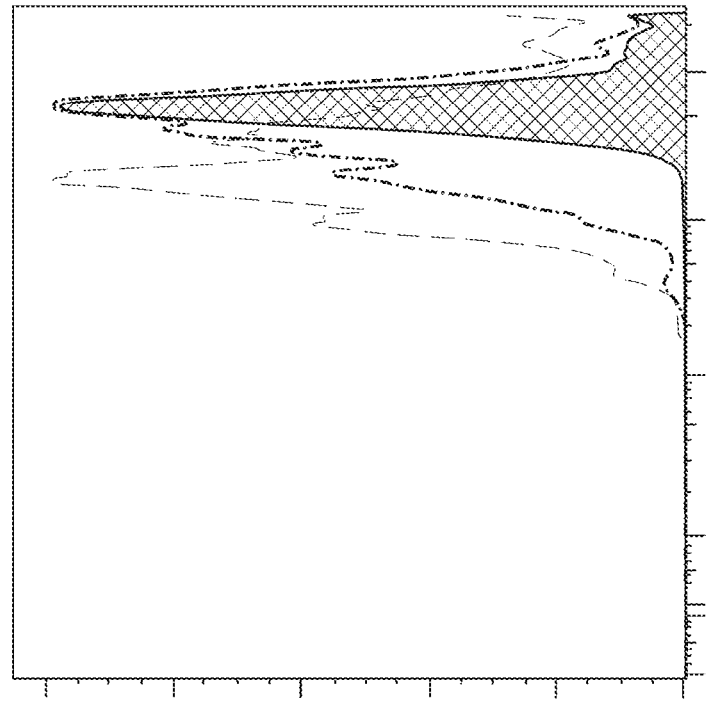
Figure 7D:
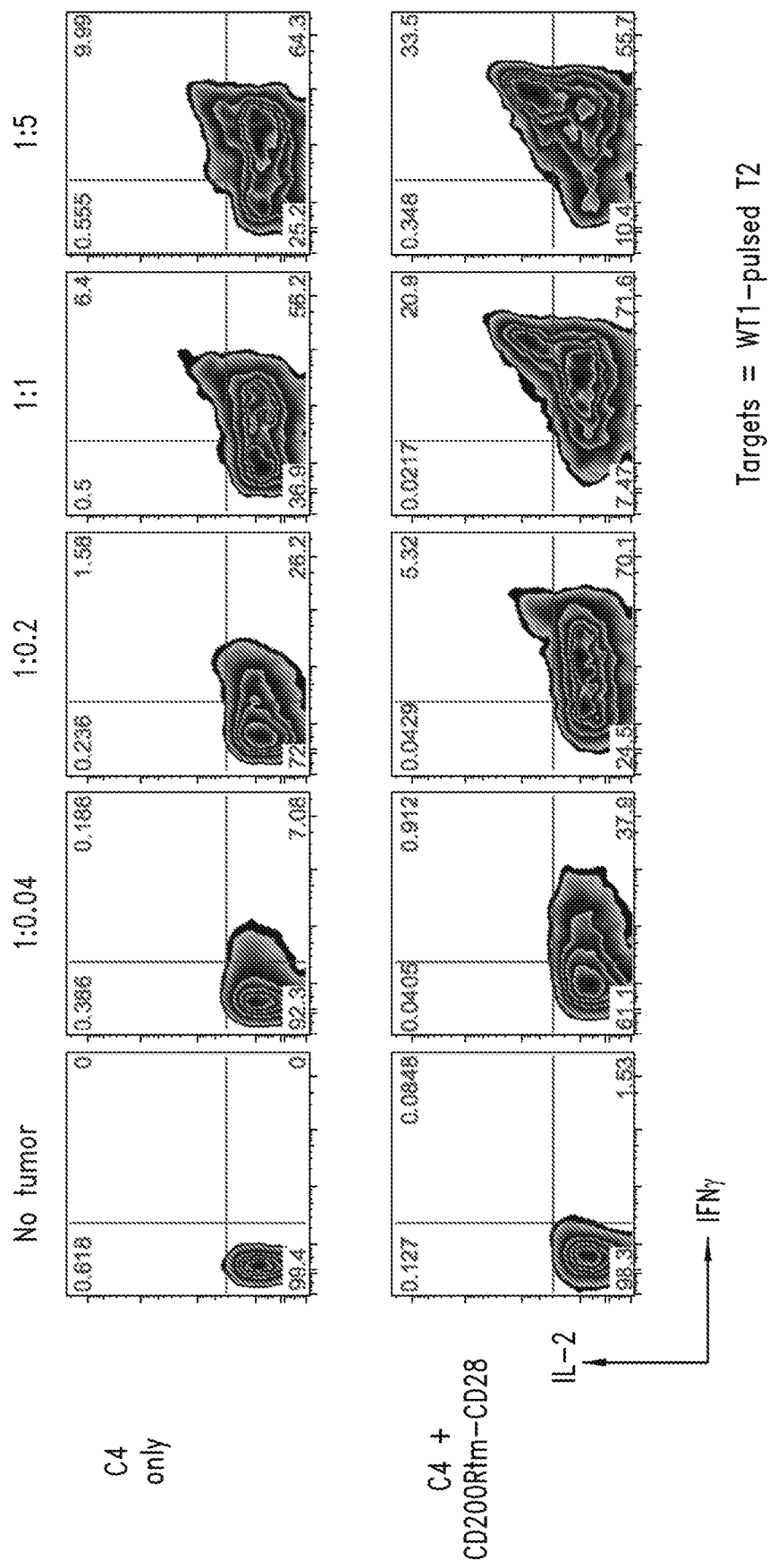

Transduced T cells were stimulated with WT1$_{126}$-pulsed T2 cells. Despite a low level of CD200 expression on the target cells, CD200Rtm-CD28-transduced T cells exhibited enhanced proliferation as compared to T cells transduced with the C4 TCR alone (FIG. 7C). In addition, stimulated CD200Rtm-CD28-transduced T cells (i.e., IFP$^+$ T cells) produced increased levels of IFNγ and IL-2 compared to control T cells when exposed to CD200dim tumor cells (FIG. 7D).

Overall, these results showed that primary T cells transduced to express a human CD200Rtm-CD28 construct and the beta and alpha chains of a WT1$_{126}$-specific TCR exhibited enhanced proliferation and increased cytokine production relative to T cells transduced with the TCR construct alone.

Example 9

Figure 8A:
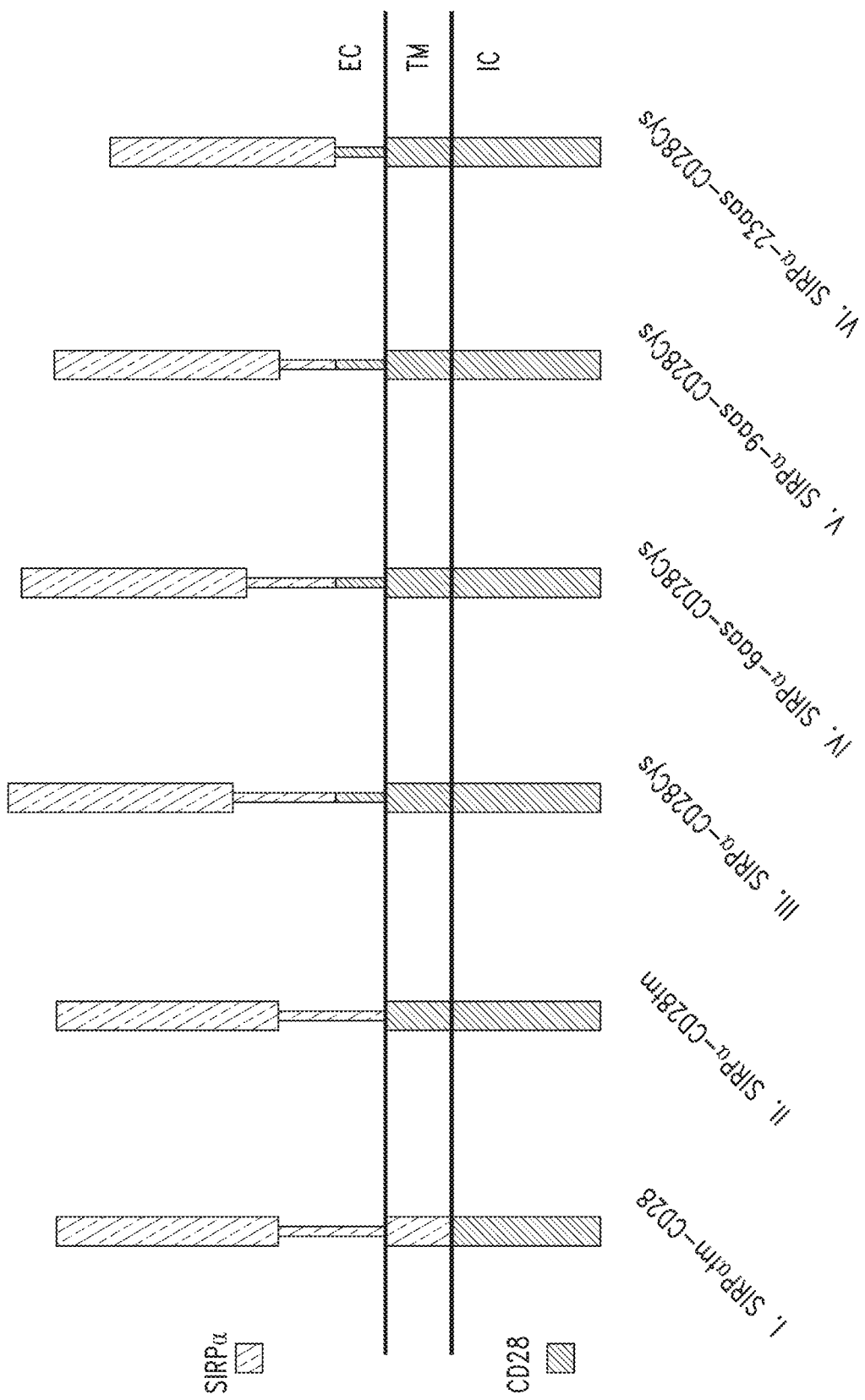
FIGS. 8A to 8E show that fusion proteins comprising SIRPα extracellular components and CD28 co-stimulatory signaling domains promote accumulation and proliferation of transduced T cells in vitro. (A) Schematic representation of exemplary SIRPα-CD28 constructs. Construct "I" contains SIRPα extracellular ("EC") and transmembrane ("TM") domains and a CD28 intracellular ("IC") signaling domain (SIRPαtm-CD28). Construct "II" contains the extracellular domain of SIRPα and the transmembrane and intracellular domains of CD28 (SIRPα-CD28tm). Constructs "III-VI" also incorporate a portion of the extracellular domain of CD28 to the transmembrane-proximal cysteine to promote multimerization and enhance CD28 signaling. To account for the extra extracellular amino acids (e.g., extra nine (9) amino acids for murine constructs, or twelve (12) amino acids for human constructs), some constructs have a truncated portion of an extracellular or intracellular domain (e.g., a SIRPα that preserves an N linked glycosylation site). Construct IV has a truncated portion of SIRPα that is truncated 6 amino acids to preserve an N linked glycosylation site. Construct V has a truncated portion of SIRPα that is truncated 9 amino acids. Construct VI has a truncated portion of SIRPα that is truncated 23 amino acids. Constructs "I", "II", and "V" maintain the short spatial distance between the cells (e.g., between a T cell and an antigen presenting cell) and may co-localize with the TCR within the cSMAC and deliver a strong co-stimulatory signal. (B) Expansion of transduced TCR$_{gag}$ T cells relative to non-transduced TCR$_{gag}$ T cells after weekly stimulation with irradiated SIRPα$^+$ FBL and splenocytes. SIRPα-CD28 constructs promote accumulation of transduced T cells in vitro, with SIRPα-9aas-CD28Cys exhibiting enhanced accumulation. (C) Proliferation of T cells transduced with SIRPα-CD28 constructs in a CellTrace Violet (CTV) dilution proliferation assay. T cells expressing SIRPα-CD28 constructs engineered to maintain T cell-tumor cell distance exhibited enhanced proliferation relative to nontransduced T cells. (D) CD47$^+$ tumor cells were killed after co-culture with SIRPα-CD28$^+$ T cells transduced to express SIRPαtm-CD28 or SIRPα-9aas-CD28Cys constructs. In contrast, tumor cells were not eradicated when cultured with T cells receiving empty vector, or a truncated SIRPα lacking its intracellular domain. (E) Results of an IncuCyte® assay used to quantify killing of CD47$^+$ tumor cells. CD47$^+$ FBL tumor cells were transduced with mCherry. Loss of red signal indicates killing of tumor cells. Killing of tumor cells was tested at the effector:target ratios of 10:1, 2:1, and 0.4:1. SIRPα-CD28$^+$ T cells killed CD47$^-$ tumor cells, even at the lowest effector-to-target ratio tested.

SIRPα-CD28 Fusion Protein Constructs Promote Accumulation of Transduced T Cells In Vitro Exemplary fusion proteins as described herein also include IFPs comprised of the extracellular domain of SIRPα, or portions thereof, and an intracellular signaling domain of CD28 (FIG. 8A). The hydrophobic component may be comprised of the transmembrane domain of either SIRPα or CD28, or portions thereof. In some exemplary SIRPα-CD28 fusion proteins, the hydrophobic component comprises the transmembrane domain of CD28 and the extracellular component further comprises an extracellular portion of CD28, particularly an extracellular cysteine residue adjacent to the hydrophobic component (e.g., SIRPα-CD28Cys, SIRPα-6aas-CD28Cys, SIRPα-9aas-CD28Cys, and SIRPα-9aas-CD28Cys). The extracellular component may comprise all or a portion of the extracellular domain of SIRPα. In some embodiments, the extracellular component comprises the entire extracellular domain of SIRPα. In other examples, the extracellular component comprises the first 367 amino acids (e.g., SIRPα-6aas-CD28Cys), the first 364 amino acids (e.g., SIRPα-9aas-CD28Cys), or the first 350 (SIRPα-23aas-CD28Cys) amino acids from the N-terminus of SIRPα. The size of the extracellular component may affect the ability of the fusion protein to enter the immunological synapse and co-localize with the TCR within the cSMAC to deliver a strong co-stimulatory signal. In some examples, the extracellular component comprises a truncated SIRPα, which may alter the size of the extracellular component. For example, to account for the additional extracellular amino acids of the extracellular domain of the fusion protein (e.g., an additional 9 or 12 amino acids), SIRPα-6aas-CD28 has a truncated portion of SIRPα that preserves a natural N-linked glycosylation site. In another example, SIRPα-23aas-CD28 has a truncated portion of SIRPα that lacks the entire stem region of the SIRPα extracellular domain. Additionally, a SIRPα-CD28 construct has the capacity to convert a signal initiated by the binding of SIRPα to its target into a positive (e.g., costimulatory) signal generated by the CD28 intracellular signaling domain.

IFPs using SIRPα extracellular components were generated (FIG. 8A) using the methods described in Example 2. TCR$_{gag}$ T cells were transduced as in Example 2, and TCR$_{gag}$ effector cells were generated in vitro as in Example 3. FBL cells were transduced with CD47 or mCherry with polybrene spinfection, similar to T cell transduction, and subsequently sorted to generate a homogenous population.

Figure 8B:
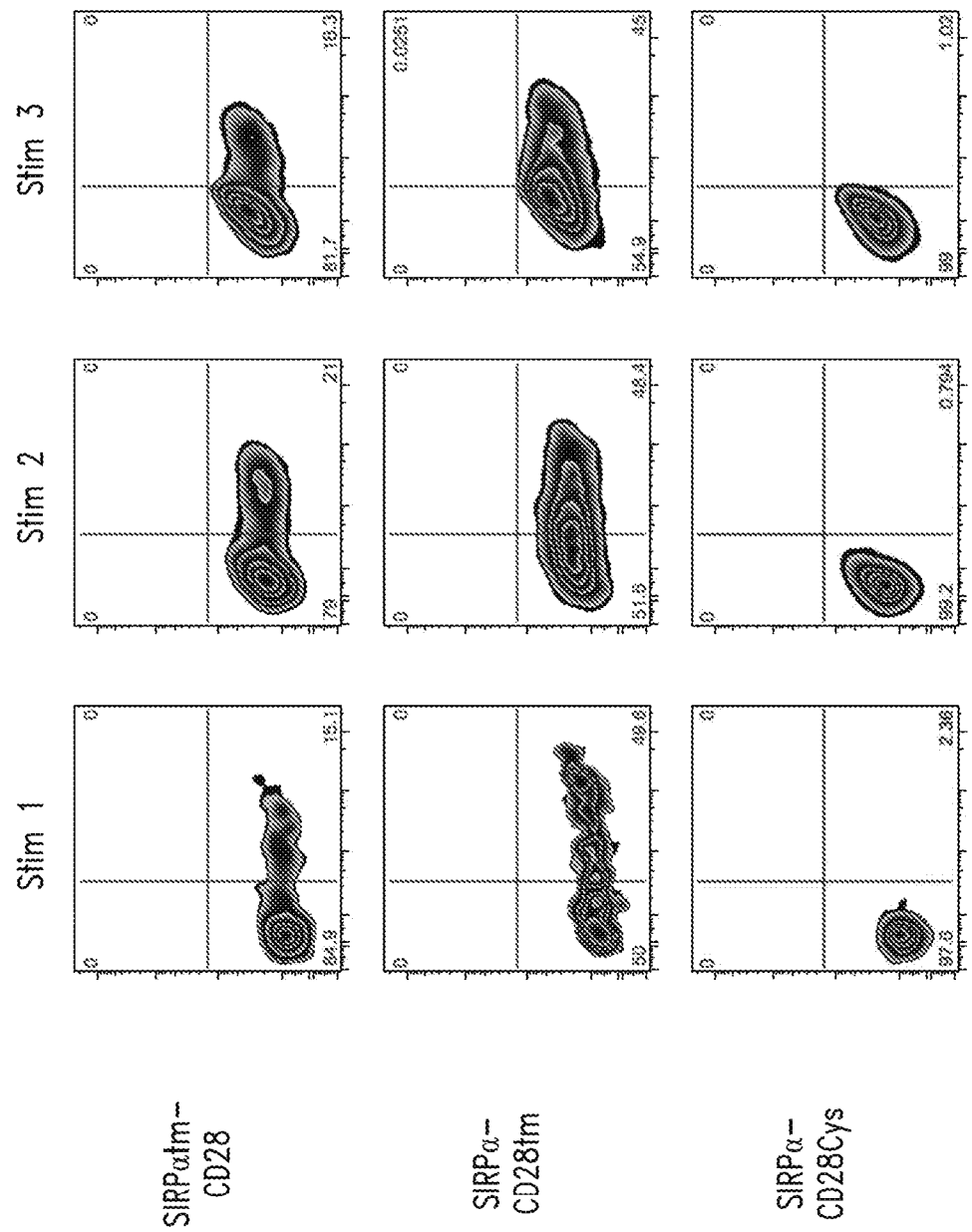
Figure 8B:
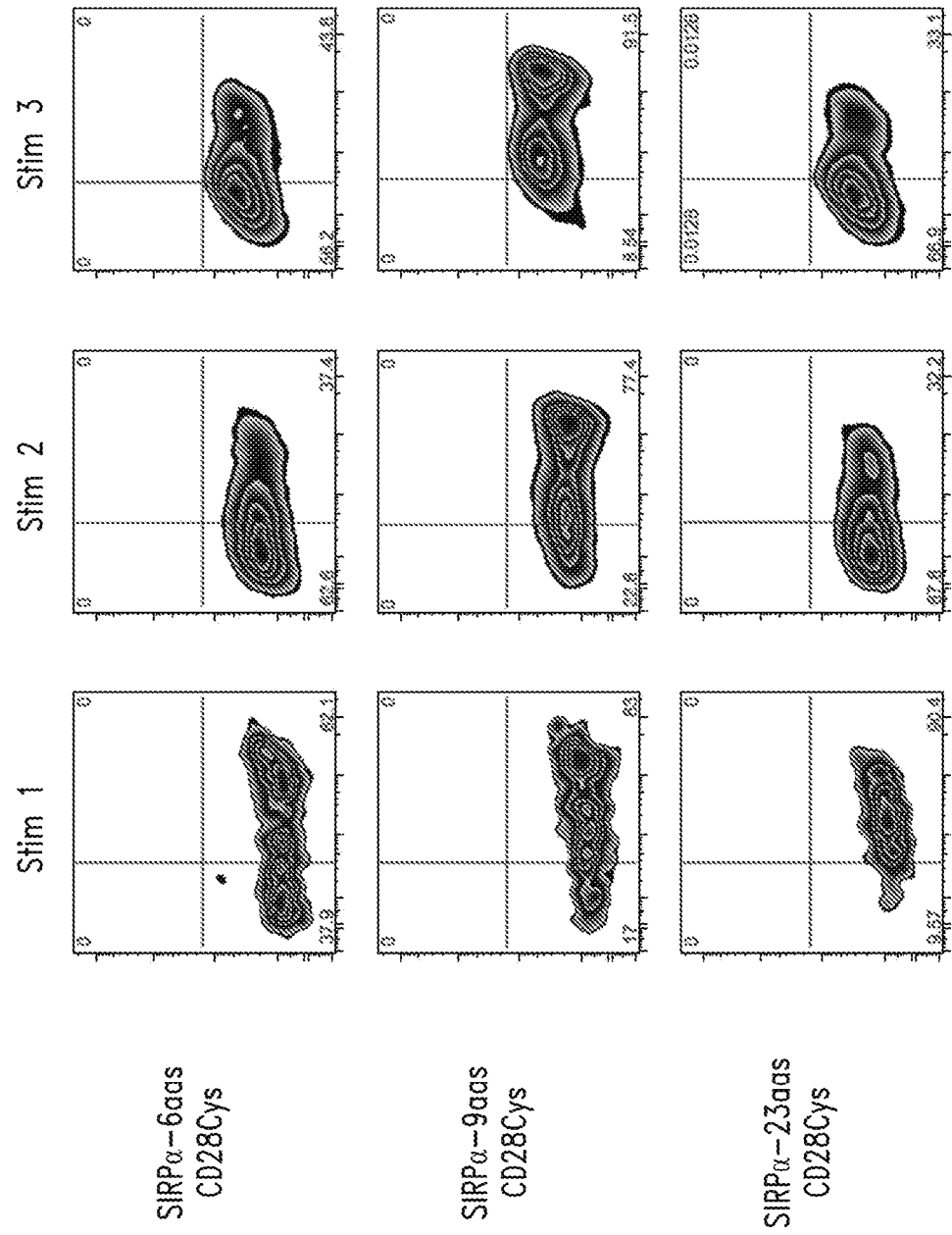

As was observed with CD200R-9aas-CD28Cys, T cells transduced with the SIRPα constructs accumulated over multiple rounds of stimulation in vitro (FIG. 8B). These data suggest that SIRPα-CD28 IFPs also promote proliferation and survival of T cells.

Figure 8C:
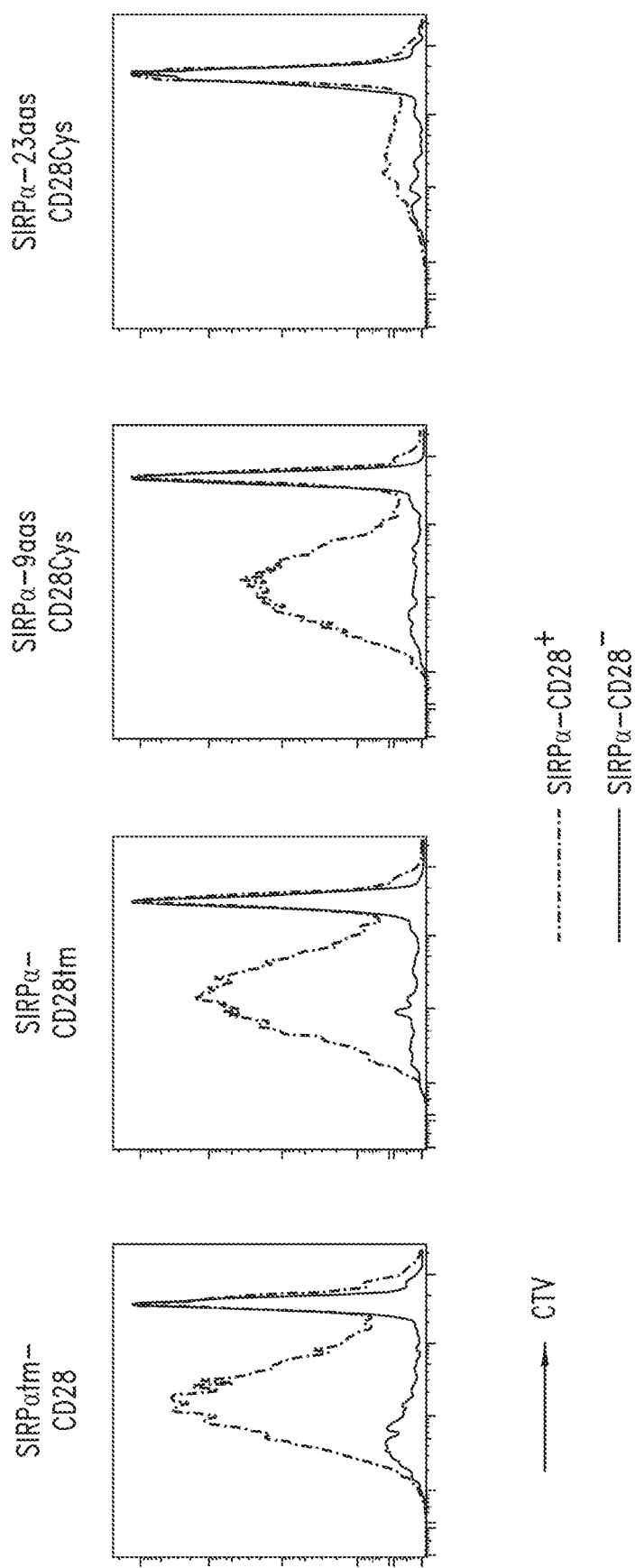
Figure 8D:
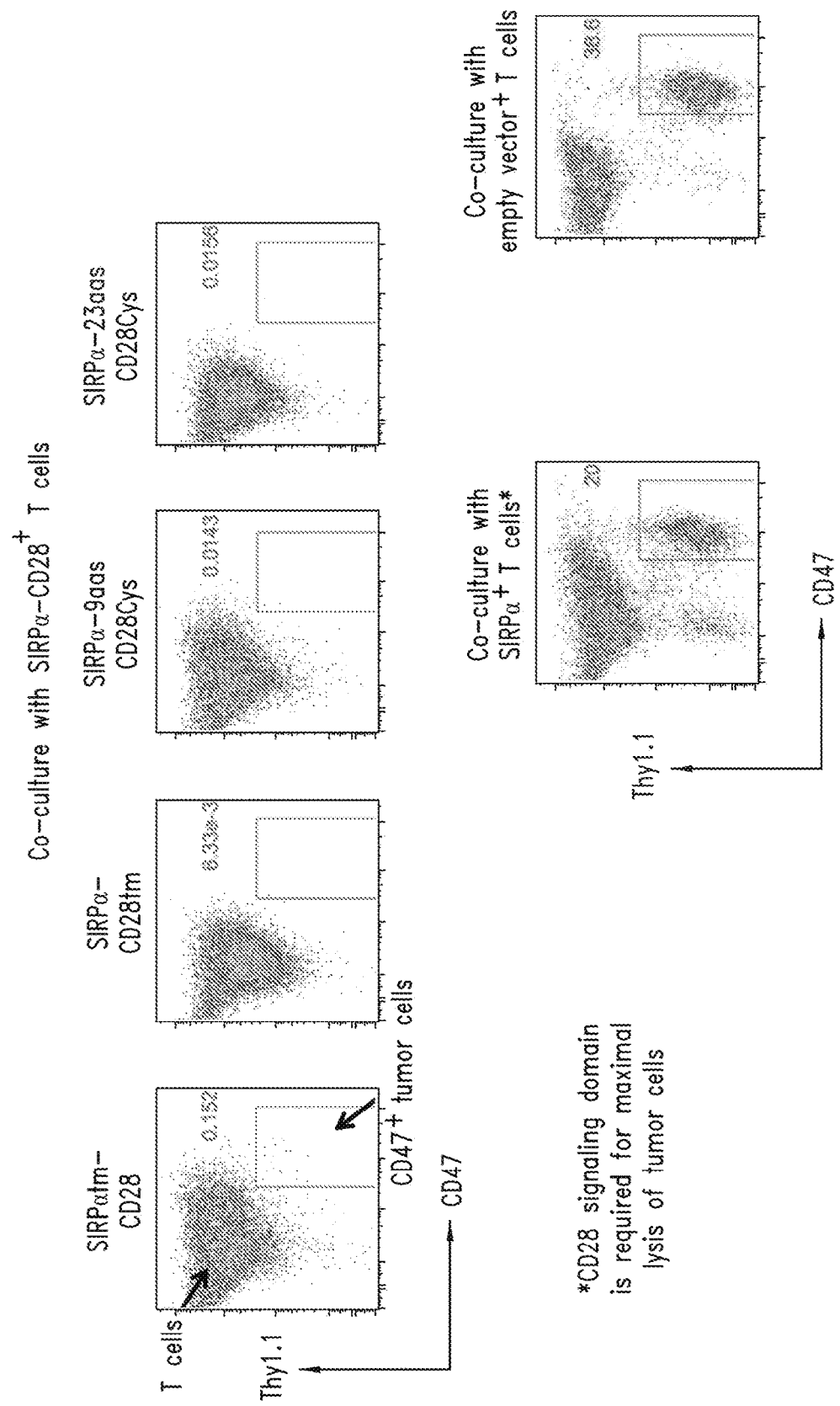
Figure 8E:
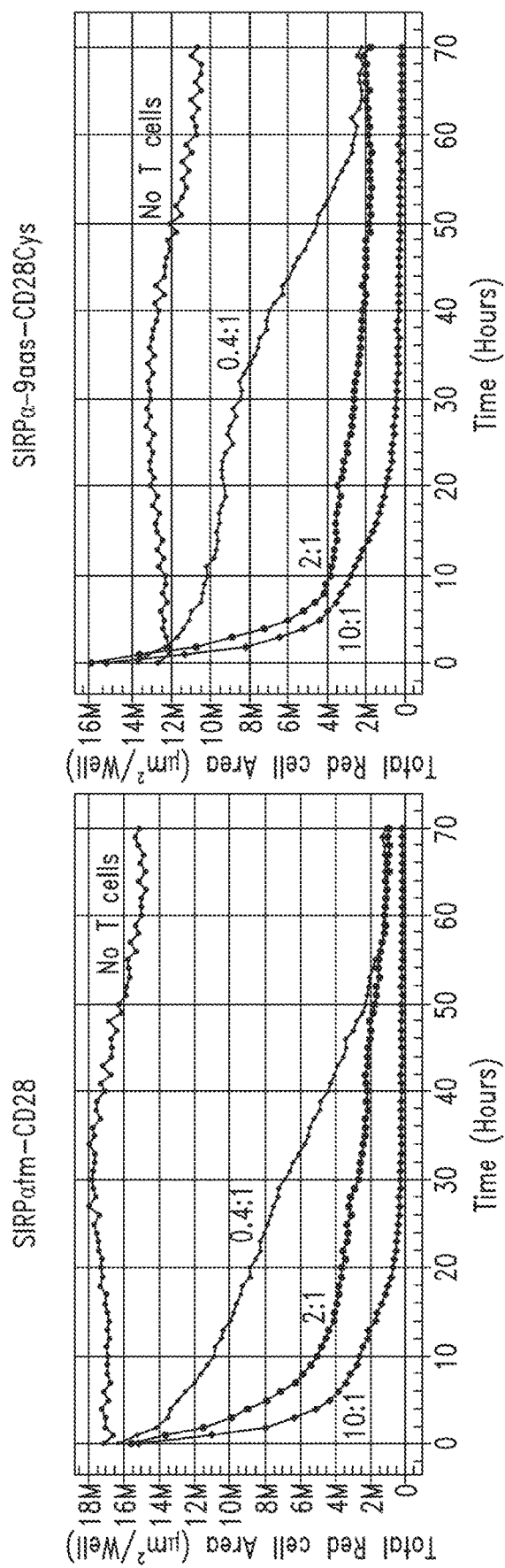

To assess T cell proliferation in vitro, a CTV Dilution Proliferation assay was performed as described in Example 2. As was observed with CD200R-9aas-CD28Cys, T cells transduced with the SIRPα constructs engineered to maintain the T cell-tumor cell synapse distance exhibited enhanced proliferation as compared to control T cells (FIG. 8C). In addition, CD47$^+$ tumor cells were efficiently killed after 3 days of co-culture with SIRPα-CD28$^+$ T cells but not control T cells or T cells transduced with a SIRPα construct that lacked an intracellular signaling domain (FIG. 8D). To further assess the lytic capacity of SIRPα-CD28$^+$ T cells, an IncuCyte® assay was used to quantify killing of CD47$^+$ FBL. A total of $10^5$ mCherry$^+$ CD47$^+$ FBL were co-cultured in 24-well plates with a titration of human T cells transduced with SIRPα-CD28 constructs. The plate was incubated in an IncuCyte® (Essen BioScience) inside a cell culture incubator for 70 hours. Images were captured every hour to monitor killing of tumor cells, as determined by loss of red signal. SIRPα-CD28$^+$αT cells killed CD47$^+$ tumor cells, even at the lowest effector-to-target ratio tested (0.4:1; FIG. 8E).

Example 10

Figure 9A:
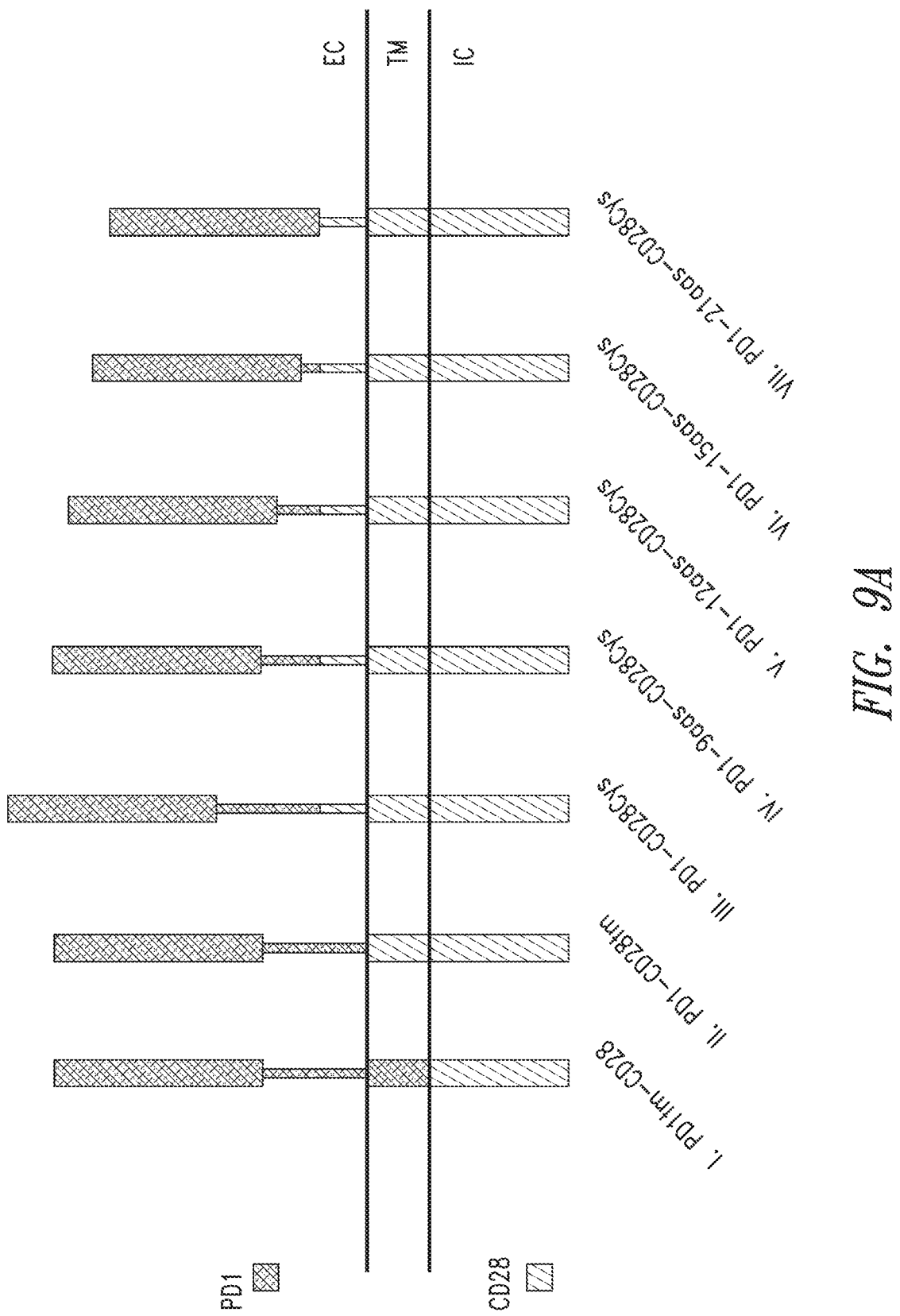
FIGS. 9A and 9B show that fusion proteins comprising PD-1 extracellular components and CD28 co-stimulatory signaling domains promote cytokine production in vitro. (A) Schematic representation of exemplary PD-1-CD28 constructs. Construct "I" contains PD-1 extracellular ("EC") and transmembrane ("TM") domains and a CD28 intracellular ("IC") signaling domain (PD1tm-CD28). Construct "II" contains the extracellular domain of PD-1 and the transmembrane and intracellular domains of CD28 (PD1-CD28tm). Constructs "III-VII" also incorporate a portion of the extracellular domain of CD28 adjacent to the transmembrane-proximal cysteine to promote multimerization and enhance CD28 signaling. To account for the extra extracellular amino acids (e.g., extra nine (9) amino acids for murine constructs, or twelve (12) amino acids for human constructs), constructs IV-VII have a truncated portion of PD-1. Construct IV has a truncated portion of PD-1 that is truncated 9 amino acids. Construct V has a truncated portion of PD-1 that is truncated 12 amino acids. Construct VI has a truncated portion of PD-1 that is truncated 15 amino acids. Construct VII has a truncated portion of PD-1 that is truncated 21 amino acids. Constructs "I", "II", and "V" maintain the short spatial distance between the cells (e.g., between a T cell and an antigen presenting cell) and may co-localize with the TCR within the cSMAC and deliver a strong co-stimulatory signal. (B) PD1-CD28$^+$ T cells exhibited increased cytokine production in response to stimulation for 5 hours in the presence of Brefeldin A with FBL cells that endogenously express the PD-1 ligands, PD-L1 and PD-L2. Stimulated T cells were assessed for intracellular expression of the effector cytokines, IFNγ and TNFα, by flow cytometry.

PD-1-CD28 Fusion Protein Constructs Promote Cytokine Production in Transduced T Cells In Vitro Exemplary fusion proteins as described herein also include IFPs comprised of the extracellular domain of PD-1, or portions thereof, and an intracellular signaling domain of CD28 (FIG. 9A). The transmembrane component may be comprised of the transmembrane domain of either PD-1 or CD28, or portions thereof. In some exemplary PD1-CD28 fusion proteins, the transmembrane component comprises the transmembrane domain of CD28 and the extracellular component further comprises an extracellular portion of CD28, particularly an extracellular cysteine residue adjacent to the transmembrane component (e.g., PD1-CD28Cys, PD1-9aas-CD28Cys, and PD1-21aas-CD28Cys) to promote inter-chain dimerization. The extracellular component may comprise all or a portion of the extracellular domain of PD-1, or may be truncated (e.g., −9aas in murine constructs, −12aas or −15aas in human constructs; lacking the stem region of PD-1, -21aas) to maintain the short spatial distance between the cells to facilitate access of the liganded receptor to the immunologic synapse. Additionally, a PD1-CD28 construct has the capacity to convert what would typically be an inhibitory signal from the binding of PD1 to its target into a positive (e.g., costimulatory) signal generated by the CD28 intracellular signaling domain.

IFPs comprising PD-1 extracellular components were generated (FIG. 9A) using the methods described in Example 2. TCR$_{gag}$ T cells were transduced as in Example 2, and TCR$_{gag}$ effector cells were generated in vitro as in Example 3.

Figure 9B:
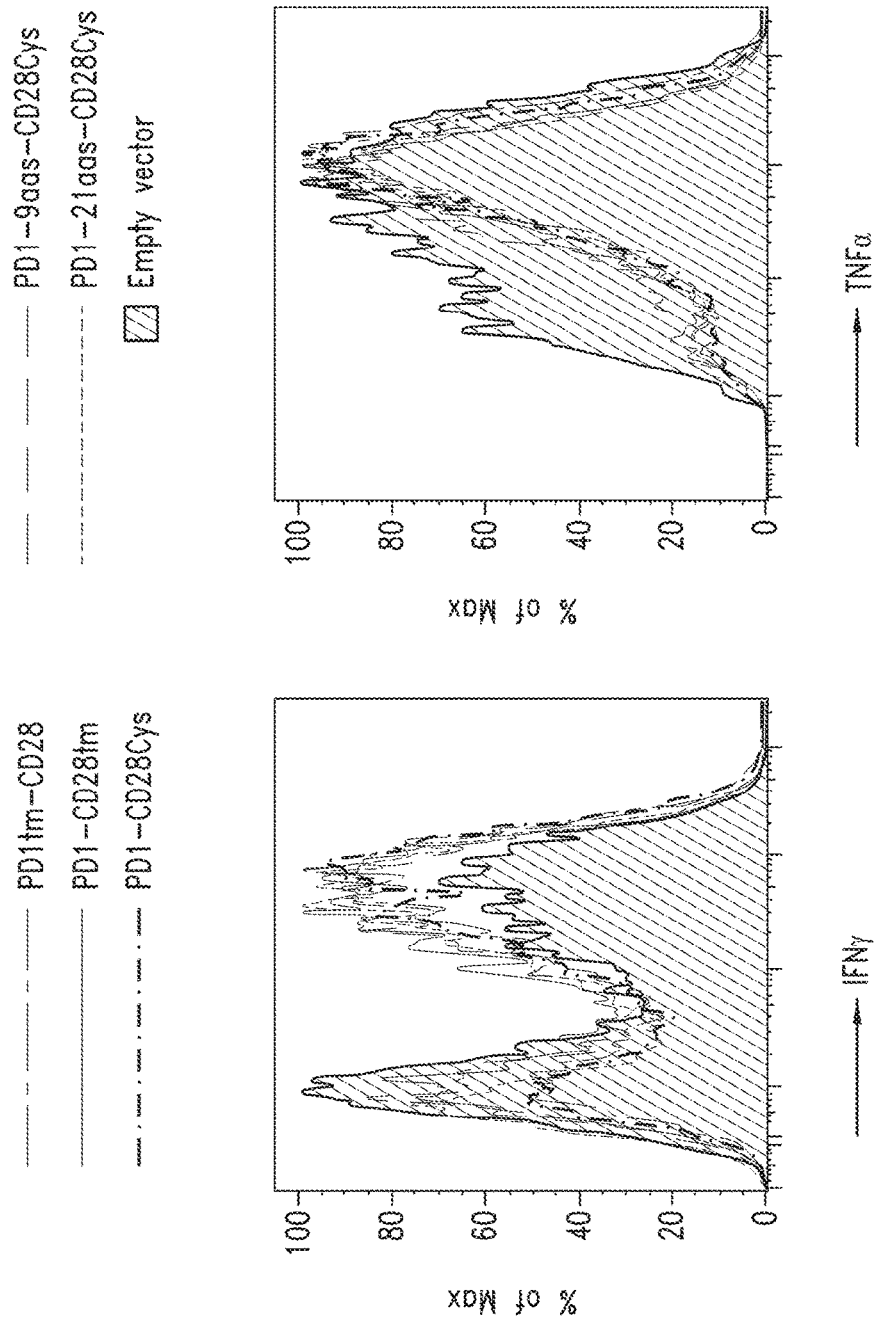

Murine PD1-CD28 IFPs were generated using constructs I-IV and VII (FIG. 9A). PD1-CD28$^+$ T cells were restimulated in the presence of Brefeldin A (to retain produced cytokines) with FBL cells endogenously expressing the PD-1 ligands, PD-L1 and PD-L2. After 5 hours, cells were fixed and treated with the BD Cytofix/Cytoperm kit, to allow intracellular staining of the effector cytokines, IFNγ and TNFα. Transduction with each of the five PD1-CD28 constructs enhanced production of intracellular cytokines compared to control T cells (FIG. 9B).

Figure 10:
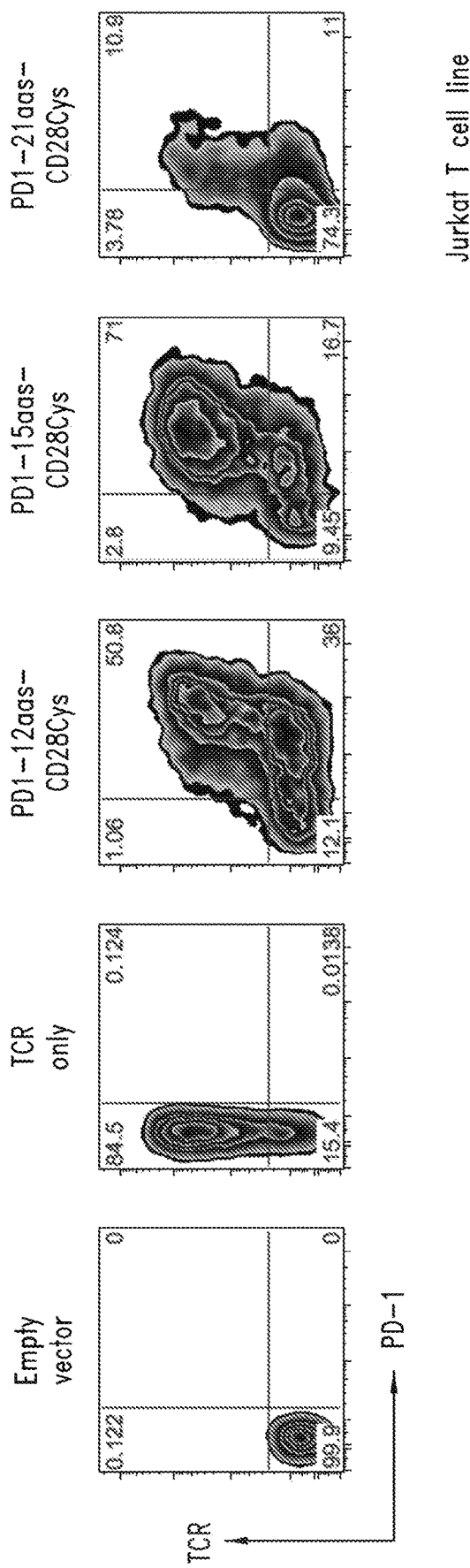
FIG. 10 shows co-expression of the TCR C4 and a PD-1 IFP (PD1-12aas-CD28Cys, PD1-15aas-CD28Cys, or PD1-21aas-CD28Cys). T cells transduced with C4 and PD1-12aas-CD28Cys or PD1-15aas-CD28Cys exhibited high transduction efficiencies and expression of both proteins.

Human PD1-CD28 IFPs were generated using constructs I-III and V-VII (FIG. 9A). Vectors containing the PD1-CD28 IFP and C4 TCR were generated as described above. Jurkat T cells were transduced as described above. T cells transduced with the TCR and PD1-12aas-CD28Cys or PD1-15aas-CD28Cys exhibited high transduction efficiencies and expression of both proteins (FIG. 10).

Example 11

Figure 11A:
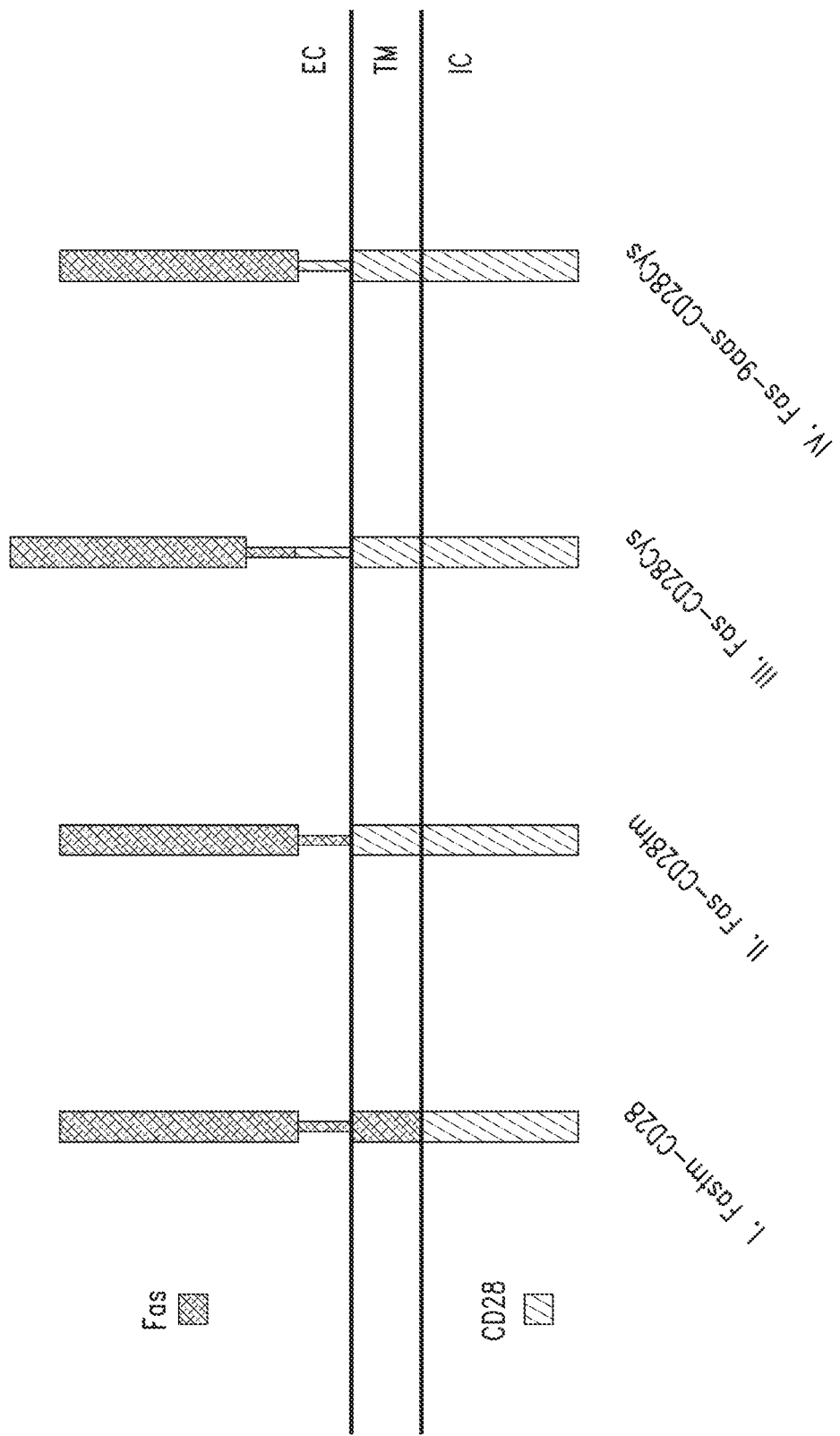
FIGS. 11A to 11C show that fusion proteins comprising Fas extracellular components and CD28 co-stimulatory signaling domains accumulate in vitro upon stimulation with irradiated FBL cells. (A) Schematic representation of exemplary Fas-CD28 constructs. Construct "I" contains Fas extracellular ("EC") and transmembrane ("TM") domains and a CD28 intracellular ("IC") signaling domain (Fastm-CD28). Construct "II" contains the extracellular domain of Fas and the transmembrane and intracellular domains of CD28 (Fas-CD28tm). Constructs "III" and "IV" also incorporate a portion of the extracellular domain of CD28 adjacent to the transmembrane-proximal cysteine to promote multimerization and enhance CD28 signaling. To account for the extra extracellular amino acids (e.g., extra nine (9) amino acids for murine constructs, or twelve (12) amino acids for human constructs), construct IV has a truncated portion of Fas, wherein the Fas extracellular domain is truncated 9 amino acids. Constructs "I", "II", and "IV" maintain the short spatial distance between the cells (e.g., between a T cell and an antigen presenting cell) and may co-localize with the TCR within the cSMAC and deliver a strong co-stimulatory signal. (B) Accumulation of TCR$_{gag}$ T cells transduced with Fas constructs over multiple stimulations with irradiated FBL cells. All of the constructs promoted accumulation of T cells relative to control T cells. (C)

FAS-CD28 Fusion Protein Constructs Promote Accumulation and Enhanced Function in Transduced T Cells In Vitro Exemplary fusion proteins as described herein also include IFPs comprised of the extracellular domain of Fas, or portions thereof, and an intracellular signaling domain of CD28 (FIG. 11A). The transmembrane component may be comprised of the domain of either Fas or CD28, or portions thereof. In some exemplary Fas-CD28 fusion proteins, the transmembrane component comprises the transmembrane domain of CD28 and the extracellular component further comprises an extracellular portion of CD28, particularly an extracellular cysteine residue adjacent to the transmembrane component (e.g., Fas-CD28Cys and Fas-9aas-CD28Cys). The extracellular component may comprise all or a portion of the extracellular domain of Fas or may be truncated to preserve maintain a short spatial distance between the cells (-9aas) upon receptor-ligand interaction. Additionally, a Fas-CD28 construct has the capacity to convert a signal initiated by the binding of Fas to its target into a positive (e.g., costimulatory) signal generated by the CD28 intracellular signaling domain.

IFPs comprising Fas extracellular components were generated (FIG. 11A) using the methods described in Example 2. TCR$_{gag}$ T cells were transduced as in Example 2, and TCR$_{gag}$ effector cells were generated in vitro as in Example 3.

Figure 11B:
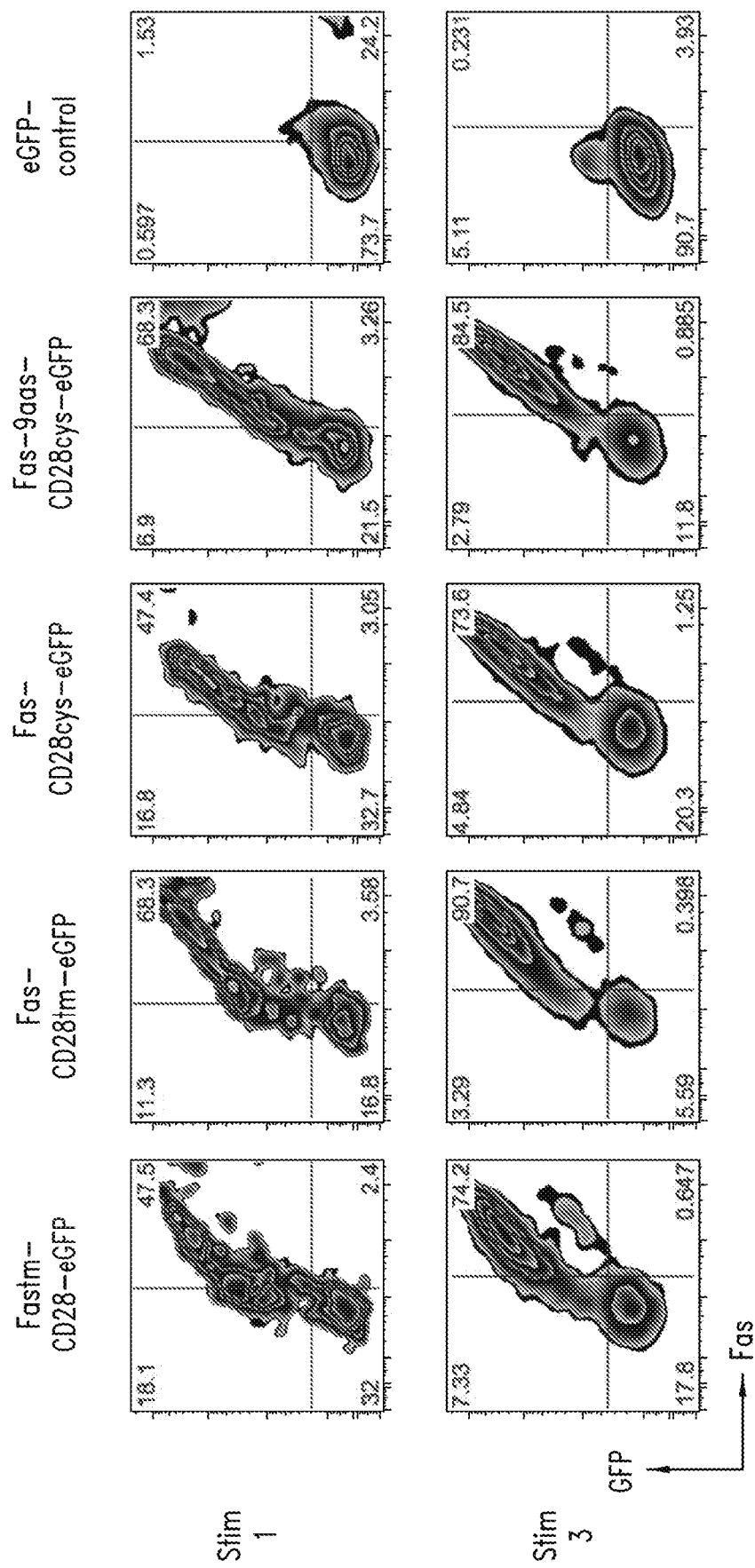
Figure 11C:
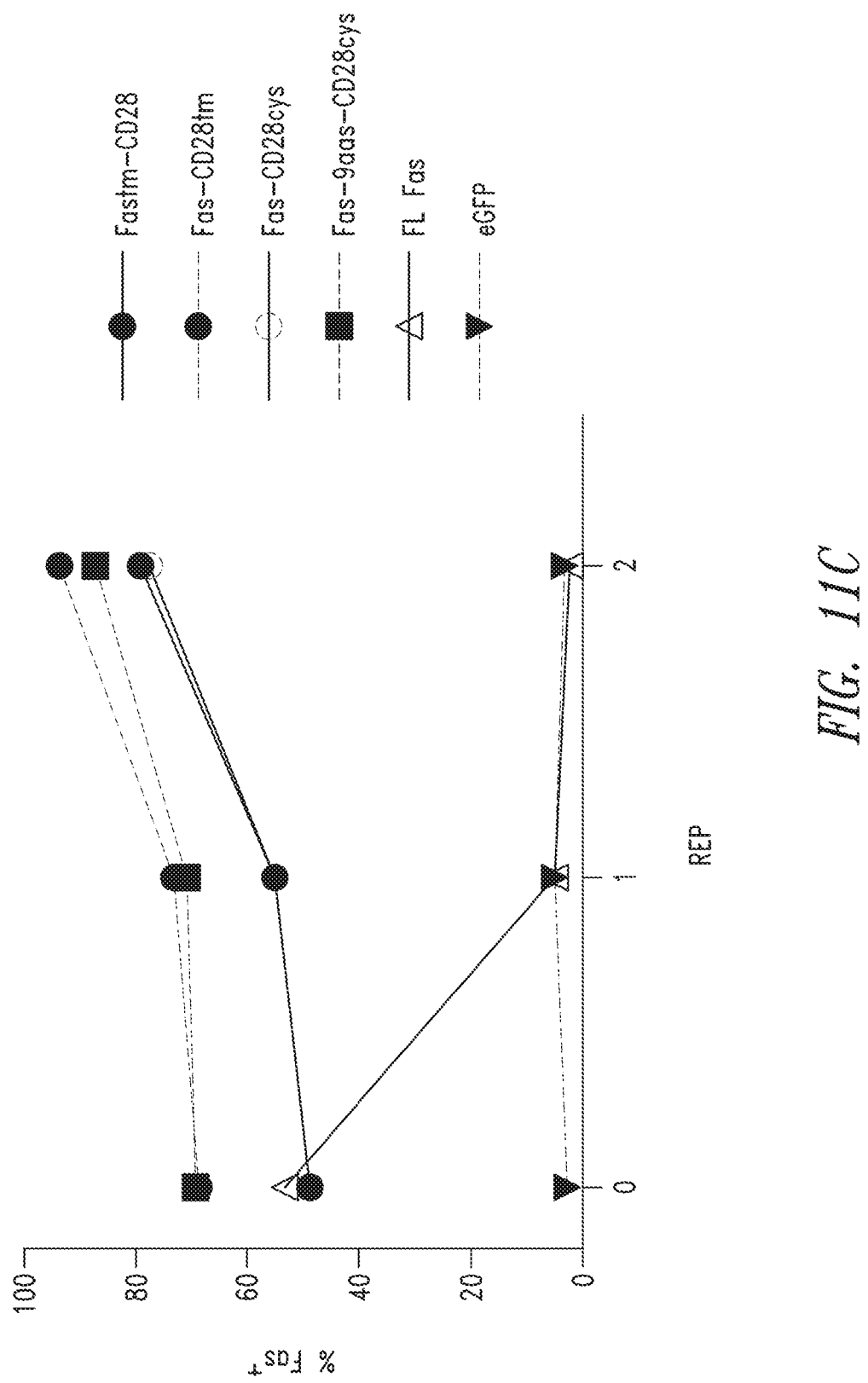

To determine if expression of the Fas-CD28 IFP results in increased accumulation of transduced cells, the proportion of transduced cells from the mixed population in the total TCR$_{gag}$ population was measured over multiple cycles of stimulation with irradiated FBL, as described in Example 3. All of the constructs promoted accumulation of transduced T cells compared to control T cells (FIG. 11B). In addition, expression of Fas-CD28 constructs but not full-length (FL) Fas promoted survival or expansion of T cells upon multiple stimulations in vitro FIG. 11C).

Example 12

LAG3-CD28 Fusion Protein Constructs

Exemplary fusion proteins as described herein also include IFPs comprised of the extracellular domain of LAG3, or portions thereof, and an intracellular signaling domain of CD28 (FIG. 12A). The transmembrane component may be comprised of the domain of either LAG3 or CD28, or portions thereof. In some exemplary LAG3-CD28 fusion proteins, the transmembrane component comprises the transmembrane domain of CD28 and the extracellular component further comprises an extracellular portion of CD28, particularly an extracellular cysteine residue adjacent to the transmembrane component (e.g., LAG3-CD28Cys and LAG3-9aas-CD28Cys). The extracellular component may comprise all or a portion of the extracellular domain of LAG3 or may be truncated to maintain a short spatial distance between the cells (e.g., −9aas) upon receptor-ligand interaction. Additionally, a LAG3-CD28 construct has the capacity to convert what would typically be an inhibitory signal from the binding of LAG3 to its target into a positive (e.g., costimulatory) signal generated by the CD28 intracellular signaling domain.

IFPs using LAG3 extracellular components were generated (FIG. 12A) using the methods described in Example 2. T cells were transduced with LAG3-eGFP constructs as described. Five days after transduction, CD8+ T cells were analyzed for construct expression by anti-LAG3 antibody staining and flow cytometry (FIG. 12B). A vector encoding only green fluorescent protein (GFP) was used as a control. All constructs exhibited expression of LAG3 (FIG. 12B).

Example 13

TIM3-CD28 Fusion Protein Constructs

Exemplary fusion proteins as described herein also include IFPs comprised of the extracellular domain of TIM3, or portions thereof, and an intracellular signaling domain of CD28 (FIG. 13A). The transmembrane component may be comprised of the domain of either TIM3 or CD28, or portions thereof. In some exemplary TIM3-CD28 fusion proteins, the transmembrane component comprises the transmembrane domain of CD28 and the extracellular component further comprises an extracellular portion of CD28, particularly an extracellular cysteine residue adjacent to the transmembrane component (e.g., TIM3-CD28Cys and TIM3-9aas-CD28Cys). The extracellular component may comprise all or a portion of the extracellular domain of TIM3 or may be truncated to maintain the short spatial distance between the cells (e.g., −9aas). Additionally, a TIM3-CD28 construct has the capacity to convert what would typically be an inhibitory signal from the binding of TIM3 to its target into a positive signal generated by the CD28 intracellular signaling domain.

New IFPs using TIM3 extracellular components were generated (FIG. 13A) using the methods described in Example 2. T cells were transduced with GFP-TIM3 constructs as described. Five days after transduction, CD8+ T cells were analyzed for construct expression by anti-TIM3 antibody staining and flow cytometry (FIG. 13B). A vector encoding only green fluorescent protein (GFP) was used as a control. Most constructs exhibited similar expression of TIM3 (FIG. 13B).

Example 14

CD200R-CD28 Fusion Protein Constructions Can Be Expressed by Primary T Cells

In a further example, exemplary fusion proteins as described herein are illustrated using schematic representations in FIG. 14A. Representative fusion proteins include IFPs comprised of the extracellular domain of CD200R or a portion thereof, and an intracellular signaling domain of CD28 or a portion thereof (FIG. 14A, constructs I-V). The hydrophobic component may be comprised of the transmembrane domain of either CD200R (FIG. 14A, construct I) or CD28 (FIG. 14A, constructs II-V), or portions thereof. In some exemplary CD200R-CD28 fusion proteins, the hydrophobic component comprises the transmembrane domain of CD28 and the extracellular component further comprises an extracellular portion of CD28, particularly an extracellular cysteine residue adjacent to the hydrophobic component (e.g., FIG. 14A construct III, CD200R-CD28Cys; construct IV, CD200R-3aas-CD28Cys; and construct V, CD200R-9aas-CD28Cys). The extracellular component may comprise all or a portion of the extracellular domain of CD200R. In some embodiments, the extracellular component comprises the entire extracellular domain of CD200R (FIG. 14A, constructs In other examples, the extracellular component comprises the first 235 amino acids (preserving an N-linked glycosylation site) (e.g., FIG. 14A, construct IV, CD200R-3aas-CD28Cys) or the first 229 amino acids (e.g., FIG. 14A, construct V, CD200R-9aas-CD28Cys) from the N-terminus of CD200R. The CD200R-CD28 constructs disclosed herein have the capacity to convert what would typically be an inhibitory signal from the binding of CD200R to its target into a positive signal generated by the CD28 intracellular signaling domain.

The size of the extracellular component, which may be manipulated by adjusting the fusion protein construct, may affect the ability of the fusion protein to enter the immunological synapse and co-localize with the TCR within the cSMAC to deliver a strong co-stimulatory signal. CD28 signaling naturally occurs in the immunological synapse, where CD28 is recruited to amplify TCR signals and lower the threshold of activation (Chen and Flies, *Nat. Rev. Immunol.* 13: 227-242, 2013; Yokosuka et al., *Immunity* 29:589-601, 2008). The spatial distance between the T cell and APC is shortest within the immunological synapse, and molecules with large ectodomains are excluded. Thus, constructs that best approximate the cell-to-cell spacing of the immunological synapse may be able to co-localize with the TCR within the immunological synapse and deliver an effective costimulatory signal. Constructs III and IV extend the CD28 transmembrane domain into the extracellular space to incorporate the membrane proximal cysteine (CD28Cys) that promotes CD28 homodimerization and enhances native CD28 signaling (Lazar-Molnar et al., *Cell Immunol.* 244: 125-129, 2006). To account for the length added by the nine amino acids of extracellular CD28 domain, the CD200R extracellular domain portion of CD200R-9aas-CD28Cys is truncated by nine amino acids, an equivalent number added by the CD28 extracellular domain. Similarly, the extracellular CD200R of CD200R-3aas-CD28Cys is truncated by 3 amino acids. The truncated extracellular CD200R is truncated from the C-terminal end, to preserve an N-linked glycosylation site. Thus, murine constructs CD200Rtm-CD28, CD200R-CD28tm, and CD200R-9aas-CD28Cys theoretically best maintain the short spatial distance between the T cell and APC needed to co-localize with the TCR in the immunological synapse.

An exemplary nucleic acid molecule encoding a CD200R-CD28 fusion protein comprises the following elements (5' to 3'): Extracellular Component (CD200R)-Multimerization Domain (CD28 Cysteine)-Hydrophobic Component (CD28 transmembrane)-Intracellular Component (CD28 intracellular). In some embodiments, a nucleic acid molecule encoding a CD200R-CD28 fusion protein comprises a nucleic acid molecule as set forth in any one of SEQ ID NOS.:47-51 or 1, 6, 7, 10, 12, 14, 15, or 183.

Nucleic acids encoding the constructs were inserted into the pMP71 retroviral vector to transduce primary mouse splenocytes stimulated with anti-CD3 and anti-CD28 antibodies. C57BL/6 (B6) mice were purchased from Jackson Laboratory. TCR$_{gag}$ transgenic mice express in CD8+ T cells a TCR transgene specific for the Friend virus gag epitope (Ohlen et al., *J. Exp. Med.* 195:1407-1418, 2002). The B6 Friend virus induced erythroleukemia (FBL) expresses the Friend virus gag epitope (peptide CCLCLTVFL (SEQ ID NO.:213)) (Teague et al., *Nat. Med.* 12:335-341, 2006). DNA constructs were ordered from Invitrogen or generated in-house by PCR. The constructs directionally TOPO-cloned into vector pENTR/D-TOPO were transferred to the retroviral vector (RV) pMP71-attR using Gateway® technology. The retroviral packaging cell line Plat-E (Cell-Bio Labs) was transduced with the RV using effectene transduction reagent (Qiagen). Viral supernatant was collected on days 2 and 3. One day prior to transfection, $TCR_{gag}$ T cells were stimulated with anti-CD3/CD28 and 100 U/mL rhIL-2. Transduction of $TCR_{gag}$ T cells was performed in 12 well plates in the presence of IL-2 and polybrene by spinfection for 90 minutes at 1000 g. Transduced cells were restimulated 7 days post stimulation in the presence of irradiated splenocytes ($5 \times 10^6$), irradiated FBL ($3 \times 10^6$), and IL-2 (IU/mL).

Five days post-transduction, CD8+ T cells were analyzed for IFP expression by flow cytometry (FIG. 14B). Fluorochrome-conjugated antibodies were purchased from eBioscience or Biolegend. Transduction efficiency ranged from 5-43%, and mean fluorescence intensity of transduced cells was similar between constructs, suggesting similar IFP expression.

Example 15

CD200R-CD28 Constructs Promote In Vitro Proliferation, Accumulation, and Effector Function of Transduced T Cells The CD200R-CD28 constructs described in Example 14 were assessed for their abilities to promote proliferation, accumulation, and effector function of $TCR_{gag}$ T cells.

In vitro T Cell Proliferation Assay

CD28 signaling promotes proliferation and survival of T cells stimulated via the TCR (Chen and Flies, *Nat. Rev. Immunol.* 13: 227-242, 2013). To determine if CD200R-CD28 IFPs improve proliferation, naïve CD8+ TCR transgenic T cells ($TCR_{gag}$ cells) specific for an epitope derived from the Friend murine leukemia virus-transformed FBL leukemia (Stromnes et al., *J Clin Invest.* 120:3722-3734, 2010), as described in Example 14, were transduced and expanded in vitro with antigen in the presence of IL-2 for 2-3 stimulation cycles to generate effector T cells and model human adoptive immunotherapy protocols. Effector T cells were labeled with CellTrace Violet (CTV), and CTV-labeled Tg T cells ($10^5$) were stimulated with either FBL, which does not naturally express CD200 (CD200− FBL) (FIG. 15A, upper panels), or an FBL line transduced to express CD200 (CD200+ FBL) for 3 days and then assessed by flow cytometry (FIG. 15A, lower panels).

At a low 25:1 T cell to FBL ratio, GFP-control transduced T cells (FIG. 15A, blue lines) exhibited minimal proliferation in response to CD200− or CD200+ FBL. In contrast, four of the five tested constructs (FIG. 15A, red lines) dramatically improved proliferation in response to CD200+ FBL but not CD200− FBL. T cells transduced with the largest ectodomain, CD200R-CD28Cys, did not improve proliferation.

To test whether the increased proliferation delivered by the CD200R interaction with the leukemia-expressed CD200 reflected enhanced adhesion and/or decoy binding rather than costimulation, a truncated non-signaling version of the construct was generated with only CD200R extracellular and CD28 transmembrane domains ("trCD200R"; FIG. 15B). Transduced $TCR_{gag}$ T cells expressing the construct (FIG. 15C) did not exhibit enhanced proliferation to CD200+ FBL (FIG. 15D), indicating a requisite role for CD28 costimulatory signals.

In vitro T Cell Enrichment Assay

It was expected that expression of the CD200-targeted IFP would result in enrichment of IFP+ T cells relative to IFP− T cells after stimulation with CD200+ FBL. The proportion of transduced cells in the total $TCR_{gag}$ population after multiple cycles of stimulation with irradiated CD200− or CD200+ FBL was assessed. Analysis of cell composition after 3 cycles of stimulation with either CD200− or CD200+ FBL revealed no change in the fraction of GFP control-expressing $TCR_{gag}$ T cells (FIG. 15E). In contrast, IFP-expressing $TCR_{gag}$ T cells were enriched following stimulation with CD200+ but not CD200− FBL (CD200R-9aas-CD28Cys, FIG. 15F). Although several constructs promoted accumulation of transduced T cells, as predicted, the construct that was sized to fit within the immunological synapse and included the dimerizing cysteine motif, CD200R-9aas-CD28Cys, produced the greatest relative increase, resulting in an average of >3-fold enrichment after 3 stimulations ($P<0.05$), in 3 separate experiments (FIG. 15G, showing fold enrichment, stimulation 3/stimulation 1, for eGFP, CD200Rtm-CD28, CD200R-CD28tm, CD200R-3aas-CD28cys, and CD200R-9aas-CD28cys-transduced T cells).

CFSE-Based Cytotoxic Assay

CD28 signaling promotes effector functions (Chen and Flies, *Nat. Rev. Immunol.* 13: 227-242, 2013). T cells transduced to express CD200R-9aas-CD28Cys were tested for increased killing of tumor target cells.

FBL and control EL4 tumors were incubated for 10 min at room temperature with 2.5 µM (hi) or 0.25 µM (lo) CFSE in PBS, respectively. Excess dye was removed by washing tumor cells in serum-containing media. A 1:1 mixture of non-specific EL4 control targets and CD200+ FBL tumor cells was incubated with titrated numbers of CD200R-9aas-CD28Cys-transduced or GFP-transduced $TCR_{gag}$ effector T cells (i.e., a range of effector to target (E:T) ratios) for 5 h in 96-well, round-bottom plates at 37° C. and 5% $CO_2$. Specific FBL lysis was determined by flow cytometric analyses of the % $CFSE_{hi}$ (FBL) of total CFSE positive cells (FBL+EL4) remaining in the well.

$TCR_{gag}$ T cells transduced with CD200R-9aas-CD28Cys killed CD200+ FBL cells better than control T cells, lysing >40% of CD200+ FBL at a low E:T ratio (0.3:1) (FIG. 15H).

In Vitro Cytokine Production Assay

To determine if T cells transduced with the CD200R-9aas-CD28Cys IFP produced increased amounts and diversity of cytokines, which represent other functions of costimulation, polyfunctional cytokine production was assessed by flow cytometry. A higher percentage of CD200R IFP+ T cells produced IFNγ, IL-2, and TNFα than control T cells following stimulation with CD200− FBL. A lower percentage of CD200R IFP+ T cells were cytokine non-producing cells (27% vs 51%, FIG. 15I, blue), while a higher percentage of CD200R IFP+ T cells were polyfunctional cells producing all 3 cytokines (22% vs 7%, FIG. 15I, purple). CD200R IFP+ T cells stimulated with CD200+ FBL had increased cytokine/cell based on mean fluorescent intensity (MFI) (FIG. 15J).

In Vitro Colocalization Assay

To more closely examine the mechanism of enhanced T cell function with IFP expression, CD200R IFP location on the T cell surface was visualized via microscopy. Localization of native CD28 to the immunological synapse after binding CD80/86 recruits signaling molecules that amplify the TCR signal (Chen and Flies, *Nat. Rev. Immunol.* 13:

227-242, 2013). To assess movement of the IFP following stimulation, FITC-conjugated cholera toxin B subunit (CTx B) was used to stain lipid rafts within the cell membrane (FIG. 15K, panel III), which are enriched at the immunological synapse (Stephan et al., *Nat Med.* 13:1440-1449, 2007), and used to define the site of immunological synapse assembly. Antibodies binding CD200 on FBL (FIG. 15K, panel II) or CD200R on the T cell (CD200R-9aas-CD28Cys, FIG. 15K, panel I) were then used to visualize these molecules in relation to the immunological synapse. CD200R IFP-transduced, in vitro expanded effector $TCR_{gag}$ cells were mixed with FBL at an E:T of 10:1 in 15 mL, then incubated at 37° C. for 20 minutes, and then loaded on a μ-Slide VI.4 chamber (Ibidi) for 15 minutes. Slides were washed with PBS and fixed with 2% paraformaldehyde for 4 minutes. Cells were then washed, stained, imaged at 60× using a Deltavision Elite Fluorescent Microscope, and analyzed using Image J (NIH).

CD200R localized with increased lipid raft staining at the region of T cell:target contact (FIGS. 15K to 15M, panel IV), suggesting that the size of the IFP can be accommodated by the immunological synapse.

LCK Phosphorylation

The tyrosine kinase, LCK, is critical for TCR signaling and recruitment of LCK to the TCR signaling complex results in phosphorylation of immunoreceptor tyrosine-based activation motif (ITAM) sequences in the CD3 complex to initiate the TCR signaling cascade (Chen and Flies, *Nat. Rev. Immunol.* 13: 227-242, 2013). LCK associates with CD28 via a proline motif in the CD28 signaling tail and T cell expression of CD28 is required for sustained phosphorylation of LCK residue Y394 (Holdorf et al., *Nat Immunol.* 3:259-264, 2002). To determine if CD200R-CD28 IFP expression provides or augments CD28 signaling, pLCK Y394 was evaluated in T cells transduced with the GFP control, the lead construct (CD200R-9aas-CD28Cys), or the ineffective construct that did not promote proliferation (CD200R-CD28Cys) (FIG. 15A). Transduced T cells were unstimulated or stimulated with PMA/ionomycin, FBL, or $CD200^+$ FBL for 10 minutes, fixed and stained for intracellular pLCK Y394, and analyzed by flow cytometry. Antibodies to phospho-LCK (Tyr394) were purchased from R&D Systems, and intracellular staining was detected via secondary labeling with anti-mouse PE from BioLegend.

The three populations of T cells achieved similar phosphorylation of LCK Y394 in response to strong stimulation (PMA/ionomycin) and $CD200^-$ FBL stimulation (FIG. 15N). T cells transduced with the GFP control or the IFP with the larger ectodomain, CD200R-CD28Cys, exhibited a similar low level of pLCK Y394 expression in response to $CD200^-$ FBL and $CD200^+$ FBL. However, when stimulated with $CD200^+$ FBL, CD200R-9aas-CD28Cys-transduced T cells exhibited sustained increased phosphorylation of LCK Y394 at 10 minutes, demonstrating that expression of CD200R-9aas-CD28cys provided a requisite function of CD28 costimulation.

Summary

Taken together, these data show that CD200R-CD28 constructs function to increase accumulation and the lytic activity of transduced T cells in response to tumor cell stimulation. Analysis of a panel CD200R-CD28 IFP constructs revealed costimulation was most effectively achieved in IFPs containing a dimerizing motif and a tumor-T cell distance that facilitates localization to the immunological synapse. T cells transduced with the such CD200R-CD28 IFPs exhibited enhanced proliferation and effector function in response to $CD200^+$ target cells in vitro.

Example 16

T Cells Transduced with CD200R-9AAS-CD28CYS Exhibit Enhanced Accumulation In Vivo in Response to Recognition of FBL In adoptive T cell therapy of malignancies, tumors commonly provide limited or no costimulatory signals and rather express ligands for inhibitory receptors. In leukemia, CD200 is a commonly expressed inhibitory ligand and is associated with a poor prognosis (Tonks et al., *Leukemia* 21:566-568, 2007). Therefore, the ability of $TCR_{gag}$ T cells expressing CD200R-9aas-CD28Cys IFP, which appeared most effective in vitro, to proliferate and accumulate when encountering $CD200^-$ FBL leukemia in vivo was assessed.

Figure 16A:
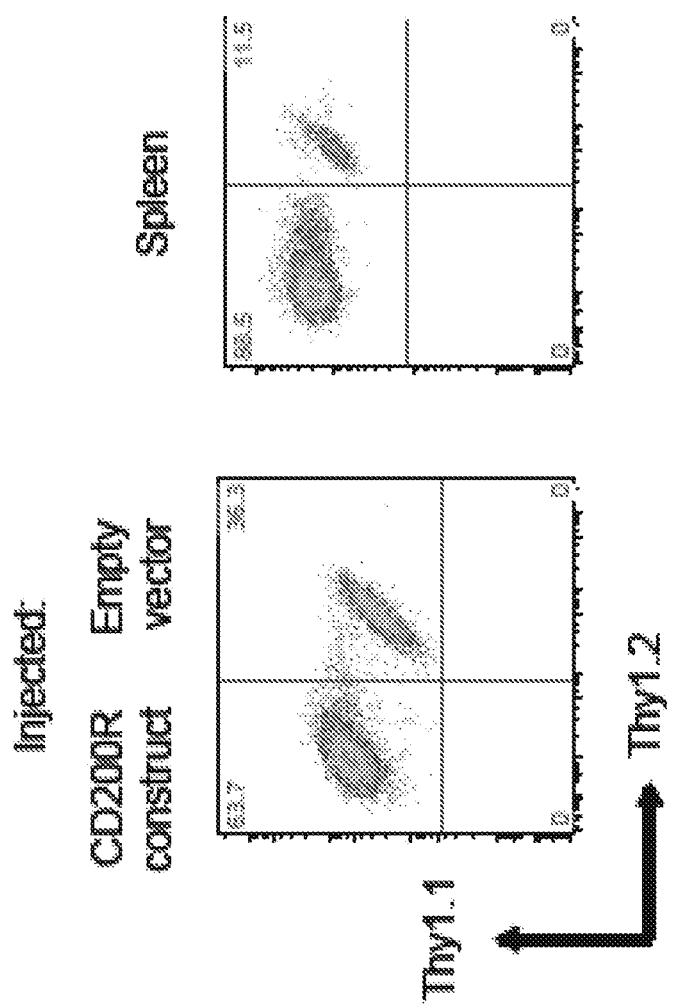
Figure 16B:
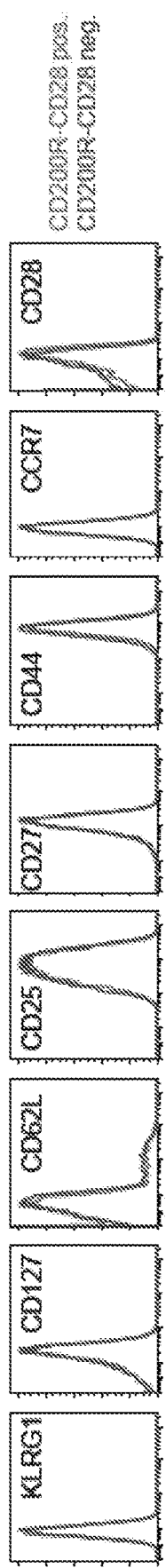

Transduced $TCR_{gag}$ T cells were generated as described in Example 15. B6 mice were injected with $4 \times 10^6$ live $CD200^+$ FBL leukemia intraperitoneal (i.p.) and, after allowing 5 days for the FBL to disseminate, mice received 180 mg/kg cyclophosphamide (Cy) i.p. 6 hours before transfer of the effector T cells to reduce tumor burden and induce lymphopenia similar to human adoptive immunotherapy protocols. To assess short-term proliferation and accumulation, $2 \times 10^6$ IFP-transduced $Thy1.1^+$ T cells were co-injected with an equal number of congenically distinct GFP-control-transduced $Thy1.1^+ Thy1.2^+$ T cells into tumor-bearing mice so that each mouse could serve as an internal control (FIG. 16A). Both T cell populations were generated in vitro and expanded with three stimulation cycles by identical methods, and appeared phenotypically similar on the day of injection, 5 days after the third stimulation (FIG. 16B). IL-2 was administered every 2 days ($2 \times 10^4$ U/dose). On day 8 post-T cell transfer, mice were euthanized and spleens and inguinal lymph nodes harvested.

For some studies, $CD8^+$ T cells were isolated by negative selection using the EasySepTM Mouse $CD8^+$ T Cell Enrichment Kit (STEMCELL). Mice were regularly monitored for increasing tumor burden and euthanized if evidence of tumor progression predicted mortality would occur within 24-48 hours.

Figure 16C:
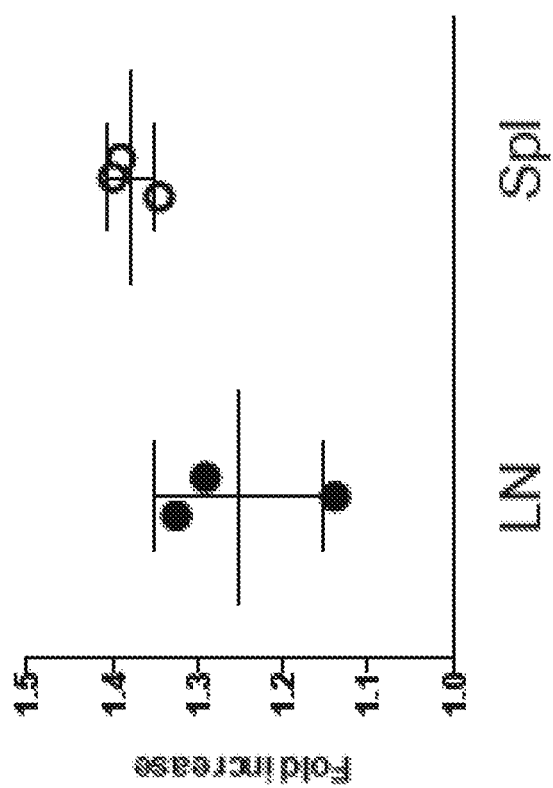
Figure 16D:
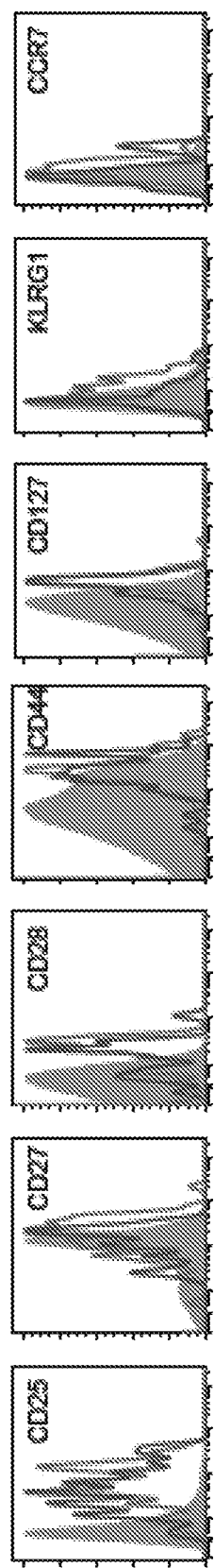
Figure 16E:
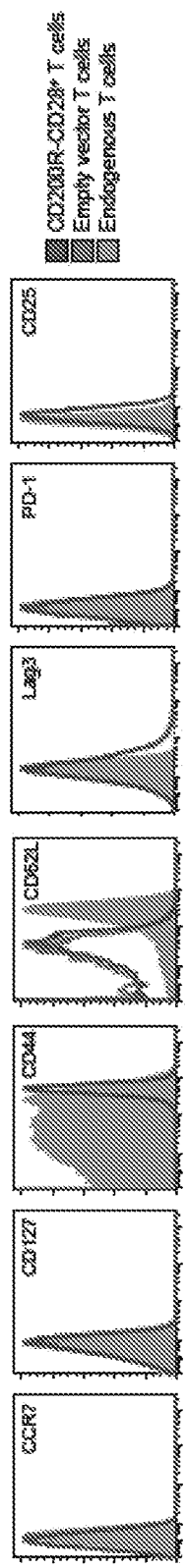

IFP-expressing T cells were 1.2- to 1.4-fold enriched in both spleen and lymph nodes compared to control cells (FIG. 16C). To assess possible phenotypic differences acquired by the transferred T cells, cohorts of mice were euthanized at early (d3) and late (d15) time points to identify effector, memory, and exhaustion markers. T cells were isolated from the spleen by untouched $CD8^+$ T cell enrichment and assessed by flow cytometry. Transduced CD200R-9aas-CD28Cys$^-$ $TCR_{gag}$ and control T cells expressed similar surface molecules consistent with an effector T cell phenotype at 3 days post-transfer (FIG. 16D). By day 15, the persisting IFP$^+$ and control T cells again appeared similar phenotypically, and did not express exhaustion markers PD-1 or Lag-3 (FIG. 16E), suggesting both cell types likely remained functional during this period.

In summary, in an in vivo study of adoptive therapy of disseminated leukemia, CD200R-CD28 transduced leukemia-specific T cells eradicated otherwise lethal disease more efficiently than wild type cells, and bypassed the requirement for IL-2 administration to sustain in vivo activity.

Example 17

Adoptive Immunotherapy with CD200R-CD28$^+$ T Cells Exhibits Greater Activity in Therapy of Disseminated Leukemia Whether the costimulation provided to cells expressing CD200R-9aas-CD28Cys IFP results in enhanced therapeutic T cell activity was evaluated in a preclinical mouse model of disseminated leukemia, which requires a T cell response lasting >25 days to achieve leukemia eradication (Cheever et al., *J Immunol.* 125:711-714, 1980). B6 mice were injected with a lethal dose (4×10⁶) of CD200⁺ FBL leukemia cells i.p., as previously described (Stromnes et al., *J Clin Invest.* 120:3722-3734, 2010). Five days later, cohorts of mice received 180 mg/kg cyclophosphamide (Cy) i.p. and received 10⁵ $TCR_{gag}$ effector T cells 6 hours later, to allow for metabolism of the drug (Cheever et al., 1980). The $TCR_{gag}$ T cells were previously stimulated 1-3× in vitro. The efficacy of therapy with T cells transduced with CD200R-9aas-CD28Cys was compared to T cells expressing a GFP control (FIGS. 17A, 17B). This approach was initially tested with a small cohort of mice that received IL-2 for 10 days following T cell transfer to enhance and sustain T cell activity (Stromnes et al., *J Clin Invest.* 120:3722-3734, 2010) (FIG. 17A).

With IL-2 injections, immunotherapy using the control T cells cured 67% of mice and CD200R-9aas-CD28Cys⁺ T cells cured 100% of mice, which did not achieve statistical significance (FIG. 17A). Subsequent studies were conducted with a larger cohort and with the IL-2 injections omitted. In these studies, only 40% of mice treated with T cells transduced with the GFP control vector survived beyond day 30 (FIG. 17B, blue line). By contrast, 89% of mice that received CD200R-9aas-CD28Cys⁺ T cells survived 100 days post-transfer of FBL (FIG. 17B, red line, P<0.05). These results indicate that an IFP with a CD200R providing a costimulatory signal not only enhances T cell immunotherapy of progressive leukemia, but can largely bypass the requirement for administration of IL-2.

Example 18

Co-Expression of CD200RTM-CD28 Enhances Function in WT1-Specific TCR Primary T Cells Adoptive therapy with engineered T cells has shown promising clinical benefit, particularly in acute lymphocytic leukemia with T cells expressing a chimeric antigen receptor (CAR) specific for the cell surface protein CD19 (Turtle et al., *J Clin Invest.* 126:2123-2138, 2016; Kalos et al., *Sci Transl Med.* 3:95ra73, 2011). T cells can alternatively be transduced to express a tumor-specific T cell receptor (TCR), which greatly expands the breadth of target antigens by including intracellular proteins such as transcription factors that often drive the oncogenic phenotype. CD8⁻ T cells specific for WT1, a transcription factor over-expressed in many malignancies (Yang et al., *Leukemia* 21:868-876, 2007; Qi et al., *Sci Rep.* 5:8924, 2015), exhibit anti-leukemic activity after transfer to patients (Chapuis et al., *Sci Transl Med.* 5:174ra127, 2013), and there are ongoing trials with CD8⁺ T cells transduced with a high affinity WT1-specific TCR in patients with leukemia, lung cancer, or mesothelioma (clinicaltrials.gov NCT01640301, NCT02408016). T cell activation with associated proliferation and survival requires a costimulatory signal concurrent with triggering the antigen receptor (Chen et al., *Nat Rev Immunol.* 13:227-242, 2013). Unlike CARs, which include a costimulatory domain in the chimeric signaling protein, cells with introduced TCRs require independent triggering of a costimulatory receptor. However, tumor cells generally not only express few if any ligands for costimulatory receptors, but commonly upregulate inhibitory receptor ligands that can interfere with costimulation and block T cell activation (Driessens et al., *Immunol Rev.* 229:126-144, 2009). Strategies to overcome inhibitory signaling and increase costimulatory/activation signaling are thus being actively pursued to promote T cell anti-tumor activity (Mellman et al., *Nature* 480:480-489, 2011).

Acute myeloid leukemia (AML) has a 5-year survival rate of 26% with current therapies (Society AC, Cancer Facts & FIG. 2016. Atlanta: American Cancer Society, 2016). As T cells naturally traffic to hematopoietic sites where AML localizes, T cell therapy has significant potential for treating this disease but overexpression of inhibitory molecules by AML cells represents a substantive barrier to success (Geiger & Rubnitz, *Discov Med.* 19:275-284, 2015). The type-1 membrane protein CD200, a member of the immunoglobulin superfamily, binds to the T cell inhibitory receptor CD200R (Hatherley et al., *Structure* 21:820-832, 2013), and increased CD200 expression is observed in AML and other malignancies, including multiple myeloma, ovarian, and prostate cancers (Siva et al., *Cancer Immunol Immunother.* 57:987-996, 2008; Stumpfova et al., *Cancer Res.* 70:2962-2972, 2010; Kawasaki et al., *Trends Immunol.* 29:464-468, 2008). Importantly for targeted therapy, increased CD200 expression has been reported in cancer stem cells (CSCs) and leukemia stem cells (LSCs), a small population of cells that initiate and maintain disease with a high proliferative capacity and resistance to radiation and chemotherapy (Snauwaert et al., *Oncoimmunology* 2:e22943, 2013; Tonks et al., *Leukemia* 21:566-568, 2007; Ho et al., 58th ASH Annual Meeting, San Diego, Calif., 2016; Kawasaki et al., *Biochem Biophys Res Commun.* 364:778-782, 2007). CD200R signaling inhibits T cell function (Coles et al., *Leukemia* 26:2148-2151, 2012; Kretz-Rommel et al., *The Journal of Immunology* 178:5595-5605, 2007) as well as other immune cells, including natural killer (NK) cells (Coles et al., *Leukemia* 25:792-799, 2011), and high levels of CD200 expression have been linked with poor outcomes in AML patients (Tonks et al., *Leukemia* 21:566-568, 2007).

Synthetic biology affords the opportunity to engineer T cells not just with tumor-reactive receptors but also molecules that abrogate negative signals and replace them with activating signals. To both overcome inhibitory CD200R signaling associated with AML and concurrently provide missing costimulatory signals to CD8⁻ T cells, immunomodulatory fusion proteins (IFPs) were designed consisting of the CD200R ectodomain fused to an intracellular T cell costimulatory signaling domain so that the IFP could take advantage of leukemia cells expressing CD200 by binding this inhibitory ligand but generating a costimulatory signal. An fusion protein comprising a PD-1 ectodomain has been shown capable of providing costimulatory signals (Prosser et al., *Mot Immunol.* 51:263-272, 2012), but principles for designing molecules to generate or even optimize costimulatory signals have not been defined.

Therapy with TCR-transduced T cells was investigated in an AML clinical trial (registered at clinicaltrials.org as NCT01640301). All clinical investigations were conducted according to the Declaration of Helsinki principles. Protocol 2498 was approved by the Fred Hutchinson Cancer Research Center (FHCRC) Institutional Review Board (IRB) and the U.S. Food and Drug Administration (FDA). AML patients were treated with TCR-transduced T cells. Peripheral blasts were obtained from 4 patients who progressed/relapsed after T cell therapy. The AML maintenance subpopulation, LSCs, reside within the $CD45^{dim}CD34^+$ $CD38^-$ population of leukemic blasts (Bachas et al., *Leukemia* 26:1313-1320, 2012; Ho et al., 58th ASH Annual Meeting, San Diego, Calif., 2016) and CD200 expression was compared with CD34⁺ cells obtained from mobilized leukaphereses from 3 healthy donors used to generate the T cells for infusion. Although CD200 expression was not detected on the normal CD34+ cells, CD200 was expressed in a large fraction of the AML blasts from each of the patients tested (range 42-97%+) (FIG. 18A), consistent with previous reports (Tonks et al., *Leukemia* 21:566-568, 2007; Coles et al., *Leukemia* 29:1952-1954, 2015).

Figure 18A:
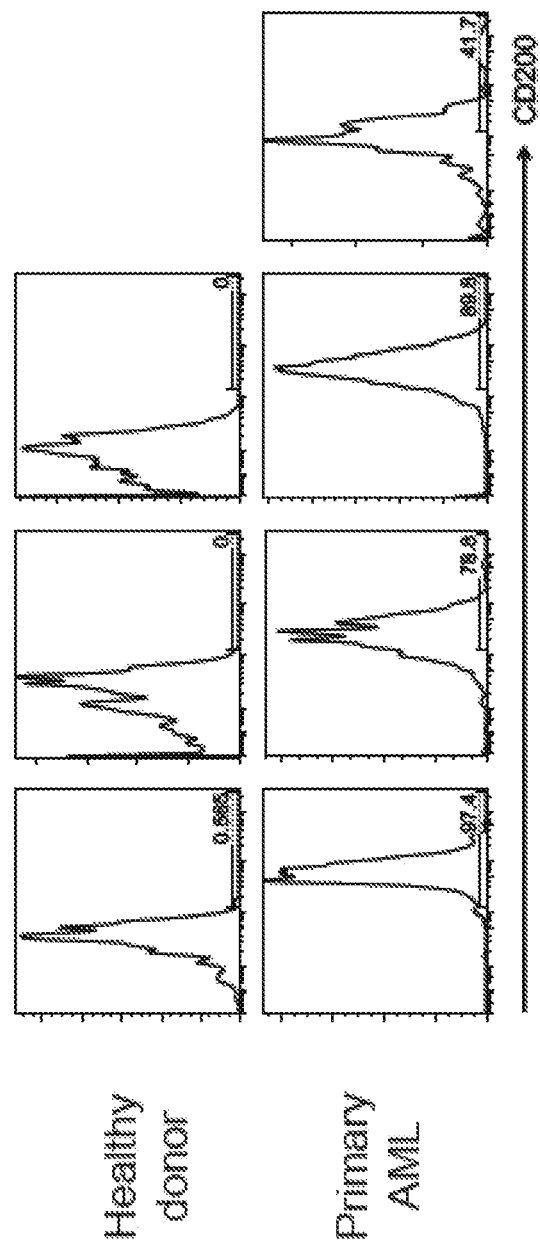
Figure 18B:
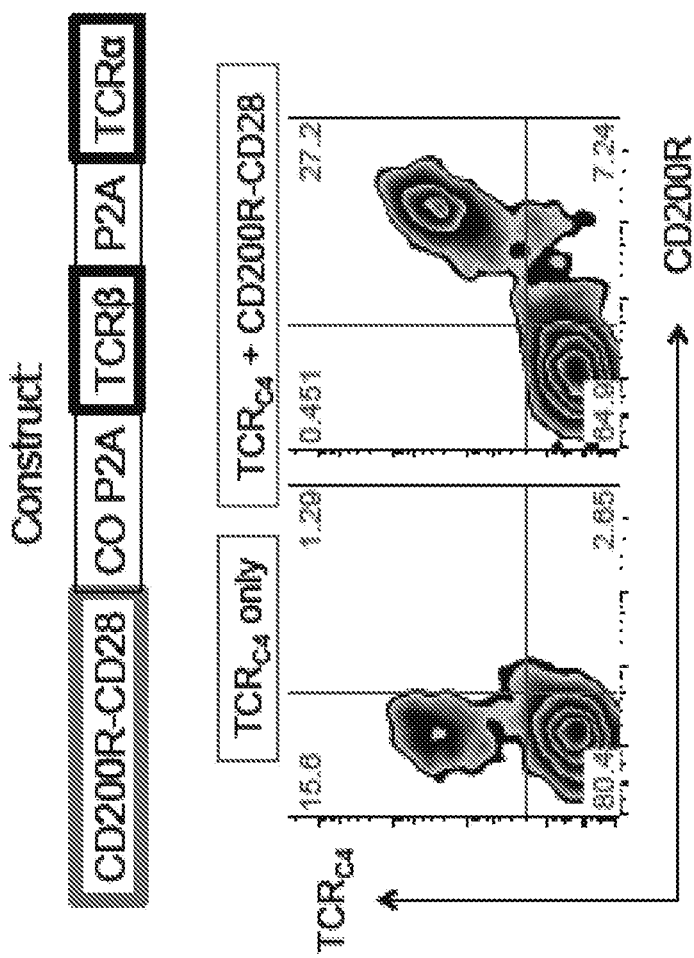

Based on the results of previous murine experiments (see Examples 14-17), human CD200Rtm-CD28 construct (SEQ ID NO.:1) was generated to maintain the spatial distance between the human T cell and tumor cell at the immunological synapse (FIG. 18B). Human primary T cells were transduced to determine if expression of this IFP could enhance function. The construct was inserted into a single lentiviral vector construct with the beta and alpha chains of the HLA-A2-restricted $WT1_{126}$-specific $TCR_{C4}$ (Stromnes et al., *Immunol Rev.* 257:145-164, 2014), which were used to transduce T cells in the clinical trial for therapy of AML, by linking each of the genes with P2A elements (FIG. 18B). The first P2A sequence was codon optimized to prevent genetic recombination with the second P2A sequence.

To generate lentiviruses, 293T/17 cells ($3 \times 10^6$ cells/plate) were transduced with human constructs in the pRRLSIN plasmid and the packaging plasmids pMDLg/pRRE, pMD2-G, and pRSV-REV using Effectene (Qiagen). Culture media was changed on day 1 post-transfection, virus-containing supernatant collected on days 2 and 3, and aliquots frozen for future use. After obtaining informed consent, peripheral blood mononuclear cells (PBMC) were harvested from normal HLA-A2+ donors. CD8+ T cells were purified using Miltenyi magnetic beads and stimulated with Human T cell Expander CD3/CD28 Dynabeads (Life Technologies) and 50 IU/mL IL-2. Four hours following stimulation, T cells were transduced by spinfection of $5$-$10 \times 10^6$ cells with 2 mL of lentiviral supernatant at 1000 g for 90 min at 32° C. T cells were restimulated every 10-14 days with a rapid expansion protocol (REP), as previously described (see Ho et al., *J. Immunol. Methods* 310:40-52, 2006).

Human primary T cells transduced to express $TCR_{C4}$ and the CD200R-CD28 fusion protein exhibited a high level of CD200R expression and equivalent levels of $TCR_{C4}$ expression relative to T cells transduced with the $TCR_{C4}$ alone (FIG. 18B).

Figure 18C:
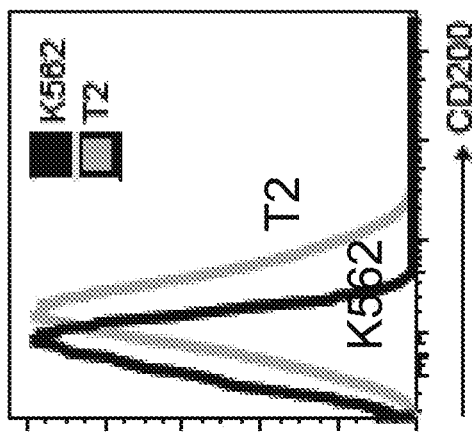
Figure 18D:
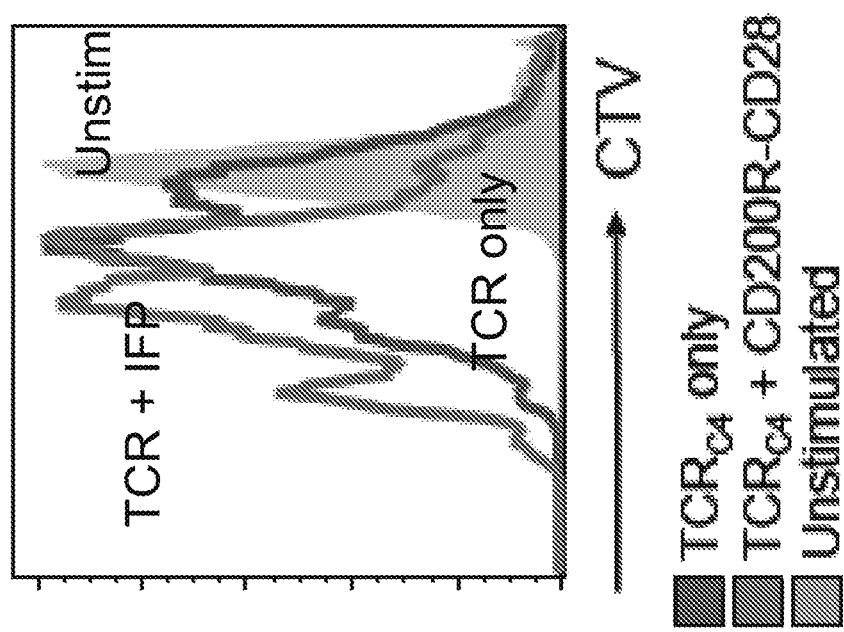
Figure 18E:
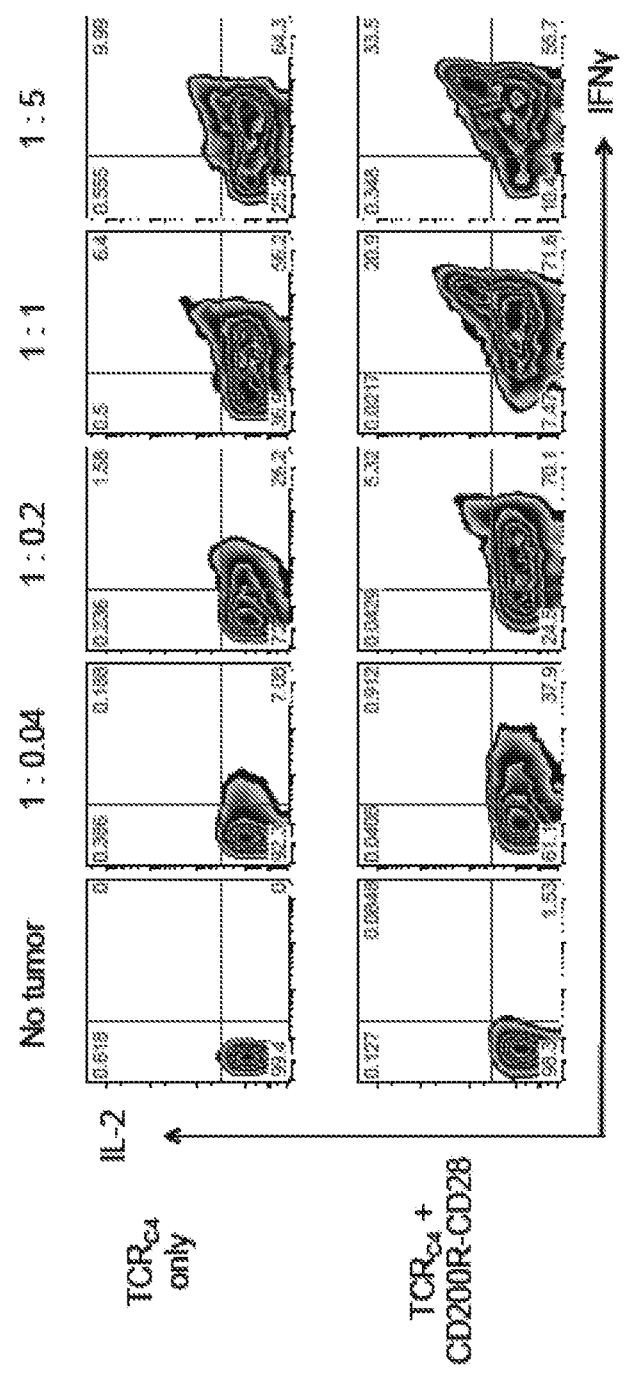

To determine if the CD200R-CD28 IFP improved the function of transduced human T cells, the cells were stimulated with peptide-pulsed T2 lymphoblastoid cells that naturally express a low level of endogenous CD200, relative to primary AML (FIG. 18A) and the CD200− CML cell line, K562 (Coles et al., *Leukemia* 25:792-799, 2011) (FIG. 18C). In response to $WT1_{126}$-pulsed T2 cells, T cells transduced with $TCR_{C4}$ plus CD200R-CD28 IFP exhibited enhanced proliferation (FIG. 18D) and increased cytokine production, particularly at low E:T ratios (FIG. 18E), suggesting tumor cells expressing even dim CD200 expression can provide costimulation.

In summary, transduction of human primary T cells with the human IFP also increased proliferation and cytokine production in response to CD200− leukemia cells. This study focused on generating an IFP to target the inhibitory molecule, CD200, which is frequently upregulated on cancer cells, particularly AML, and LSC cells, and known to suppress T cell immune responses. In addition to AML, increased CD200 expression had been reported for other heme malignancies and solid tumors such as breast, colon, ovarian, and prostate cancers. In certain embodiments, a CD200 IFP may be used in the treatment of heme malignancies and solid tumors, including breast, colon, ovarian, and prostate cancer. These results show that genetic engineering of tumor-specific T cells with IFP containing the CD200R ectodomain can efficiently convert an inhibitory signal delivered by leukemic cells to a costimulatory one in a cell intrinsic fashion, thus obviating the requirement to globally block this inhibitory receptor with the associated risk of promoting activation of endogenous autoreactive T cells. In addition, IFPs can be used to improve sensitivity without manipulating TCRs.

Example 19

Co-Expression of CD200RTM-CD28 or CD200R-9AAS-CD28CYS with WT1—Specific TCR Enhances Function in Primary T Cells In a further example, exemplary fusion proteins as described herein are illustrated using schematic representations in FIG. 19A. Representative fusion proteins include IFPs comprised of the extracellular domain of human CD200R or a portion thereof, and an intracellular signaling domain of human CD28 or a portion thereof (FIG. 19A, constructs II-VII). The hydrophobic component may be comprised of the transmembrane domain of either human CD200R (FIG. 19A, constructs I, II, and VIII) or human CD28 (FIG. 19A, constructs III-VII), or portions thereof. In some exemplary CD200R-CD28 fusion proteins, the hydrophobic component comprises the transmembrane domain of human CD28 and the extracellular component further comprises an extracellular portion of human CD28, particularly an extracellular cysteine residue adjacent to the hydrophobic component (e.g., FIG. 19A construct IV, CD200R-CD28Cys; construct V, CD200R-9aas-CD28Cys; construct VI, CD200R-12aas-CD28Cys; and construct VII, CD200R-15aas-CD28Cys). Construct VIII comprises an extracellular domain and a transmembrane domain, but does not include an intracellular signaling domain (FIG. 19A). The extracellular component may comprise all or a portion of the extracellular domain of human CD200R. In some embodiments, the extracellular component comprises the entire extracellular domain of CD200R (FIG. 19A, constructs II-IV and VIII). In some other examples, the extracellular component comprises the first 234 amino acids (e.g., FIG. 19A, construct V, CD200R-9aas-CD28Cys), the first 231 amino acids (e.g., FIG. 19A, construct VI, CD200R-12aas-CD28Cys), or the first 228 amino acids (e.g., FIG. 19A, construct VII, CD200R-15aas-CD28Cys) from the N-terminus of CD200R. The human CD200R-CD28 constructs disclosed herein have the capacity to convert what would typically be an inhibitory signal from the binding of CD200R to its target into a positive signal generated by the CD28 intracellular signaling domain.

The size of the extracellular component, which may be manipulated by adjusting the fusion protein construct, may affect the ability of the fusion protein to enter the immunological synapse and co-localize with the TCR within the cSMAC to deliver a strong co-stimulatory signal. CD28 signaling naturally occurs in the immunological synapse, where CD28 is recruited to amplify TCR signals and lower the threshold of activation (Chen and Flies, *Nat. Rev. Immunol.* 13: 227-242, 2013; Yokosuka et al., *Immunity* 29:589-601, 2008). The spatial distance between the T cell and APC is shortest within the immunological synapse, and molecules with large ectodomains are excluded. Thus, constructs that best approximate the cell-to-cell spacing of the immunological synapse may be able to co-localize with the TCR within the immunological synapse and deliver an effective costimulatory signal. Constructs IV-VII extend the CD28 transmembrane domain into the extracellular space to incorporate the membrane proximal cysteine (CD28Cys) that promotes CD28 homodimerization and enhances native CD28 signaling (Lazar-Molnar et al., Cell Immunol. 244: 125-129, 2006). In some embodiments, to account for the length added by the additional amino acids of extracellular CD28 domain, the CD200R extracellular portion is truncated by an equivalent number; for example, the CD200R extracellular domain portion of CD200R-9aas-CD28Cys is truncated by nine amino acids, an equivalent number added by the CD28 extracellular domain. Similarly, the extracellular CD200R of CD200R-12aas-CD28Cys is truncated by 12 amino acids and the extracellular CD200R of CD200R-15aas-CD28Cys is truncated by 15 amino acids. In constructs V-VII, the truncated extracellular CD200R is truncated from the C-terminal end, to preserve an N-linked glycosylation site. For the representative fusion proteins illustrated in FIG. 19A, CD200Rtm-CD28, CD200R-CD28tm, and CD200R-12aas-CD28cys theoretically best maintain the short spatial distance between the T cell and APC needed to co-localize with the TCR in the immunological synapse.

All clinical investigations were conducted according to the Declaration of Helsinki principles. Protocol 2498 was approved by the Fred Hutchinson Cancer Research Center (FHCRC) Institutional Review Board (IRB) and the U.S. Food and Drug Administration (FDA). The trial was registered at clinicaltrials.org as NCT01640301.

To generate lentiviruses, 293T/17 cells ($3 \times 10^6$ cells/plate) were transduced with human constructs (FIG. 19B) in the pRRLSIN plasmid and the packaging plasmids pMDLg/pRRE, pMD2-G, and pRSV-REV using Effectene (Qiagen). Culture media was changed on day 1 post-transfection, virus-containing supernatant collected on days 2 and 3, and aliquots frozen for future use.

Human CD200R-CD28 IFP constructs were generated that theoretically maintained the spatial distance between the T cell and tumor cell at the immunological synapse (FIG. 19B). The construct was inserted into a single lentiviral vector construct with the beta and alpha chains of the HLA-A2-restricted $WT1_{126}$-specific $TCR_{C4}$ (Stromnes et al., Immunol Rev. 257:145-164, 2014), which were used to transduce T cells in the clinical trial for therapy of AML, by linking each of the genes with P2A elements The first P2A sequence was codon optimized to prevent genetic recombination with the second P2A sequence.

After obtaining informed consent, peripheral blood mononuclear cells (PBMC) were harvested from normal HLA-A2$^+$ donors. CD8$^+$ T cells were purified using Miltenyi magnetic beads and stimulated with Human T cell Expander CD3/CD28 Dynabeads (Life Technologies) and 50 IU/mL IL-2. Four hours following stimulation, T cells were transduced by spinfection of $5-10 \times 10^6$ cells with 2 mL of lentiviral supernatant at 1000 g for 90 min at 32° C. T cells were restimulated every 10-14 days with a rapid expansion protocol (REP), as has been previously described (Ho et al., J Immunol Methods 310:40-52, 2006).

Transduced CD8$^+$ T cells were analyzed for IFP expression by flow cytometry (FIG. 19C). The results show that, when transduced with constructs encoding an IFP and a WT1-specific TCR, primary human T cells co-expressed the CD200R-CD28 IFPs and WT1-specific TCRs.

Example 20

Cells Expressing CD200-Targeted IFPS are Enriched Relative to IFP$^-$ T Cells After Stimulation with CD200$^+$ Cells To test whether expression of a CD200-targeted IFP would result in enrichment of IFP$^+$ T cells relative to IFP$^-$ T cells after stimulation with CD200$^+$ cells, the relative proportion of CD200R$^+$ cells was measured before and after stimulation with CD200$^+$ LCL cells.

Figure 20A:
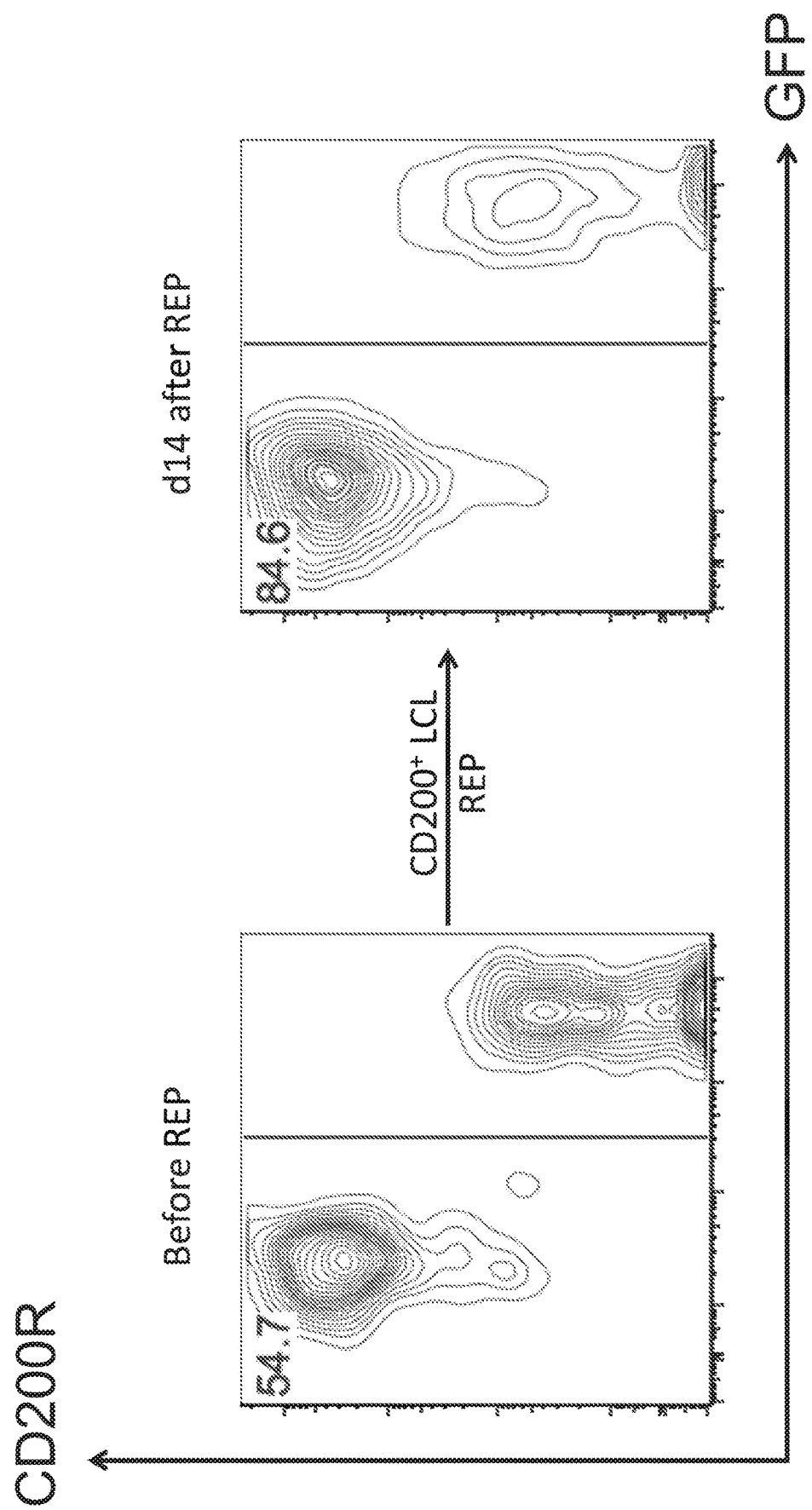

As shown in FIG. 20A, expression of the IFP CD200R-CD28tm (construct III in FIG. 19A) results in enrichment of IFP$^+$ T cells (CD200R$^+$) relative to IFP$^-$ T cells (CD200R$^-$) after restimulation with CD200-transduced LCL.

Figure 20B:
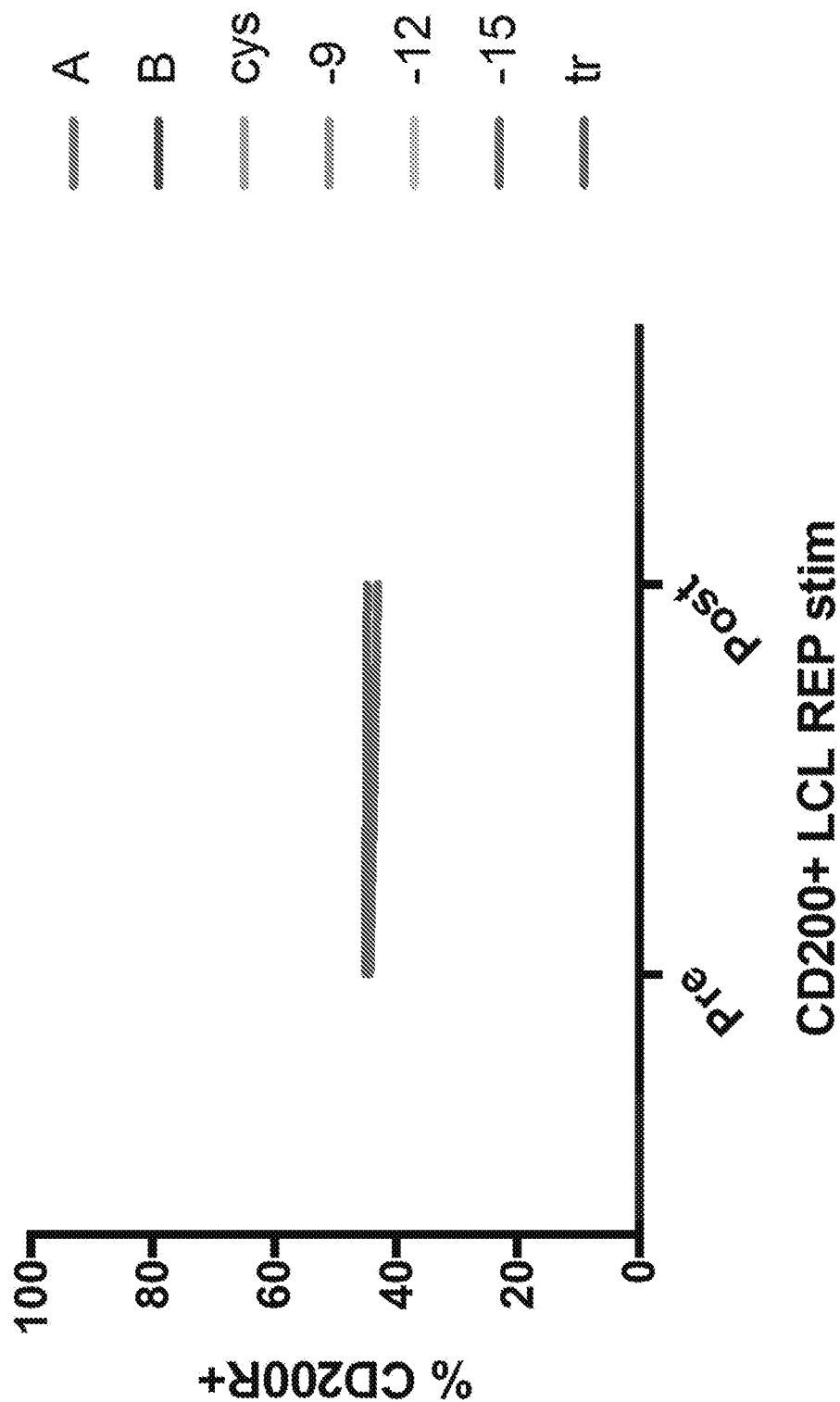
Figure 20C:
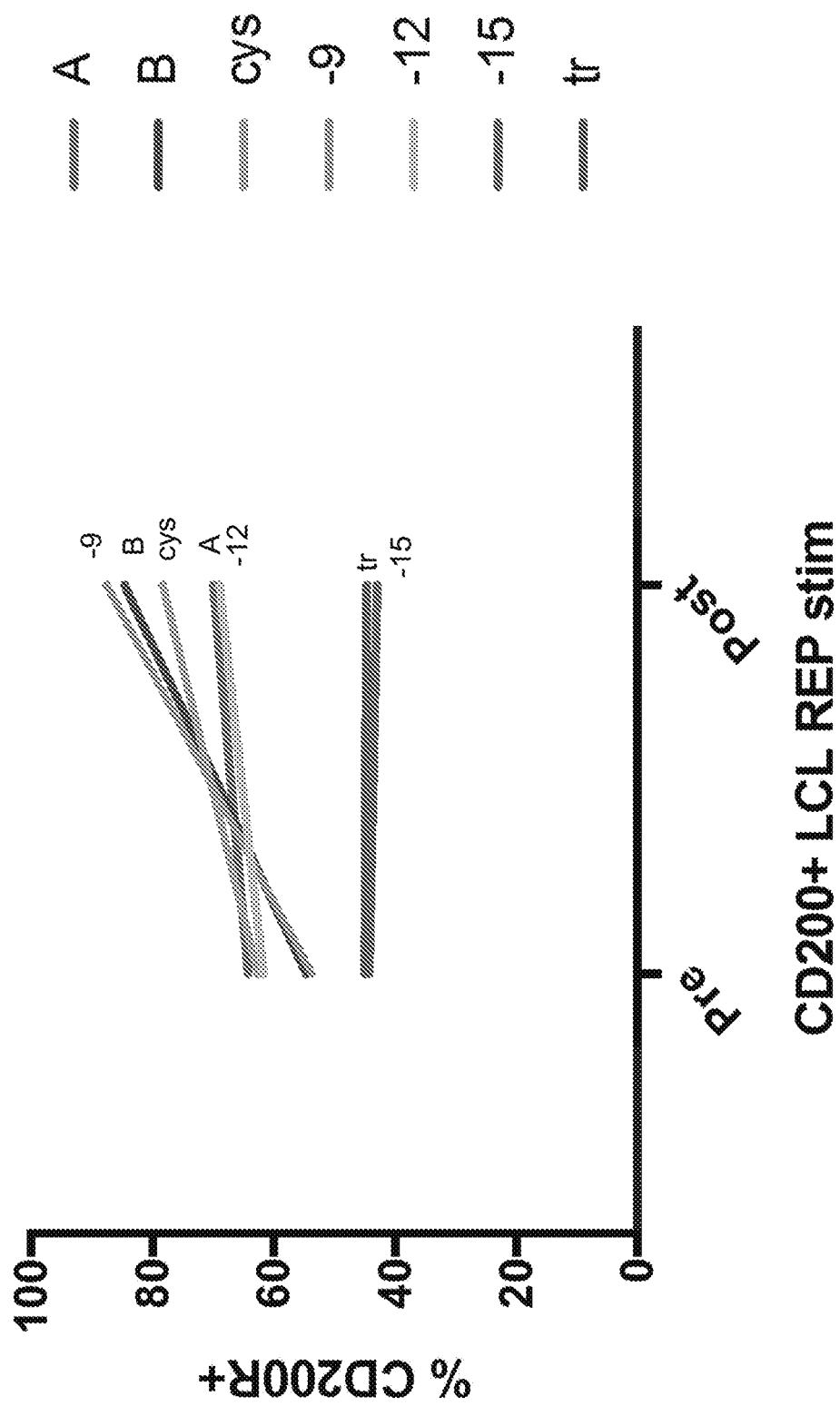
Figure 20D:
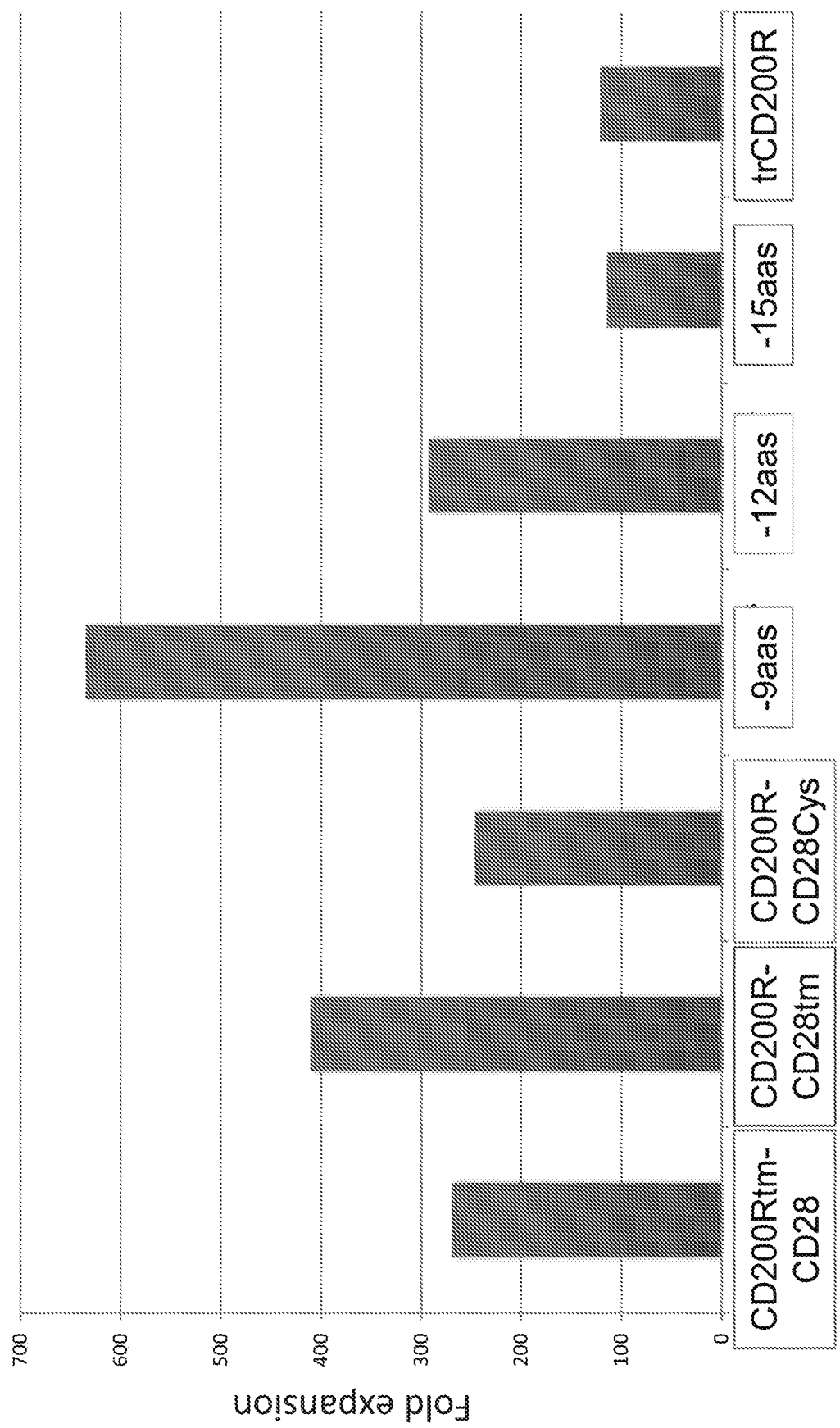

T cells transduced with trCD200R (construct VIII in FIG. 19A) and CD200R-15aas-CD28Cys (construct VII FIG. 19A) were not enriched, suggesting lack of costimulation (FIGS. 20B and 20C). T cells expressing several other constructs, however, increase in ratio after CD200$^+$ LCL REP, especially CD200R-CD28tm (construct III in FIG. 19A) and CD200R-9aas-CD28Cys (construct V in FIG. 19A) (FIGS. 20C and 20D).

Example 21

Figure 21A:
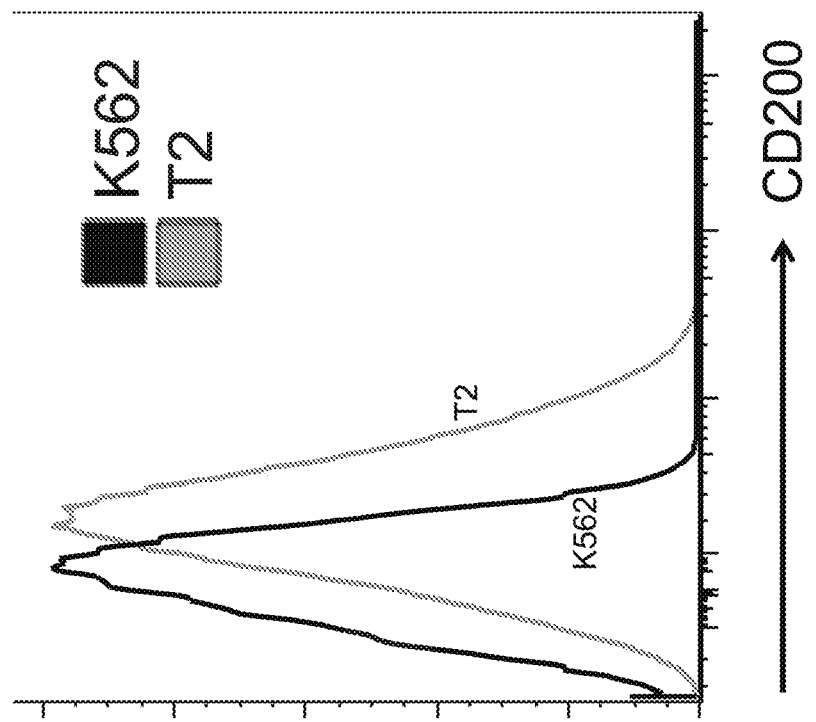
Figure 21B:
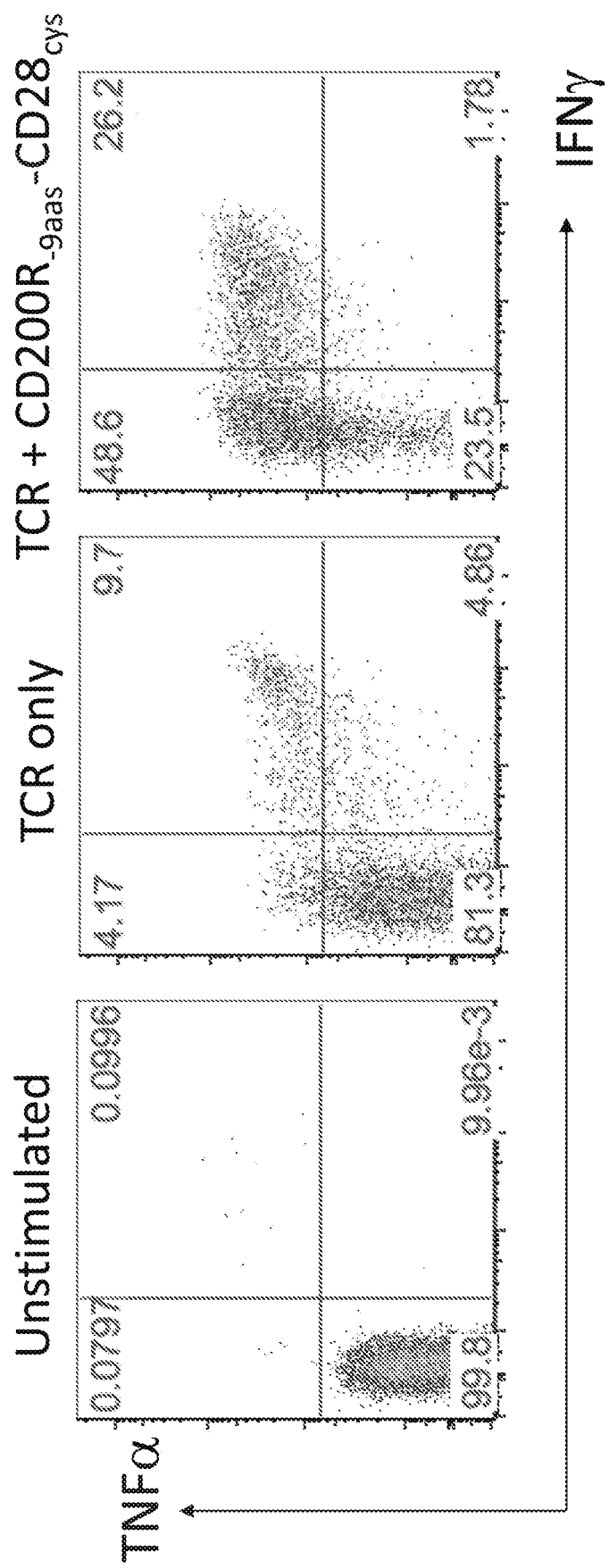

Human T Cells Expressing CD200R-CD28TM and CD200R-9AAS-CD28CYS IFP Exhibit Greater Effector Function Human T cells expressing the CD200-targeted IFP CD200R-9aas-CD28Cys, had increased cytokine production relative to IFP$^-$ cells. The TAP-deficient tumor cell line, T2, expresses endogenous CD200 (FIG. 21A). CD200R-9aas-CD28Cys expression enhanced cytokine production to peptide-pulsed T2 cells (pulsed with 1 ug/mL $WT1_{1-126}$), relative to unstimulated cells and stimulated cells expressing a TCR but not the IFP (FIG. 21B).

Figure 21C:
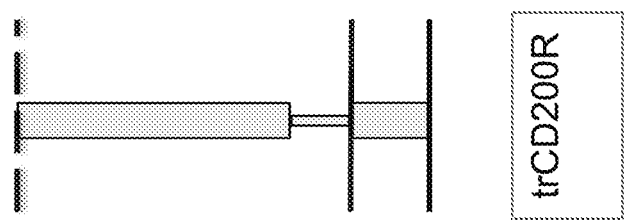
Figure 21D:
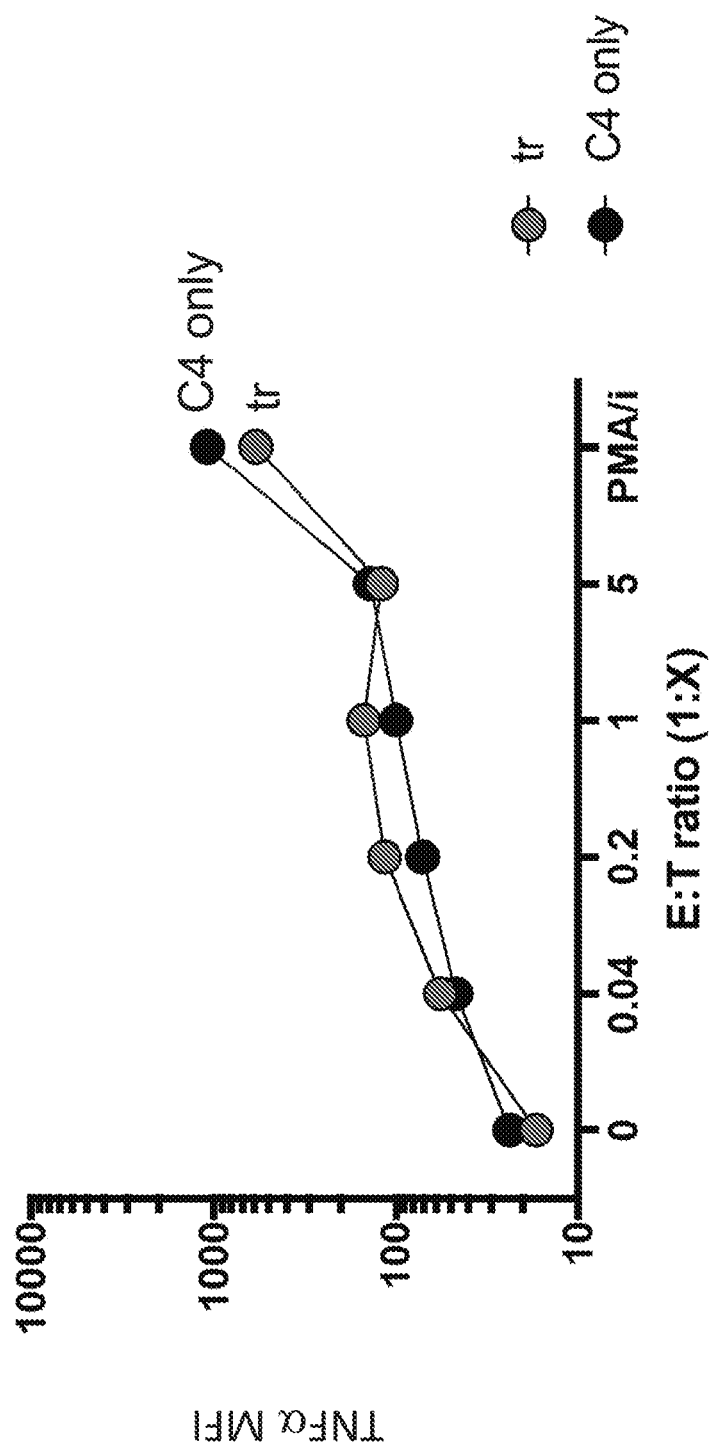

To test whether the increased effector function associated with CD200R-9aas-CD28Cys expression reflected enhanced adhesion and/or decoy binding rather than costimulation, a truncated non-signaling version of the construct was generated with only CD200R extracellular and CD28 transmembrane domains ("trCD200R"; FIG. 19A, construct VIII; FIG. 21C). Transduced T cells expressing the construct did not exhibit enhanced cytokine production relative to cells expressing $TCR_{C4}$ alone (FIG. 21D), indicating that CD200R-9aas-CD28Cys provides costimulatory signals.

Figure 21E:
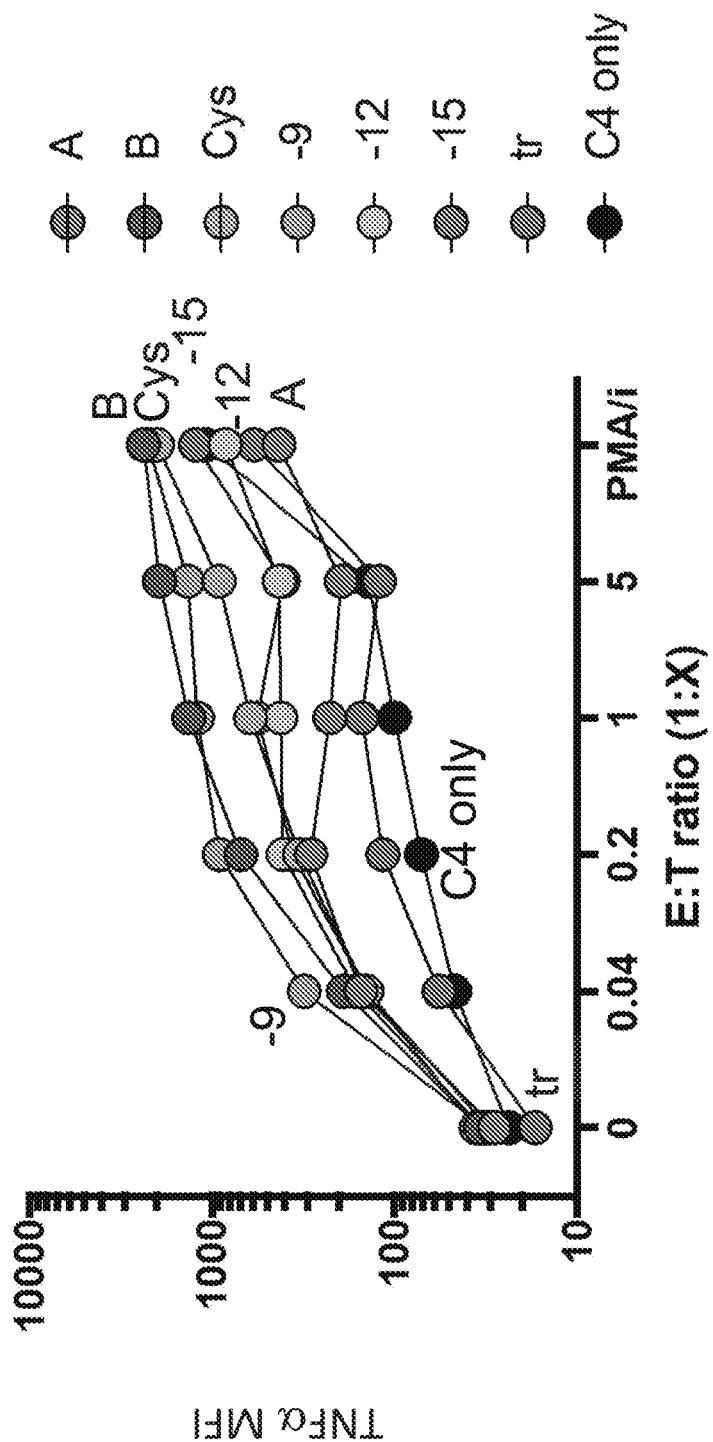
Figure 21F:
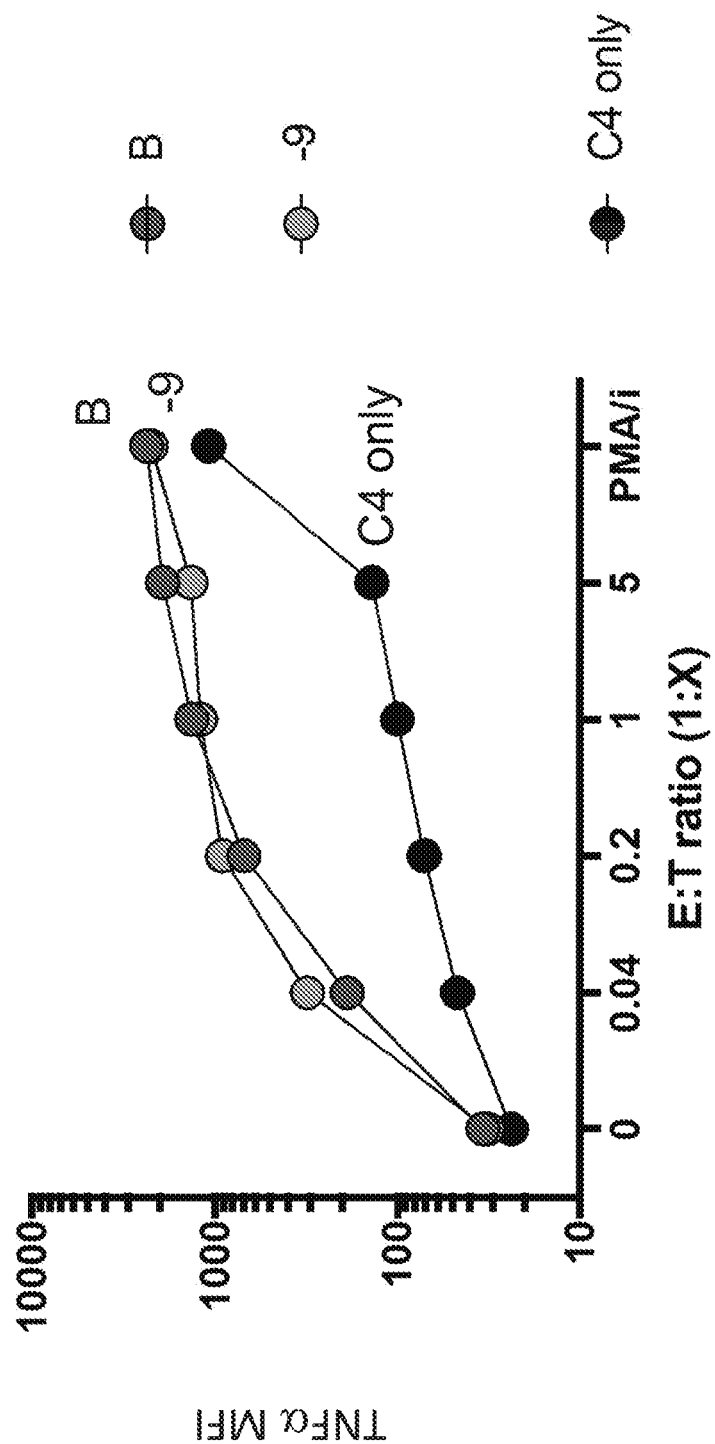
Figure 21G:
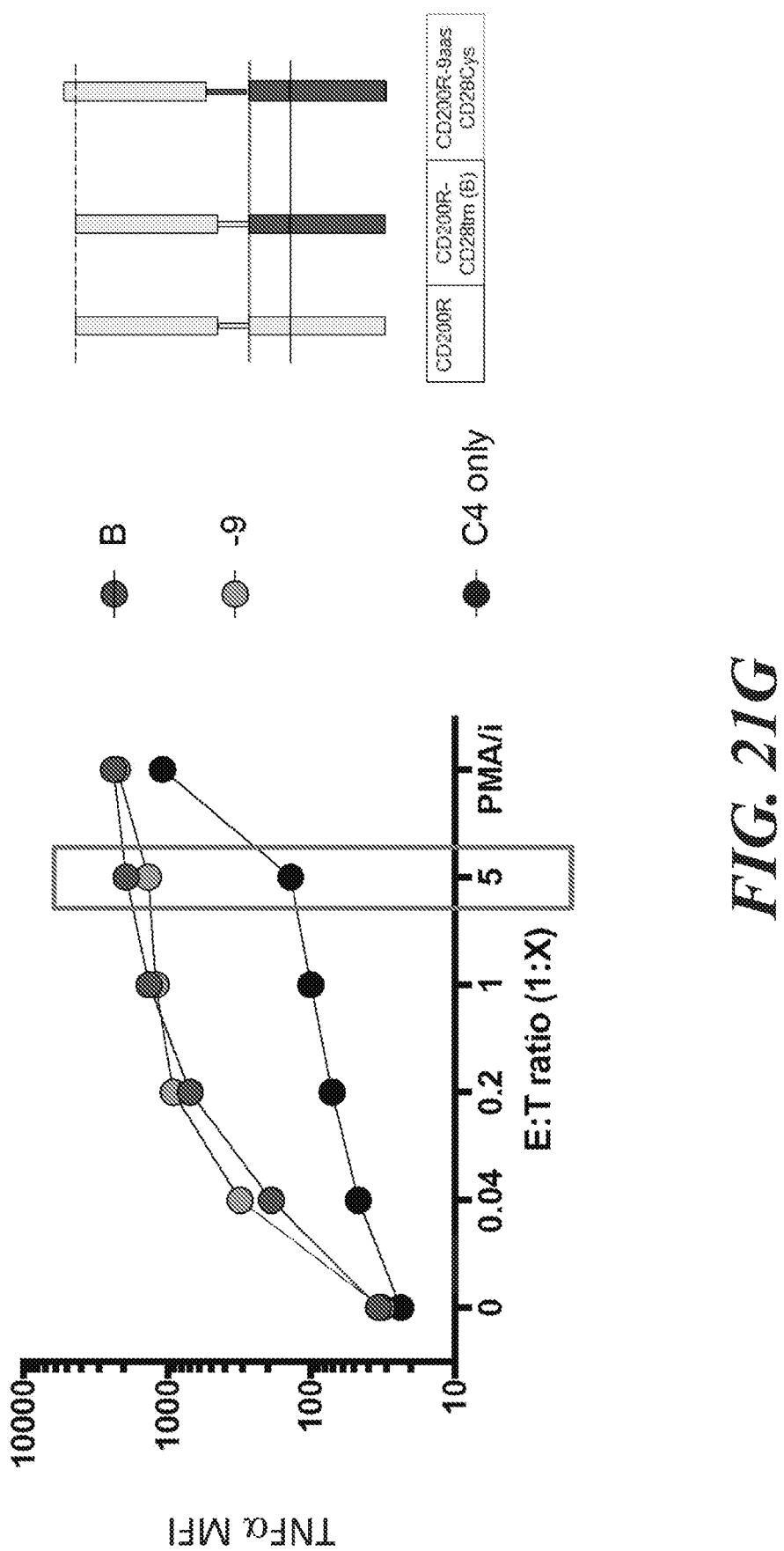
Figure 21H:
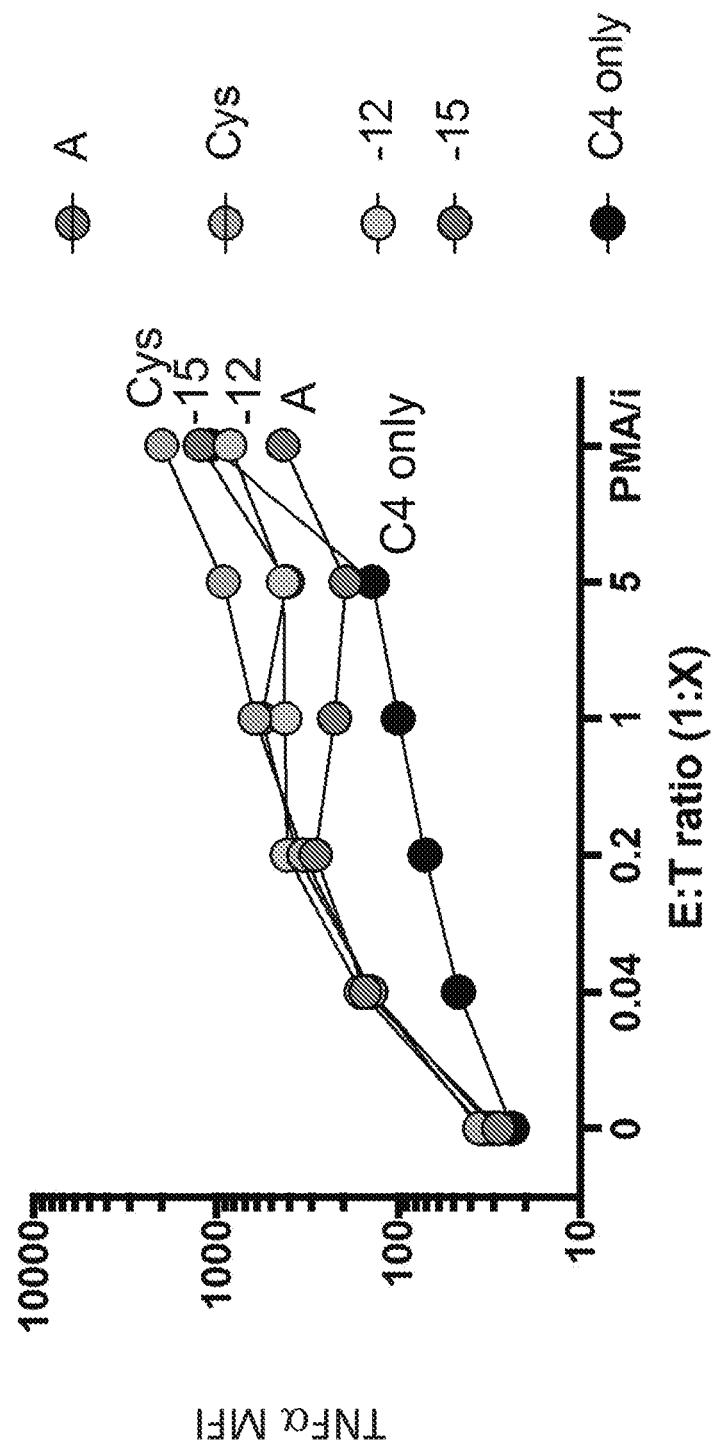
Figure 21I:
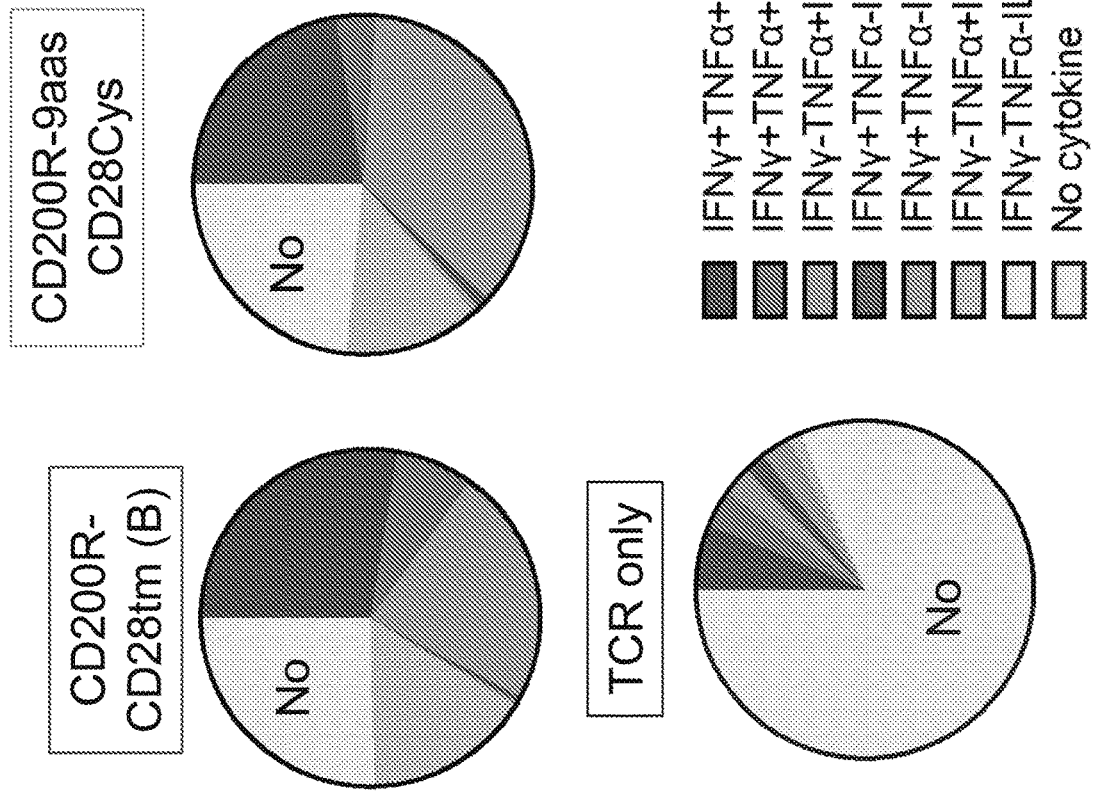

The ability of other CD200R-targeted constructs to increase cytokine production is shown in FIGS. 21E. CD200R-CD28tm (FIGS. 21F and 21G, labeled "B") and CD200R-9aas-CD28Cys (FIGS. 21F and 21G, labeled "-9") notably improved cytokine production. CD200-targeted IFPs exhibited increased and polyfunctional cytokine production (FIG. 21I).

Figure 21J:
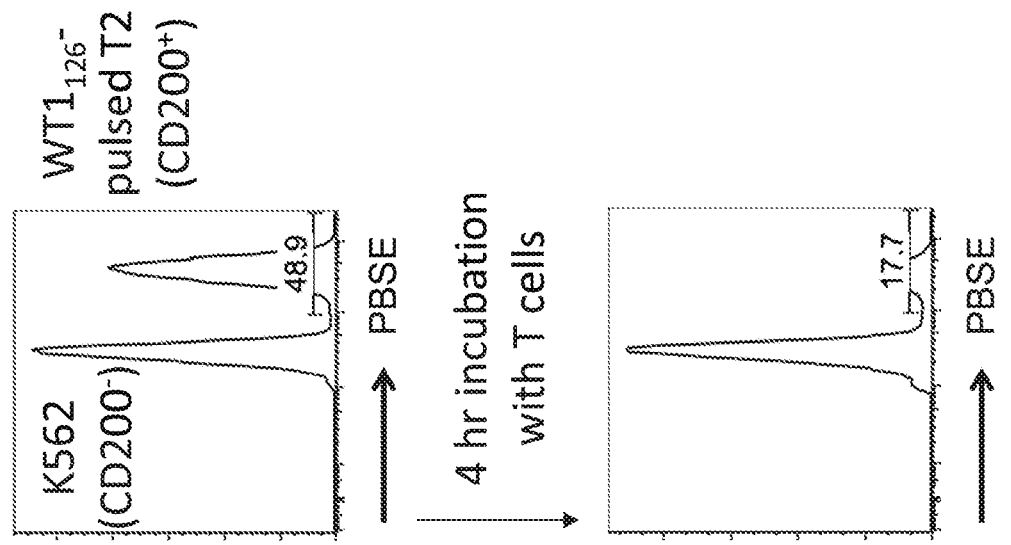
Figure 21K:
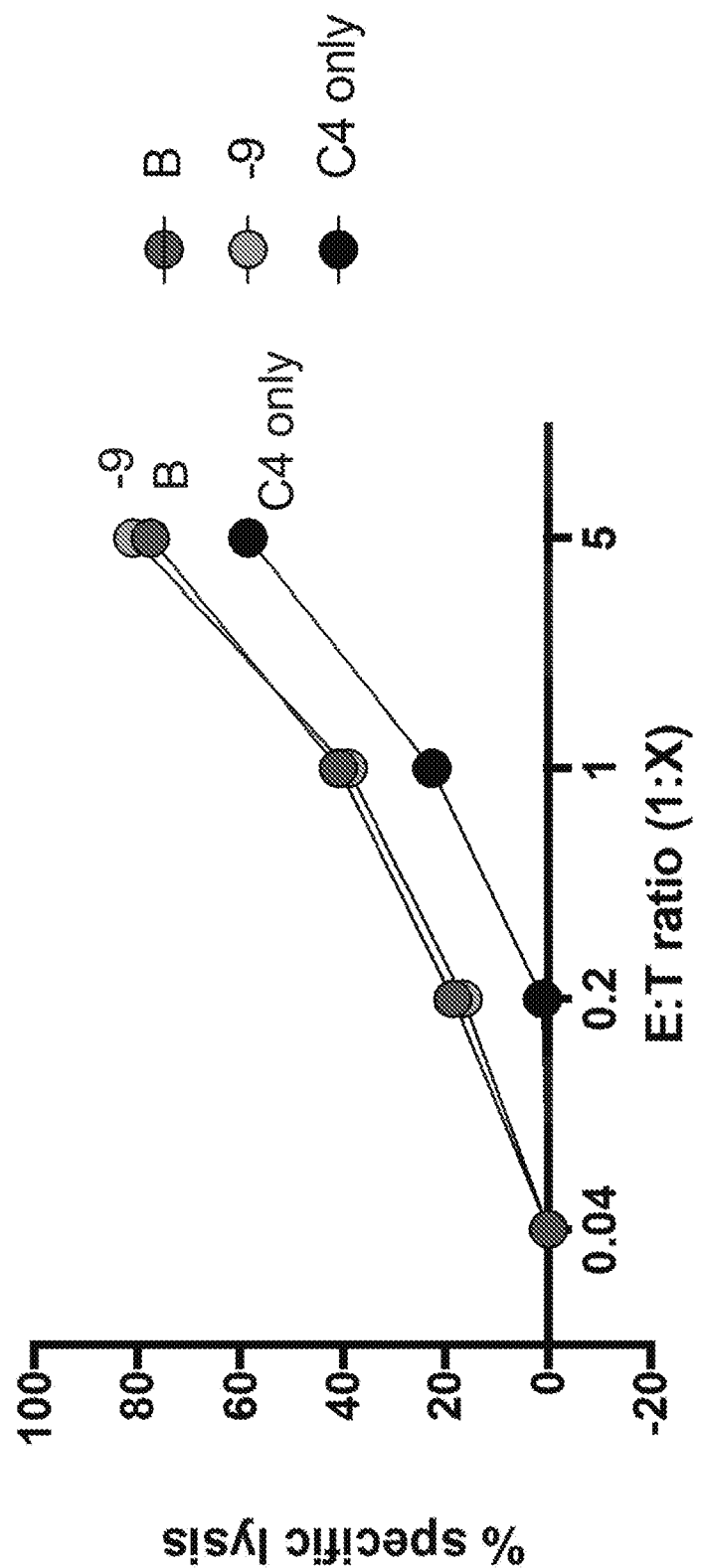

Effector function was also assessed in a flow cytometry-based cytotoxicity assay similar to that described in Example 15 (FIG. 21J). T cells transduced with CD200R-CD28 constructs lysed targets more effectively than control T cells (FIG. 21K, CD200R-CD28tm, labeled "B", and CD200R-9aas-CD28Cys, labeled "-9").

Example 22

In Vivo Testing of FAS IFPS

Fas-CD28 constructs were designed as in Example 11 and tested in an in vivo mouse model of leukemia (FIG. 22A). C57BL/6 mice were inoculated intraperitoneally with $4\times10^6$ tumor cells (day 0) and treated with cyclophosphamide, and subsequently provided with (1) no additional treatment, (2) adoptive transfer of $10^6$ GFP-transduced $TCR_{gag}$ transgenic $CD8^+$ T cells (day 5), or (3) adoptive transfer of $10^6$ Fas-CD28-transduced $TCR_{gag}$ transgenic $CD8^+$ T cells (day 5). In vivo bioluminescence imaging of firefly luciferase$^+$ FBL tumors was used to measure leukemia in the mice at various time points.

T cells transduced with Fas IFP tended to eradicate disease quicker (FIG. 22B) and provide protection over time (FIGS. 22B, 22C).

Example 23

FAS-4-1BB Fusion Protein Constructs

Figure 23A:
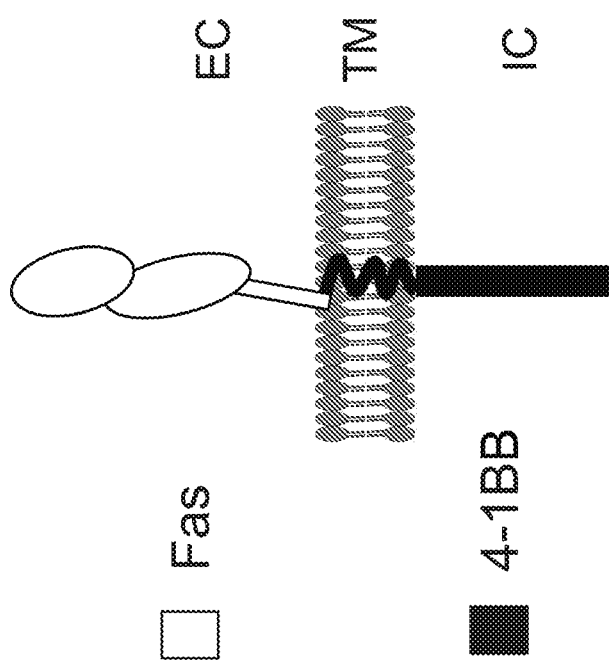

Exemplary fusion proteins as described herein also include IFPs comprised of the extracellular domain of Fas, or portions thereof, and an intracellular signaling domain of 4-1BB. The extracellular component may comprise all or a portion of the extracellular domain of Fas. In some embodiments, the transmembrane component may be comprised of the domain of Fas, 4-1BB, or CD28, or portions thereof. In some exemplary Fas-4-1BB fusion proteins, the transmembrane component comprises the transmembrane domain of CD28 and the extracellular component further comprises an extracellular portion of CD28, particularly an extracellular cysteine residue adjacent to the transmembrane component (e.g., Fas-CD28Cys-4-1BBic and Fas-9aas-CD28Cys-4-1BBic). The extracellular component may comprise all or a portion of the extracellular domain of Fas or may be truncated to preserve maintain a short spatial distance between the cells (~9aas) upon receptor-ligand interaction. In some other exemplary Fas-4-1BB fusion proteins, the transmembrane component comprises the transmembrane domain of 4-1BB (e.g., Fas-4-1BBtm; FIG. 23A). Additionally, a Fas-4-1BB construct has the capacity to convert a signal initiated by the binding of Fas to its target into a positive (e.g., costimulatory) signal generated by the 4-1BB intracellular signaling domain.

Figure 23B:
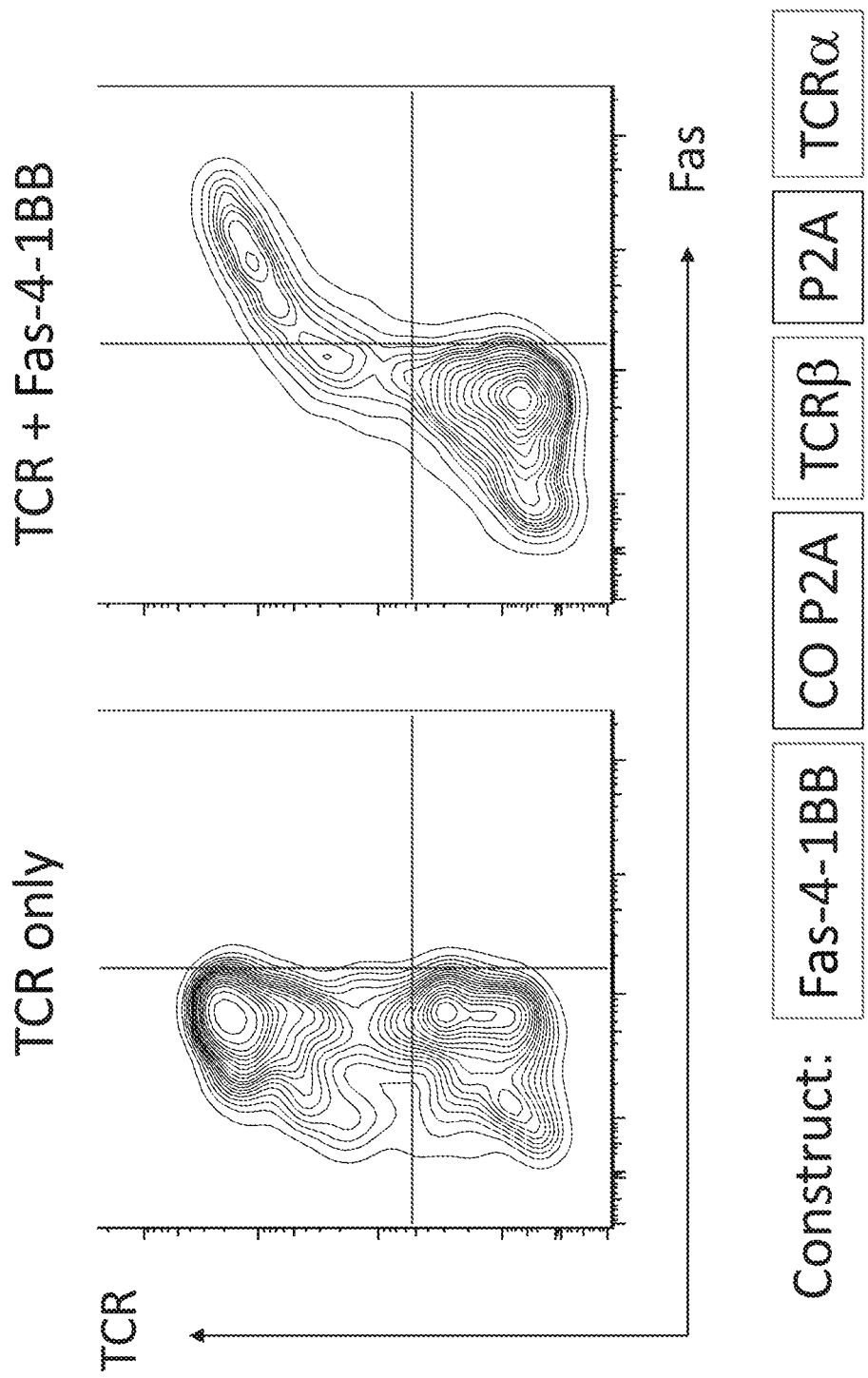

Fas-4-1BB IFP and a transgenic TCR can be co-expressed in transduced murine T cells. IFPs comprising a Fas extracellular component were generated using the general methods described in Example 2. P14 T cells were transduced to co-express the Fas-4-1BBtm IFP and a transgenic TCR ($TCR_{gag}$, specific for an epitope derived from the Friend murine leukemia virus-transformed FBL leukemia (Stromnes et al., *J Clin Invest.* 120:3722-3734, 2010)). Retroviral supernatant was generated by transfection of Plat-E cells with DNA constructs encoding either $TCR_{gag}$ alone, or $TCR_{gag}$ and Fas-4-1BBtm. Naïve P14 T cells were stimulated with anti-CD3 and anti-CD28, then transduced for 2 days with retroviral supernatant. Five days post-stimulation, transduced T cells were stained with specific antibodies to the TCR and to Fas, and analyzed by flow cytometry. P14 T cells transduced with constructs encoding $TCR_{gag}$ and Fas-4-1BBtm expressed similar levels of TCR, and also expressed high levels of the Fas-4-1BBtm IFP construct (FIG. 23B).

Figure 23C:
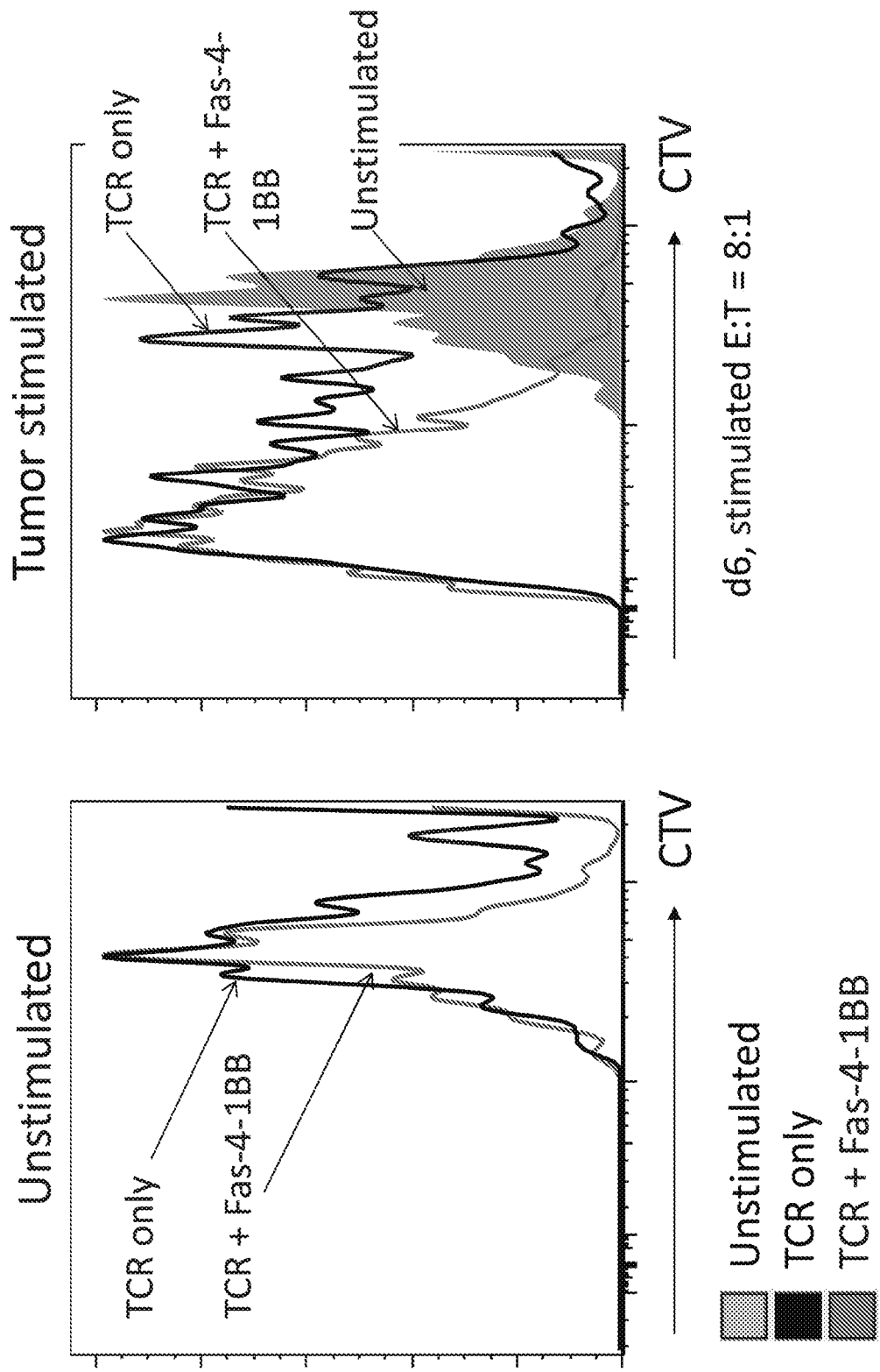

Fas-4-1BB$^+$ T cells were found to exhibit enhanced proliferation in vitro. Transduced P14 T cells were stained with CellTrace Violet (CTV) proliferation dye and stimulated with FBL tumor cells for 6 days at an effector-to-target (E:T) ratio of 8:1. T cells were then harvested and analyzed by flow cytometry. Without stimulation, T cells transduced with the $TCR_{gag}$ only exhibited a lack of proliferation, as did T cells transduced with both $TCR_{gag}$ and Fas-4-1BBtm (TCR+Fas-4-1BBtm) (FIG. 23C, left). With an E:T of 8:1, some TCR-only T cells exhibited proliferation; however, all TCR+Fas-4-1BB$^+$ T cells exhibited robust proliferation, supporting increased stimulation and proliferative capacity (FIG. 23C, right).

Figure 23D:
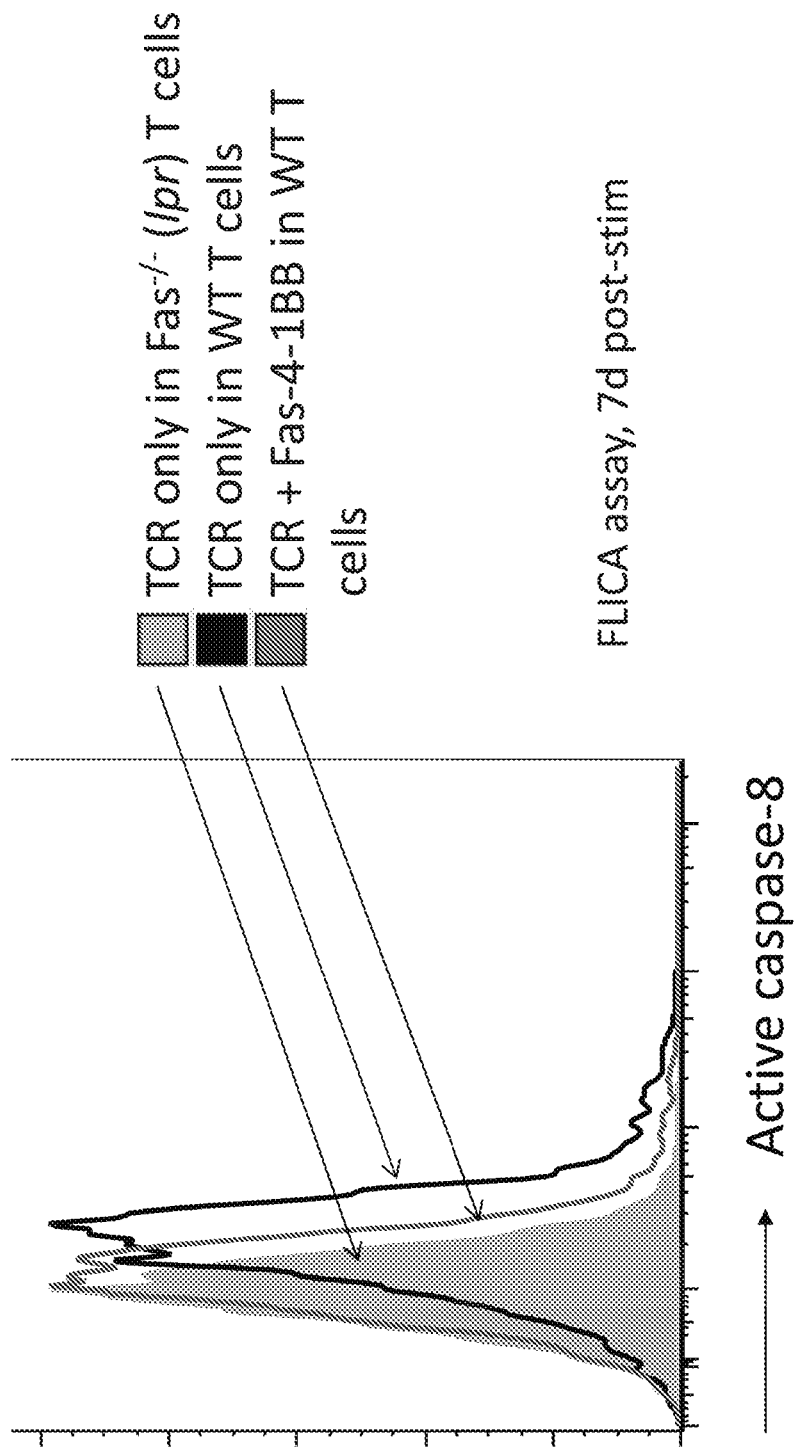

Additionally, Fas-4-1BB$^+$ T cells exhibited reduced cell death Fas pathway signaling, indicating that binding of the Fas extracellular domain did not result in activation of the Fas signaling pathway, as expected for the IFP wherein the Fas intracellular domain was replaced with a 4-1BB intracellular domain. Cell death Fas signaling pathway activity in (i) T cells expressing transgenic $TCR_{gag}$ but lacking Fas expression; (ii) wild-type T cells expressing transgenic $TCR_{gag}$; and (iii) T cells expressing transgenic $TCR_{gag}$ and Fas-4-1BBtm is shown in FIG. 23D. P14 T cells were stimulated and transduced with $TCR_{gag}$ or $TCR_{gag}$+Fas-4-1BB IFP. Seven days later, T cells were stained for active caspase-8 expression using the fluorescent inhibitor of caspases (FLICA) methodology, as a measure of cell death by the Fas pathway. Fas-deficient T cells (grey) exhibited no active caspase-8 expression, whereas TCR-transduced T cells exhibited elevated expression. TCR+Fas-4-1BB T cells had less active caspase-8 expression relative to TCR-only T cells, indicating less cell death by the Fas pathway (FIG. 23D).

Overall, these data indicate that Fas-4-1BBtm fusion proteins are able to convert negative/cell death signaling associated with binding of Fas into positive co-stimulatory signals.

Example 24

FAs-4-1BB Fusion Proteins Enhance Control of Tumor Growth and Improve Survival in an ID8 Ovarian Cancer Model T cells transduced with Fas-4-1BBtm controlled tumor growth and promoted survival in an ID8 model of ovarian cancer.

The ID8 model is a transplantable murine model of ovarian cancer (Walton et al., *Cancer Res* 76: 6118-29, 2016). An IncuCyte® assay used to quantify killing of ID8 ovarian tumor cells. Murine transduced T cells (TCR or TCR+4-1BB) were co-incubated with red fluorescent ID8 ovarian tumor cells for two days and ID8 cell growth was quantified by IncuCyte® analysis. Loss of red signal indicates killing of tumor cells. TCR+Fas-4-1BB T cells exhibited increased control of ID8 tumor cell growth, relative to TCR-only T cells, as indicated by less red signal (FIG. 24A).

Additionally, mice treated T cells transduced with anti-mesothelin TCR+Fas-4-1BBtm had increased survival relative to mice treated with T cells transduced with anti-mesothelin TCR only. In the ID8 murine ovarian cancer model, 5e6 ID8 tumor cells were implanted and allowed to disseminate for 6 weeks. Following cyclophosphamide treatment, mice received $10^7$ T cells and 50e7 mesothelin-pulsed splenocytes, followed by IL-2 injections for 10 days. Mice were treated every two weeks until euthanized according to IACUC-approved endpoint criteria. Survival was improved with T cells transduced with TCR+Fas-4-1BBtm relative to TCR-only T cells (FIG. 24B).

Example 25

T Cells Expressing FAS-4-1BB Fusion Proteins Exhibit T Cell Persistence and Improve Survival in a KPC Mouse Model of Pancreatic Cancer It has previously been shown that immunotherapy with TCR-T cells targeting mesothelin can significantly prolong survival in the murine pancreatic KPC tumor model. In this study, the KPC model was used to determine whether immunotherapy with T cells expressing Fas-4-1BB fusion proteins can improve survival.

The autochthonous KPC pancreatic cancer model was used to model human disease (Lee et al., *Curr. Protoc. Pharmacol.* 73:14.39.1-14.39.20, 2016). In patients, >90% of pancreatic ductal adenoma (PDA) cases exhibit activating mutations in KRAS and >75% have mutations in p53. The KPC model uses a pancreas-specific Cre recombinase ("C") to create mutations in Kras ("K") and p53 ("P") in the pancreatic epithelium. The KPC model (i) reproduces many of the key features of the immune microenvironment observed in human PDA including a robust inflammatory reaction and exclusion of effector T cells, (ii) is the most extensively studied genetic model of PDA for evaluation of immunotherapy, and (iii) it has reproduced clinical observations seen in PDA patients treated with several immune oncology drugs including CD40 agonists and anti-PDL1 antibodies. The model has also been useful in screening drugs as a predictor of therapeutic efficacy in patients.

Figure 25A:
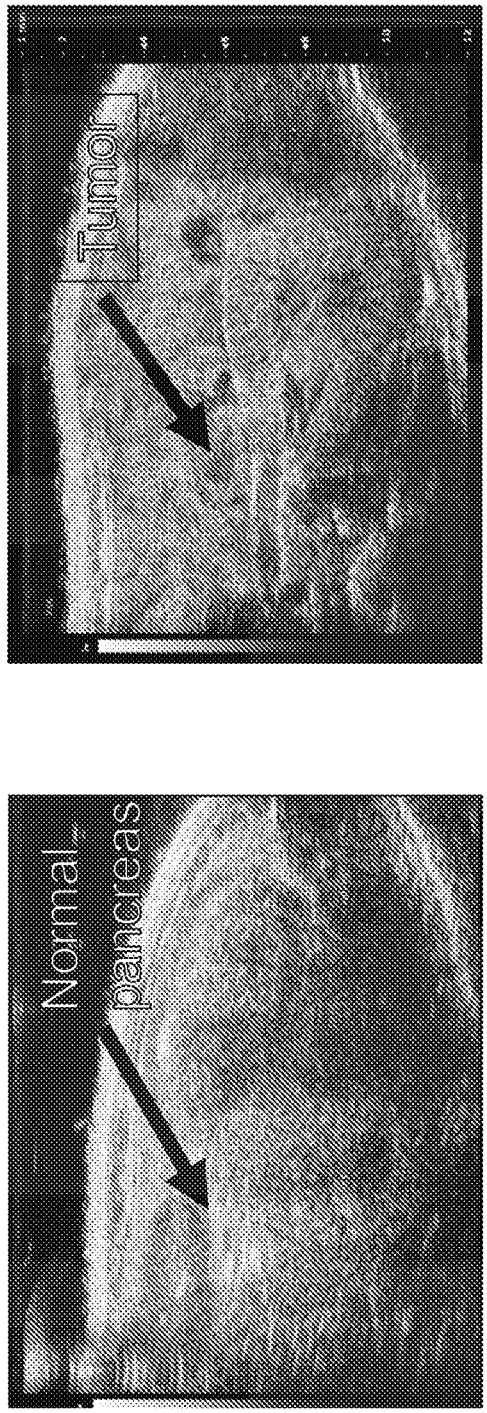
Figure 25B:
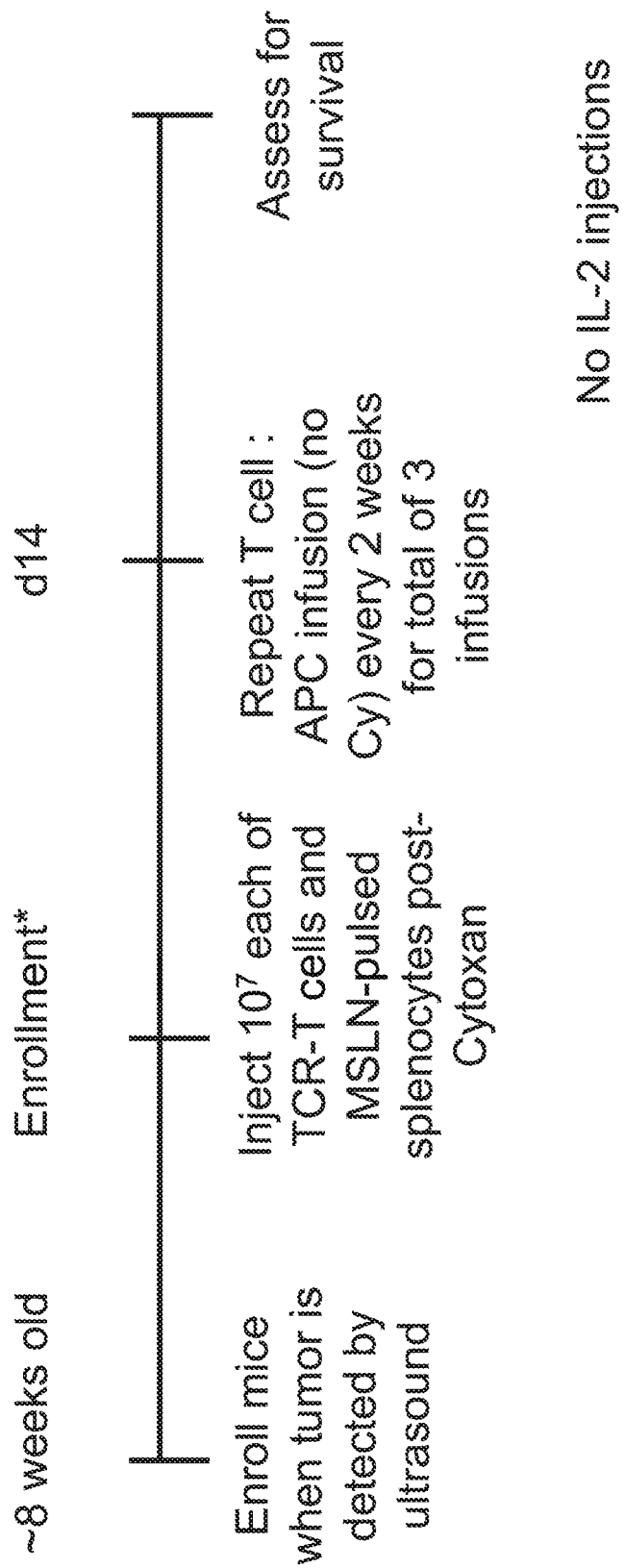

KPC mice were screened by ultrasound to determine when tumors arise, and were enrolled in the study when a tumor was detected, at approximately 8 weeks of age. FIG. 25A shows an ultrasound image of a healthy mouse with normal pancreas and a pancreatic tumor in an "enrolled" mouse (a KPC genetically engineered mouse). Mice were randomly assigned to treatment groups. Mice were treated with cyclophosphamide, and those receiving TCR-T cells were injected with $10^7$ each of mesothelin-specific-T cells (transduced with anti-mesothelin TCR cells or with anti-mesothelin TCR+Fas-4-1BBtm) and mesothelin peptide-pulsed splenocytes post-cyclophosphamide. Beginning 14 days post-enrollment, the T cell/APC infusion (but without cyclophosphamide) was repeated every 2 weeks for a total of 3 infusions, without IL-2 injections. Mice that survived 28 days after the final T cell infusion were bled and the persistence of transferred T cells was assessed by detection of congenically marked T cells using flow cytometry. At the end of the study, the mice were assessed for survival and euthanized according to IACUC-approved endpoint criteria. A summary of the experimental design used in this example is shown in FIG. 25B.

Figure 25C:
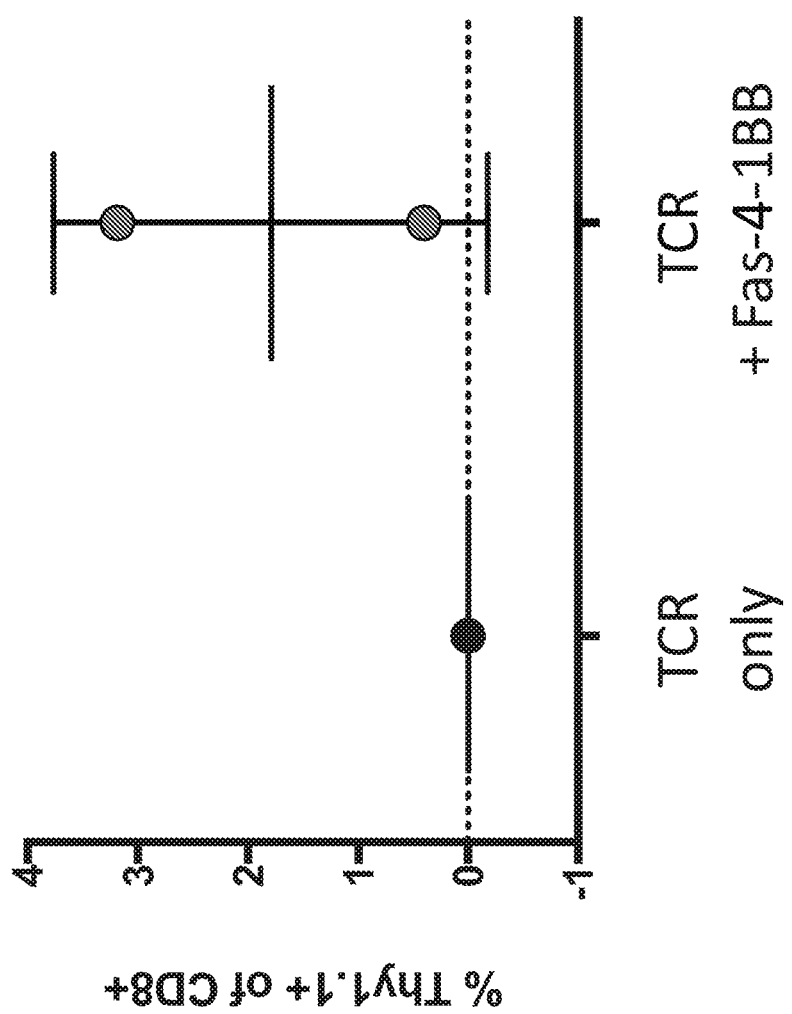
Figure 25D:
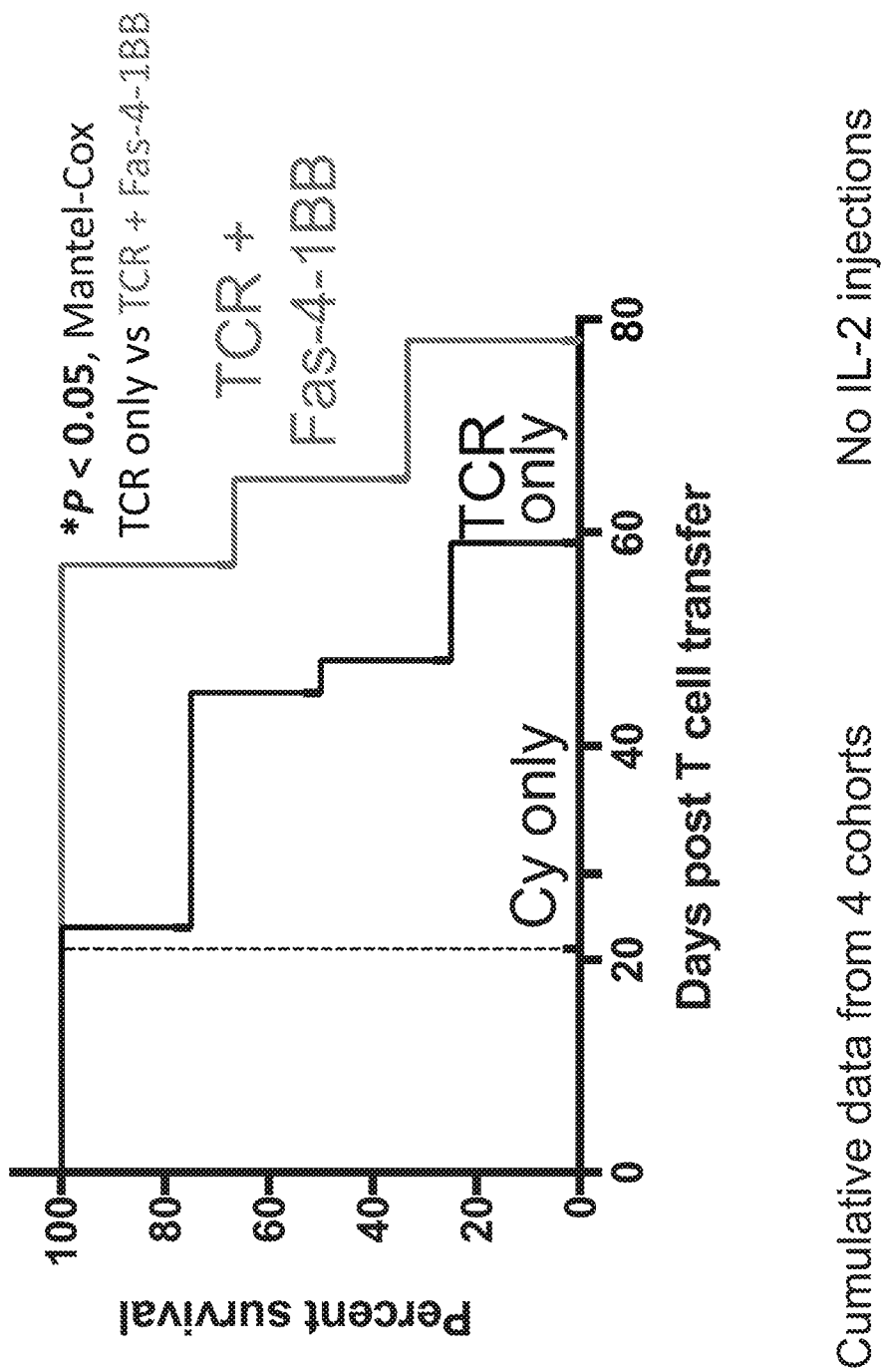

Fas-4-1BB$^+$ T cells exhibited greater persistence in the blood 28 days after the third T cell infusion (FIG. 25C). All of the mice (100%) that received Fas-4-1BB$^+$ T cells exhibited T cell persistence whereas TCR-only T cells did not persist (FIG. 25C). Survival of mice treated with mesothelin-specific TCR and Fas-4-1BB$^+$ T cells was significantly improved over mesothelin-specific TCR only T cell immunotherapy (Mantel-Cox test, P<0.05; FIG. 25D).

Example 26

FAS-4-1BB Expression Enhances Adoptive Immunotherapy in a Mouse Model of AML As was shown in Example 24 for solid tumors, treatment with Fas-4-1BB$^+$ T cells improves survival in liquid tumors. In the murine AML model (Teague et al., *Nature Medicine* 12: 335-341, 2006; Oda et al., *Blood* 130: 2410-2419, 2017), FBL cells were injected and allowed to disseminate for 5 days. On day 5, mice were treated with cyclophosphamide with or without $10^6$ T cells. Survival was improved with T cells transduced with TCR+Fas-4-1BBtm relative to TCR-only T cells (FIG. 26).

While specific embodiments of the invention have been illustrated and described, it will be readily appreciated that the various embodiments described above can be combined to provide further embodiments, and that various changes can be made therein without departing from the spirit and scope of the invention.

All of the U.S. patents, U.S. patent application publications, U.S. patent applications, foreign patents, foreign patent applications, and non-patent publications referred to in this specification or listed in the Application Data Sheet, including but not limited to U.S. Provisional Patent Application No. 62/128,979 filed Mar. 5, 2015, U.S. Provisional Patent Application No. 62/473,282 filed Mar. 17, 2017, U.S. Provisional Patent Application No. 62/629,663 filed Feb. 12, 2018, International Application No. PCT/US2016/021064 filed Mar. 4, 2016, and International Application No. PCT/US2018/022998 filed Mar. 16, 2018, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A fusion protein, comprising (a) an extracellular component comprising a binding domain that specifically binds a target, (b) an intracellular component comprising an intracellular signaling domain, and (c) a hydrophobic component connecting the extracellular and intracellular components, wherein the extracellular component is or comprises (i) a CD95 (Fas) ectodomain that binds to CD95L (FasL) or (ii) a CD95L (FasL)-binding fragment of (i), and the intracellular component is or comprises a CD137 (4-1BB) intracellular signaling domain or a signal-producing portion thereof.

2. The fusion protein according to claim 1, wherein the extracellular component comprises a full length mature extracellular portion of a Fas protein.

3. A fusion protein, comprising (a) an extracellular component comprising a binding domain that specifically binds a target, (b) an intracellular component comprising an intracellular signaling domain, and (c) a hydrophobic component connecting the extracellular and intracellular components, wherein the binding domain is, or has at least 95% identity to, an inhibitory molecule binding domain and the intracellular signaling domain is, or contains at least 95% identity to, a costimulatory or stimulatory molecule binding domain, and wherein the inhibitory molecule is or comprises (i) a CD95 (Fas) ectodomain that binds to CD95L (FasL) or (ii) a CD95L (FasL)-binding fragment of (i), and the costimulatory or stimulatory molecule is or comprises an intracellular signaling domain or a signal-producing portion thereof from CD137 (4-1BB).

4. The fusion protein according to claim 1, wherein the expression of the fusion protein in a T cell comprising an antigen-specific TCR or an antigen-specific chimeric antigen receptor results in at least about a 1.5-fold, 2-fold, or 3-fold increase in survival, expansion, cytotoxicity, and/or cytokine secretion by the T cell in response to the antigen, as compared to a response to the antigen by a cell substantially the same as the T cell but not containing the fusion protein.

5. The fusion protein according to claim 1, wherein the extracellular component further comprises an additional extracellular portion, wherein (a) the additional extracellular portion optionally is from or shares identity with an extracellular portion of a molecule that is distinct from the binding domain source molecule or does not contain the binding domain or (b) the additional extracellular portion is from a hydrophobic component, or contains the hydrophobic component or a portion thereof.

6. The fusion protein according to claim 5, wherein the extracellular component or additional extracellular portion comprises a multimerization domain or a spacer.

7. The fusion protein according to claim 6, wherein the multimerization domain comprises an extracellular component modified to contain a cysteine residue within about 2 to about 15 amino acids from the hydrophobic component.

8. The fusion protein according to claim 1, wherein the hydrophobic component comprises a transmembrane domain of a CD2, CD3ε, CD3δ, CD3ζ, CD25, CD27, CD28, CD40, CD79A, CD79B, CD80, CD86, CD95 (Fas), CD134 (OX40), CD137 (4-1BB), CD150 (SLAMF1), CD152 (CTLA4), CD200R, CD223 (LAG3), CD270 (HVEM), CD272 (BTLA), CD273 (PD-L2), CD274 (PD-L1), CD278 (ICOS), CD279 (PD-1), CD300, CD357 (GITR), A2aR, DAP10, FcRα, FcRβ, FcRγ, Fyn, GAL9, KIR, Lck, LAT, LRP, NKG2D, NOTCH1, NOTCH2, NOTCH3, NOTCH4, PTCH2, ROR2, Ryk, Slp76, SIRPα, pTα, TCRα, TCRβ, TIM3, TRIM, LPA5, or Zap70.

9. The fusion protein according to claim 1, wherein (a) the extracellular component comprises the CD95 (Fas) ectodomain, (b) the hydrophobic component comprises a transmembrane domain of a CD137 (4-1BB), and (c) the intracellular component comprises the CD137 (4-1BB) intracellular signaling domain.

10. The fusion protein according to claim 1, wherein (a) the extracellular component comprises an amino acid sequence encoded by a nucleic acid molecule selected from the group consisting of SEQ ID NOs:71, 73, and 75, (b) the hydrophobic component comprises an amino acid sequence encoded by a nucleic acid molecule selected from the group consisting of SEQ ID NOs.:4, 77, and 197, and (c) the intracellular component comprises the amino acid sequence encoded by a nucleic acid molecule selected from the group consisting of SEQ ID NO.:13.

11. The fusion protein according to claim 10, wherein the intracellular component comprises a second intracellular signaling domain.

12. The fusion protein according to claim 11, wherein the second intracellular signaling domain is or comprises an intracellular signaling domain of a CD28.

13. The fusion protein according to claim 10, wherein the extracellular component further comprises a multimerization domain with an amino acid sequence encoded by a nucleic acid molecule as set forth in SEQ ID NO.:9.

14. The fusion protein according to claim 1, wherein (a) the extracellular component comprises an amino acid sequence selected from the group consisting of SEQ ID NOs.:72, 74, and 76 (b) the hydrophobic component comprises an amino acid sequence selected from the group consisting of SEQ ID NOs.:27, 78, and 198, and (c) the intracellular component comprises an amino acid sequence as set forth in SEQ ID NO.:36.

15. The fusion protein according to claim 1, wherein the extracellular component further comprises a multimerization domain with an amino acid sequence as set forth in SEQ ID NO.:32.

16. A nucleic acid molecule encoding a fusion protein according to claim 1.

17. A vector comprising a nucleic acid molecule according to claim 16.

18. The vector according to claim 17, further encoding an antigen-specific TCR.

19. A host cell, comprising a fusion protein according to claim 1.

20. The fusion protein of claim 1, wherein the extracellular portion of a complex formed by specific binding of the fusion protein to the target (fusion protein::target complex) is of a size, or spans a distance, of (i) up to about a distance between two cell membranes of an immunological synapse, (ii) up to about or substantially the same as a distance spanned by the extracellular portion of a complex between a T cell receptor (TCR) and an MHC-peptide complex specifically bound by the TCR, (iii) up to about or substantially the same as a distance spanned by the extracellular portion of a complex between a natural molecule comprising the binding domain and its cognate binding partner; (iii) less than or up to about 40 nm, 25 nm, 20 nm, 15 nm, or 14 nm; or (iv) any combination thereof.

21. The fusion protein of claim 1, wherein (a) the extracellular component comprises the amino acid sequence set forth in SEQ ID NO: 72, (b) the hydrophobic component comprises the amino acid sequence set forth in SEQ ID NO: 78, and (c) the intracellular component comprises the amino acid sequence set forth in SEQ ID NO: 36.

22. The fusion protein of claim 1, wherein the fusion protein comprises the amino acid sequence set for in SEQ ID NO: 186.

\* \* \* \* \*